United States Patent
Maier et al.

(10) Patent No.: US 11,633,480 B2
(45) Date of Patent: *Apr. 25, 2023

(54) BIODEGRADABLE LIPIDS FOR THE DELIVERY OF ACTIVE AGENTS

(71) Applicant: ALNYLAM PHARMACEUTICALS, INC., Cambridge, MA (US)

(72) Inventors: Martin Maier, Cambridge, MA (US); Muthusamy Jayaraman, Cambridge, MA (US); Akin Akinc, Cambridge, MA (US); Shigeo Matsuda, Cambridge, MA (US); Pachamuthu Kandasamy, Cambridge, MA (US); Kallanthottathil G. Rajeev, Cambridge, MA (US); Muthiah Manoharan, Cambridge, MA (US)

(73) Assignee: ALNYLAM PHARMACEUTICALS, INC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/651,023

(22) Filed: Feb. 14, 2022

(65) Prior Publication Data
US 2022/0175928 A1 Jun. 9, 2022

Related U.S. Application Data

(63) Continuation of application No. 17/302,311, filed on Apr. 29, 2021, now Pat. No. 11,246,933, which is a
(Continued)

(51) Int. Cl.
| | |
|---|---|
| *A61K 47/18* | (2017.01) |
| *A61K 9/127* | (2006.01) |
| *A61K 9/51* | (2006.01) |
| *A61K 31/713* | (2006.01) |
| *C07D 317/30* | (2006.01) |
| *C07C 211/09* | (2006.01) |
| *C07C 211/10* | (2006.01) |
| *C07C 211/11* | (2006.01) |
| *C07C 217/08* | (2006.01) |
| *C07C 229/12* | (2006.01) |
| *C07C 327/22* | (2006.01) |
| *C07C 327/28* | (2006.01) |
| *C07C 327/32* | (2006.01) |
| *C07C 235/06* | (2006.01) |
| *C07C 251/38* | (2006.01) |
| *C07F 5/02* | (2006.01) |
| *C07D 233/54* | (2006.01) |
| *C07D 207/32* | (2006.01) |
| *C07D 295/08* | (2006.01) |
| *C07D 295/12* | (2006.01) |

(Continued)

(52) U.S. Cl.
CPC ............ *A61K 47/18* (2013.01); *A61K 9/1272* (2013.01); *A61K 9/5123* (2013.01); *A61K 31/7088* (2013.01); *A61K 31/713* (2013.01); *A61K 31/7105* (2013.01); *C07C 31/125* (2013.01); *C07C 211/09* (2013.01); *C07C 211/10* (2013.01); *C07C 211/11* (2013.01); *C07C 217/08* (2013.01); *C07C 229/12* (2013.01); *C07C 235/06* (2013.01); *C07C 251/38* (2013.01); *C07C 323/12* (2013.01); *C07C 323/58* (2013.01); *C07C 327/22* (2013.01); *C07C 327/28* (2013.01); *C07C 327/32* (2013.01); *C07D 207/32* (2013.01); *C07D 233/54* (2013.01); *C07D 295/08* (2013.01); *C07D 295/12* (2013.01); *C07D 295/14* (2013.01); *C07D 317/30* (2013.01); *C07F 5/022* (2013.01)

(58) Field of Classification Search
CPC .... A61K 9/1272; A61K 9/5123; A61K 47/18; A61K 48/00; C07C 211/00; C07C 217/00; C07C 229/00; C07C 235/00; C07C 251/00; C07C 323/00; C07C 327/88
See application file for complete search history.

(56) References Cited

U.S. PATENT DOCUMENTS

| | | |
|---|---|---|
| 2,466,678 A | 4/1949 | Bruson et al. |
| 2,856,420 A | 10/1958 | Crawford, Jr. |

(Continued)

FOREIGN PATENT DOCUMENTS

| | | |
|---|---|---|
| AU | 2011245987 A1 | 12/2012 |
| CA | 2081119 A1 | 10/1991 |

(Continued)

OTHER PUBLICATIONS

Aberle, et al., A Novel Tetraester Construct That Reduces Cationic Lipid-Associated Cytotoxicity Implications for the Onset of Cytotoxicity, Biochemistry, 1998, 6533-6540.

Alexidis et al., "Novel 1,4 Substituted Piperidine Derivatives. Synthesis and Correlation of Antioxidant Activity with Structure and Lipophilicity," J. Pharm. Pharmacol. 47:131-137,1995.

(Continued)

*Primary Examiner* — Theodore R. Howell
(74) *Attorney, Agent, or Firm* — Blank Rome LLP

(57) ABSTRACT

The present invention relates to a cationic lipid having one or more biodegradable groups located in a lipidic moiety (e.g., a hydrophobic chain) of the cationic lipid. These cationic lipids may be incorporated into a lipid particle for delivering an active agent, such as a nucleic acid. The invention also relates to lipid particles comprising a neutral lipid, a lipid capable of reducing aggregation, a cationic lipid of the present invention, and, optionally, a sterol. The lipid particle may further include a therapeutic agent such as a nucleic acid.

28 Claims, No Drawings

Specification includes a Sequence Listing.

Related U.S. Application Data continuation of application No. 16/520,183, filed on Jul. 23, 2019, now Pat. No. 11,071,784, which is a continuation of application No. 14/677,801, filed on Apr. 2, 2015, now Pat. No. 10,369,226, which is a continuation of application No. 13/708,383, filed on Dec. 7, 2012, now Pat. No. 9,061,063.

(60) Provisional application No. 61/623,274, filed on Apr. 12, 2012, provisional application No. 61/568,133, filed on Dec. 7, 2011.

(51) Int. Cl.
| | |
|---|---|
| C07D 295/14 | (2006.01) |
| C07C 323/12 | (2006.01) |
| C07C 323/58 | (2006.01) |
| C07C 31/125 | (2006.01) |
| A61K 31/7088 | (2006.01) |
| A61K 31/7105 | (2006.01) |

(56) References Cited

U.S. PATENT DOCUMENTS

| | | |
|---|---|---|
| 3,340,299 A | 9/1967 | Weintraub et al. |
| 3,729,564 A | 4/1973 | Chang et al. |
| 3,872,171 A | 3/1975 | Cronin et al. |
| 3,931,430 A | 1/1976 | Tada et al. |
| 4,121,898 A | 10/1978 | Kirschnek et al. |
| 4,694,084 A | 9/1987 | Breuninger et al. |
| 5,155,260 A | 10/1992 | Zubovics et al. |
| 5,705,385 A | 1/1998 | Bally et al. |
| 5,756,785 A | 5/1998 | O'Lenick, Jr. |
| 5,807,861 A | 9/1998 | Klein et al. |
| 5,820,873 A | 10/1998 | Choi et al. |
| 5,919,743 A | 7/1999 | O'Lenick, Jr. |
| 5,965,542 A | 10/1999 | Wasan et al. |
| 5,976,567 A | 11/1999 | Wheeler et al. |
| 5,981,501 A | 11/1999 | Wheeler et al. |
| 5,994,517 A | 11/1999 | Ts et al. |
| 6,013,813 A | 1/2000 | O'Lenick, Jr. |
| 6,077,509 A | 6/2000 | Weiner et al. |
| 6,107,286 A | 8/2000 | Byk et al. |
| 6,287,591 B1 | 9/2001 | Semple et al. |
| 6,300,321 B1 | 10/2001 | Scherman et al. |
| 6,320,017 B1 | 11/2001 | Ansell |
| 6,333,433 B1 | 12/2001 | Banerjee et al. |
| 6,346,516 B1 | 2/2002 | Banerjee et al. |
| 6,410,328 B1 | 6/2002 | Maclachlan et al. |
| 6,458,381 B1 | 10/2002 | Sourovoi et al. |
| 6,503,945 B2 | 1/2003 | Banerjee et al. |
| 6,534,484 B1 | 3/2003 | Wheeler et al. |
| 6,541,649 B2 | 4/2003 | Banerjee et al. |
| 6,586,410 B1 | 7/2003 | Wheeler et al. |
| 6,620,794 B1 | 9/2003 | O'Lenick, Jr. et al. |
| 6,734,171 B1 | 5/2004 | Saravolac et al. |
| 6,815,432 B2 | 11/2004 | Wheeler et al. |
| 6,858,224 B2 | 2/2005 | Wheeler et al. |
| 6,858,225 B2 | 2/2005 | Semple et al. |
| 6,986,902 B1 | 1/2006 | Chen et al. |
| 7,112,337 B2 | 9/2006 | Huang et al. |
| 7,341,738 B2 | 3/2008 | Semple et al. |
| 7,470,781 B2 | 12/2008 | Crouzet et al. |
| 7,514,099 B2 | 4/2009 | Chen et al. |
| 7,553,830 B2 | 6/2009 | Beigelman et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,811,602 B2 | 10/2010 | Cullis et al. |
| 7,901,708 B2 | 3/2011 | MacLachlan et al. |
| 7,982,027 B2 | 7/2011 | MacLachlan et al. |
| 8,034,376 B2 | 10/2011 | Manoharan et al. |
| 8,058,069 B2 | 11/2011 | Yaworski et al. |
| 8,158,601 B2 | 4/2012 | Chen et al. |
| 8,283,333 B2 | 10/2012 | Yaworski et al. |
| 8,329,070 B2 | 12/2012 | MacLachlan et al. |
| 8,466,122 B2 | 6/2013 | Heyes et al. |
| 8,569,256 B2 | 10/2013 | Heyes et al. |
| 8,575,123 B2 | 11/2013 | Manoharan et al. |
| 8,642,076 B2 | 2/2014 | Manoharan et al. |
| 8,691,750 B2 | 4/2014 | Constien et al. |
| 8,722,082 B2 | 5/2014 | Manoharan et al. |
| 8,754,062 B2 | 6/2014 | de Fougerolles et al. |
| 8,802,644 B2 | 8/2014 | Chen et al. |
| 8,822,668 B2 | 9/2014 | Yaworski et al. |
| 9,006,487 B2 | 4/2015 | Anderson et al. |
| 9,012,498 B2 | 4/2015 | Manoharan et al. |
| 9,029,590 B2 | 5/2015 | Colletti et al. |
| 9,061,063 B2 | 6/2015 | Maier et al. |
| 9,139,554 B2 | 9/2015 | Hope et al. |
| 9,394,234 B2 | 7/2016 | Chen et al. |
| 9,463,247 B2 | 10/2016 | Ansell et al. |
| 9,604,908 B2 | 3/2017 | Stanton et al. |
| 9,682,922 B2 | 6/2017 | Manoharan et al. |
| 10,369,226 B2 | 8/2019 | Maier et al. |
| 11,382,979 B2 * | 7/2022 | Maier ............ A61K 47/18 |
| 2003/0031704 A1 | 2/2003 | Huang et al. |
| 2003/0153081 A1 | 8/2003 | Tagawa et al. |
| 2003/0187114 A1 | 10/2003 | Breitscheidel et al. |
| 2003/0229037 A1 | 12/2003 | Massing et al. |
| 2004/0032037 A1 | 2/2004 | Katinger et al. |
| 2004/0142025 A1 | 7/2004 | MacLachlan et al. |
| 2004/0142474 A1 | 7/2004 | Mahato et al. |
| 2004/0241855 A1 | 12/2004 | Cullis et al. |
| 2005/0064595 A1 | 3/2005 | MacLachlan et al. |
| 2005/0234270 A1 | 10/2005 | Kaizik et al. |
| 2006/0051405 A1 | 3/2006 | MacLachlan et al. |
| 2006/0083780 A1 | 4/2006 | Heyes et al. |
| 2006/0100177 A1 | 5/2006 | Nishimura et al. |
| 2007/0042031 A1 | 2/2007 | MacLachlan et al. |
| 2009/0023673 A1 | 1/2009 | Manoharan et al. |
| 2009/0209037 A1 | 8/2009 | Tagawa et al. |
| 2009/0247608 A1 | 10/2009 | Manoharan et al. |
| 2010/0010066 A1 | 1/2010 | Fitzgerald et al. |
| 2010/0035974 A1 | 2/2010 | Lehn et al. |
| 2010/0076055 A1 | 3/2010 | Dande et al. |
| 2010/0130588 A1 | 5/2010 | Yaworski et al. |
| 2010/0285112 A1 | 11/2010 | Novobrantseva et al. |
| 2010/0305198 A1 | 12/2010 | Bradley et al. |
| 2010/0324120 A1 | 12/2010 | Chen et al. |
| 2011/0009641 A1 | 1/2011 | Anderson et al. |
| 2011/0045473 A1 | 2/2011 | De Fougerolles et al. |
| 2011/0091525 A1 | 4/2011 | Heyes et al. |
| 2011/0097720 A1 | 4/2011 | Ciufolini et al. |
| 2011/0117125 A1 | 5/2011 | Hope et al. |
| 2011/0200582 A1 | 8/2011 | Baryza et al. |
| 2011/0256175 A1 | 10/2011 | Hope et al. |
| 2011/0262527 A1 | 10/2011 | Heyes et al. |
| 2011/0300205 A1 | 12/2011 | Geall et al. |
| 2011/0305770 A1 | 12/2011 | Zhao et al. |
| 2011/0311582 A1 | 12/2011 | Manoharan et al. |
| 2011/0311583 A1 | 12/2011 | Manoharan et al. |
| 2012/0017411 A1 | 1/2012 | Groszkiewicz et al. |
| 2012/0027796 A1 | 2/2012 | Manoharan et al. |
| 2012/0027803 A1 | 2/2012 | Manoharan et al. |
| 2012/0046478 A1 | 2/2012 | Manoharan et al. |
| 2012/0058144 A1 | 3/2012 | Manoharan et al. |
| 2012/0058188 A1 | 3/2012 | MacLachlan et al. |
| 2012/0095075 A1 | 4/2012 | Manoharan et al. |
| 2012/0101148 A1 | 4/2012 | Aking et al. |
| 2012/0128760 A1 | 5/2012 | Manoharan et al. |
| 2012/0136073 A1 | 5/2012 | Yang et al. |
| 2012/0183602 A1 | 7/2012 | Chen et al. |
| 2012/0225434 A1 | 9/2012 | Ciufolini et al. |
| 2012/0244207 A1 | 9/2012 | Fitzgerald et al. |
| 2012/0251618 A1 | 10/2012 | Schrum et al. |
| 2012/0264810 A1 | 10/2012 | Lin et al. |
| 2012/0295832 A1 | 11/2012 | Constien et al. |
| 2013/0017223 A1 | 1/2013 | Hope et al. |
| 2013/0022649 A1 | 1/2013 | Yaworski et al. |
| 2013/0108685 A1 | 5/2013 | Kuboyama et al. |
| 2013/0122104 A1 | 5/2013 | Yaworski et al. |
| 2013/0123338 A1 | 5/2013 | Heyes et al. |
| 2013/0129811 A1 | 5/2013 | Kuboyama et al. |

(56) References Cited

U.S. PATENT DOCUMENTS

| | | |
|---|---|---|
| 2013/0261172 A1 | 10/2013 | Kariko et al. |
| 2013/0274504 A1 | 10/2013 | Colletti et al. |
| 2013/0280305 A1 | 10/2013 | Kuboyama et al. |
| 2013/0323269 A1 | 12/2013 | Manoharan et al. |
| 2013/0338210 A1 | 12/2013 | Manoharan et al. |
| 2014/0044772 A1 | 2/2014 | MacLachlan et al. |
| 2014/0121393 A1 | 5/2014 | Manoharan et al. |
| 2014/0134260 A1 | 5/2014 | Heyes et al. |
| 2014/0179761 A1 | 6/2014 | Manoharan et al. |
| 2014/0256785 A1 | 9/2014 | Manoharan et al. |
| 2014/0294937 A1 | 10/2014 | MacLachlan et al. |
| 2014/0295449 A1 | 10/2014 | Ciufolini et al. |
| 2014/0308304 A1 | 10/2014 | Manoharan et al. |
| 2014/0323548 A1 | 10/2014 | Budzik et al. |
| 2015/0174260 A1 | 6/2015 | Yang et al. |
| 2015/0174261 A1 | 6/2015 | Kuboyama et al. |
| 2015/0284317 A1 | 10/2015 | Colletti et al. |
| 2015/0343062 A1 | 12/2015 | Kuboyama et al. |
| 2016/0009637 A1 | 1/2016 | Manoharan et al. |
| 2016/0009657 A1 | 1/2016 | Anderson et al. |
| 2016/0095924 A1 | 4/2016 | Hope et al. |

FOREIGN PATENT DOCUMENTS

| | | |
|---|---|---|
| DE | 3402146 A1 | 7/1985 |
| EP | 0685234 A1 | 12/1995 |
| EP | 0685457 A1 | 12/1995 |
| FR | 02909378 A1 | 6/2008 |
| GB | 1277947 A | 6/1972 |
| JP | H05286824 A | 11/1993 |
| JP | H09110814 A | 4/1997 |
| JP | H09278726 A | 10/1997 |
| JP | H09301936 A | 11/1997 |
| JP | 2007230789 A | 9/2007 |
| JP | 4681425 B2 | 5/2011 |
| JP | 5-331118 B2 | 10/2013 |
| WO | WO-91016024 A1 | 10/1991 |
| WO | WO-9528146 A1 | 10/1995 |
| WO | 9534531 A1 | 12/1995 |
| WO | WO-9730024 A2 | 8/1997 |
| WO | WO-9816599 A1 | 4/1998 |
| WO | WO-98017757 A2 | 4/1998 |
| WO | WO-9933493 A1 | 7/1999 |
| WO | WO-0003683 A2 | 1/2000 |
| WO | WO-0107548 A1 | 2/2001 |
| WO | WO-0148233 A1 | 7/2001 |
| WO | 02072068 A2 | 9/2002 |
| WO | WO-03053409 A1 | 7/2003 |
| WO | WO-2005060934 A1 | 7/2005 |
| WO | WO-2005120461 A2 | 12/2005 |
| WO | WO-2006052767 A2 | 5/2006 |
| WO | 2006138380 A2 | 12/2006 |
| WO | WO-2006138380 A2 | 12/2006 |
| WO | 2007073489 A2 | 6/2007 |
| WO | WO-2008001505 A1 | 1/2008 |
| WO | WO-2008042973 A2 | 4/2008 |
| WO | 2008078102 A2 | 7/2008 |
| WO | WO-2009086228 A1 | 7/2009 |
| WO | WO-2009086558 A1 | 7/2009 |
| WO | WO-2009088891 A1 | 7/2009 |
| WO | WO-2009088892 A1 | 7/2009 |
| WO | 2009127060 A1 | 10/2009 |
| WO | WO-2009129385 A1 | 10/2009 |
| WO | WO-2009129395 A1 | 10/2009 |
| WO | WO-2009132131 A1 | 10/2009 |
| WO | WO-2010030739 A1 | 3/2010 |
| WO | 2010048228 A2 | 4/2010 |
| WO | WO-2010042877 A1 | 4/2010 |
| WO | WO-2010048536 A2 | 4/2010 |
| WO | WO-2010054384 A1 | 5/2010 |
| WO | WO-2010054401 A1 | 5/2010 |
| WO | WO-2010054405 A1 | 5/2010 |
| WO | WO-2010054406 A1 | 5/2010 |
| WO | WO-2010057150 A1 | 5/2010 |
| WO | WO-2010057160 A1 | 5/2010 |
| WO | WO-2010088537 A2 | 8/2010 |
| WO | 2010129687 A1 | 11/2010 |
| WO | 2010129709 A1 | 11/2010 |
| WO | WO-2010129709 A1 | 11/2010 |
| WO | 2010144740 A1 | 12/2010 |
| WO | 2011000106 A1 | 1/2011 |
| WO | WO-2011000107 A1 | 1/2011 |
| WO | 2011022460 A1 | 2/2011 |
| WO | WO-2011036557 A1 | 3/2011 |
| WO | WO-2011056682 A1 | 5/2011 |
| WO | 2011066651 A1 | 6/2011 |
| WO | 2011071860 A2 | 6/2011 |
| WO | WO-2011066651 A1 | 6/2011 |
| WO | WO-2011075656 A1 | 6/2011 |
| WO | 2011090965 A1 | 7/2011 |
| WO | 2011127255 A1 | 10/2011 |
| WO | WO-2011136368 A1 | 11/2011 |
| WO | WO-2011136369 A1 | 11/2011 |
| WO | WO-2011140627 A1 | 11/2011 |
| WO | WO-2011141703 A1 | 11/2011 |
| WO | WO-2011141704 A1 | 11/2011 |
| WO | WO-2011141705 A1 | 11/2011 |
| WO | WO-2011143230 A1 | 11/2011 |
| WO | 2011149733 A2 | 12/2011 |
| WO | 2011153120 A1 | 12/2011 |
| WO | WO-2011153493 A2 | 12/2011 |
| WO | WO-2012000104 A1 | 1/2012 |
| WO | WO-2012019630 A1 | 2/2012 |
| WO | 2012040184 A2 | 3/2012 |
| WO | 2012044638 A1 | 4/2012 |
| WO | WO-2012054365 A2 | 4/2012 |
| WO | 2012061259 A2 | 5/2012 |
| WO | WO-2012068176 A1 | 5/2012 |
| WO | 2012099755 A1 | 7/2012 |
| WO | 2012162210 A1 | 11/2012 |
| WO | WO-2013014073 A1 | 1/2013 |
| WO | WO-2013016058 A1 | 1/2013 |
| WO | WO-2013059496 A1 | 4/2013 |
| WO | WO-2013086322 A1 | 6/2013 |
| WO | WO-2013086354 A1 | 6/2013 |
| WO | WO-2013086373 A1 | 6/2013 |
| WO | 2013116126 A1 | 8/2013 |
| WO | 2013148541 A1 | 10/2013 |
| WO | WO-2013143555 A1 | 10/2013 |
| WO | WO-2014007398 A1 | 1/2014 |
| WO | WO-2014008334 A1 | 1/2014 |
| WO | WO-2014028487 A1 | 2/2014 |
| WO | WO-2014089239 A1 | 6/2014 |

OTHER PUBLICATIONS

Basha et al., Influence of cationic lipid composition on gene silencing properties of lipid nanoparticle formulations of siRNA in antigen-presenting cells. Mol Ther. Dec. 2011;19(12):2186-200.

Cattanach et al., "Studies in the Indole Series. Part IV. Tetrahydro-1 H-pyrido[4,3-b]-indoles as Serotonin Antagonists," J. Chem. Soc. Perkin 1. 10:1235-1243, 1968.

Cook et al., "Synthesis and Characterization of cis-Dioxomolybdenum(IV) Complexes with Sterically Bulky Tripodal Tetradentate Ligands," Inorganica Chimica Acta 144:81-87, 1988.

Farhood, et al., Effect of Cationic Cholesterol. Derivatives on Gene Transer and Protein Kinase C Activity, Biochimica et Biophysica Acta 1992, 1111:239-246.

Frisch et al., "A New Triantennary Galactose-Targeted PEGylated Gene Carrier, Characterization of Its Complex with DNA, and Transfection of Hepatoma Cells," Bioconjugate Chem. 15:754-764, 2004.

Hafez et al., "On the mechanism whereby cationic lipids promote intracellular delivery of polynucleic acids," Gene Therapy 8:1188-1196, 2001.

Jayaraman et al., "Maximizing the Potency of siRNA Lipid Nanoparticles for Hepatic Gene Silencing In Vivo," Angew. Chem. Int. Ed. 51:8529-8533, 2012.

Koh et al., "Delivery of antisense oligodeoxyribonucleotide lipopolyplex nanoparticles assembled by microfluidic hydrodynamic focusing," Journal of Controlled Release 141(1):62-69, 2010.

(56) References Cited

OTHER PUBLICATIONS

Lee et al., Lipid nanoparticle siRNA systems for silencing the androgen receptor in human prostate cancer in vivo, Int. J. Cancer: 131, E781-E790 (2012).
Leventis, et al., Interactions of Mammalian Cells with Lipid Dispersions Containing Novel Metabolizable Cationic Amphiphiles, Biochimica et Biophysica Acta (1990) 1023:124-132.
Lin P.J.C., et al., Influence of cationic lipid composition on uptake and intracellular processing of lipid nanoparticle formulations of siRNA. Nanomedicine: NBM 2013;9:233-246.
Lv, et al., Toxicity of Cationic Lipids and Cationic Polymers in Gene Delivery, Journal of Controlled Release, 2006, 114:100-109.
Novobrantseva et al., "Systemic RNAi-mediated Gene Silencing in Nonhuman Primate and Rodent Myeloid Cells," Molecular Therapy-Nucleic Acids 1(e4), 2012.
Nuhn et al., Synthesis, calorimetry, and X-ray diffraction of lecithins containing branched fatty acid chains, Chemistry and Physics of Lipids, 1986, 39, 221-236.
Obika et al., Symmetrical cationic triglycerides: an efficient synthesis and application to gene transfer, Bioorganic & Medicinal Chemistry, 2001, 9(2), 245-254.
Schar et al., "Long Chain Linear Fatty Alcohols from ZIEGLER—Synthesis, their Mixtures, Derivatives and Use," IP.com Prior Art Database Technical Disclosure, Jan. 17, 2011.
Semple et al., "Interactions of liposomes and lipid-based carrier systems with blood proteins: Relation to clearance behaviour in vivo," Advanced Drug Delivery Reviews 32:3-17, 1998.
Semple et al., Rational design of cationic lipids for siRNA delivery, Nature Biotechnology vol. 28, pp. 172-176 (2010).
Sheikh et al.. In vitro lipofection with novel series of symmetric 1,3-dialkoylamidopropane-based cationic surfactants containing single primary and tertiary amine polar head groups, Chemistry and Physics of Lipids, 2003, 124(1), p. 49-61.
Spelios et al., Effect of spacer attachment sites and pH-sensitive headgroup expansion on cationic lipid-mediated gene delivery of three novel myristoyl derivatives. Biophysical Chemistry 2007, 129 (2-3), 137-147.
Tang F, Hughes JA. Synthesis of a single-tailed cationic lipid and investigation of its transfection. J Control Release. Dec. 6, 1999;62(3):345-58.
Wilson et al., "The combination of stabilized plasmid lipid particles and lipid nanoparticle encapsulated CpG containing oligodeoxynucleotides as a systemic genetic vaccine," J Gene Med 11:14-25, 2009.
Yamada et al. CAS:120:27761, 1994. (151923-87-4).
Chesnoy, et al., Structure and Function of Lipid-DNA Complexes For Gene Delivery, Annu. Rev. Biophys. Biomol. Struct., 2009, 29:27-47.
International Search Report issued in PCT/US2012/068491 dated Apr. 5, 2013.
Debal, et al., Synthesis 6, 391-93 (1976).
Akinc et al., A combinatorial library of lipid-like materials for delivery of RNAi therapeutics, Nature Biotechnology 2008, 26(5), 561-569.
Banerjee et al. Novel Series of Non-Glycerol-Based Cationic Transfection Lipids for Use in Liposomal Gene Delivery, J. Med. Chem. 1999, 42(21), 4292-4299.
Mahidhar et al. Distance of Hydroxyl Functionality from the Quaternized Center Influence DNA Binding and in Vitro Gene Delivery Efficacies of Cationic Lipids with Hydroxyalkyl Headgroups, J. Med. Chem. 2004, 47(23), 5721-5728.
Mukherjee et al. Covalent Grafting of Common Trihydroxymethylaminomethane in the Headgroup Region Imparts High Serum Compatibility and Mouse Lung Transfection Property to Cationic Amphiphile, J. Med. Chem. 2008. 51(6), 1967-1971.
Nguyen et al., Lipid-derived nanoparticles for immunostimulatory RNA adjuvant delivery, Proc. Natl. Acad. Sci, 2012, 109(14), E797-E803.
Rajesh et al., Dramatic Influence of the Orientation of Linker between Hydrophilic and Hydrophobic Lipid Moiety in Liposomal Gene Delivery, J. Am. Chem. Soc. 2007, 129, 11408-11420.
Srinivas et al. Cationic Amphiphile with Shikimic Acid Headgroup Shows More Systemic Promise Than Its Mannosyl Analogue as DNA Vaccine Carrier in Dendritic Cell Based Genetic Immunization, J. Med. Chem. 2010, 53(3), 1387-1391.
Whitehead et al. Synergistic silencing: combinations of lipid-like materials for efficacious siRNA delivery, Mol Ther., 2011, 19(9), 1688-94.
Akinc, et al., "Development of lipidoid-siRNA formulations for systemic delivery to the liver", Mol Ther., May 17, 2009, 17(5):872-9. doi: 10.1038/mt.2009.36. Epub Mar. 3, 2009.
Bhattacharya, et al., "Advances in gene delivery through molecular design of cationic lipids", Chem Commun (Camb), Aug. 21, 2009, (31):4632-56. Epub Jul. 3, 2009.
Braun, et al., "Structure/function relationships of polyamidoamine/DNA dendrimers as gene delivery vehicles", J Pharm Sci, Feb. 2005, 94(2):423-36.
Chen, et al., "Novel cationic lipid that delivers siRNA and enhances therapeutic effect in lung cancer cells", Mol Pharm., May-Jun. 2009, 6(3):696-705.
Crawford, et al., "Analysis of lipid nanoparticles by Cryo-EM for characterizing siRNA delivery vehicles", Int J Pharm, Jan. 17, 2011, 403(1-2):237-44. doi: 10.1016/j.ijpharm.2010.10.025. Epub Oct. 23, 2010.
Gjetting, et al., "In vitro and in vivo effects of polyethylene glycol (PEG)-modified lipid in DOTAP/cholesterol-mediated gene transfection", Int J Nanomedicine, Aug. 9, 2010, 5:371-83.
Jeffs, et al., "A scalable, extrusion-free method for efficient liposomal encapsulation of plasmid DNA", Pharm Res., Mar. 2005, 22(3):362-72.
Kumar, et al., "Single histidine residue in head-group region is sufficient to impart remarkable gene transfection properties to cationic lipids: evidence for histidine-mediated membrane fusion at acidic pH", Gene Ther., Aug. 2003, 10(15):1206-15.
Labas, et al., "Nature as a source of inspiration for cationic lipid synthesis", Genetica, Feb. 2010, 138(2):153-68. Epub Sep. 11, 2009.
Love, et al., "Lipid-like materials for low-dose, in vivo gene silencing", Proc Natl Acad Sci U S A. Feb. 2, 2010;107(5):1864-9. Epub Jan. 11, 2010. Erratum in: Proc Natl Acad Sci U S A. May 25, 2010;107(21):9915.
Manoharan, et al., "Oligonucleotide conjugates as potential antisense drugs with improved uptake, biodistribution, targeted delivery, and mechanism of action", Antisense Nucleic Acid Drug Dev Apr. 2002;12(2):103-28.
Manoharan, et al., "RNA interference and chemically modified small interfering RNAs", Curr Opin Chem Biol. Dec. 2004;8(6):570-9.
Martin, et al., "The design of cationic lipids for gene delivery", Curr Pharm Des. 2005;11(3):375-94.
Mukherjee, et al., "Common co-lipids, in synergy, impart high gene transfer properties to transfection-incompetent cationic lipids", FEBS Lett Feb. 14, 2005;579(5):1291-300. doi: 10.1016/j.febslet.2004.11.116. Epub Jan. 26, 2005.
Smisterova, et al., "Molecular shape of the cationic lipid controls the structure of cationic lipid/dioleylphosphatidylethanolamine-DNA complexes and the efficiency of gene delivery", J Biol Chem. Dec. 14, 2001;276(50):47615-22Epub Oct. 2, 2001.
Sparks, et al., "838. Flexible Cationic Lipids for siRNA Delivery", Mol Ther. May 1, 2011;19(Supplement 1:S320). 1 page.
Stanton, et al., "Medicinal chemistry of siRNA delivery", J Med Chem. Nov. 25, 2010;53(22):7887-901. Epub Aug. 31, 2010.
Zhang, et al., "Macropinocytosis is the major pathway responsible for DNA transfection in CHO cells by a charge-reversal amphiphile", Mol Pharm. Jun. 6, 2011;8(3):758-66. doi: 10.1021/mp100366h. Epub Mar. 30, 2011.
Zhang, et al., "Self-assembling DNA-lipid particles for gene transfer", Pharm Res. Feb. 1997; 14(2): 190-6.

(56) References Cited

OTHER PUBLICATIONS

Zhang, et al., "Synthesis, characterization, and in vitro transfection activity of charge-reversal amphiphiles for DNA delivery", Bioconjug Chem. Apr. 20, 2011;22(4):690-9. doi: 10.1021/bc1004526. Epub Apr. 1, 2011.
Zhu, et al., "Systemic gene expression after intravenous DNA delivery into adult mice", Science. Jul. 9, 1993;261(5118):209-11.
Simões S, et al., "Cationic liposomes for gene delivery", Expert Opin Drug Deliv. 2005, 2(2):237-254.
Xu, et al., "Mechanism of DNA Release from Cationic Lipsome/DNA Complexes Used in Cell Transfection", 35 Biochemistry 5616-5623 (1996).
Zhang, et al., "Functional Lipids and Lipoplexes for Improved Gene Delivery", 94(1) Biochimie 42-58 (May 20, 2011).
Zhi, et al., "Transfection Efficiency of Cationic Lipids with Different Hydrophobic Domains in Gene Delivery", 21 Bioconjugate Chem. 563-577 (2010).
Zhou, et al., Efficient Intracellular Delivery of Oligonucleotides Formulated in Folate Receptor-Targeted Lipid Vesicles, 13 Bioconjugate Chemistry 1220-1225 (2002).
Zhu, L, et al., Mahato RL Structural and formulation factors influencing pyridinium lipid-based gene transfer. Bioconjug Chem. Dec. 2008;19(12):2499-512. doi: 10.1021/bc8004039. PMID: 19053309; PMCID: PMC2681295.
Zuhorn, et al., "Nonbilayer phase of lipoplex-membrane mixture determines endosomal escape of genetic cargo and transfection efficiency", 11 Molecular Therapy 801-810, 2005.
Defendants' Invalidity Contentions Regarding U.S. Pat. Nos. 11,246,933 and 11,382,979, *Alnylam Pharmaceuticals, Inc.* v. *Pfizer Inc et al.*, Civil Action No. 22-336, Dec. 19, 2022 (999 pages).
Exhibit A to Defendants' Invalidity Contentions Regarding U.S. Pat. Nos. 11,246,933 and 11,382,979, *Alnylam Pharmaceuticals, Inc.* v. *Pfizer Inc et al.*, Civil Action No. 22-336, Dec. 19, 2022 (247 pages).
Exhibit B to Defendants' Invalidity Contentions Regarding U.S. Pat. Nos. 11,246,933 and 11,382,979, *Alnylam Pharmaceuticals, Inc.* v. *Pfizer Inc et al.*, Civil Action No. 22-336, Dec. 19, 2022 (611 pages).
Moderna's Invalidity Contentions and Document Production Accompanying Invalidity Contentions, *Alnylam Pharmaceuticals, Inc.* v. *Moderna, Inc et al.*, Civil Action No. 22-cv-335, , Dec. 16, 2022 (includes Exbhit 1) (490 pages).
Wasunga, et al., "Cationic lipids, lipoplexes and intracellular delivery of genes", 166 J. of Controlled Release, 255-264 (2006).
Akinc, et al., "Targeted Delivery of RNAi Therapeutics With Endogenous and Exogenous Ligand Based Mechanisms", 18 Molecular Therapy 1357-1364, May 11, 2010.
Arpicco, et al., "Synthesis, Characterization and Transfection Activity of New Saturated and Unsaturated Cationic Lipids", II Farmaco 59:769-878 (2004).
Barani, et al., "A Review on Applications of Liposomes in Textile Processing", 18(3) Journal of Liposome Res. 249-262 (Dec. 16, 2008).
Choudhary, et al., "An Evaluation of Peptide-Bond Isoteres", 12 ChemBioChem 1801-1807 (2011).
Coderch, et al., "Application of Liposomes in Textile Dyeing", 1 Recent Res. Devel. In Oil Chem. 17-29 (1997).
Felgner, et al., "Lipofection: A highly efficient, lipid-mediated DNA-transfection procedure", 84 Proc. Natl. Acad. Sci. U.S.A. 7413-7417 (1987).
Ferrari, et al., "Synergy between cationic lipid and co-lipid determines the macroscopic structure and transfection activity of lipoplexes", 30(8) Nucleic Acids Res. 1808-1816 (2002).
Floch, et al., "Cation Substitution in Cationic Phosphonolipids: A New Concept To Improve Transfection Activity and Decrease Cellular Toxicity", 43 J. Med Chem., 4617-4628 (2000).
Hashim, et al., "Nature-like synthetic alkyl branched-chain glycolipids: a review on chemical structures and selfassembly properties", 39(1) Liquid Crystals, 1-17 (2012).
Herringson, et al., "Convenient Targeting of Stealth siRNA-Lipoplexes to Cells with Chelator Lipid-Anchored Molecules", 139 J. Controlled Release 229-238 (2009).
Heyes, et al., "Cationic lipid saturation influences intracellular delivery of encapsulated nucleic acids", 107 Journal of Controlled Release 276-287 (2005).
Huang, et al., "Asymmetric 1-alkyl-2-acyl Phsophatdyl Choline: A Helper Lipid for Enhanced Non-Viral Gene Delivery", 427 International Journal of Pharmaceutics 64-70 (2012) (available online Jun. 21, 2011).
Ilies, et al., "Cationic lipids in gene delivery: principles, vector design and therapeutically applications", 8 Current Pharmaceutical Design, 2441-2473 (2002).
Jenkins, et al., "Peptide Bond Isoteres: Ester or (E)-Alkene in the Backbone of the Collagen Triple Helix", 7(13) Drganic Letters 2619-2622 (2005).
Koltover, et al., "An Inverted Hexagonal Phase of Cationic Liposome-DNA Complexes Related to DNA Release and Delivery", 281 Science 78-81 (1998).
Kosswig, "Surfactants", Ullmann's Encyclopedia of Industrial Chemistry, Wiley-VCH Verlag GmbH & Co. KGaA, 2012, p. 431-505.
Koynova, et al., "An Intracellular Lamellar-Nonlamellar Phase Transition Rationalizes the Superior Performance of Cationic Lipid Transfection Agents", 103 PNAS 14373-14378 (2006).
Wilson, et al., "Targeted Delivery of Oligodeoxynucleotides to Mouse Lung Endothelial Cells in Vitro and in Vivo", 12 Molecular Therapy 510-518 (2005).
Ma, et al., "Cationic Lipids Enhance siRNA-Mediated Interferon Response in Mice", 330 Biochemical and Biophysical Res. Communs. 775-759 (Mar. 17, 2005).
Ma, et al., "Lipoplex morphologies and their influences on transfection efficiency in gene delivery", 123 Journal of Controlled Release 184-194 (2007).
Maier, et al., Biodegradable lipids enabling rapidly eliminated lipid nanoparticles for systemic delivery of RNAi therapeutics, 21(8) Molecular Therapy 1570-1578 (2013).
Masotti, et al., "Comparison of Different Commercially Available Cationic Liposome-DNA Lipoplexes: Parameters Influencing Toxicity and Transfection Efficiency", 68 Colloids and Surfaces B: Biointerfaces 136-144 (2009).
Maurer, et al., "Spontaneous Entrapment of Polynucleotides upon Electrostatic Interaction with Ethanol-Destabilized Cationic Liposomes", 80 Biophysical J. 2310-2326 (2001).
Medvedeva, et al., "Novel Cholesterol-Based Cationic Lipids for Gene Delivery", 52 Journal of Medicinal Chemistry, 6558-6568 (2009).
Mishra, et al., "Ester Quats: The Novel Class of Cationic Fabric Softness", 56(6) J. Oleo Sci. 269-276 (2007).
Montier, et al., "Progress in cationic lipid-mediated gene transfection: a series of bio-inspired lipids as an example", 8 Current Gene Therapy 296-312 (2008).
Morrison & Boyd, "Organic Chemistry—Functional Derivatives of Carboxylic Acids Edition", Allyn and Bacon Inc., Chapter 24, p. 857-865 (1987).
Nguyen, et al., "Complex Formation with Plasmid DNA Increases the Cytotoxicity of Cationic Liposomes", 30(4) Biol. Pharm Bull. 751-757 (2007).
Niculescu-Duvaz, et al., "Structure-Activity Relationship in Cationic Lipid Mediated Gene Transfection", 10 Current Med. Chem. 1233-1261 (2003).
Obata, et al., "Plasmid DNA-Encapsulating Liposomes: Effect of a Spacer between Cationic Head Group and Hydrophobic Moieties of the Lipids on Gene Expression Efficiency", 1788 Biochimica et Biophysica Acta 1148-1158 (2009).
Ouyang, et al., "Controlled Template-Assisted Assembly of Plasmid DNA into Nanometric Particles with High DNA Concentration", 11 Bioconjugate Chem. 104-112 (2000).
Patani, et al., "Bioisosterism: A Rational Approach in Drug Design", 96 Chem. Rev. 3147-3176 (1996).
Pinnaduwage, et al., "Use of a quaternary ammonium detergent in liposome mediated DNA transfection of mouse L-cells", 985 Biochimica et Biophysica Acta 33-37 (1989).

(56) References Cited

OTHER PUBLICATIONS

Prata, et al., "A New Helper Phospholipid for Gene Delivery", 13 Chem Comm. 1566-1568 (2008).

Sato, et al., "A pH-Sensitive Cationic Lipid Facilitates the Delivery of Liposomal siRNA and Gene Silencing Acitivity in Vitro and In Vivo", 163 J. of Controlled Release 267-276 (2012).

Scarzello, et al., "Polymorphism of Pyridinium Amphiphiles for Gene Delivery: Influence of Ionic Strength, Helper Lipid Content and Plasmid DNA Complexation", 88 Biophysical Journal, 2104-2113 (2005).

Semple, et al., "Efficient Encapsulation of Antisense Oligonucleotides in Lipid Vesicles Using Ionizable Aminolipids: Formation of Novel Small Multilamellar Vesicle Structures", 1510 Biochimica et Biophysica Acta 152-166 (2001).

Simberg, et al., "DOTAP (and other cationic lipids): chemistry, biophysics, and transfection", 21(4) Critical Reviews in Therapeutic Drug Carrier-Systems 257-317 (2004).

Tadros, "Applied Surfactants: Principles and Applications", WILEY-VCH Vedag GmbH & Co. KGA, Weinheim (2005) ISBN: 3-527-30629-3, 1-17.

Tamaddon, et al., "Modeling Cytoplasmic Release of Encapsulated Oligonucleotides from Cationic Liposomes", 336 Pharmaceutical Nanotechnology 174-182 (2007).

Tranchant, et al., "Physiochemical Optimisation of Plasmid Delivery by Cationic Lipid", 6 J. Gene. Med. S24-S35 (2004).

Tristam-Nagle, et al., "Structure and Water Permeability of Fully Hydrated DiphytanolPC", 163 Chemistry and Physics of Lipids 630-637 (2010) (available online May 4, 2010).

Tros De Ilarduya, et al., "Gene Delivery by Lipoplexes and Polyplexes", 40 European J. Pharmaceutical Sciences 159-170 (2010) (available online Mar. 30, 2010).

Xu, et al., "Mechanism of DNA Release from Cationic Lipsome/DNA Complexes Used in Cell Transfection May 7, 1996".

Zhang, et al., "Functional Lipids and Lipoplexes for Improved Gene Delivery May 20, 2011".

\* cited by examiner

BIODEGRADABLE LIPIDS FOR THE DELIVERY OF ACTIVE AGENTS

This application is a continuation of U.S. patent application Ser. No. 17/302,311, filed Apr. 29, 2021, which is a continuation of Ser. No. 16/520,183, filed Jul. 23, 2019, now U.S. Pat. No. 11,071,784, which is a continuation of U.S. patent application Ser. No. 14/677,801, filed Apr. 2, 2015, now U.S. Pat. No. 10,369,226, which is a continuation of U.S. patent application Ser. No. 13/708,383, filed Dec. 7, 2012, now U.S. Pat. No. 9,061,063, which claims the benefit of U.S. Provisional Application No. 61/568,133, filed Dec. 7, 2011, and U.S. Provisional Application No. 61/623,274, filed Apr. 12, 2012, each of which is hereby incorporated by reference.

TECHNICAL FIELD

The present invention relates to biodegradable lipids and to their use for the delivery of active agents such as nucleic acids.

BACKGROUND

Therapeutic nucleic acids include, e.g., small interfering RNA (siRNA), micro RNA (miRNA), antisense oligonucleotides, ribozymes, plasmids, immune stimulating nucleic acids, antisense, antagomir, antimir, microRNA mimic, supermir, U1 adaptor, and aptamer. In the case of siRNA or miRNA, these nucleic acids can down-regulate intracellular levels of specific proteins through a process termed RNA interference (RNAi). The therapeutic applications of RNAi are extremely broad, since siRNA and miRNA constructs can be synthesized with any nucleotide sequence directed against a target protein. To date, siRNA constructs have shown the ability to specifically down-regulate target proteins in both in vitro and in vivo models. In addition, siRNA constructs are currently being evaluated in clinical studies.

However, two problems currently faced by siRNA or miRNA constructs are, first, their susceptibility to nuclease digestion in plasma and, second, their limited ability to gain access to the intracellular compartment where they can bind the protein RISC when administered systemically as the free siRNA or miRNA. Lipid nanoparticles formed from cationic lipids with other lipid components, such as cholesterol and PEG lipids, and oligonucleotides (such as siRNA and miRNA) have been used to facilitate the cellular uptake of the oligonucleotides.

There remains a need for improved cationic lipids and lipid nanoparticles for the delivery of oligonucleotides. Preferably, these lipid nanoparticles would provide high drug:lipid ratios, protect the nucleic acid from degradation and clearance in serum, be suitable for systemic delivery, and provide intracellular delivery of the nucleic acid. In addition, these lipid-nucleic acid particles should be well-tolerated and provide an adequate therapeutic index, such that patient treatment at an effective dose of the nucleic acid is not associated with significant toxicity and/or risk to the patient.

SUMMARY

The present invention relates to a cationic lipid and PEG lipid suitable for forming nucleic acid-lipid particles. Each of the cationic and PEG lipids of the present invention includes one or more biodegradable groups. The biodegradable groups are located in a lipidic moiety (e.g., a hydrophobic chain) of the cationic or PEG lipid. These cationic and PEG lipids may be incorporated into a lipid particle for delivering an active agent, such as a nucleic acid (e.g., an siRNA). The incorporation of the biodegradable group(s) into the lipid results in faster metabolism and removal of the lipid from the body following delivery of the active agent to a target area. As a result, these lipids have lower toxicity than similar lipids without the biodegradable groups.

In one embodiment, the cationic lipid is a compound of formula (I), which has a branched alkyl at the alpha position adjacent to the biodegradable group (between the biodegradable group and the tertiary carbon):

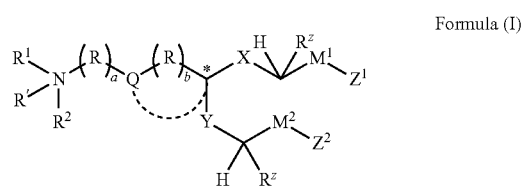

Formula (I)

or a salt thereof (e.g., a pharmaceutically acceptable salt thereof), wherein
R' is absent, hydrogen, or alkyl (e.g., $C_1$-$C_4$ alkyl);
with respect to $R^1$ and $R^2$,
(i) $R^1$ and $R^2$ are each, independently, optionally substituted alkyl, alkenyl, alkynyl, cycloalkylalkyl, heterocycle, or $R^{10}$;
(ii) $R^1$ and $R^2$, together with the nitrogen atom to which they are attached, form an optionally substituted heterocylic ring; or
(iii) one of $R^1$ and $R^2$ is optionally substituted alkyl, alkenyl, alkynyl, cycloalkyl, cycloalkylalkyl, or heterocycle, and the other forms a 4-10 member heterocyclic ring or heteroaryl (e.g., a 6-member ring) with (a) the adjacent nitrogen atom and (b) the $(R)_a$ group adjacent to the nitrogen atom;
each occurrence of R is, independently, —$(CR^3R^4)$—;
each occurrence of $R^3$ and $R^4$ are, independently H, halogen, OH, alkyl, alkoxy, —$NH_2$, $R^{10}$, alkylamino, or dialkylamino (in one preferred embodiment, each occurrence of $R^3$ and $R^4$ are, independently H or $C_1$-$C_4$ alkyl);
each occurrence of $R^{10}$ is independently selected from PEG and polymers based on poly(oxazoline), poly(ethylene oxide), poly(vinyl alcohol), poly(glycerol), poly(N-vinylpyrrolidone), poly[N-(2-hydroxypropyl)methacrylamide] and poly(amino acid)s, wherein (i) the PEG or polymer is linear or branched, (ii) the PEG or polymer is polymerized by n subunits, (iii) n is a number-averaged degree of polymerization between 10 and 200 units, and (iv) wherein the compound of formula has at most two $R^{10}$ groups (preferably at most one $R^{10}$ group);
the dashed line to Q is absent or a bond;
when the dashed line to Q is absent then Q is absent or is —O—, —NH—, —S—, —C(O)—, —C(O)O—, —OC(O)—, —C(O)N($R^4$)—, —N($R^5$)C(O)—, —S—S—, —OC(O)O—, —O—N=C($R^5$)—, —C($R^5$)=N—O—, —OC(O)N($R^5$)—, —N($R^5$)C(O)N($R^5$)—, —N($R^5$)C(O)O—, —C(O)S—, —C(S)O— or —C($R^5$)=N—O—C(O)—; or
when the dashed line to Q is a bond then (i) b is 0 and (ii) Q and the tertiary carbon adjacent to it (C*) form a substituted or unsubstituted, mono- or bi-cyclic heterocyclic group having from 5 to 10 ring atoms (e.g., the heteroatoms in the heterocyclic group are selected from O and S, preferably O);

each occurrence of $R^5$ is, independently, H or alkyl (e.g. $C_1$-$C_4$ alkyl);

X and Y are each, independently, alkylene or alkenylene (e.g., $C_4$ to $C_{20}$ alkylene or $C_4$ to $C_{20}$ alkenylene);

$M^1$ and $M^2$ are each, independently, a biodegradable group (e.g., —OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)(C$R^3R^4$)C(O)O—, —OC(O)(C$R^3R^4$)C(O)—, or

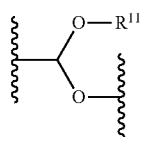

(wherein $R^{11}$ is a $C_2$-$C_8$ alkyl or alkenyl));

each occurrence of $R^z$ is, independently, $C_1$-$C_8$ alkyl (e.g., methyl, ethyl, isopropyl, n-butyl, n-pentyl, or n-hexyl);

a is 1, 2, 3, 4, 5 or 6;

b is 0, 1, 2, or 3; and $Z^1$ and $Z^2$ are each, independently, $C_8$-$C_{14}$ alkyl or $C_8$-$C_{14}$ alkenyl, wherein the alkenyl group may optionally be substituted with one or two fluorine atoms at the alpha position to a double bond which is between the double bond and the terminus of $Z^1$ or $Z^2$ (e.g., 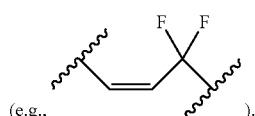 ).

The $R'R^1R^2N$—$(R)_a$-Q-$(R)_b$— group can be any of the head groups described herein, including those shown in Table 1 below, and salts thereof. In one preferred embodiment, $R'R^1R^2N$—$(R)_a$-Q-$(R)_b$— is $(CH_3)_2N$—$(CH_2)_3$—C(O)O—, $(CH_3)_2N$—$(CH_2)_2$—NH—C(O)O—, $(CH_3)_2N$—$(CH_2)_2$—OC(O)—NH—, or $(CH_3)_2N$—$(CH_2)_3$—C($CH_3$)=N—O—.

In one embodiment, $R^1$ and $R^2$ are both alkyl (e.g., methyl).

In a further embodiment, a is 3. In another embodiment, b is 0.

In a further embodiment, a is 3, b is 0 and R is —$CH_2$—. In yet a further embodiment, a is 3, b is 0, R is —$CH_2$— and Q is —C(O)O—. In another embodiment, $R^1$ and $R^2$ are methyl, a is 3, b is 0, R is —$CH_2$— and Q is —C(O)O—.

In another embodiment, X and Y are each, independently —$(CH_2)_n$— wherein n is 4 to 20, e.g., 4 to 18, 4 to 16, or 4 to 12. In one embodiment, n is 4, 5, 6, 7, 8, 9, or 10. In one exemplary embodiment, X and Y are —$(CH_2)_6$—. In another embodiment, X and Y are —$(CH_2)_7$—. In yet another embodiment, X and Y are —$(CH_2)_9$—. In yet another embodiment, X and Y are —$(CH_2)_8$—.

In further embodiments, $M^1$ and $M^2$ are each, independently, —OC(O)— or —C(O)O—. For example, in one embodiment, $M^1$ and $M^2$ are each —C(O)O—.

In another embodiment, the cationic lipid is a compound of formula (II), which has a branched alkyl at the alpha position adjacent to the biodegradable group (between the biodegradable group and the terminus of the tail, i.e., $Z^1$ o $Z^2$)

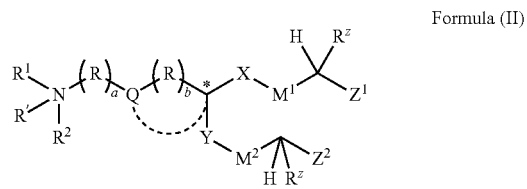

Formula (II)

or a salt thereof (e.g., a pharmaceutically acceptable salt thereof), wherein

R' is absent, hydrogen, or alkyl (e.g., $C_1$-$C_4$ alkyl);

with respect to $R^1$ and $R^2$, (i) $R^1$ and $R^2$ are each, independently, optionally substituted alkyl, alkenyl, alkynyl, cycloalkylalkyl, heterocycle, or $R^{10}$;

(ii) $R^1$ and $R^2$, together with the nitrogen atom to which they are attached, form an optionally substituted heterocylic ring; or (iii) one of $R^1$ and $R^2$ is optionally substituted alkyl, alkenyl, alkynyl, cycloalkyl, cycloalkylalkyl, or heterocycle, and the other forms a 4-10 member heterocyclic ring or heteroaryl (e.g., a 6-member ring) with (a) the adjacent nitrogen atom and (b) the $(R)_a$ group adjacent to the nitrogen atom;

each occurrence of R is, independently, —(C$R^3R^4$)—;

each occurrence of $R^3$ and $R^4$ are, independently H, halogen, OH, alkyl, alkoxy, —$NH_2$, $R^{10}$, alkylamino, or dialkylamino (in one preferred embodiment, each occurrence of $R^3$ and $R^4$ are, independently H or $C_1$-$C_4$ alkyl);

each occurrence of $R^{10}$ is independently selected from PEG and polymers based on poly(oxazoline), poly(ethylene oxide), poly(vinyl alcohol), poly(glycerol), poly(N-vinylpyrrolidone), poly[N-(2-hydroxypropyl)methacrylamide] and poly(amino acid)s, wherein (i) the PEG or polymer is linear or branched, (ii) the PEG or polymer is polymerized by n subunits, (iii) n is a number-averaged degree of polymerization between 10 and 200 units, and (iv) wherein the compound of formula has at most two $R^{10}$ groups (preferably at most one $R^{10}$ group);

the dashed line to Q is absent or a bond;

when the dashed line to Q is absent then Q is absent or is —O—, —NH—, —S—, —C(O)—, —C(O)O—, —OC(O)—, —C(O)N($R^4$)—, —N($R^5$)C(O)—, —S—S—, —OC(O)O—, —O—N=C($R^5$)—, —C($R^5$)=N—O—, —OC(O)N($R^5$)—, —N($R^5$)C(O)N($R^5$)—, —N($R^5$)C(O)O—, —C(O)S—, —C(S)O— or —C($R^5$)=N—O—C(O)—; or when the dashed line to Q is a bond then (i) b is 0 and (ii) Q and the tertiary carbon adjacent to it (C*) form a substituted or unsubstituted, mono- or bi-cyclic heterocyclic group having from 5 to 10 ring atoms (e.g., the heteroatoms in the heterocyclic group are selected from O and S, preferably O);

each occurrence of $R^5$ is, independently, H or alkyl;

X and Y are each, independently, alkylene (e.g., $C_6$-$C_8$ alkylene) or alkenylene, wherein the alkylene or alkenylene group is optionally substituted with one or two fluorine atoms at the alpha position to the $M^1$ or $M^2$ group (e.g., 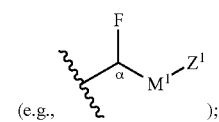 );

$M^1$ and $M^2$ are each, independently, a biodegradable group (e.g., —OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)(C$R^3R^4$)C(O)O—, —OC(O)(C$R^3R^4$)C(O)—, or

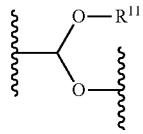

(wherein $R^{11}$ is a $C_2$-$C_8$ alkyl or alkenyl));

each occurrence of $R^z$ is, independently, $C_1$-$C_8$ alkyl (e.g., methyl, ethyl, isopropyl);

a is 1, 2, 3, 4, 5 or 6;

b is 0, 1, 2, or 3; and $Z^1$ and $Z^2$ are each, independently, $C_8$-$C_{14}$ alkyl or $C_8$-$C_{14}$ alkenyl, wherein (i) the alkenyl group may optionally be substituted with one or two fluorine atoms at the alpha position to a double bond which is between the double bond and the terminus of $Z^1$ or $Z^2$

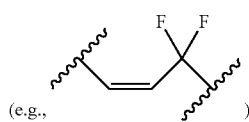 [SMILES: */C=C\C(*)(F)F]

and (ii) the terminus of at least one of $Z^1$ and $Z^2$ is separated from the group M or $M^2$ by at least 8 carbon atoms.

In another embodiment, X and Y are each, independently —(CH$_2$)$_n$— wherein n is 4 to 20, e.g., 4 to 18, 4 to 16, or 4 to 12. In one embodiment, n is 4, 5, 6, 7, 8, 9, or 10. In one exemplary embodiment, X and Y are —(CH$_2$)$_6$—. In another embodiment, X and Y are —(CH$_2$)$_7$—. In yet another embodiment, X and Y are —(CH$_2$)$_9$—. In yet another embodiment, X and Y are —(CH$_2$)$_8$—.

The R'$R^1R^2$N—(R)$_a$-Q-(R)$_b$— group can be any of the head groups described herein, including those shown in Table 1 below, and salts thereof. In one preferred embodiment, R'$R^1R^2$N—(R)$_a$-Q-(R)$_b$— is (CH$_3$)$_2$N—(CH$_2$)$_3$—C(O)O—, (CH$_3$)$_2$N—(CH$_2$)$_2$—NH—C(O)O—, (CH$_3$)$_2$N—(CH$_2$)$_2$—OC(O)—NH—, or (CH$_3$)$_2$N—(CH$_2$)$_3$—C(CH$_3$)=N—O—.

In another embodiment, the cationic lipid is a compound of formula (III), which has a branching point at a position that is 2-6 carbon atoms (i.e., at the beta (β), gamma (γ), delta (δ), epsilon (ε) or zeta position (ζ)) adjacent to the biodegradable group (between the biodegradable group and the terminus of the tail, i.e., $Z^1$ or $Z^2$

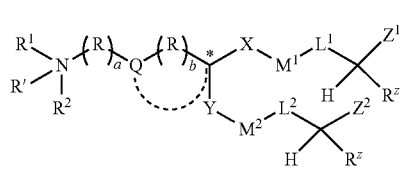

Formula (III)

or a salt thereof (e.g., a pharmaceutically acceptable salt thereof), wherein

R', $R^1$, $R^2$, R, $R^3$, $R^4$, $R^{10}$, Q, $R^5$, $M^1$, $M^2$, $R^z$, a, and b are defined as in formula (I);

$L^1$ and $L^2$ are each, independently, $C_1$-$C_5$ alkylene or $C_2$-$C_5$ alkenylene;

X and Y are each, independently, alkylene (e.g., $C_4$ to $C_{20}$ alkylene or $C_6$-$C_8$ alkylene) or alkenylene (e.g., $C_4$ to $C_{20}$ alkenylene); and $Z^1$ and $Z^2$ are each, independently, $C_8$-$C_{14}$ alkyl or $C_8$-$C_{14}$ alkenyl, wherein the alkenyl group may optionally be substituted with one or two fluorine atoms at the alpha position to a double bond which is between the double bond and the terminus of $Z^1$ or $Z^2$

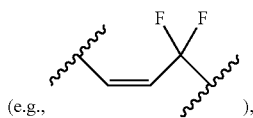 [SMILES: */C=C\C(*)(F)F]

and with the proviso that the terminus of at least one of $Z^1$ and $Z^2$ is separated from the group M or $M^2$ by at least 8 carbon atoms.

In one embodiment, $L^1$ and $L^2$ are each —CH$_2$—. In another embodiment, $L^1$ and $L^2$ are each —(CH$_2$)$_2$—. In one embodiment, $L^1$ and $L^2$ are each —(CH$_2$)$_3$—. In yet another embodiment, $L^1$ and $L^2$ are each —(CH$_2$)$_4$—. In yet another embodiment, $L^1$ and $L^2$ are each —(CH$_2$)$_5$—. In yet another embodiment, $L^1$ and $L^2$ are each —CH$_2$—CH=CH—. In a preferred embodiment, $L^1$ and $L^2$ are each —CH$_2$— or —(CH2)$_2$.

In one embodiment, X and Y are each, independently —(CH$_2$)$_n$ wherein n is 4 to 20, e.g., 4 to 18, 4 to 16, or 4 to 12. In one embodiment, n is 4, 5, 6, 7, 8, 9, or 10. In one exemplary embodiment, X and Y are —(CH$_2$)$_7$—. In another exemplary embodiment, X and Y are —(CH$_2$)$_8$—. In yet another exemplary embodiment, X and Y are —(CH$_2$)$_9$—.

The R'$R^1R^2$N—(R)$_a$-Q-(R)$_b$— group can be any of the head groups described herein, including those shown in Table 1 below, and salts thereof. In one preferred embodiment, R'$R^1R^2$N—(R)$_a$-Q-(R)$_b$— is (CH$_3$)$_2$N—(CH$_2$)$_3$—C(O)O—, (CH$_3$)$_2$N—(CH$_2$)$_2$—NH—C(O)O—, (CH$_3$)$_2$N—(CH$_2$)$_2$—OC(O)—NH—, or (CH$_3$)$_2$N—(CH$_2$)$_3$—C(CH$_3$)=N—O—.

In another embodiment, the cationic lipid is a compound of formula (IIIA), which has a branching point at a position that is 2-6 carbon atoms (i.e., at the beta (β), gamma (γ), delta (δ), epsilon (ε) or zeta position (ζ)) from the biodegradable groups $M^1$ and $M^2$ (i.e., between the biodegradable group and the terminus of the tail, i.e., $Z^1$ or $Z^2$):

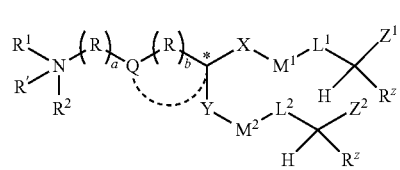

Formula (IIIA)

or a salt thereof (e.g., a pharmaceutically acceptable salt thereof), wherein

R', $R^1$, $R^2$, R, $R^3$, $R^4$, $R^{10}$, Q, $R^5$, $M^1$, $M^2$, a, and b are defined as in formula (I);

each $R^z$ is, independently, $C_1$-$C_8$ alkyl (e.g., $C_3$-$C_6$ alkyl or $C_2$-$C_3$ alkyl);

$L^1$ and $L^2$ are each, independently, $C_1$-$C_5$ alkylene (e.g., $C_2$-$C_3$ alkylene) or $C_2$-$C_5$ alkenylene;

X and Y are each, independently, alkylene (e.g., $C_4$ to $C_{20}$ alkylene or $C_7$-$C_9$ alkylene) or alkenylene (e.g., $C_4$ to $C_{20}$ alkenylene or $C_7$-$C_9$ alkenylene); and $Z^1$ and $Z^2$ are each, independently, $C_1$-$C_8$ alkyl (e.g., $C_1$-$C_6$ alkyl, such as $C_1$, $C_3$ or $C_5$ alkyl) or $C_2$-$C_8$ alkenyl (such as $C_2$-$C_6$ alkenyl);

wherein said cationic lipid is not one selected from:

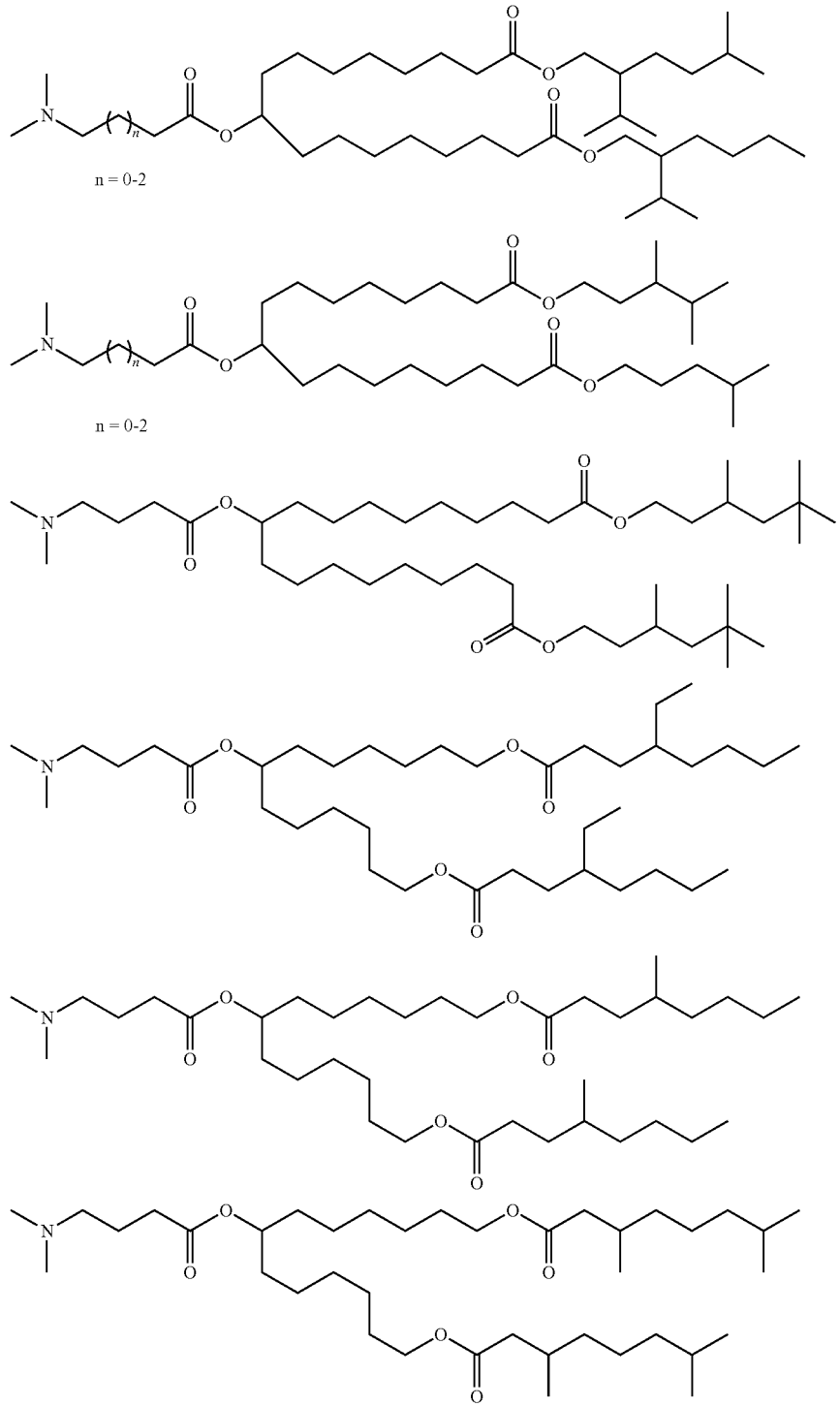

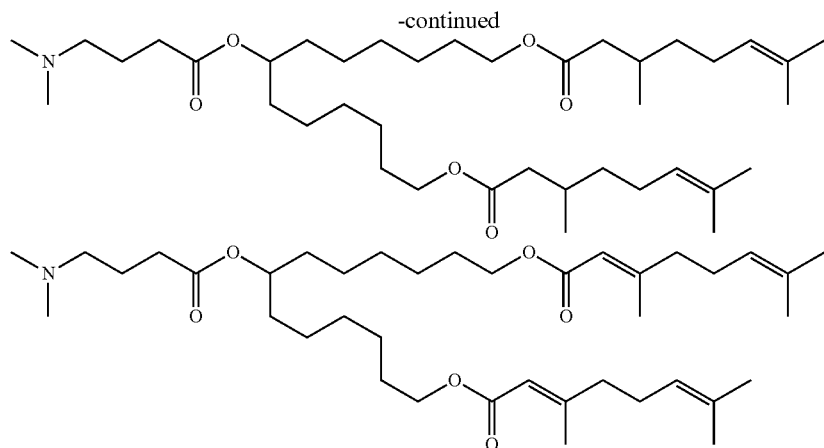

In one embodiment, $L^1$ and $L^2$ are each —$(CH_2)_2$—. In another embodiment, $L^1$ and $L^2$ are each —$(CH_2)_3$—.

In one embodiment, X and Y are each, independently —$(CH_2)_n$ wherein n is 4 to 20, e.g., 4 to 18, 4 to 16, 4 to 12 or 7-9. In one embodiment, n is 4, 5, 6, 7, 8, 9, or 10. In one exemplary embodiment, X and Y are —$(CH_2)_7$—. In yet another exemplary embodiment, X and Y are —$(CH_2)_9$.

In one preferred embodiment, $M^1$ and $M^2$ are —C(O)O— (where the carbonyl group in $M^1$ and $M^2$ is bound to the variable X, and the oxygen atom in $M^1$ and $M^2$ is bound to the variable $L^1$ and $L^2$).

The $R'R^1R^2N$—$(R)_a$-Q-$(R)_b$— group can be any of the head groups described herein, including those shown in Table 1 below, and salts thereof. In one preferred embodiment, $R'R^1R^2N$—$(R)_a$-Q-$(R)_b$— is $(CH_3)_2N$—$(CH_2)_3$—C(O)O—, $(CH_3)_2N$—$(CH_2)_2$—NH—C(O)O—, $(CH_3)_2N$—$(CH_2)_2$—OC(O)—NH—, or $(CH_3)_2N$—$(CH_2)_3$—C(CH_3)=N—O—.

In one preferred embodiment, $Z^1$ and $Z^2$ are branched alkyl or branched alkenyl groups.

In one embodiment of formula (IIIA), $Z^1$, $Z^2$, and each $R^z$ are $C_3$-$C_8$ alkyl (such as a $C_3$-$C_6$ alkyl). In another embodiment of formula (IIIA), $Z^1$, $Z^2$, and each $R^z$ are $C_3$-$C_8$ branched alkyl (such as a $C_3$-$C_6$ branched alkyl). In yet another embodiment of formula (IIIA), $Z^1$, $Z^2$, and each $R^z$ are $C_3$-$C_8$ straight alkyl (such as a $C_3$-$C_6$ straight alkyl).

In one embodiment of formula (IIIA), the branching point is at the second position (the 3-position) from the biodegradable groups $M^1$ and $M^2$ in each tail. $Z^1$, $Z^2$, and each $R^z$ can be $C_3$-$C_8$ alkyl (e.g., a $C_3$-$C_6$ alkyl), such as a $C_3$-$C_8$ branched alkyl (e.g., a $C_3$-$C_6$ branched alkyl) or a $C_3$-$C_8$ straight alkyl (e.g., a $C_3$-$C_6$ straight alkyl). In one preferred embodiment, $M^1$ and $M^2$ are —C(O)O— (where the carbonyl group in $M^1$ and $M^2$ is bound to the variable X, and the oxygen atom in $M^1$ and $M^2$ is bound to the variable $L^1$ and/or $L^2$).

In one embodiment of formula (IIIA), the branching point is at the third position (the γ-position) from the biodegradable groups $M^1$ and $M^2$ in each tail. $Z^1$, $Z^2$, and each $R^z$ can be $C_3$-$C_8$ alkyl (e.g., a $C_3$-$C_6$ alkyl), such as a $C_3$-$C_8$ branched alkyl (e.g., a $C_3$-$C_6$ branched alkyl) or a $C_3$-$C_8$ straight alkyl (e.g., a $C_3$-$C_6$ straight alkyl). In one preferred embodiment, $M^1$ and $M^2$ are —C(O)O— (where the carbonyl group in $M^1$ and $M^2$ is bound to the variable X, and the oxygen atom in $M^1$ and $M^2$ is bound to the variable $L^1$ and/or $L^2$).

In one embodiment of formula (IIIA), the branching point is at the third position (the γ-position) from the biodegradable groups $M^1$ and $M^2$ in each tail.

In another embodiment of formula (IIIA), $M^1$ and/or $M^2$ are not —O(C(O)— (where the oxygen atom in $M^1$ and/or $M^2$ is bound to the variable X, and the carbonyl in $M^1$ and/or $M^2$ is bound to the variable $L^1$ and/or $L^2$). In yet another embodiment of formula (IIIA), $Z^1$, $Z^2$, and $R^z$ are not $C_3$-$C_{10}$ cycloalkyl($C_1$-$C_6$ alkyl).

In another embodiment, the cationic lipid is a compound of formula (IV), which has a branching point at a position that is 2-6 carbon atoms (i.e., at beta (β), gamma (γ), delta (δ), epsilon (ε) or zeta position (ζ)) adjacent to the biodegradable group (between the biodegradable group and the terminus of the tail, i.e., $Z^1$ or $Z^2$ Formula (IV)

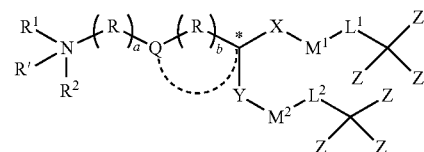

or a salt thereof (e.g., a pharmaceutically acceptable salt thereof), wherein

R', $R^1$, $R^2$, R, $R^3$, $R^4$, $R^{10}$, Q, $R^5$, $M^1$, $M^2$, $R^z$, a, and b are defined as in formula (I);

$L^1$ and $L^2$ and are each, independently, $C_1$-$C_5$ alkylene or $C_2$-$C_5$ alkenylene;

X and Y are each, independently, alkylene or alkenylene (e.g., $C_{12}$-$C_{20}$ alkylene or $C_{12}$-$C_{20}$ alkenylene); and each occurrence of Z is independently $C_1$-$C_4$ alkyl (preferably, methyl).

For example, in one embodiment, -$L^1$-C(Z)$_3$ is —$CH_2C(CH_3)_3$. In another embodiment, -$L^1$-C(Z)$_3$ is —$CH_2CH_2C(CH_3)_3$.

In one embodiment, the total carbon atom content of each tail (e.g., —X-$M^1$-$L^1$-C(Z)$_3$ or —Y-$M^2$-$L^2$-C(Z)$_3$) is from about 17 to about 26. For example, the total carbon atom content can be from about 19 to about 26 or from about 21 to about 26.

In another embodiment, X and Y are each, independently —$(CH_2)_n$— wherein n is 4 to 20, e.g., 4 to 18, 4 to 16, or 4 to 12. In one embodiment, n is 4, 5, 6, 7, 8, 9, or 10. In one exemplary embodiment, X and Y are —$(CH_2)_6$—. In another embodiment, X and Y are —(CH$_2$)$_7$—. In yet another embodiment, X and Y are —(CH$_2$)$_9$—. In yet another embodiment, X and Y are —(CH$_2$)$_8$—.

In one embodiment, the cationic lipid is a compound of formula (V), which has an alkoxy or thioalkoxy (i.e., —S-alkyl) group substitution on at least one tail:

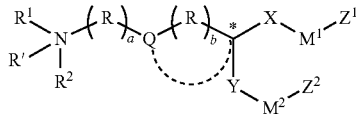

Formula (V)

or a salt thereof (e.g., a pharmaceutically acceptable salt thereof), wherein

R', R$^1$, R$^2$, R, R$^3$, R$^4$, R$^{10}$, Q, R$^5$, M$^1$, M$^2$, a, and b are defined as in formula (I);

X and Y are each, independently, alkylene (e.g., C$_6$-C$_8$ alkylene) or alkenylene, wherein the alkylene or alkenylene group is optionally substituted with one or two fluorine atoms at the alpha position to the M$^1$ or M$^2$ group (e.g., 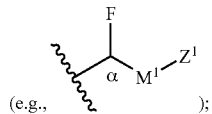 );

Z$^1$ and Z$^2$ are each, independently, C$_8$-C$_{14}$ alkyl or C$_8$-C$_{14}$ alkenyl, wherein (i) the C$_8$-C$_{14}$ alkyl or C$_8$-C$_{14}$ alkenyl of at least one of Z$^1$ and Z$^2$ is substituted by one or more alkoxy (e.g., a C$_1$-C$_4$ alkoxy such as —OCH$_3$) or thioalkoxy (e.g., a C$_1$-C$_4$ thioalkoxy such as —SCH$_3$) groups, and (ii) the alkenyl group may optionally be substituted with one or two fluorine atoms at the alpha position to a double bond which is between the double bond and the terminus of Z$^1$ or Z$^2$ (e.g., 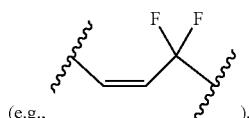 ).

In one embodiment, the alkoxy substitution on Z$^1$ and/or Z$^2$ is at the beta position from the M$^1$ and/or M$^2$ group.

In another embodiment, X and Y are each, independently —(CH$_2$)$_n$— wherein n is 4 to 20, e.g., 4 to 18, 4 to 16, or 4 to 12. In one embodiment, n is 4, 5, 6, 7, 8, 9, or 10. In one exemplary embodiment, X and Y are —(CH$_2$)$_6$—. In another embodiment, X and Y are —(CH$_2$)$_7$—. In yet another embodiment, X and Y are —(CH$_2$)$_9$—. In yet another embodiment, X and Y are —(CH$_2$)$_8$—.

The R'R$^1$R$^2$N—(R)$_a$-Q-(R)$_b$— group can be any of the head groups described herein, including those shown in Table 1 below, and salts thereof. In one preferred embodiment, R'R$^1$R$^2$N—(R)$_a$-Q-(R)$_b$— is (CH$_3$)$_2$N—(CH$_2$)$_3$—C(O)O—, (CH$_3$)$_2$N—(CH$_2$)$_2$—NH—C(O)O—, (CH$_3$)$_2$N—(CH$_2$)$_2$—OC(O)—NH—, or (CH$_3$)$_2$N—(CH$_2$)$_3$—C(CH$_3$)=N—O—.

In one embodiment, the cationic lipid is a compound of formula (VIA), which has one or more fluoro substituents on at least one tail at a position that is either alpha to a double bond or alpha to a biodegradable group:

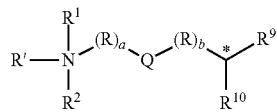

Formula (VIA)

or a salt thereof (e.g., a pharmaceutically acceptable salt thereof), wherein

R$^1$, R$^2$, R, a, and b are as defined with respect to formula (I);

Q is absent or is —O—, —NH—, —S—, —C(O)—, —C(O)O—, —OC(O)—, —C(O)N(R$^4$)—, —N(R$^5$)C(O)—, —S—S—, —OC(O)O—, —O—N=C(R$^5$)—, —C(R$^5$)=N—O—, —OC(O)N(R$^5$)—, —N(R$^5$)C(O)N(R$^5$)—, —N(R$^5$)C(O)O—, —C(O)S—, —C(S)O— or —C(R$^5$)=N—O—C(O)—;

R' is absent, hydrogen, or alkyl (e.g., C$_1$-C$_4$ alkyl); and each of R$^9$ and R$^{10}$ are independently C$_{12}$-C$_{24}$ alkyl (e.g., C$_{12}$-C$_{20}$ alkyl), C$_{12}$-C$_{24}$ alkenyl (e.g., C$_{12}$-C$_{20}$ alkenyl), or C$_{12}$-C$_{24}$ alkoxy (e.g., C$_{12}$-C$_{20}$ alkoxy) (a) having one or more biodegradable groups and (b) optionally substituted with one or more fluorine atoms at a position which is (i) alpha to a biodegradable group and between the biodegradable group and the tertiary carbon atom marked with an asterisk (*), or (ii) alpha to a carbon-carbon double bond and between the double bond and the terminus of the R$^9$ or R$^{10}$ group; each biodegradable group independently interrupts the C$_{12}$-C$_{24}$ alkyl, alkenyl, or alkoxy group or is substituted at the terminus of the C$_{12}$-C$_{24}$ alkyl, alkenyl, or alkoxy group, wherein (i) at least one of R$^9$ and R$^{10}$ contains a fluoro group;
(ii) the compound does not contain the following moiety:

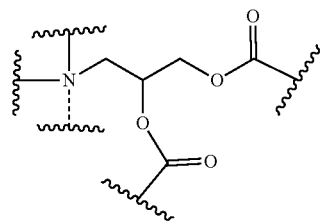

wherein ---- is an optional bond; and (iii) the terminus of R$^9$ and R$^{10}$ is separated from the tertiary carbon atom marked with an asterisk (*) by a chain of 8 or more atoms (e.g., 12 or 14 or more atoms).

In one preferred embodiment, the terminus of R$^9$ and R$^{10}$ is separated from the tertiary carbon atom marked with an asterisk (*) by a chain of 18-22 carbon atoms (e.g., 18-20 carbon atoms).

In another embodiment, the terminus of the R$^9$ and/or R$^{10}$ has the formula —C(O)O—CF$_3$.

In another embodiment, the cationic lipid is a compound of formula (VIB), which has one or more fluoro substituents on at least one tail at a position that is either alpha to a double bond or alpha to a biodegradable group:

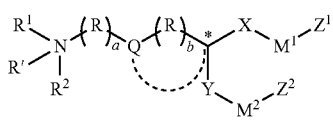

Formula (VIB)

or a salt thereof (e.g., a pharmaceutically acceptable salt thereof), wherein

R', R$^1$, R$^2$, R, R$^3$, R$^4$, R$^{10}$, Q, R$^5$, M$^1$, M$^2$, a, and b are defined as in formula (I);

X and Y are each, independently, alkylene (e.g., C$_6$-C$_8$ alkylene) or alkenylene, wherein the alkylene or alkenylene group is optionally substituted with one or two fluorine atoms at the alpha position to the M$^1$ or M$^2$ group (e.g., 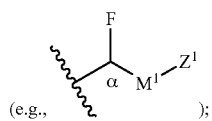);

and

Z$^1$ and Z$^2$ are each, independently, C$_8$-C$_{14}$ alkyl or C$_8$-C$_{14}$ alkenyl, wherein said C$_8$-C$_{14}$ alkenyl is optionally substituted by one or more fluorine atoms at a position that is alpha to a double bond (e.g., 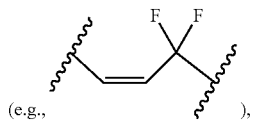 [SMILES: */C=C\C(*)(F)F]), wherein at least one of X, Y, Z$^1$, and Z$^2$ contains a fluorine atom.

In one embodiment, at least one of Z$^1$ and Z$^2$ is substituted by two fluoro groups at a position that is either alpha to a double bond or alpha to a biodegradable group. In one embodiment, at least one of Z$^1$ and Z$^2$ has a terminal —CF$_3$ group at a position that is alpha to a biodegradable group (i.e., at least one of Z$^1$ and Z$^2$ terminates with an —C(O)OCF$_3$ group).

For example, at least one of Z$^1$ and Z$^2$ may include one or more of the following moieties:

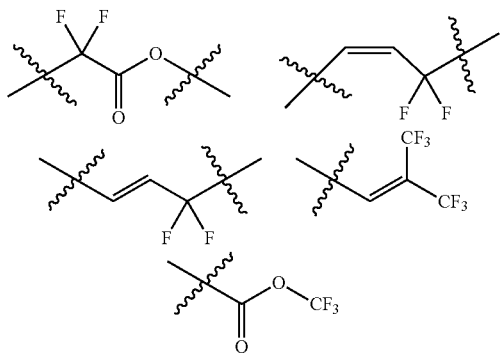

In one embodiment, X and Y are each, independently —(CH$_2$)$_n$ wherein n is 4 to 20, e.g., 4 to 18, 4 to 16, or 4 to 12. In one embodiment, n is 4, 5, 6, 7, 8, 9, or 10. In one exemplary embodiment, X and Y are —(CH$_2$)$_7$—. In another exemplary embodiment, X and Y are —(CH$_2$)$_9$—. In yet another embodiment, X and Y are —(CH$_2$)$_8$—.

The R'R$^1$R$^2$N—(R)$_a$-Q-(R)$_b$— group can be any of the head groups described herein, including those shown in Table 1 below, and salts thereof. In one preferred embodiment, R'R$^1$R$^2$N—(R)$_a$-Q-(R)$_b$— is (CH$_3$)$_2$N—(CH$_2$)$_3$—C(O)O—, (CH$_3$)$_2$N—(CH$_2$)$_2$—NH—C(O)O—, (CH$_3$)$_2$N—(CH$_2$)$_2$—OC(O)—NH—, or (CH$_3$)$_2$N—(CH$_2$)$_3$—C(CH$_3$)=N—O—.

In one embodiment, the cationic lipid is a compound of formula (VII), which has an acetal group as a biodegradable group in at least one tail:

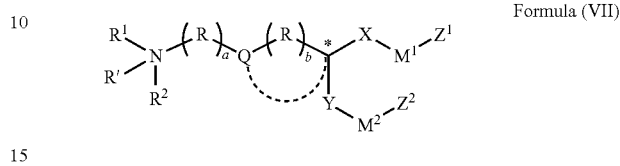

Formula (VII)

or a salt thereof (e.g., a pharmaceutically acceptable salt thereof), wherein

R', R$^1$, R$^2$, R, R$^3$, R$^4$, R$^{10}$, Q, R$^5$, a, and b are defined as in formula (I);

X and Y are each, independently, alkylene (e.g., C$_6$-C$_8$ alkylene) or alkenylene, wherein the alkylene or alkenylene group is optionally substituted with one or two fluorine atoms at the alpha position to the M$^1$ or M$^2$ group (e.g., 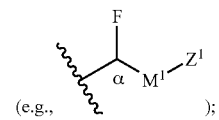);

M$^1$ and M$^2$ are each, independently, a biodegradable group (e.g., —OC(O)—, —C(O)O—, —SC(O)—, —C(O)S—, —OC(S)—, —C(S)O—, —S—S—, —C(R$^5$)=N—, —N=C(R$^5$)—, —C(R$^5$)=N—O—, —O—N=C(R$^5$)—, —C(O)(NR$^5$)—, —N(R$^5$)C(O)—, —C(S)(NR$^5$)—, —N(R$^5$)C(O)—, —N(R$^5$)C(O)N(R$^5$)—, —OC(O)O—, —OSi(R$^5$)$_2$O—, —C(O)(CR$^3$R$^4$)C(O)O—, —OC(O)(CR$^3$R$^4$)C(O)—, or

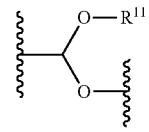

(wherein R$^{11}$ is a C$_4$-C$_{10}$ alkyl or C$_4$-C$_{10}$ alkenyl));

with the proviso that at least one of M$^1$ and M$^2$ is

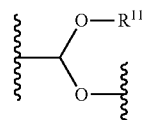;

and

Z$^1$ and Z$^2$ are each, independently, C$_4$-C$_{14}$ alkyl or C$_4$-C$_{14}$ alkenyl, wherein the alkenyl group may optionally be substituted with one or two fluorine atoms at the alpha position to a double bond which is between the double bond and the terminus of Z$^1$ or Z$^2$ (e.g.,

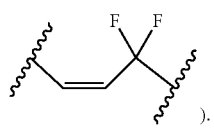

In one embodiment, each of $M^1$ and $M^2$ is

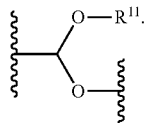

In another embodiment, X and Y are each, independently —$(CH_2)_n$— wherein n is 4 to 20, e.g., 4 to 18, 4 to 16, or 4 to 12. In one embodiment, n is 4, 5, 6, 7, 8, 9, or 10. In one exemplary embodiment, X and Y are —$(CH_2)_6$—. In another embodiment, X and Y are —$(CH_2)_7$—. In yet another embodiment, X and Y are —$(CH_2)_9$—. In yet another embodiment, X and Y are —$(CH_2)_8$—.

The $R'R^1R^2N$—$(R)_a$-Q-$(R)_b$— group can be any of the head groups described herein, including those shown in Table 1 below, and salts thereof. In one preferred embodiment, $R'R^1R^2N$—$(R)_a$-Q-$(R)_b$— is $(CH_3)_2N$—$(CH_2)_3$—C(O)O—, $(CH_3)_2N$—$(CH_2)_2$—NH—C(O)O—, $(CH_3)_2N$—$(CH_2)_2$—OC(O)—NH—, or $(CH_3)_2N$—$(CH_2)_3$—C($CH_3$)=N—O—.

In another embodiment, the present invention relates to a cationic lipid or a salt thereof having:

(i) a central carbon atom, (ii) a nitrogen containing head group directly bound to the central carbon atom, and (iii) two hydrophobic tails directly bound to the central carbon atom, wherein each hydrophobic tail is of the formula —$R^e$-M-$R^f$ where $R^e$ is a $C_4$-$C_{14}$ alkyl or alkenyl, M is a biodegradable group, and $R^f$ is a branched alkyl or alkenyl (e.g., a $C_{10}$-$C_{20}$ alkyl or $C_{10}$-$C_{20}$ alkenyl), such that (i) the chain length of —$R^e$-M-$R^f$ is at most 20 atoms (i.e. the total length of the tail from the first carbon atom after the central carbon atom to a terminus of the tail is at most 20), and (ii) the group —$R^e$-M-$R^f$ has at least 20 carbon atoms (e.g., at least 21 atoms). Optionally, the alkyl or alkenyl group in $R^e$ may be substituted with one or two fluorine atoms at the alpha position to the $M^1$ or $M^2$ group (e.g., 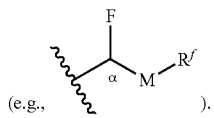).

Also, optionally, the alkenyl group in $R^f$ may be substituted with one or two fluorine atoms at the alpha position to a double bond which is between the double bond and the terminus of $R^f$ (e.g., 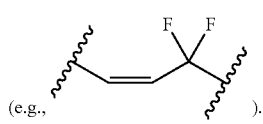).

In one embodiment, the cationic lipid of the present invention (such as of formulas I-VII) has asymmetrical hydrophobic groups (i.e., the two hydrophobic groups have different chemical formulas). For example, the cationic lipid can have the formula:

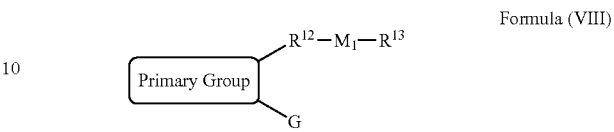

Formula (VIII)

or a salt thereof (e.g., a pharmaceutically acceptable salt thereof), wherein

G is branched or unbranched $C_3$-$C_{15}$ alkyl, alkenyl or alkynyl (e.g., a n-$C_8$ alkyl n-$C_9$ alkyl, or n-$C_{10}$ alkyl);

$R^{12}$ is a branched or unbranched alkylene or alkenylene (e.g., $C_6$-$C_{20}$ alkylene or $C_6$-$C_{20}$ alkenylene such as $C_{12}$-$C_{20}$ alkylene or $C_{12}$-$C_{20}$ alkenylene);

$M_1$ is a biodegradable group (e.g., —OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)(C$R^3R^4$)C(O)O—, —OC(O)(C$R^3R^4$)C(O)—, or

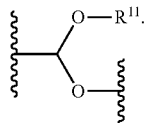

(wherein $R^{11}$ is a $C_2$-$C_8$ alkyl or alkenyl));

$R^3$ and $R^4$ are defined as in formula (I);

each occurrence of $R^5$ is, independently, H or alkyl (e.g., $C_1$-$C_4$ alkyl);

$R^3$ is branched or unbranched $C_3$-$C_{15}$ alkyl, alkenyl or alkynyl;

Primary Group comprises a protonatable group having a $pK_a$ of from about 4 to about 13, more preferably from about 5 to about 8 (e.g. from about 5 to about 7, or from about 5 to about 6.5, or from about 5.5 to about 6.5, or from about 6 to about 6.5).

In one embodiment, the primary group includes (i) a head group, and (ii) a central moiety (e.g., a central carbon atom) to which both the hydrophobic tails are directly bonded. Representative central moieties include, but are not limited to, a central carbon atom, a central nitrogen atom, a central carbocyclic group, a central aryl group, a central hetrocyclic group (e.g., central tetrahydrofuranyl group or central pyrrolidinyl group) and a central heteroaryl group.

Representative Primary Group's

's include, but are not limited to,
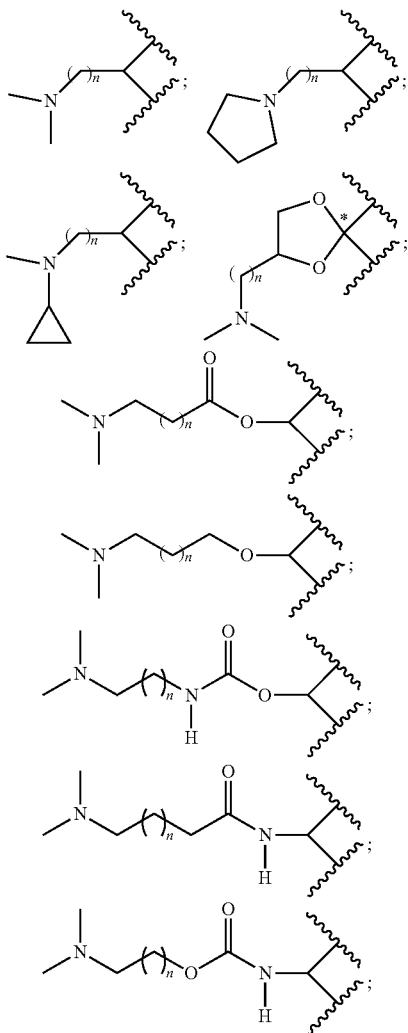
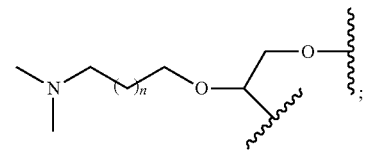
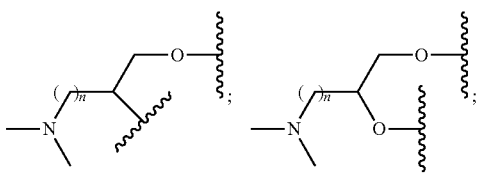
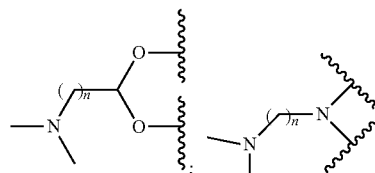
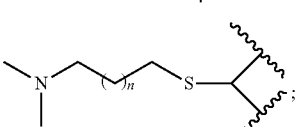
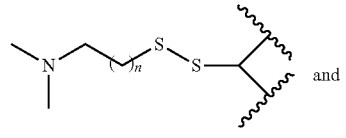
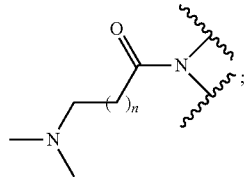
where n is 0-6.
Representative asymmetrical cationic lipids include:
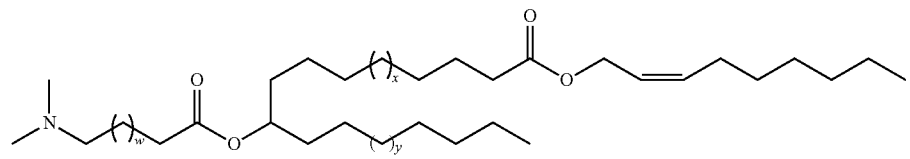
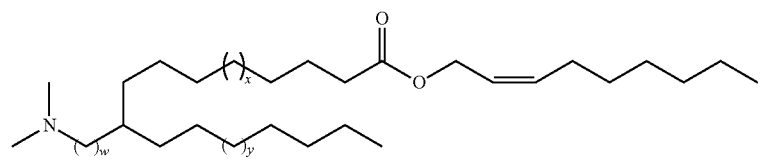
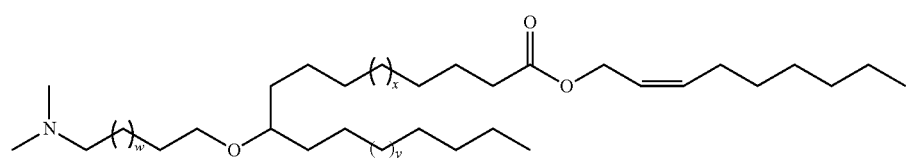

wherein w is 0, 1, 2, or 3; and x and y are each independently 1, 2, 3, 4, 5, 6, or 7.

In a preferred embodiment of the aforementioned biodegradable cationic lipids, the biodegradable cationic lipid has a log P value of at least 10.1 (as calculated by the software available at http://www.molinspiration.com/services/logp.html from Molinspiration Cheminformatics of Slovensky Grob, Slovak Republic). More preferably, the log P value is at least 10.2 or 10.3.

In another preferred embodiment of the aforementioned biodegradable cationic lipids, the biodegradable cationic lipid in the lipid nanoparticle has a HPLC retention time (relative to the retention time of cholesterol in the lipid nanoparticle), hereafter referred to as $t_{lipid} - t_{chol}$, of at least 1.4. (The HPLC parameters are provided in the examples below. Unless otherwise specified, the formulation of the lipid nanoparticle used is that described in Example 31). More preferably, the $t_{lipid} - t_{chol}$ value is at least 1.75, 2.0, or 2.25.

In another embodiment, the biodegradable cationic lipid of the present invention is not one selected from:

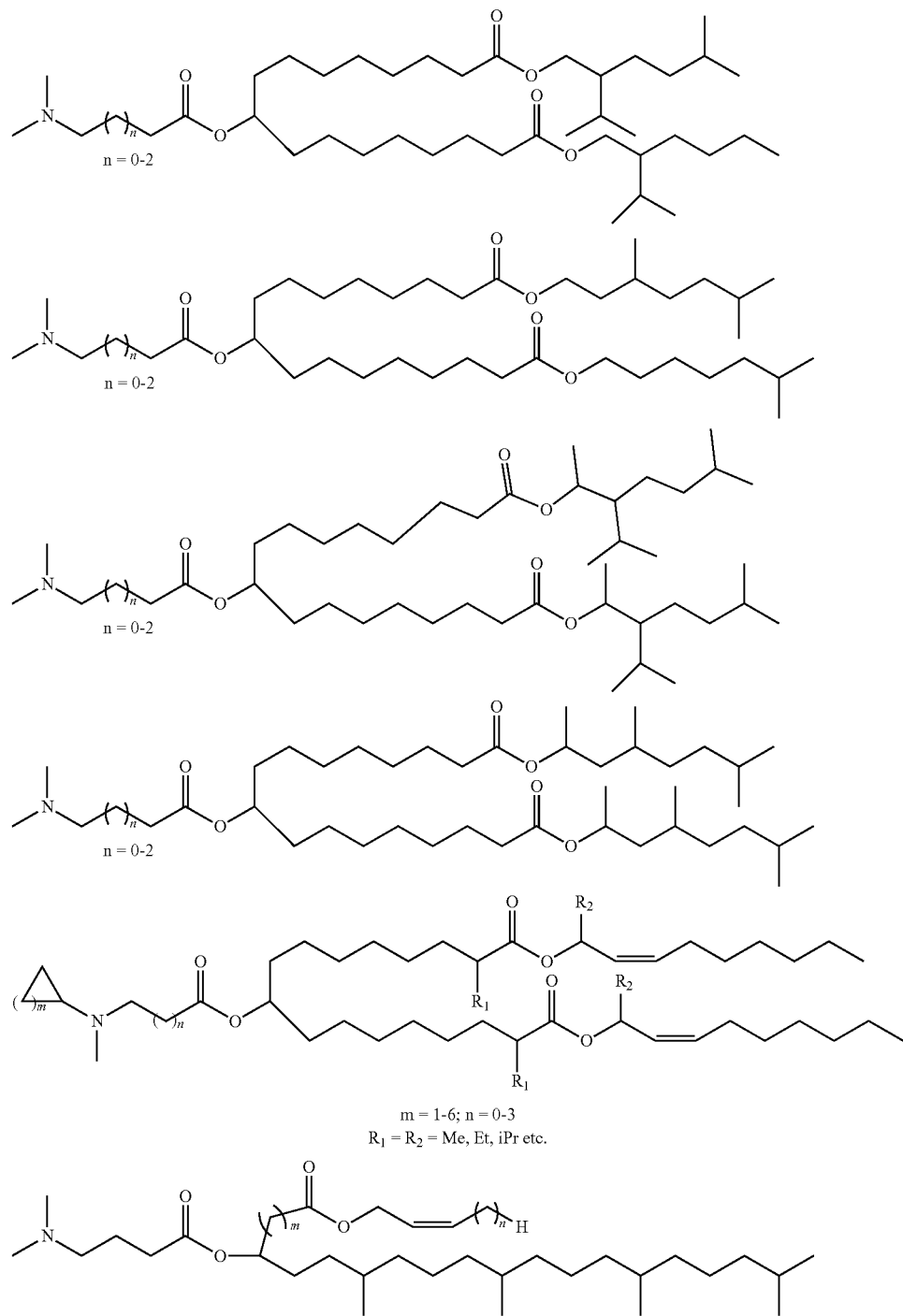

where m and n are integers, and m+n=13

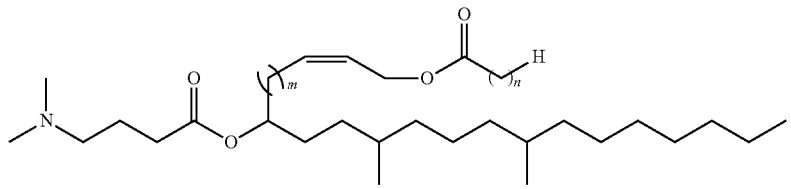

where m and n are integers, and m+n=13

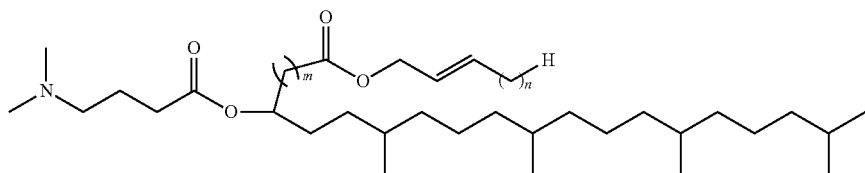

where m and n are integers, and m+n=13

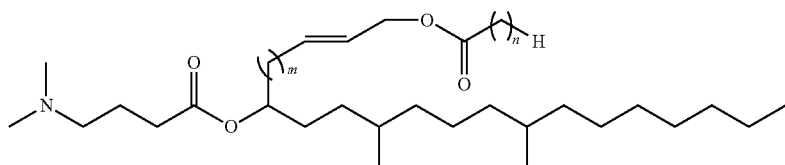

where m and n are integers, and m+n=13

In yet another embodiment, the biodegradable cationic lipid is not one selected from those disclosed in International Publication No. WO 2011/153493 and U.S. Patent Publication No. 2012/0027803, both of which are hereby incorporated by reference.

Yet another embodiment is a biodegradable cationic lipid having (i) a log P value of at least 10.1 and/or a $t_{lipid}-t_{chol}$, of at least 1.4, and (2) one or more biodegradable groups (such as an ester group) located in the mid- or distal section of a lipidic moiety (e.g., a hydrophobic chain) of the cationic lipid, with the proviso that the compound is not selected from

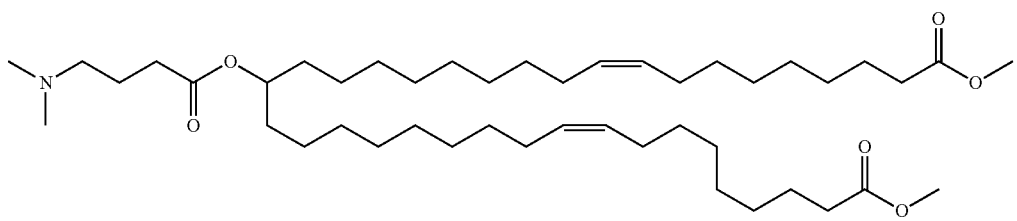

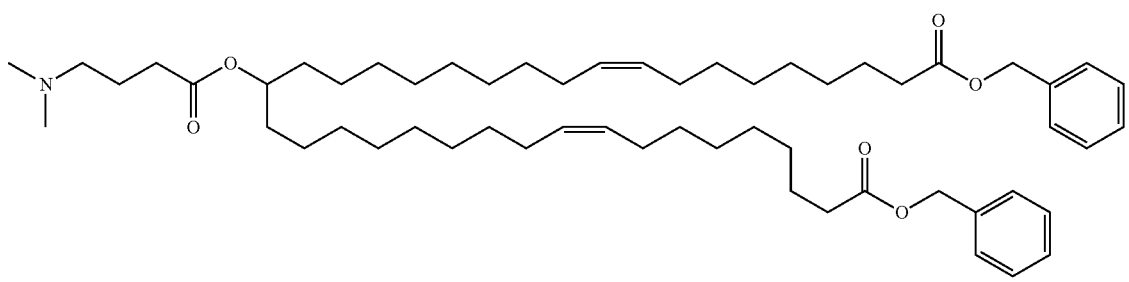

-continued

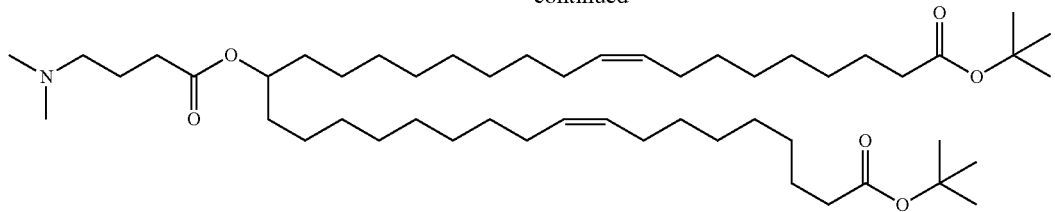

In another embodiment, the biodegradable cationic lipid is not one selected from those disclosed in International Publication No. WO 2011/153493 and U.S. Patent Publication No. 2012/0027803, both of which are hereby incorporated by reference. The incorporation of the biodegradable group(s) into the cationic lipid results in faster metabolism and removal of the cationic lipid from the body following delivery of the active pharmaceutical ingredient to a target area. In a preferred embodiment, the cationic lipid includes a branched alkyl or branched alkenyl group in its biodegradable group(s). In another preferred embodiment, the cationic lipd has a log P of at least 10.2 or 10.3. In yet another preferred embodiment, the cationic lipid has a $t_{lipid}-t_{chol}$, of at least 1.75, 2.0, or 2.25. The cationic lipid preferably has a pKa of from about 4 to about 7 (such as 6.0 to 6.5).

In one embodiment, the cationic lipid having a log P value of at least 10.1 and/or a $t_{lipid}-t_{chol}$, of at least 1.4 comprises (a) a head group (preferably a nitrogen containing head group, such as the head groups described herein), (b) at least two hydrophobic tails, each of the formula -(hydrophobic chain)-(biodegradable group)-(hydrophobic chain), and (c) a linker group (for instance, a single central carbon atom) which is bound to the head group and the hydrophobic tails. The cationic lipid preferably has one, two, three, four or more of the properties listed below:

(i) a pKa of from about 4 to about 7 (such as 6.0 to 6.5);

(ii) in at least one hydrophobic tail (and preferably all hydrophobic tails), the biodegradable group is separated from the terminus of the hydrophobic tail by from about 6 to about 12 carbon atoms (for instance, 6 to 8 carbon atoms or 8 to 12 carbon atoms), (iii) for at least one hydrophobic tail (and preferably all hydrophobic tails), the chain length from the linker group to the terminus of the hydrophobic tail is at most 21 (e.g., at most 20, or from about 17 to about 21, from about 18 to about 20, or from about 16 to about 18) (The atom(s) in the linker group are not counted when calculating the chain length.);

(iv) for at least one hydrophobic tail (and preferably all hydrophobic tails), the total number of carbon atoms in the hydrophobic tail is from about 17 to about 26 (such as from about 19 to about 26, or from about 21 to about 26);

(v) for at least one hydrophobic tail (and preferably all hydrophobic tails), the number of carbon atoms between the linker group and the biodegradable group ranges from about 5 to about 10 (for example, 6 to 10, or 7 to 9);

(vi) for at least one hydrophobic tail (and preferably all hydrophobic tails), the total number of carbon atoms between the linker group and the terminus of the hydrophobic tail is from about 15 to about 20 (such as from 16 to 20, 16 to 18, or 18 to 20);

(vii) for at least one hydrophobic tail (and preferably all hydrophobic tails), the total number of carbon atoms between the biodegradable group and the terminus of the hydrophobic tail is from about 12 to about 18 (such as from 13 to 25);

(viii) for at least one hydrophobic tail (and preferably all hydrophobic tails), the terminal hydrophobic chain in the hydrophobic tail is a branched alkyl or alkenyl group, for example, where the branching occurs at the α, β, γ, or δ position on the hydrophobic chain relative to the biodegradable group;

(ix) when formulated as a lipid nanoparticle (such as in Example 35), the cationic lipid has an in vivo half life ($t_{1/2}$) in the liver of less than about 3 hours, such as less than about 2.5 hours, less than about 2 hours, less than about 1.5 hours, less than about 1 hour, less than about 0.5 hour or less than about 0.25 hours;

(x) when formulated as a lipid nanoparticle (such as in Example 35), the cationic lipid is eliminated from the liver in mice with a greater than 10-fold reduction in lipid levels relative to $C_{max}$ within the first 24 hours post-dose;

(xi) when formulated as a lipid nanoparticle (such as in Example 35), the cationic lipid is eliminated from the spleen in mice with an equal or greater than 10-fold reduction in lipid levels relative to $C_{max}$ within the first 168 hours post-dose; and (xii) when formulated as a lipid nanoparticle (such as in Example 35), the cationic lipid is eliminated from plasma with a terminal plasma half-life (t½β) in rodents and non-human primates of 48 hours or shorter.

The present invention embodies compounds having any combination of some or all of the aforementioned properties. These properties provide a cationic lipid which remains intact until delivery of an active agent, such as a nucleic acid, after which cleavage of the hydrophobic tail occurs in vivo. For instance, the compounds can have all of properties (i) to (viii) (in addition to the log P or $t_{lipid}-t_{chol}$ value). In another embodiment, the compounds have properties (i), (ii), (iii), and (viii). In yet another embodiment, the compounds have properties (i), (ii), (iii), (v), (vi), and (viii).

Another embodiment is a method of preparing a cationic lipid comprising:

(a) designing a cationic lipid having a log P value of at least 10.1 and/or a $t_{lipid}-t_{chol}$, of at least 1.4, and optionally also having one, two, three, four, or more properties from the list above (i.e., properties (i)-(xii)); and (b) synthesizing the cationic lipid of step (a). The cationic lipid in step (a) may comprises (a) a head group (preferably a nitrogen containing head group, such as the head groups described herein), (b) at least two hydrophobic tails, each of the formula -(hydrophobic chain)-(biodegradable group)-(hydrophobic chain), and (c) a linker group (for instance, a single central carbon atom) which is bound to the head group and the hydrophobic tails. Step (a) may comprise:

(a)(i) preparing one or more cationic lipids having a log P value of at least 10.1 and/or a $t_{lipid}-t_{chol}$, of at least 1.4, and optionally also having one, two, three, four, or more properties from the list above (i.e., properties (i)-(xii);

(a)(ii) screening the cationic lipids to determine their efficacy and/or toxicity in lipid nanoparticles; and (a)(iii) selecting a cationic lipid for synthesis.

Yet another embodiment is a method of designing a cationic lipid comprising:

(a) selecting a cationic lipid having a log P value of at least 10.1 and/or a $t_{lipid}$–$t_{chol}$, of at least 1.4, and optionally also having one, two, three, four, or more properties from the list above (i.e., properties (i)-(xii)); and (b) optionally,
(i) preparing one or more cationic lipids having a log P value of at least 10.1 and/or a $t_{lipid}$–$t_{chol}$, of at least 1.4, and optionally also having one, two, three, four, or more properties from the list above (i.e., properties (i)-(xii);
(ii) screening the cationic lipids to determine their efficacy and/or toxicity in lipid nanoparticles; and
(iii) optionally, selecting a cationic lipid for further development or use.

In one embodiment, the PEG lipid has the formula:

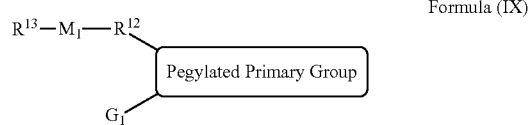

Formula (IX)

wherein $G_1$ is branched or unbranched $C_3$-$C_{15}$ alkyl, alkenyl or alkynyl (e.g., a n-$C_8$ alkyl n-$C_9$ alkyl, or n-$C_{10}$ alkyl); or $G_1$ is —$R^2$-$M_1$-$R^3$;

$R^{12}$ is a branched or unbranched alkylene or alkenylene (e.g., $C_6$-$C_{20}$ alkylene or $C_6$-$C_{20}$ alkenylene such as $C_{12}$-$C_{20}$ alkylene or $C_{12}$-$C_{20}$ alkenylene);

$M_1$ is a biodegradable group (e.g., —OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)(C$R^3R^4$)C(O)O—, —OC(O)(C$R^3R^4$)C(O)—, or

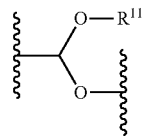

(wherein $R^{11}$ is a $C_2$-$C_8$ alkyl or alkenyl));

$R^3$ and $R^4$ are defined as in formula (I);

each occurrence of $R^5$ is, independently, H or alkyl (e.g., $C_1$-$C_4$ alkyl);

$R^{13}$ is branched or unbranched $C_3$-$C_{15}$ alkyl, alkenyl or alkynyl;

Pegylated Primary Group comprises a PEG moiety, such as

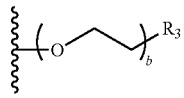

moiety wherein b is an integer from 10 to 1,000 (e.g., 5-100, 10-60, 15-50, or 20-45); $R^3$ is —H, —$R^c$, or —O$R^c$; and $R^c$ is —H, alkyl, acyl, cycloalkyl, alkenyl, alkynyl, aryl, heteroaryl, or heterocyclyl.

In one embodiment, the pegylated primary group includes (i) a head group having a PEG moiety, and (ii) a central moiety (e.g., a central carbon atom) to which both the hydrophobic tails are directly bonded. Representative central moieties include, but are not limited to, a central carbon atom, a central nitrogen atom, a central carbocyclic group, a central aryl group, a central hetrocyclic group (e.g., central tetrahydrofuranyl group or central pyrrolidinyl group) and a central heteroaryl group.

Representative Pegylated Primary Group's include, but are not limited to,

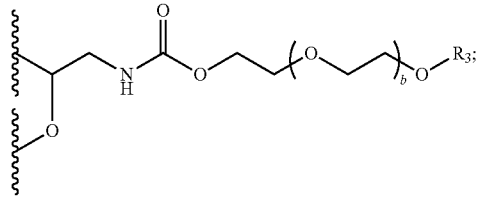

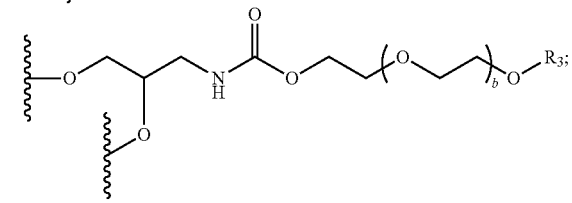

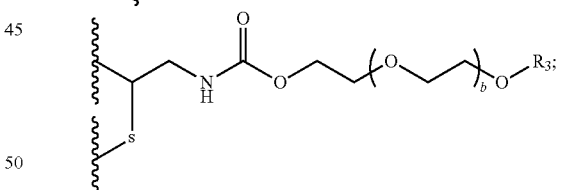

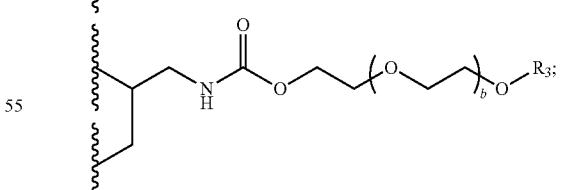

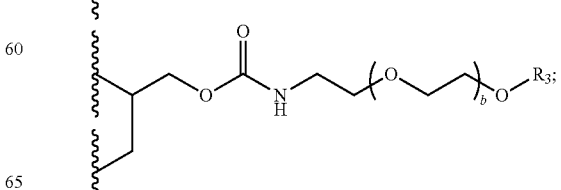

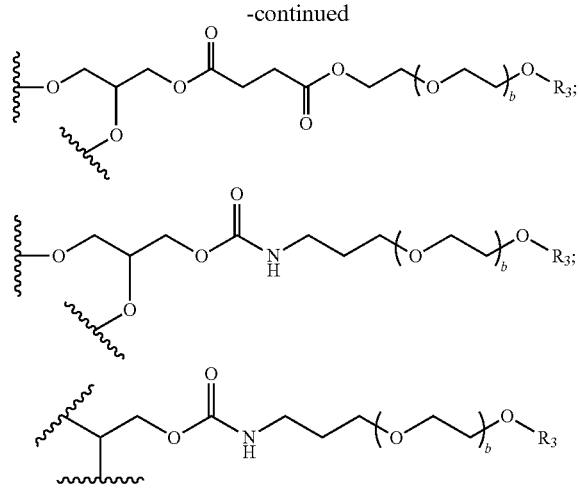

where b is 10-100 (e.g., 20-50 or 40-50)

Another embodiment of the present invention is a PEG lipid (or a salt thereof) having:

(i) a pegylated primary group including a head group which includes a PEG moiety (e.g., having from 10 to 1000 repeating units such as ethoxy units)), and (iii) one or more hydrophobic tails (preferably, two hydrophobic tails) directly bound to the pegylated primary group, wherein at least one hydrophobic tail is of the formula —$R^e$-M-$R^f$ where $R^e$ is a $C_4$-$C_{14}$ alkyl or alkenyl, M is a biodegradable group, and $R^f$ is a branched alkyl or alkenyl (e.g., a $C_{10}$-$C_{20}$ alkyl or $C_{10}$-$C_{20}$ alkenyl), such that (i) the chain length of —$R^e$-M-$R^f$ is at most 20 atoms (i.e. the total length of the tail from the first carbon atom after the central carbon atom to a terminus of the tail is at most 20), and (ii) the group —$R^e$-M-$R^f$ has at least 20 carbon atoms (e.g., at least 21 atoms). Optionally, the alkyl or alkenyl group in $R^e$ may be substituted with one or two fluorine atoms at the alpha position to the $M^1$ or $M^2$ group

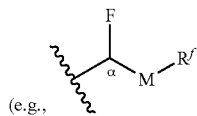

(e.g., )

Also, optionally, the alkenyl group in $R^f$ may be substituted with one or two fluorine atoms at the alpha position to a double bond which is between the double bond and the terminus of R

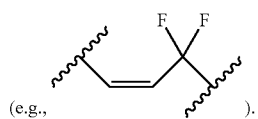

(e.g., ).

In one embodiment, the pegylated primary group includes (i) a head group having a PEG moiety, and (ii) a central moiety (e.g., a central carbon atom) to which the hydrophobic tails are directly bound. The PEG moiety may have 5-100, 10-60, 15-50, or 20-45 repeating units. For example, the PEG moiety may have the formula moiety wherein b is an integer from 10 to 1,000 (e.g., 5-100, 10-60, 15-50, or 20-45); $R^3$ is —H, —$R^c$, or —$OR^c$; and $R^c$ is —H, alkyl (e.g., $C_1$-$C_4$ alkyl), acyl, cycloalkyl, alkenyl, alkynyl, aryl, heteroaryl, or heterocyclyl.

Yet another embodiment is a lipid particle that includes a cationic lipid and/or PEG lipid of the present invention. In one embodiment, the lipid particle includes a cationic lipid of the present invention (e.g., of one of formulas (I)-(VIII)). In another embodiment, the lipid particle includes a PEG lipid of the present invention (e.g., of formula (IX)). In yet another embodiment, the lipid particle includes a cationic lipid of the present invention and a PEG lipid of the present invention.

In a preferred embodiment, the lipid particle includes a neutral lipid, a lipid capable of reducing aggregation, a cationic lipid, and optionally, a sterol (e.g., cholesterol). Suitable neutral lipids include, but are not limited to, distearoylphosphatidylcholine (DSPC), dipalmitoylphosphatidylcholine (DPPC), POPC, DOPE, and SM. Suitable lipids capable of reducing aggregation include, but are not limited to, a PEG lipid, such as PEG-DMA, PEG-DMG, and those of the present invention (e.g., of formula (IX)) or a combination thereof.

The lipid particle may further include an active agent (e.g., a therapeutic agent). The active agent can be a nucleic acid such as a plasmid, an immunostimulatory oligonucleotide, an siRNA, an antisense oligonucleotide, a microRNA, an antagomir, an aptamer, or a ribozyme. In a preferred embodiment, the nucleic acid is a siRNA. In another preferred embodiment, the nucleic acid is a miRNA.

In another embodiment, the lipid particle includes a cationic lipid of the present invention, a neutral lipid and a sterol. The lipid particle may further include an active agent, such as a nucleic acid (e.g., an siRNA or miRNA).

In yet another embodiment, the lipid particle includes a PEG lipid of the present invention, a cationic lipid, a neutral lipid, and a sterol. The lipid particle may further include an active agent, such as a nucleic acid (e.g., an siRNA or miRNA).

The lipid particles described herein may be lipid nanoparticles.

Yet another embodiment of the invention is a pharmaceutical composition which includes a lipid particle of the present invention and a pharmaceutically acceptable carrier.

In one embodiment, the cationic lipid remains intact until delivery of the nucleic acid molecule after which cleavage of the hydrophobic tail occurs in vivo.

In another embodiment, the PEG lipid remains intact until delivery of the nucleic acid molecule after which cleavage of the hydrophobic tail occurs in vivo.

In another embodiment, the present invention relates to a method of delivering a nucleic acid molecule comprising administering a nucleic lipid particle comprising (i) the nucleic acid molecule and (ii) a cationic lipid and/or a PEG lipid of the present invention. In one embodiment, the cationic lipid and/or a PEG lipid remains intact until delivery of the nucleic acid molecule after which cleavage of the hydrophobic tail occurs in vivo.

Yet another aspect is a method of modulating the expression of a target gene in a cell by providing to the cell a lipid particle of the present invention. The active agent can be a nucleic acid selected from a plasmid, an immunostimulatory oligonucleotide, an siRNA, an antisense oligonucleotide, a microRNA, an antagomir, an aptamer, and a ribozyme. In a preferred embodiment, the nucleic acid is a siRNA or miRNA.

Yet another aspect is a method of treating a disease or disorder characterized by the overexpression of a polypeptide in a subject by providing to the subject a pharmaceutical composition of the present invention, wherein the active agent is a nucleic acid selected from an siRNA, a microRNA, and an antisense oligonucleotide, and wherein the siRNA, microRNA, or antisense oligonucleotide includes a polynucleotide that specifically binds to a polynucleotide that encodes the polypeptide, or a complement thereof. In a preferred embodiment, the nucleic acid is a siRNA or miRNA.

Yet another aspect is a method of treating a disease or disorder characterized by underexpression of a polypeptide in a subject by providing to the subject a pharmaceutical composition of the present invention, wherein the active agent is a plasmid that encodes the polypeptide or a functional variant or fragment thereof.

Yet another aspect is a method of inducing an immune response in a subject by providing to the subject a pharmaceutical composition wherein the active agent is an immunostimulatory oligonucleotide.

Yet another aspect is a transfection agent that includes the composition or lipid particles described above, where the composition or lipid particles include a nucleic acid. The agent, when contacted with cells, can efficiently deliver nucleic acids to the cells. Yet another aspect is a method of delivering a nucleic acid to the interior of a cell, by obtaining or forming a composition or lipid particles described above, and contacting the composition or lipid particles with a cell.

DETAILED DESCRIPTION

In one aspect, the present invention relates to a lipid particle that includes a neutral lipid, a lipid capable of reducing aggregation (e.g., a PEG lipid), a cationic lipid, and optionally a sterol. In certain embodiments, the lipid particle further includes an active agent (e.g., a therapeutic agent). Various exemplary embodiments of these lipids, lipid particles and compositions comprising the same, and their use to deliver therapeutic agents and modulate gene and protein expression are described in further detail below.

The Cationic Lipid

In one embodiment, the cationic lipid is a compound of any one of Formulas I-VIII. The following disclosure represents various embodiments of the compounds described above, including the compounds of Formulas I-VIII.

In one embodiment, $M^1$ and $M^2$ are each, independently: —OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)(C$R^3R^4$)C(O)O—, —OC(O)(C$R^3R^4$)C(O)—, or

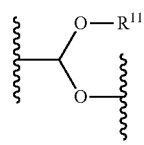

(wherein $R^{11}$ is a $C_2$-$C_8$ alkyl or alkenyl).

In another embodiment, $M^1$ and $M^2$ are each, independently:
—OC(O)—, —C(O)—O—, —C($R^5$)=N—, —N=C($R^5$)—, —C($R^5$)=N—O—, —O—N=C($R^5$)—, —O—C(O)O—, —C(O)N($R^5$)—, —N($R^5$)C(O)—, —C(O)S—, —SC(O)—, —C(S)O—, —OC(S)—, —OSi($R^5$)$_2$O—, —C(O)(C$R^3R^4$)C(O)O—, or —OC(O)(C$R^3R^4$)C(O)—.

In yet another embodiment, $M^1$ and $M^2$ are each, independently:
—C(O)—O—, —OC(O)—, —C($R^5$)=N—, —C($R^5$)=N—O—, —O—C(O)O—, —C(O)N($R^5$)—, —C(O)S—, —C(S)O—, —OSi($R^5$)$_2$O—, —C(O)(C$R^3R^4$)C(O)O—, or —OC(O)(C$R^3R^4$)C(O)—.

In another embodiment, $M^1$ and $M^2$ are each —C(O)O—.

In one embodiment, $R^1$ and $R^2$ are each, individually, optionally substituted alkyl, cycloalkyl, cycloalkylalkyl, or heterocycle. In one embodiment, $R^1$ is alkyl and $R^2$ is alkyl, cycloalkyl or cycloalkylalkyl. In one embodiment, $R^1$ and $R^2$ are each, individually, alkyl (e.g., $C_1$-$C_4$ alkyl, such as methyl, ethyl, or isopropyl). In one embodiment, $R^1$ and $R^2$ are both methyl. In another embodiment, $R^1$ and $R^2$, together with the nitrogen atom to which they are attached, form an optionally substituted heterocyclic ring (e.g., N-methylpiperazinyl). In another embodiment, one of $R^1$ and $R^2$ is

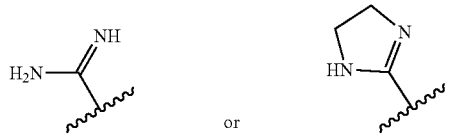

(e.g., $R^1$ is one of the two aforementioned groups and $R^2$ is hydrogen).

In one embodiment, R' is hydrogen or alkyl. In another embodiment, R' is hydrogen or methyl. In one embodiment, R' is absent. In one embodiment, R' is absent or methyl.

For cationic lipid compounds which contain an atom (e.g., a nitrogen atom) that carries a positive charge, the compound also contains a negatively charged counter ion. The counterion can be any anion, such as an organic or inorganic anion. Suitable examples of anions include, but are not limited to, tosylate, methanesulfonate, acetate, citrate, malonate, tartarate, succinate, benzoate, ascorbate, α-ketoglutarate, α-glycerophosphate, halide (e.g., chloride), sulfate, nitrate, bicarbonate, and carbonate. In one embodiment, the counterion is a halide (e.g., Cl).

In one embodiment each R is, independently, —(C$R^3R^4$)—, wherein $R^3$ and $R^4$ are each, independently, H or alkyl (e.g., $C_1$-$C_4$ alkyl). For example, in one embodiment each R is, independently, —(CH$R^4$)—, wherein each $R^4$ is, independently H or alkyl (e.g., $C_1$-$C_4$ alkyl). In another embodiment, each R is, independently, —CH$_2$—, —C(CH$_3$)$_2$— or —CH(iPr)- (where iPr is isopropyl). In another embodiment, each R is —CH$_2$—.

In another embodiment $R^5$ is, in each case, hydrogen or methyl. For example, $R^5$ can be, in each case, hydrogen.

In one embodiment, Q is absent, —C(O)O—, —OC(O)—, —C(O)N($R^5$)—, —N($R^5$)C(O)—, —S—S—, —OC(O)O—, —C($R^5$)=N—O—, —OC(O)N($R^5$)—, —N($R^5$)C(O)N($R^5$)—, —N($R^5$)C(O)O—, —C(O)S—, —C(S)O— or —C($R^5$)=N—O—C(O)—. In one embodiment, Q is —C(O)O—.

In one embodiment, the dashed line to Q is absent, b is 0 and R'R¹R²N—(R)$_a$-Q- and the tertiary carbon adjacent to it (C*) form the following group:

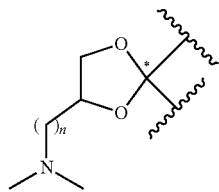

where n is 1 to 4 (e.g., n is 2).

In one embodiment, the dashed line to Q is absent, b is 0 and R'R¹R²N—(R)$_a$-Q- and the tertiary carbon adjacent to it form the following group:

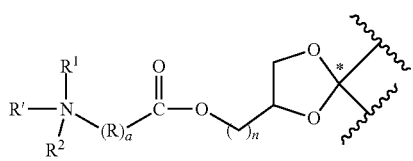

where n is 1 to 4 (e.g., n is 2), and R¹, R², R, a, and b are as defined with respect to formula (I).

In one embodiment, a is 3.

In one embodiment, the dashed line to Q is absent, b is 0 and R'R¹R²N—(R)$_a$-Q- and the tertiary carbon adjacent to it form the following group:

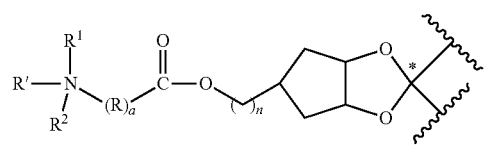

where n is 1 to 4 (e.g., n is 2), and R¹, R², R, a, and b are as defined with respect to formula (I). In one embodiment, a is 0. For example, the group can be:

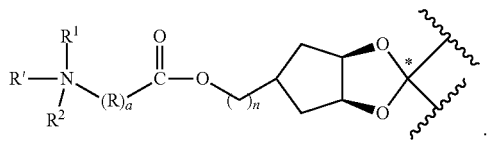

In one embodiment, b is 0. In another embodiment, a is 2, 3, or 4 and b is 0. For example, in one embodiment, a is 3 and b is 0. In another embodiment, a is 3, b is 0, and Q is —C(O)O—.

In certain embodiments, the biodegradable group present in the cationic lipid is selected from an ester (e.g., —C(O)O— or —OC(O)—), disulfide (—S—S—), oxime (e.g., —C(H)=N—O— or —O—N=C(H)—), —C(O)—O—, —OC(O)—, —C(R⁵)=N—, —N=C(R⁵)—, —C(R⁵)=N—O—, —O—N=C(R⁵)—, —O—C(O)O—, —C(O)N(R⁵), —N(R⁵)C(O)—, —C(S)(NR⁵)—, (NR⁵)C(S)—, —N(R⁵)C(O)N(R⁵)—, —C(O)S—, —SC(O)—, —C(S) O—, —OC(S)—, —OSi(R⁵)$_2$O—, —C(O)(CR³R⁴)C(O) O—, or —OC(O)(CR³R⁴)C(O)—.

A suitable cholesterol moiety for the cationic lipids of the present invention (including compounds of formulas I-VI) has the formula:

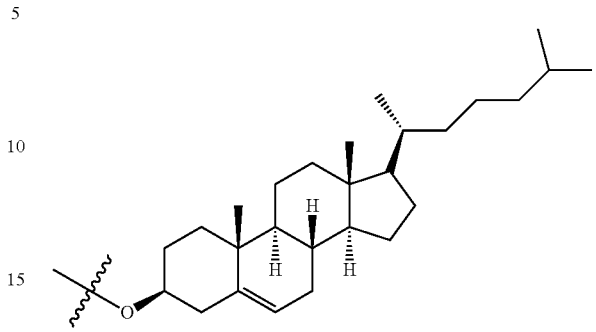

Additional embodiments include a cationic lipid having a head group, one or more hydrophobic tails, and a central moiety between the head group and the one or more tails. The head group can include an amine; for example an amine having a desired pK$_a$. The pK$_a$ can be influenced by the structure of the lipid, particularly the nature of head group; e.g., the presence, absence, and location of functional groups such as anionic functional groups, hydrogen bond donor functional groups, hydrogen bond acceptor groups, hydrophobic groups (e.g., aliphatic groups), hydrophilic groups (e.g., hydroxyl or methoxy), or aryl groups. The head group amine can be a cationic amine; a primary, secondary, or tertiary amine; the head group can include one amine group (monoamine), two amine groups (diamine), three amine groups (triamine), or a larger number of amine groups, as in an oligoamine or polyamine. The head group can include a functional group that is less strongly basic than an amine, such as, for example, an imidazole, a pyridine, or a guanidinium group. The head group can be zwitterionic. Other head groups are suitable as well.

Representative central moieties include, but are not limited to, a central carbon atom, a central nitrogen atom, a central carbocyclic group, a central aryl group, a central hetrocyclic group (e.g., central tetrahydrofuranyl group or central pyrrolidinyl group) and a central heteroaryl group. Additionally, the central moiety can include, for example, a glyceride linker, an acyclic glyceride analog linker, or a cyclic linker (including a spiro linker, a bicyclic linker, and a polycyclic linker). The central moiety can include functional groups such as an ether, an ester, a phosphate, a phosphonate, a phosphorothioate, a sulfonate, a disulfide, an acetal, a ketal, an imine, a hydrazone, or an oxime. Other central moieties and functional groups are suitable as well.

In one embodiment, the cationic lipid is a racemic mixture. In another embodiment, the cationic lipid is enriched in one diastereomer, e.g. the cationic lipid has at least 95%, at least 90%, at least 80% or at least 70% diastereomeric excess. In yet another embodiment, the cationic lipid is enriched in one enantiomer, e.g. the lipid has at least 95%, at least 90%, at least 80% or at least 70% enantiomer excess. In yet another embodiment, the cationic lipid is chirally pure, e.g. is a single optical isomer. In yet another embodiment, the cationic lipid is enriched for one optical isomer.

Where a double bond is present (e.g., a carbon-carbon double bond or carbon-nitrogen double bond), there can be isomerism in the configuration about the double bond (i.e. cis/trans or E/Z isomerism). Where the configuration of a double bond is illustrated in a chemical structure, it is understood that the corresponding isomer can also be present. The amount of isomer present can vary, depending on the relative stabilities of the isomers and the energy required to convert between the isomers. Accordingly, some double bonds are, for practical purposes, present in only a single configuration, whereas others (e.g., where the relative stabilities are similar and the energy of conversion low) may be present as inseparable equilibrium mixture of configurations.

In some cases, a double-bonded unsaturation is replaced by a cyclic unsaturation. The cyclic unsaturation can be a cycloaliphatic unsaturation, e.g., a cyclopropyl, cyclobutyl, cyclopentyl, cyclohexyl, cycloheptyl, or cyclooctyl group. In some cases, the cyclic group can be a polycyclic group, e.g., a bicyclic group or tricyclic group. A bicyclic group can be bridged, fused, or have a spiro structure. In some cases, a double bond moiety can be replaced by a cyclopropyl moiety, e.g.,

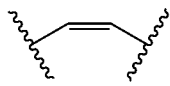

can be replaced by

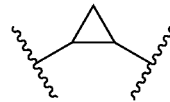

The cationic lipid includes one or more biodegradable groups. The biodegradable group(s) include one or more bonds that may undergo bond breaking reactions in a biological environment, e.g., in an organism, organ, tissue, cell, or organelle. Functional groups that contain a biodegradable bond include, for example, esters, dithiols, and oximes. Biodegradation can be a factor that influences the clearance of the compound from the body when administered to a subject. Biodegredation can be measured in a cell based assay, where a formulation including a cationic lipid is exposed to cells, and samples are taken at various time points. The lipid fractions can be extracted from the cells and separated and analyzed by LC-MS. From the LC-MS data, rates of biodegradation (e.g., as $t_{1/2}$ values) can be measured.

For example, the compound

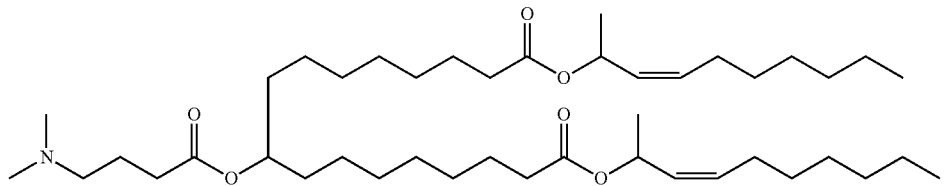

(Compound 1)

includes an ester linkage in each aliphatic chain, which can undergo hydrolysis in a biological environment, for example, when exposed to, e.g., a lipase or an esterase. The structure of the compound, of course, influences the rate at which the compound undergoes biodegradation. Thus, a compound where the methyl substituent is on the other side of the biodegradable group such as

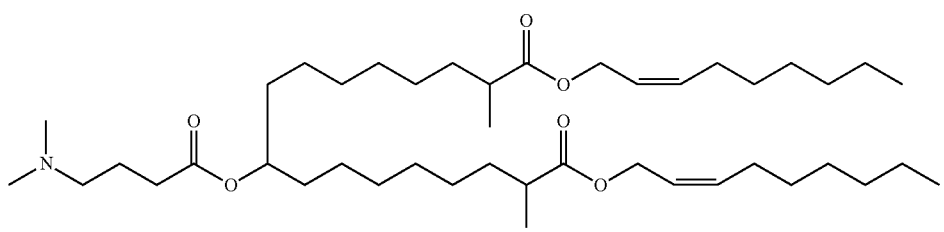 [SMILES: CCCCCC/C=C\COC(=O)C(C)CCCCCCC(CCCCCCC(C)C(=O)OC/C=C\CCCCCC)OC(=O)CCCN(C)C]

would be expected to exhibit a different rate of biodegradation. Greater effects on that rate would be expected from changes in the structure of the compound at the site of hydrolysis. One modification that can influence the rate of hydrolysis, and thereby influence the rate of biodegradation and clearance from a subject's body, is to make the leaving group of the hydrolysis reaction have a secondary, rather than primary, alcohol.

For example, without wishing to be bound by theory, Compound 1 shown above may be metabolized as shown in the scheme below:

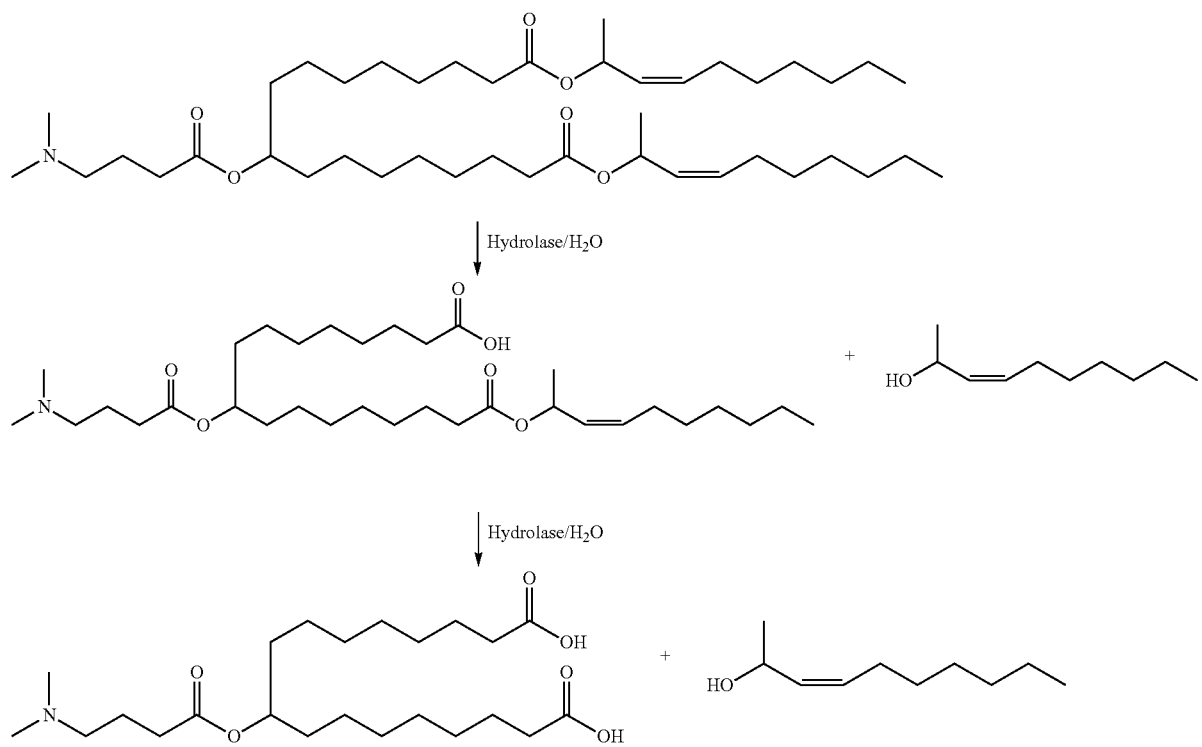

In one embodiment, a cationic lipid of any of the embodiments described herein has an in vivo half life ($t_{1/2}$) (e.g., in the liver, spleen or plasma) of less than about 3 hours, such as less than about 2.5 hours, less than about 2 hours, less than about 1.5 hours, less than about 1 hour, less than about 0.5 hour or less than about 0.25 hours. The cationic lipid preferably remains intact, or has a half-life sufficient to form a stable lipid nanoparticle which effectively delivers the desired active pharmaceutical ingredient (e.g., a nucleic acid) to its target but thereafter rapidly degrades to minimize any side effects to the subject. For instance, in mice, the cationic lipid preferably has a $t_{1/2}$ in the spleen of from about 1 to about 7 hours.

In another embodiment, a cationic lipid of any of the embodiments described herein containing a biodegradable group or groups has an in vivo half life ($t_{1/2}$) (e.g., in the liver, spleen or plasma) of less than about 10% (e.g., less than about 7.5%, less than about 5%, less than about 2.5%) of that for the same cationic lipid without the biodegradable group or groups.

Some cationic lipids can be conveniently represented as a hydrophobic group combined via a central moiety (such as a carbon atom) with a headgroup. By way of example, the compound:

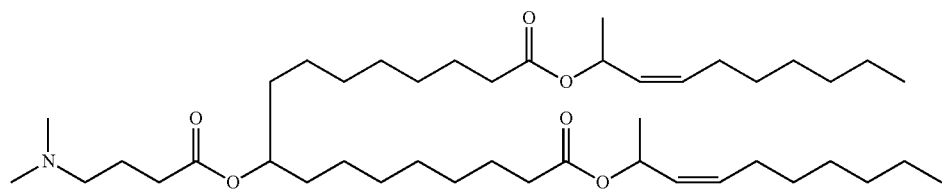 [SMILES: CCCCCC/C=C\C(C)OC(=O)CCCCCCCC(CCCCCCCC(=O)OC(C)/C=C\CCCCCC)OC(=O)CCCN(C)C]

can be thought of as a combination of a headgroup, a central moiety, and two hydrophobic groups as follows:

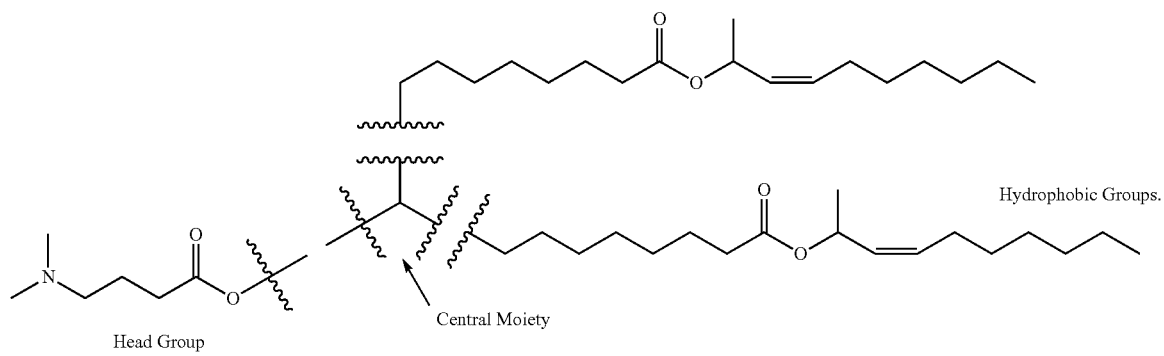
Head Group · Central Moiety · Hydrophobic Groups.
The present invention includes compounds composed of any combination of the head and hydrophobic groups listed below (in combination with a central moiety (such as a central carbon atom).
Some suitable head groups include those depicted in Table 1A:
TABLE 1A
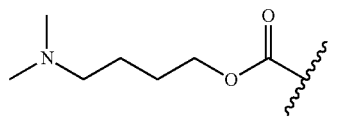 [SMILES: *C(=O)OCCCCN(C)C]
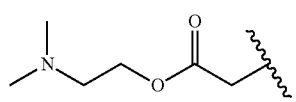 [SMILES: *CC(=O)OCCN(C)C]
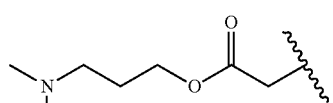
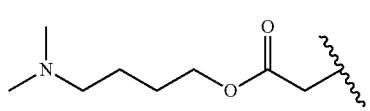 [SMILES: *CC(=O)OCCCCN(C)C]
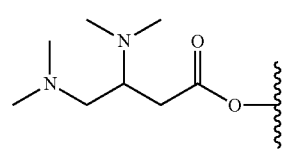 [SMILES: *OC(=O)CC(CN(C)C)N(C)C]
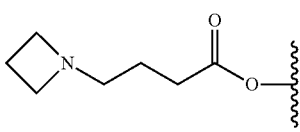 [SMILES: *OC(=O)CCCN1CCC1]
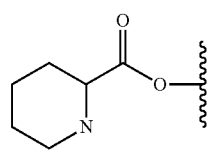 [SMILES: *OC(=O)C1CCCCN1]
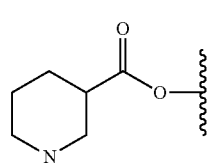 [SMILES: *OC(=O)C1CCCNC1]
TABLE 1A-continued TABLE 1A-continued
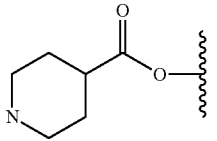 [SMILES: *OC(=O)C1CCNCC1]
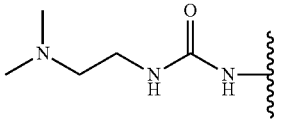 [SMILES: *NC(=O)NCCN(C)C]
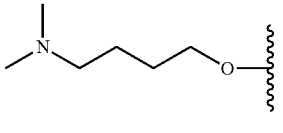 [SMILES: *OCCCCN(C)C]
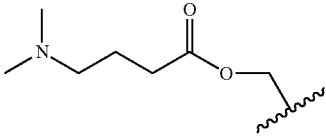 [SMILES: *COC(=O)CCCN(C)C]
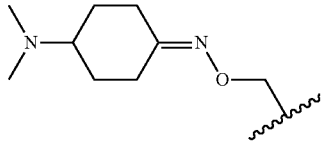 [SMILES: *CON=C1CCC(N(C)C)CC1]
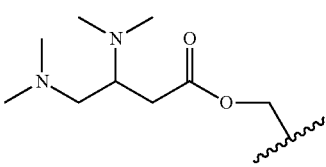 [SMILES: *COC(=O)CC(CN(C)C)N(C)C]
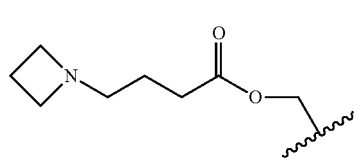 [SMILES: *COC(=O)CCCN1CCC1]
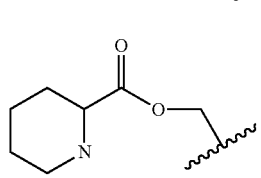
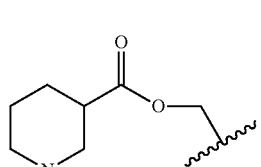
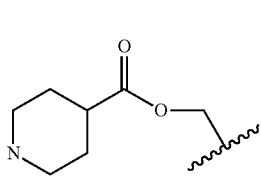 [SMILES: *COC(=O)C1CCNCC1]
TABLE 1A-continued
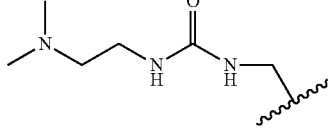
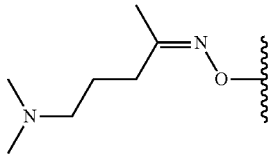 [SMILES: *O/N=C(/C)CCCN(C)C]
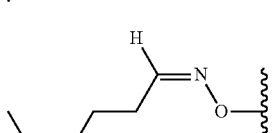
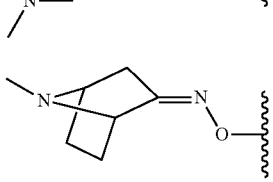
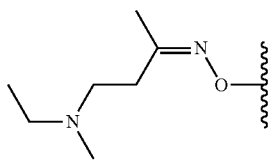 [SMILES: *O/N=C(/C)CCN(C)CC]
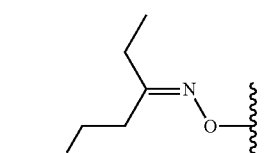
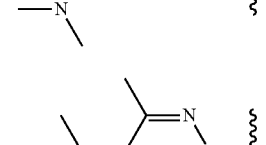
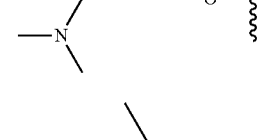
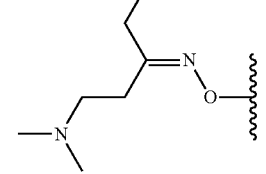

TABLE 1A-continued

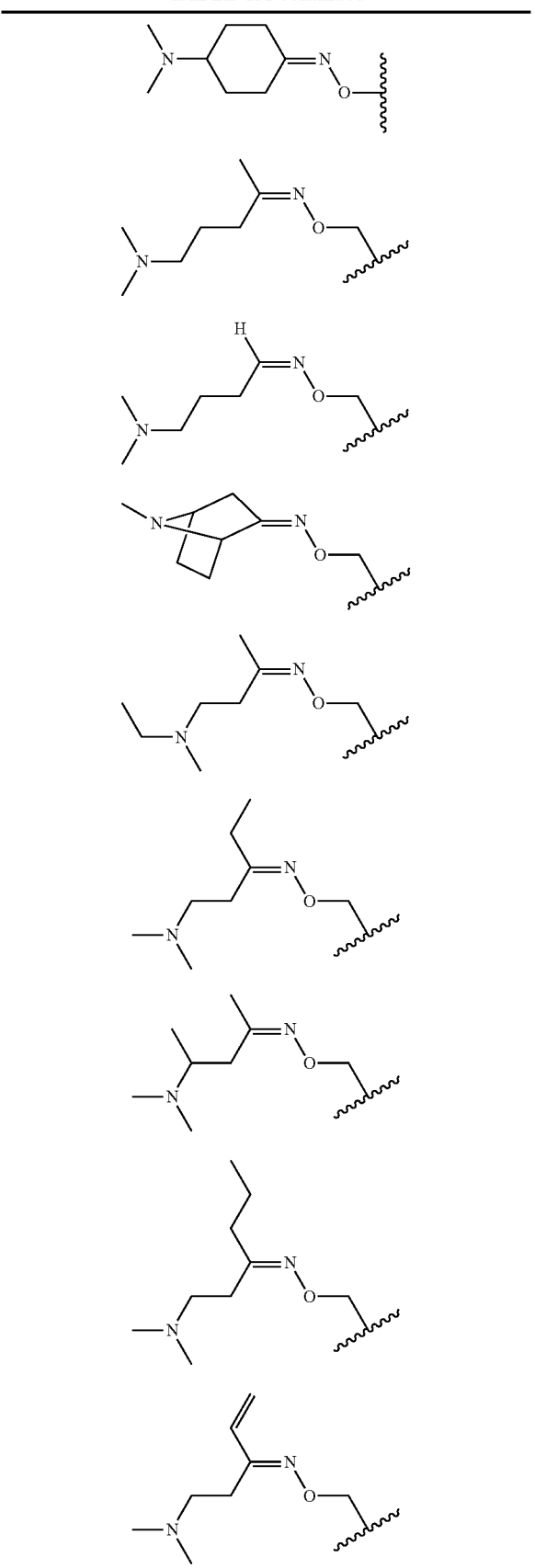

TABLE 1A-continued

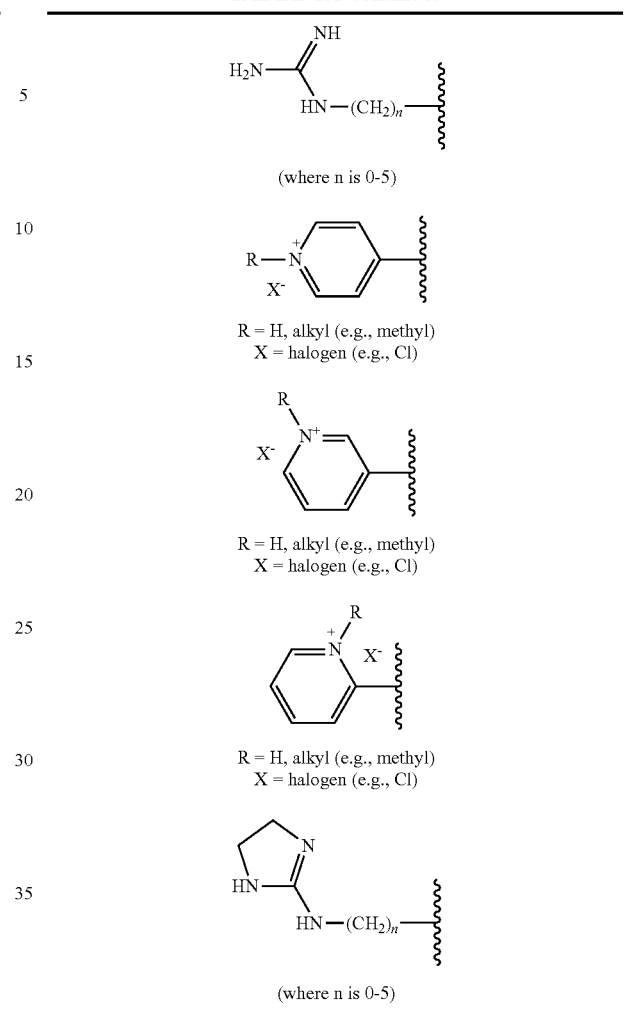

(where n is 0-5)

R = H, alkyl (e.g., methyl)
X = halogen (e.g., Cl)

R = H, alkyl (e.g., methyl)
X = halogen (e.g., Cl)

R = H, alkyl (e.g., methyl)
X = halogen (e.g., Cl)

(where n is 0-5)

Suitable primary groups include, but are not limited to, those that are a combination of a head group from table 1A with a central carbon atom. Other suitable primary groups include those in table 1B below:

TABLE 1B

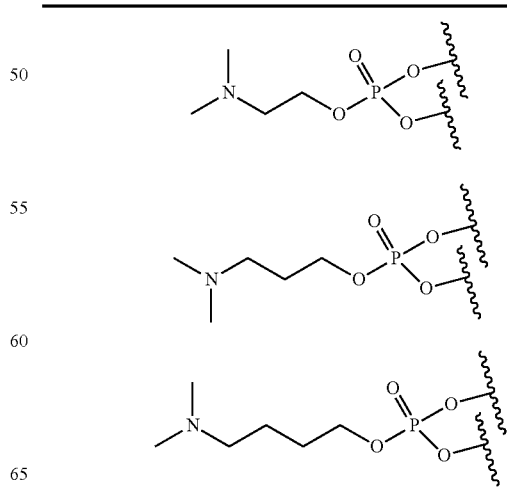

TABLE 1B-continued
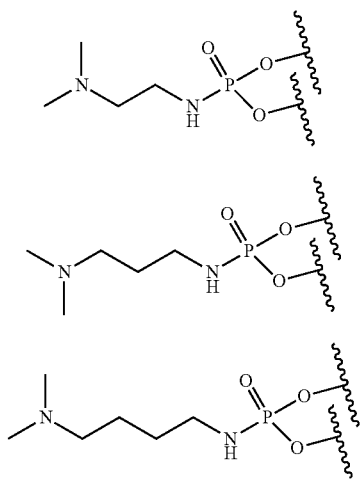
TABLE 1B-continued
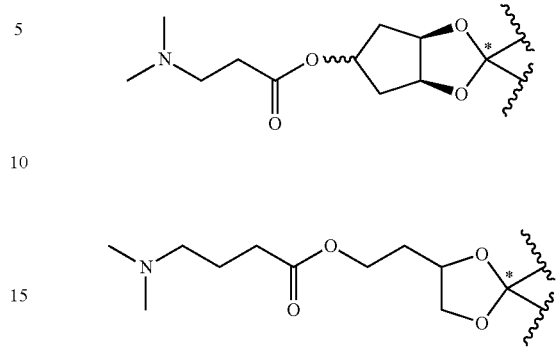
Some suitable hydrophobic tail groups include those depicted in Table 1C:
TABLE 1C
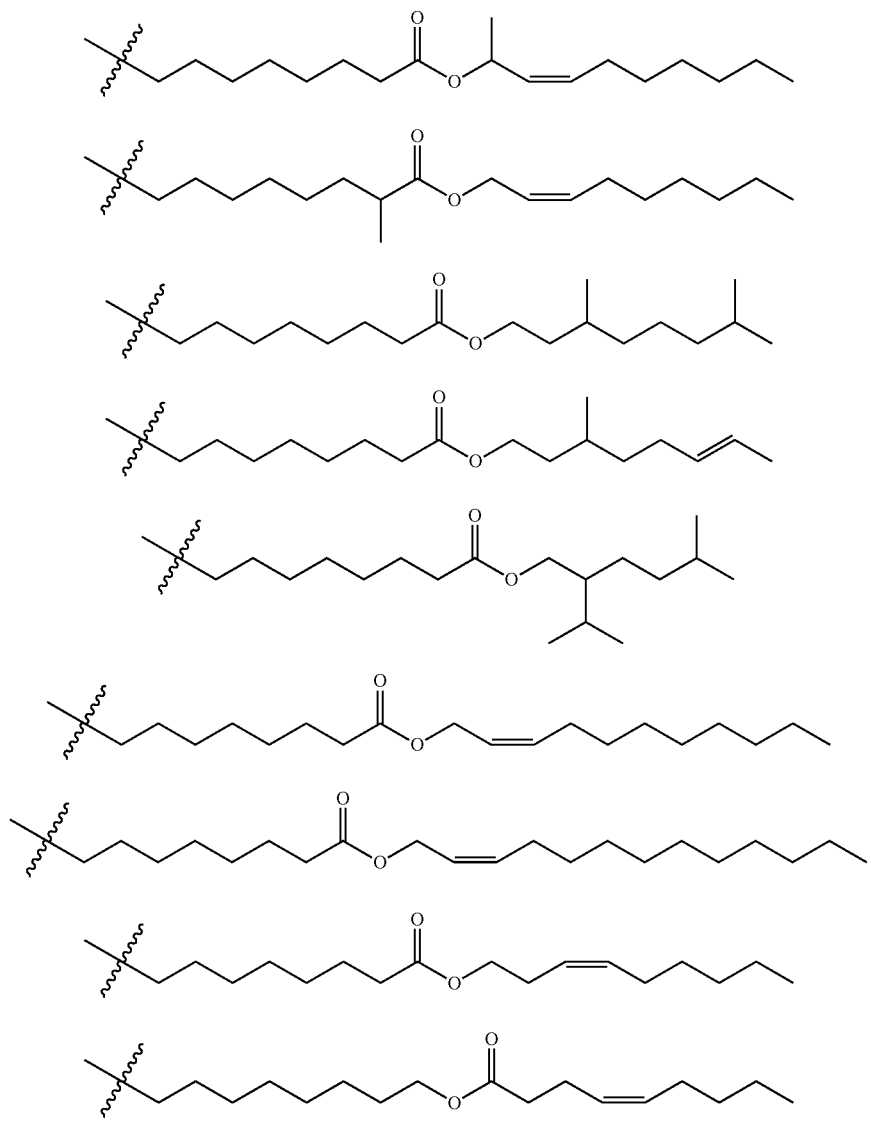

TABLE 1C-continued
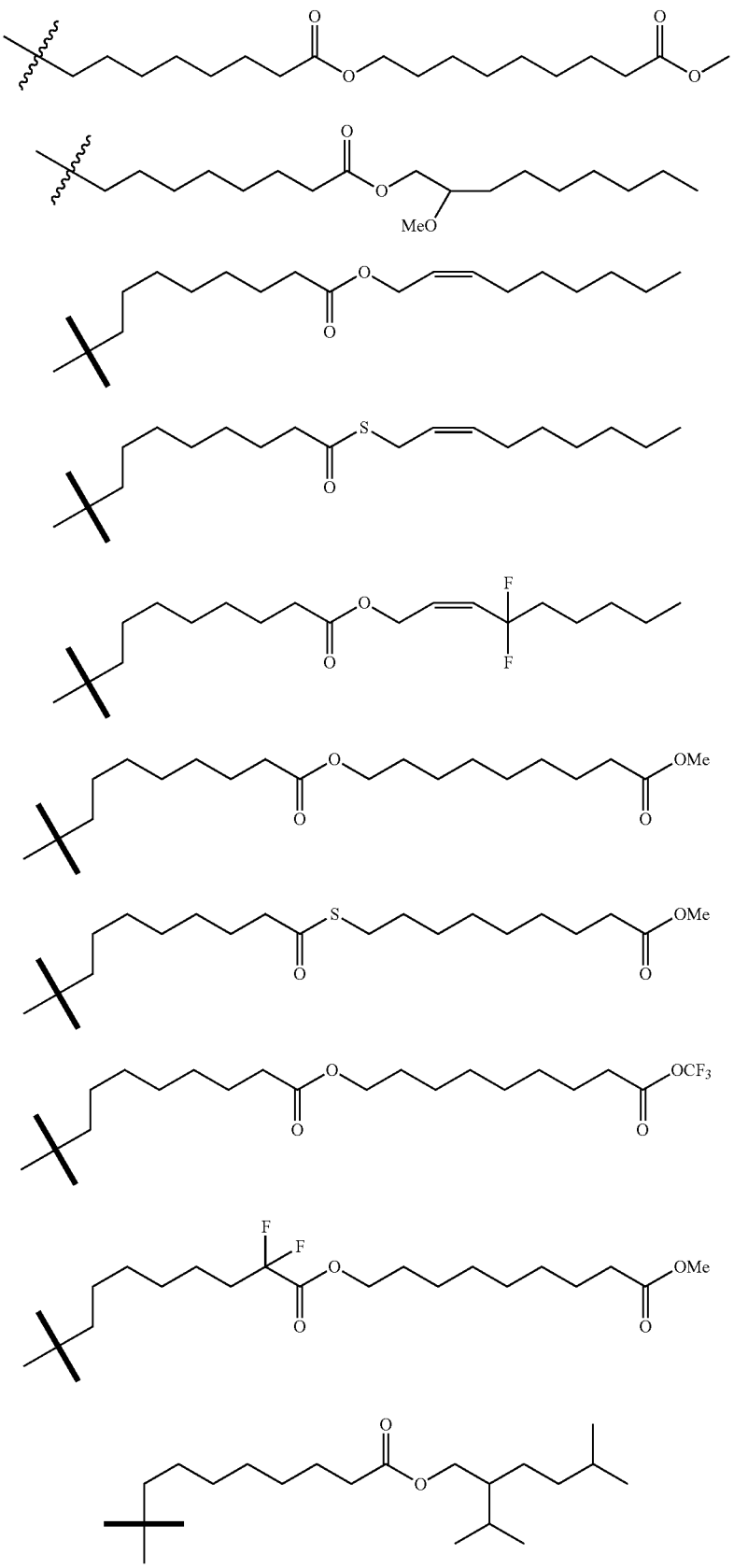

TABLE 1C-continued
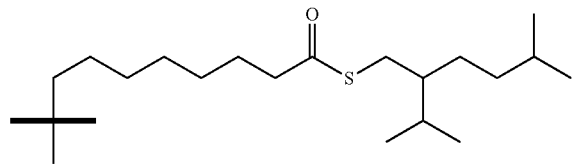
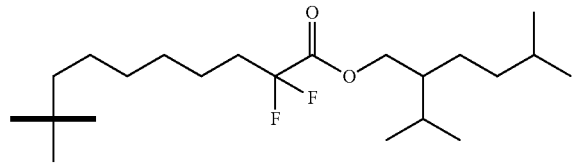
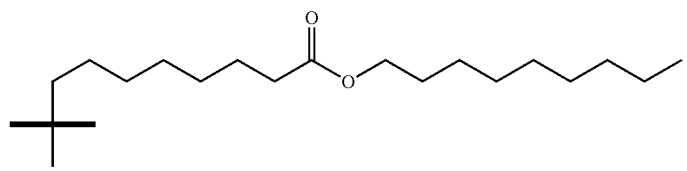
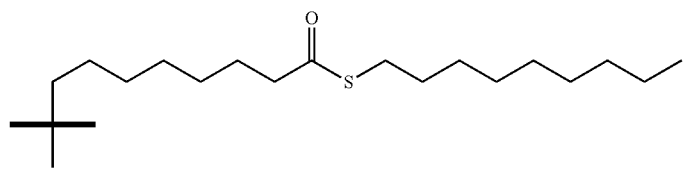
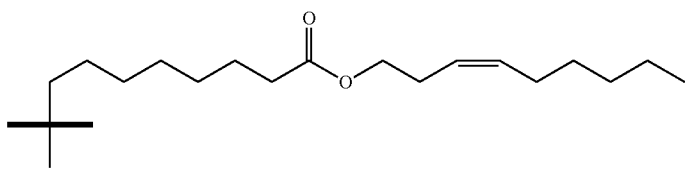
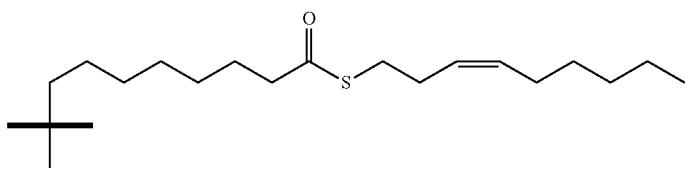
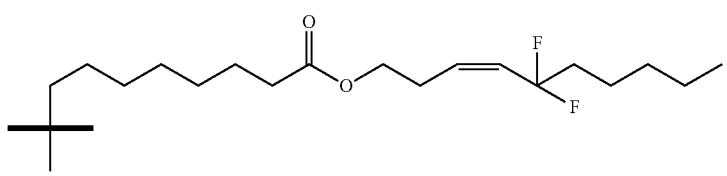
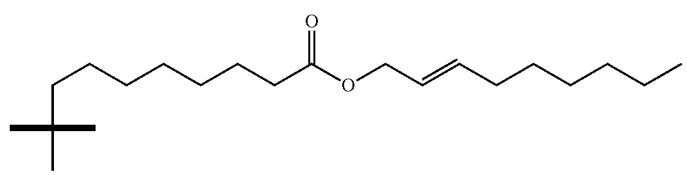
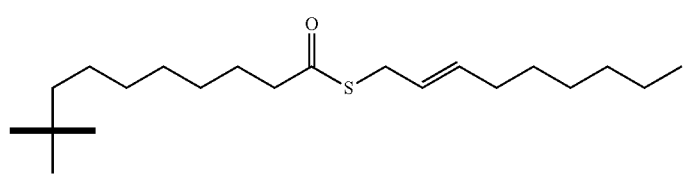

TABLE 1C-continued
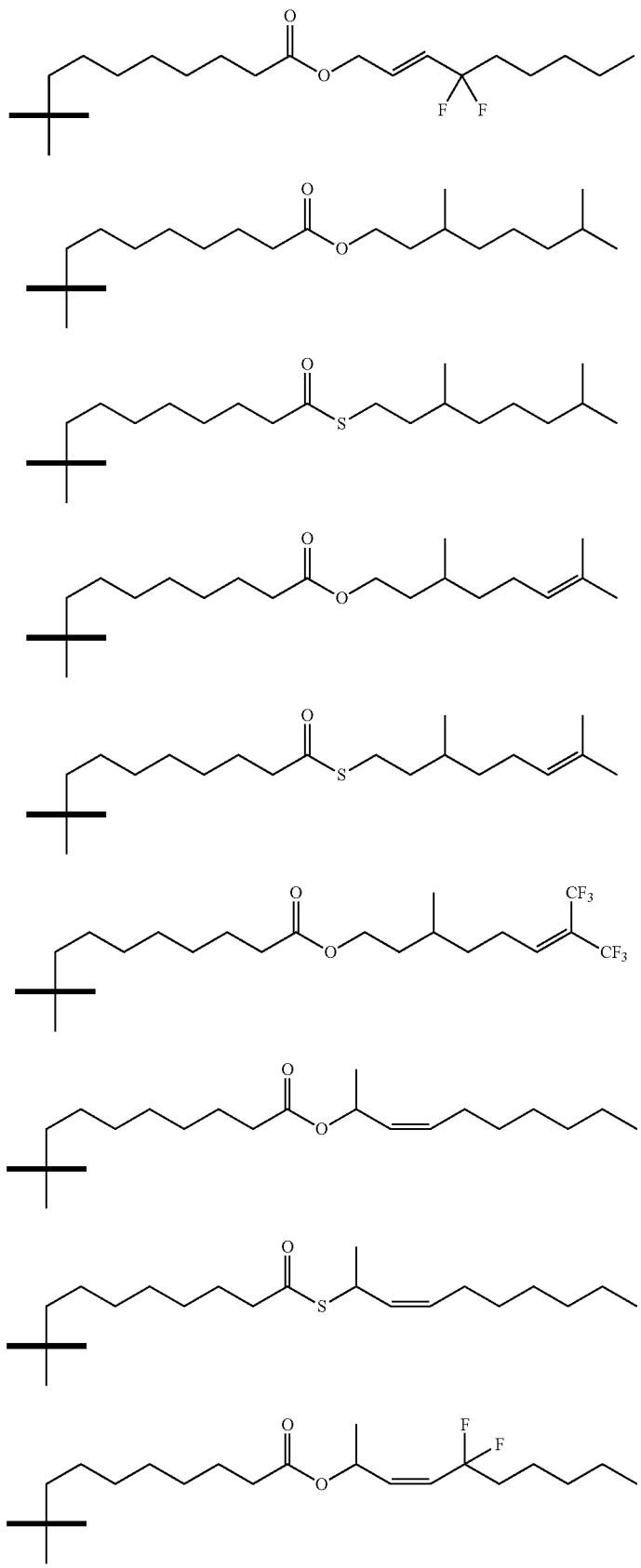

TABLE 1C-continued
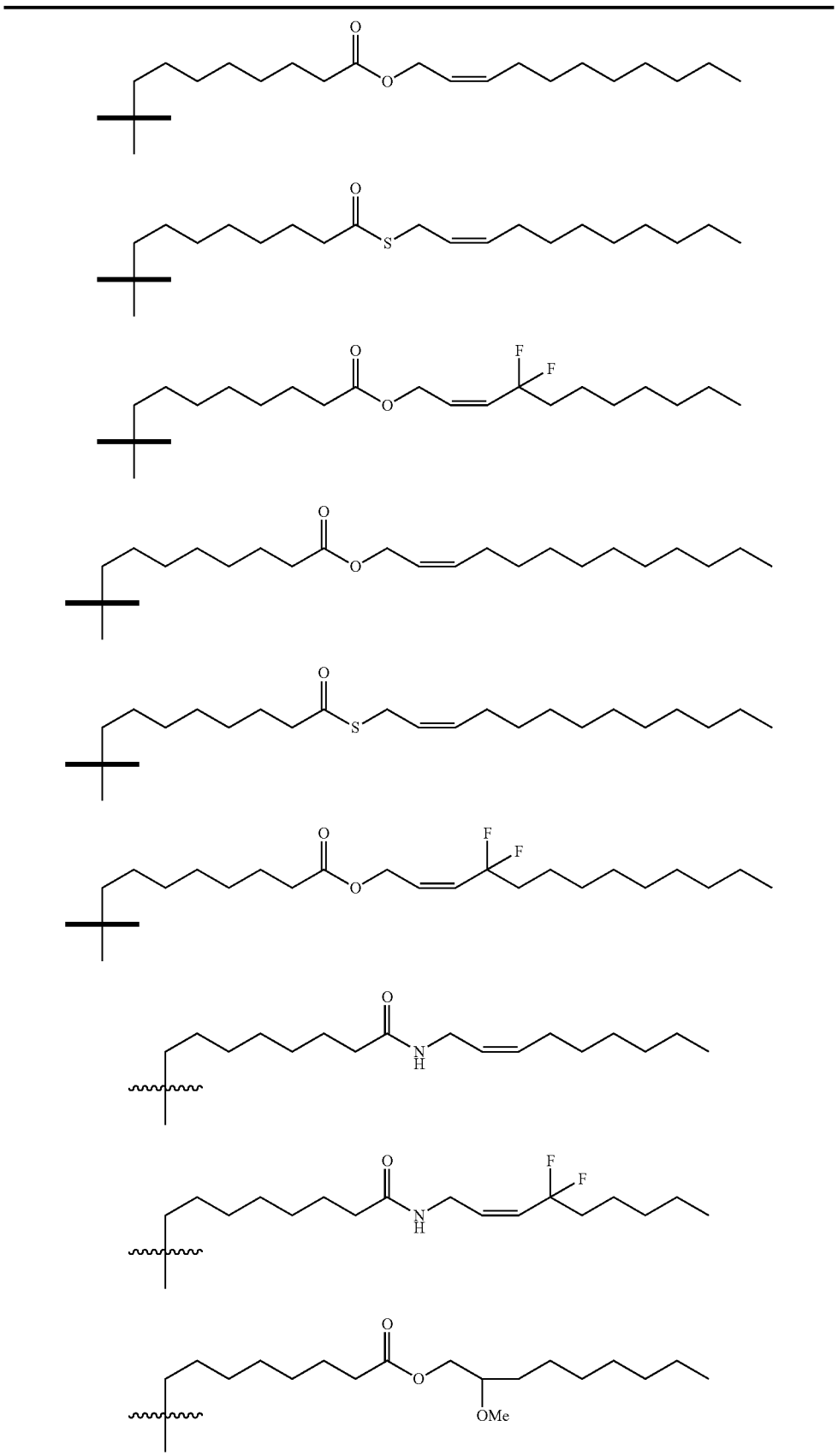

TABLE 1C-continued
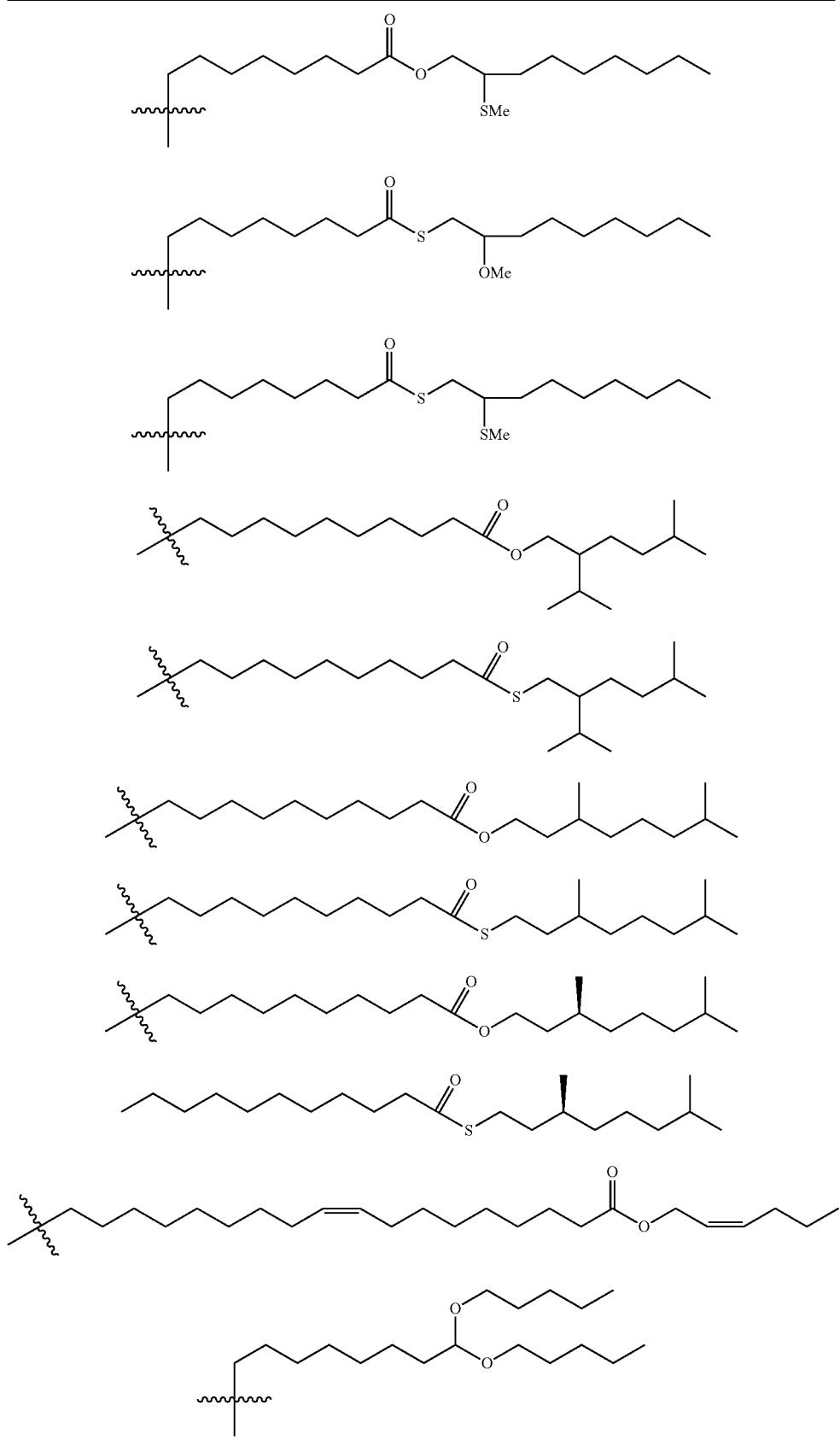

TABLE 1C-continued

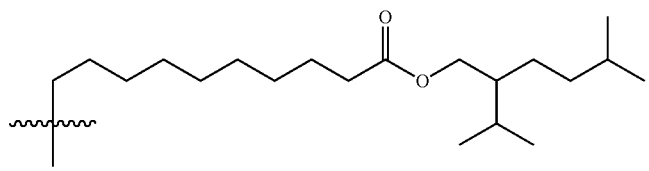 [SMILES: *CCCCCCCCCC(=O)OCC(CCC(C)C)C(C)C]

Other suitable tail groups includes those of the formula —$R^{12}$-$M^1$-$R^{13}$ where $R^{12}$ is a $C_4$-$C_{14}$ alkyl or $C_4$-$C_{14}$ alkenyl, $M^1$ is a biodegradable group as defined above, and $R^{13}$ is a branched alkyl or alkenyl (e.g., a $C_{10}$-$C_{20}$ alkyl or $C_{10}$-$C_{20}$ alkenyl), such that (i) the chain length of —$R^{12}$-$M^1$-$R^{13}$ is at most 21 atoms (i.e., the total length of the tail from the first carbon after the tertiary carbon (marked with an asterisk) to a terminus of the tail is at most 21), and (ii) the group —$R^{12}$-$M^1$-$R^{13}$ has at least 20 carbon atoms (e.g., at least 21 or 22 carbon atoms).

In one preferred embodiment, the chain length of —$R^{12}$-$M^1$-$R^{13}$ is at most 21 (e.g., at most 20). For example, the chain length can be from about 17 to about 24 or from about 18 to about 20.

In one embodiment, the total carbon atom content of each tail (—$R^{12}$-$M^1$-$R^{13}$) is from about 17 to about 26. For example, the total carbon atom content can be from about 19 to about 26 or from about 21 to about 26.

In one embodiment, the tail has the formula:

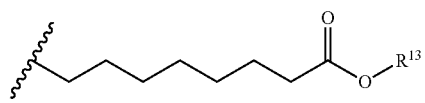

where $R^{13}$ is an alkyl or alkenyl group having from about 13 to about 17 carbon atoms, and the total carbon length of the tail from the first carbon (the leftmost carbon atom above) to a terminus of the tail is at most 20. Preferably, the tail has from about 22 to about 26 carbon atoms. In one embodiment, the maximum length of $R^{13}$ from its attachment point to the ester group of the compound is 12 carbon atoms (e.g., the maximum length can be 11 carbon atoms). In one preferred embodiment, the branch in the alkyl or alkenyl group is at the 6-position or later from the point of attachment of $R^{13}$ to the ester group. Suitable $R^{13}$ groups include, but are not limited to

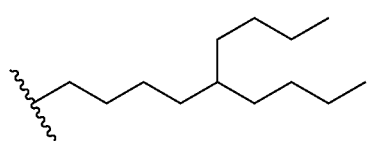

C13 (C21)
Length: C9 (18)

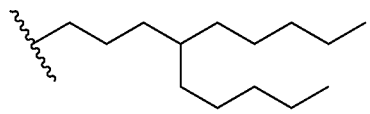

C14 (C22)
Length: C9 (18)

-continued

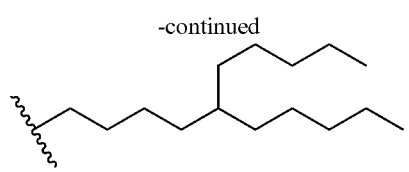

C15 (C23)
Length: C10 (19)

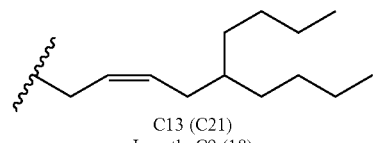

C13 (C21)
Length: C9 (18)

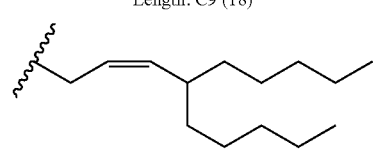

C14 (C22)
Length: C9 (18)

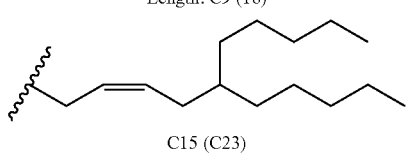

C15 (C23)
Length: C10 (19)

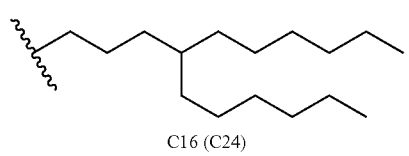

C16 (C24)
Length: C10 (19)

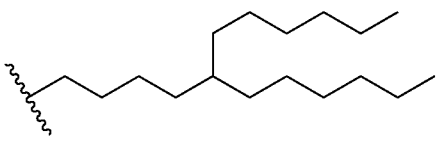

C17 (C25)
Length: C11 (20)

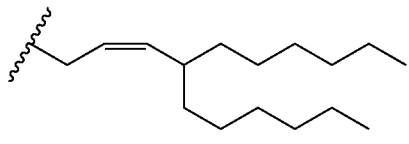

C16 (C24)
Length: C10 (19)

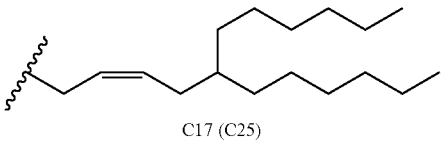

C17 (C25)
Length: C11 (20)

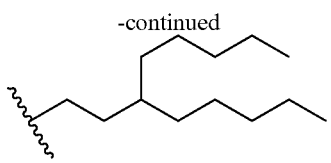

C13 (C21)
Length: C8 (17)

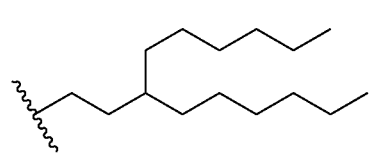

C15 (C23)
Length: C9 (18)

For example, the cationic lipid can be

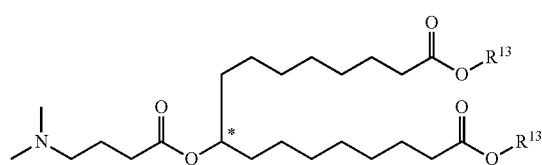

or a salt thereof (e.g., a pharmaceutically acceptable salt thereof), where $R^{13}$ is selected from the groups mentioned above.

Another example is a tail of the formula

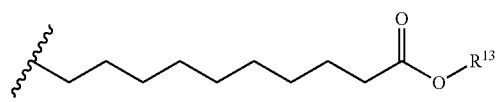

where $R^{13}$ is an alkyl or alkenyl group having from about 13 to about 15 carbon atoms, and the total carbon length of the tail from the first carbon (i.e., the leftmost carbon atom, which is attached to a tertiary carbon) to a terminus of the tail is at most 20. Preferably, the tail has from about 24 to about 26 carbon atoms. In one embodiment, the maximum length of $R^{13}$ from its attachment point to the ester group of the compound is 10 carbon atoms (e.g., the maximum length can be 9 carbon atoms). In one preferred embodiment, the branch in the alkyl or alkenyl group is at the 6-position or later from the point of attachment of $R^{13}$ to the ester group. Suitable $R^{13}$ groups include, but are not limited to

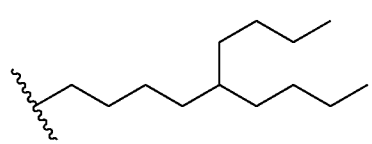

C13 (C23)
Length: C9 (20)

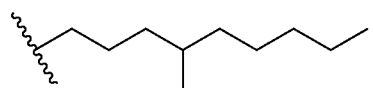

C14 (C24)
Length: C9 (20)

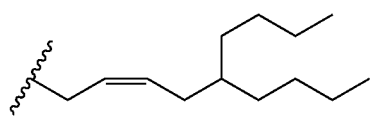

C13 (C23)
Length: C9 (20)

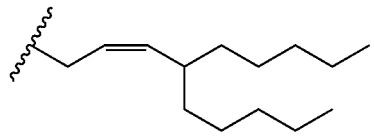

C14 (C24)
Length: C9 (20)

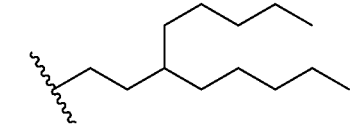

C13 (C24)
Length: C8 (19)

For example, the cationic lipid can be

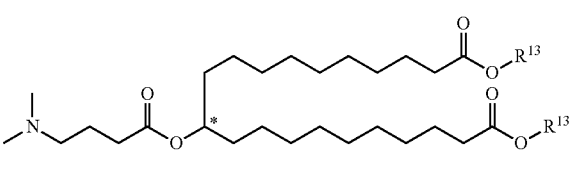

or a salt thereof (e.g., a pharmaceutically acceptable salt thereof), where $R^{13}$ is selected from the groups above.

The $R^{13}$ group may be derived from a natural product, such as dihydrocitgronellol, lavandulol, phytol, or dihydrophytol. In one embodiment, the $R^{13}$ group in the tails above is a dihydrocitronellol group (either as a racemic group or a chirally pure group):

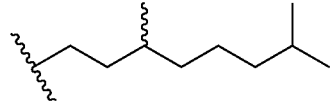 [SMILES: *CCC(C)CCCC(C)C]

For example, the cationic lipid having a dihydroitronellol group can be
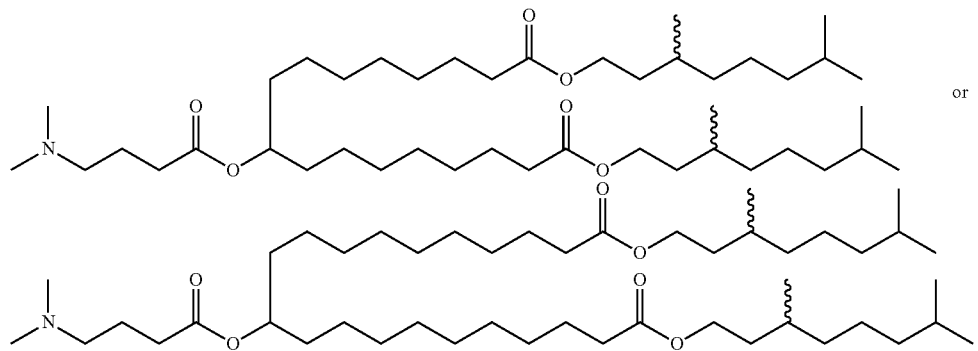
or a salt thereof.
In another embodiment, the $R^{13}$ group in the tails above is a lavandulol group or a homolog of it as shown below:
In another embodiment, the $R^{13}$ group in the tails above is a phytol or dihydrophytol group:
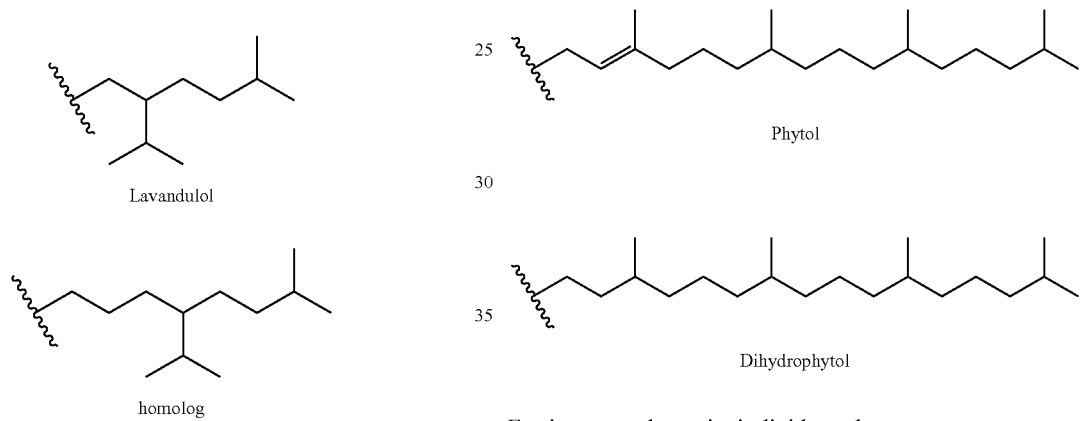
For instance, the cationic lipid can be:
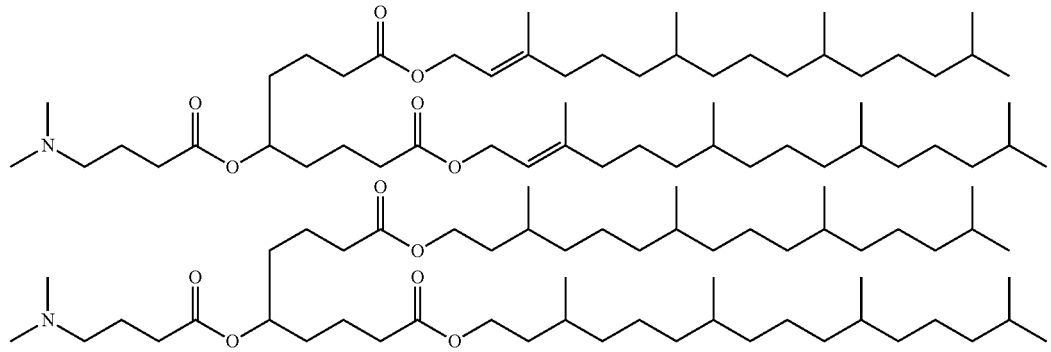
A cationic lipid of the formula:
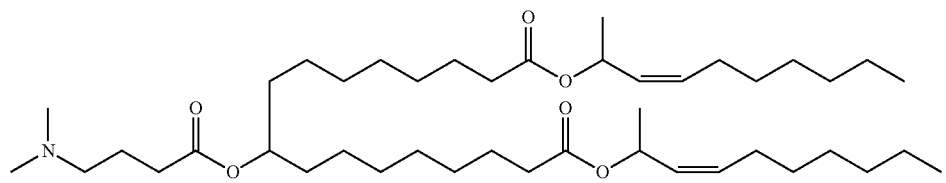 [SMILES: CCCCCC/C=C\C(C)OC(=O)CCCCCCCC(CCCCCCCC(=O)OC(C)/C=C\CCCCCC)OC(=O)CCCN(C)C]

can also be thought of as a combination of a headgroup, a linker moiety, and two parts of the hydrophobic chains as follows:

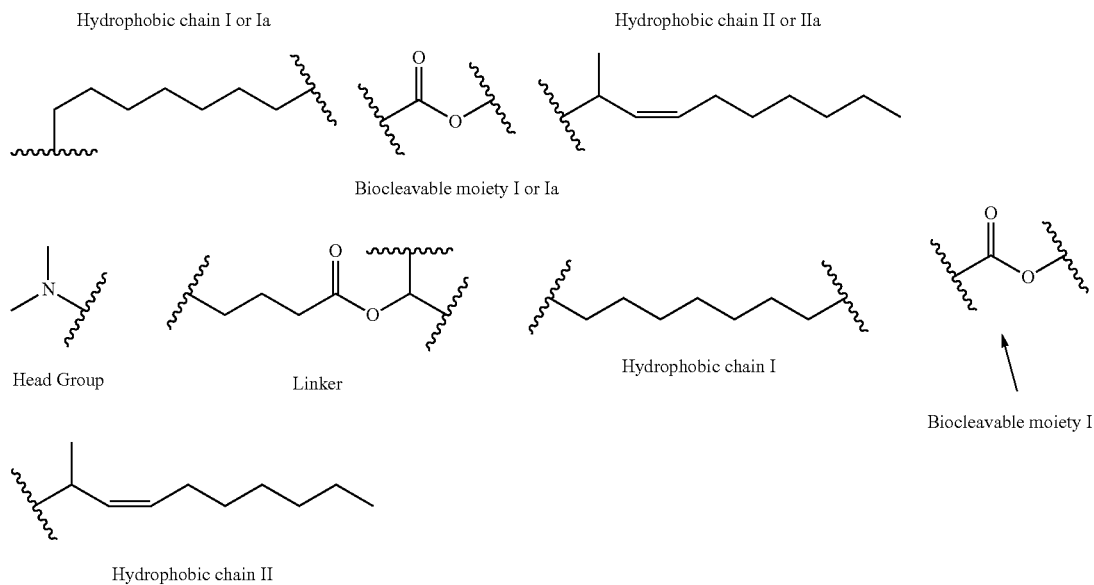

Various headgrops, linker moieties, and hydrophobic chains I and II are listed below. The present invention includes compounds composed of any combination of the head, linker, hydrophobic chain I, and hydrophobic chain II groups listed below.

TABLE 2A

Representative headgroups

TABLE 2A-continued
Representative headgroups
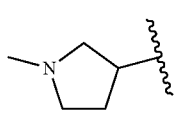 [SMILES: *C1CCN(C)C1]
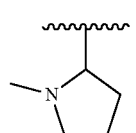
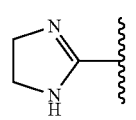
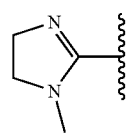 [SMILES: *C1=NCCN1C]
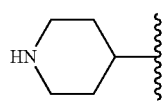
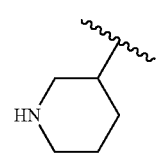
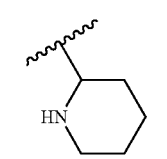
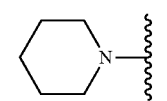
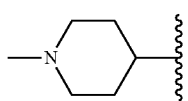
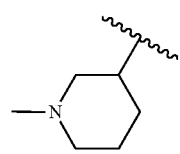 [SMILES: *C1CCCN(C)C1]
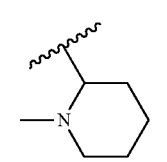 [SMILES: *C1CCCCN1C]
TABLE 2A-continued
Representative headgroups
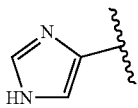
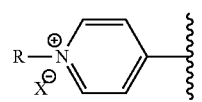
R = H, alkyl; X = halogen
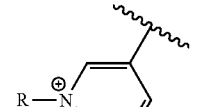
R = H, alkyl; X = halogen
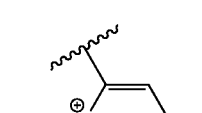
R = H, alkyl; X = halogen
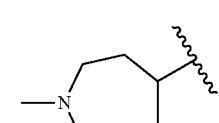
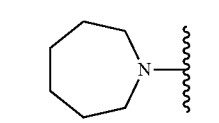
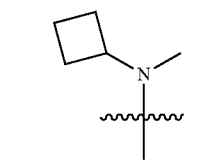 [SMILES: *N(C)C1CCC1]
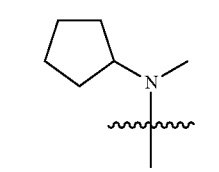 [SMILES: *N(C)C1CCCC1]
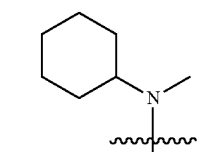
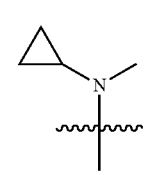 [SMILES: *N(C)C1CC1]

TABLE 2A-continued

Representative headgroups (where n is 0-5)

TABLE 2A-continued

Representative headgroups

[Chemical structure: N-methyl-N-(pyridin-3-ylmethyl)amine]

[Chemical structure: N-methyl-N-(pyridin-2-ylmethyl)amine]

[Chemical structure: N,N-dimethylpyridin-2-amine]

[Chemical structure: N,N-dimethylpyridin-3-amine]

[Chemical structure: N,N-dimethylpyridin-4-amine]

TABLE 2B

Representative linker groups

[Chemical structure: ester linker]
m = 1-5; n = 0-3

[Chemical structure: ether linker]
m = 0-5; n = 0-3

[Chemical structure: alkyl linker]
n = 0-5

[Chemical structure: reverse ester linker]
m = 0-5; n = 0-3

[Chemical structure: thioester linker]
m = 0-5; n = 0-3

TABLE 2B-continued

Representative linker groups

[Chemical structure: cyclohexyl ester linker]

[Chemical structure: cyclohexyl ether linker]
n = 0-3

[Chemical structure: cyclohexyl alkyl linker]
n = 0-3

[Chemical structure: branched linker with X]
m = 1-4; n/o = 0-3
X = O or S

[Chemical structure: amide linker]
m = 0-5; n = 0-3

[Chemical structure: carbamate linker]
m = 0-5; n = 0-3

[Chemical structure: reverse carbamate linker]
m = 0-5; n = 0-3

[Chemical structure: urea linker]
m = 0-5; n = 0-3

[Chemical structure: thioester linker]
m = 0-5; n = 0-3

TABLE 2B-continued
Representative linker groups
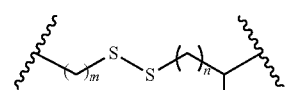
m = 0-5; n = 0-3
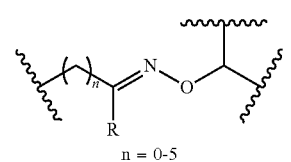
n = 0-5
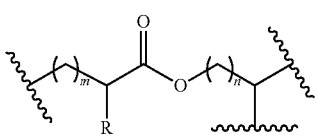
m = 1-4; n = 0-3
R = COOH, COOMe,
COOEt, CN, CONH2
CONHMe
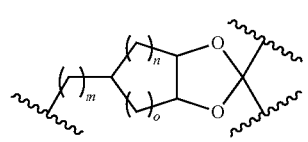
m = 1-4; n/o = 1-3
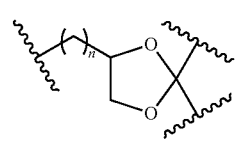
n = 1-5
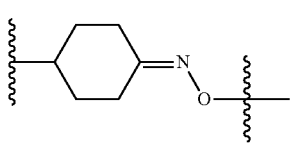 [SMILES: *ON=C1CCC(*)CC1]
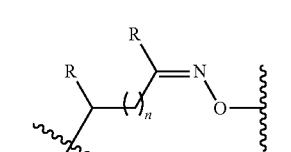
n = 0-5
R = H, Me, Et, Pr, allyl
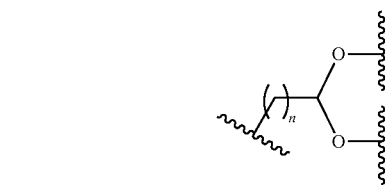
n = 0-5
R = Me, Et, Pr, allyl
R1 = Me, Et, Pr, allyl
TABLE 2B-continued
Representative linker groups
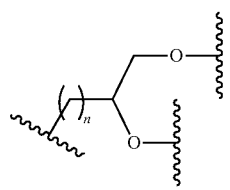
n = 0-6
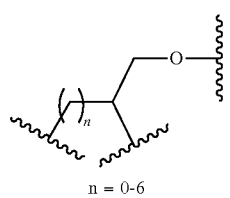
n = 0-6
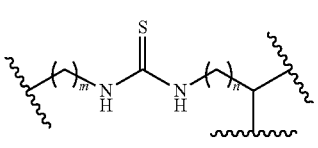
n = 0-6
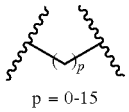
m = 0-5; n = 0-3
TABLE 2C
Representative hydrophobic chain I and/or Ia, and combination thereof
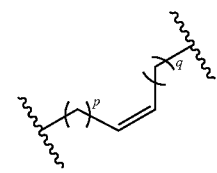
p = 0-15
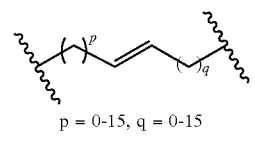
p = 0-15, q = 0-15
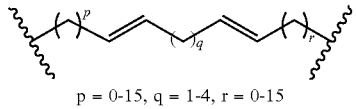
p = 0-15, q = 0-15
p = 0-15, q = 1-4, r = 0-15

TABLE 2C-continued
Representative hydrophobic chain I and/or Ia, and combination thereof
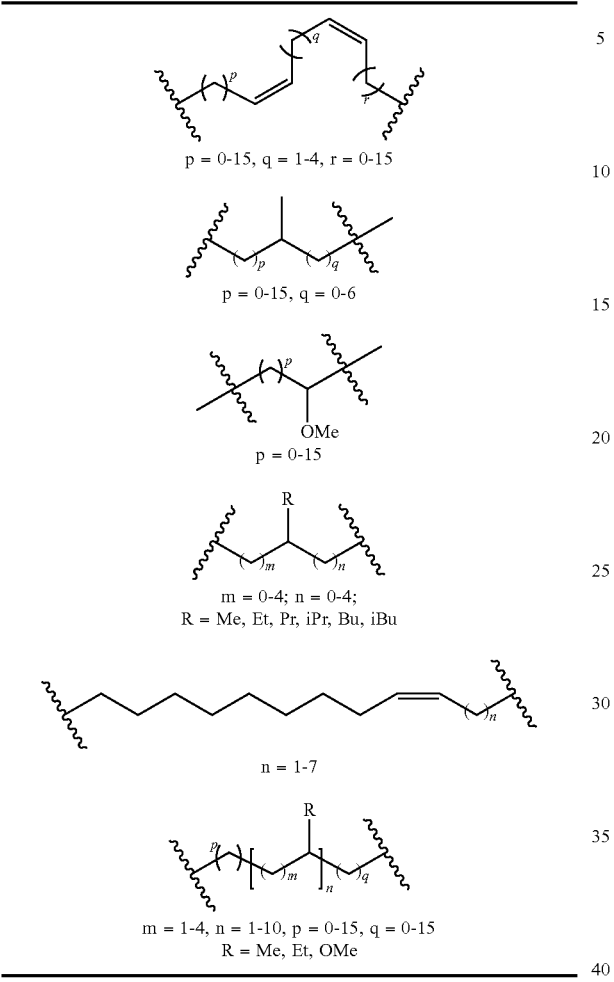
TABLE 2D
Representative biodegradable moieties I and/or Ia and combinations thereof
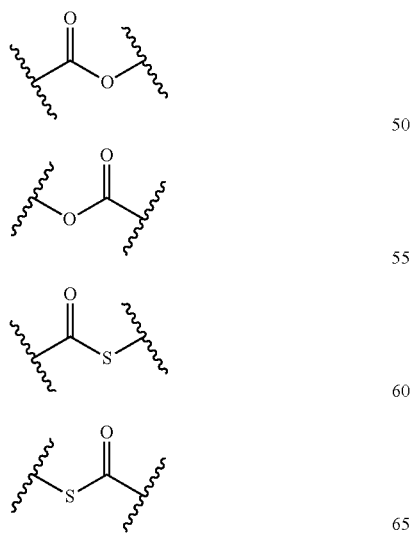
TABLE 2D-continued
Representative biodegradable moieties I and/or Ia and combinations thereof
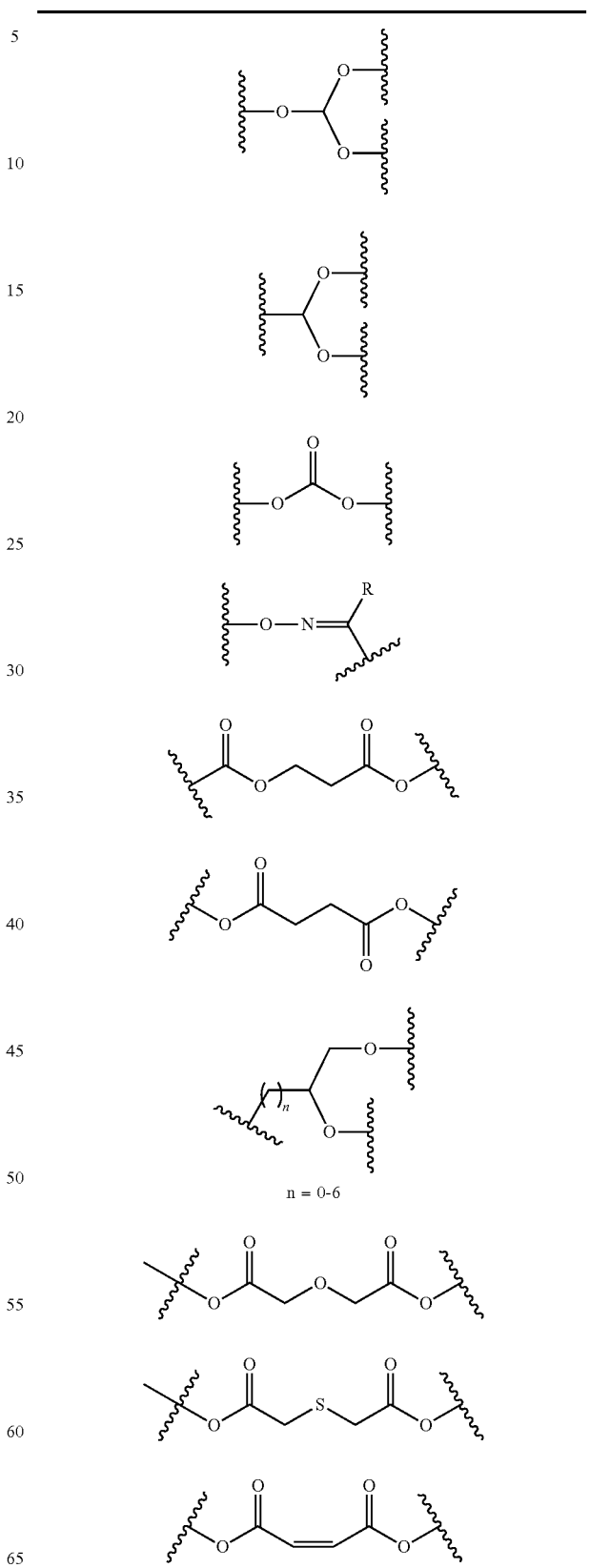

TABLE 2D-continued

Representative biodegradable moieties I and/or Ia and combinations thereof

[chemical structure: ethylene glycol diester]

[chemical structure: disulfide -S-S-]

[chemical structure: oxime R-C(=N-O-)-]

[chemical structure: acetal -O-CHR-O-]
R = H, Me, Et, cyclic alkyl, alicylic, aromatic

[chemical structure: cyclic ketal with X]
X = CH$_2$, O, S

TABLE 2E

Representative hydrophobic chain II and/or IIa and combinations thereof

[chemical structure: cis-alkene chain]
n = 0-6; m = 0-16

[chemical structure: branched alkyl]

[chemical structure: branched alkyl with n]
n = 0-6

[chemical structure: chiral methyl branched chain]

[chemical structure: isoprenoid chain]

TABLE 2E-continued

Representative hydrophobic chain II and/or IIa and combinations thereof

[chemical structure: chiral branched chain]

[chemical structure: alkyl chain]
n = 0-8

[chemical structure: alkene chain]
n = 0-8; m = 0-6

[chemical structure: chain with R substituent]
n = 0-8
R = OMe, Me, Et, n-Pr, n-Bu

[chemical structure: chain with R]
n = 0-8
R = OMe, Me, Et, Pr

[chemical structure: chain with R]
n = 0-8
R = OMe, Me, Et, Pr

[chemical structure: branched chain]
m = 0-6; n = 0-6; p = 0-6

[chemical structure: branched chain with double bond]
m = 0-6; n = 0-6; p = 0-6

[chemical structure: branched chain with cis double bond]
m = 0-6; n = 0-6; p = 0-6

[chemical structure: branched chain with two double bonds]
m = 0-6; n = 0-6; p = 0-6; q = 0-6

Other cationic lipids of the present invention include those in Table 3 below. Each asymmetric carbon atom in the compounds below can be either chirally pure (R or S) or racemic. These cationic lipids as well as those in the working examples (such as Examples 36 and 37) are suitable for forming nucleic acid-lipid particles.
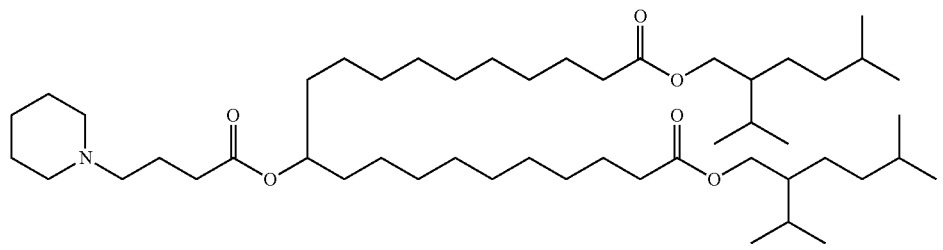
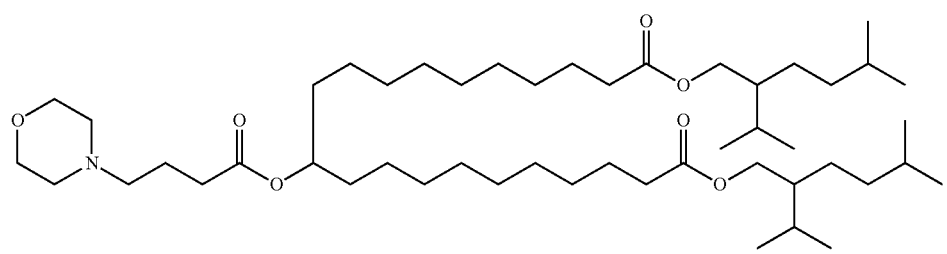
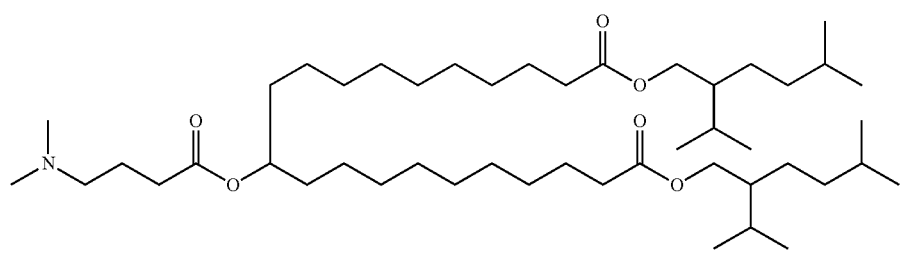
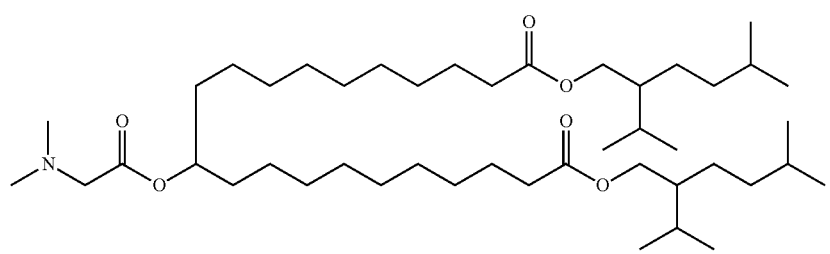
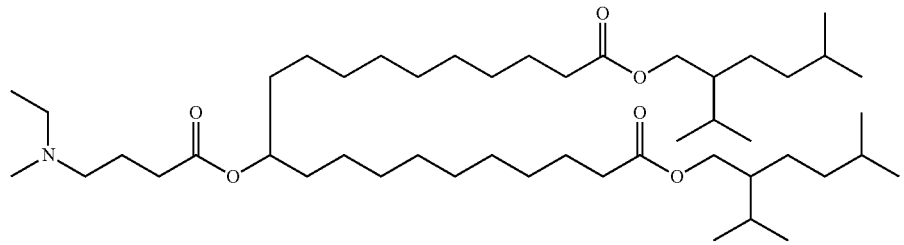
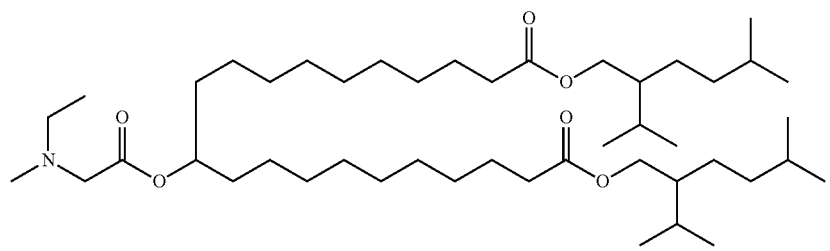

-continued
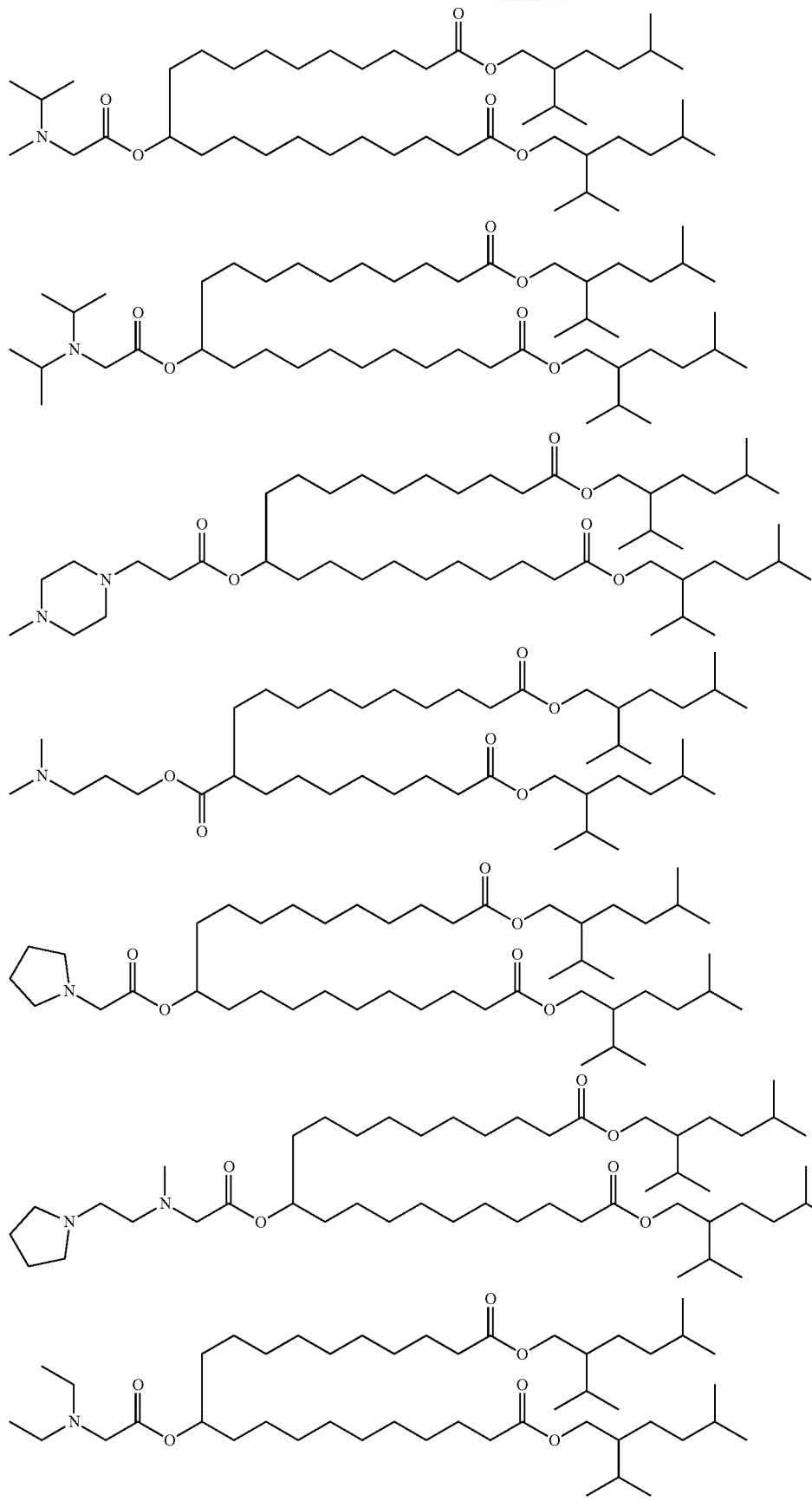

-continued
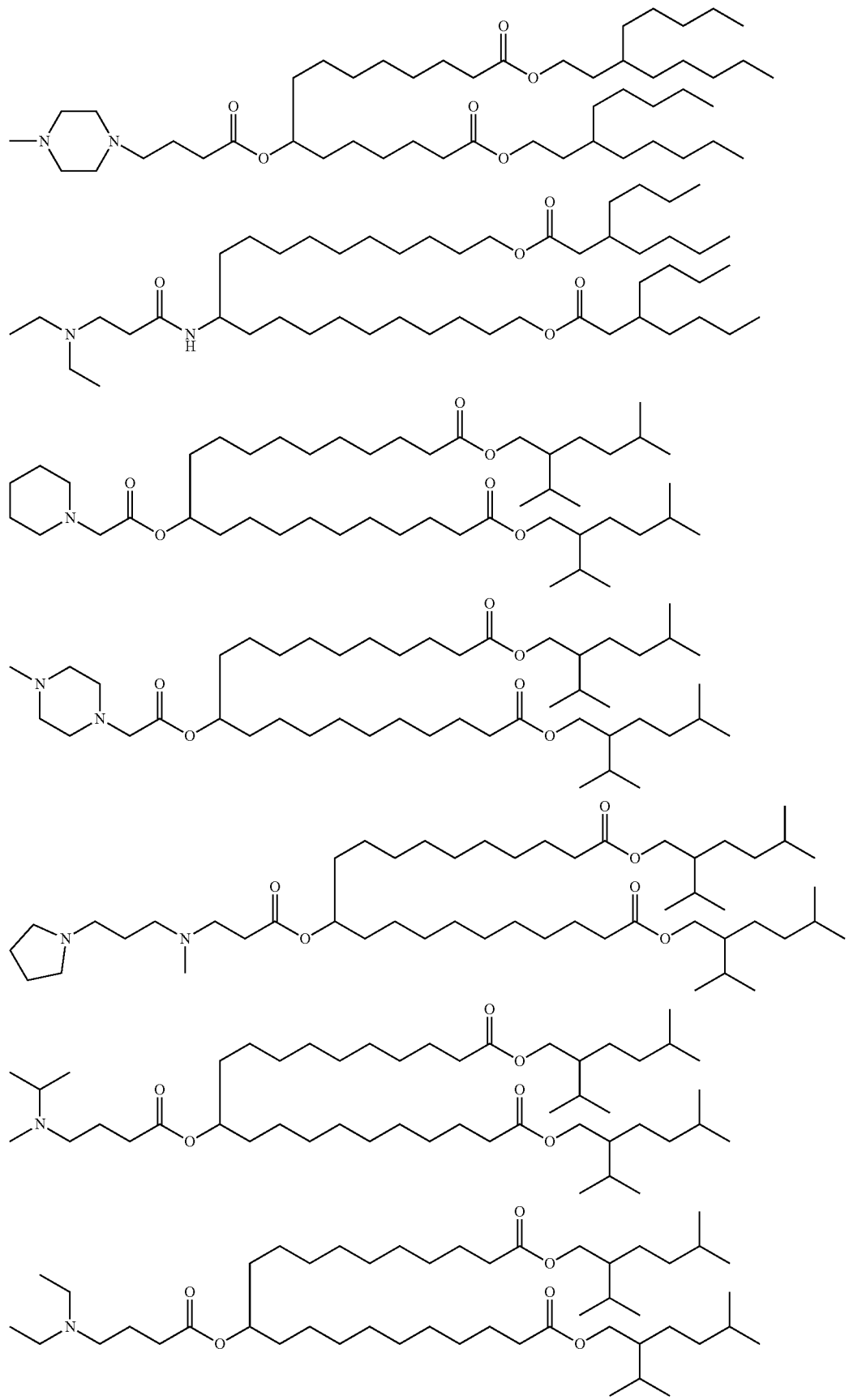

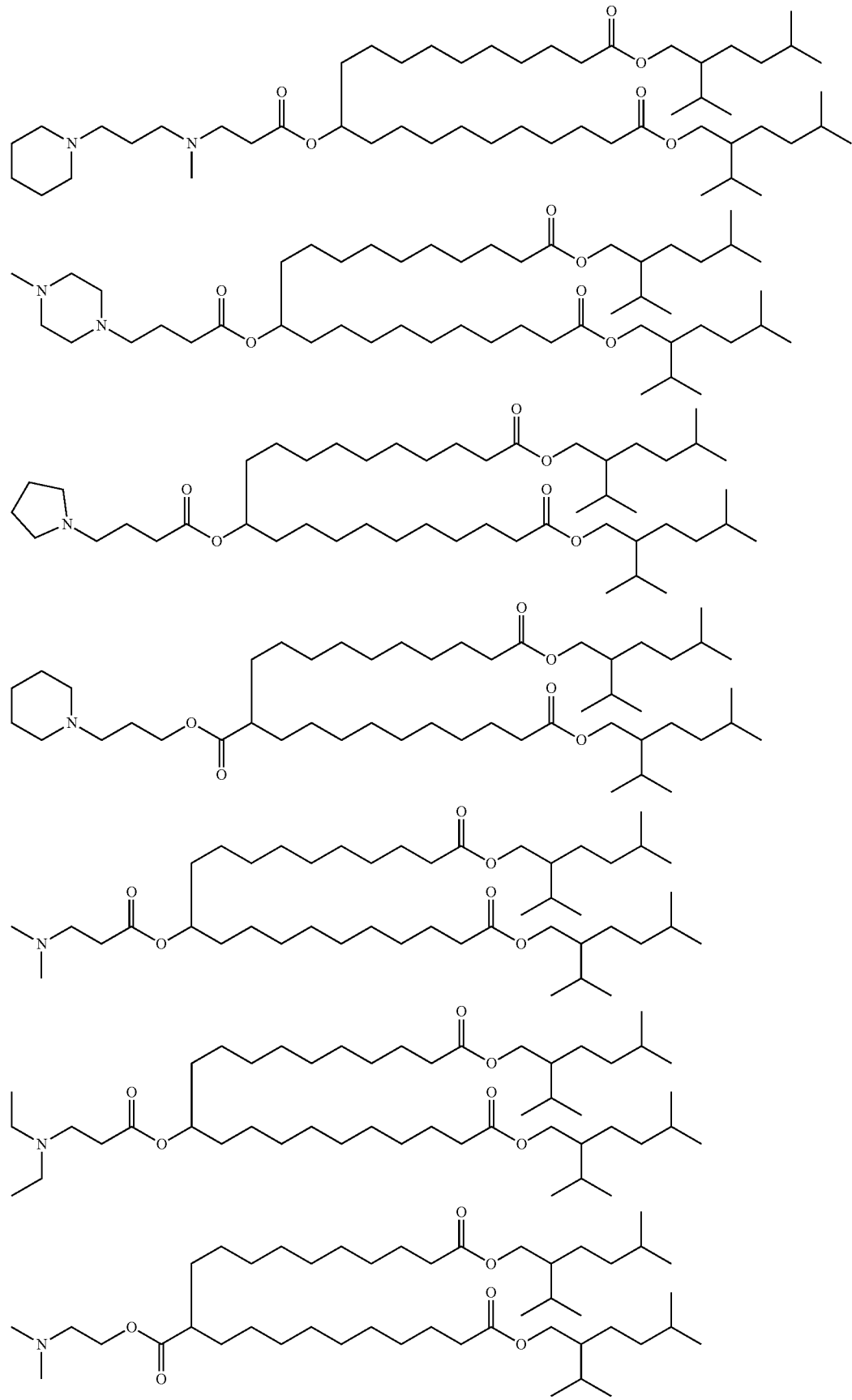

-continued
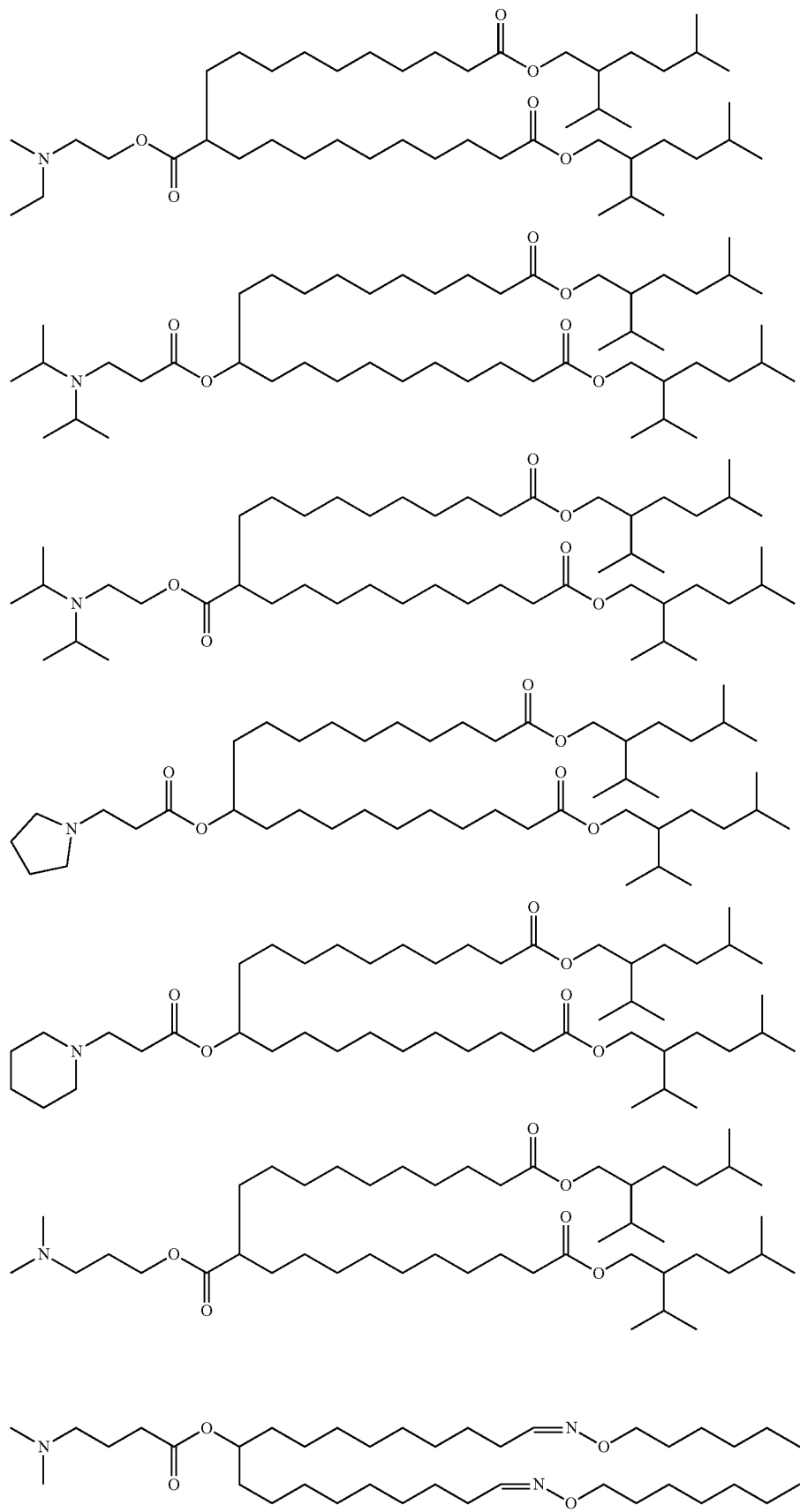

-continued
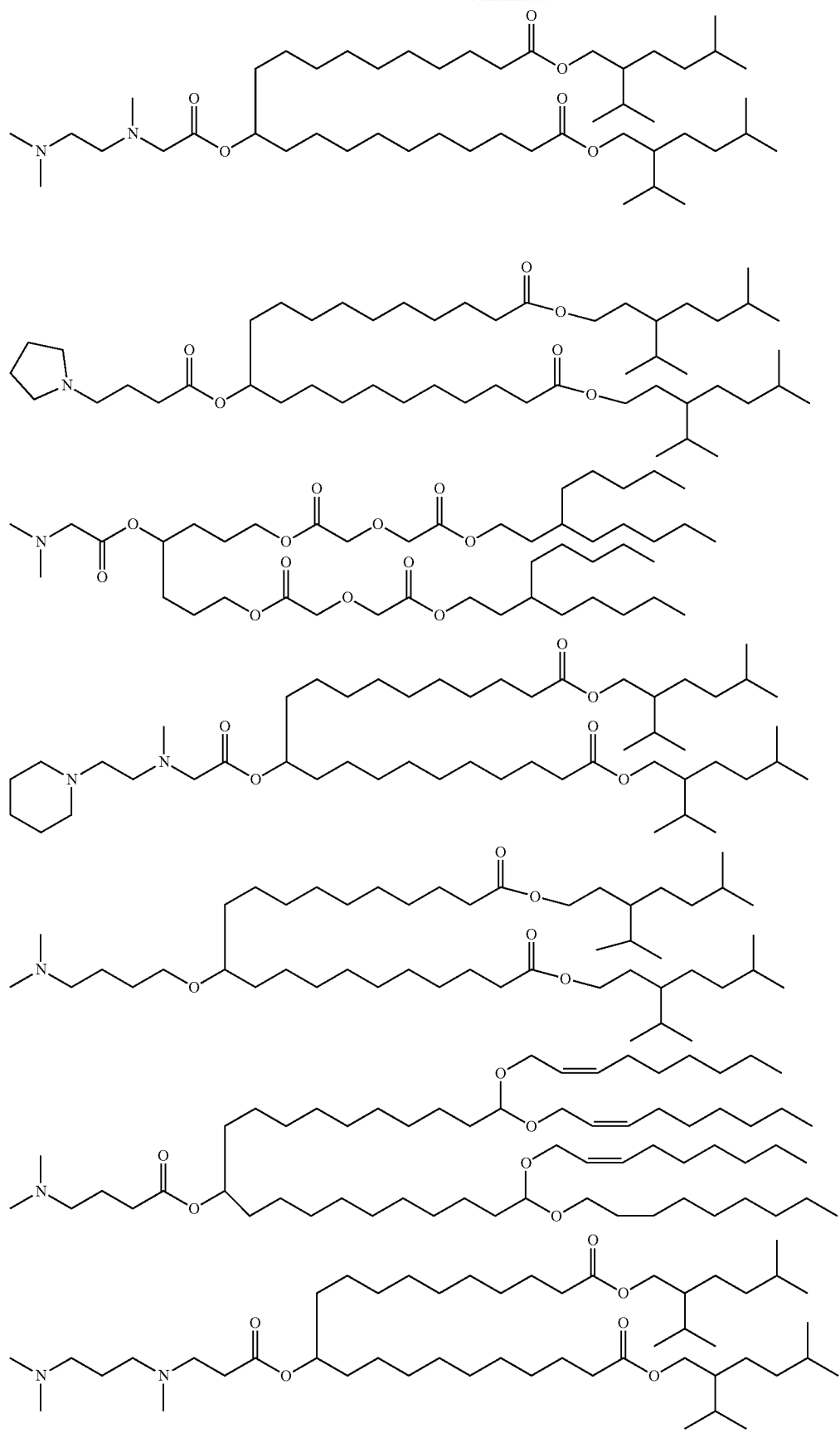

-continued
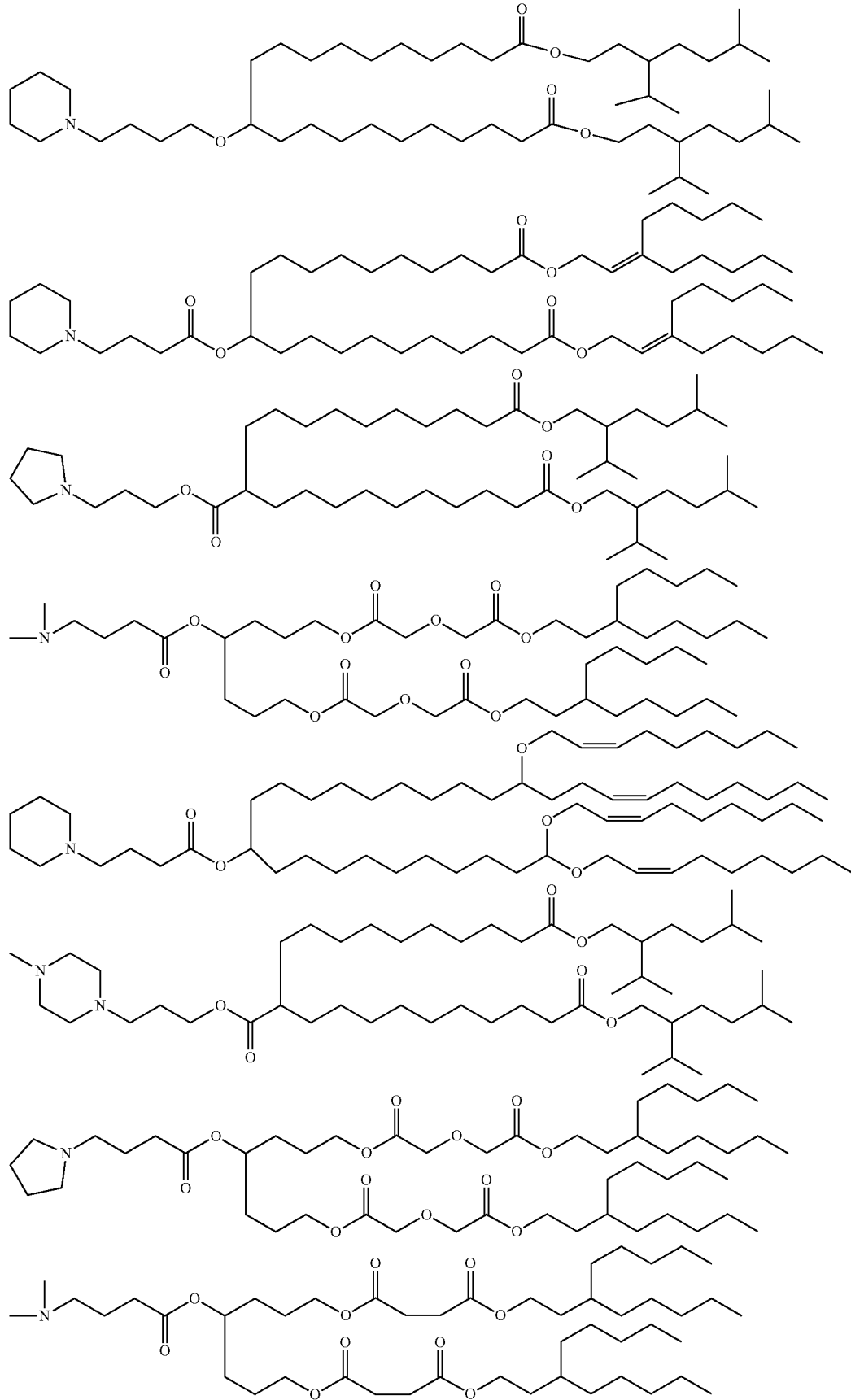

-continued
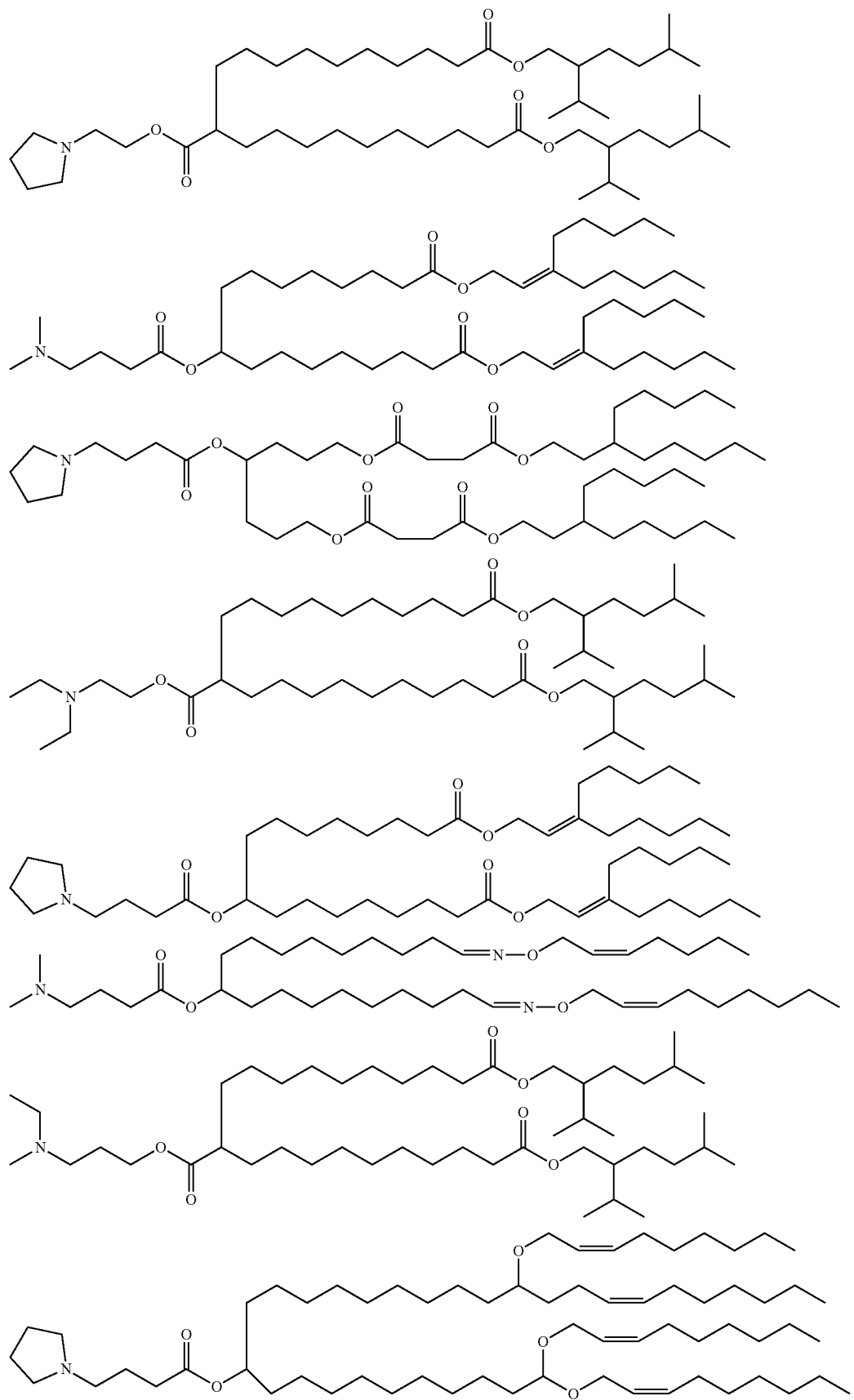

-continued
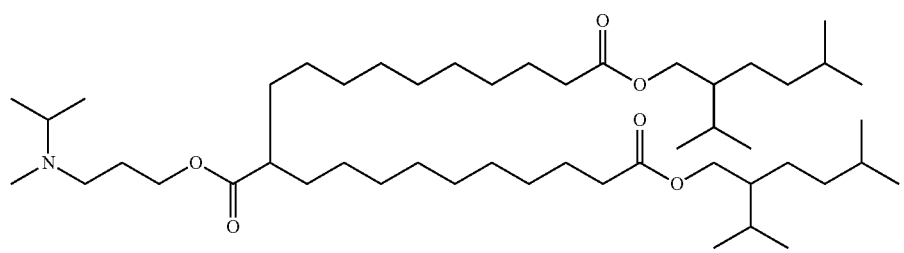
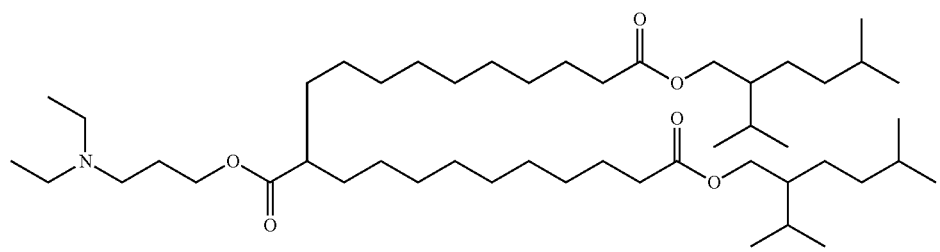
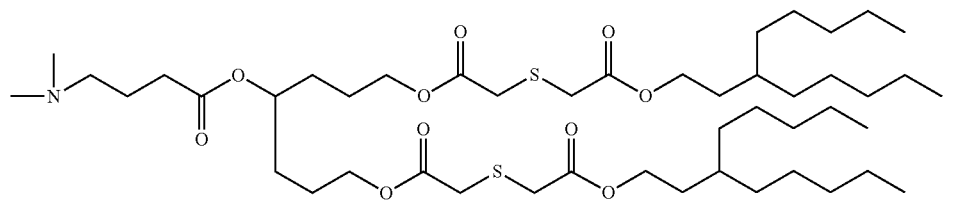
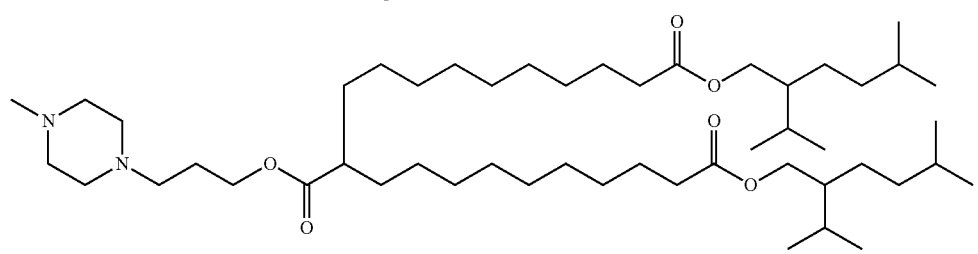
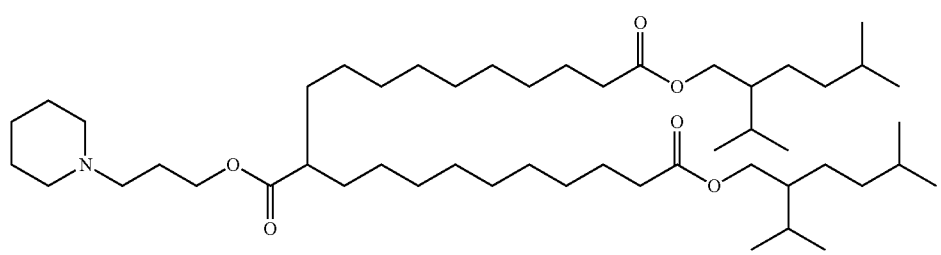
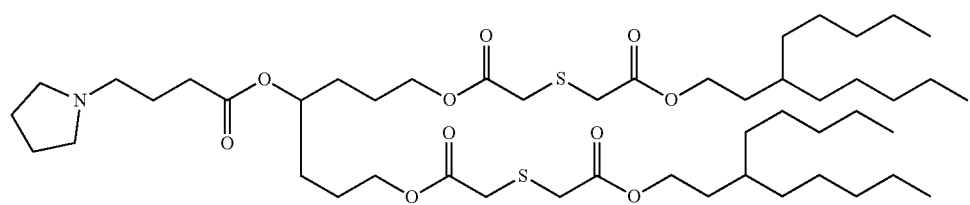
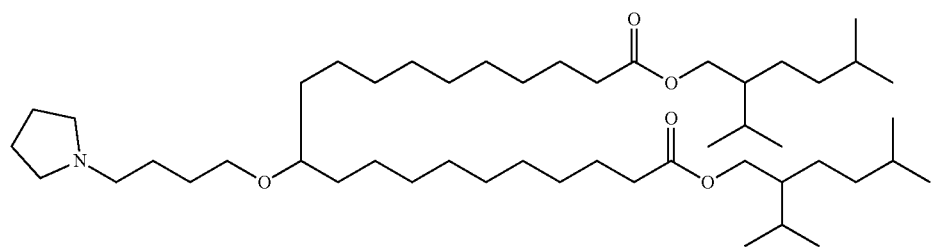

-continued
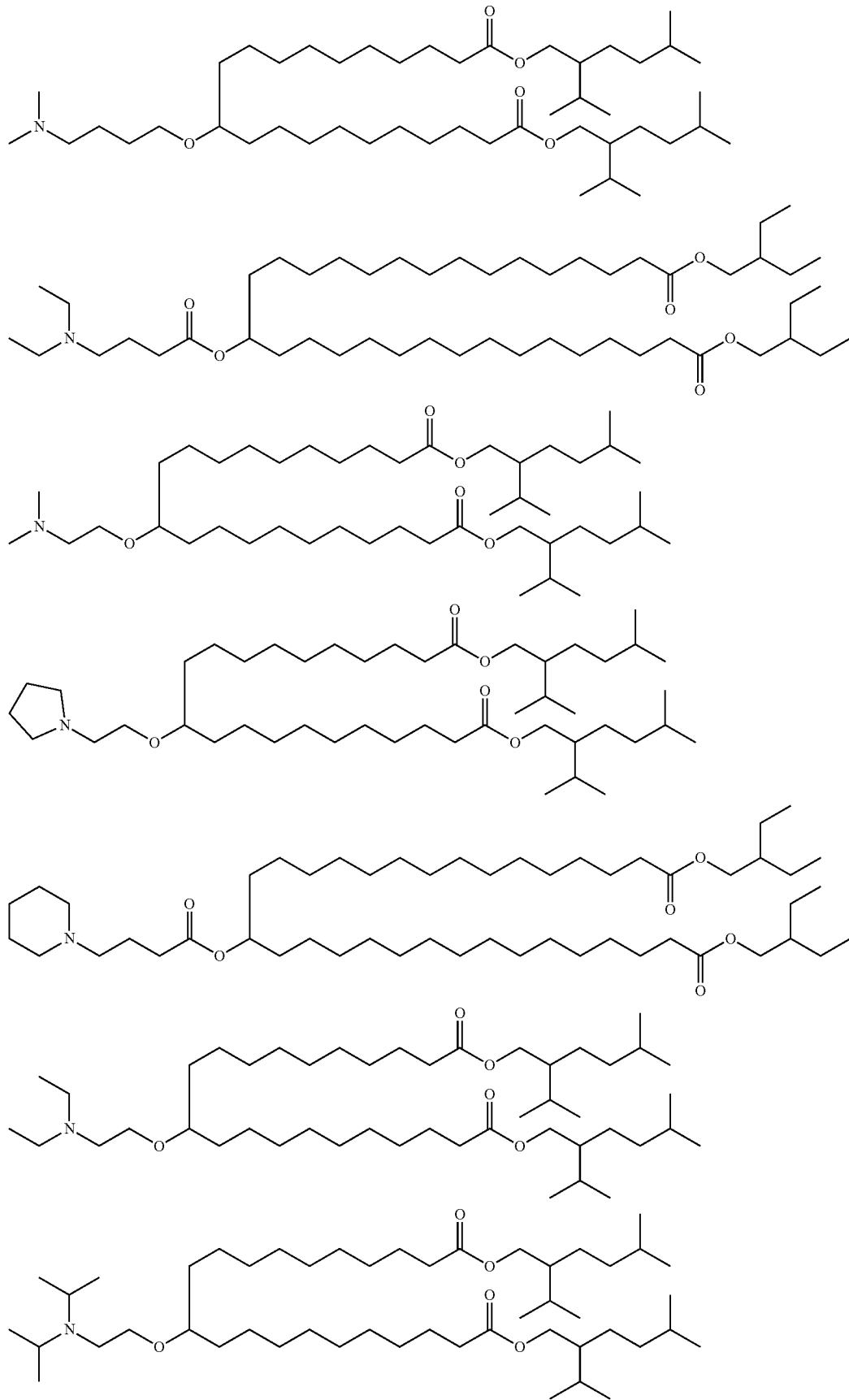

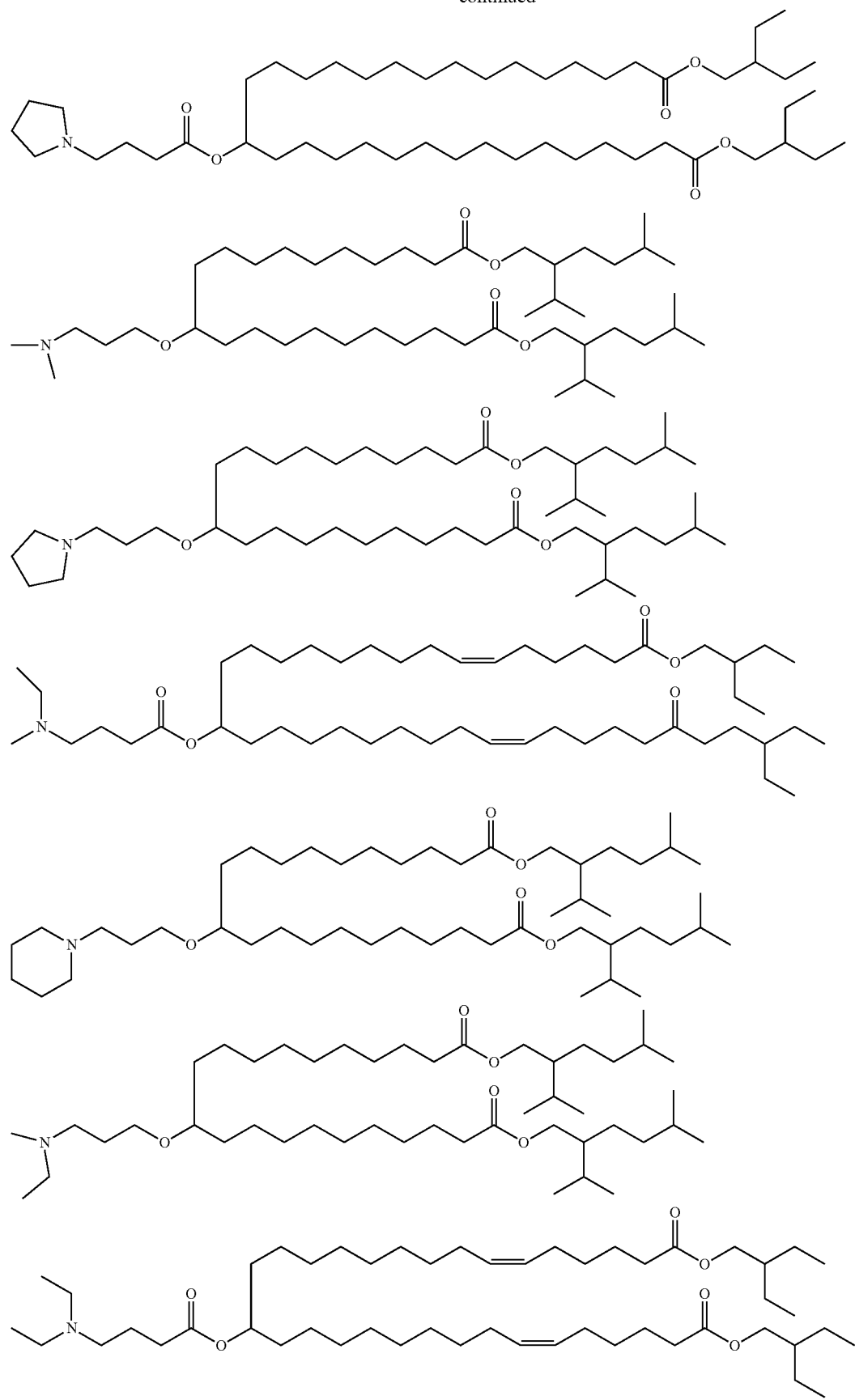

-continued
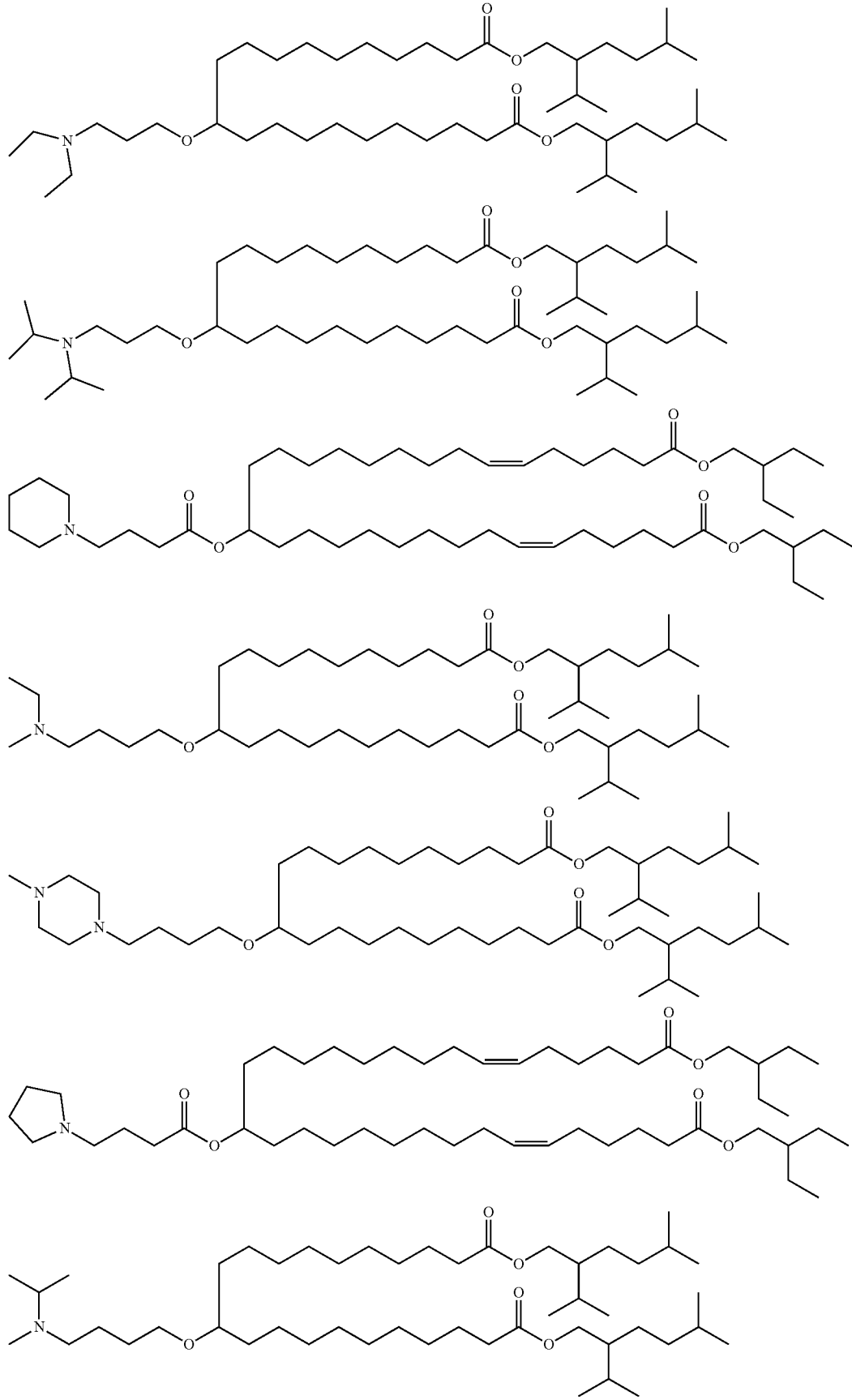

-continued
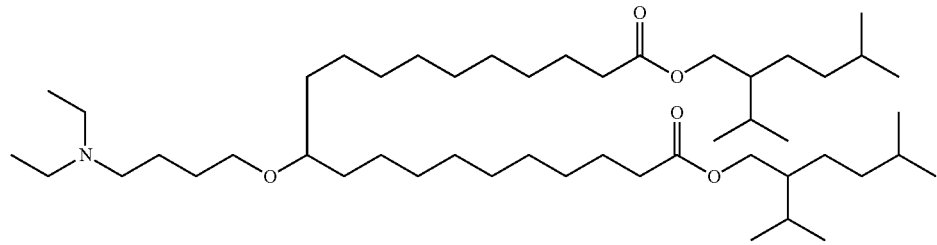
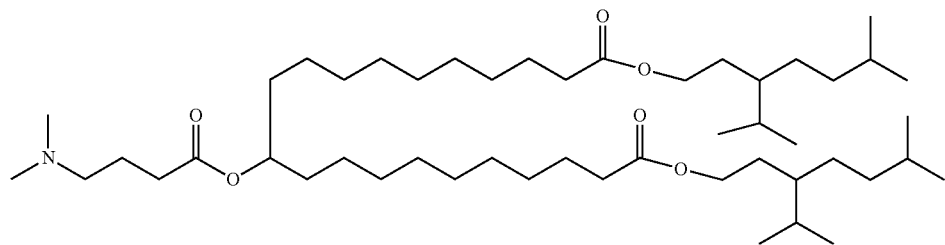
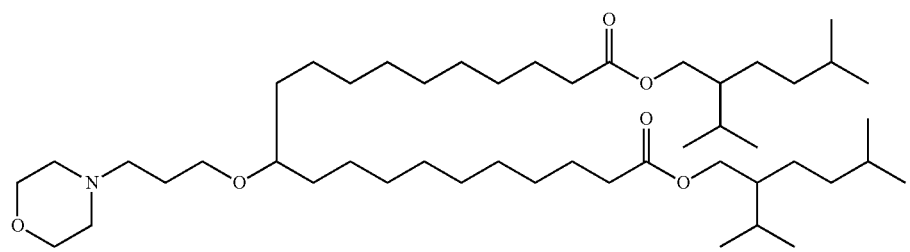
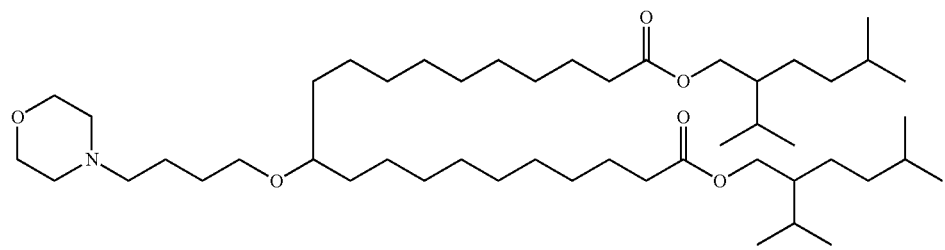
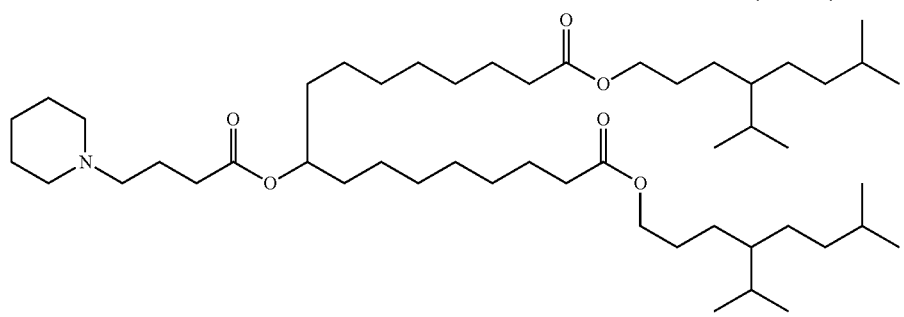
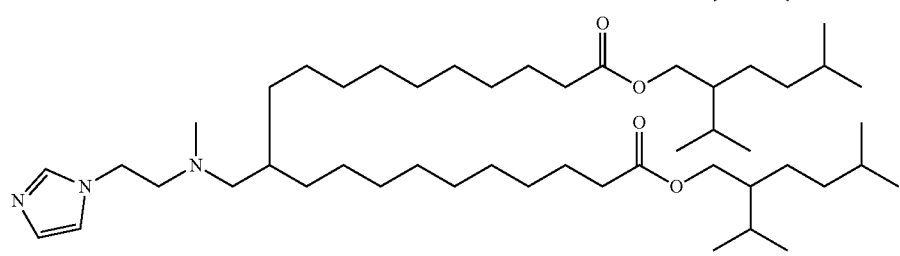

-continued
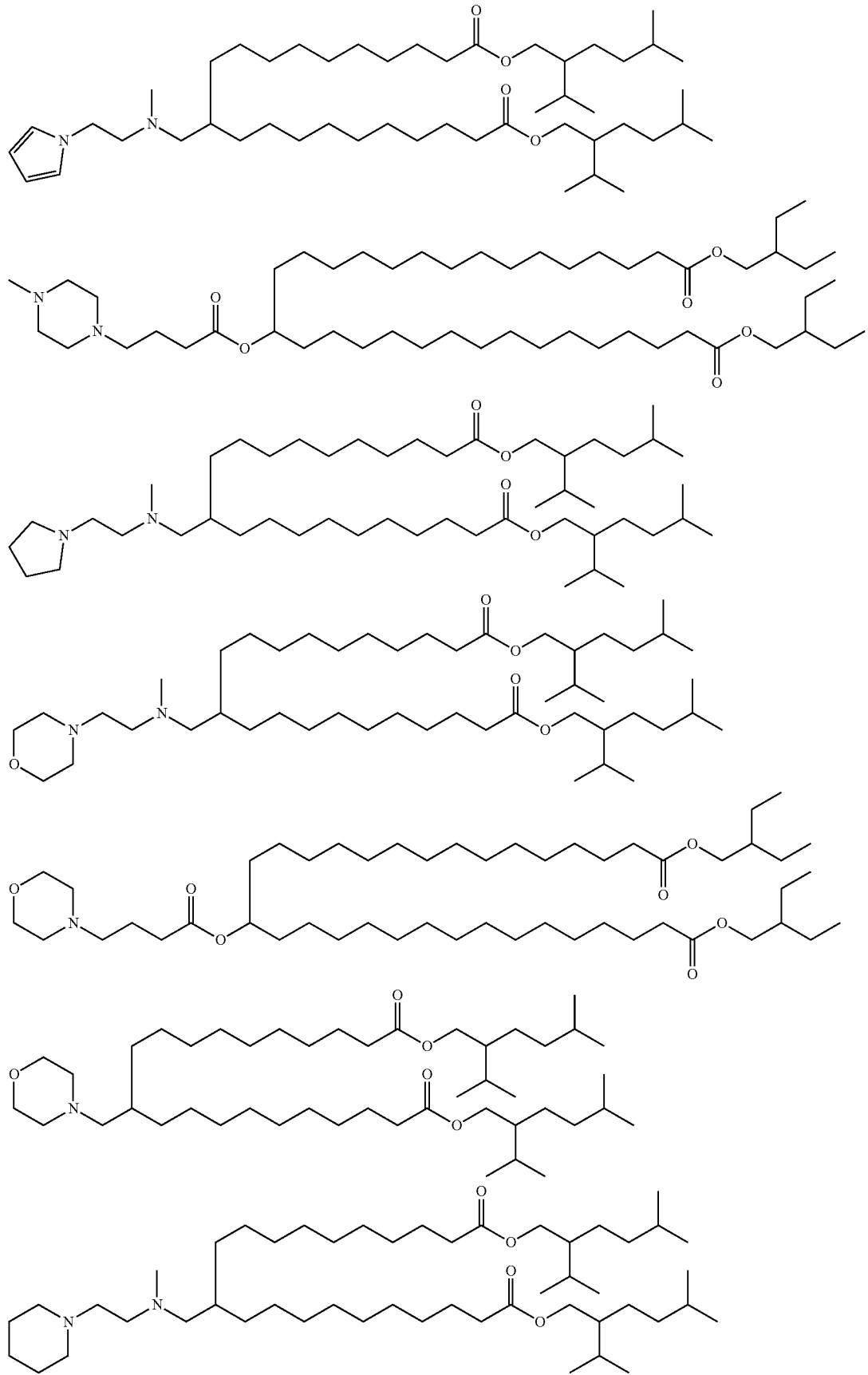

-continued
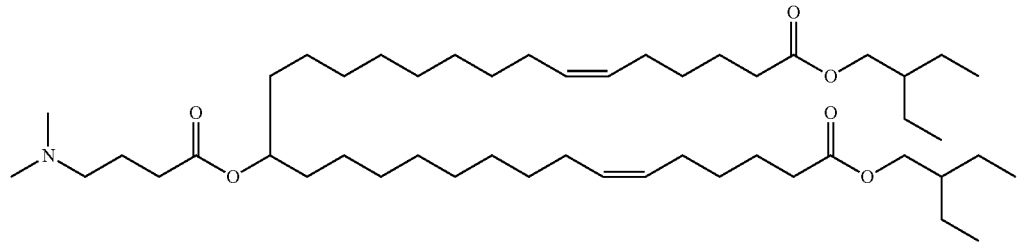
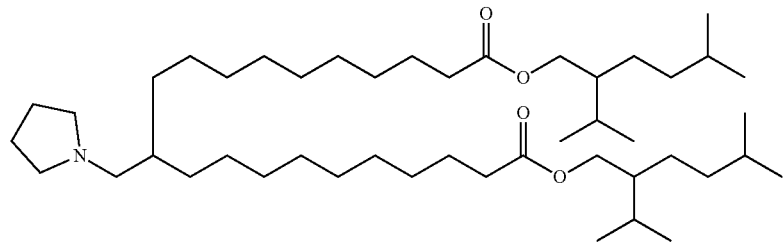
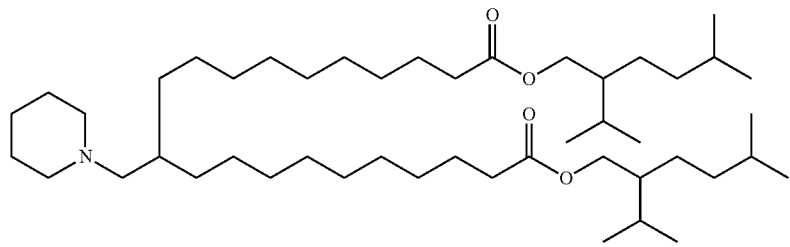
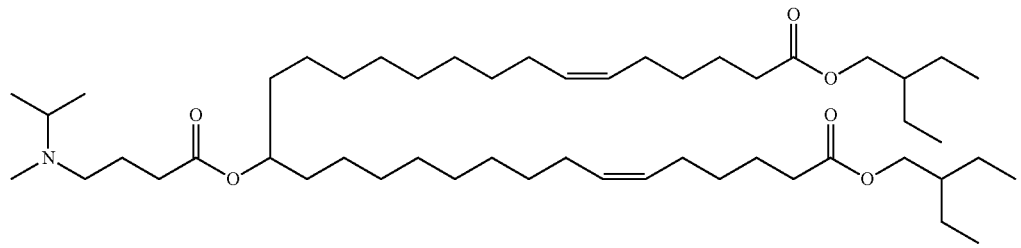
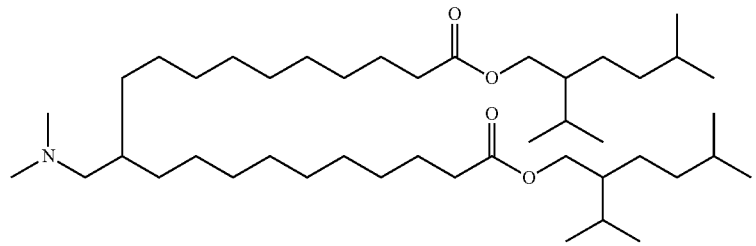
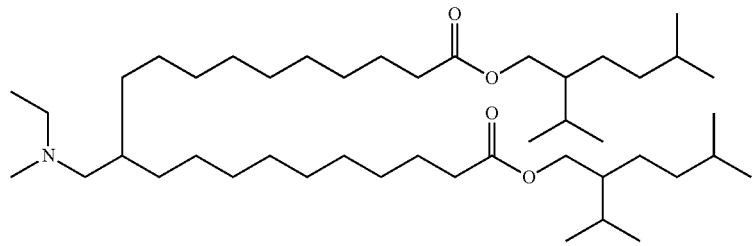
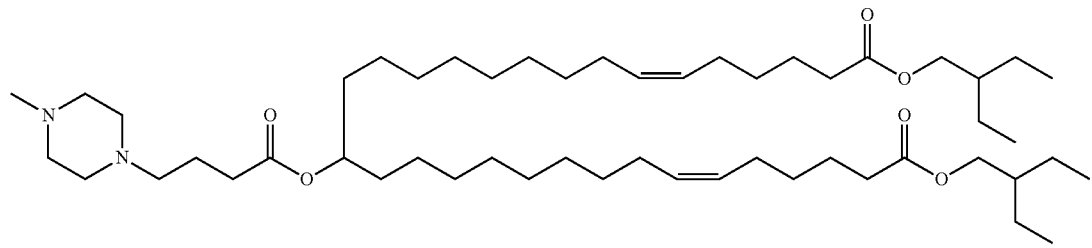

-continued
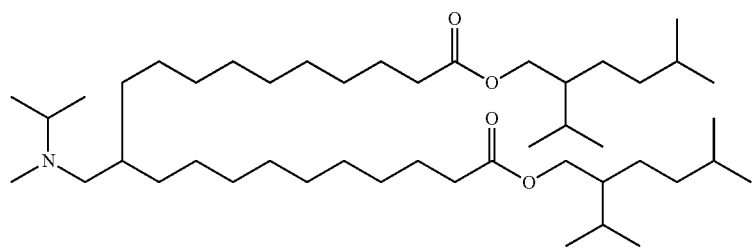
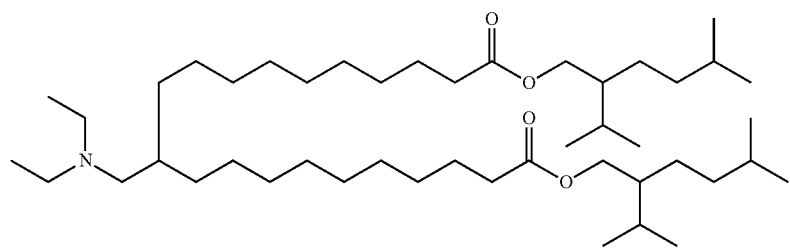
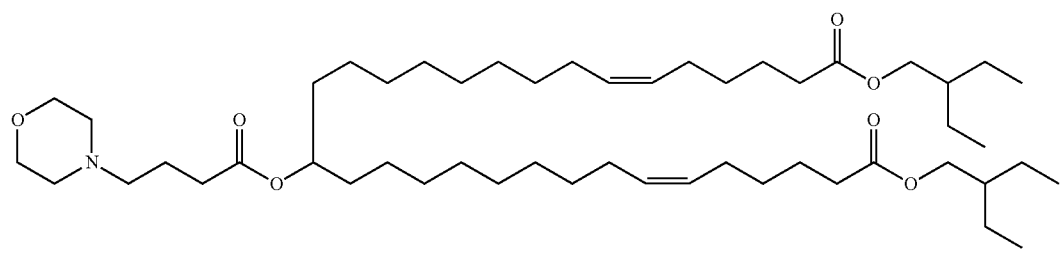
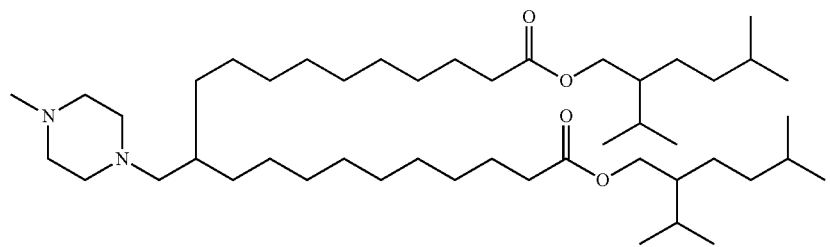
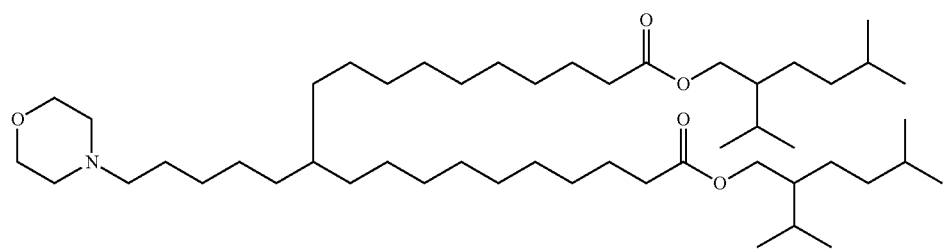
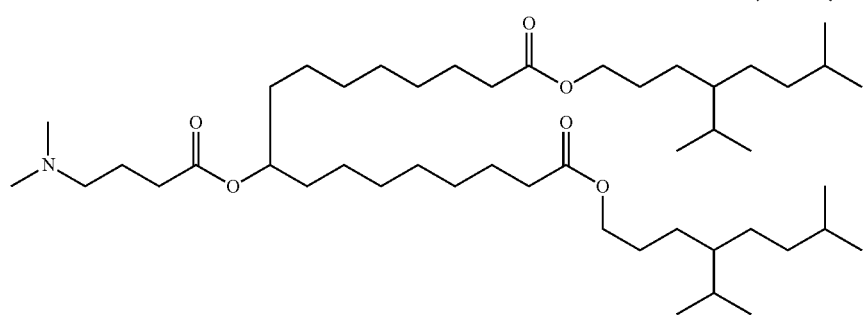

-continued
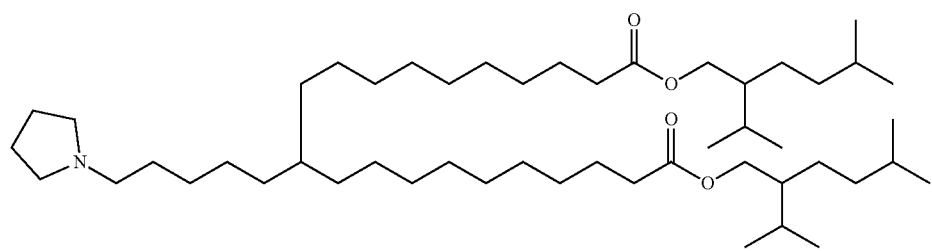
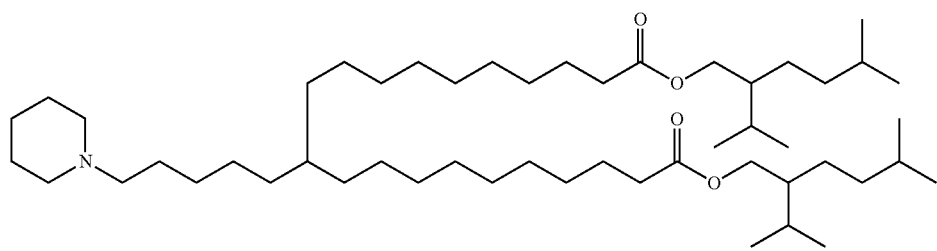
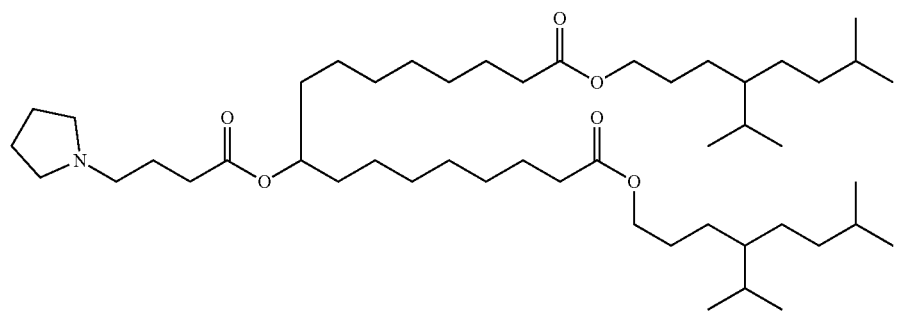
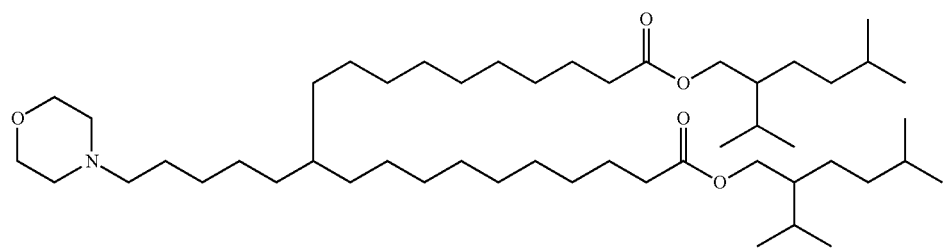
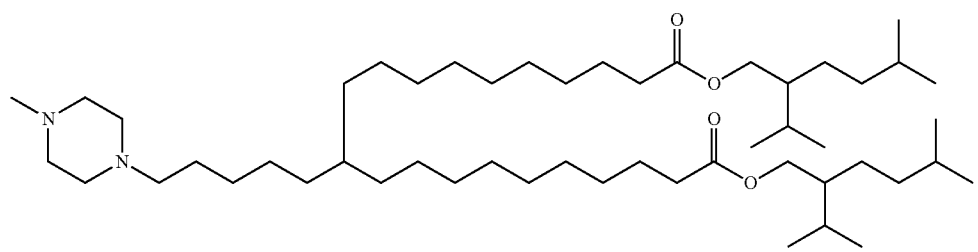
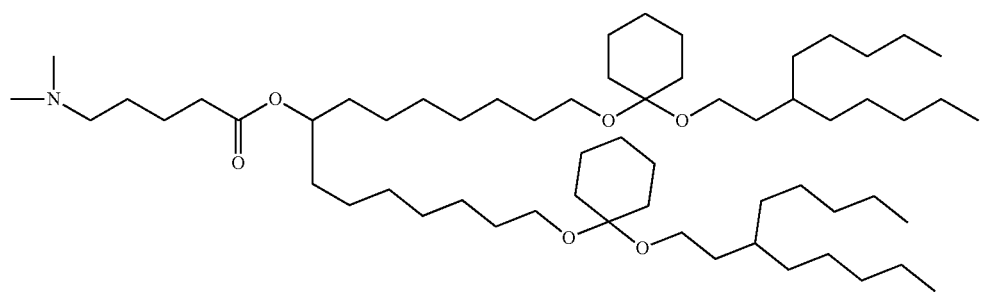

-continued
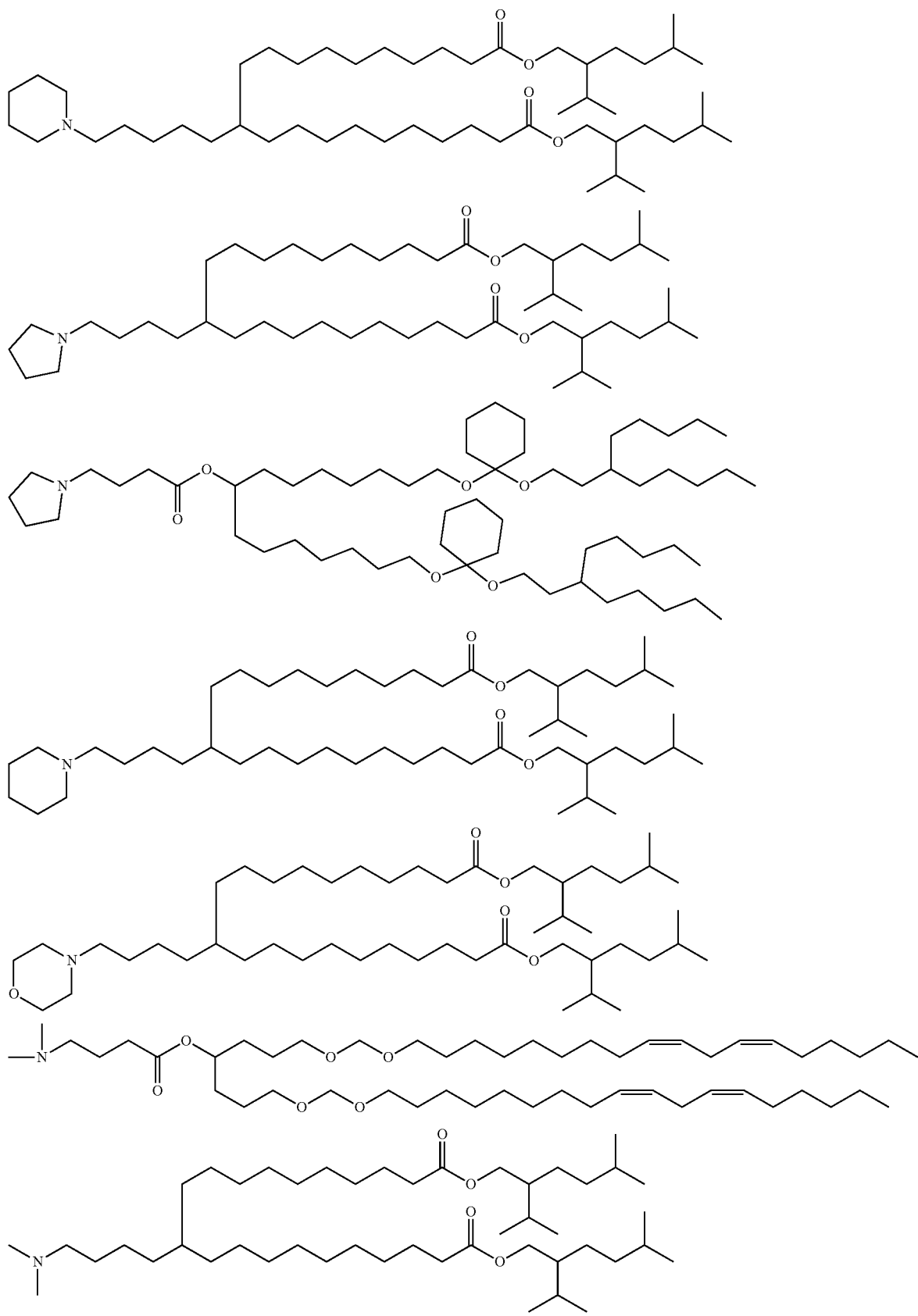

-continued
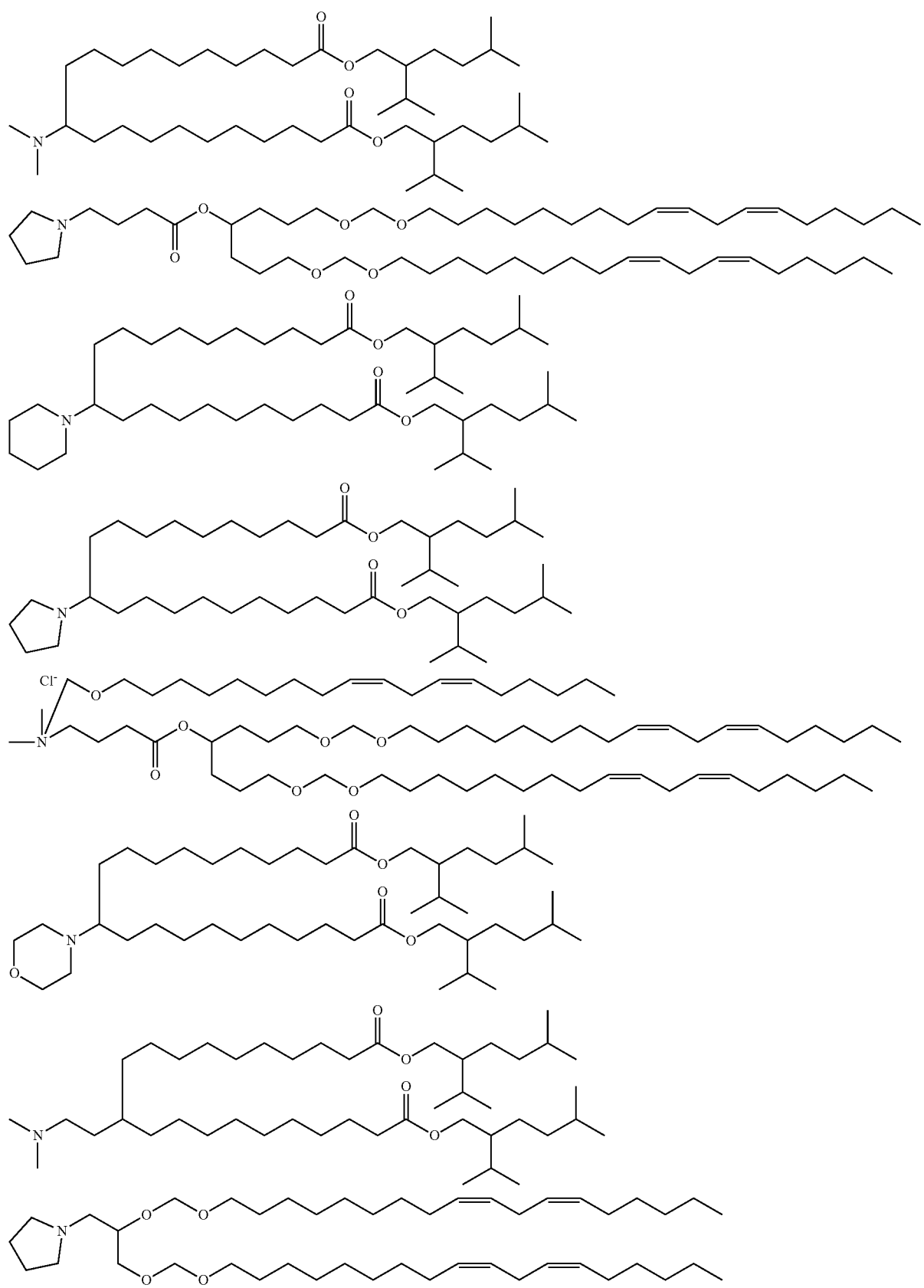

-continued
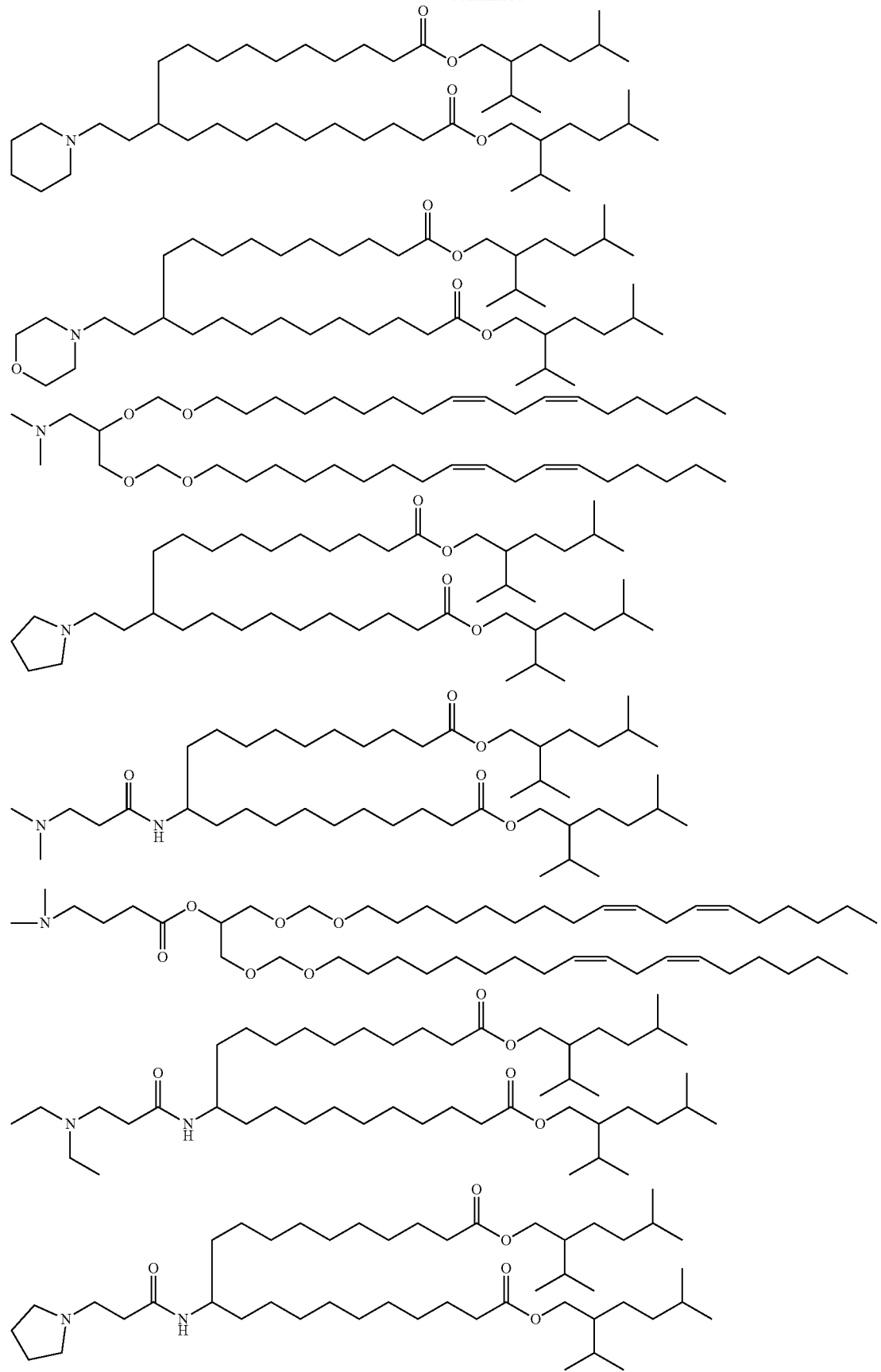

-continued
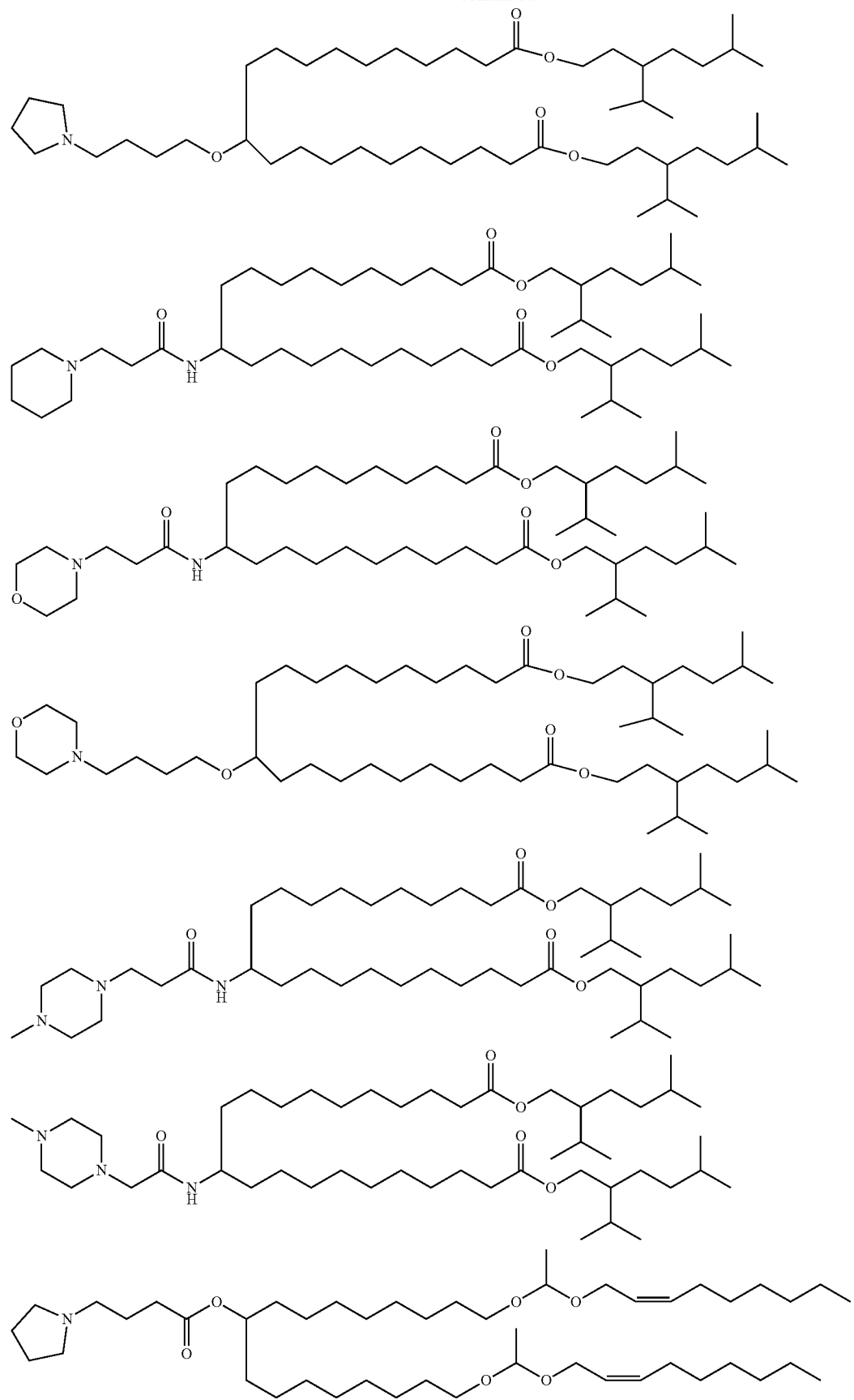

-continued
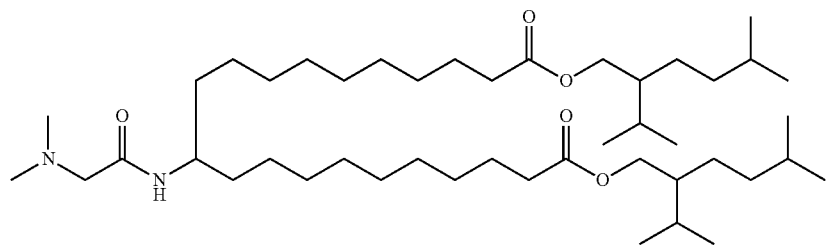
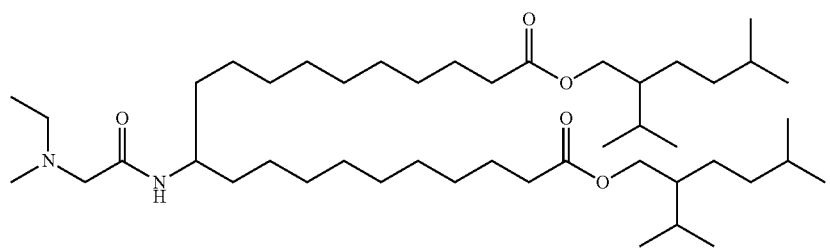
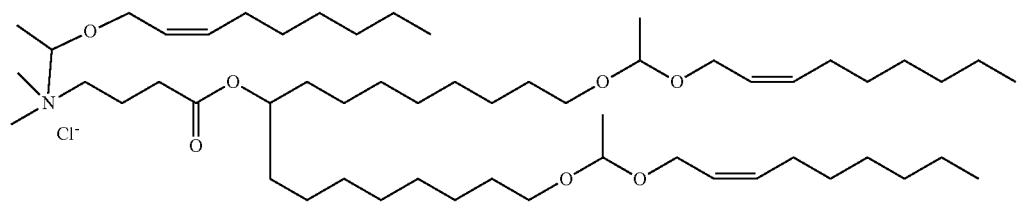
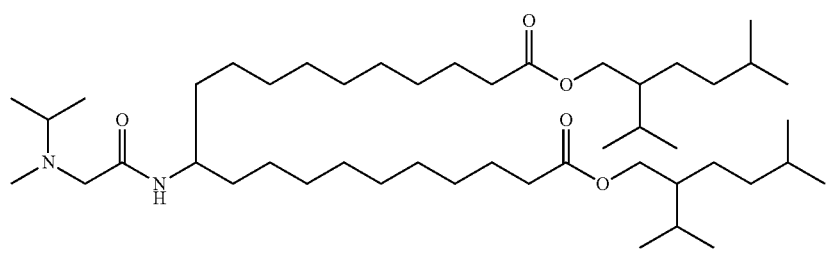
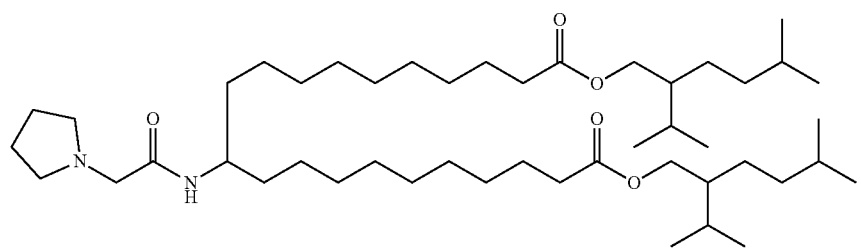
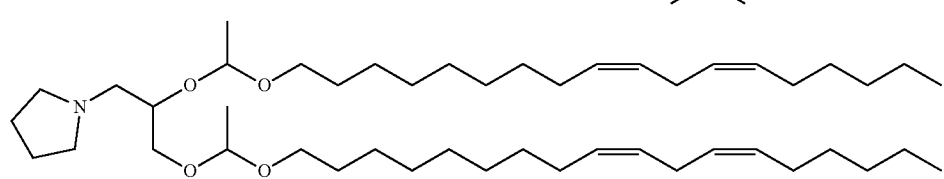
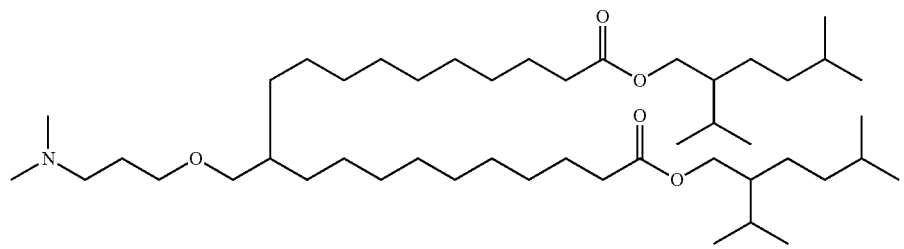

-continued
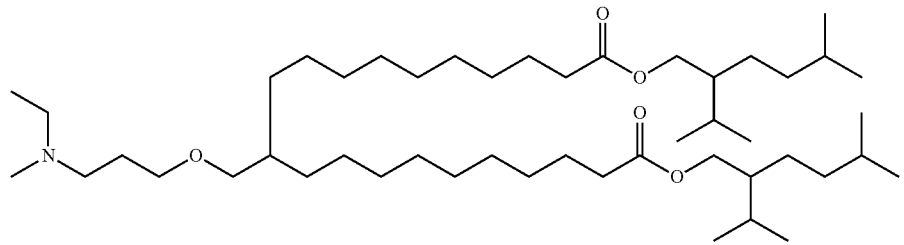
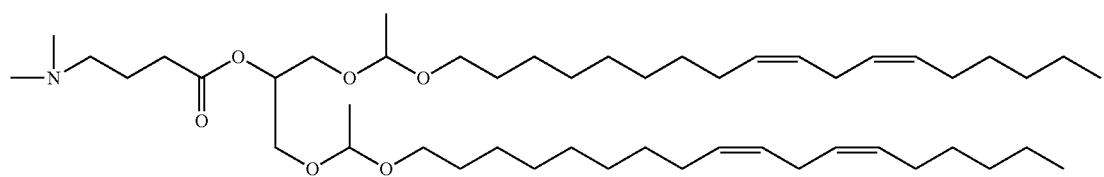
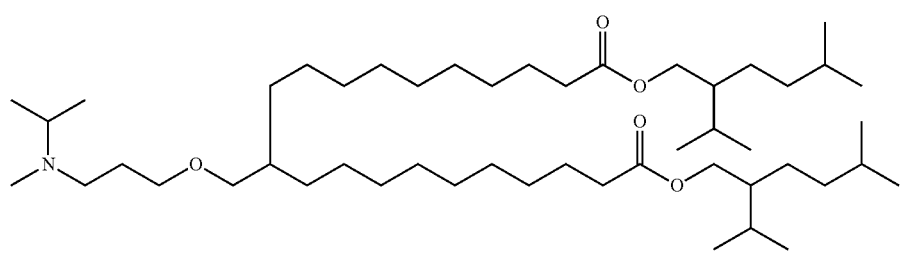
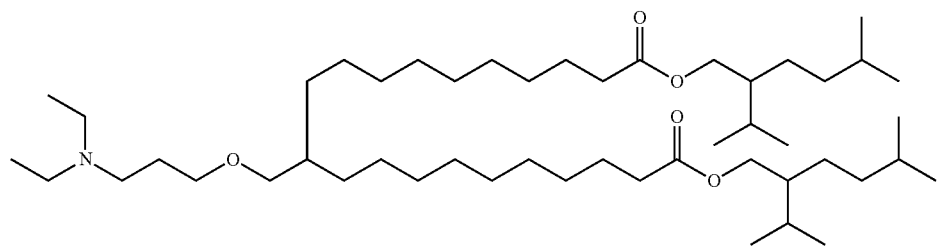
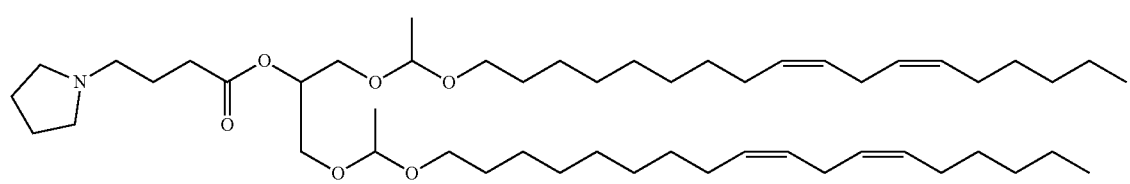
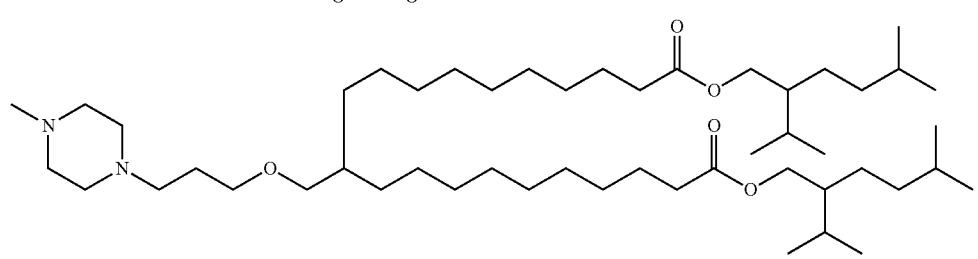
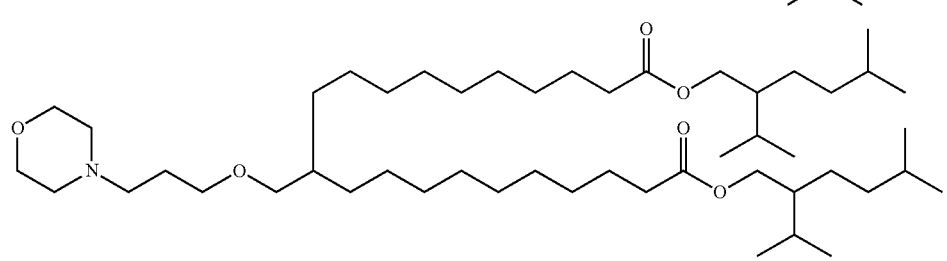

-continued
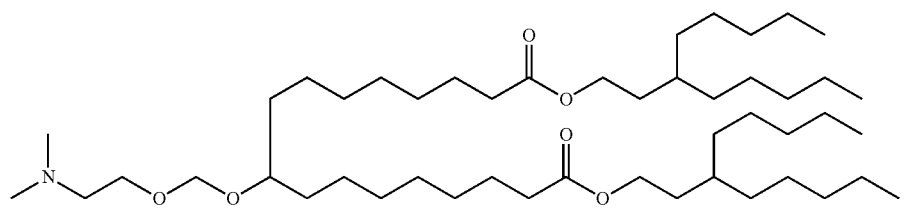
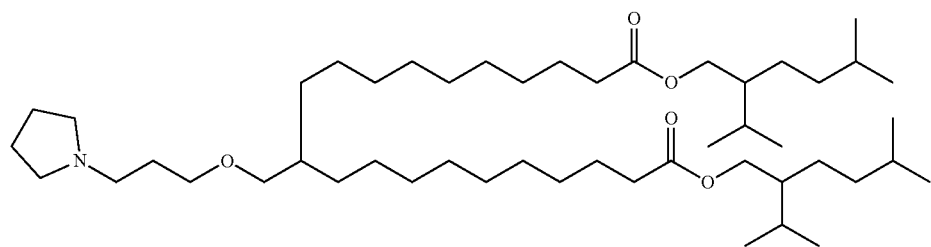
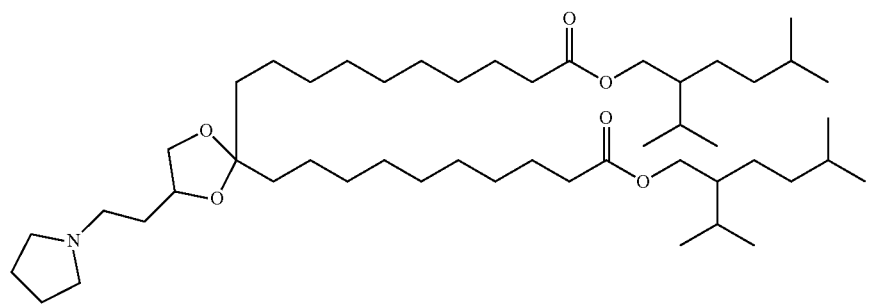
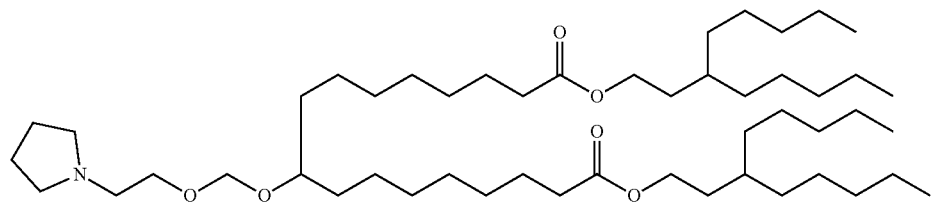
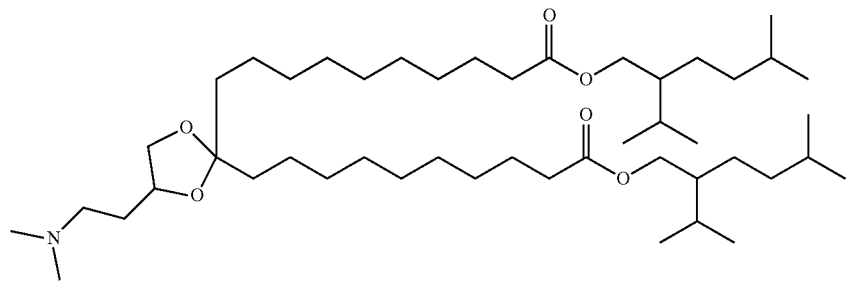
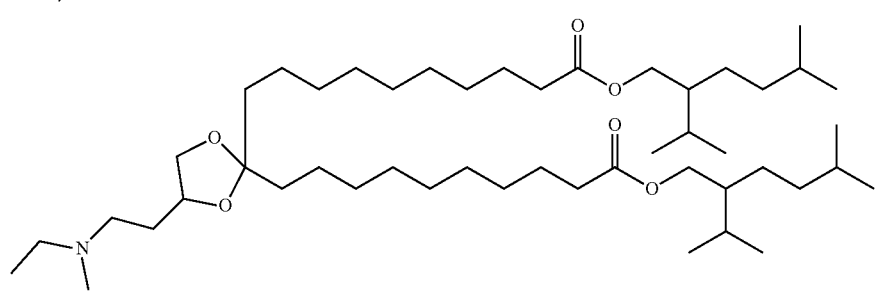

-continued
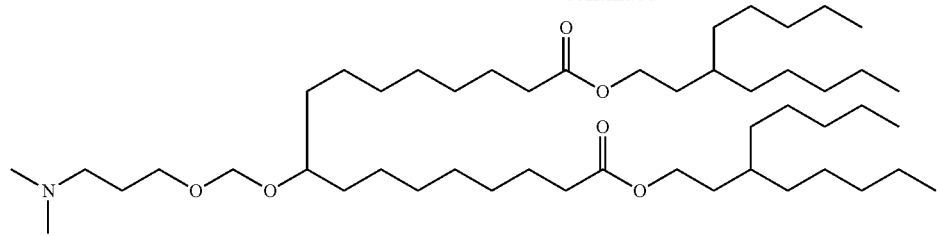
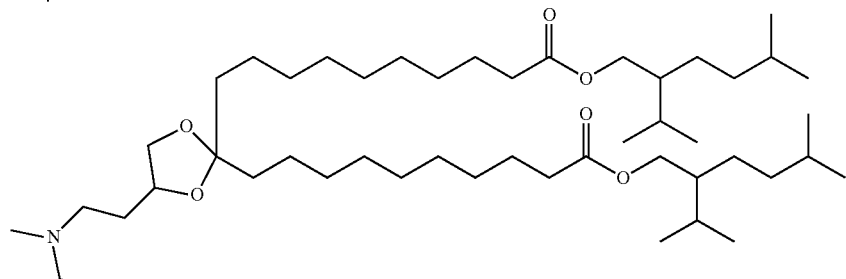
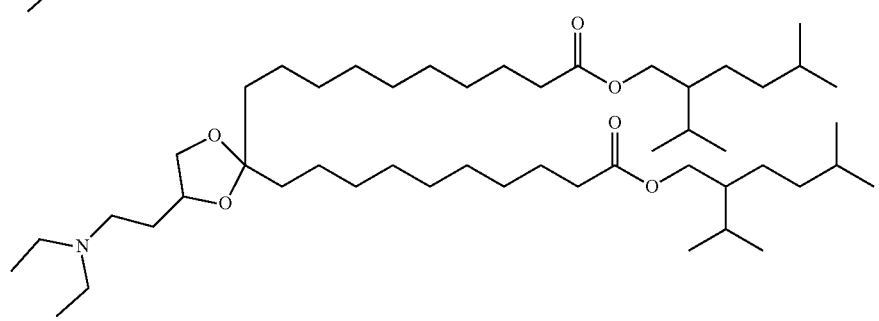
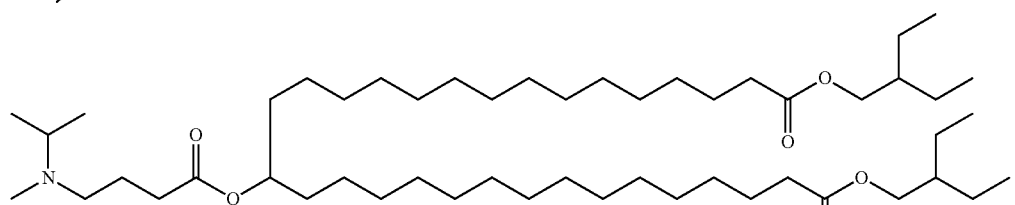
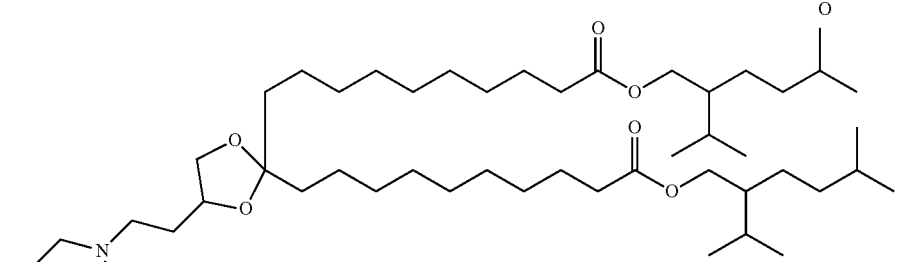
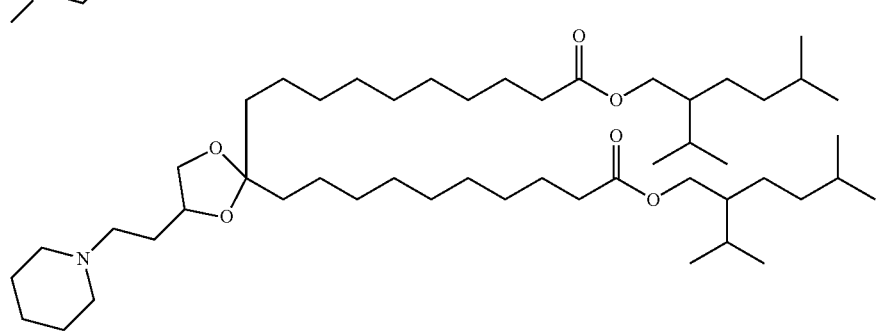

-continued
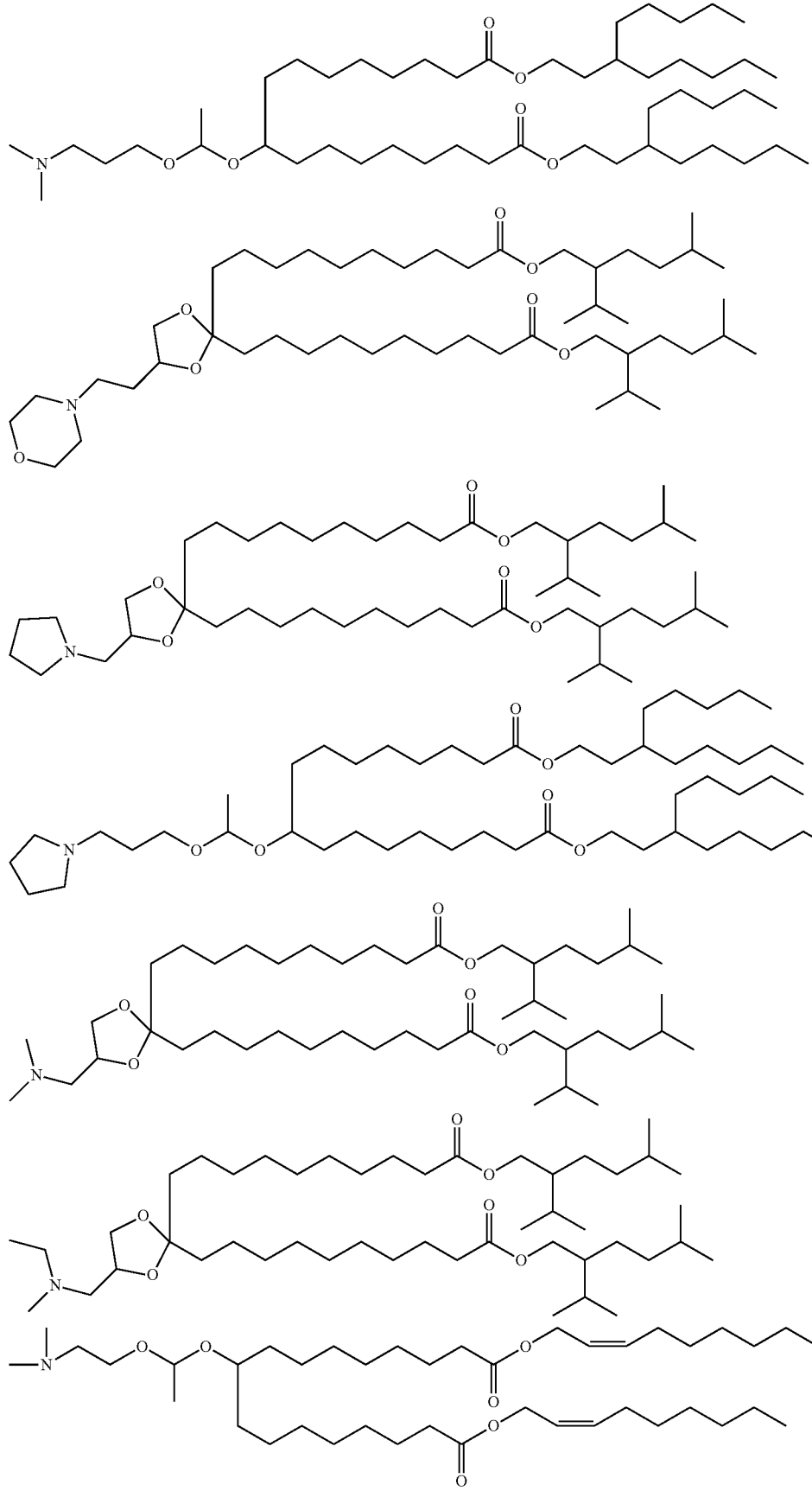

-continued
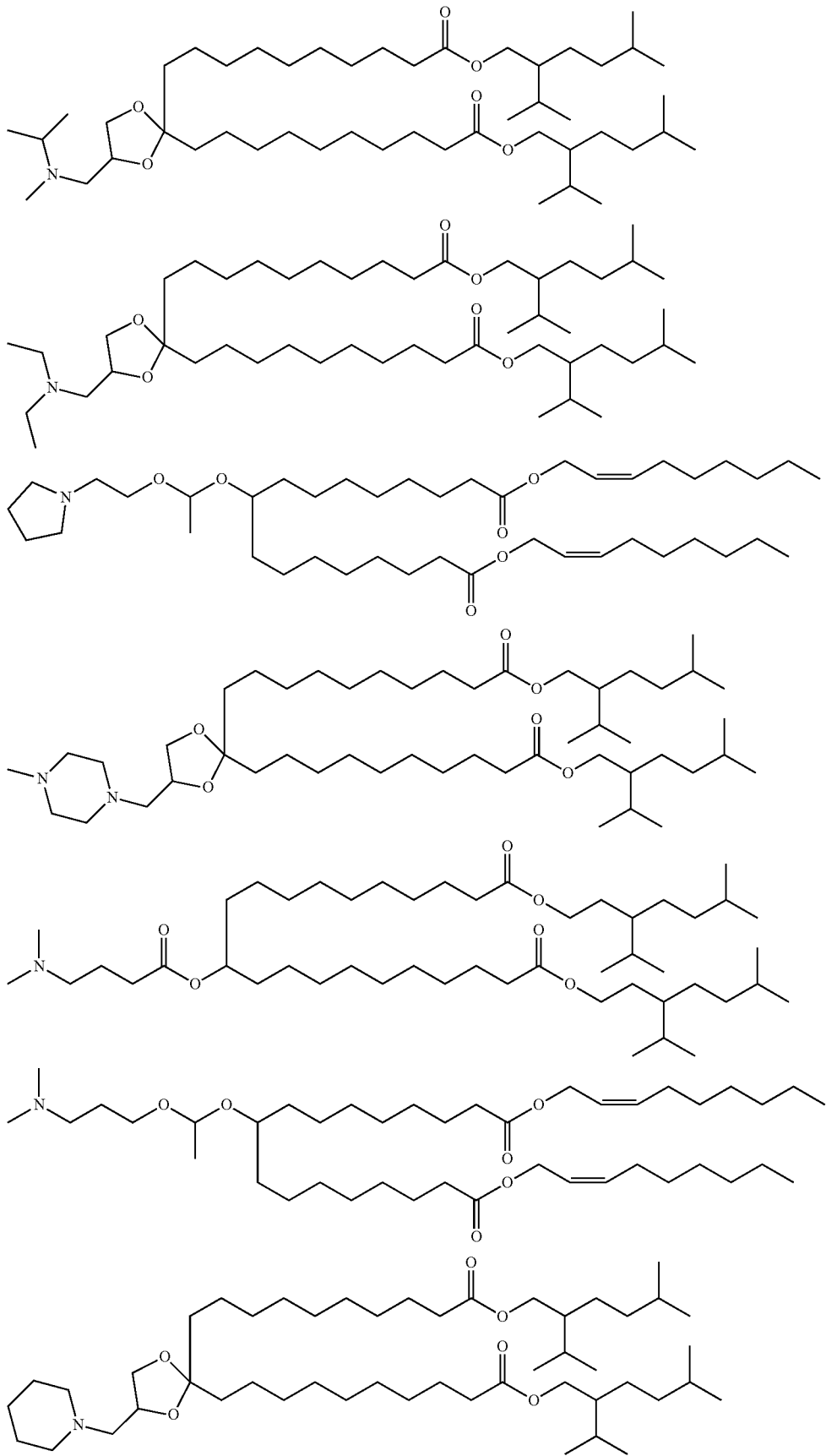

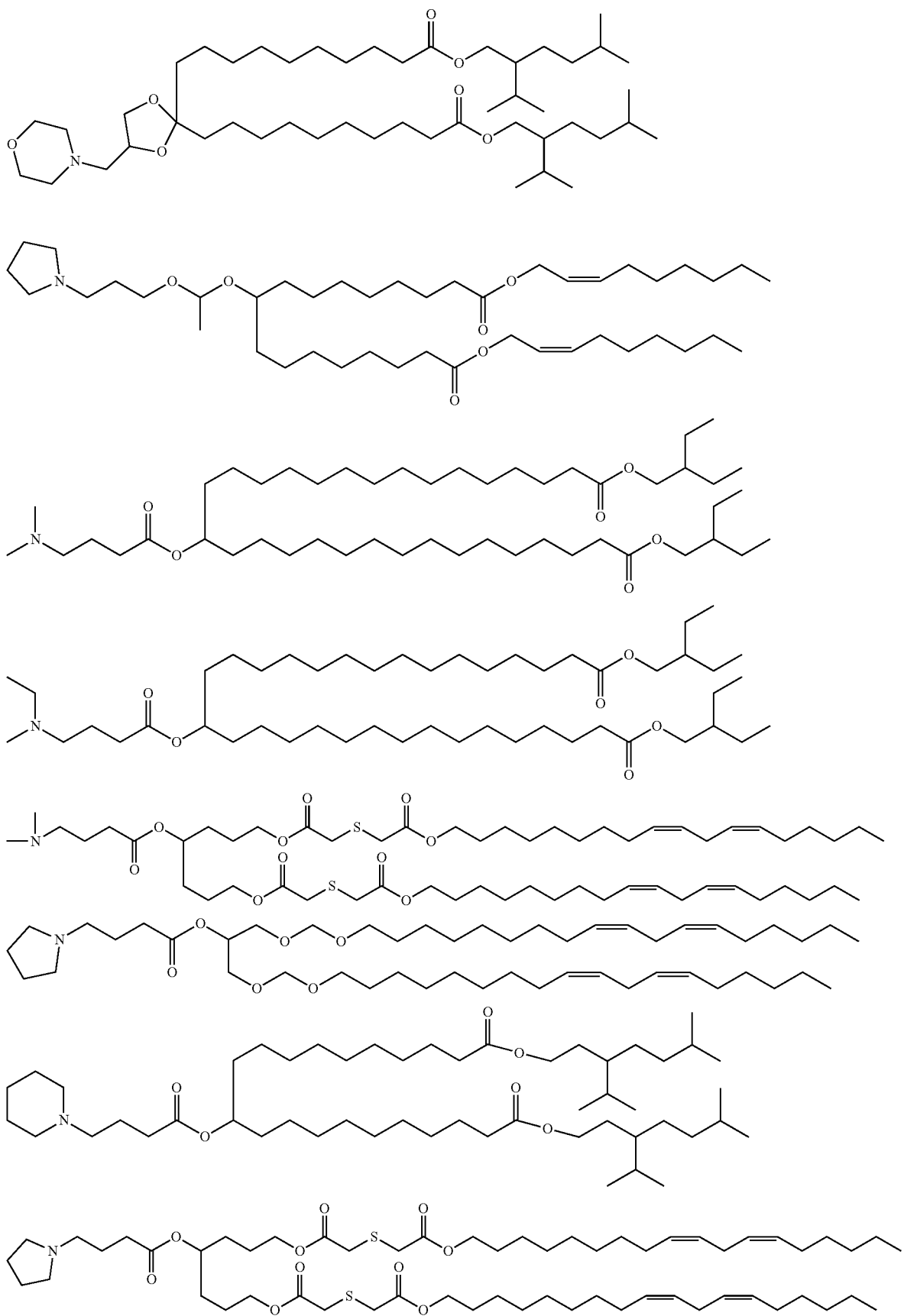

-continued
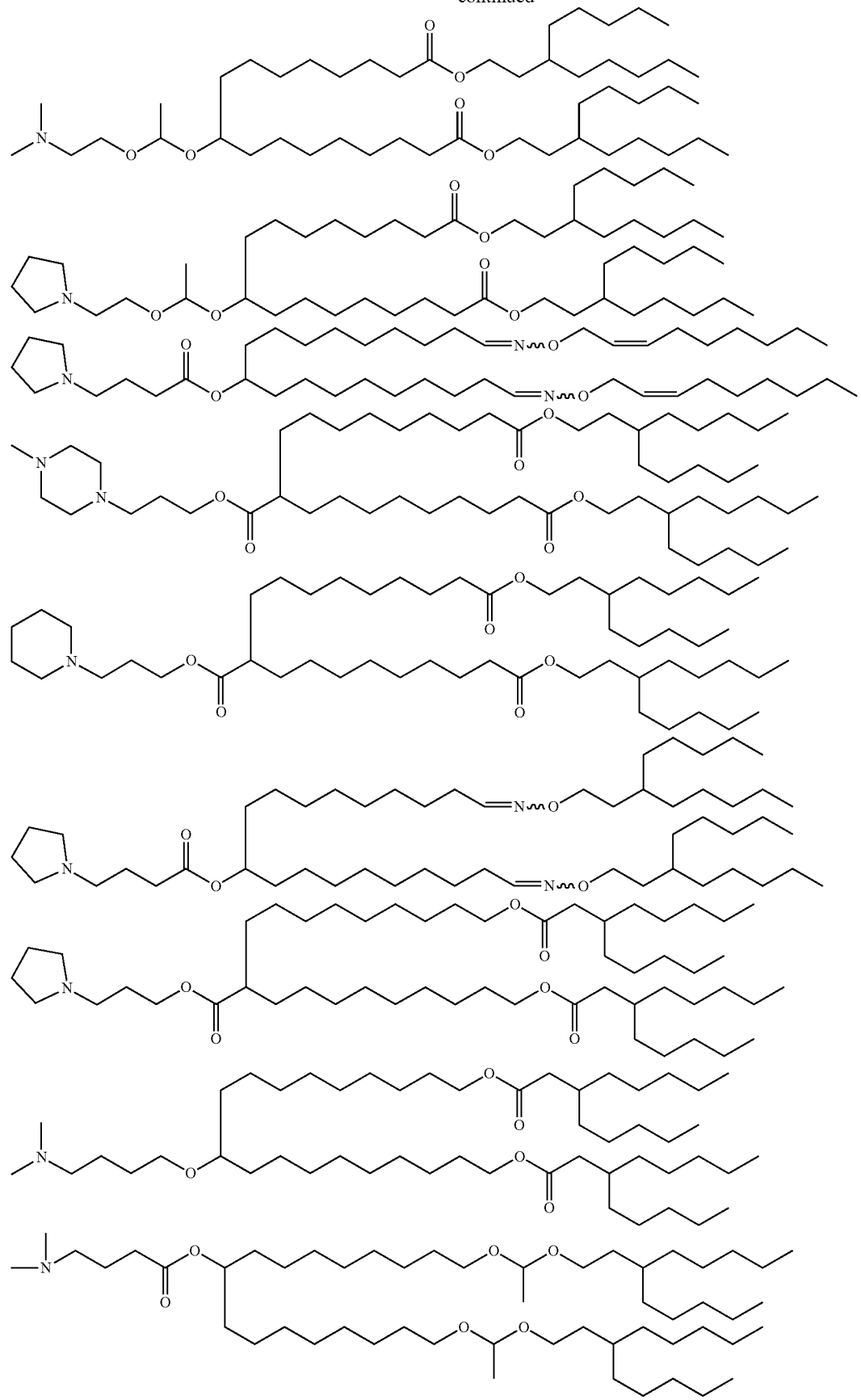

-continued
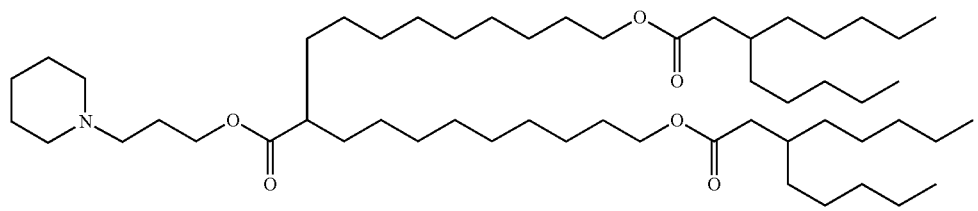
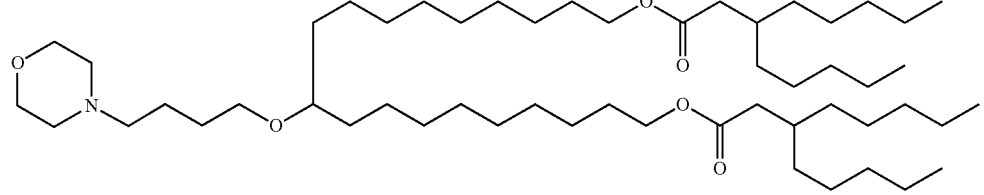
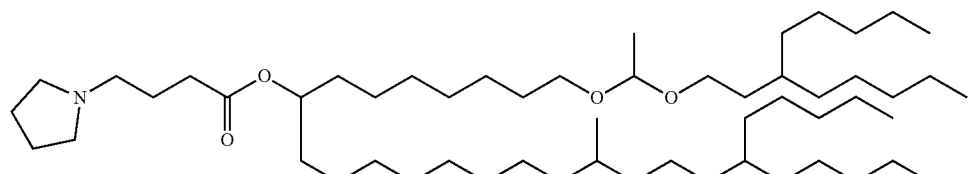
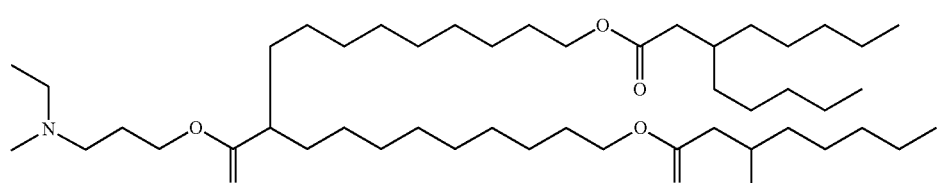
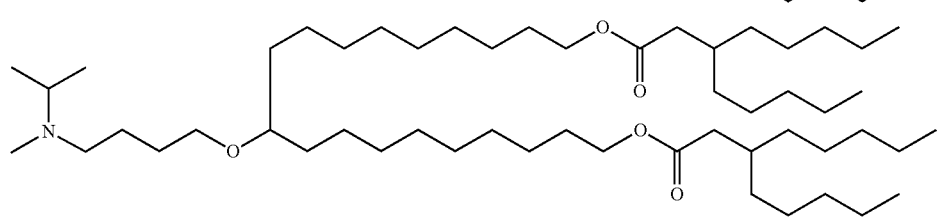
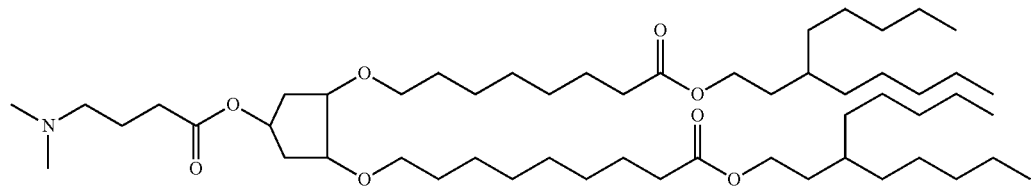
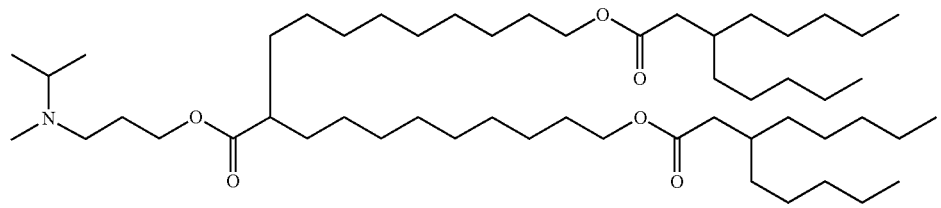
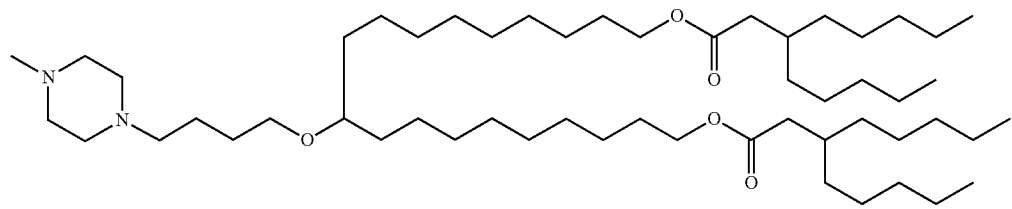

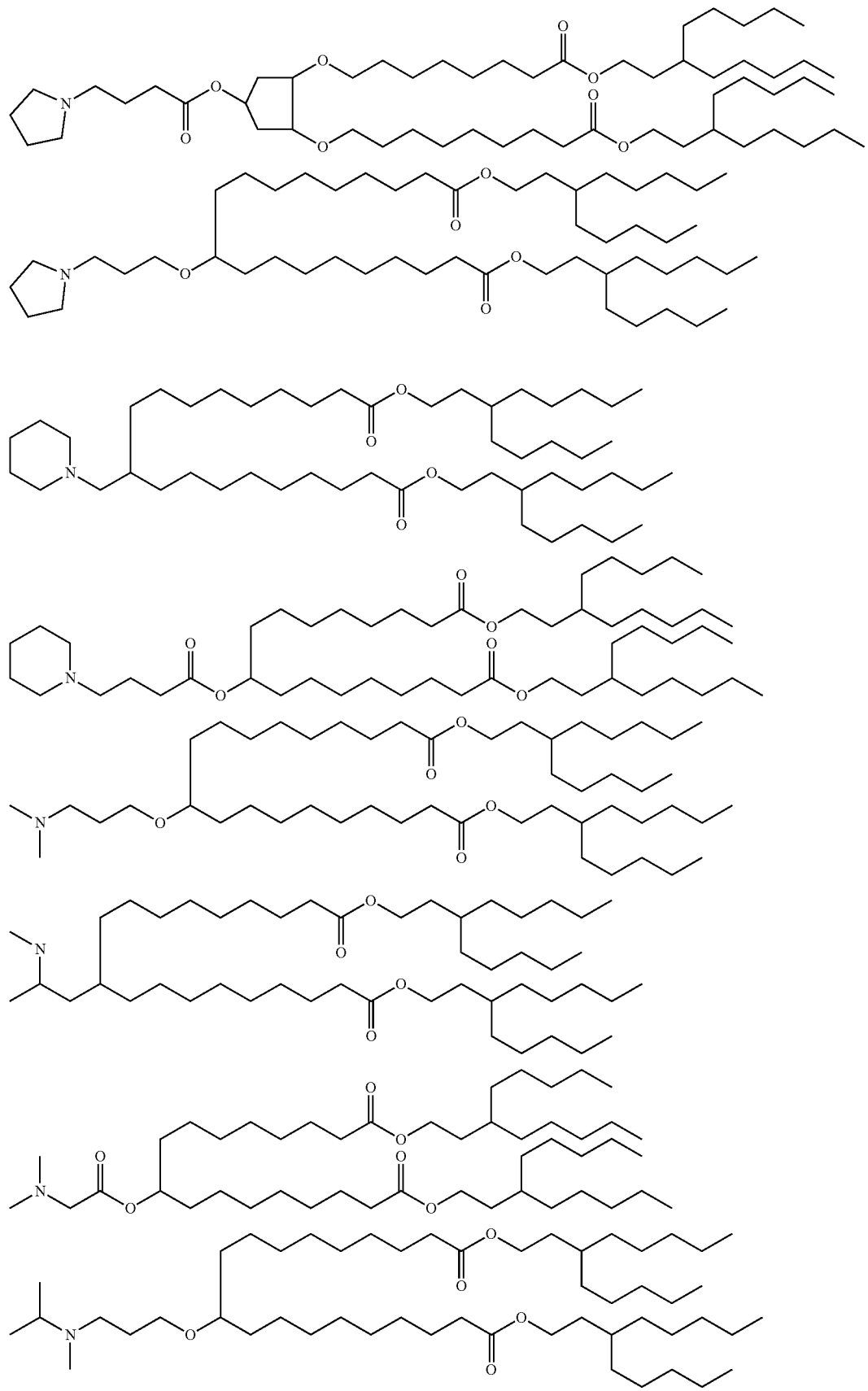

-continued
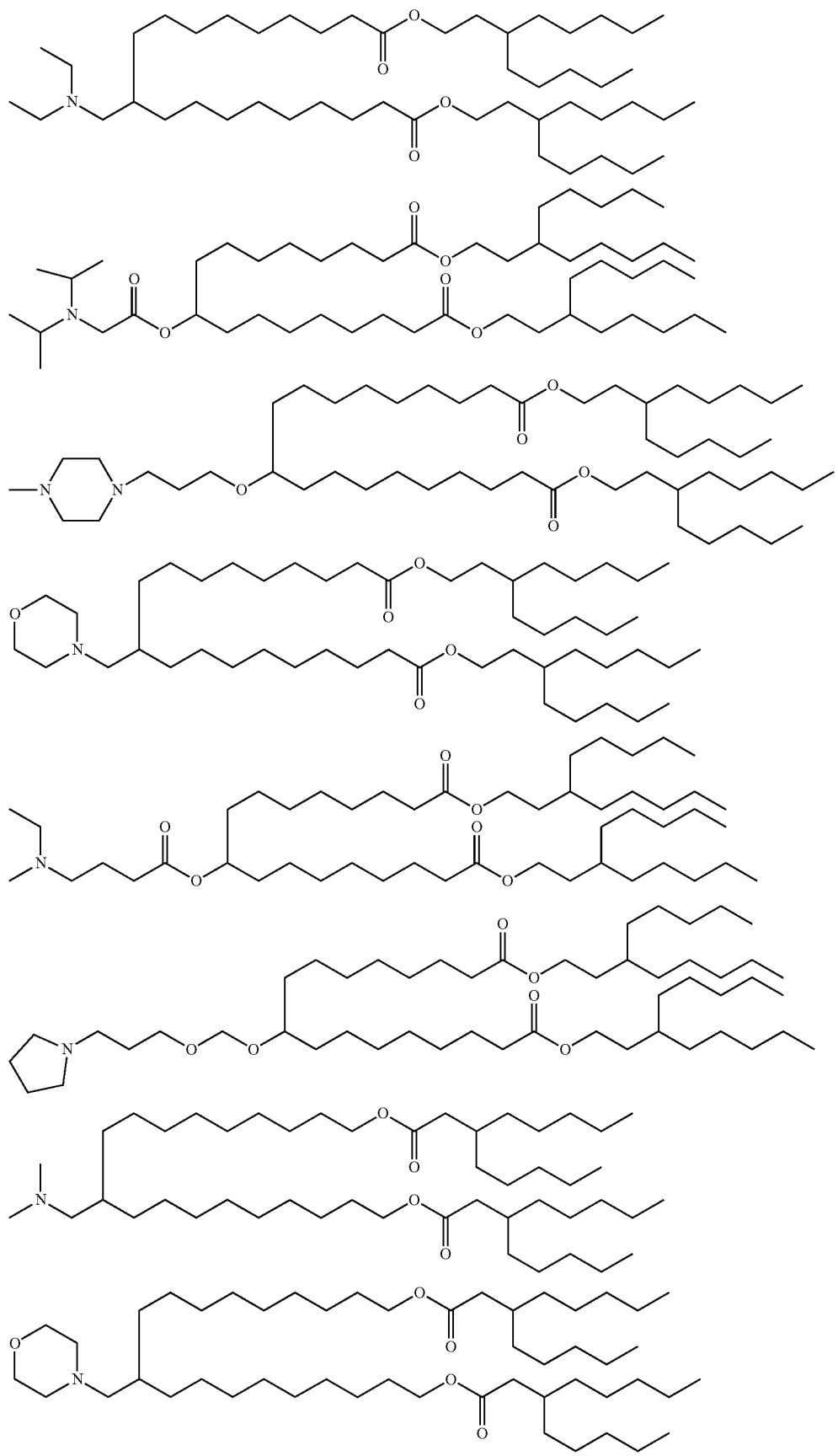

-continued
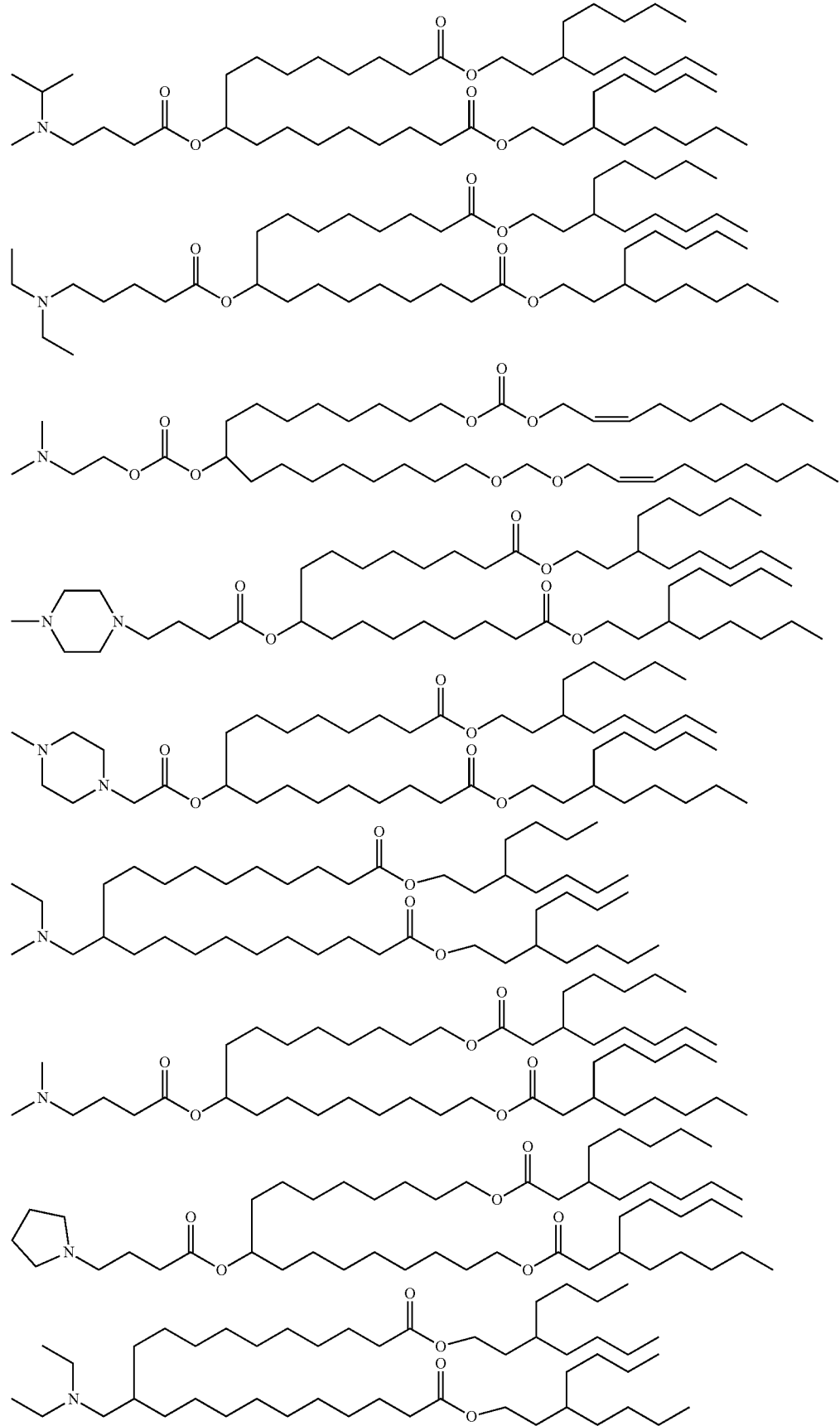

-continued
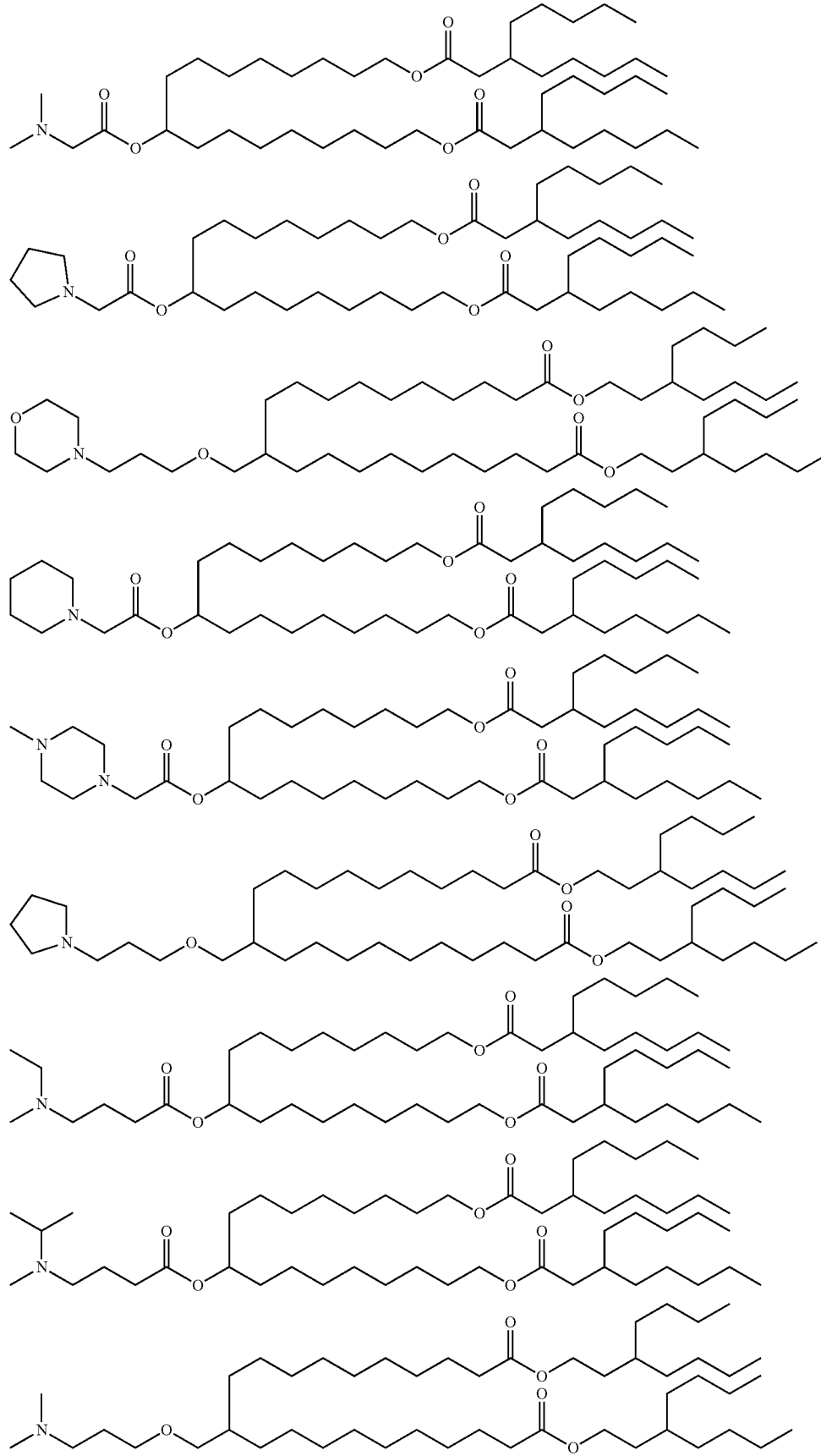

-continued
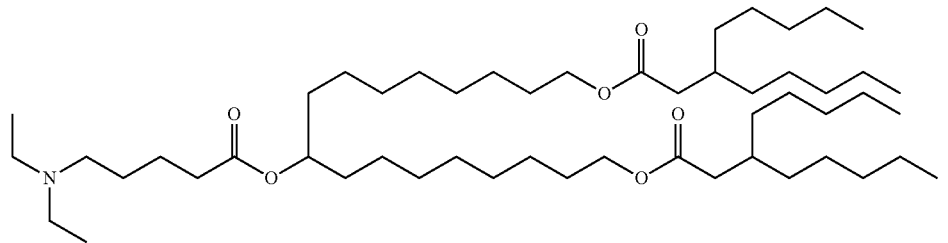
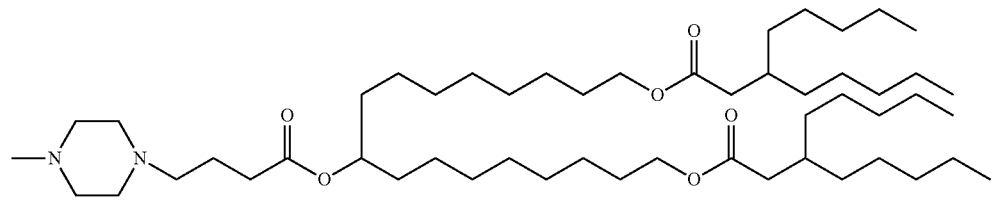
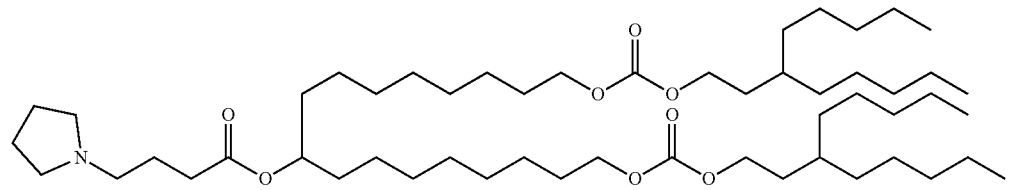
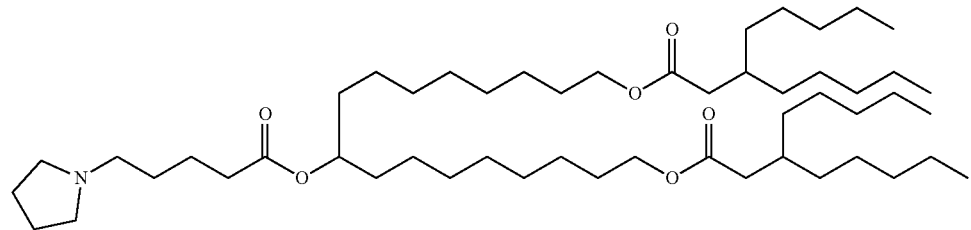
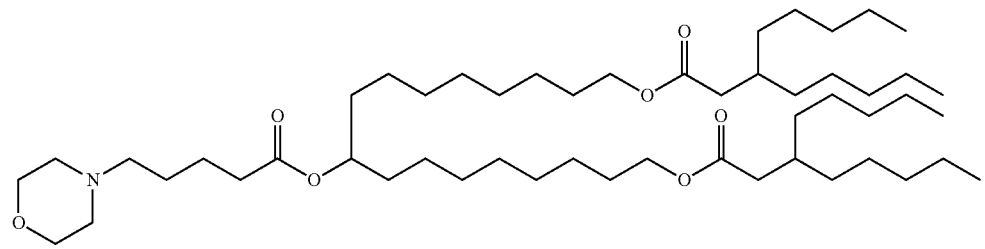
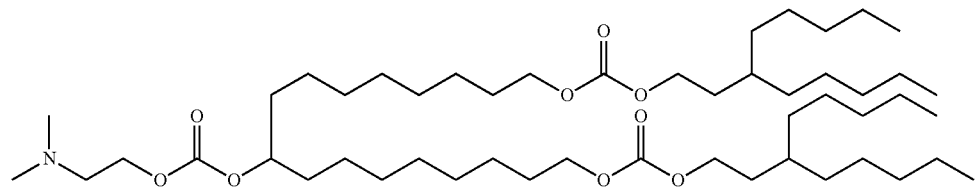
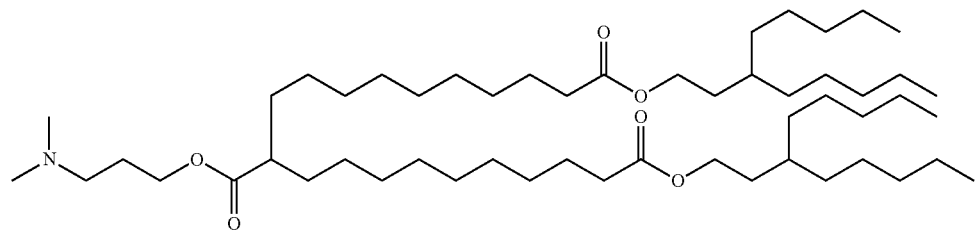

-continued
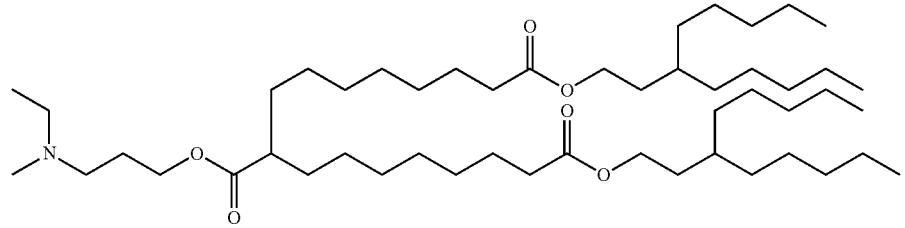
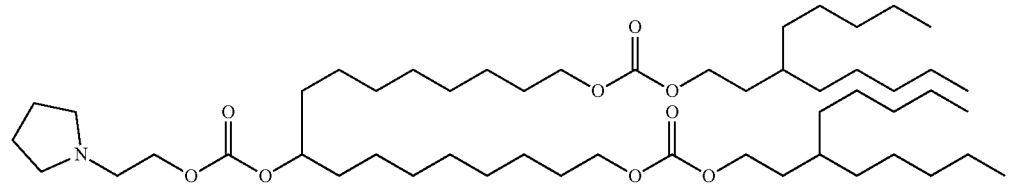
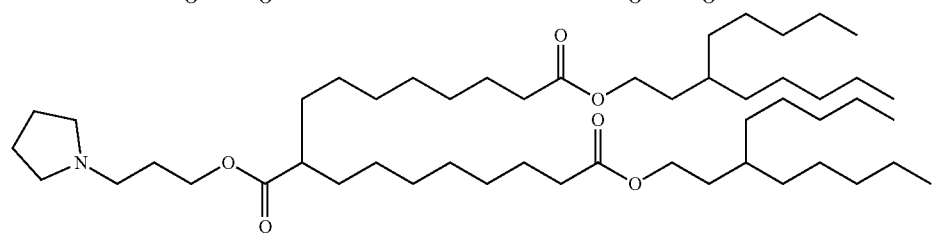
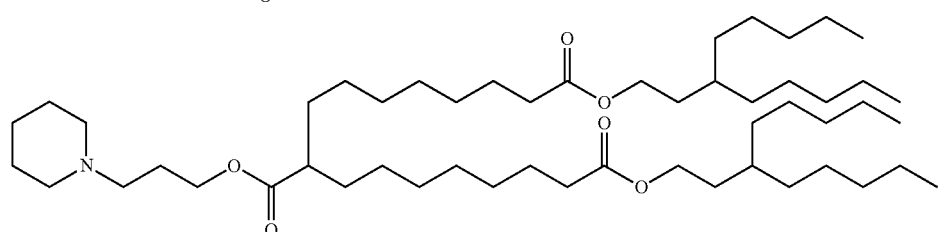
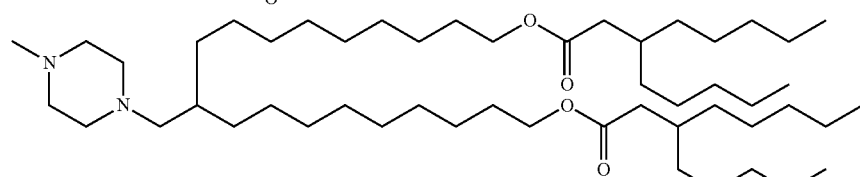
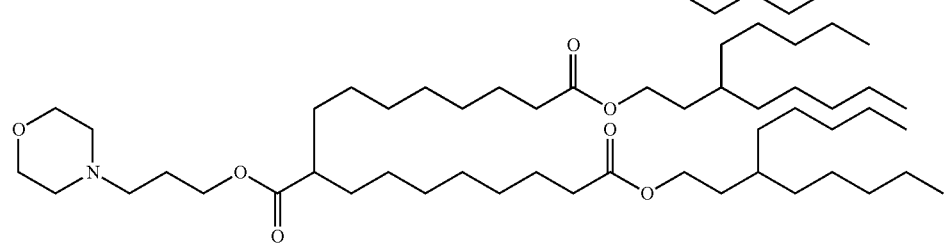
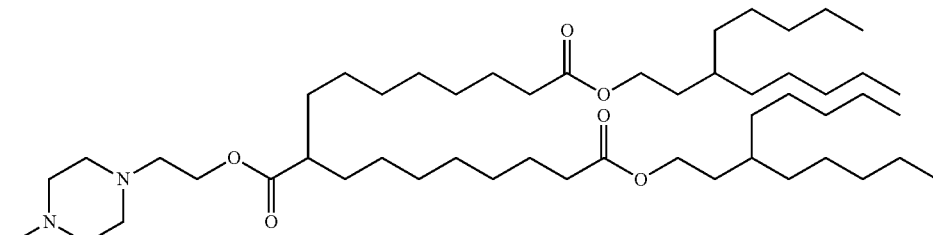
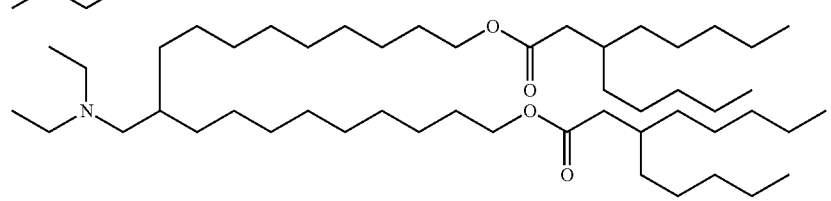

-continued
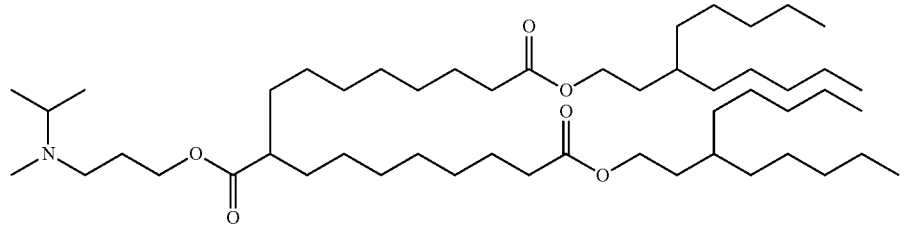
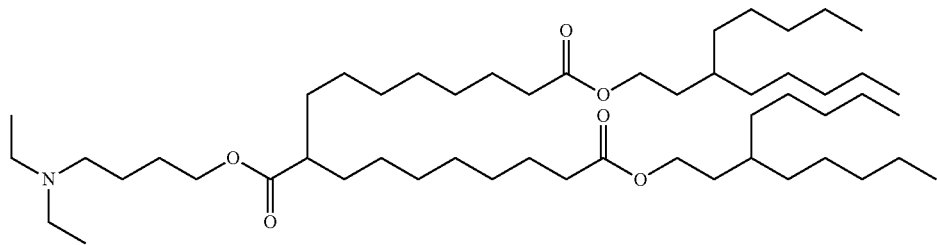
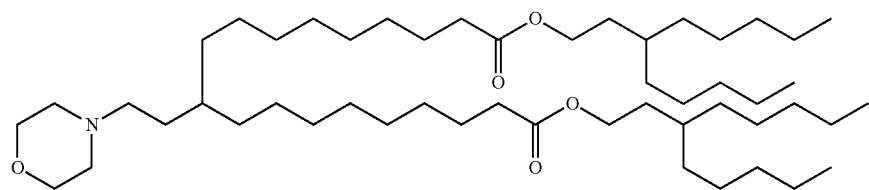
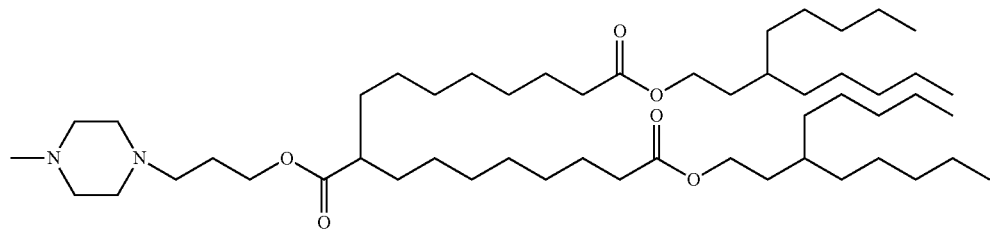
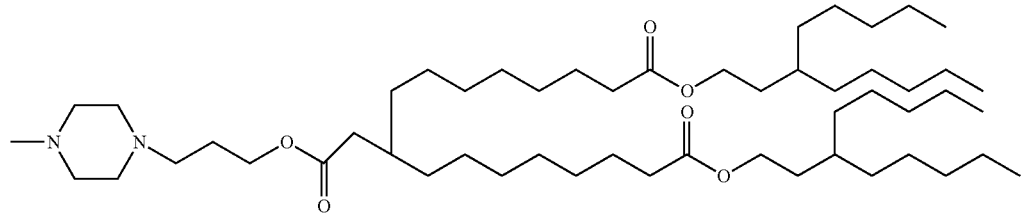
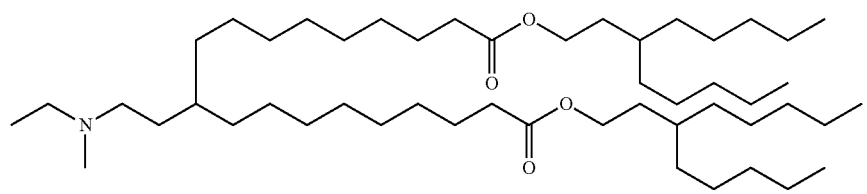
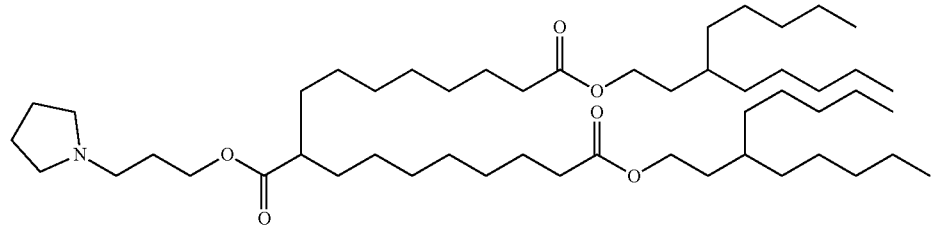

-continued
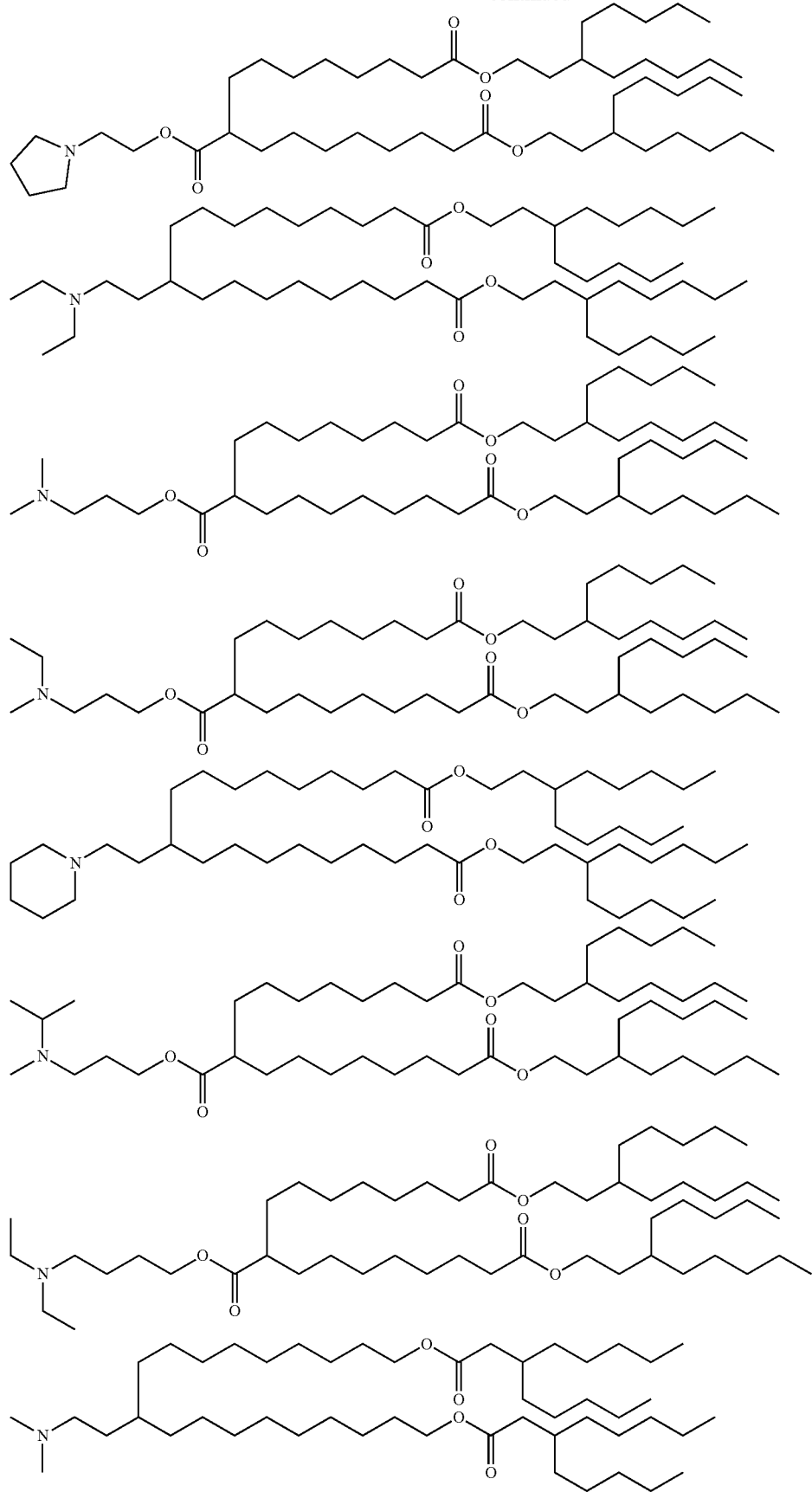

-continued
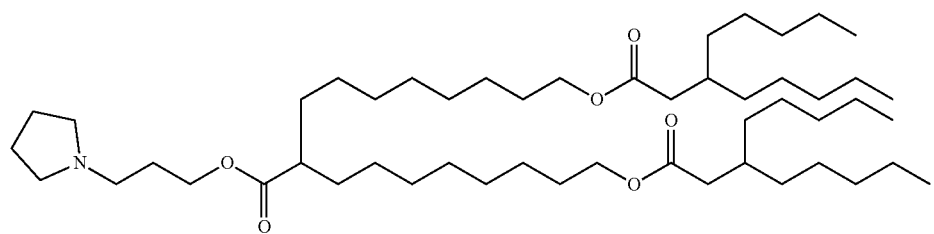
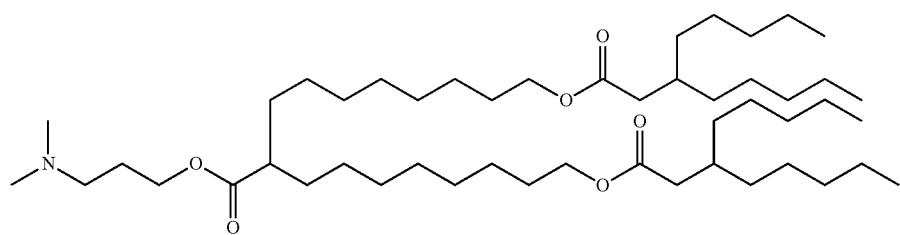
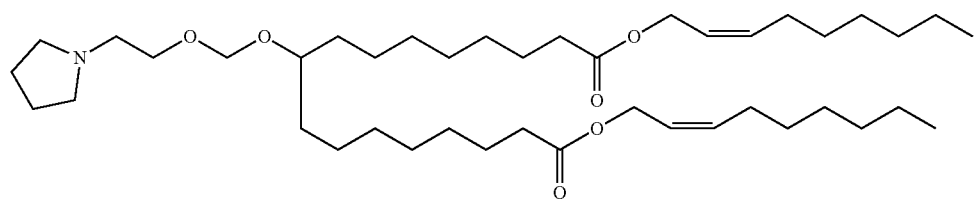
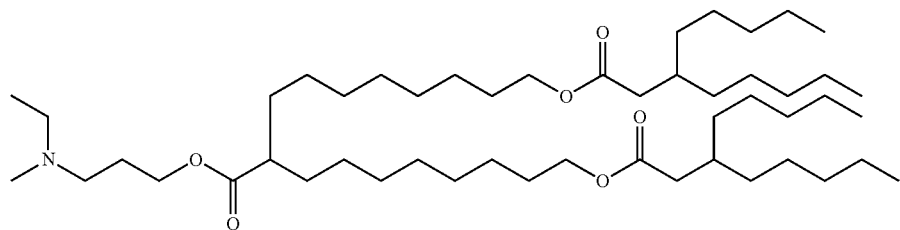
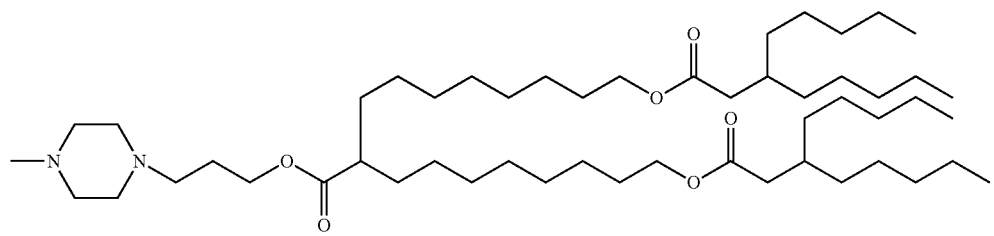
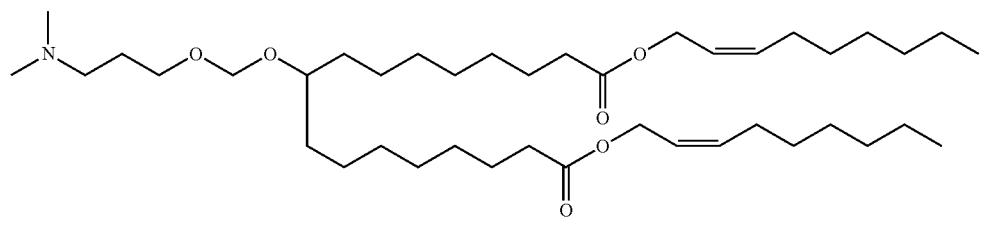
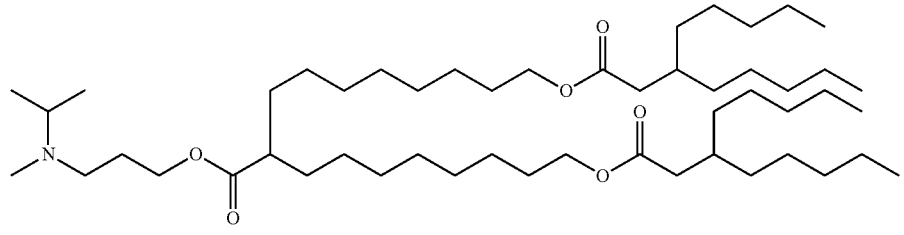

-continued
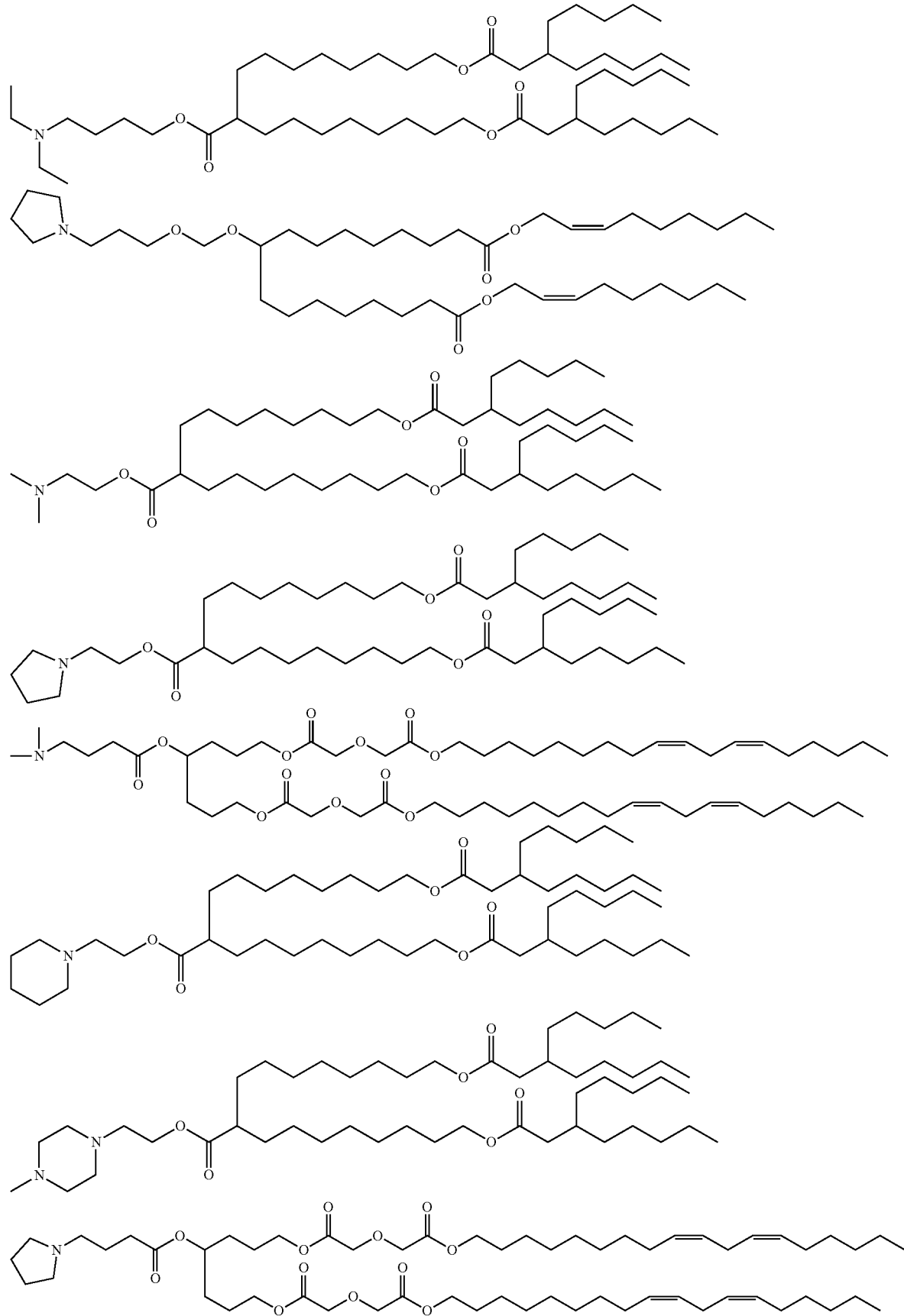

-continued
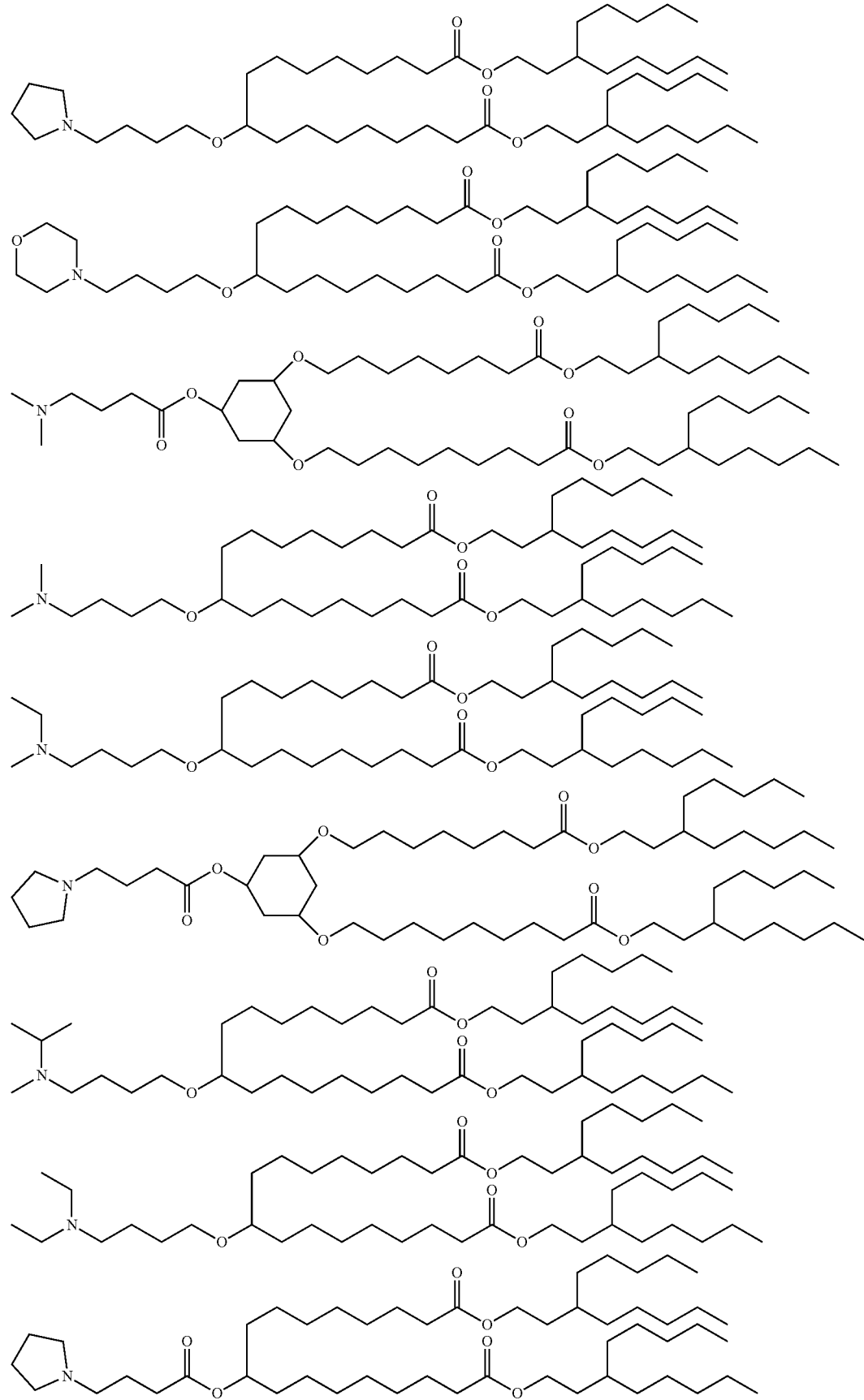

-continued
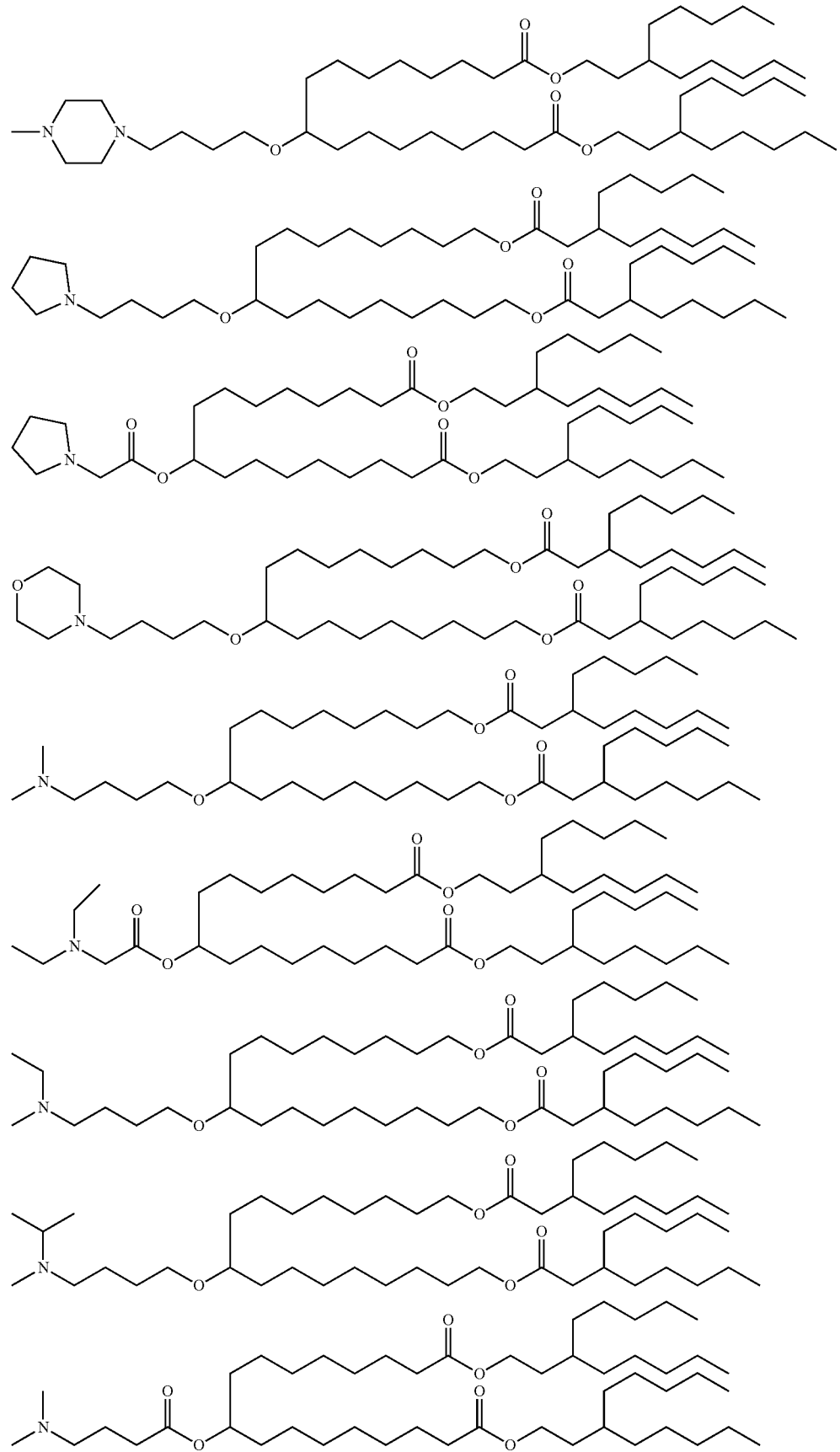

-continued
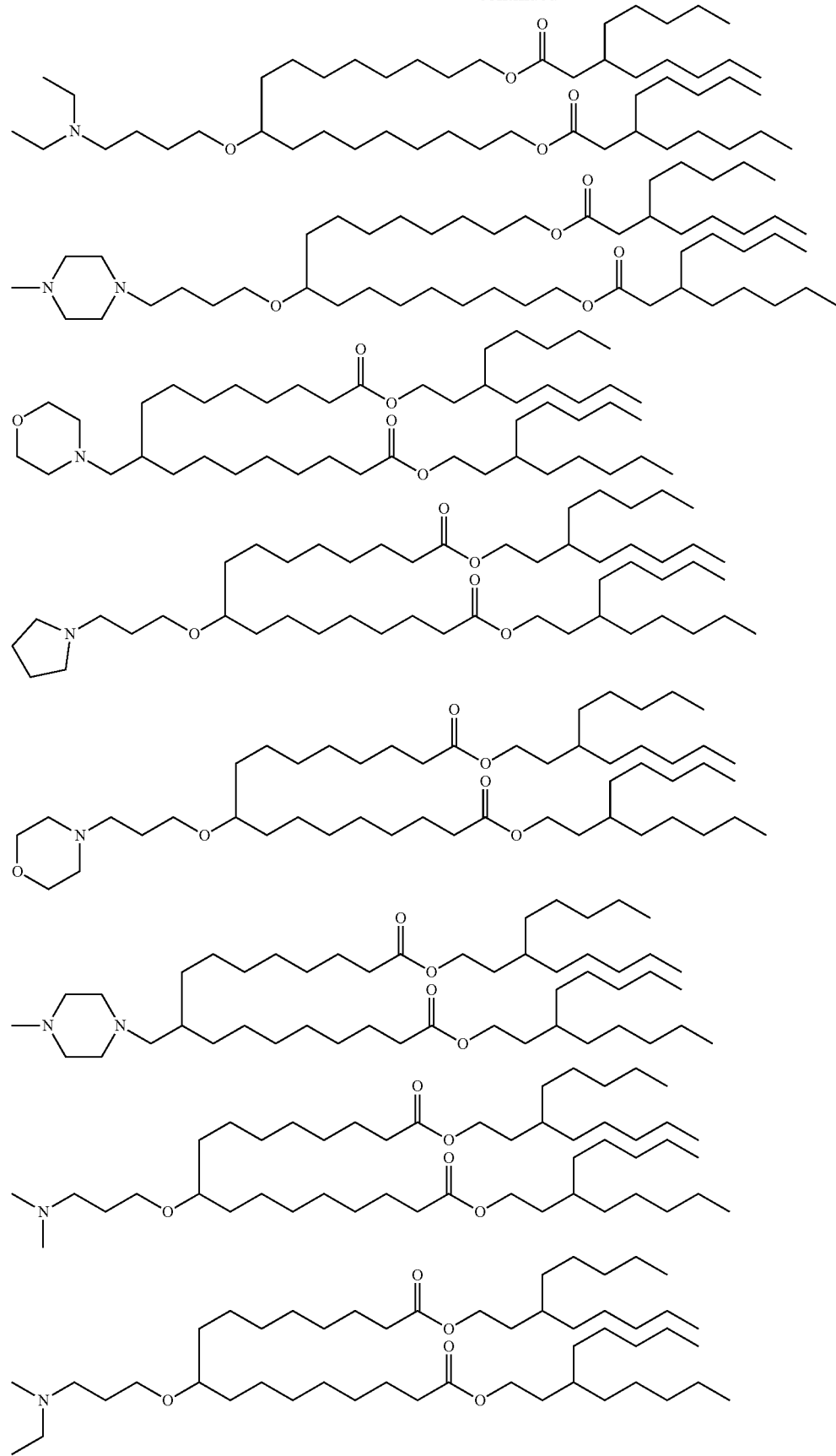

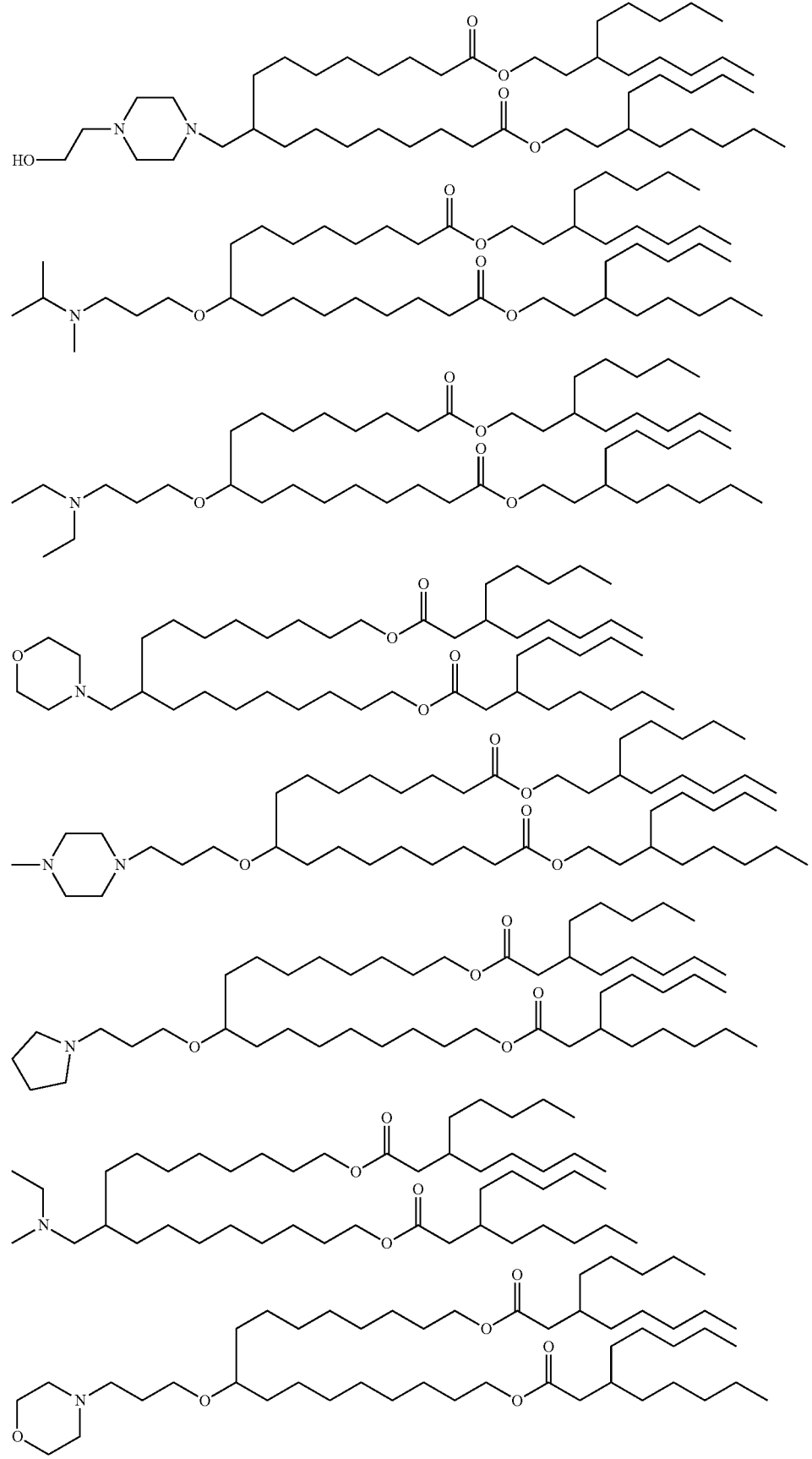

-continued
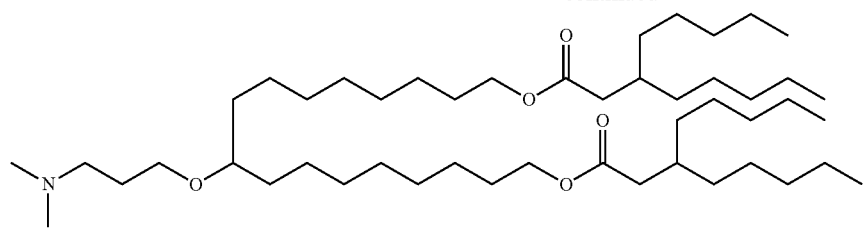
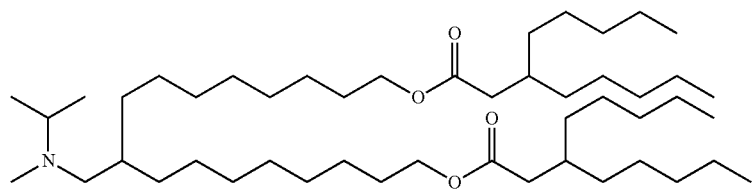
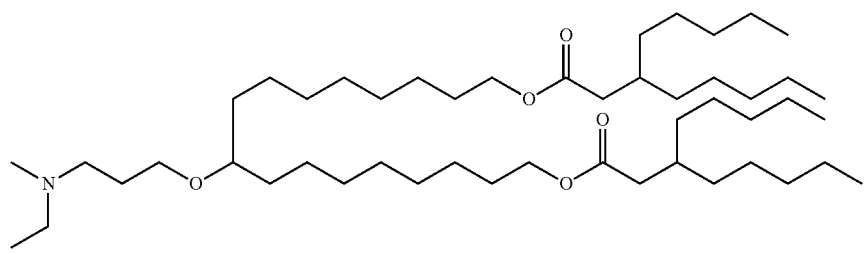
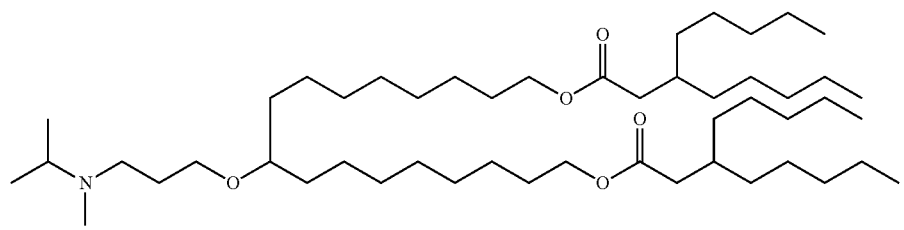
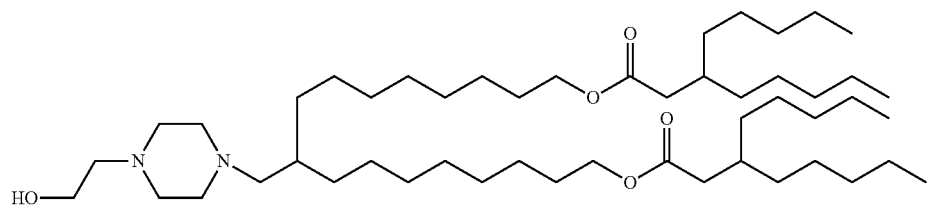
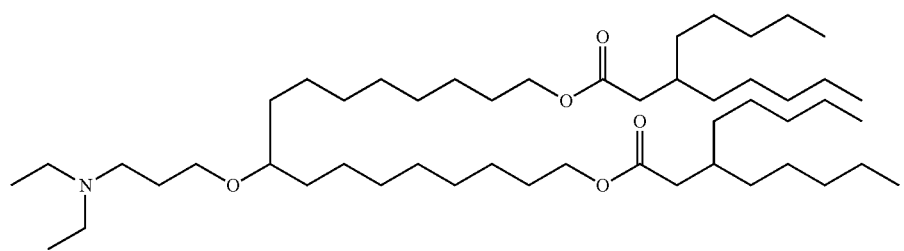
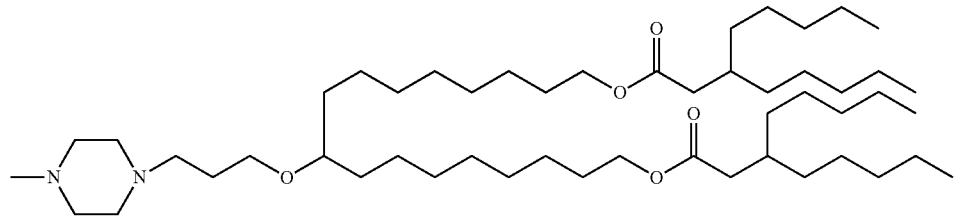

-continued
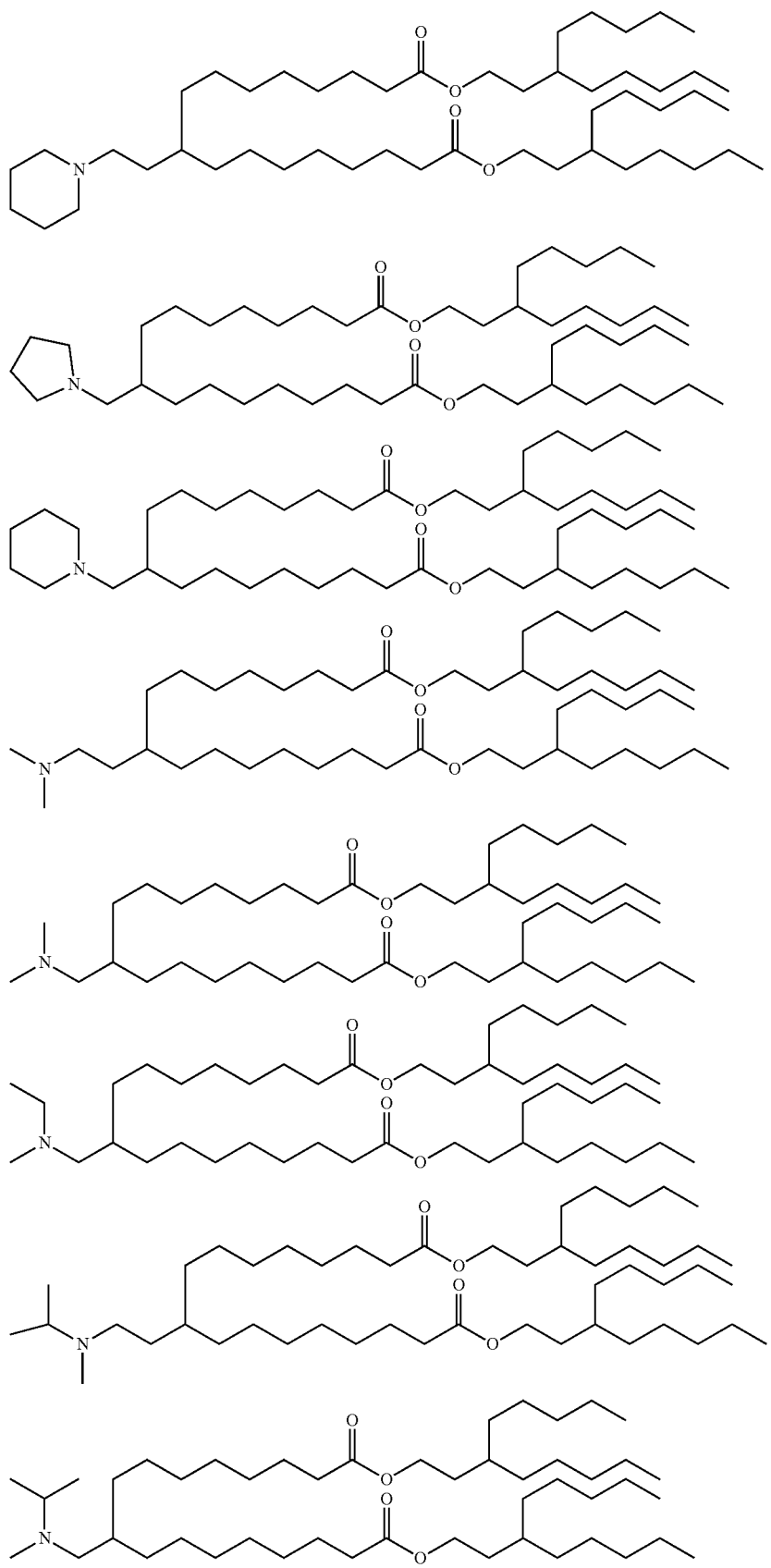

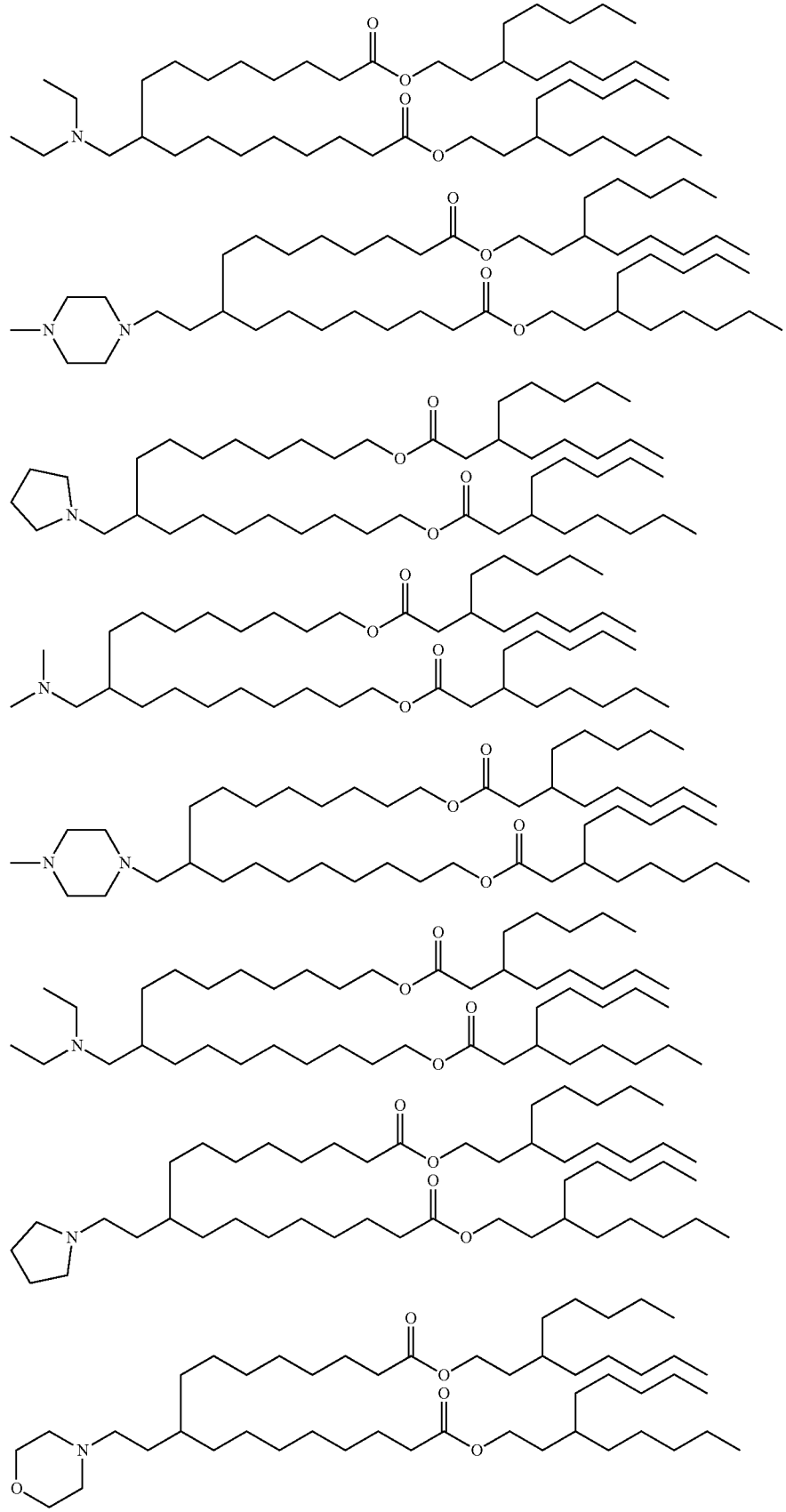

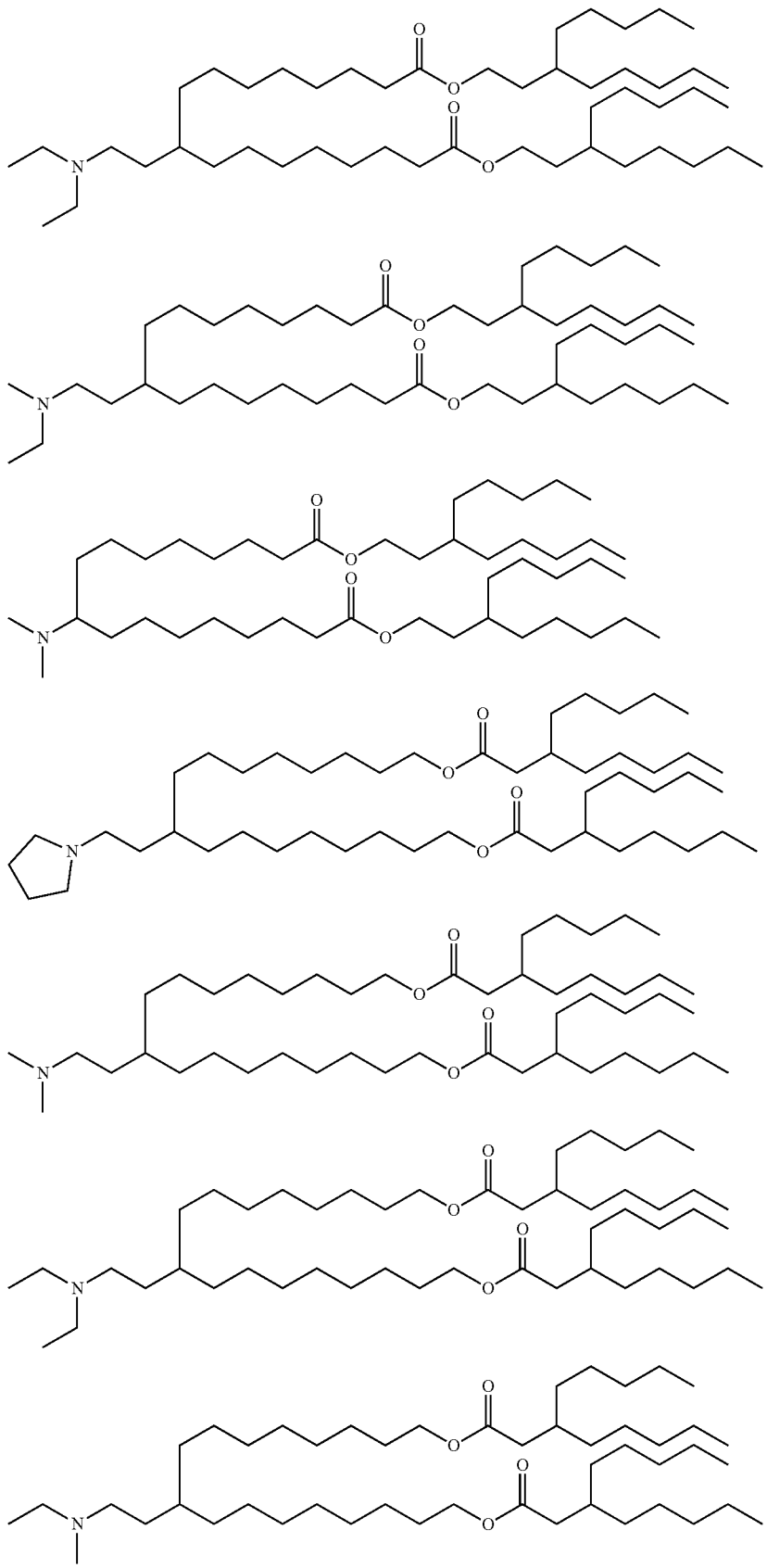

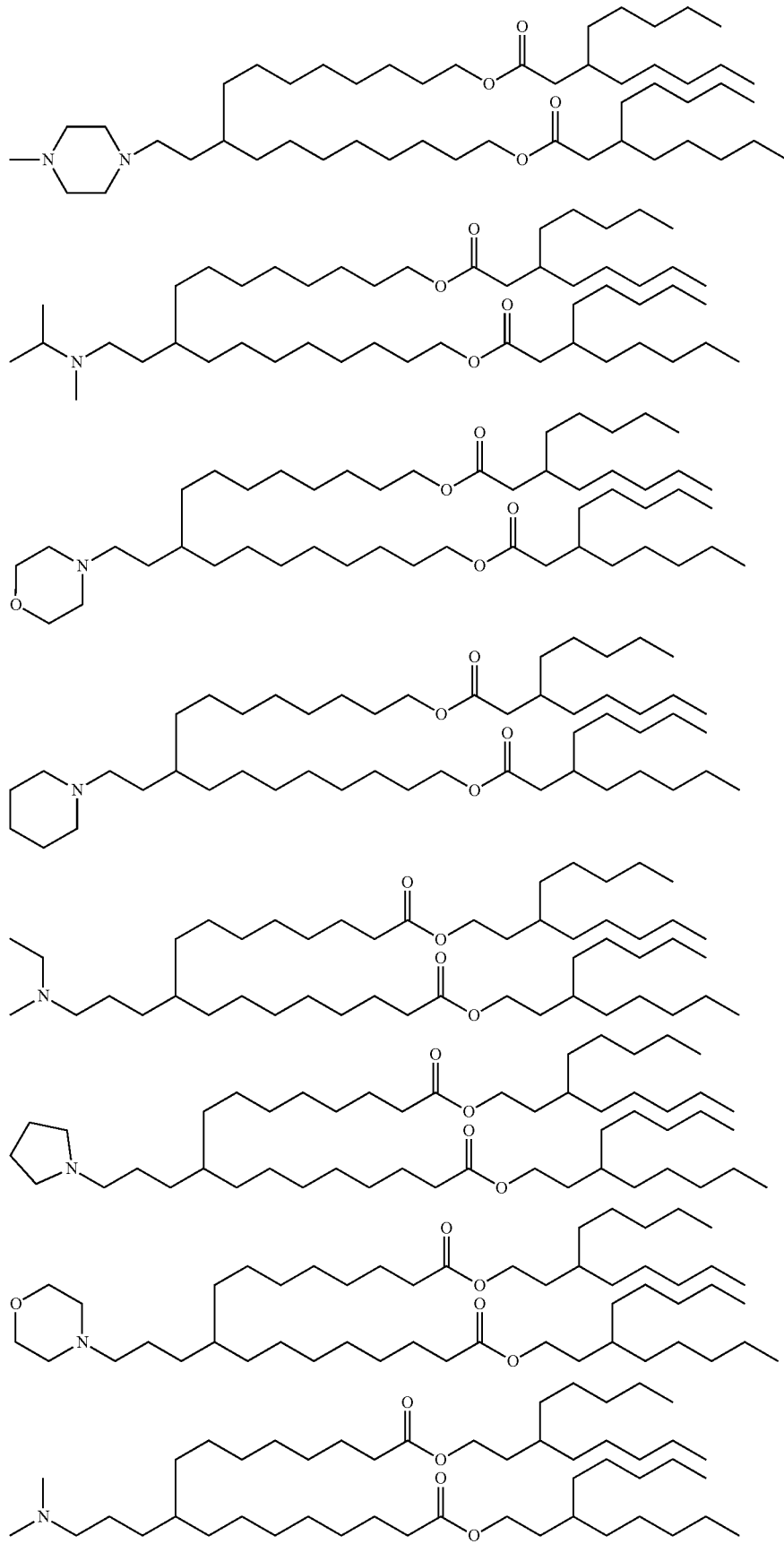

-continued
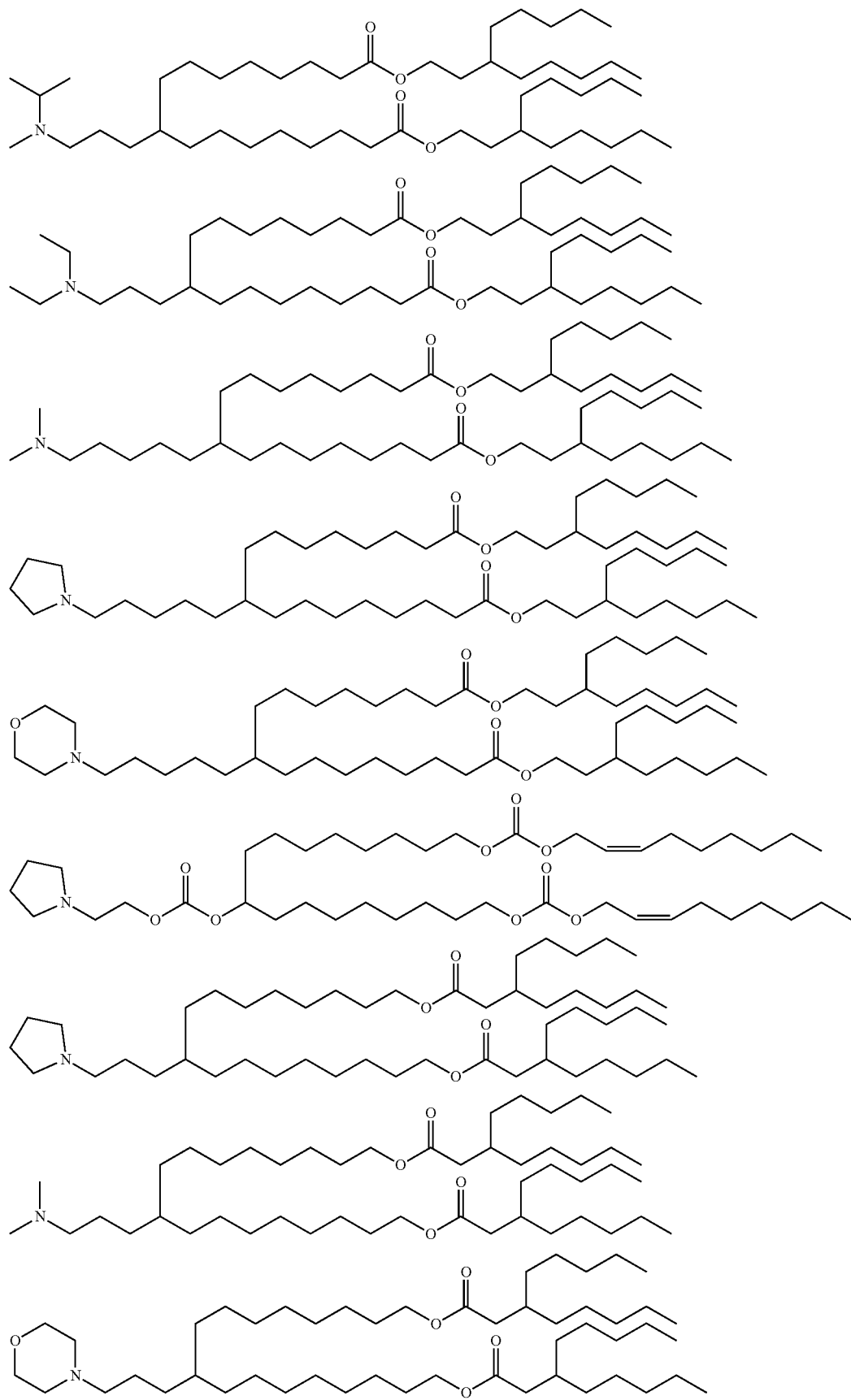

-continued
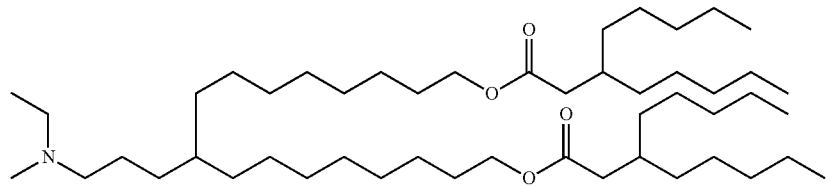
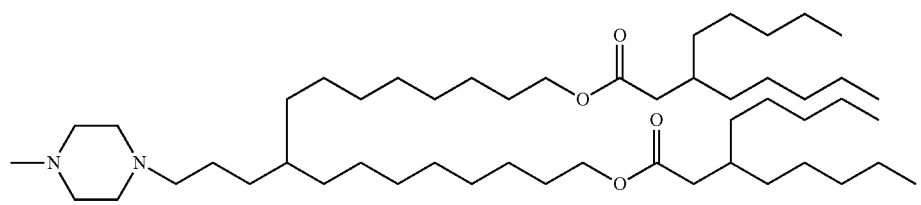
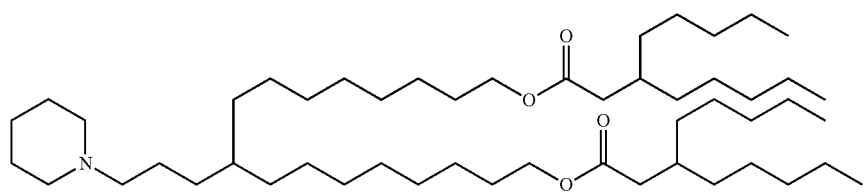
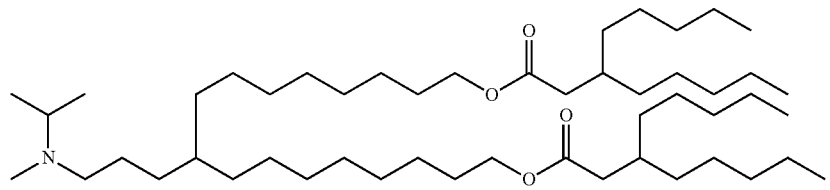
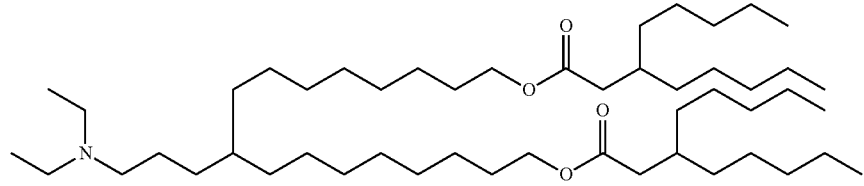
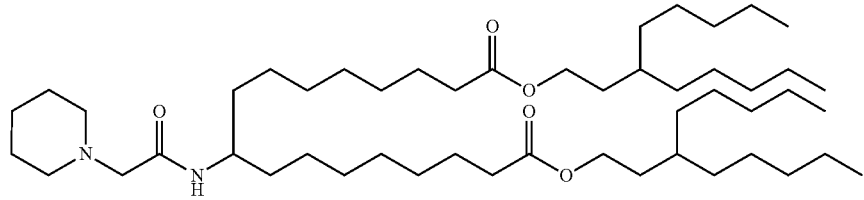
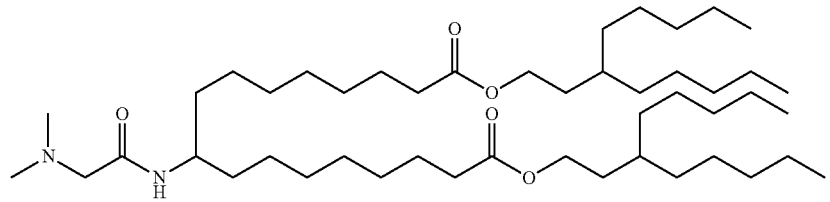
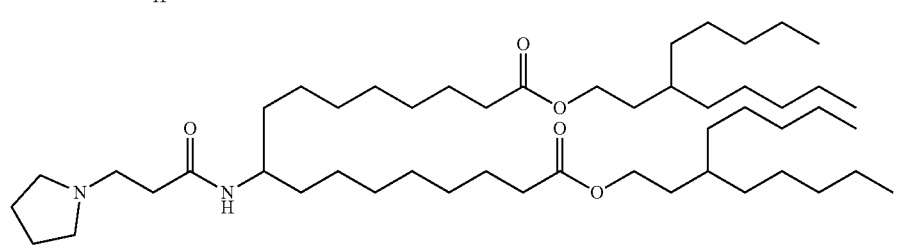

-continued
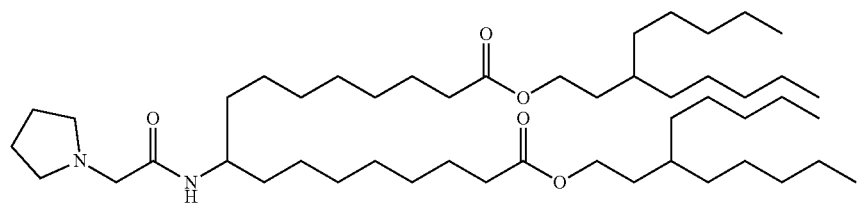
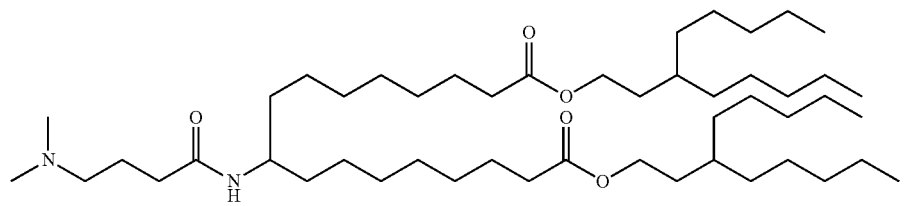
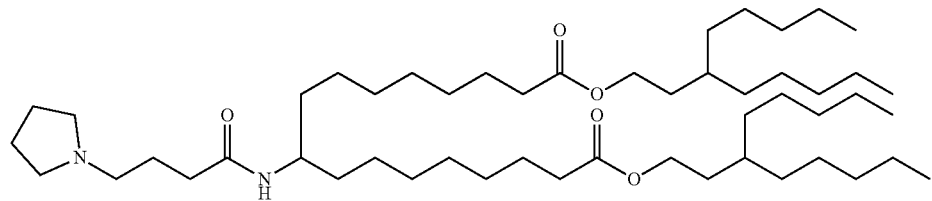
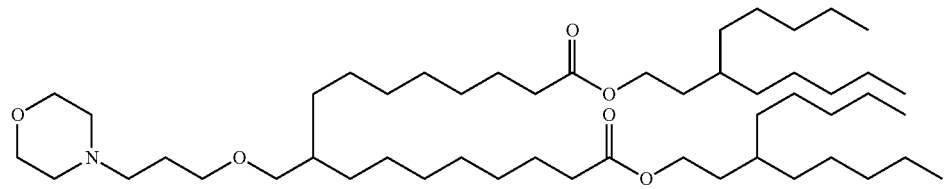
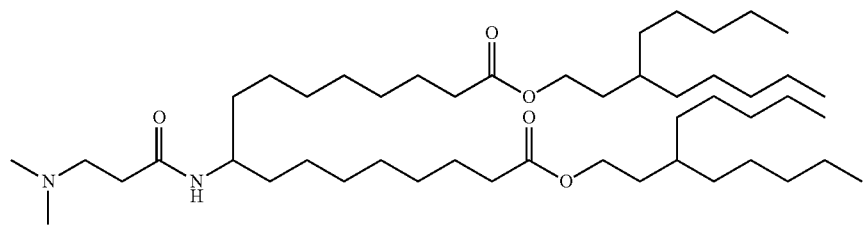
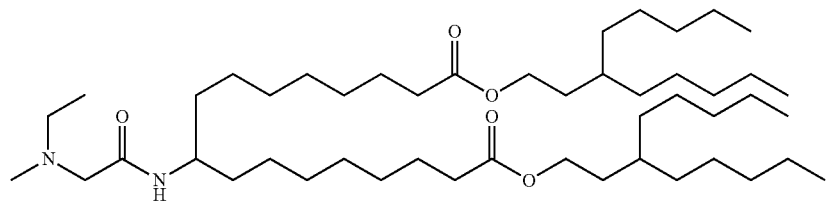
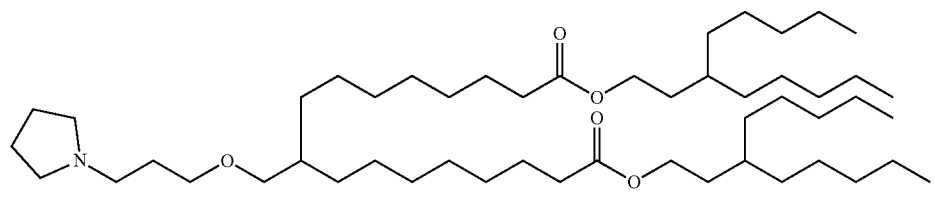
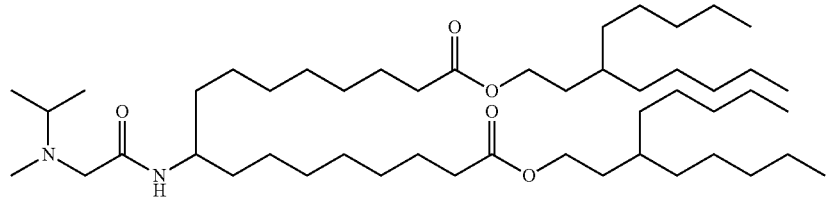

-continued
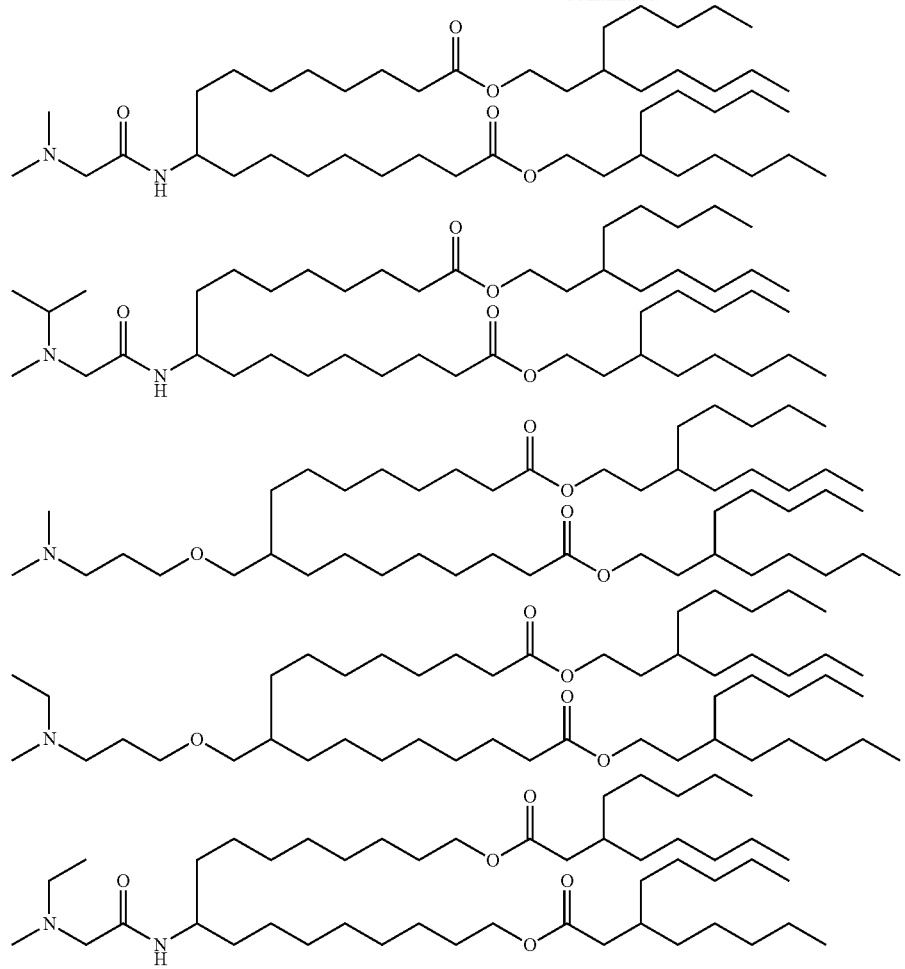
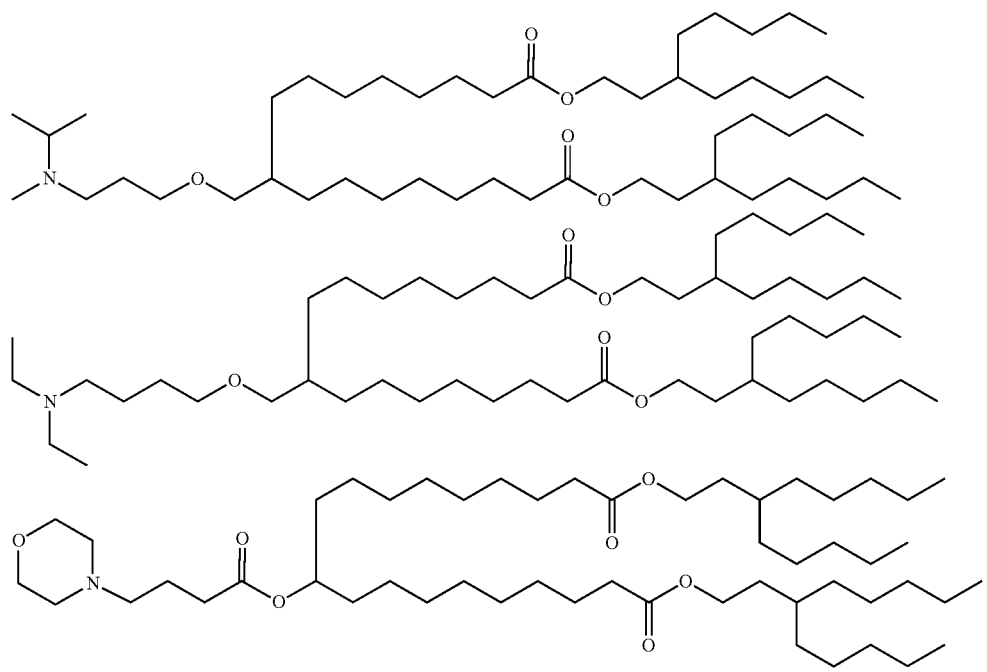

-continued
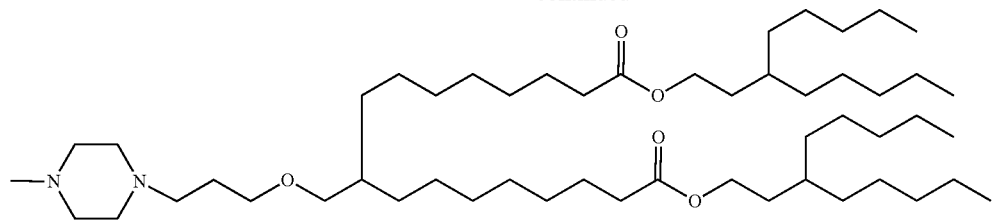
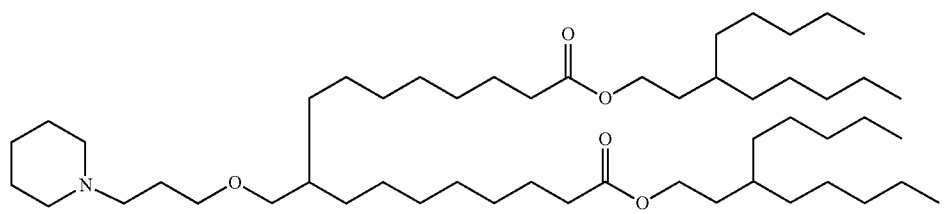
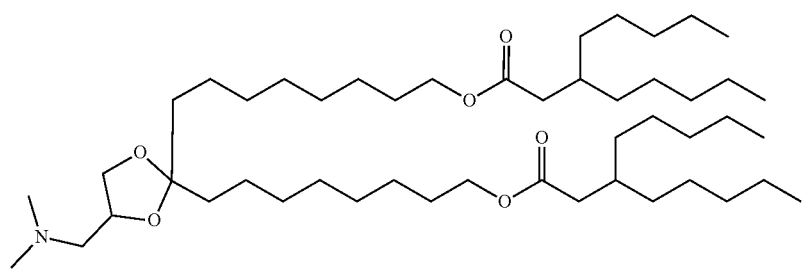
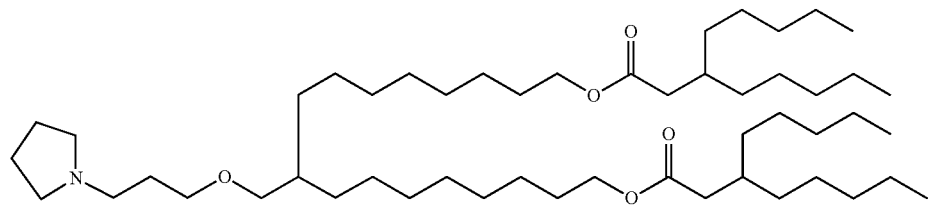
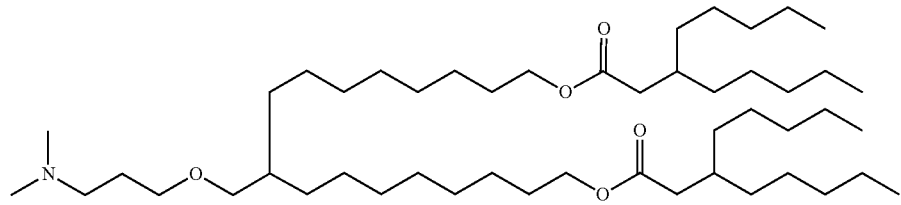
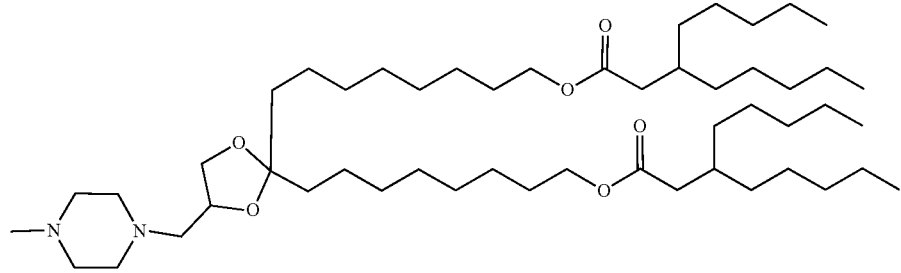
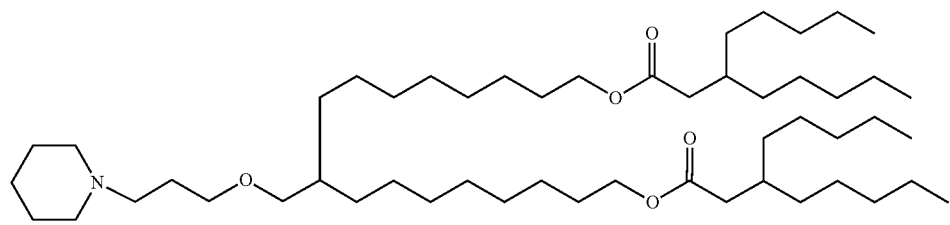

-continued
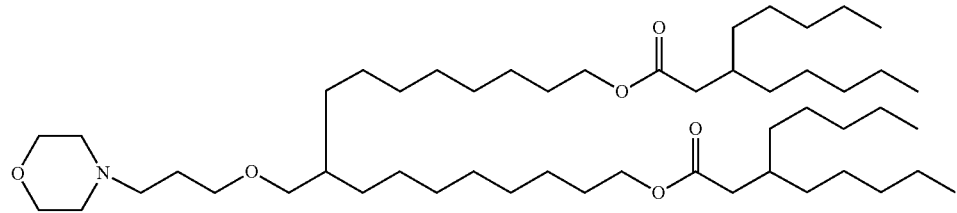
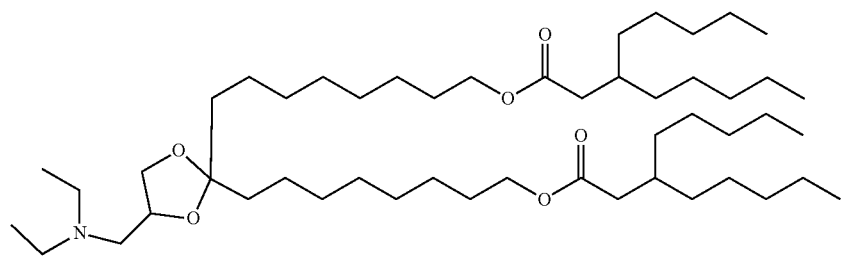
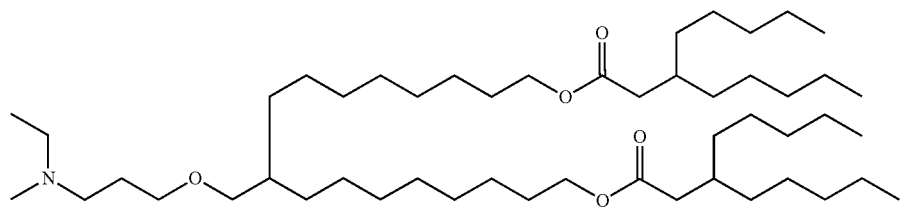
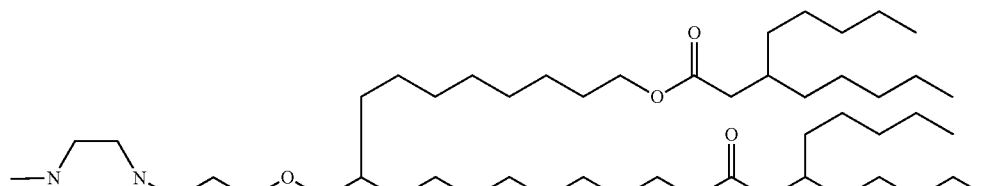
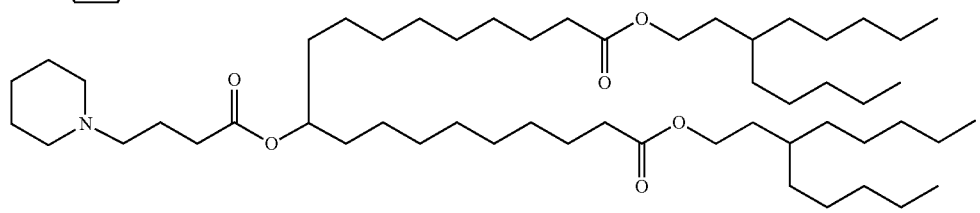
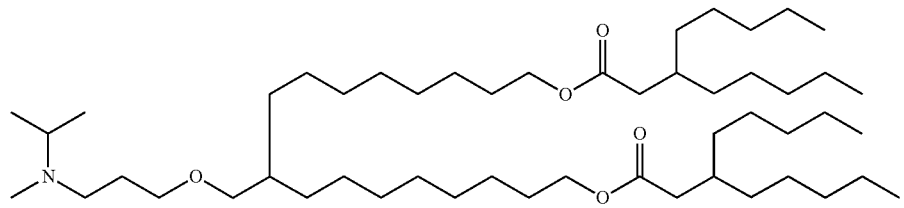
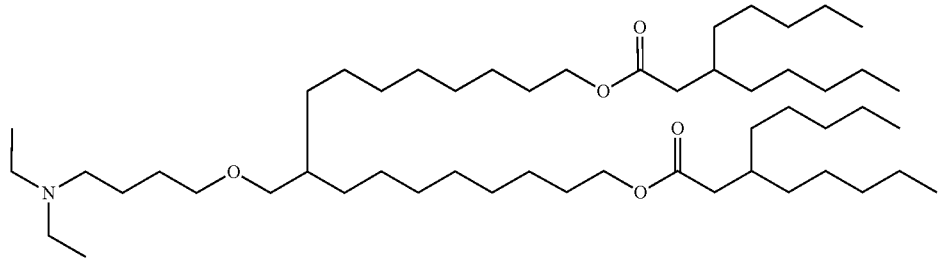

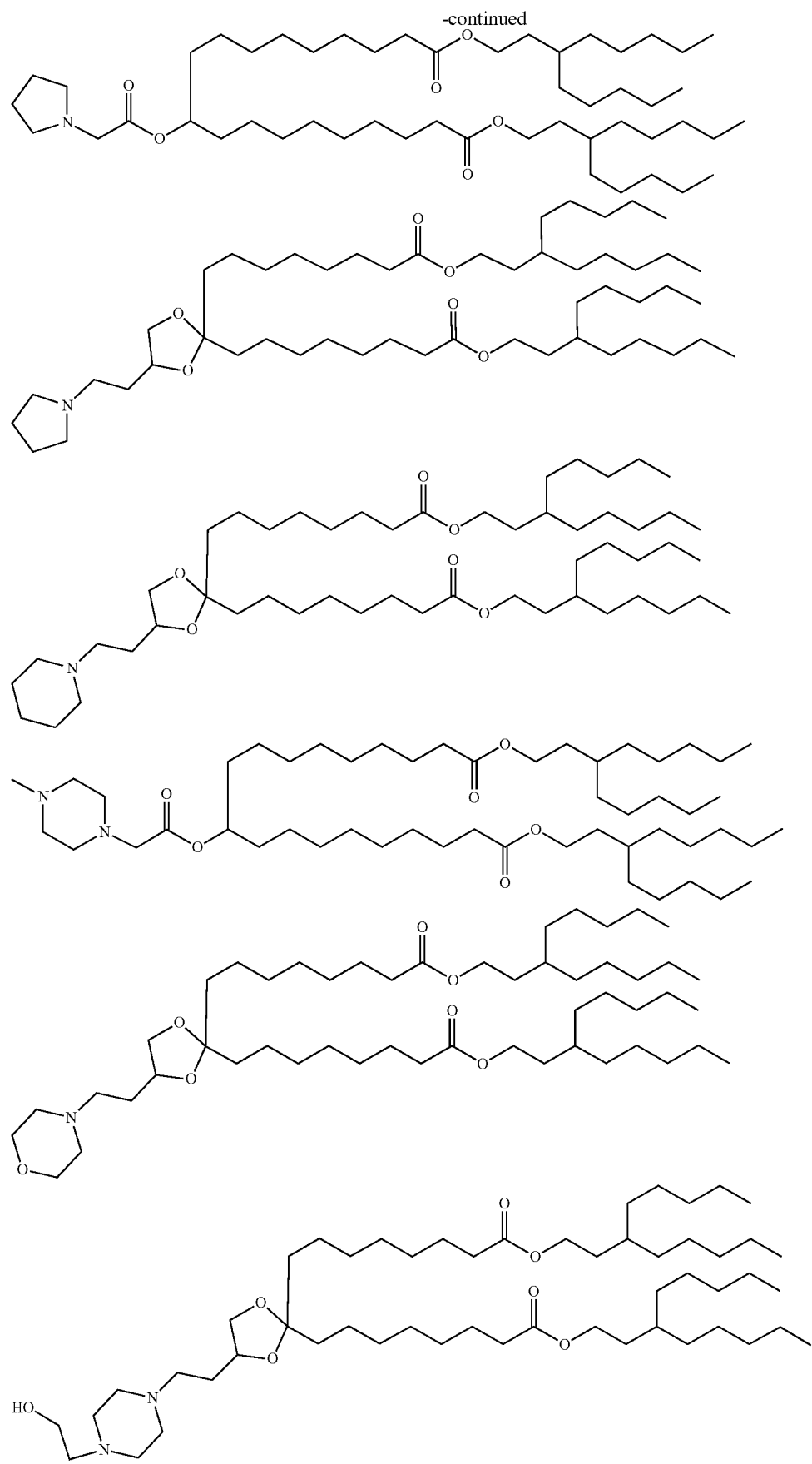

-continued
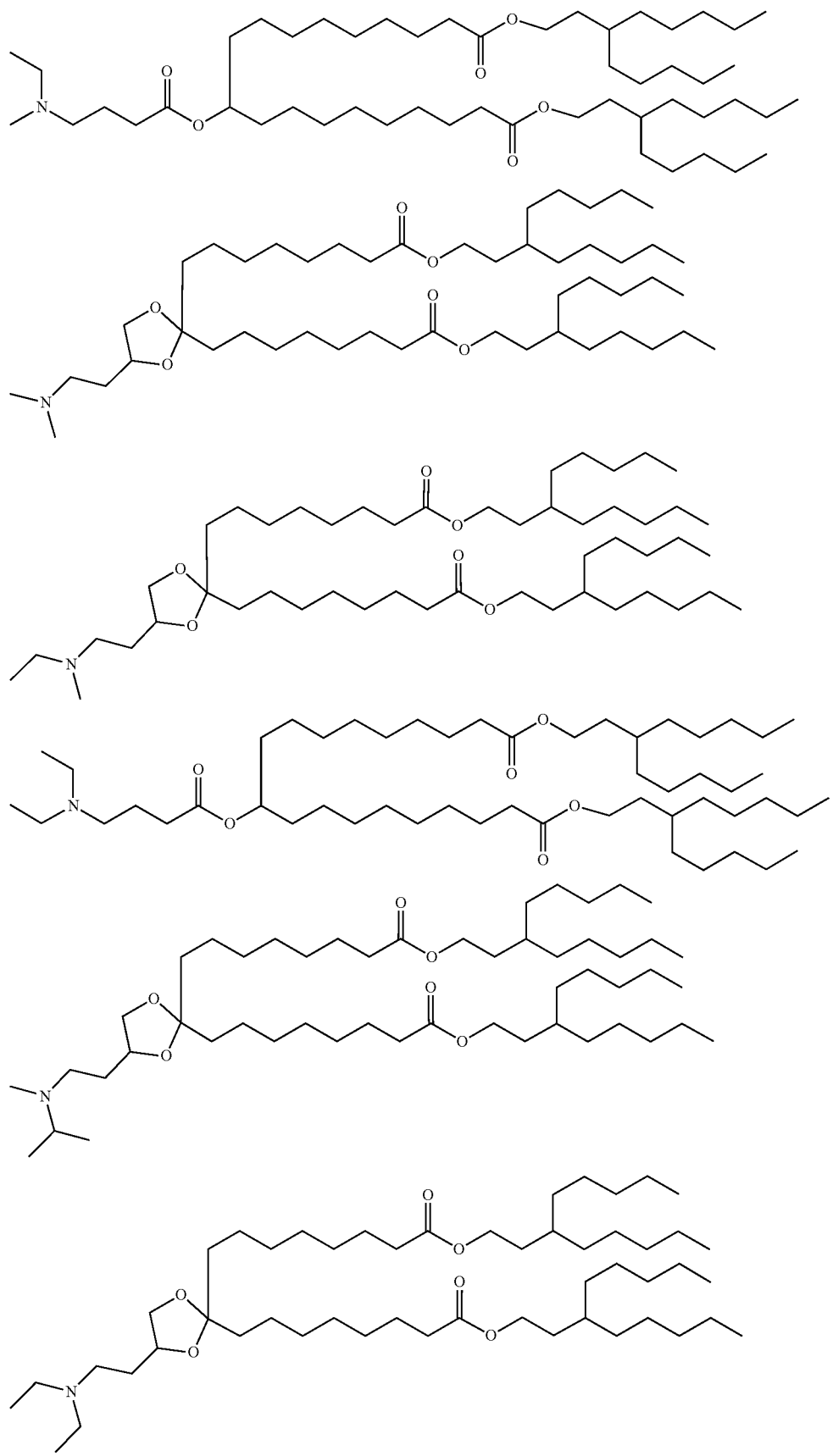

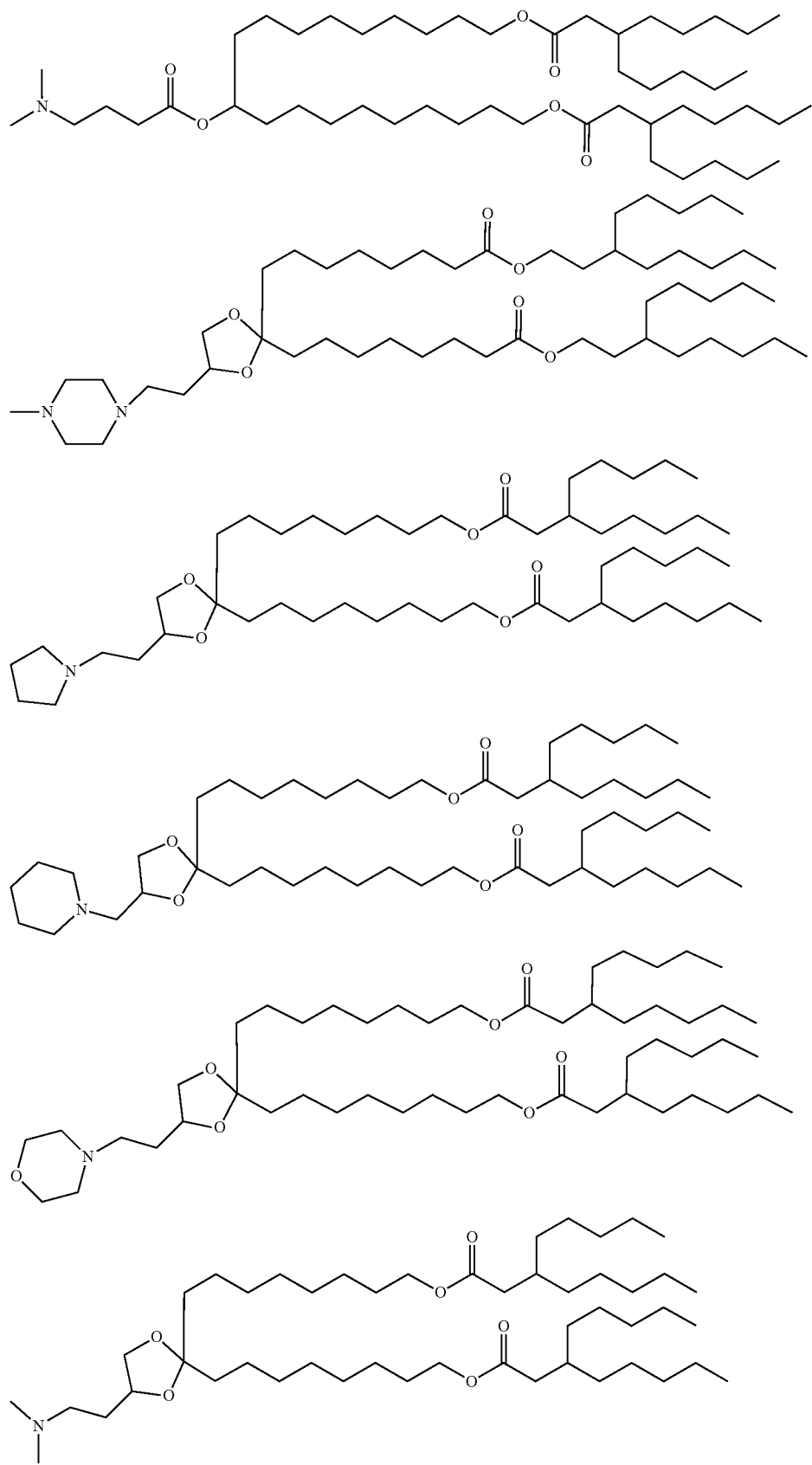

-continued
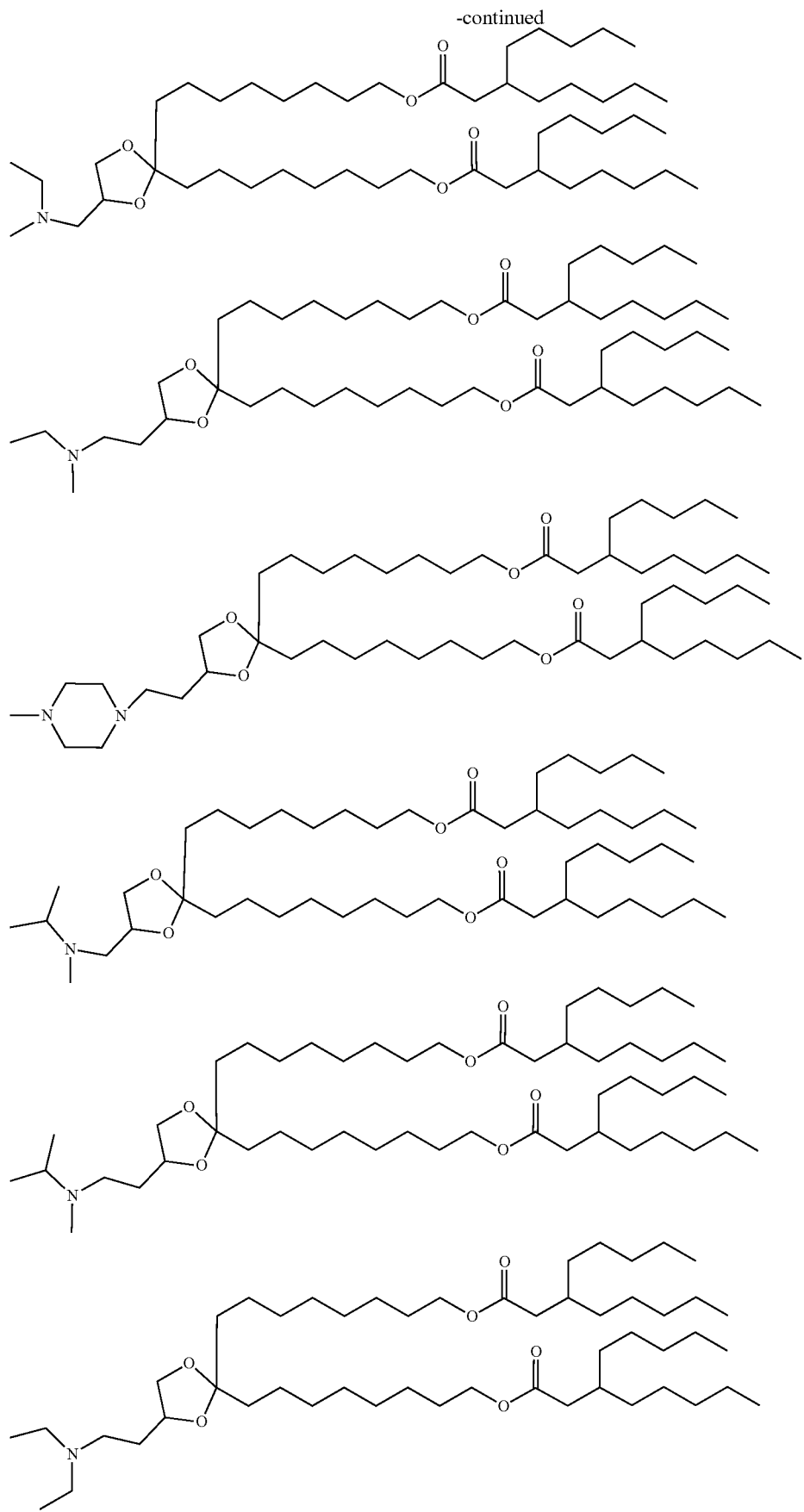

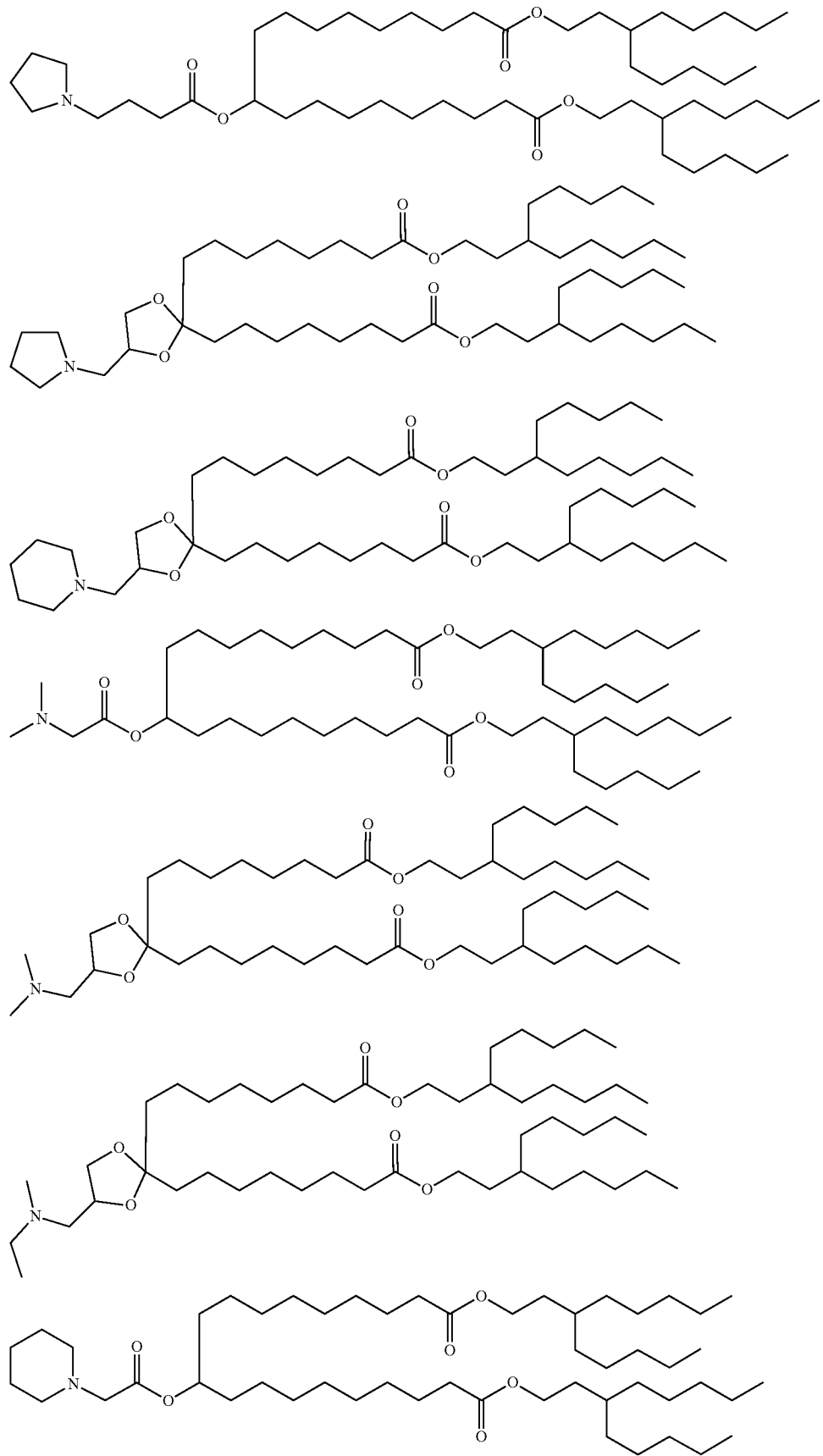

-continued
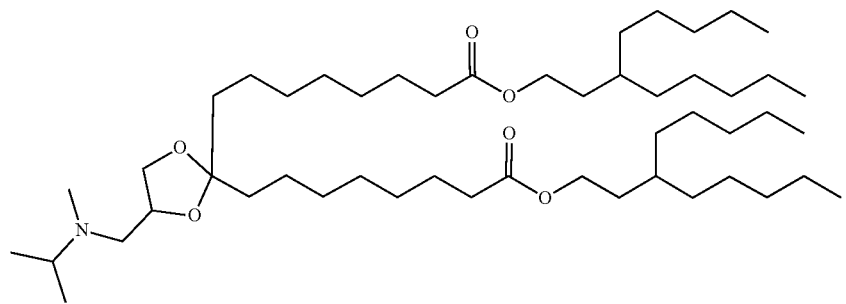
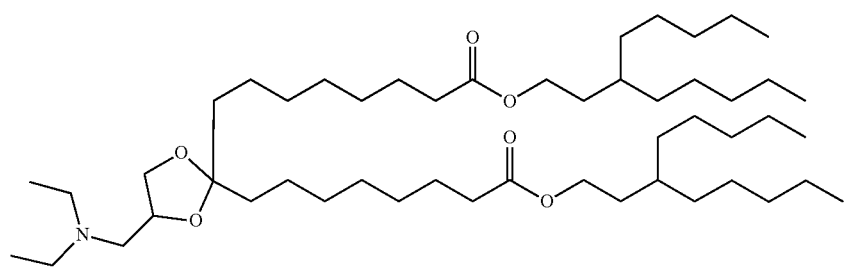
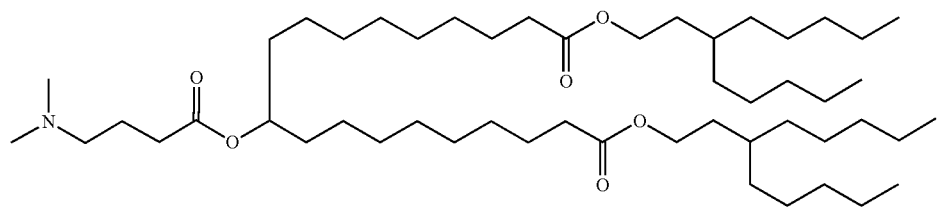
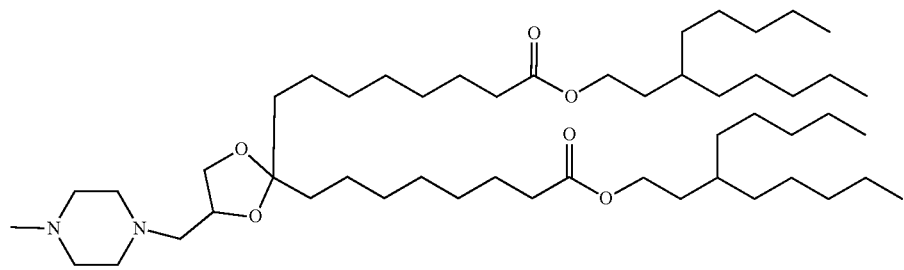
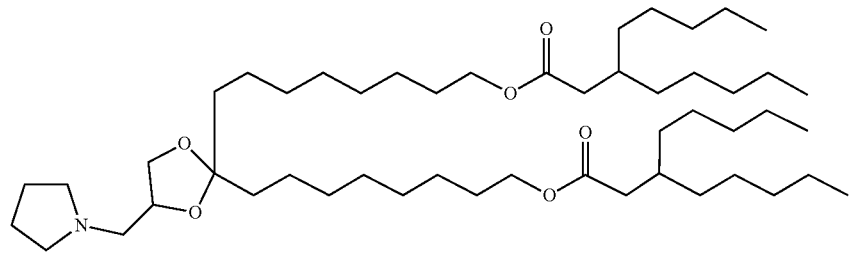
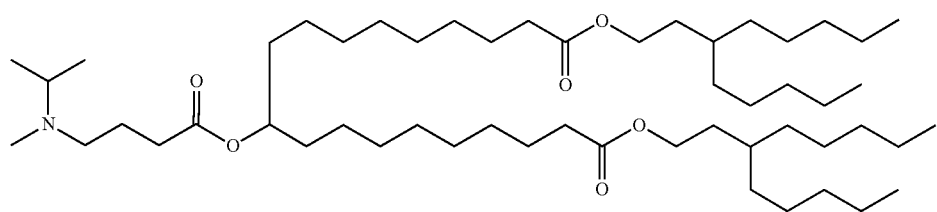

-continued
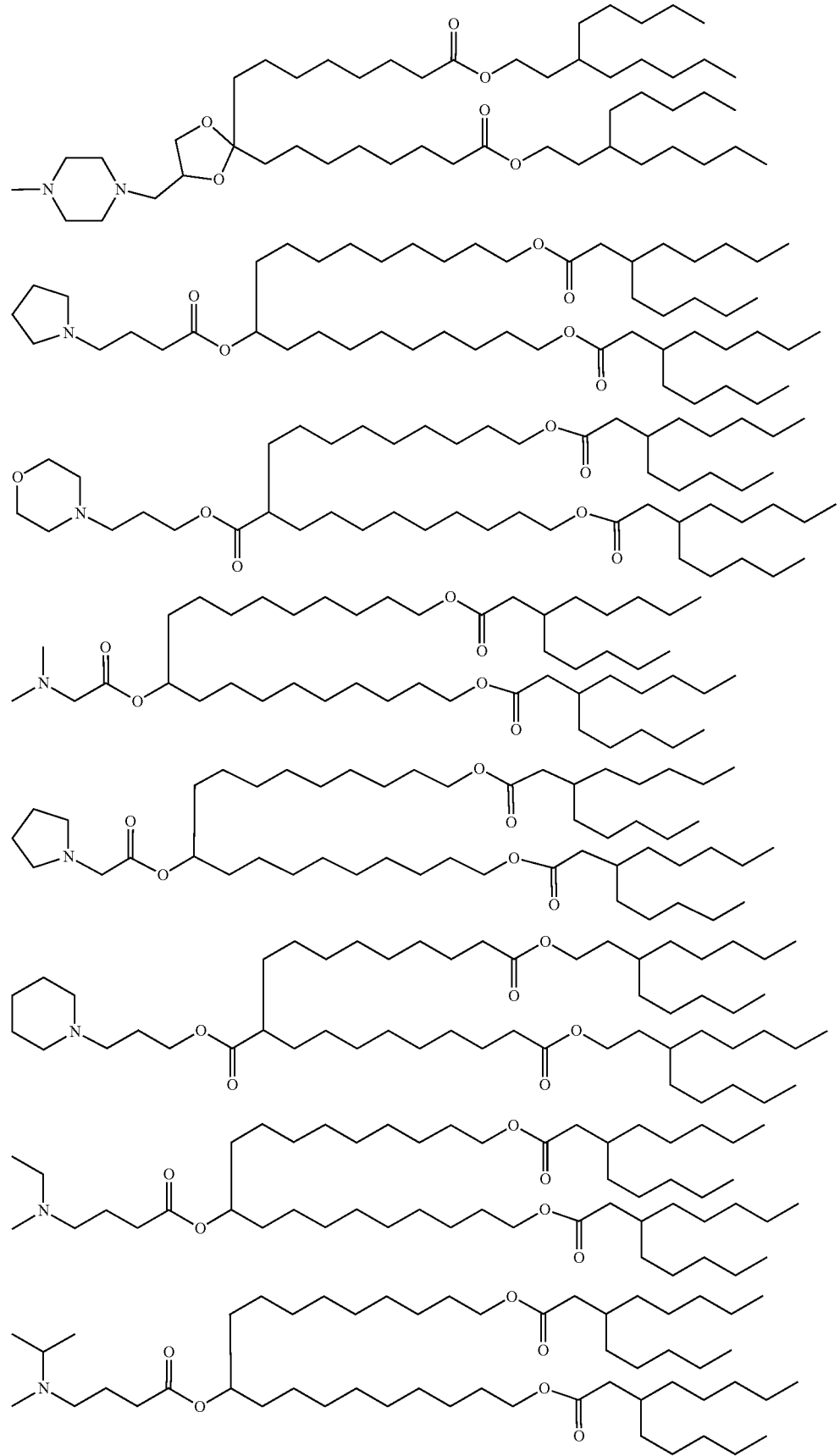

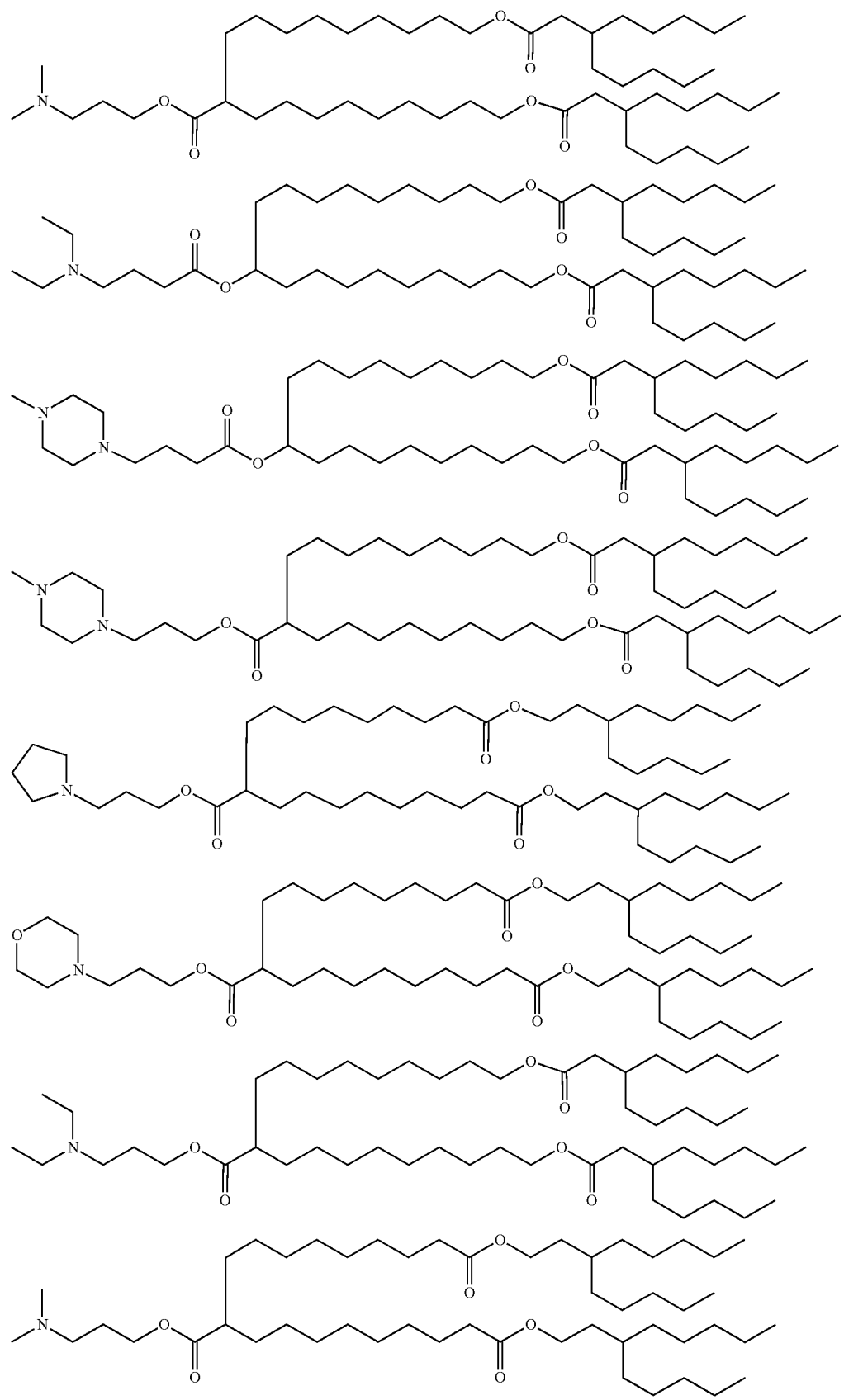

-continued
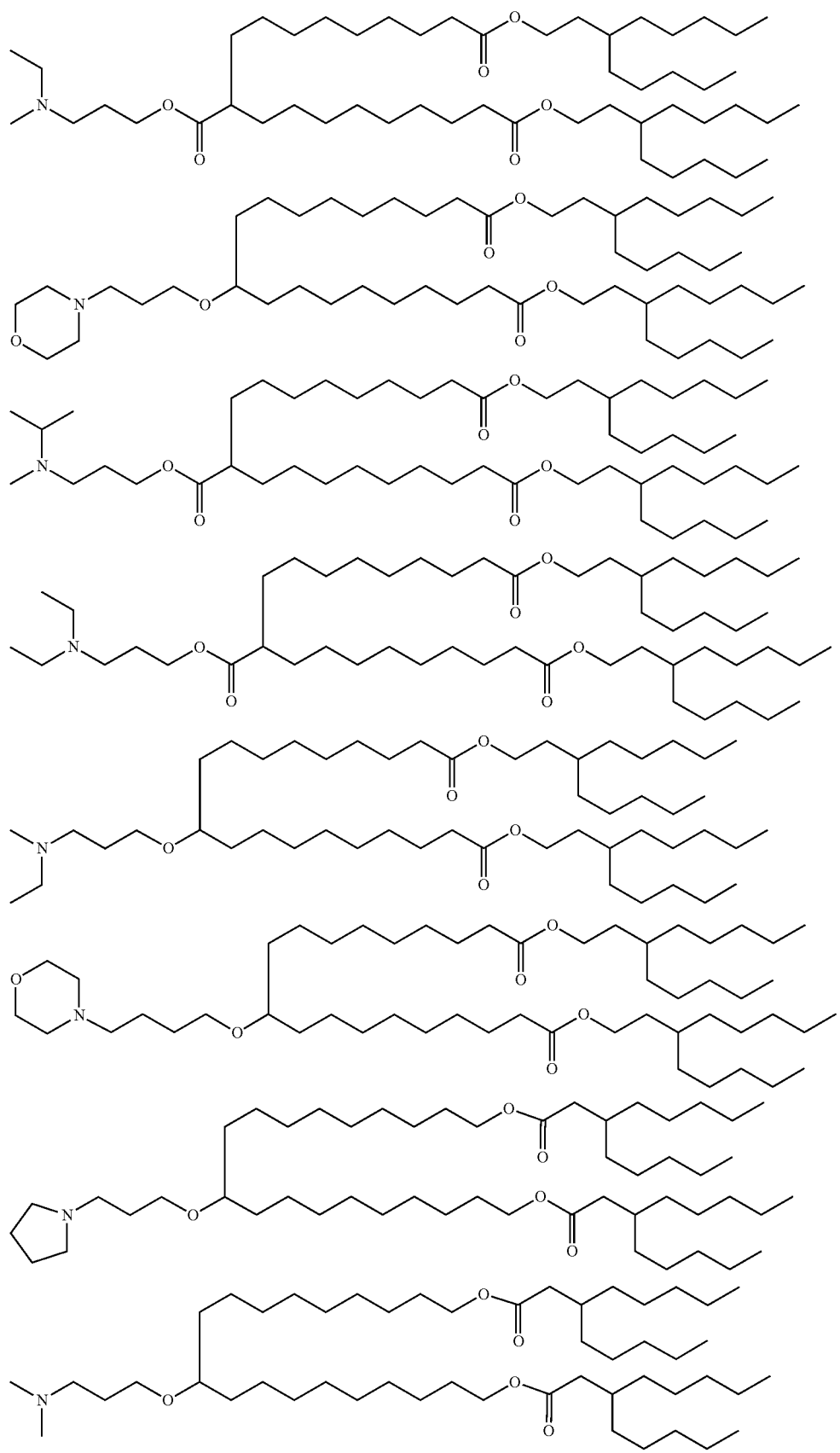

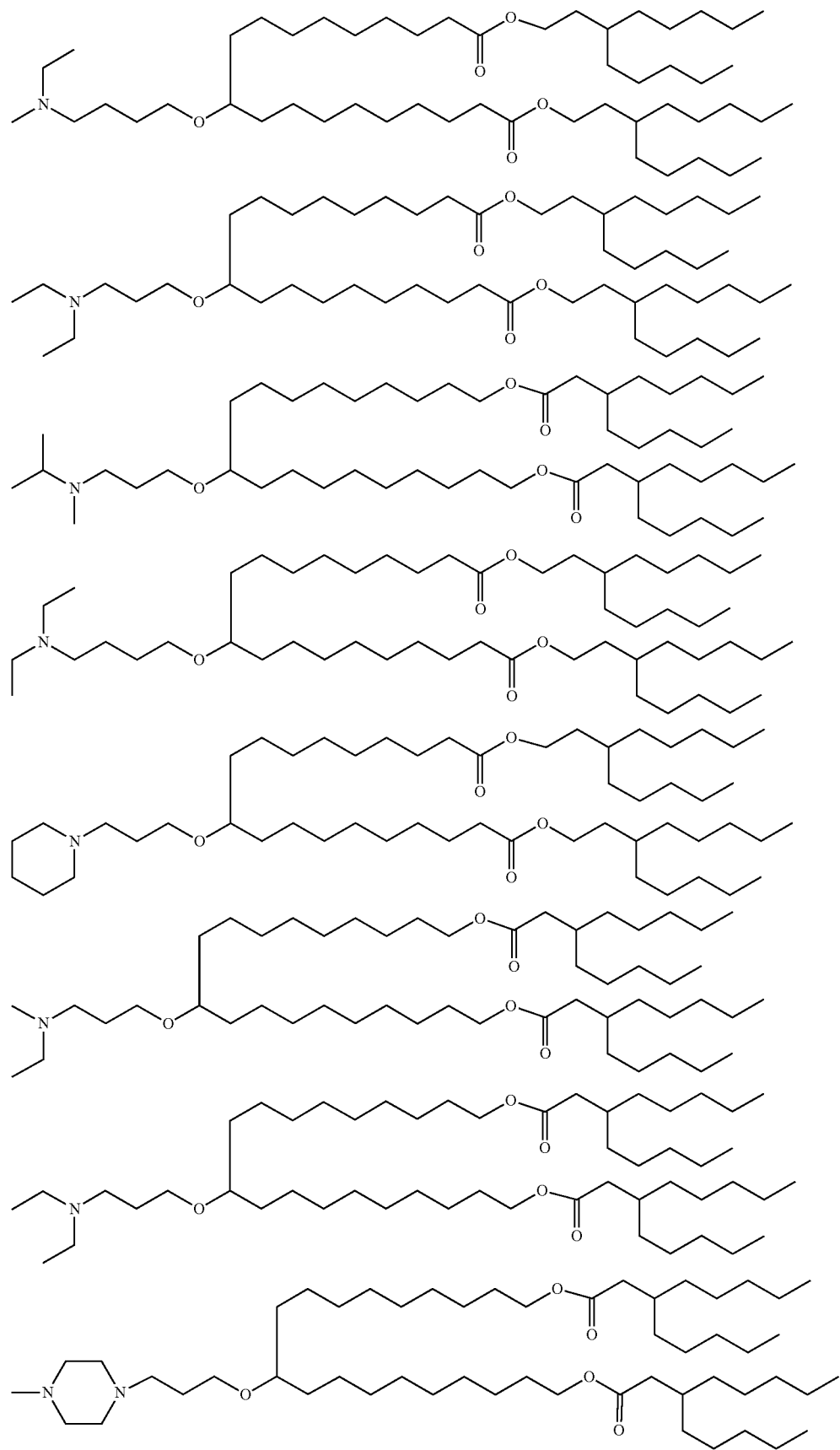
-continued

-continued
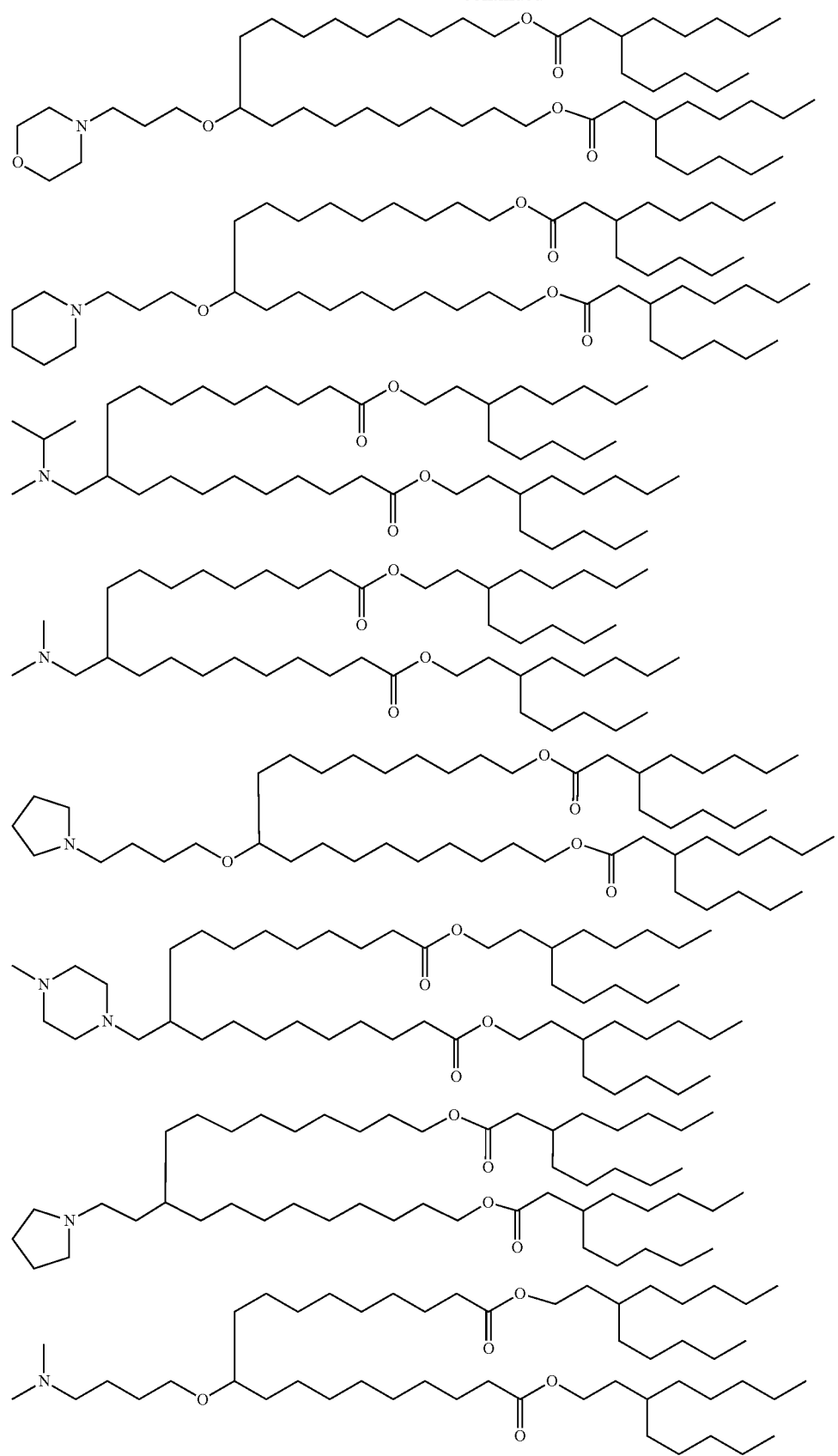

-continued
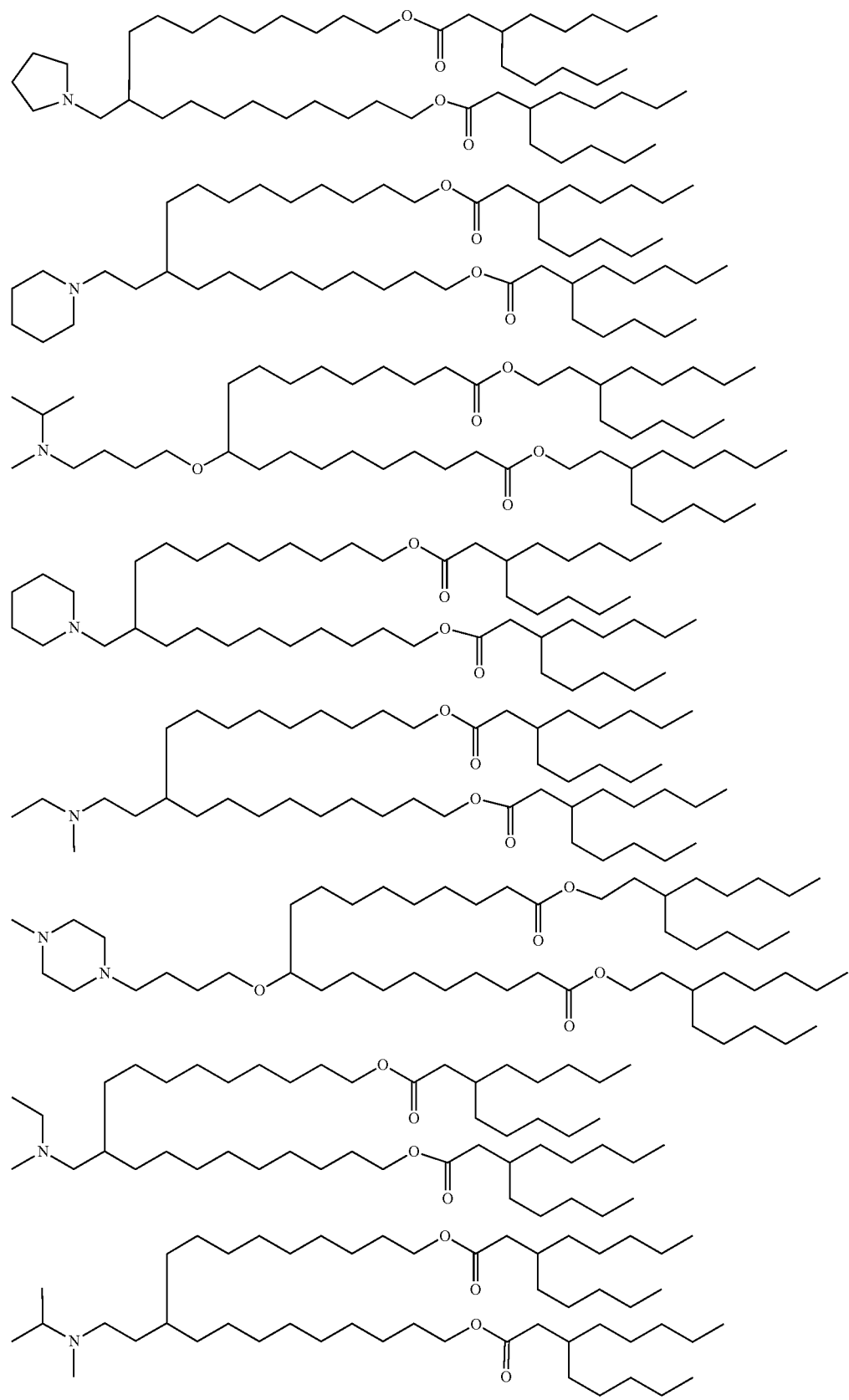

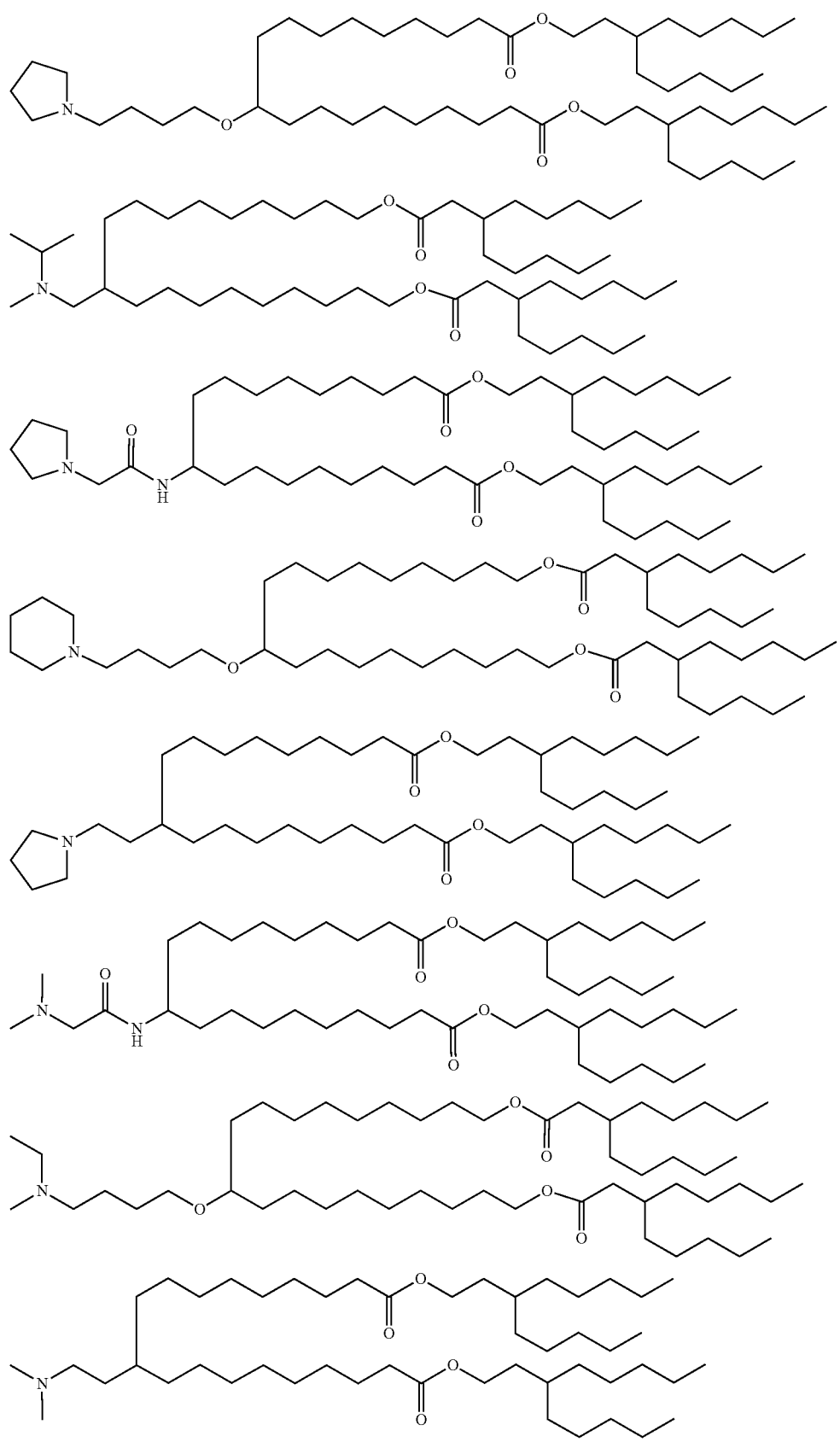

-continued
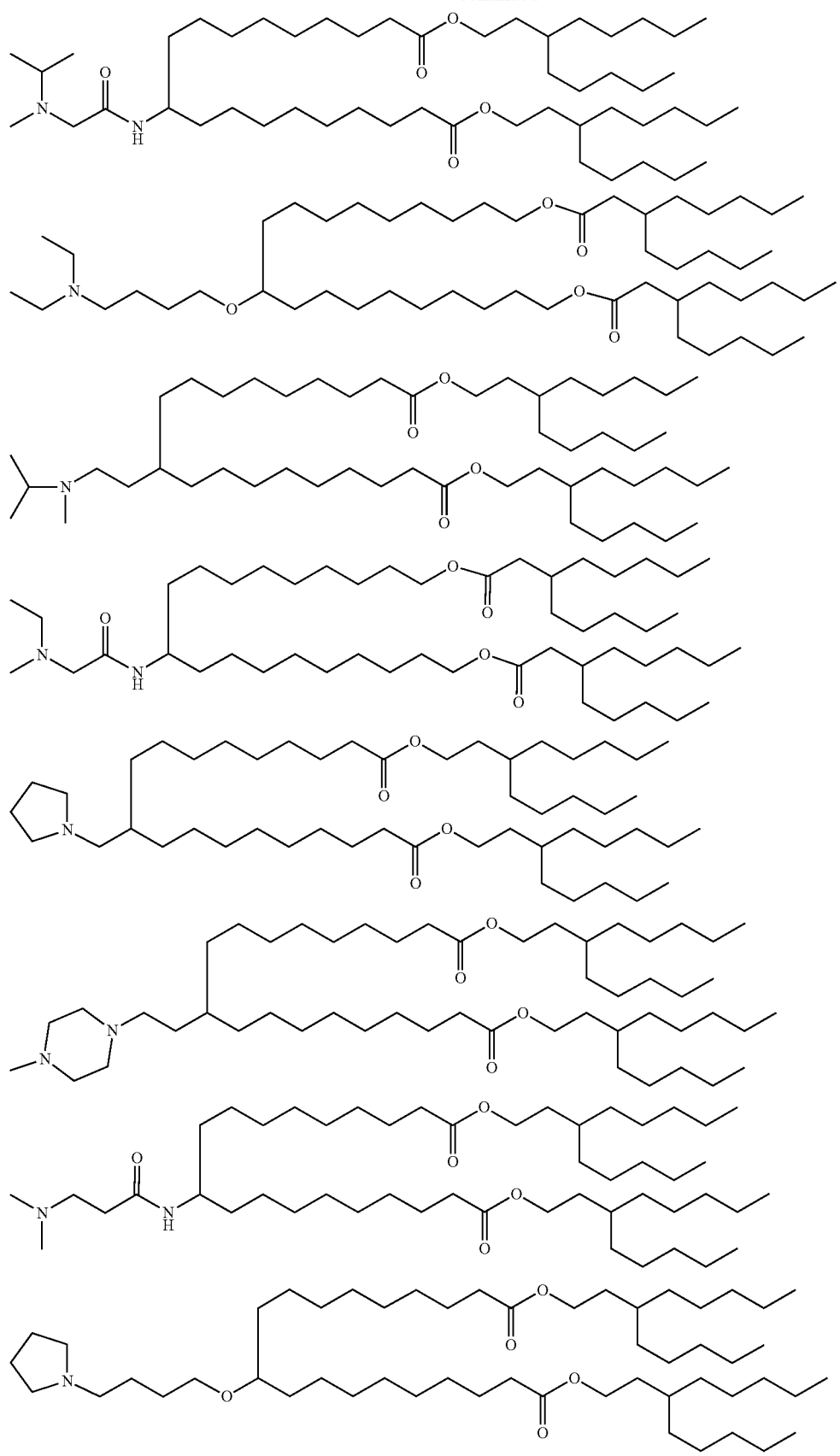

-continued
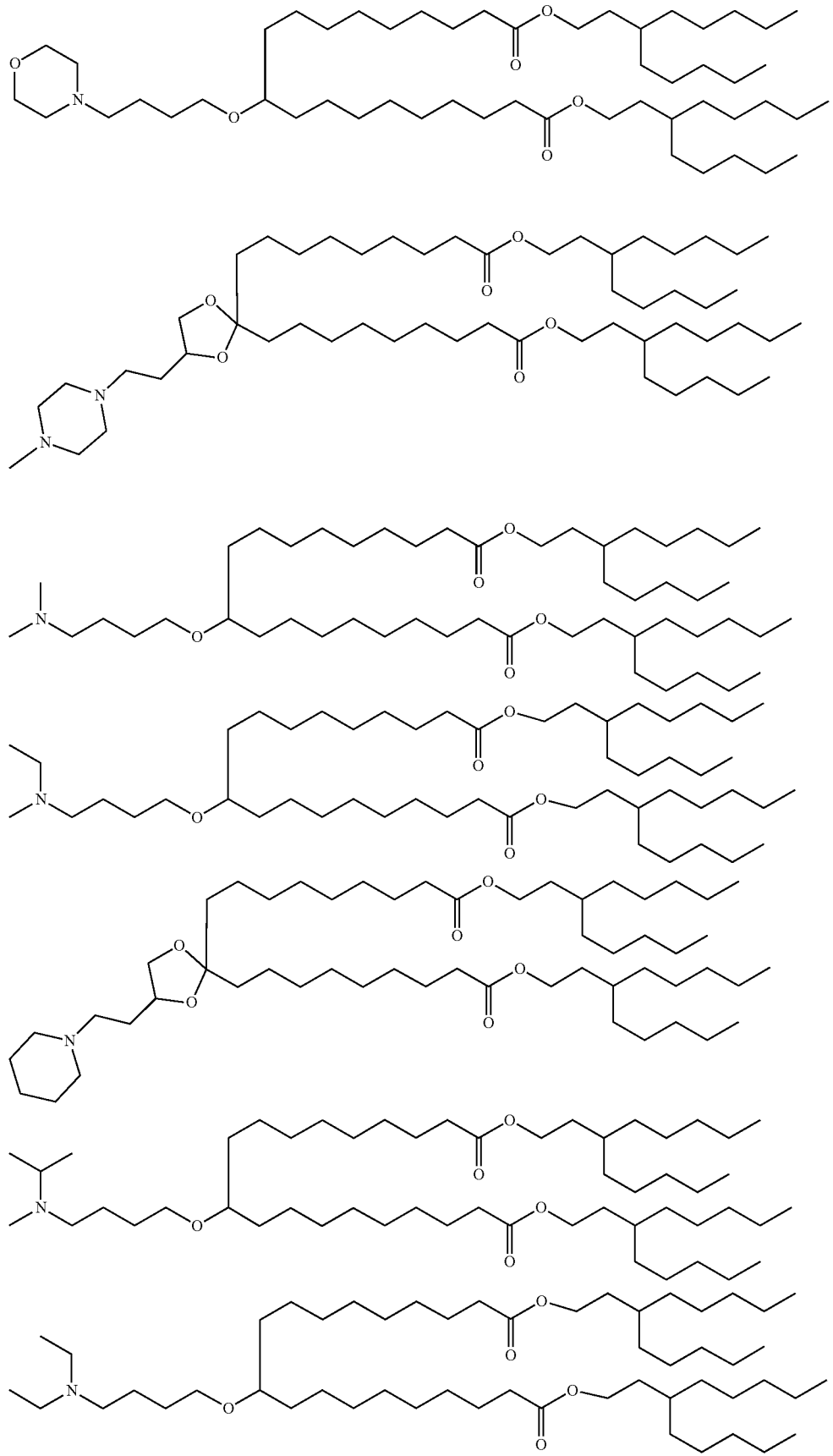

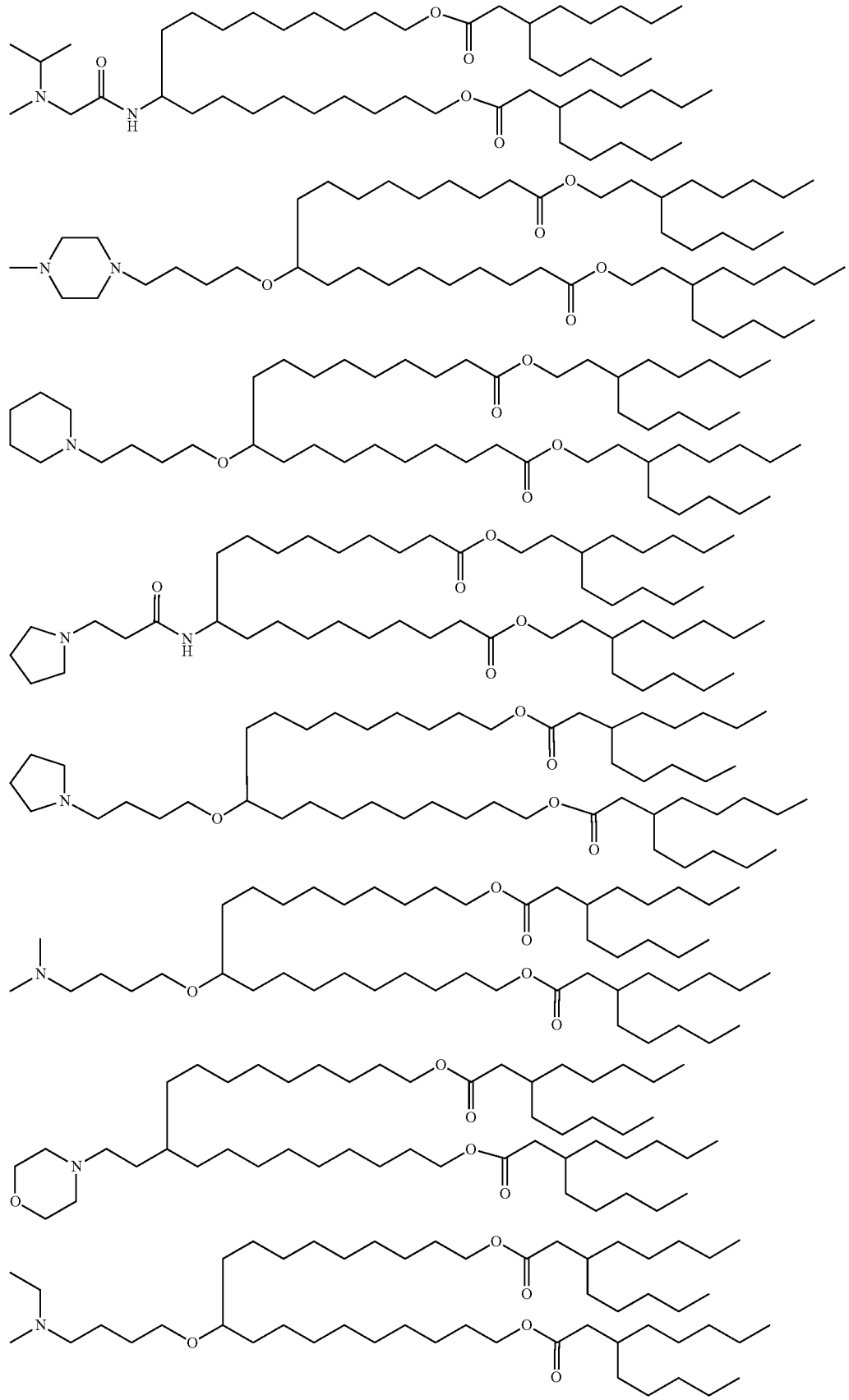

-continued
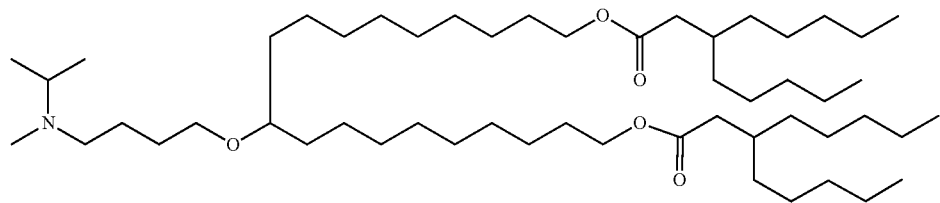
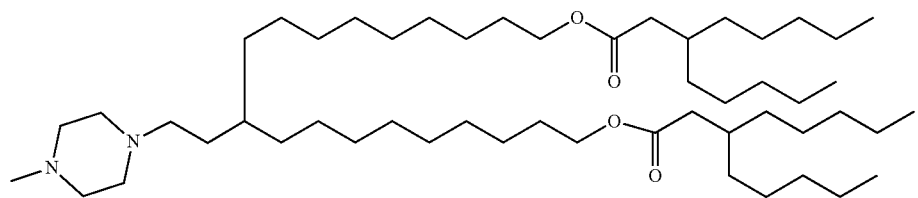
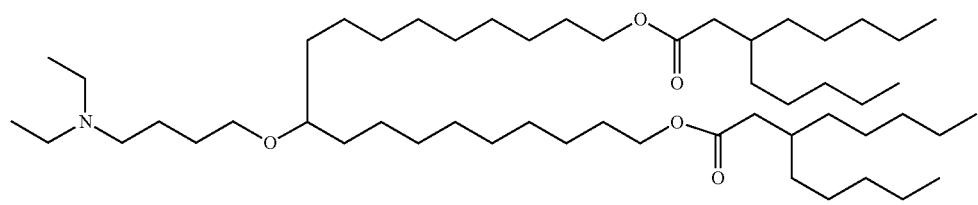
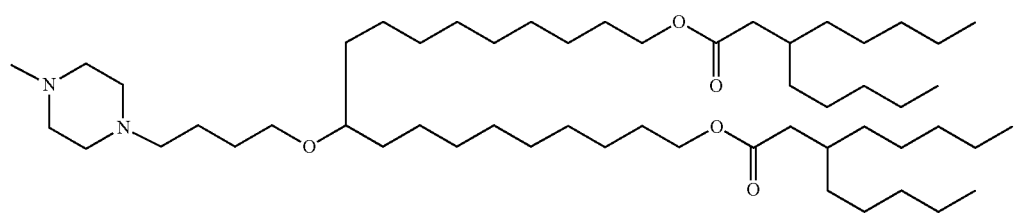
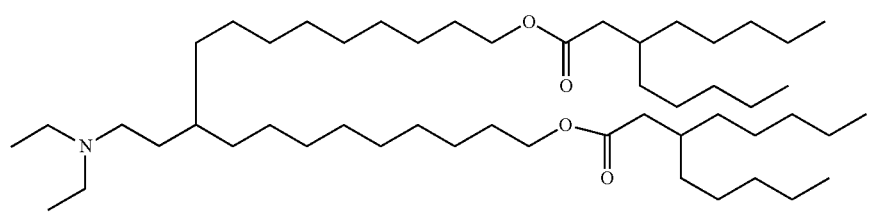
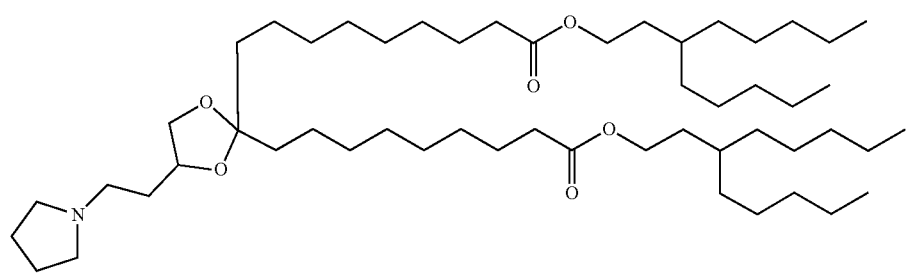
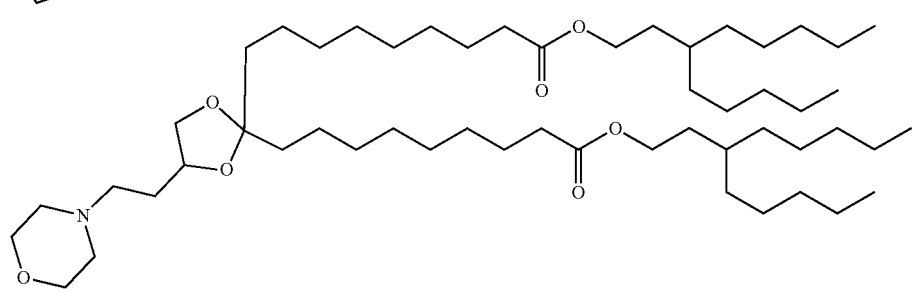

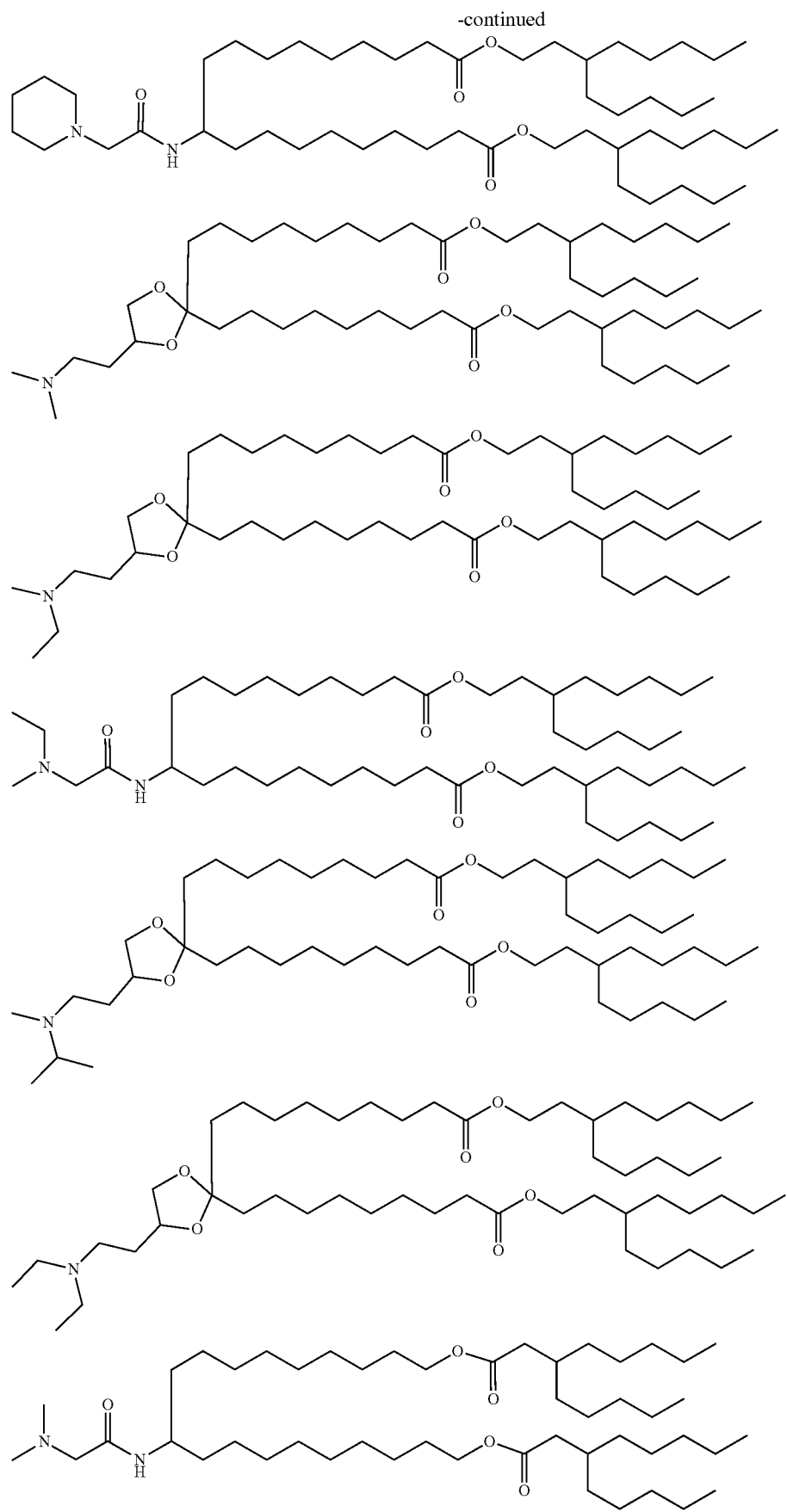

-continued
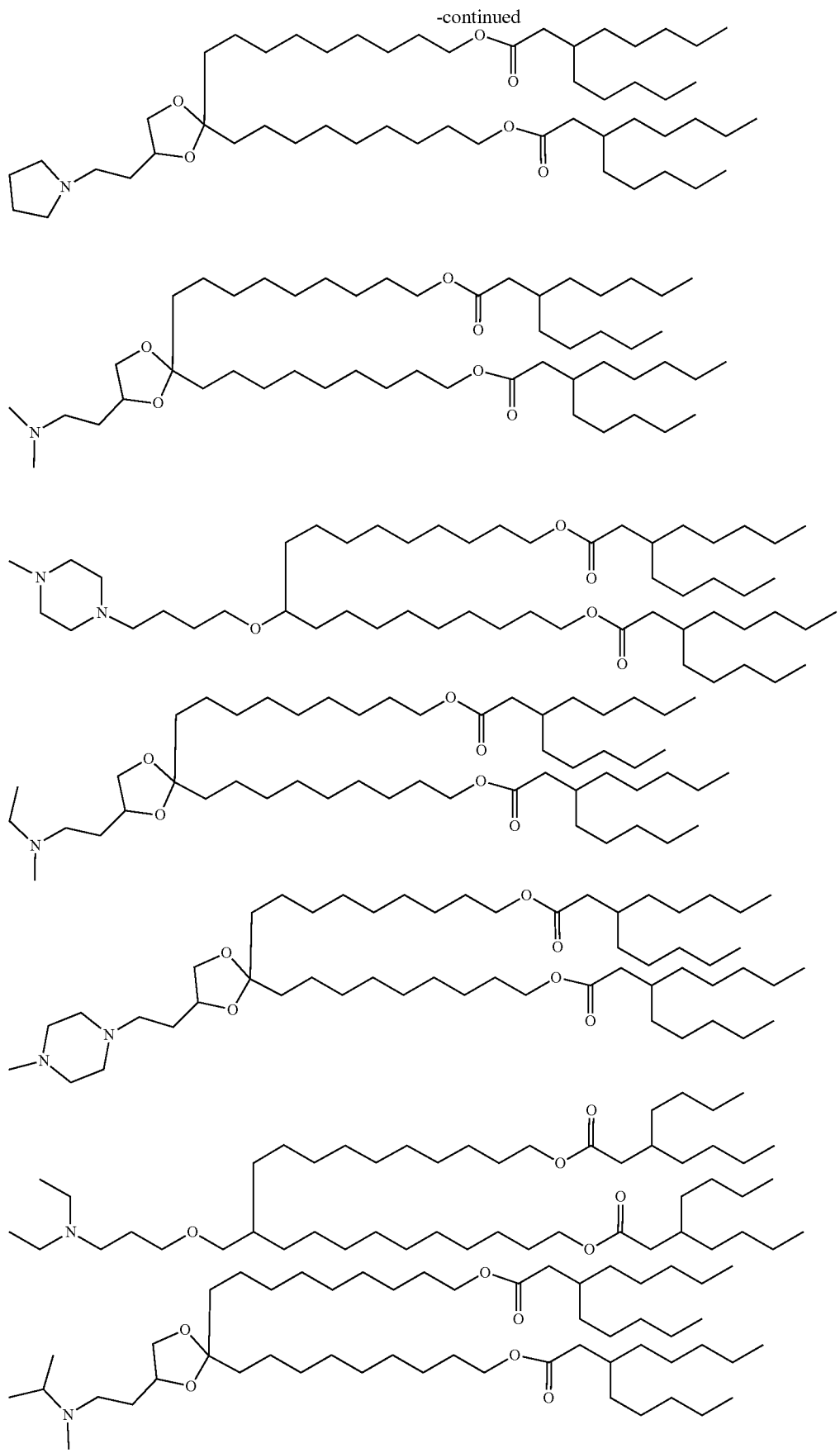

-continued
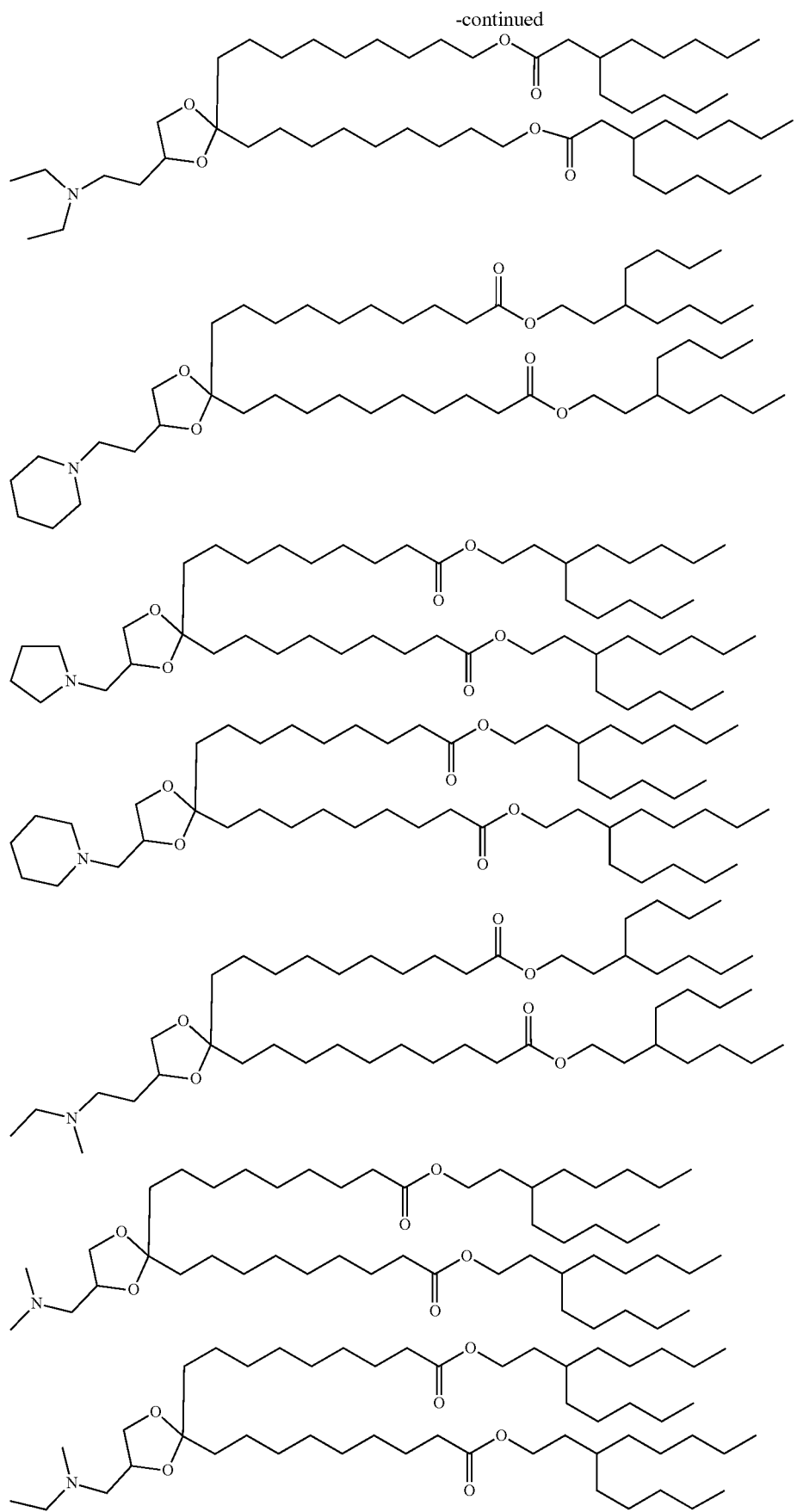

-continued
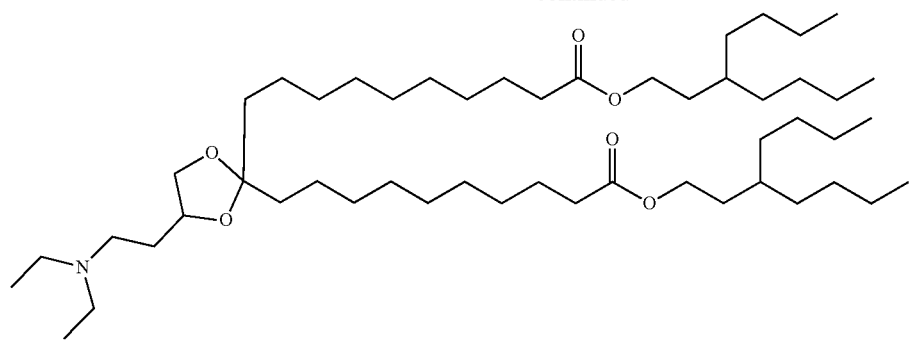
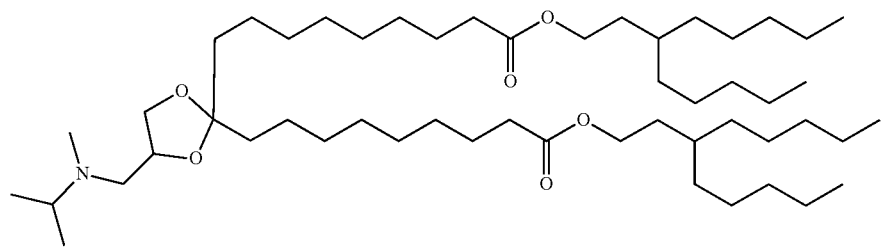
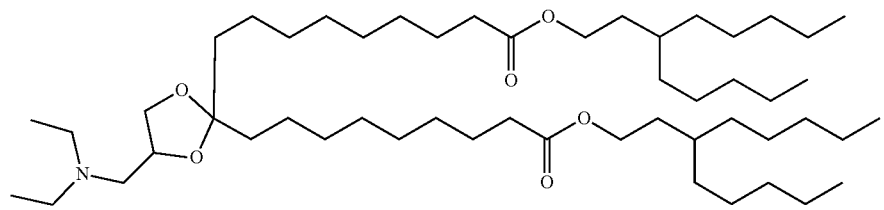
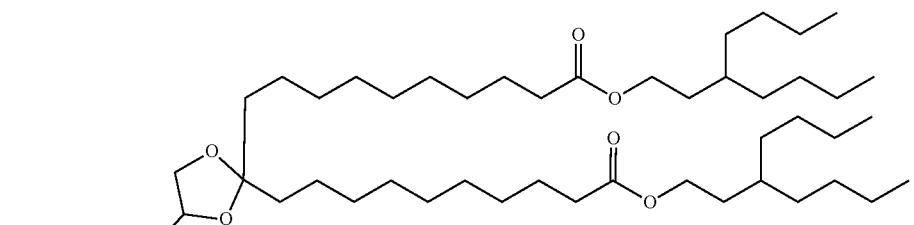
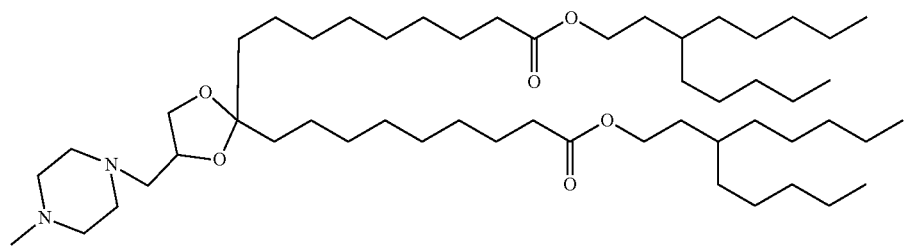
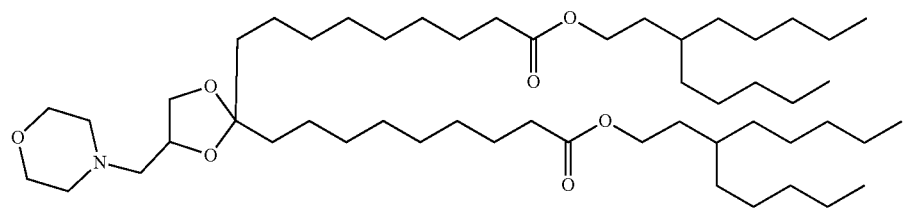

-continued
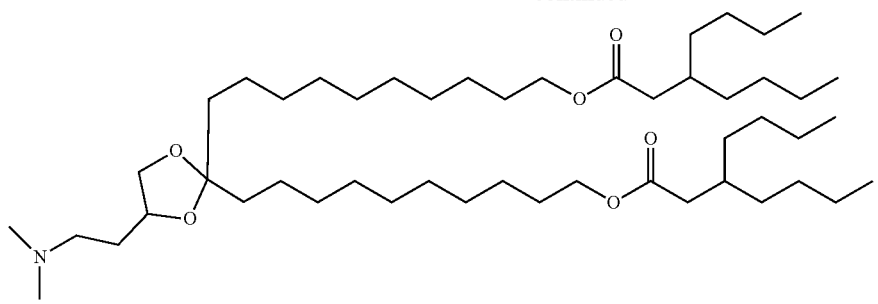
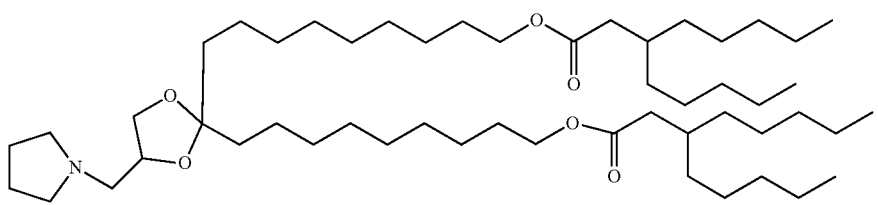
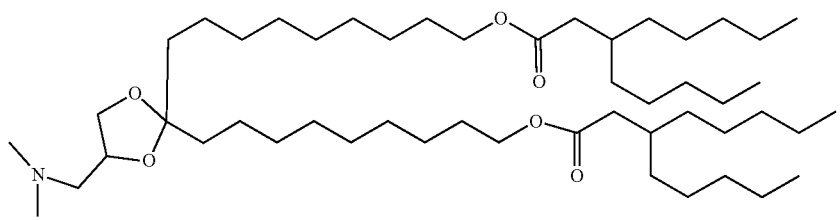
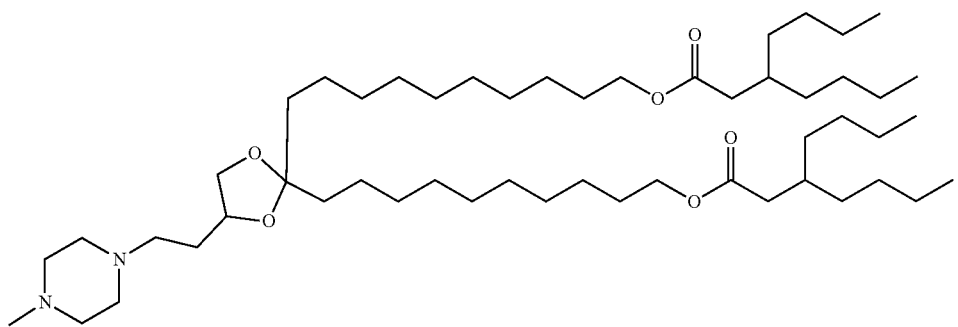
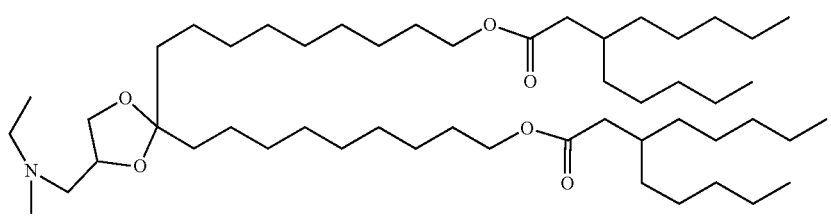
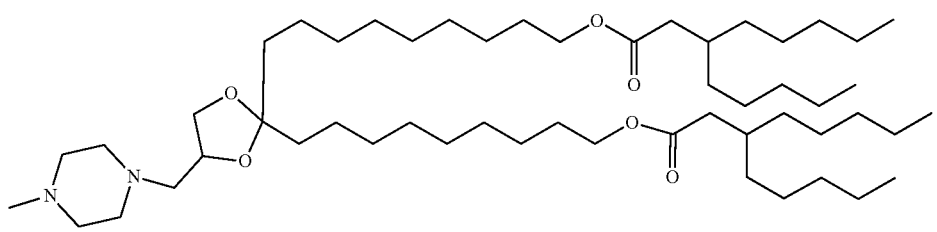

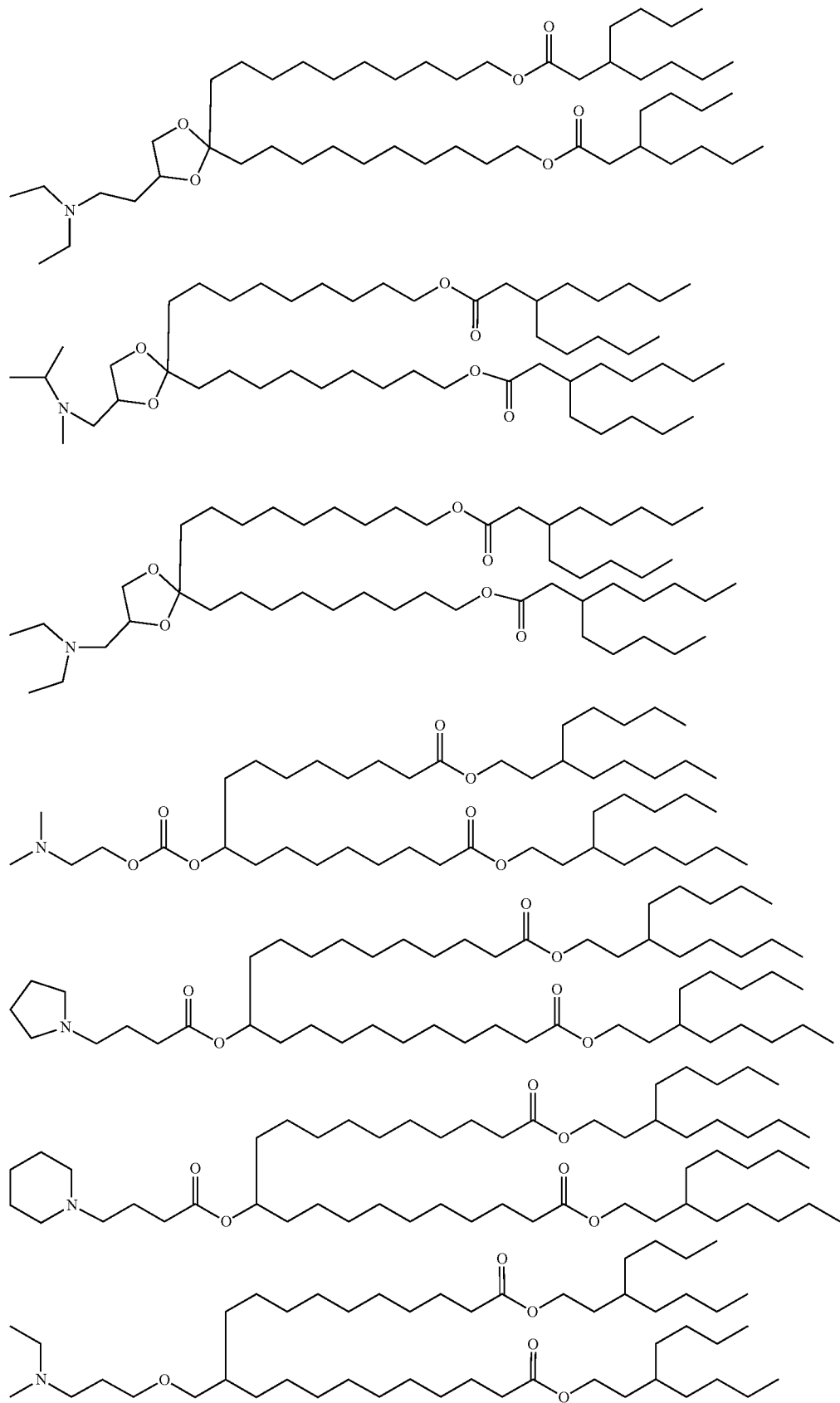

-continued
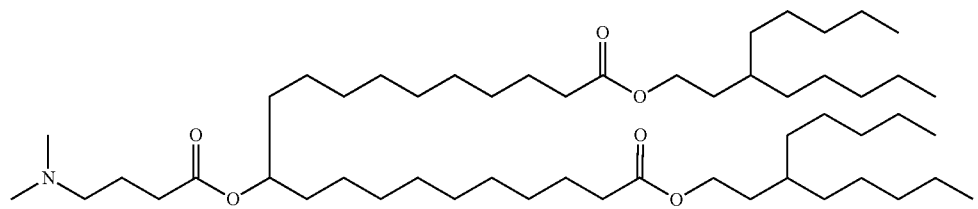
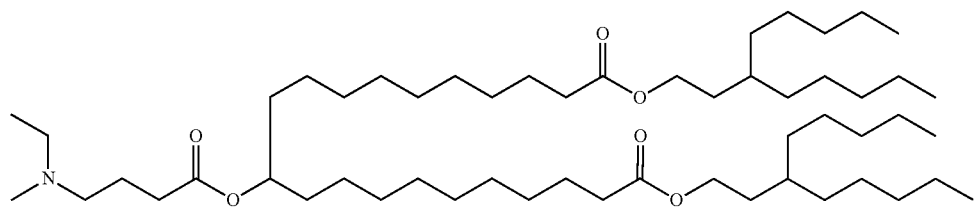
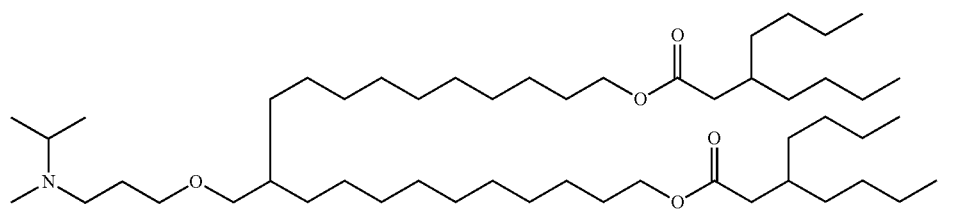
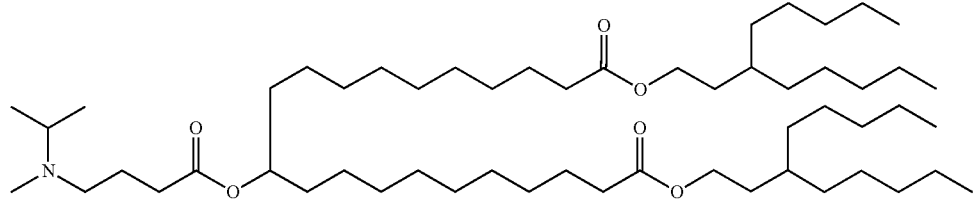
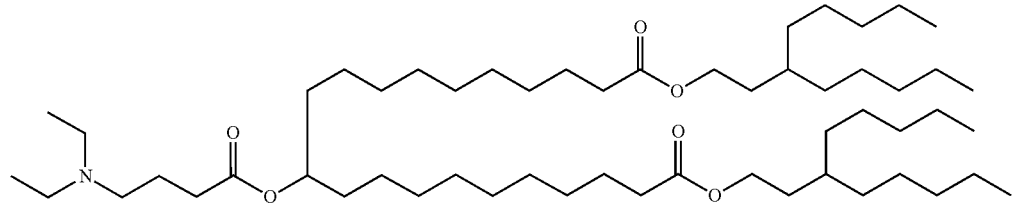
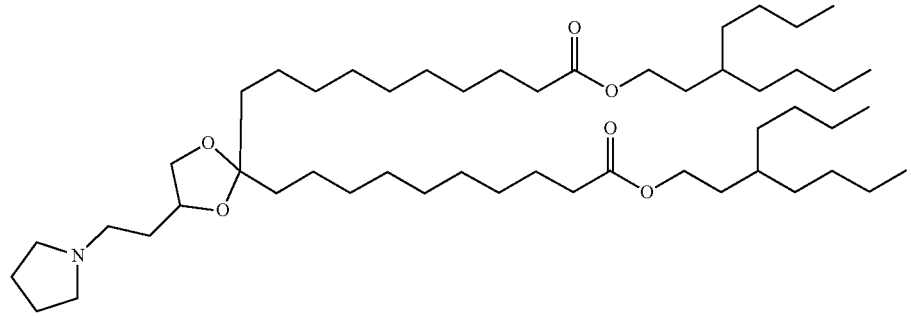
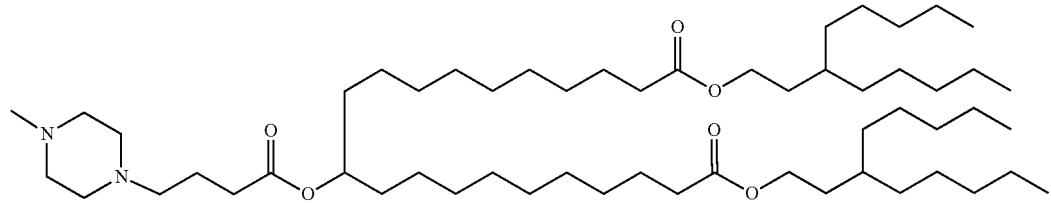

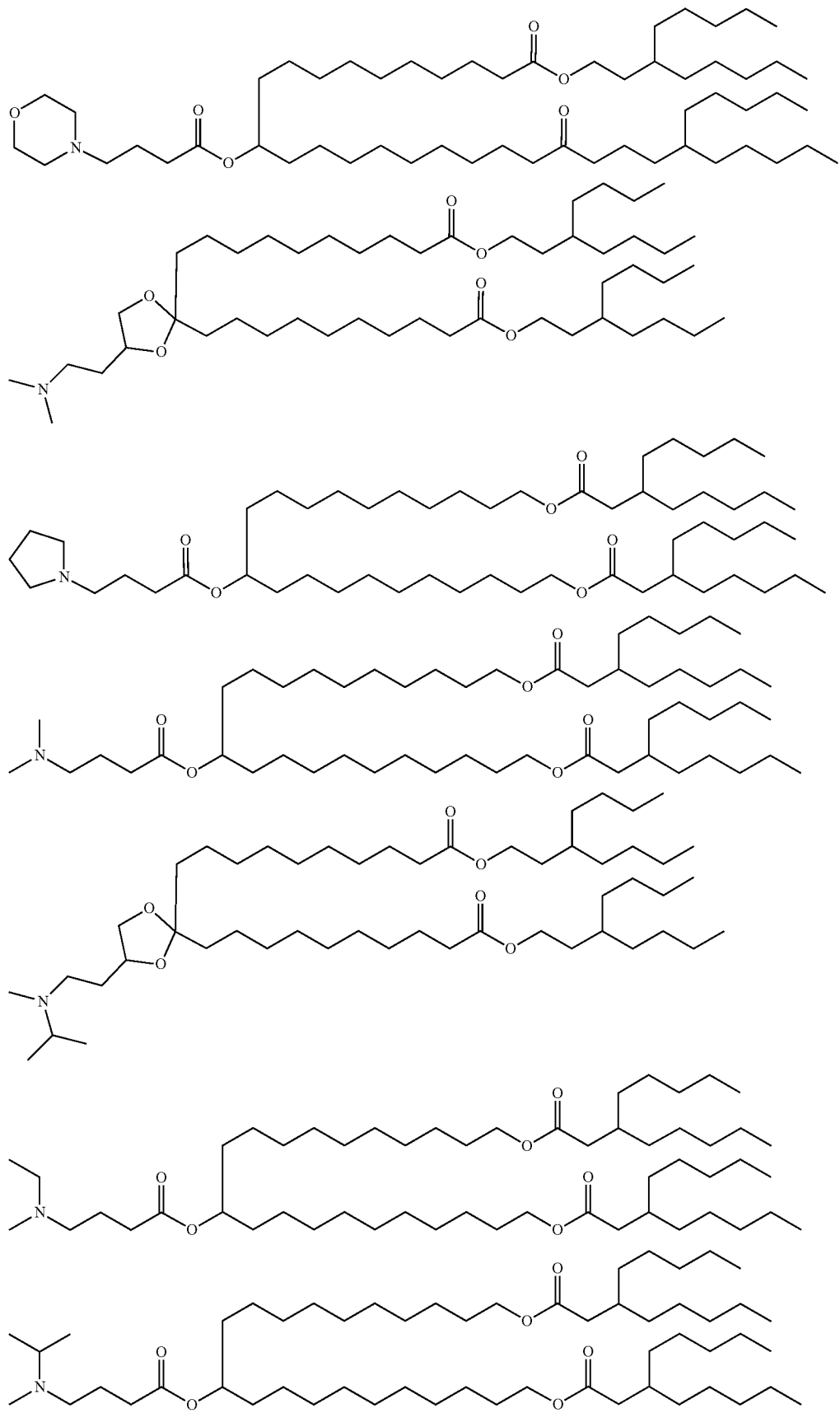

-continued
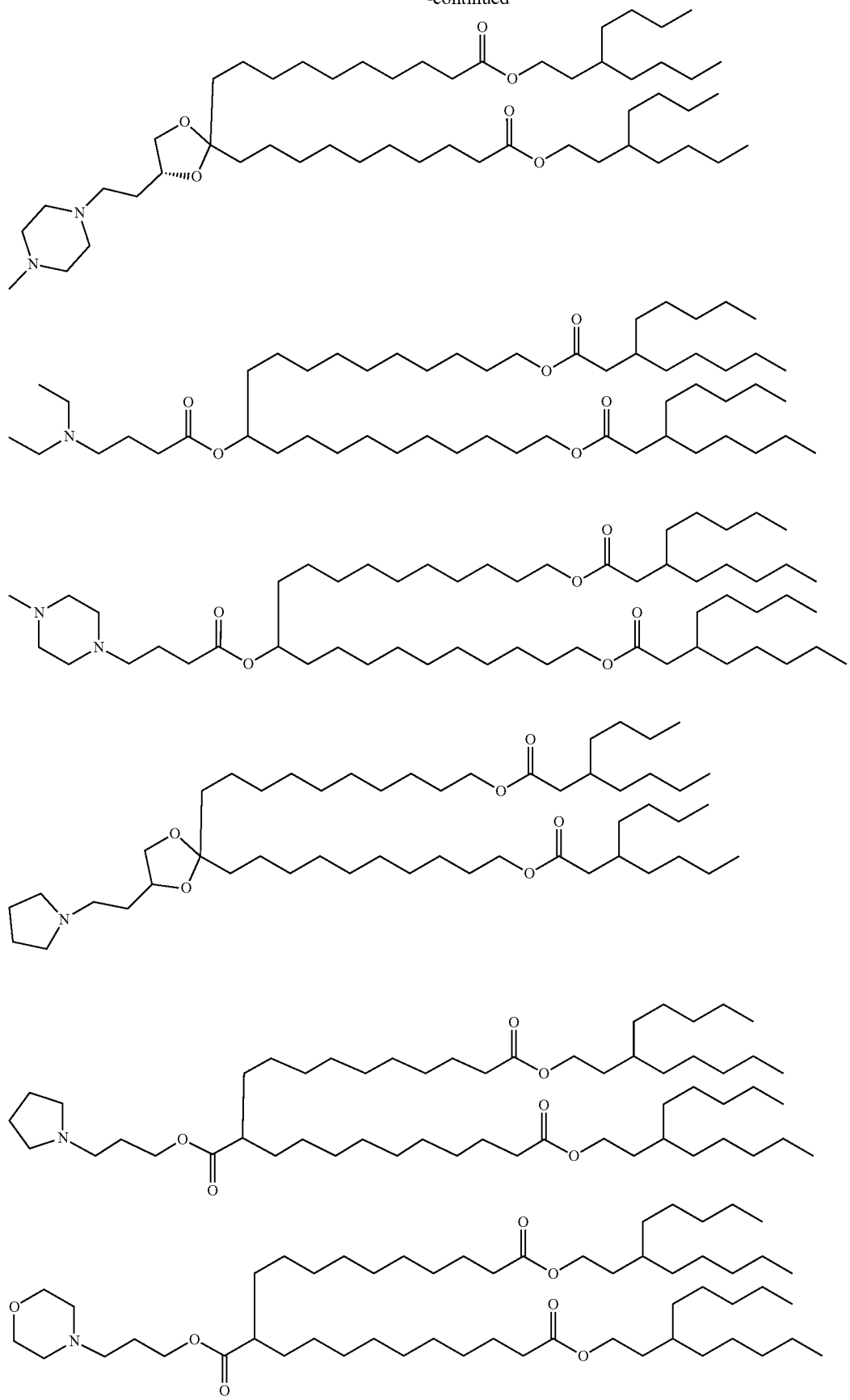

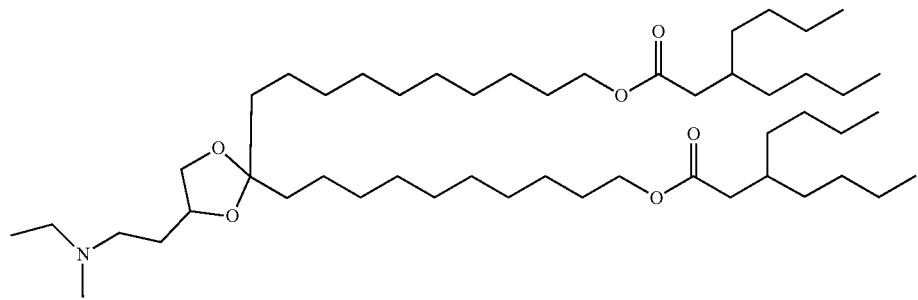
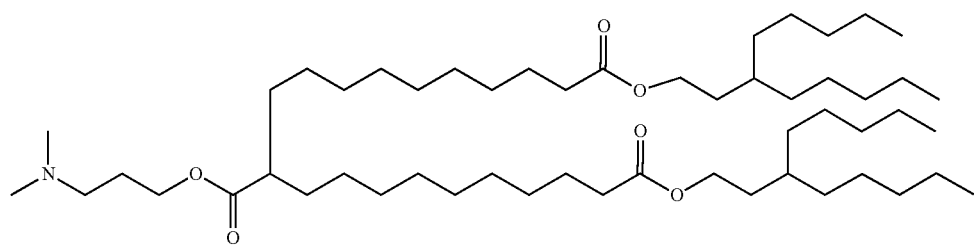
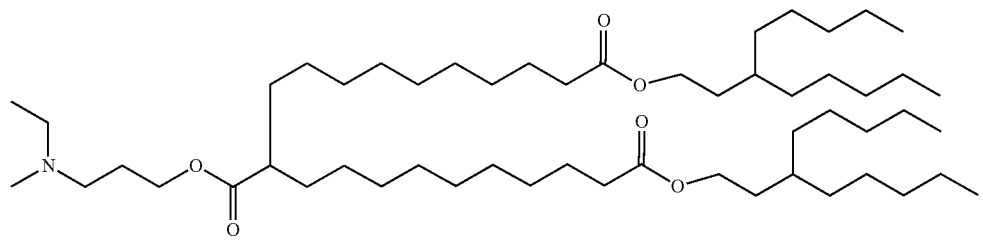
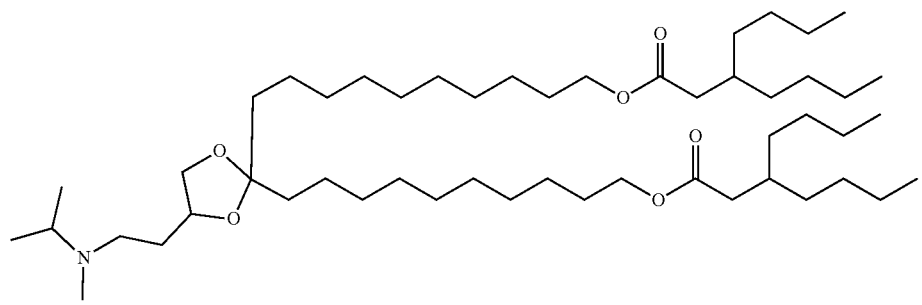
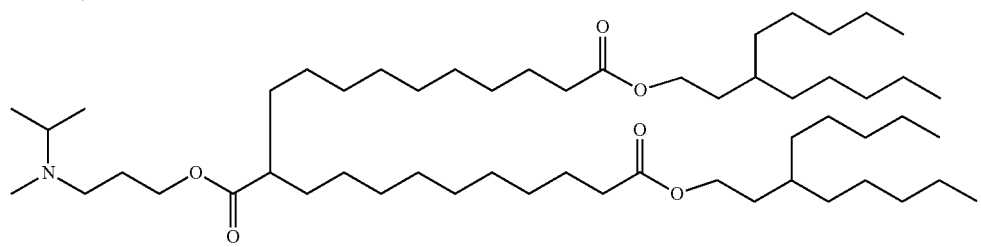
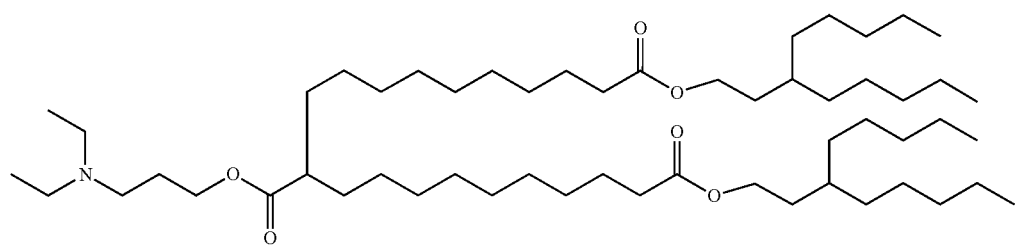

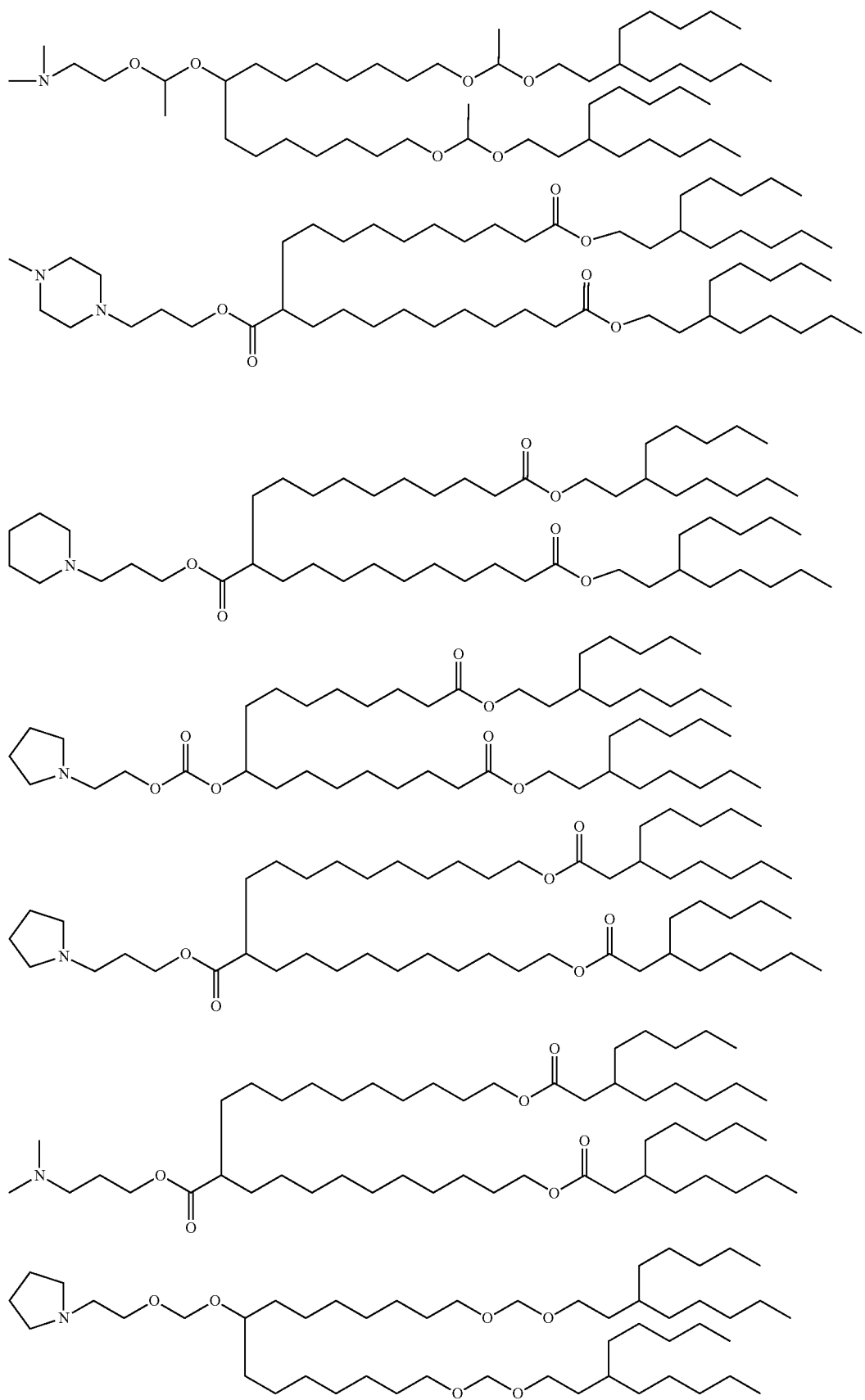

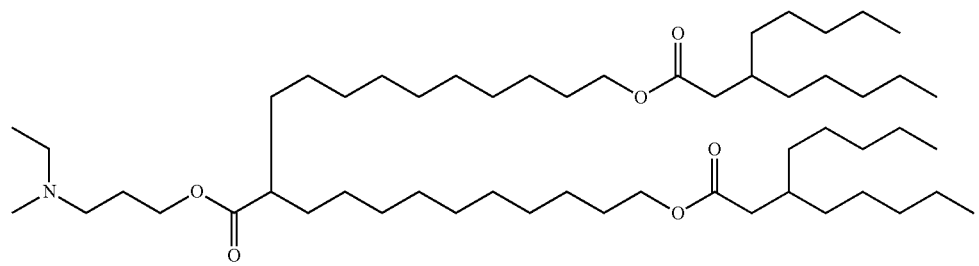
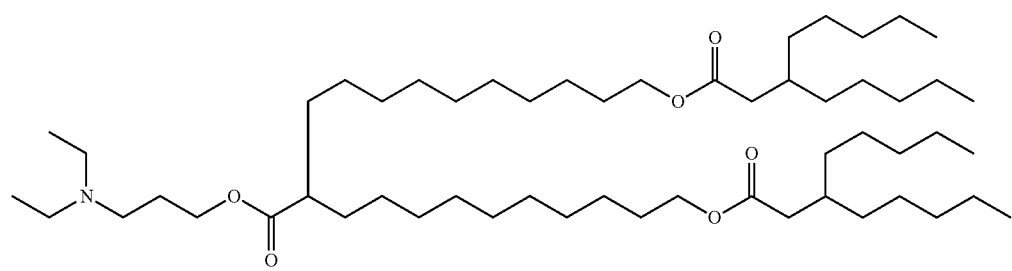
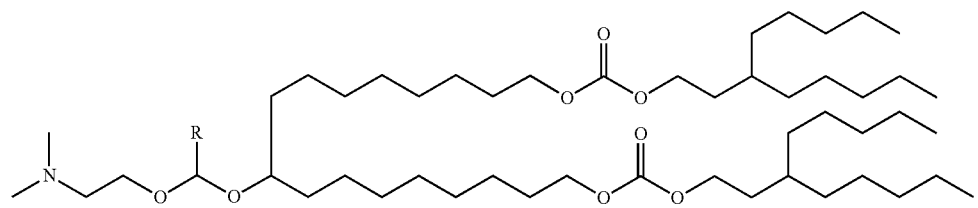
R = H, Me
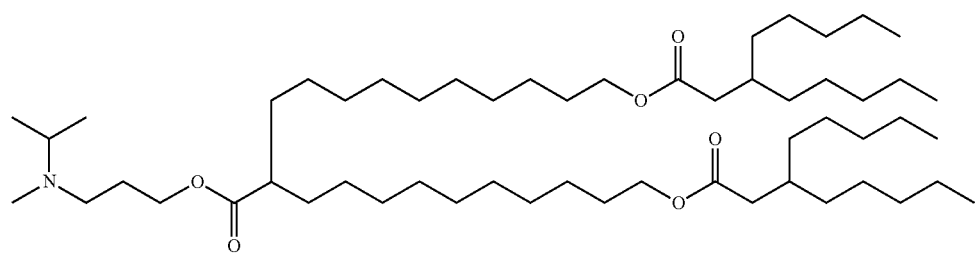
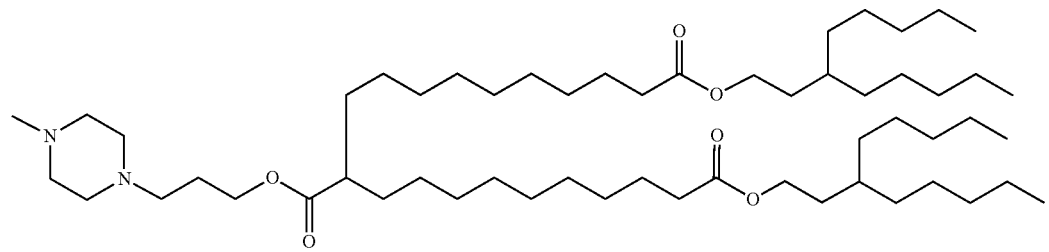
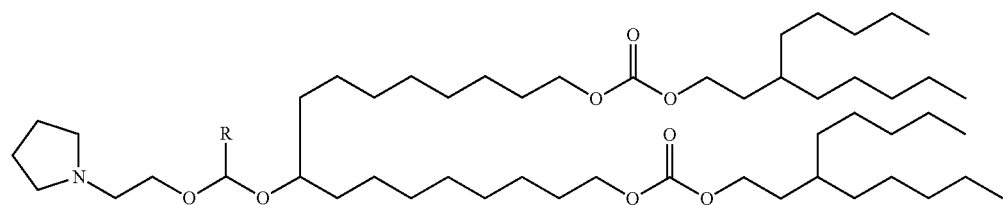
R = H, Me

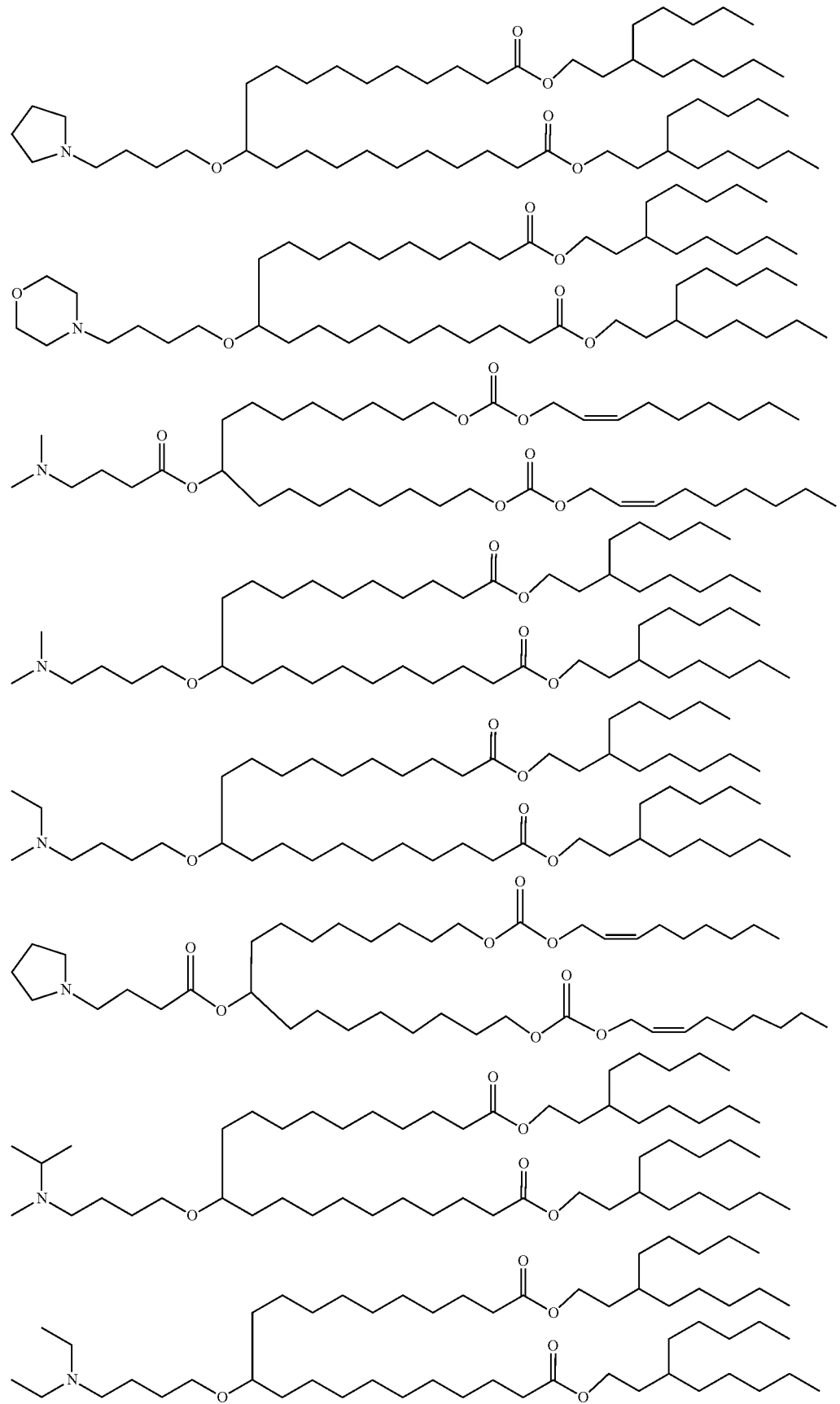

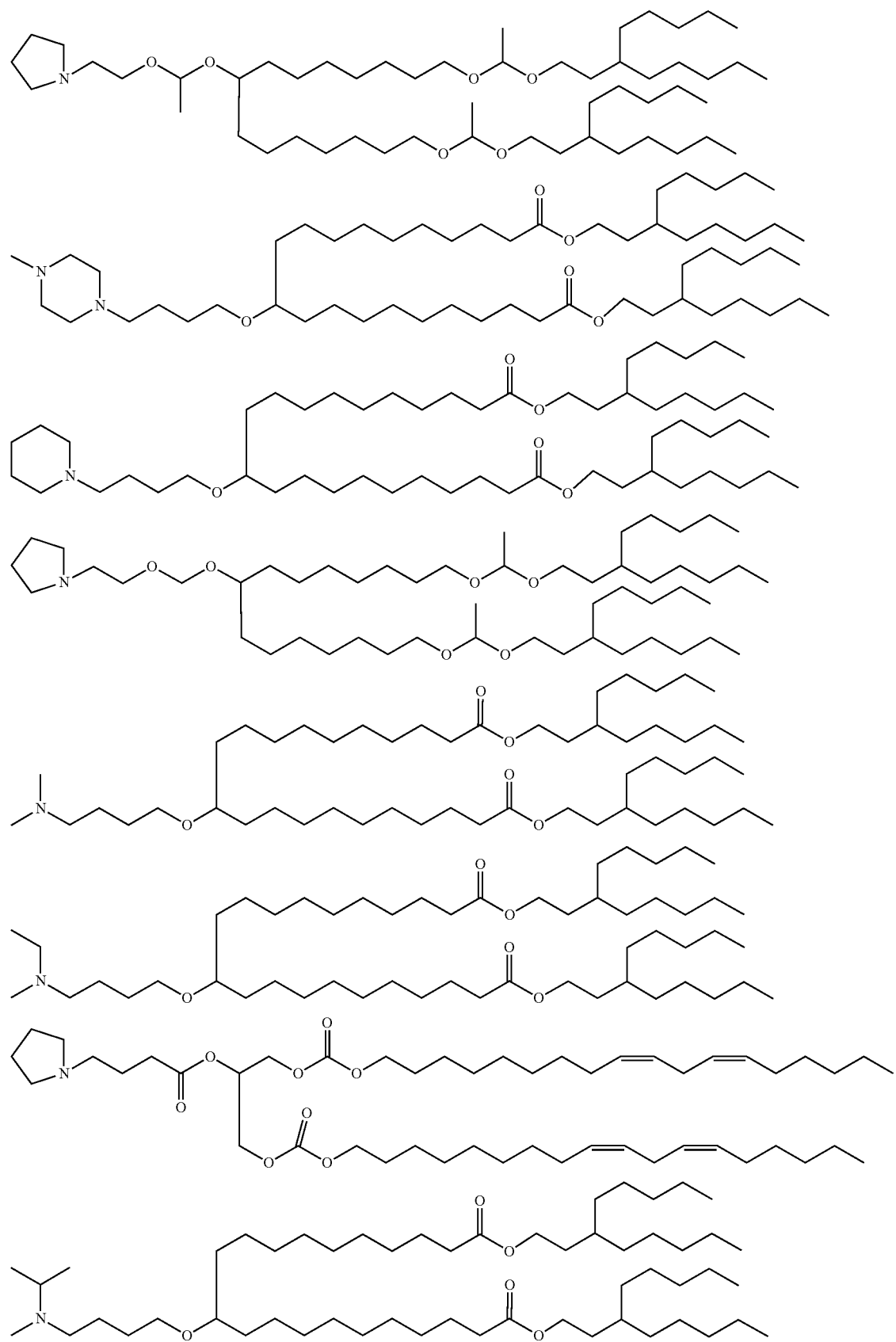

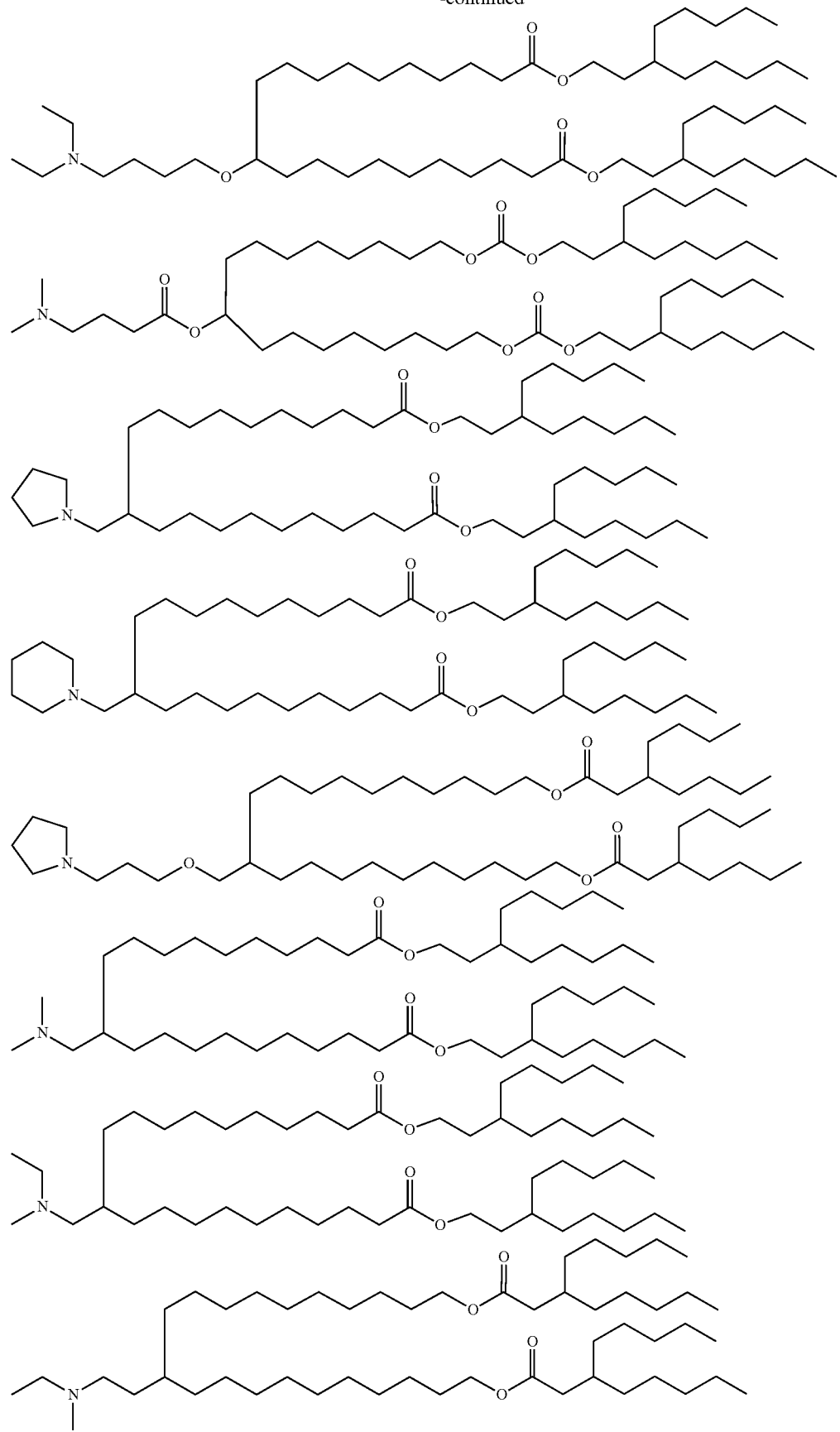

-continued
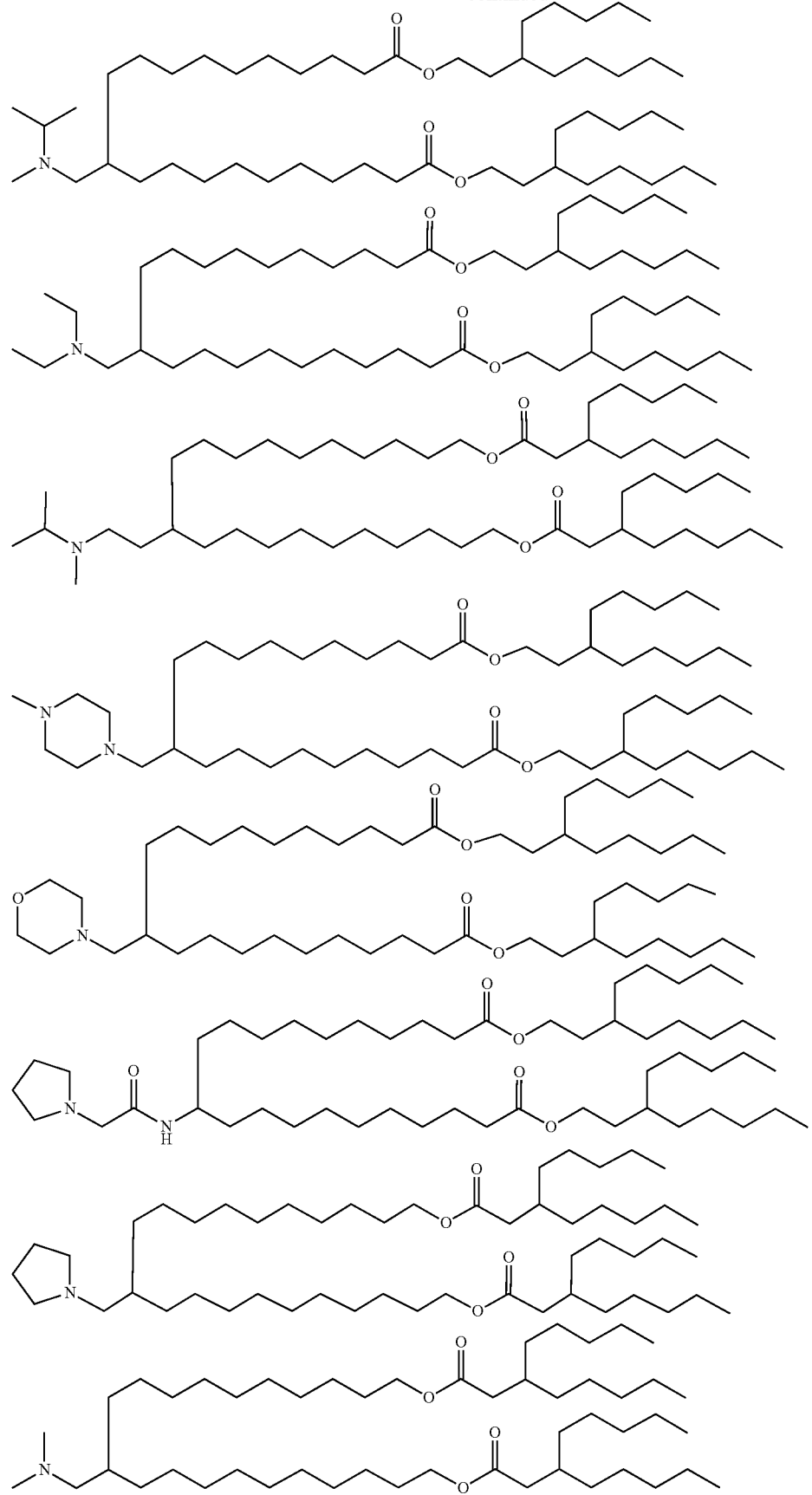

-continued
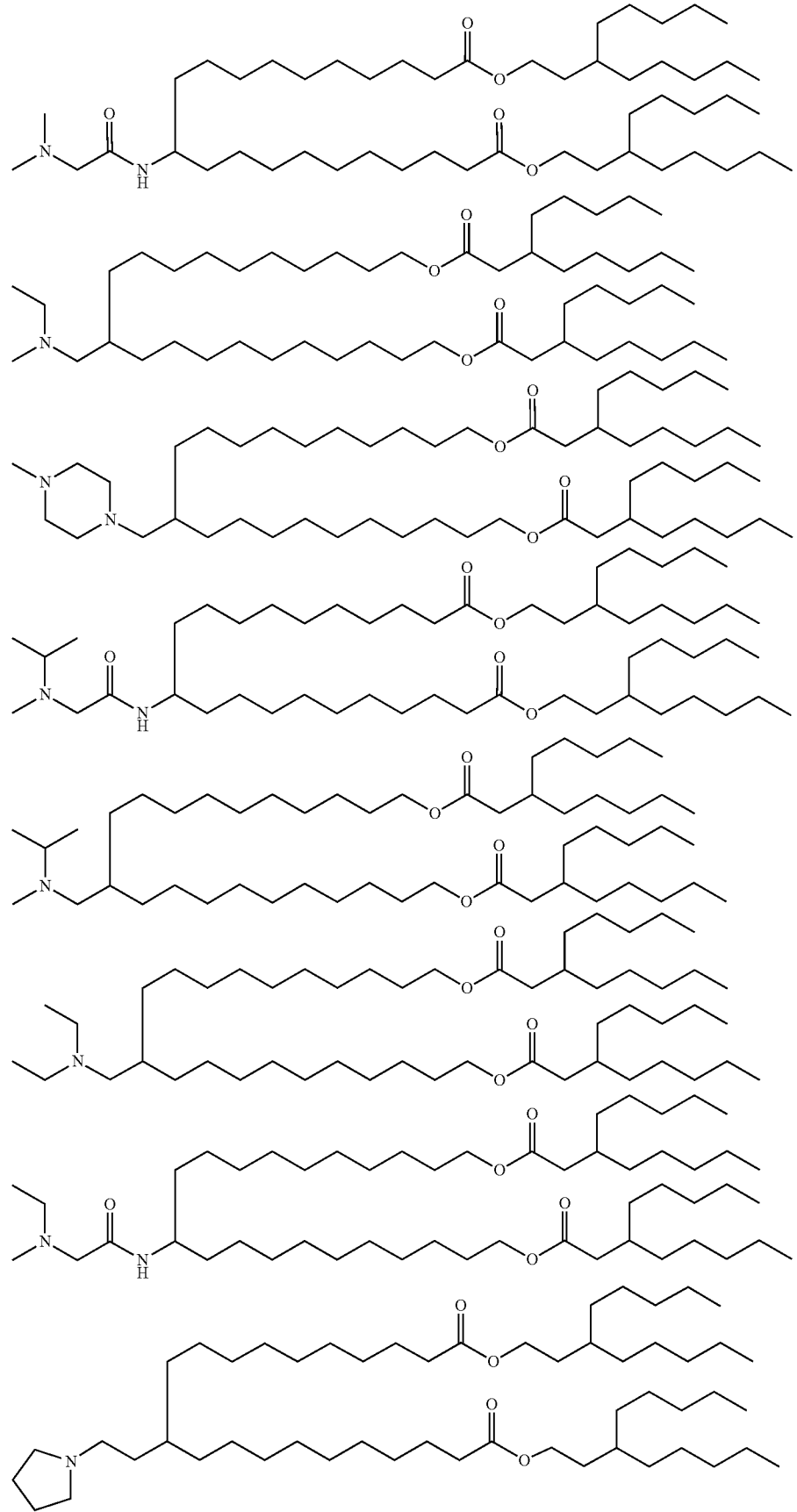

-continued
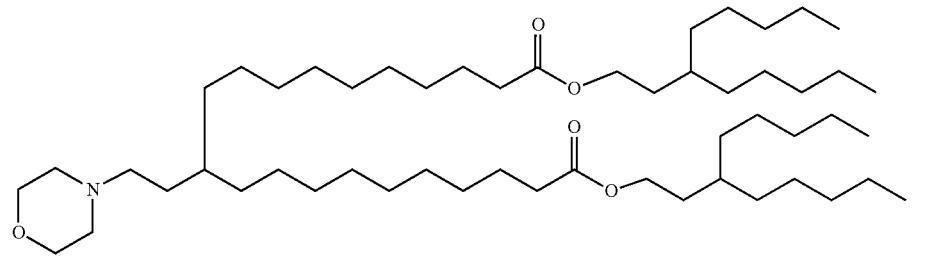
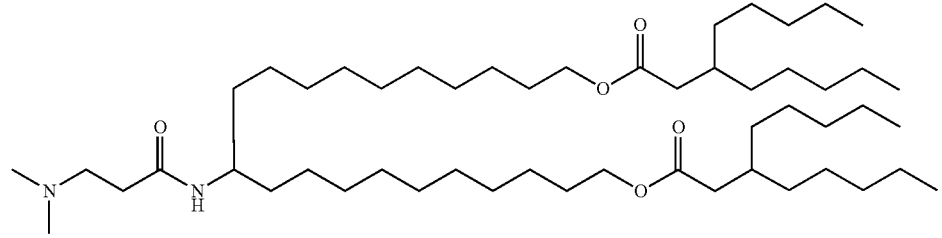
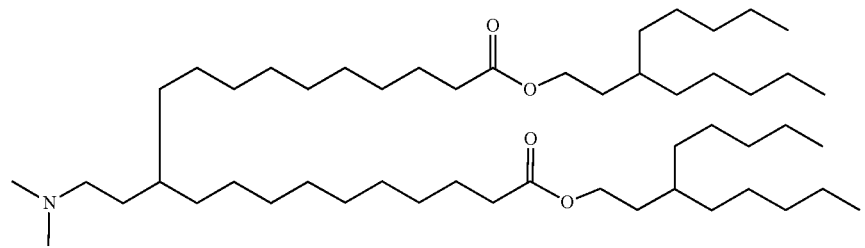
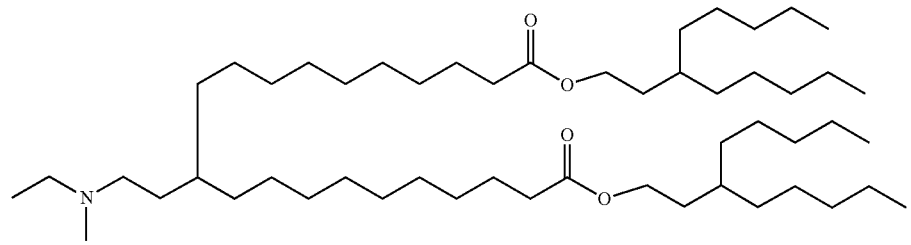
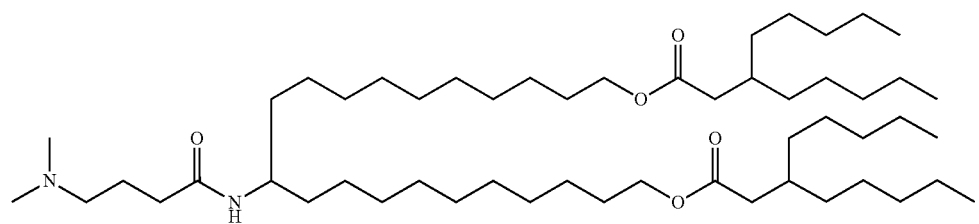
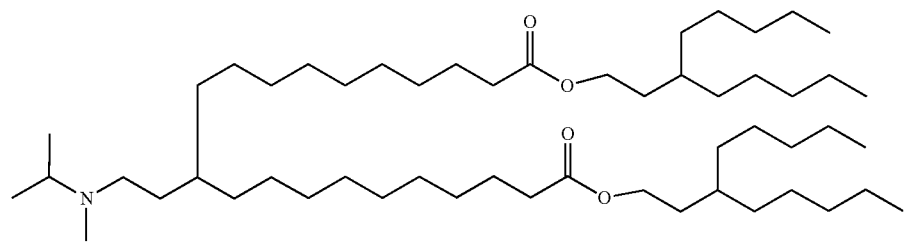
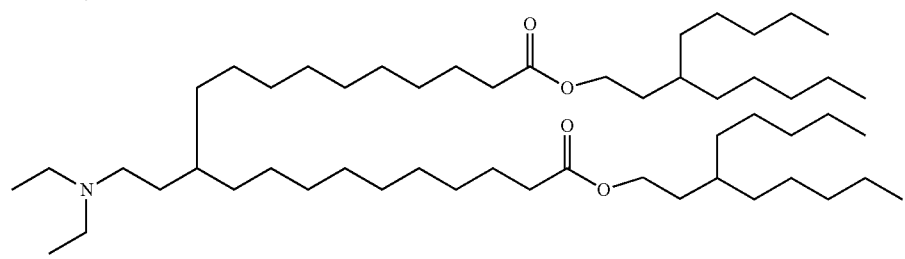

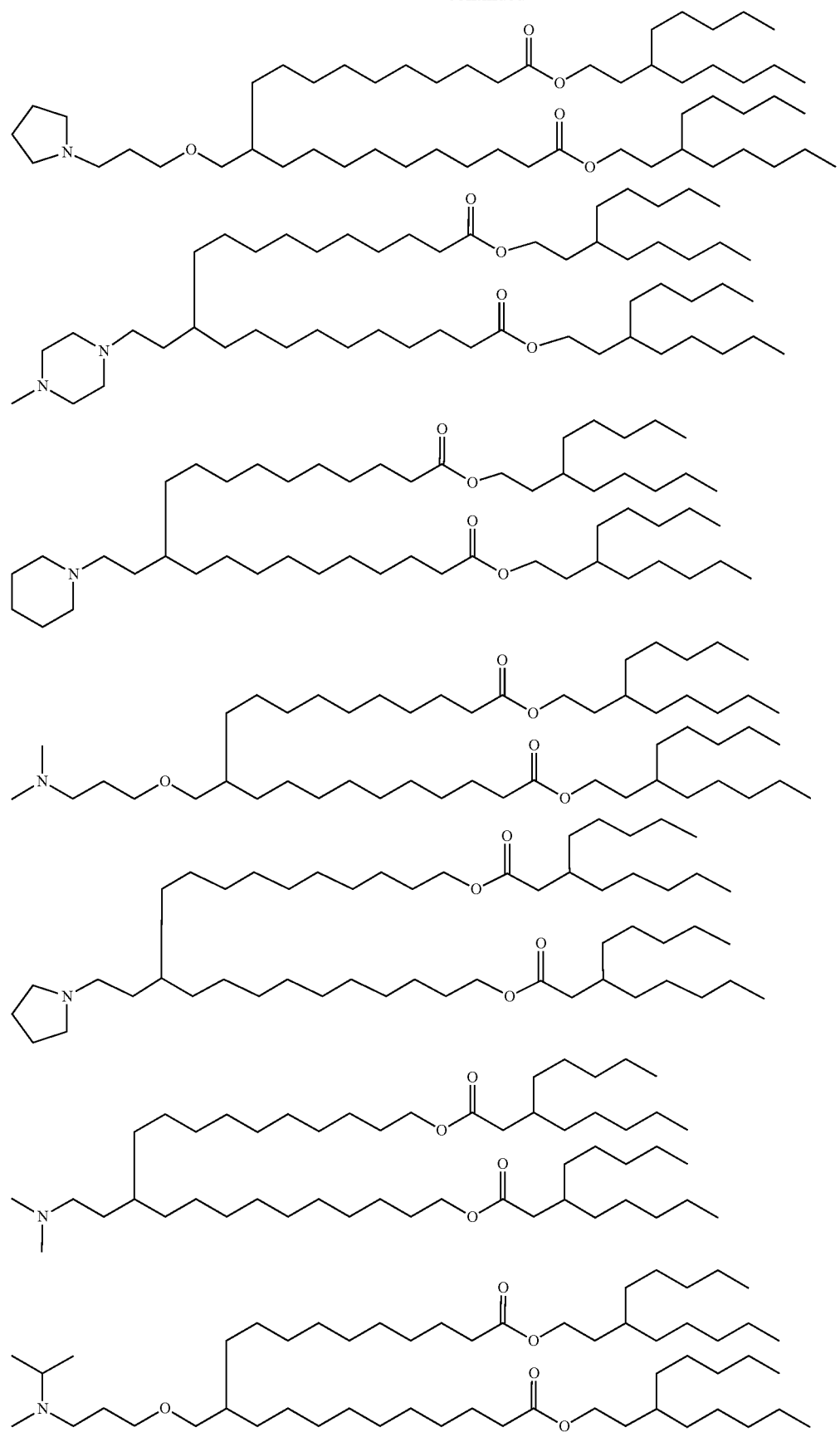

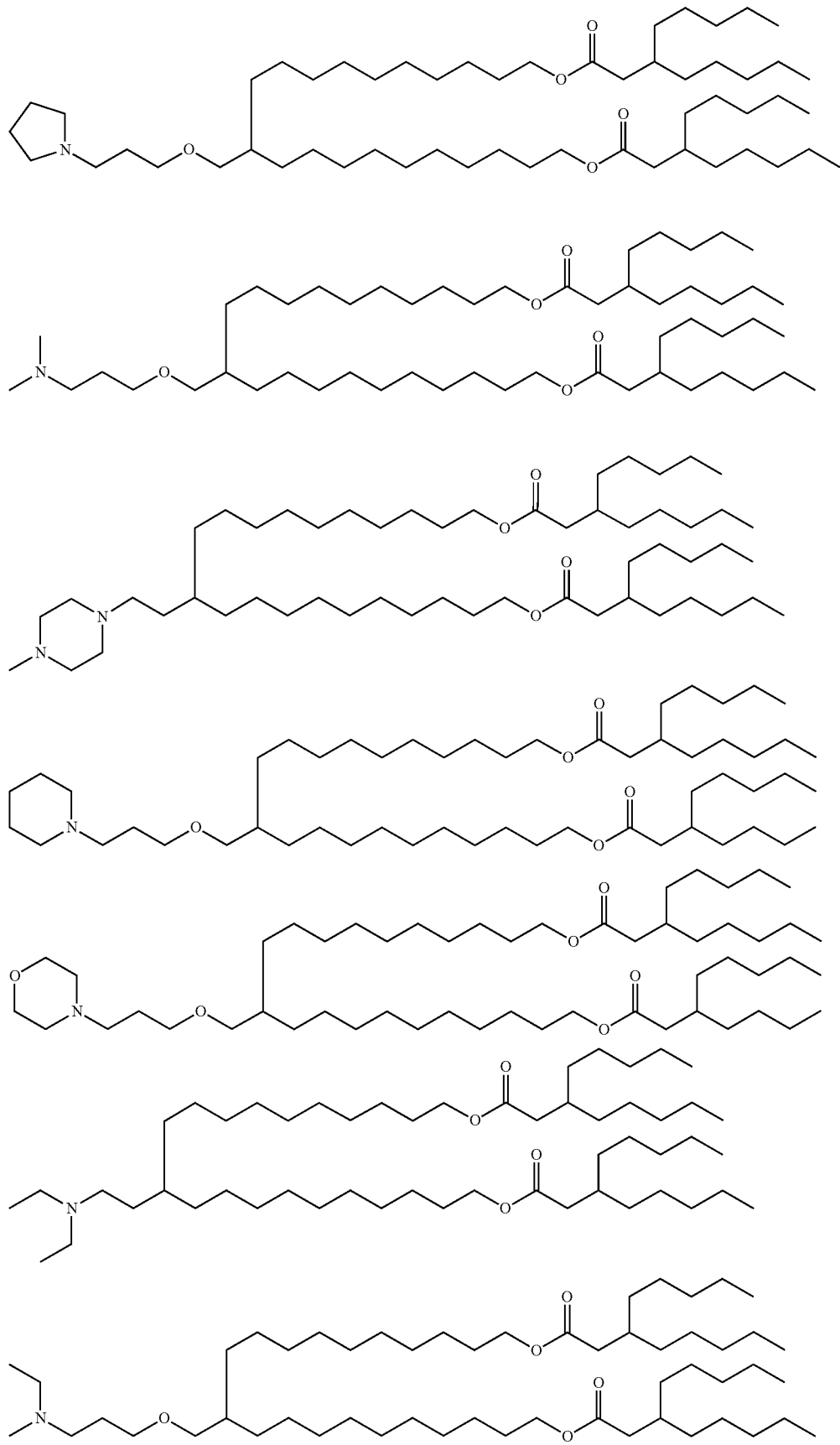

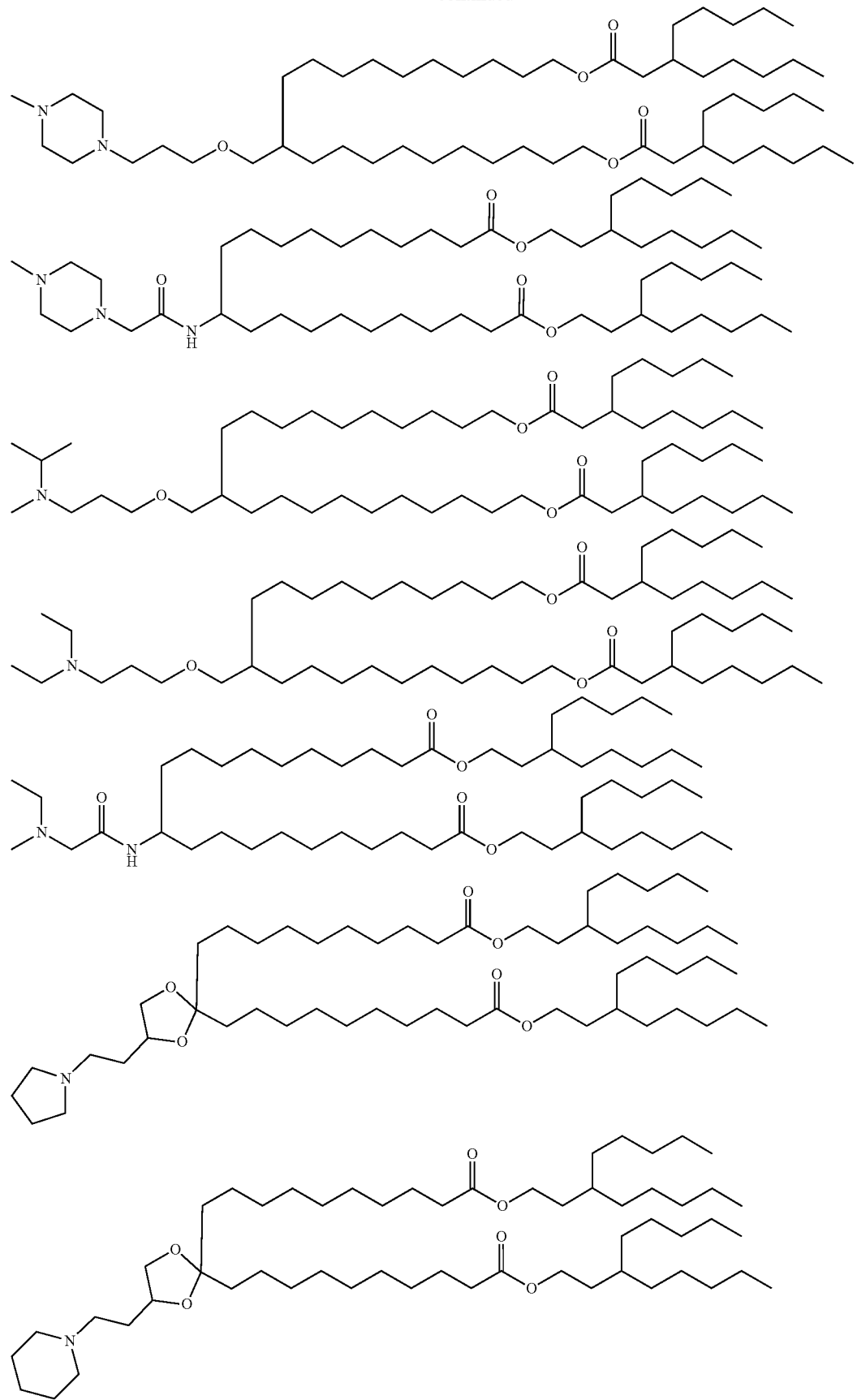

-continued
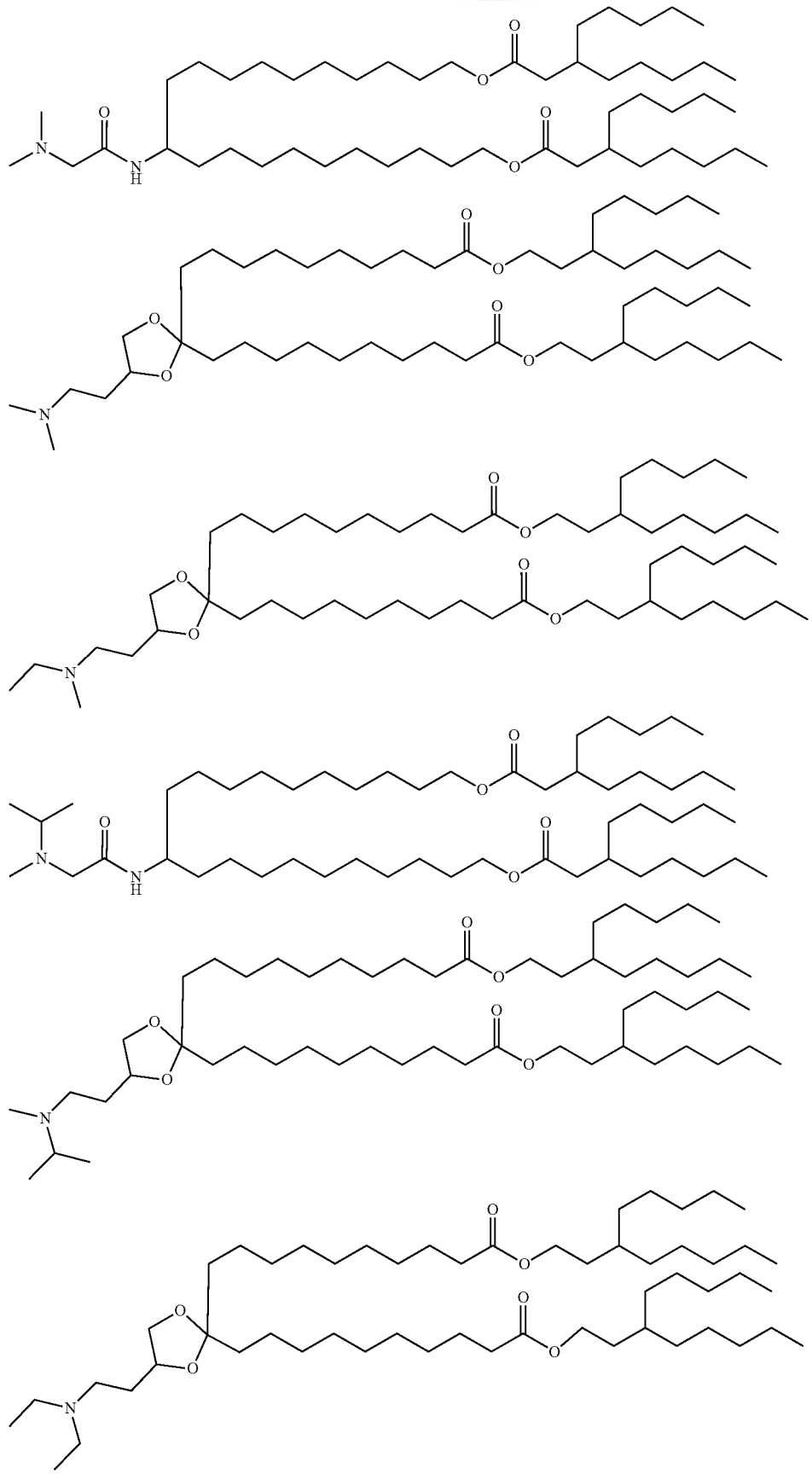

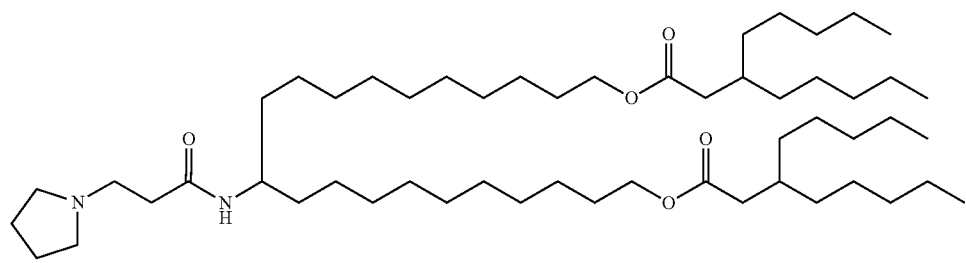
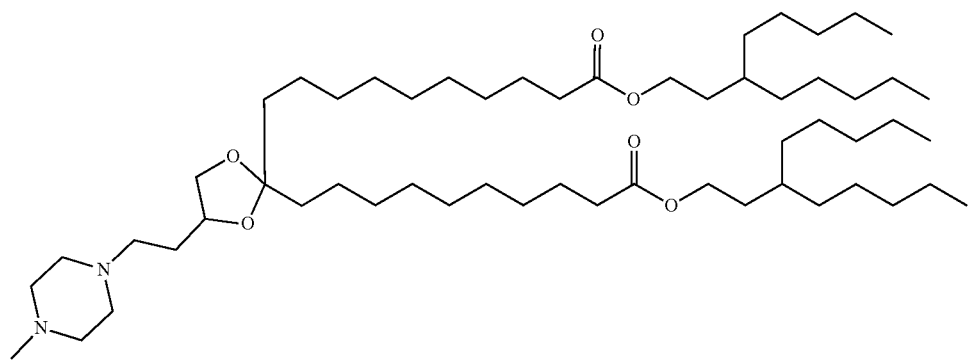
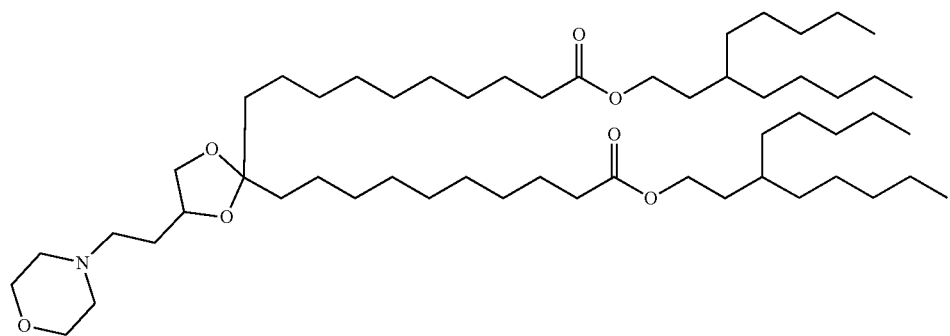
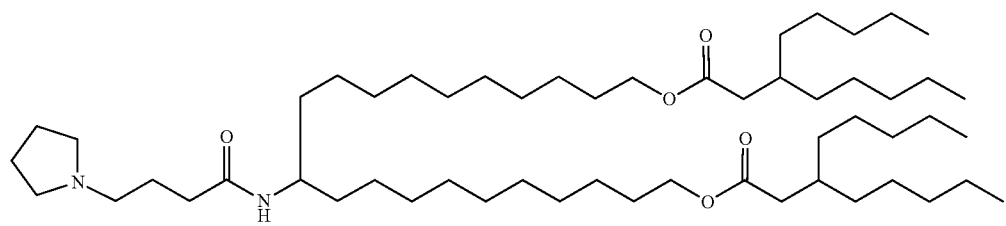
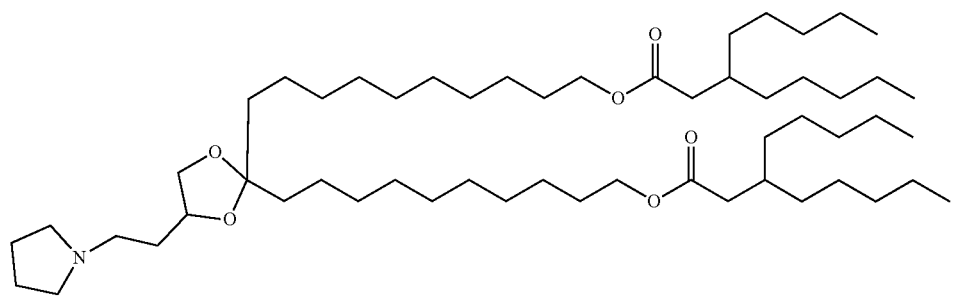

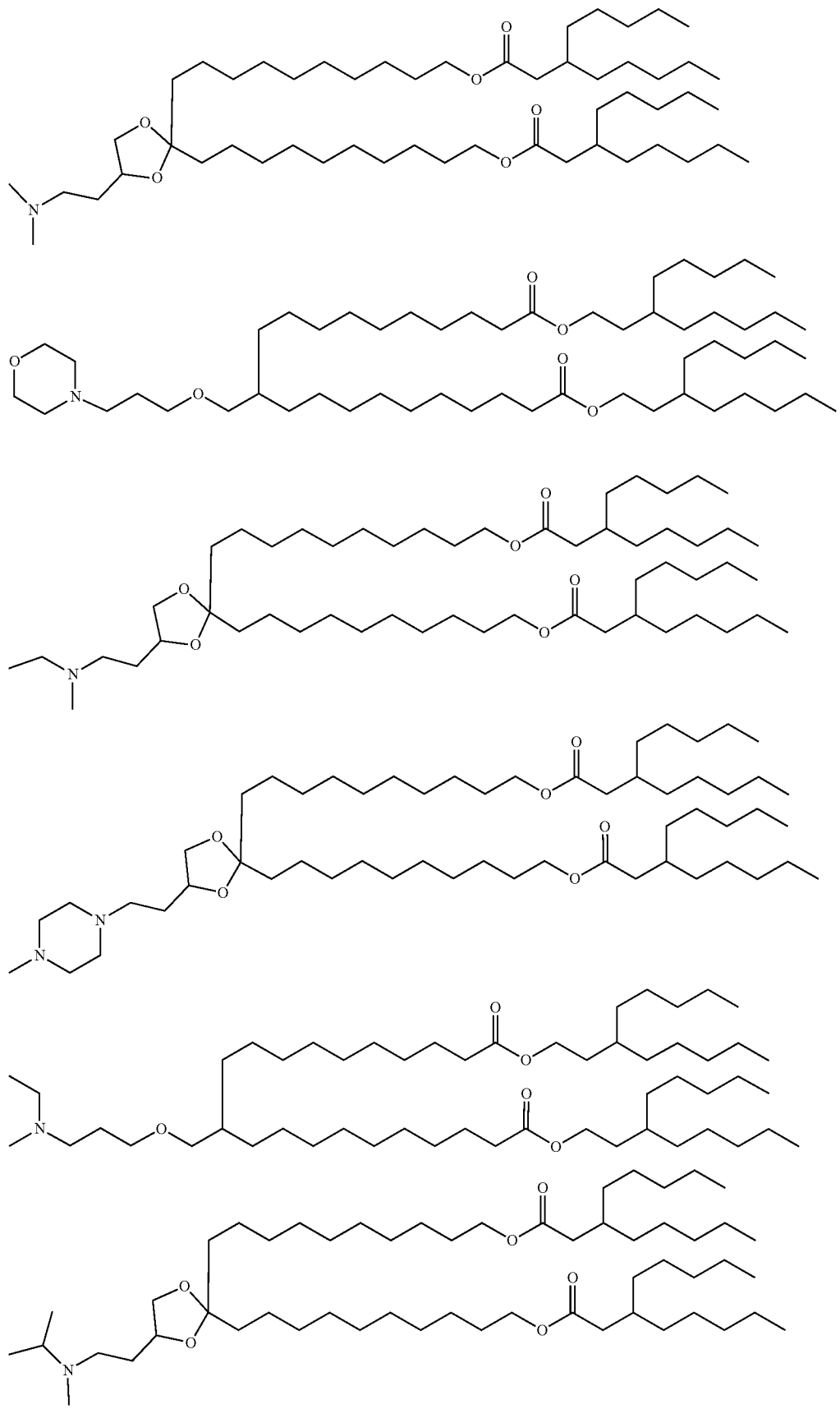

-continued
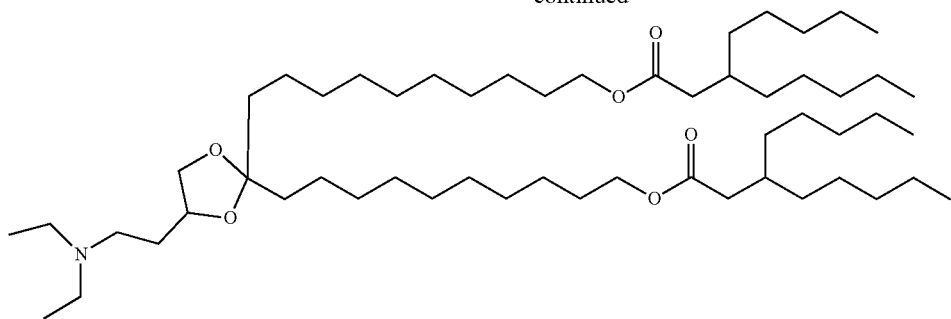
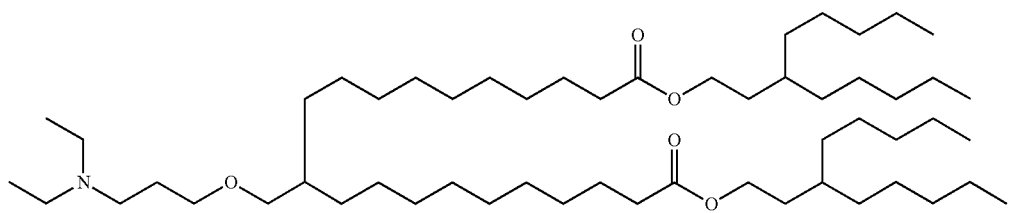
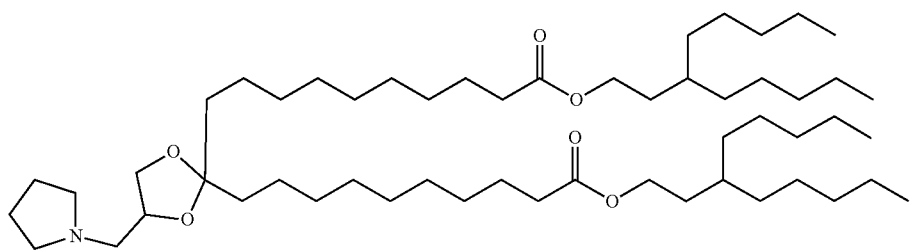
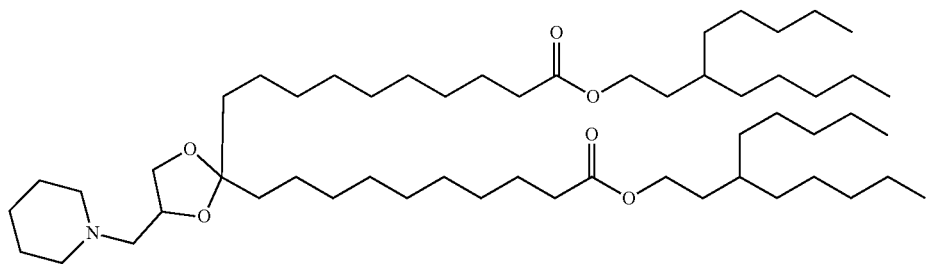
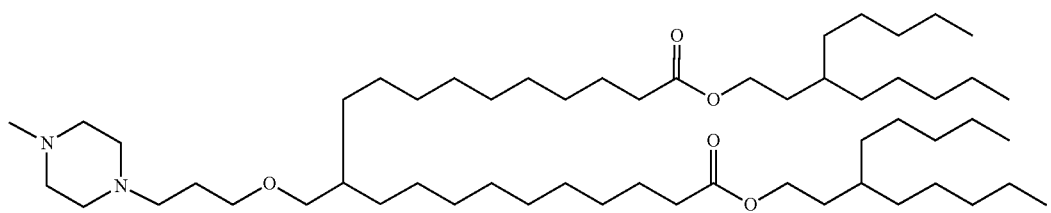
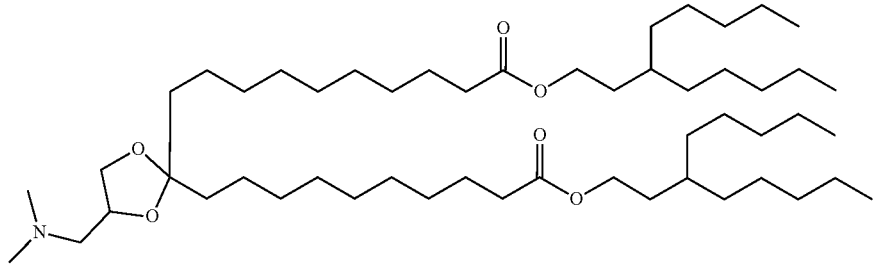

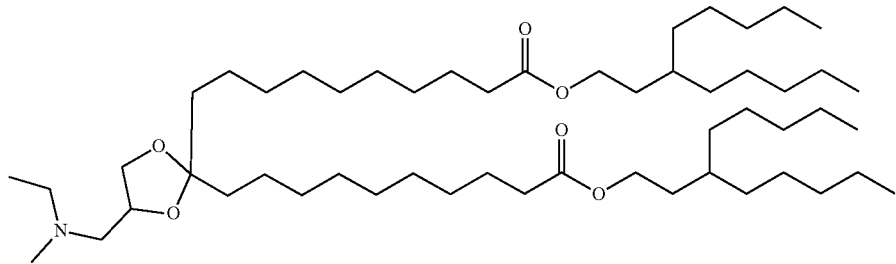
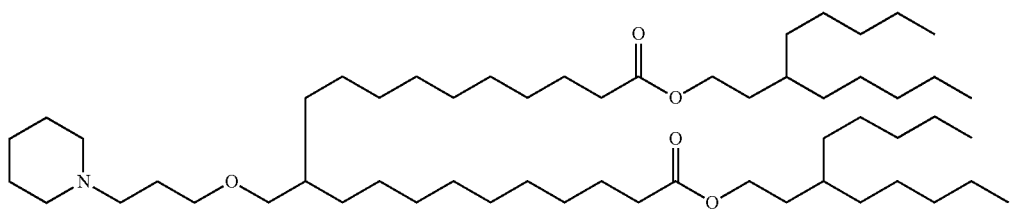
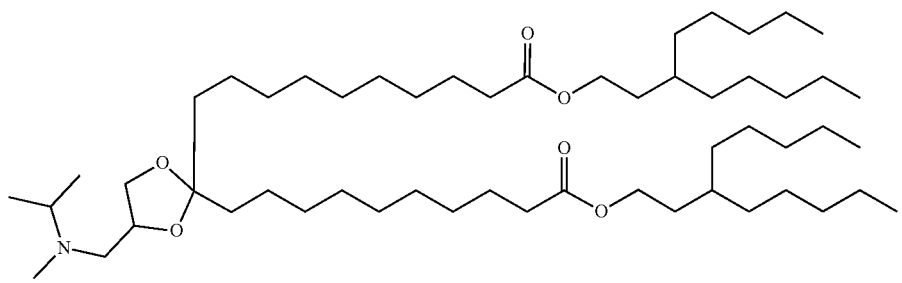
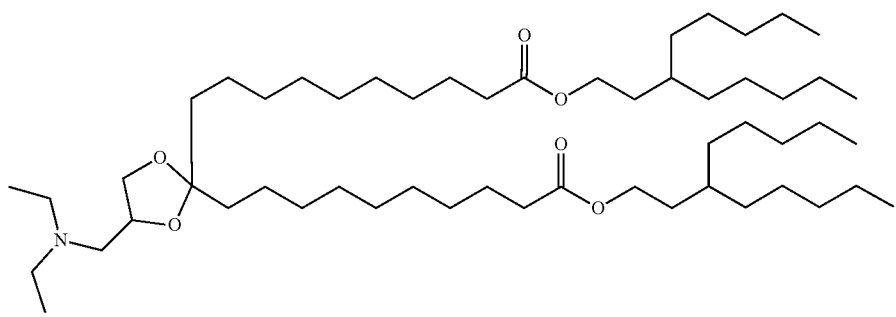
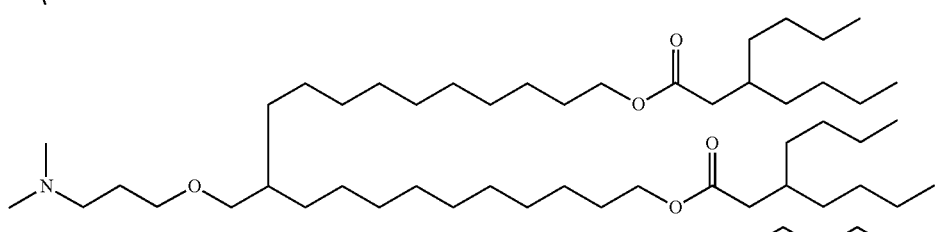
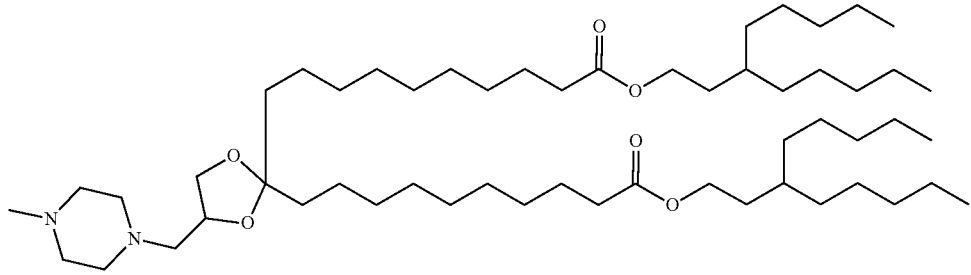

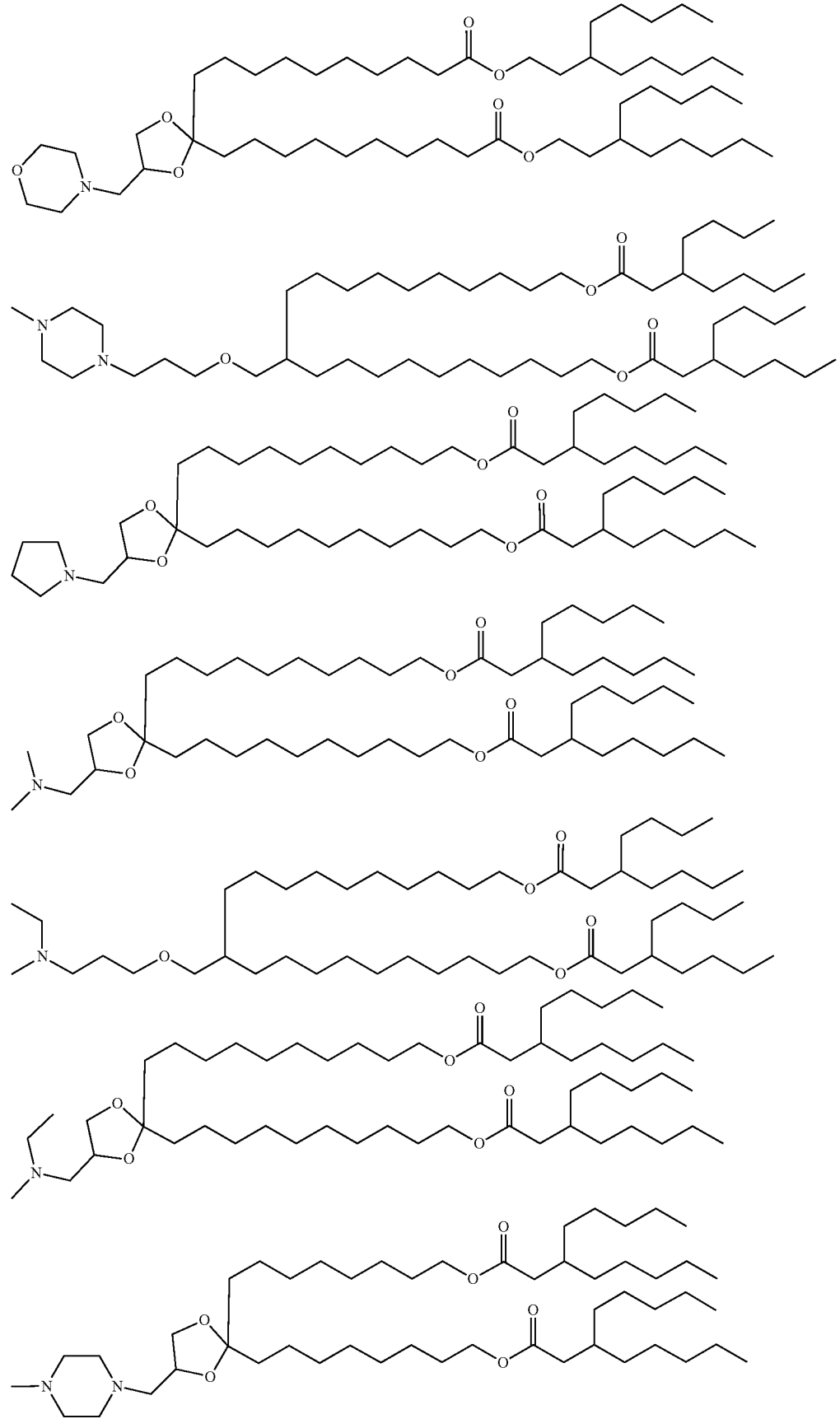

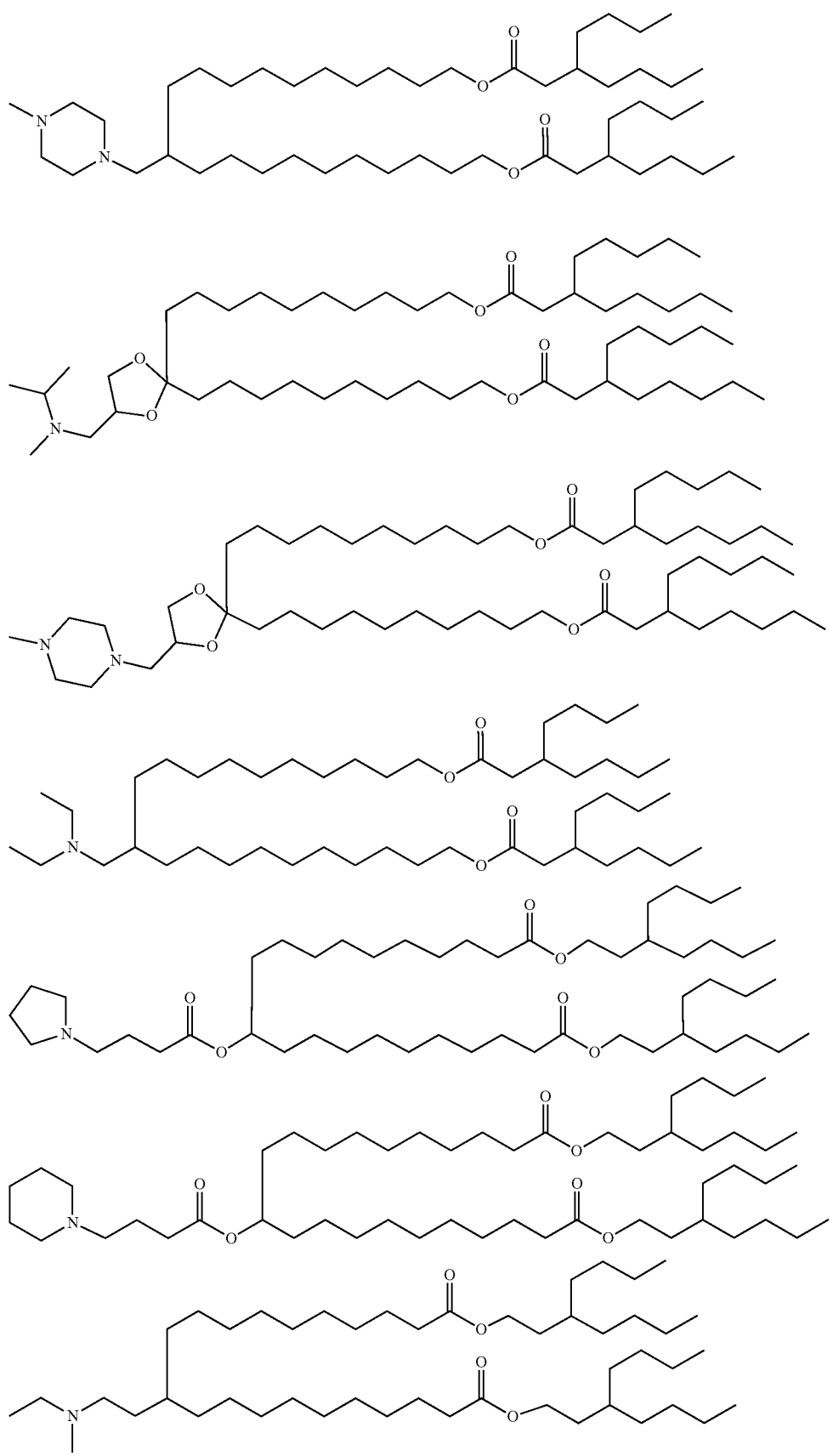

-continued
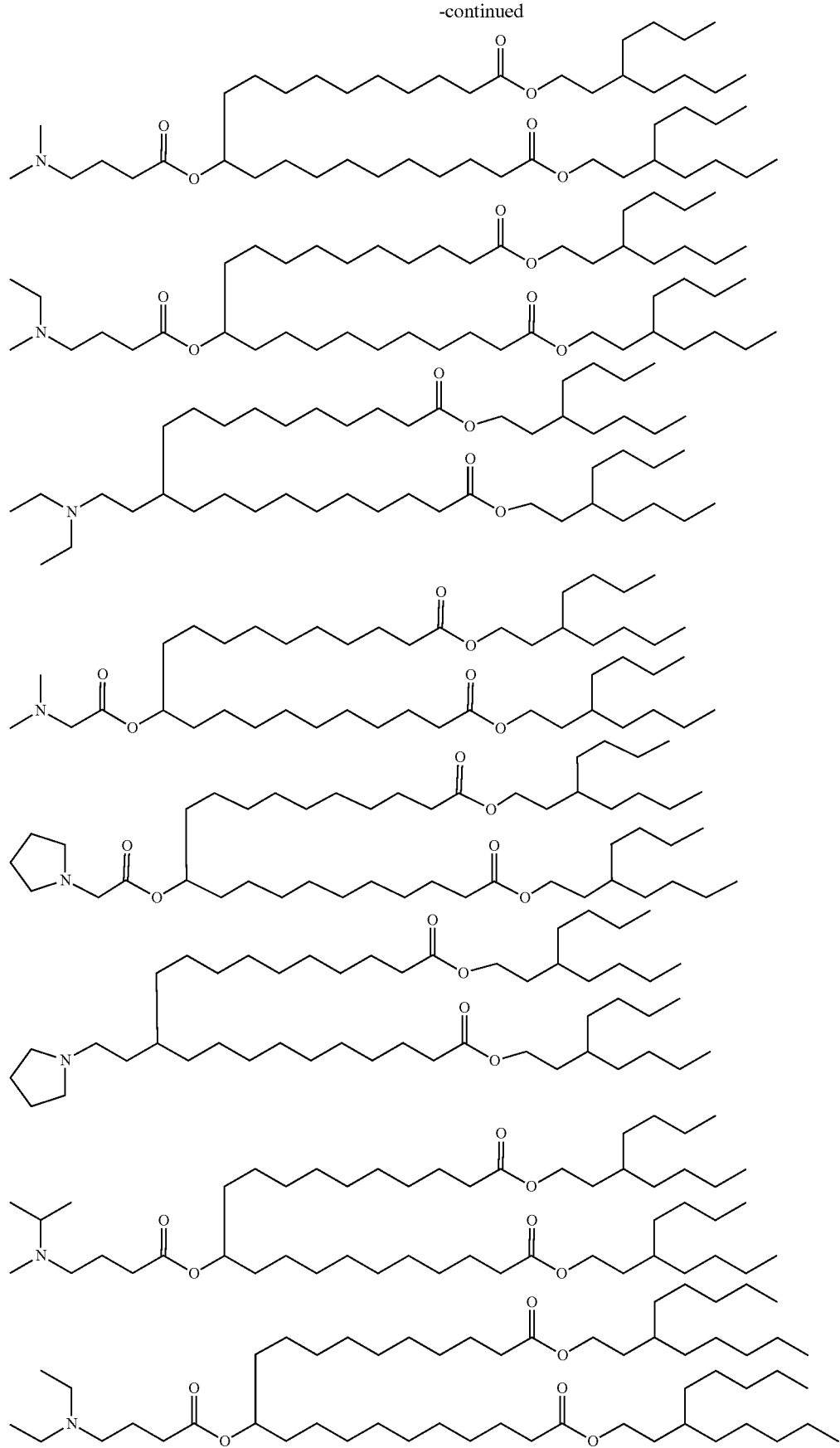

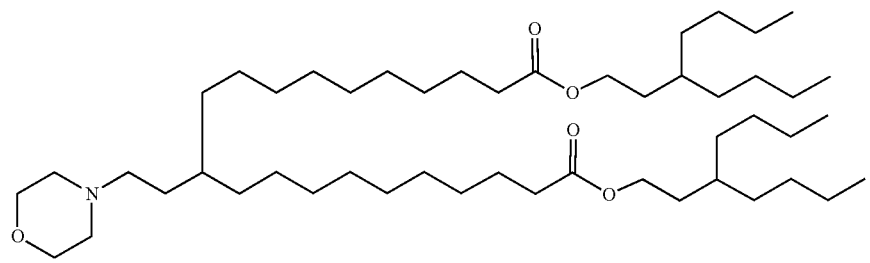
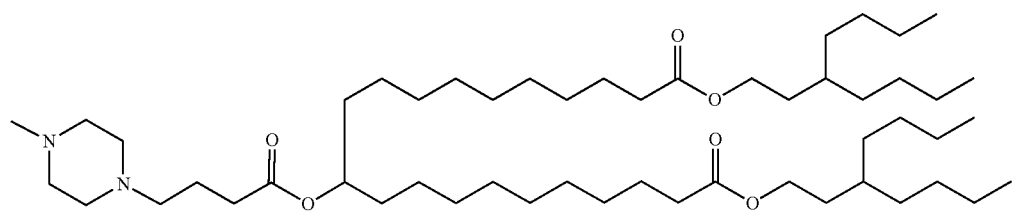
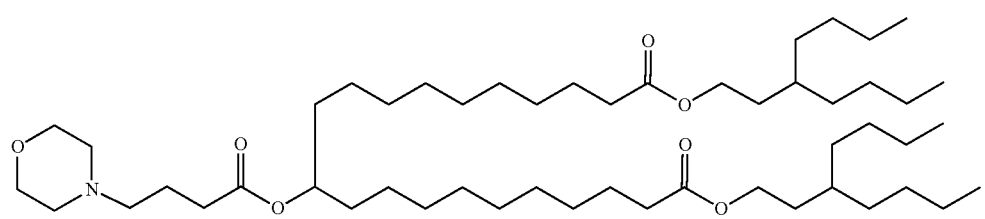
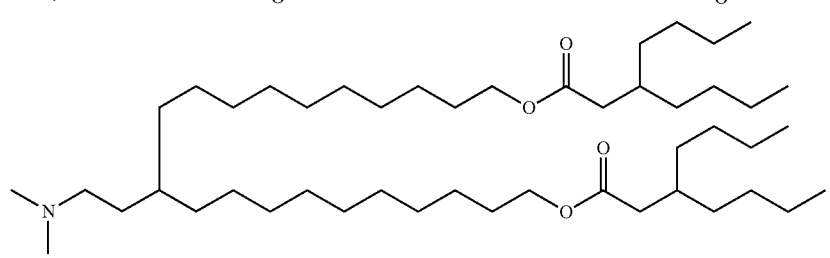
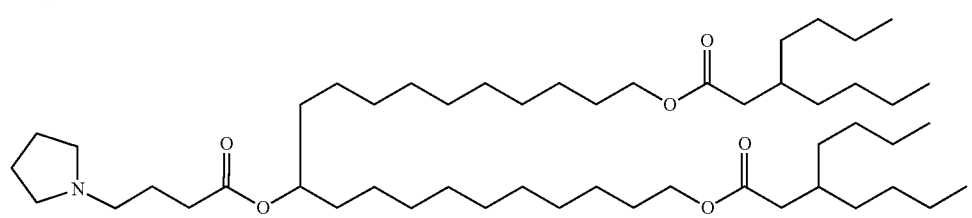
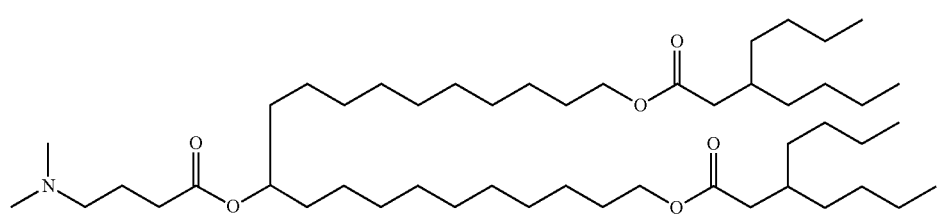
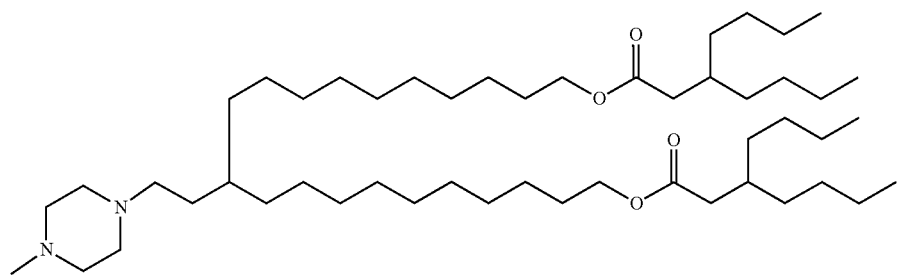

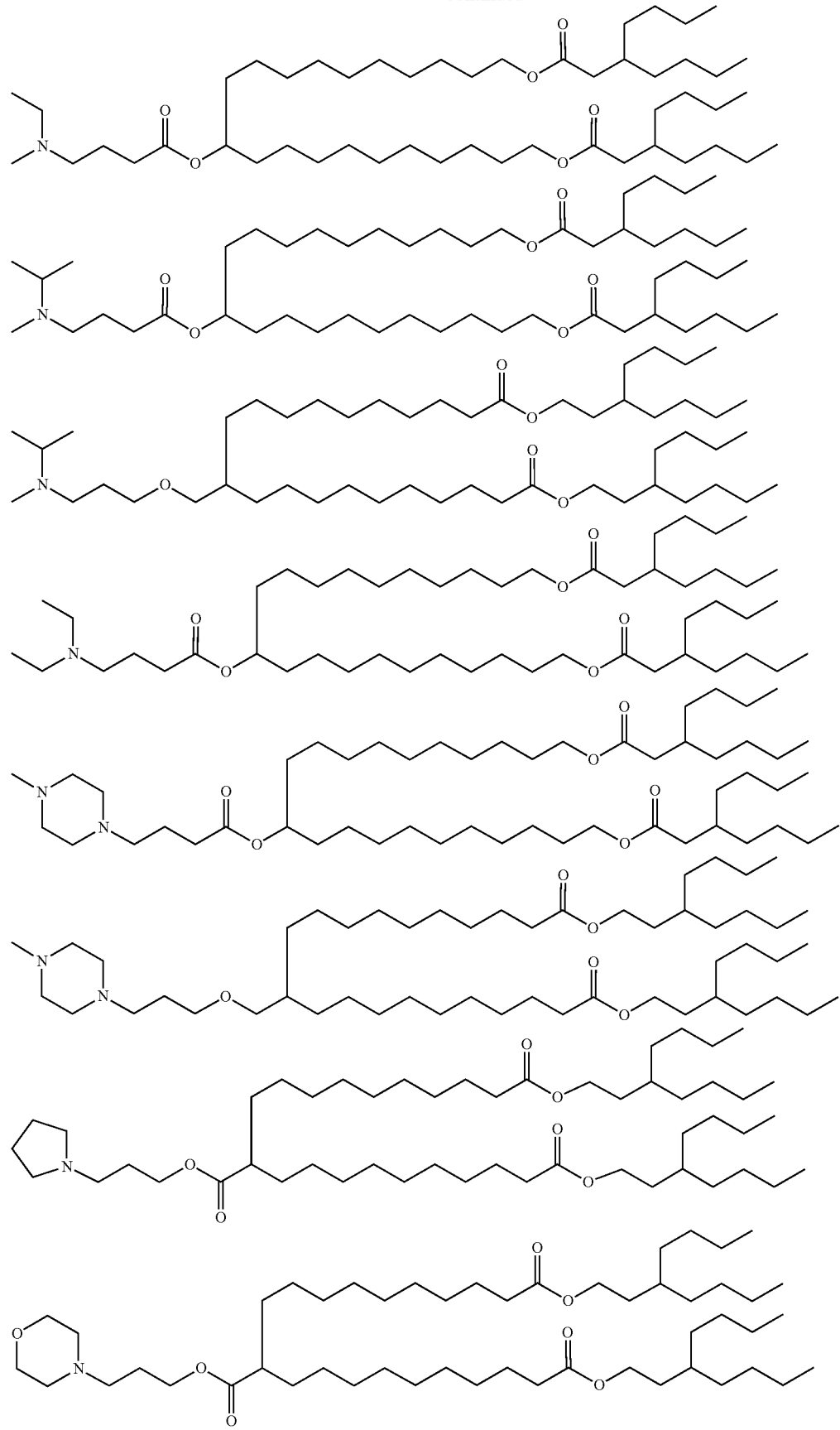

-continued
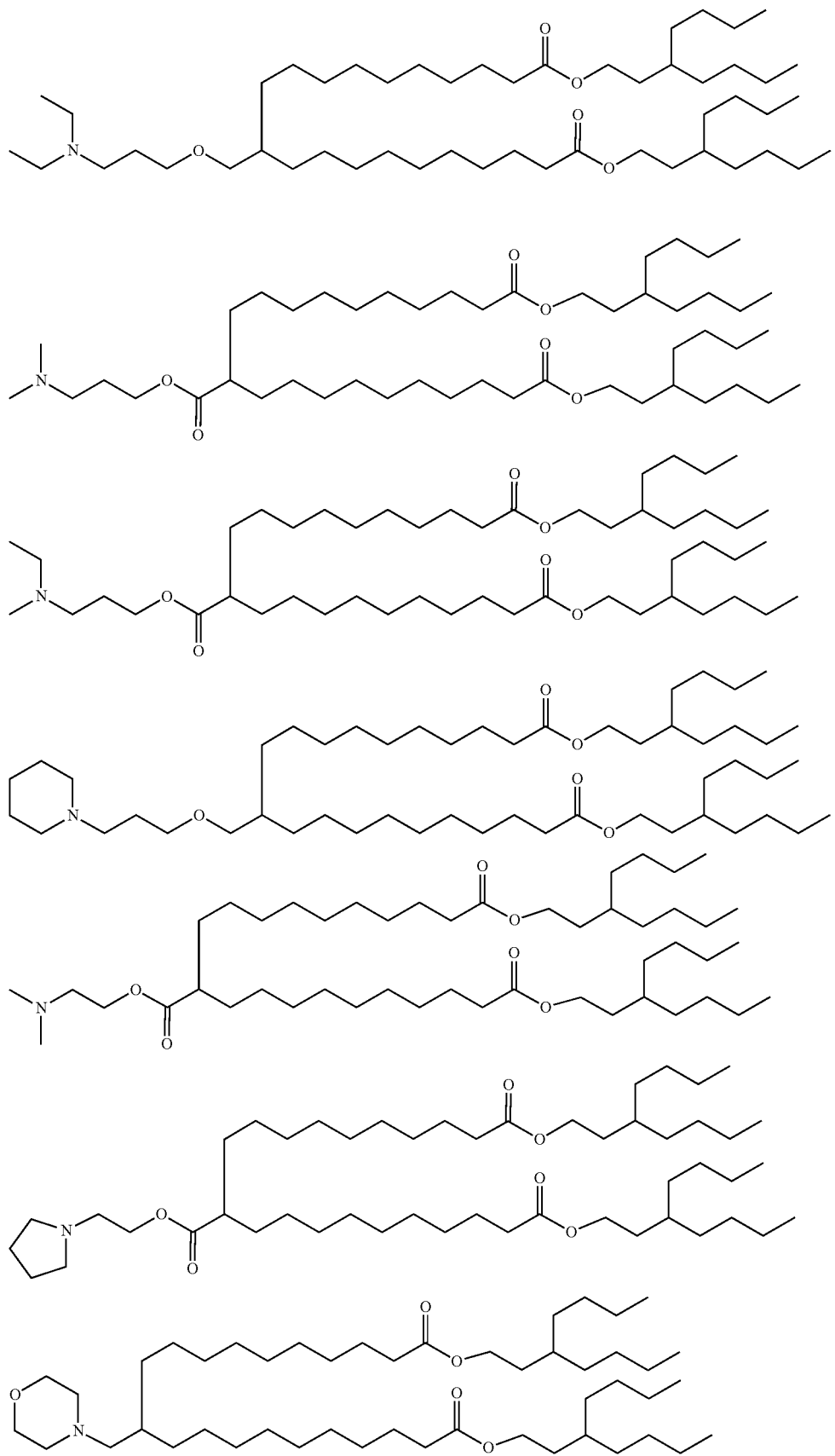

-continued
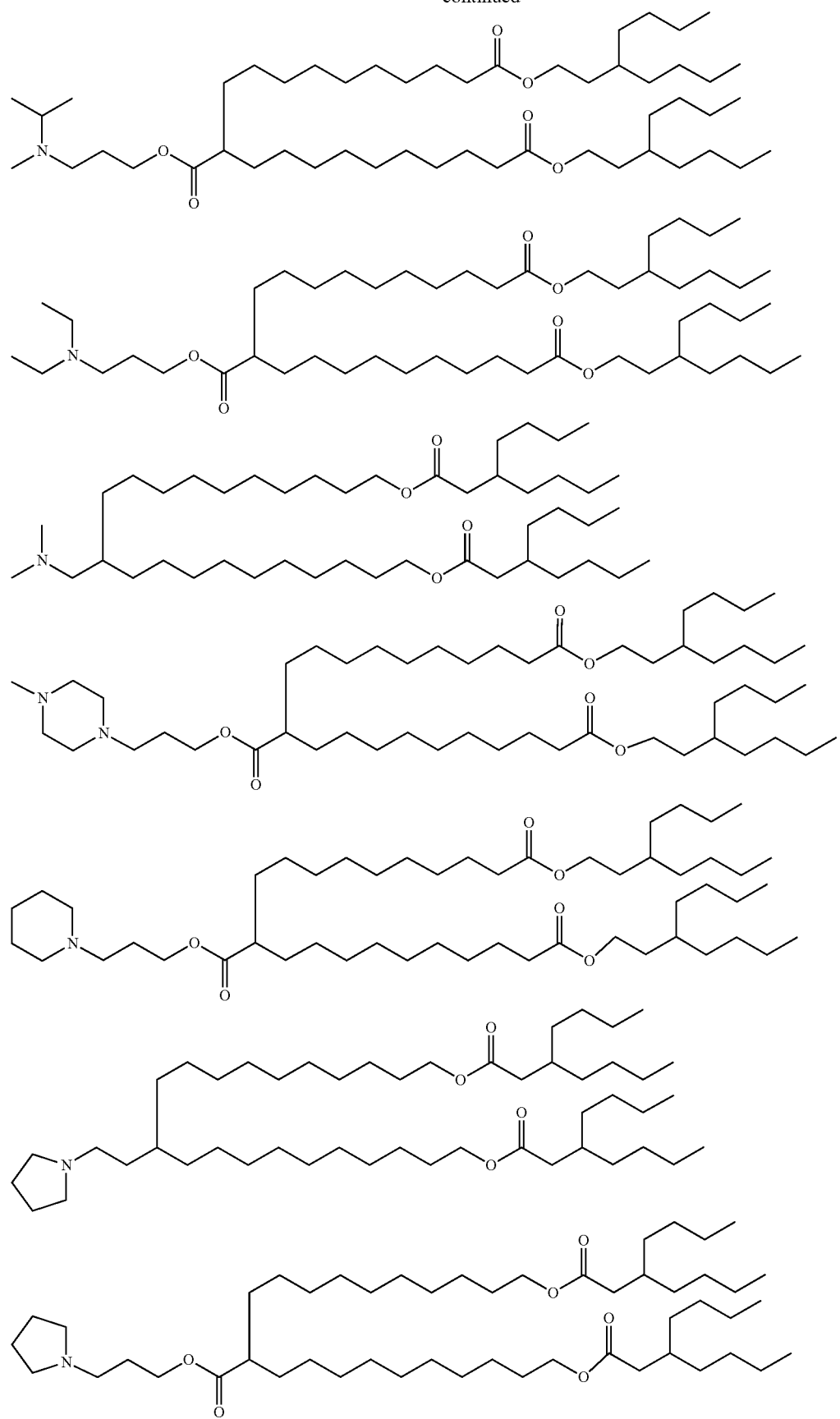

-continued
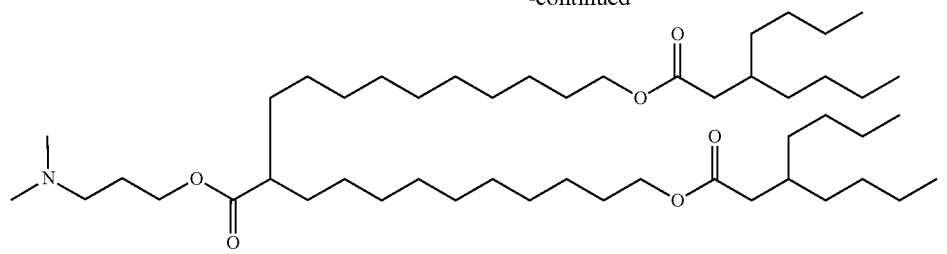
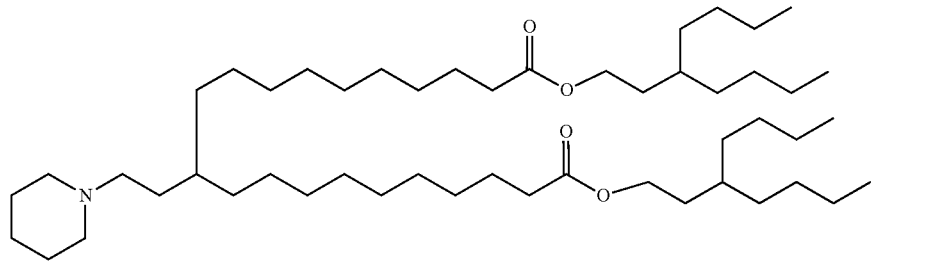
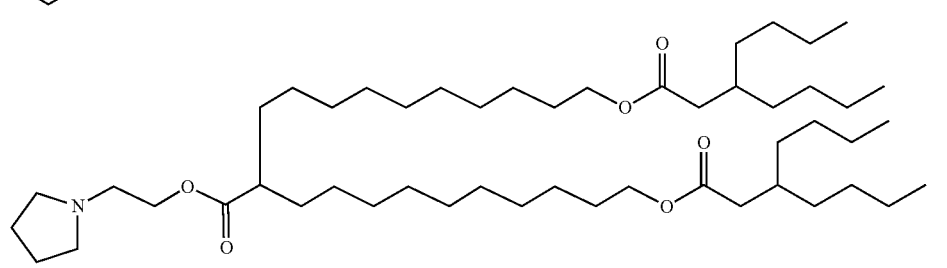
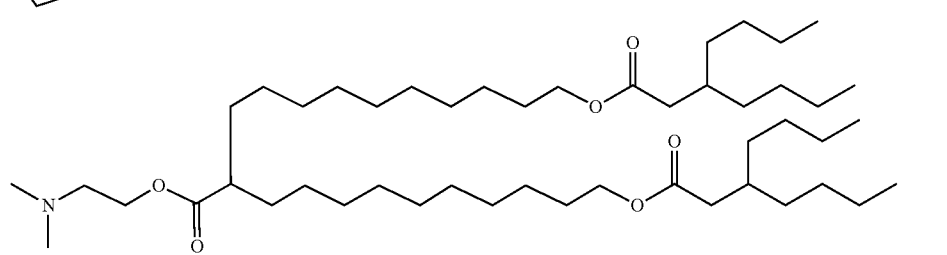
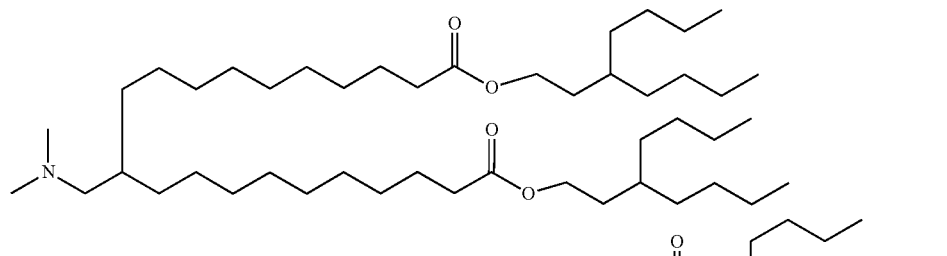
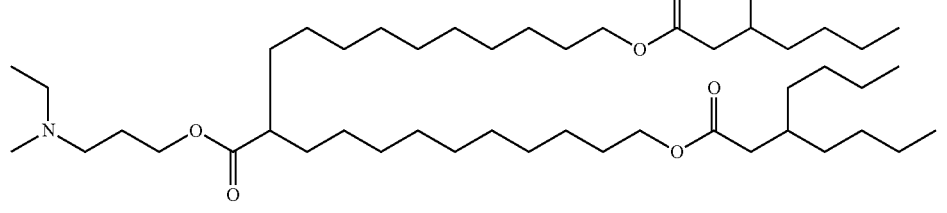
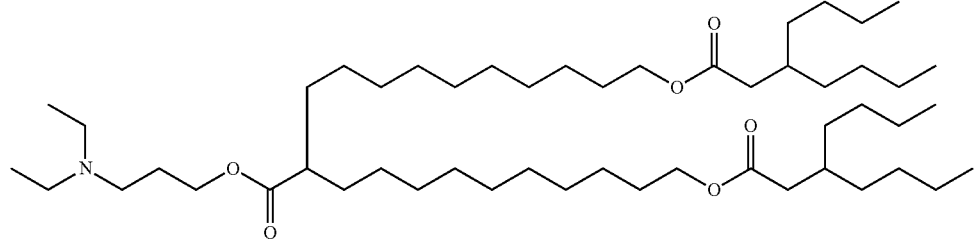

-continued
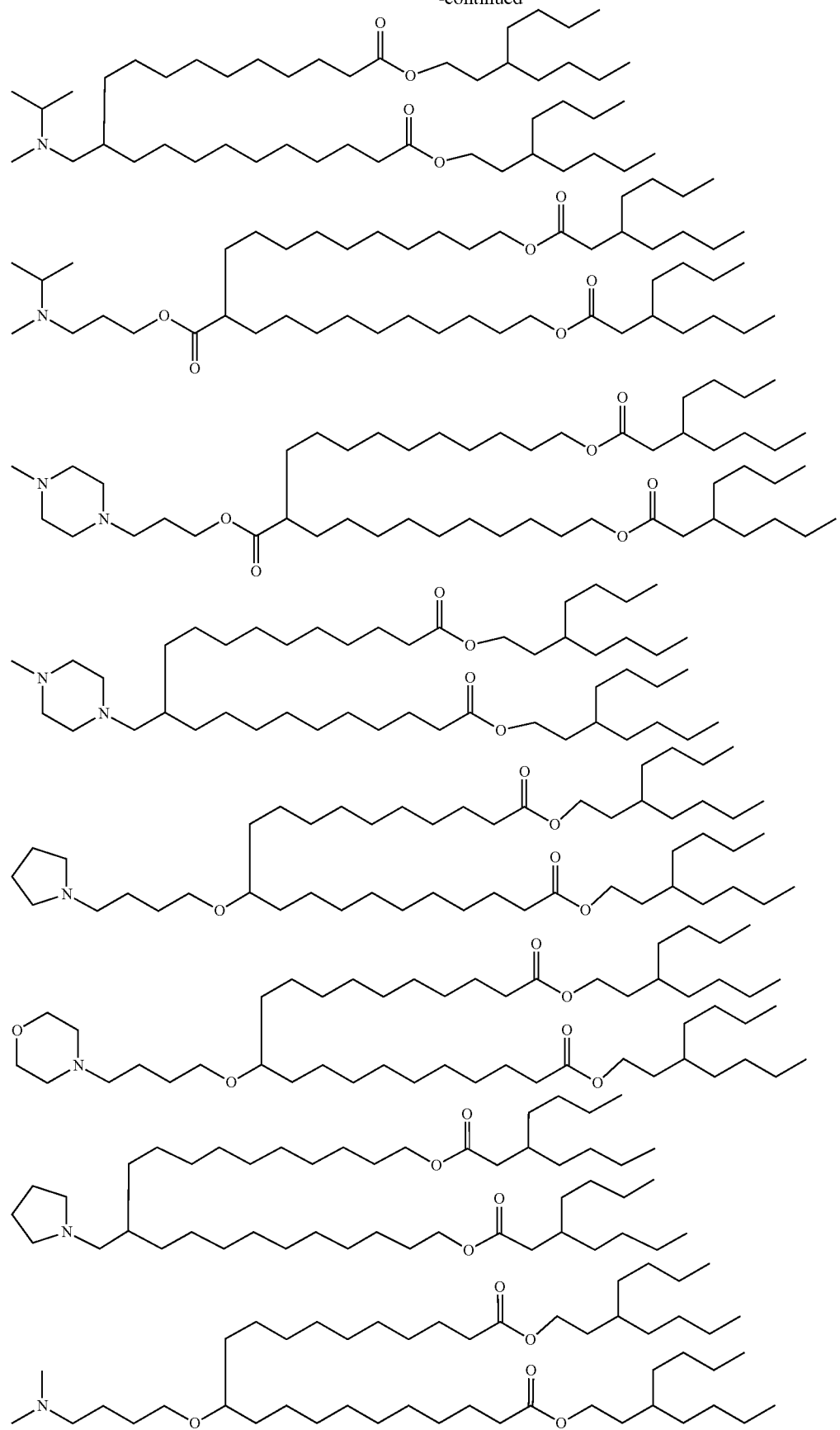

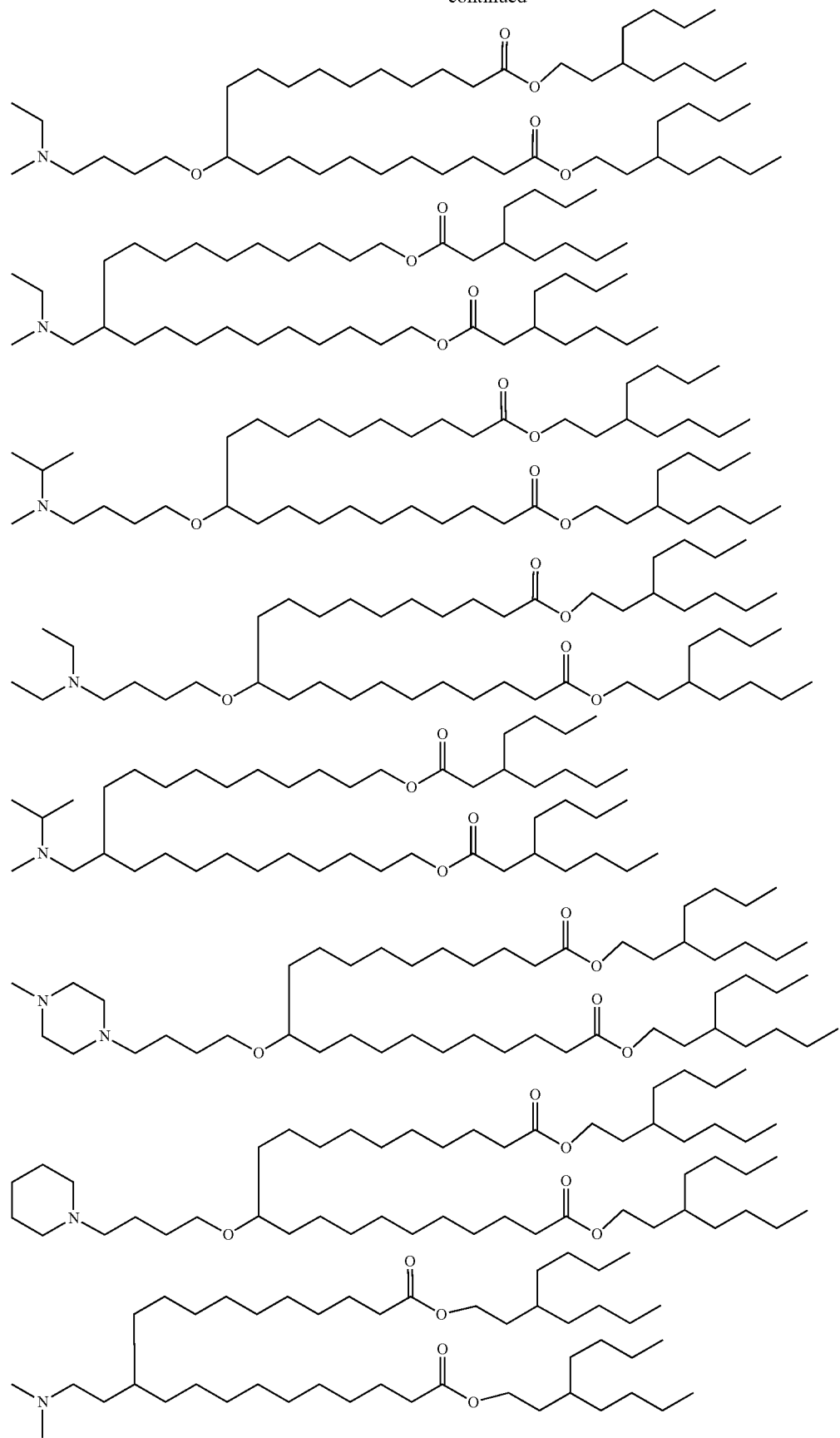

-continued
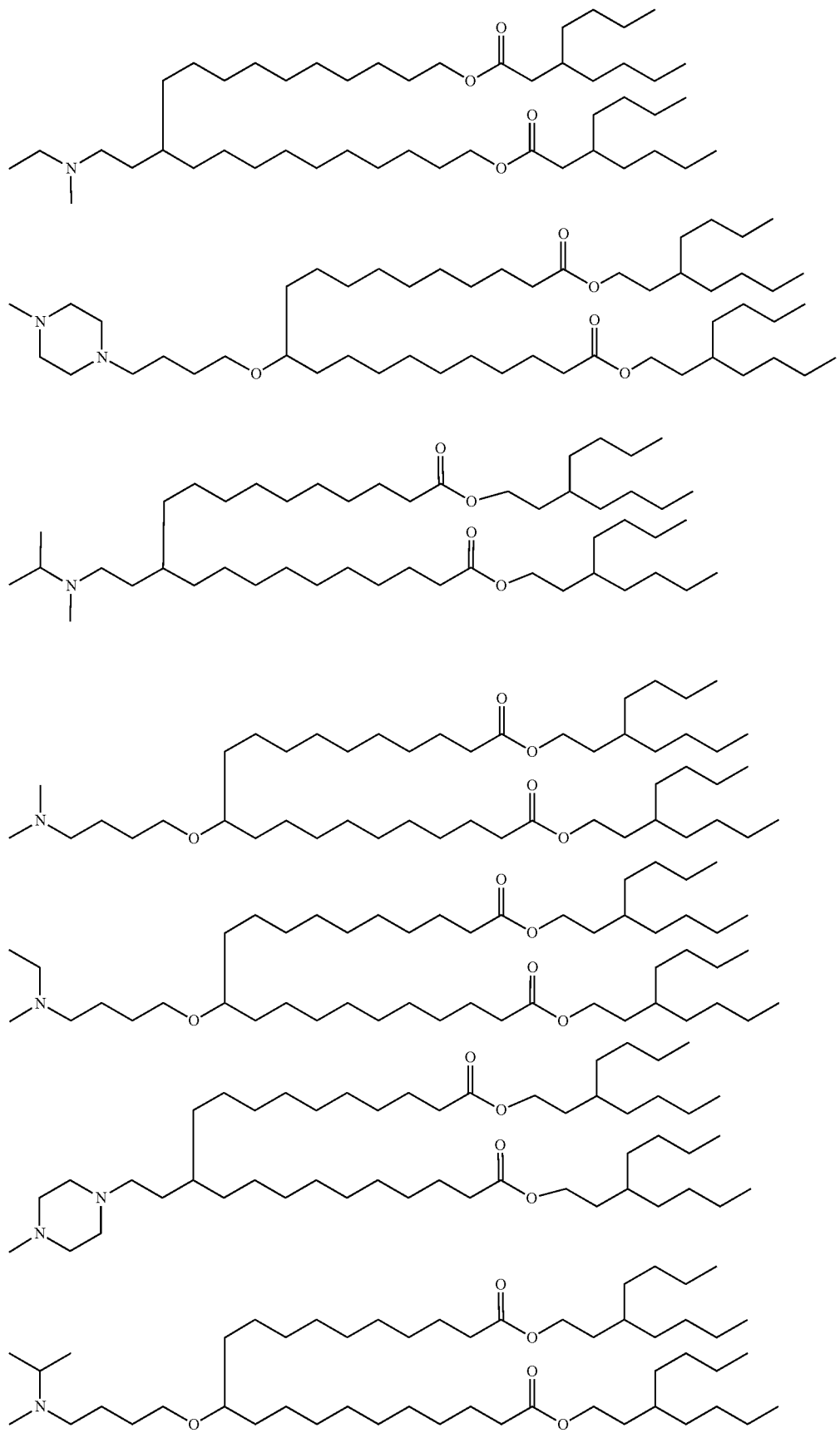

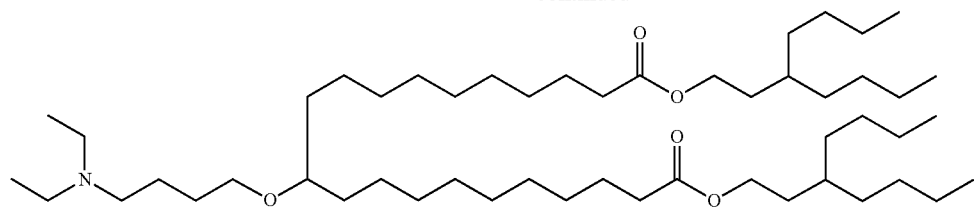
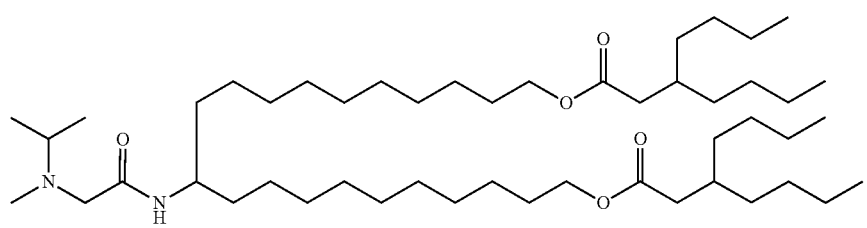
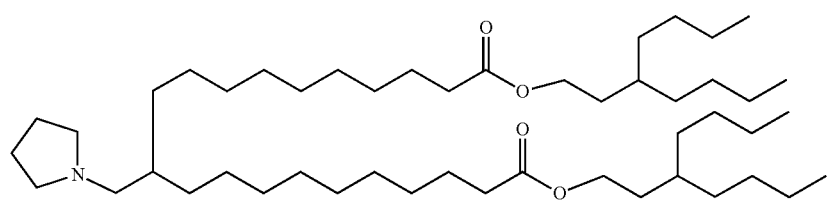
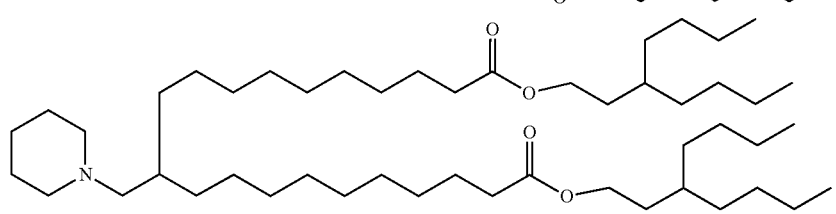
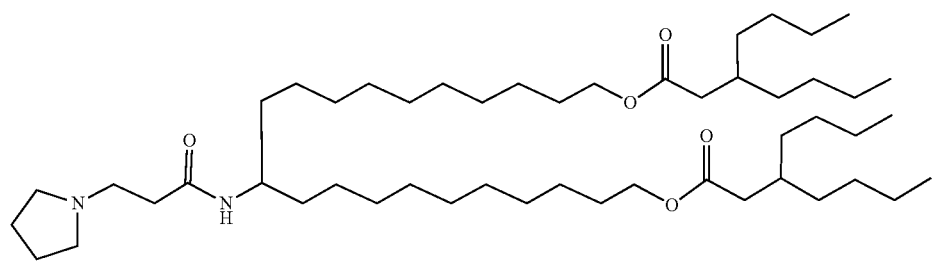
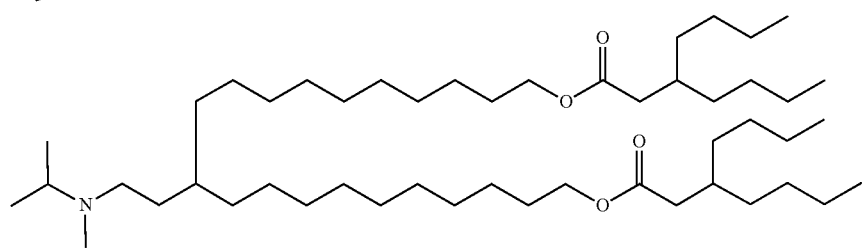
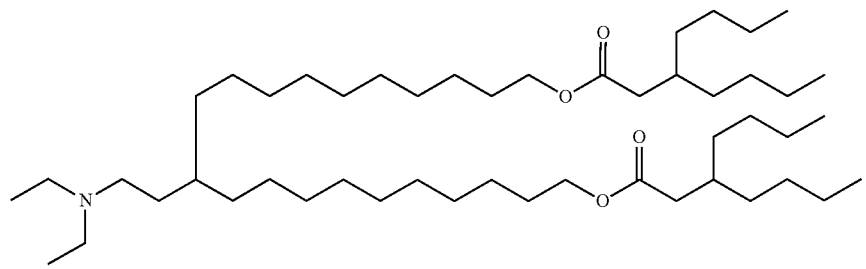

-continued
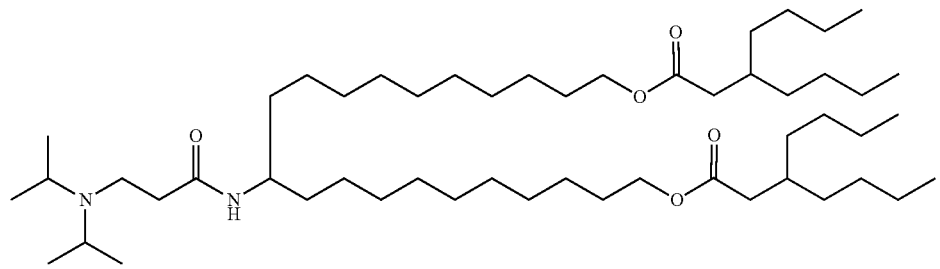
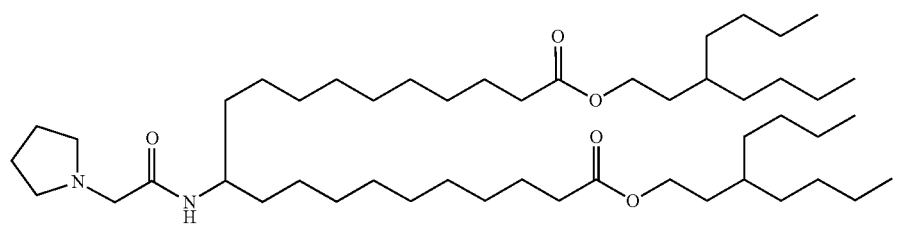
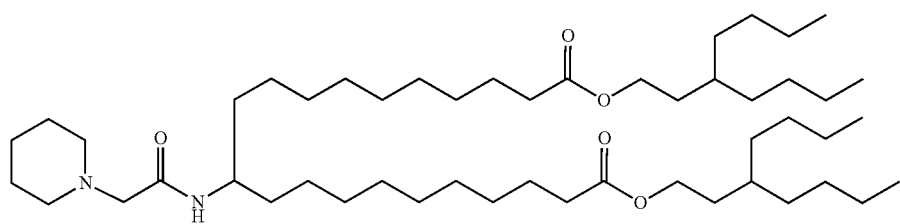
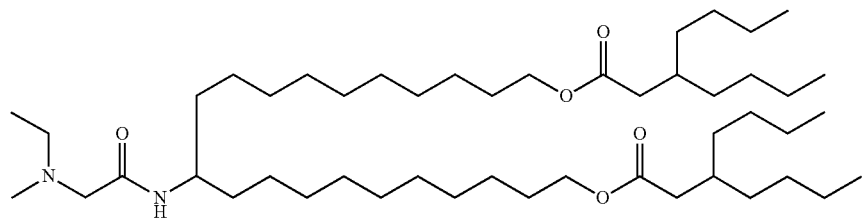
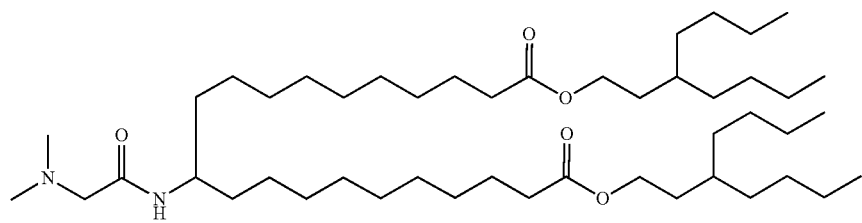
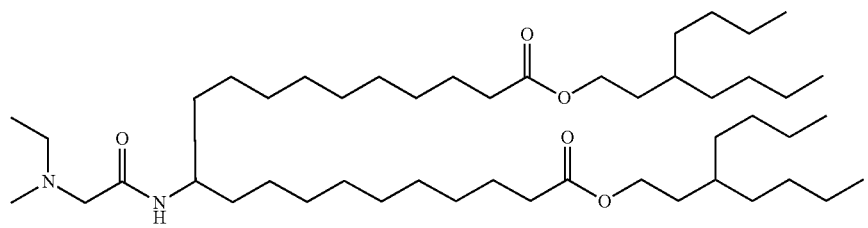
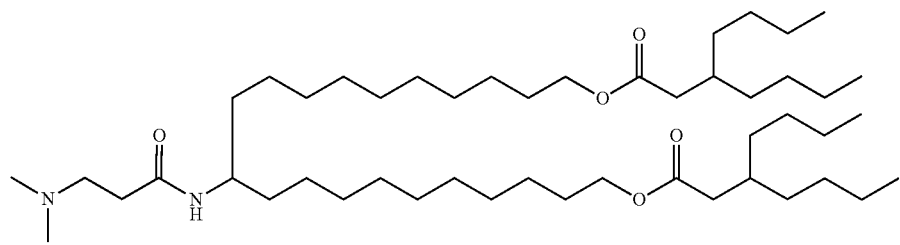

-continued
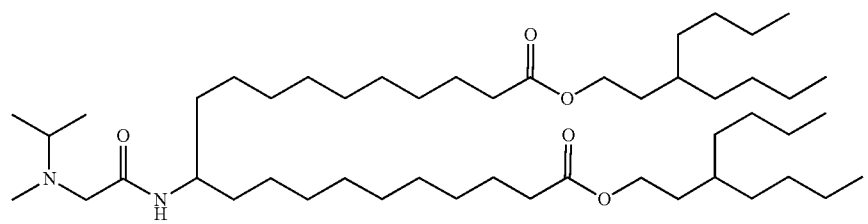
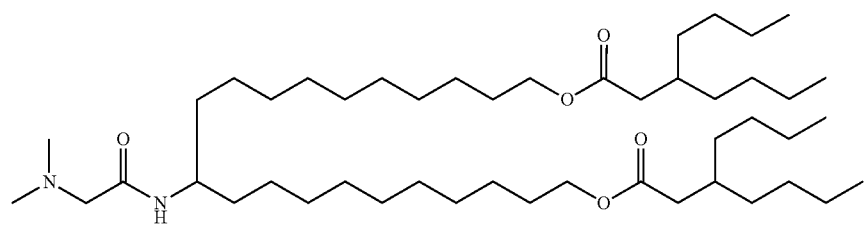
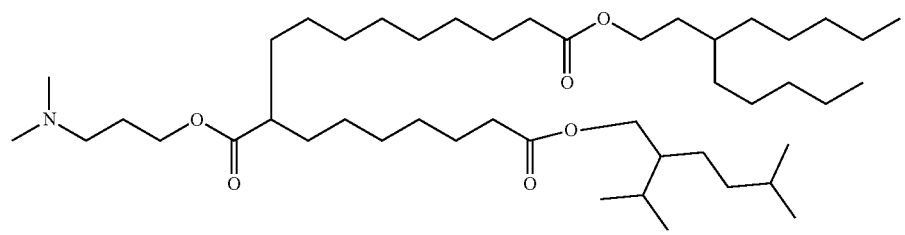
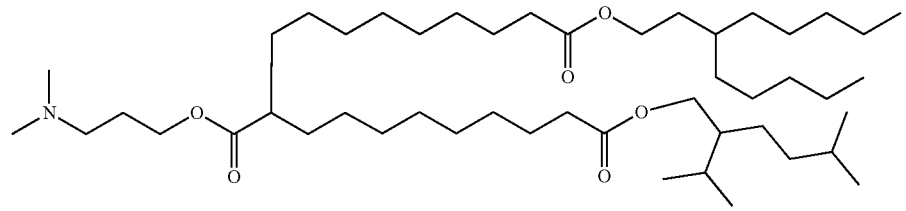
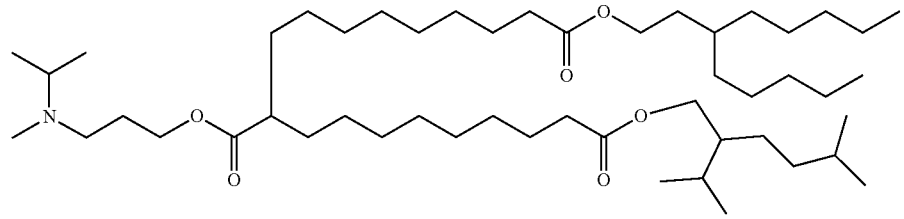
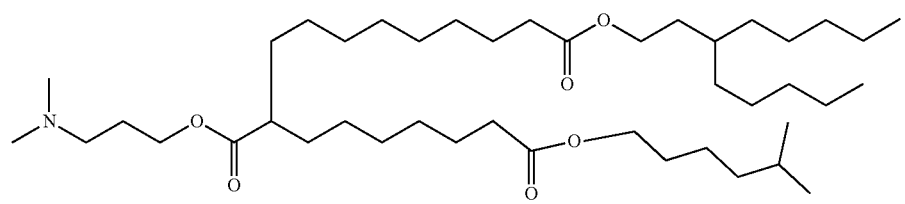
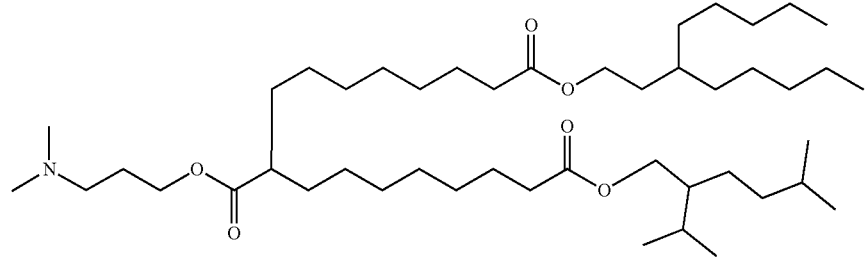

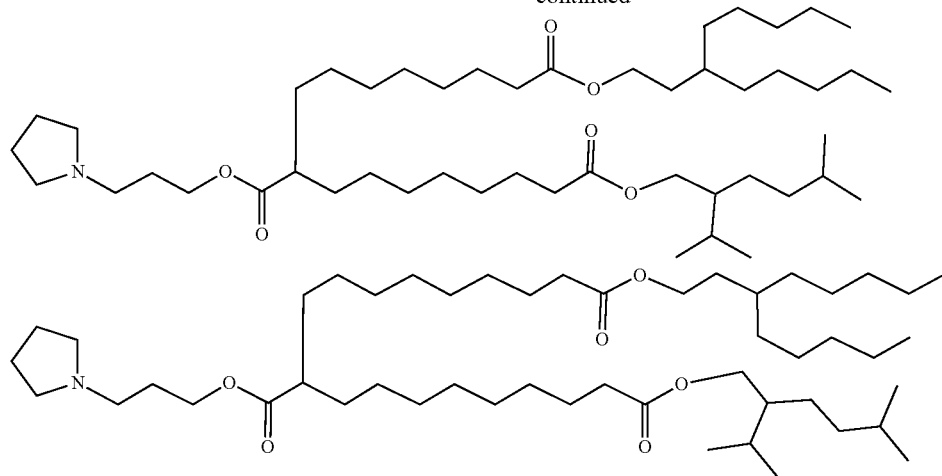

In another aspect, the present invention relates to a method of preparing a compound of Formula I-VII. Suitable exemplary synthetic methods are illustrated in Schemes 1-27 shown in the Examples section below.

In one embodiment, the cationic lipid of the present invention is selected from the following compounds, and salts thereof (including pharmaceutically acceptable salts thereof). These cationic lipids are suitable for forming nucleic acid-lipid particles.

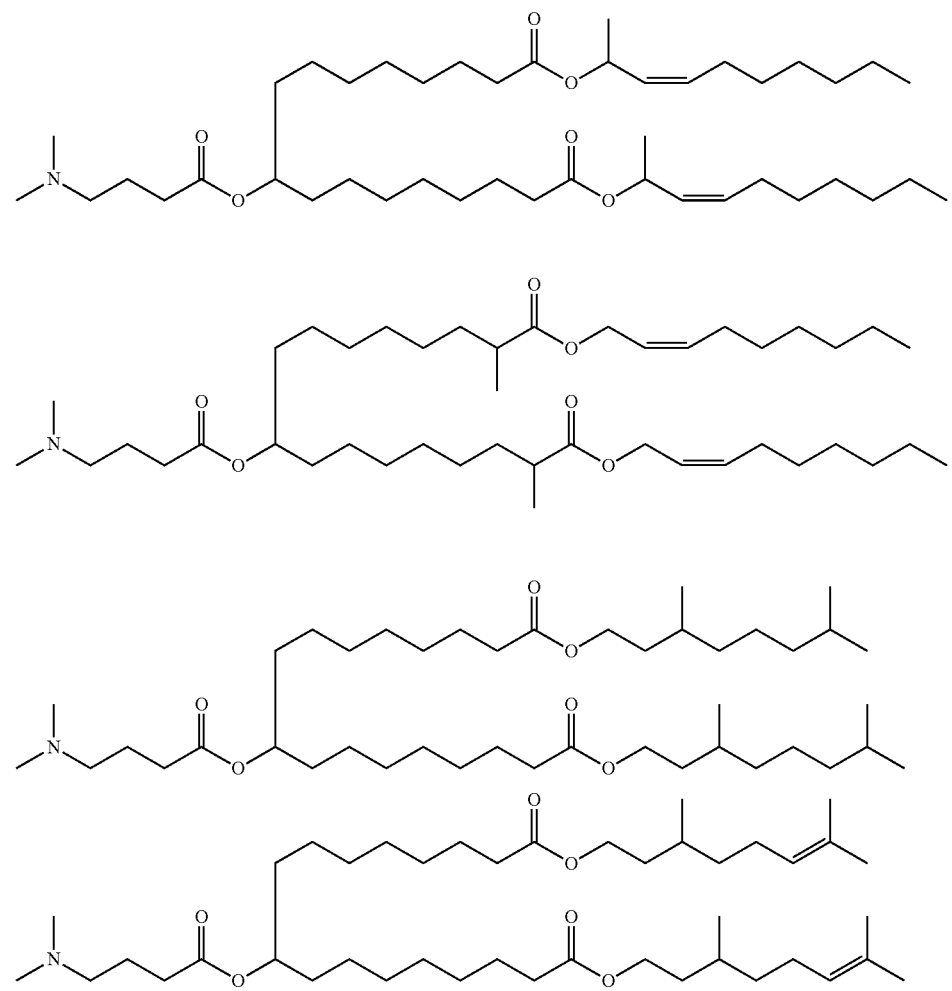

-continued
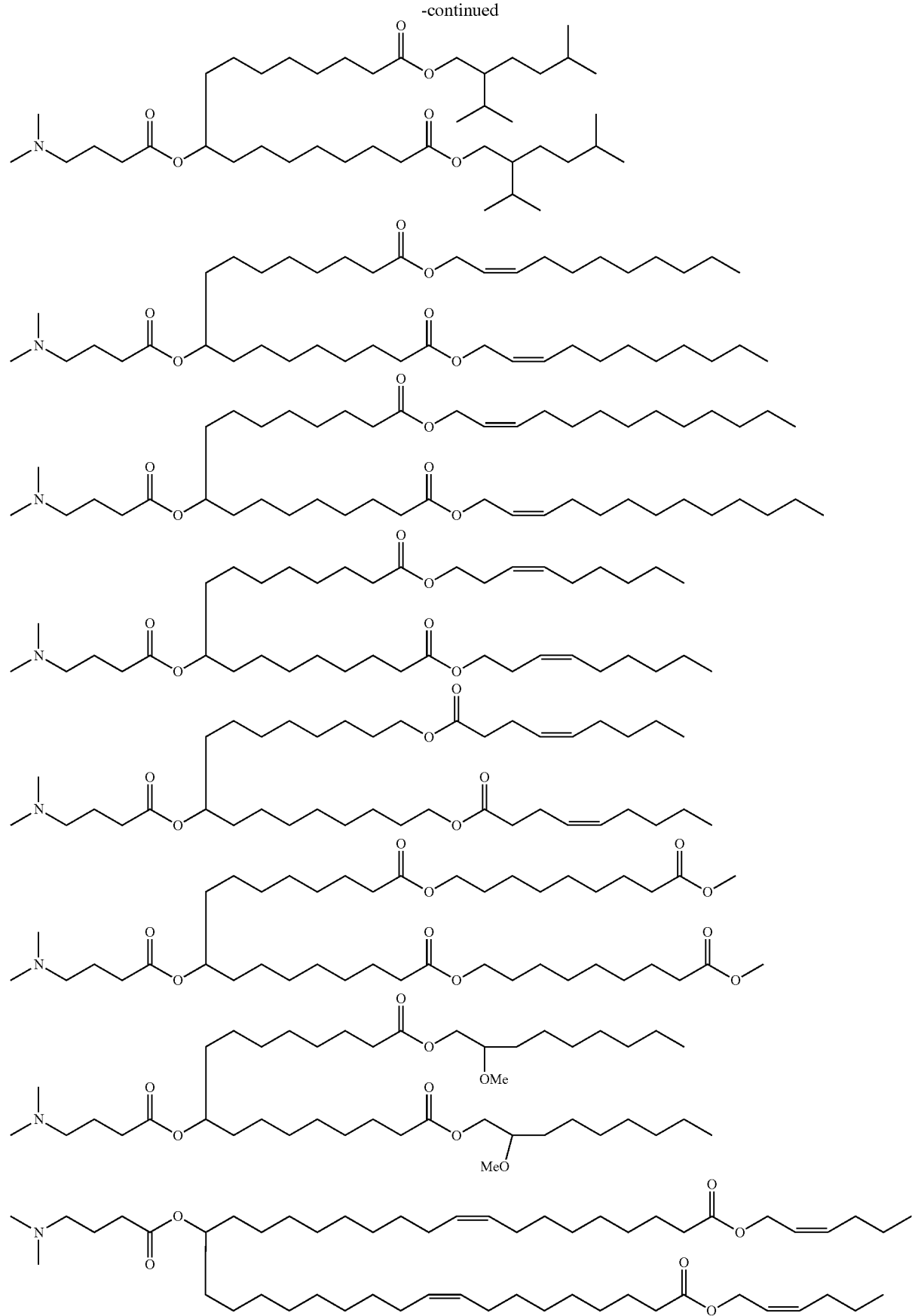

-continued
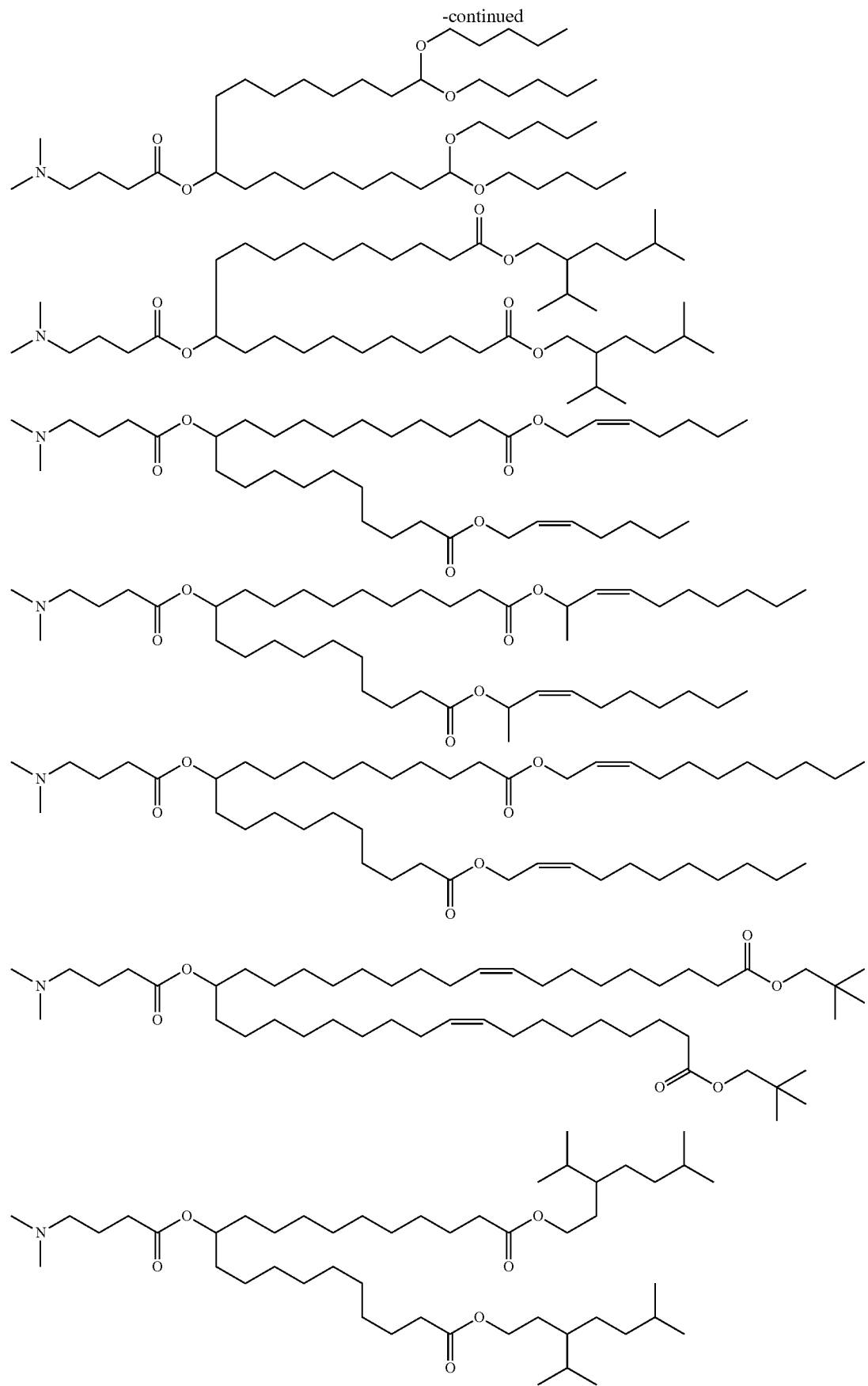

-continued
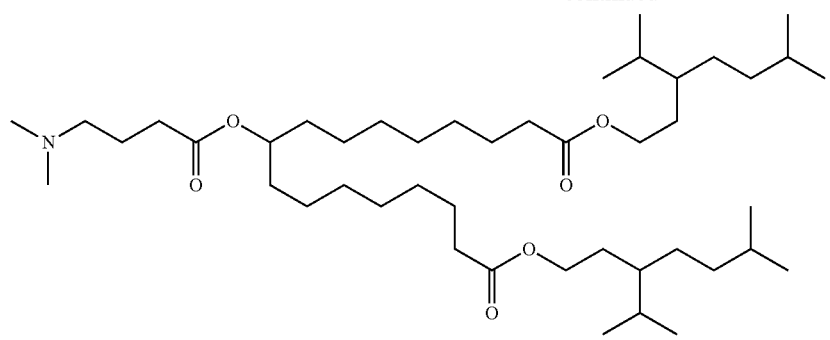
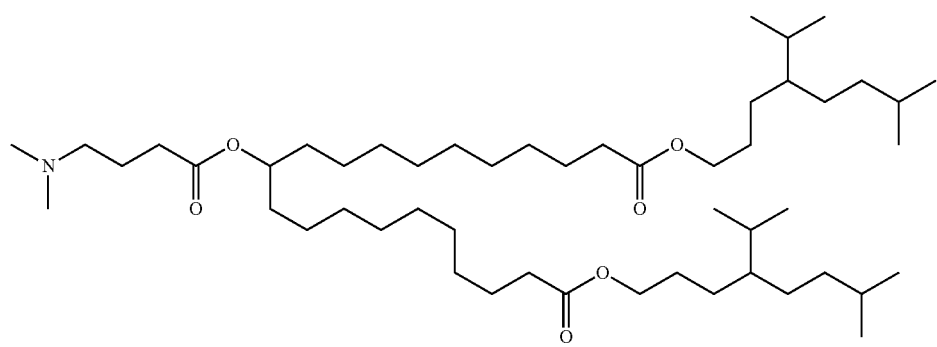
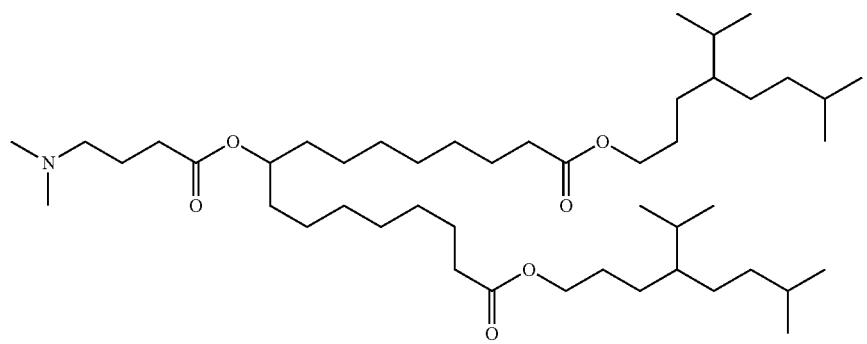
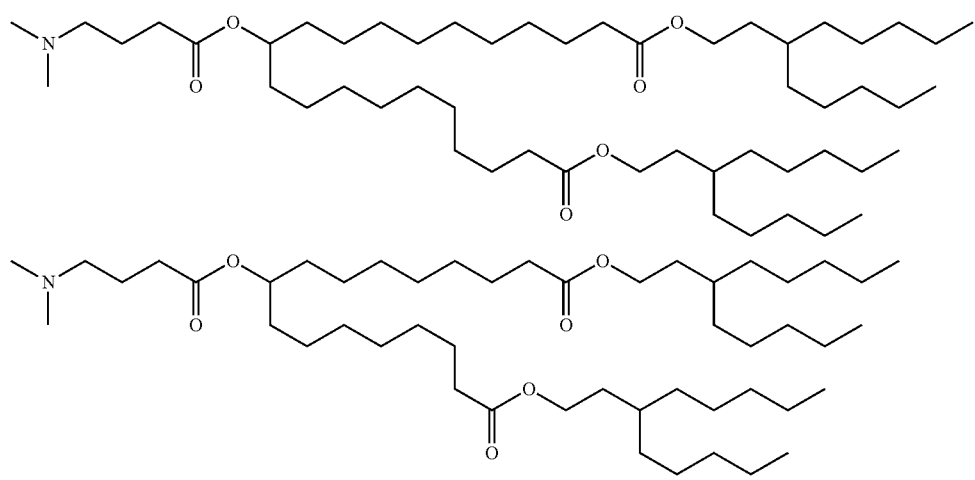

In another embodiment, the cationic lipid of the present invention is selected from the following compounds, and salts thereof (including pharmaceutically acceptable salts thereof):
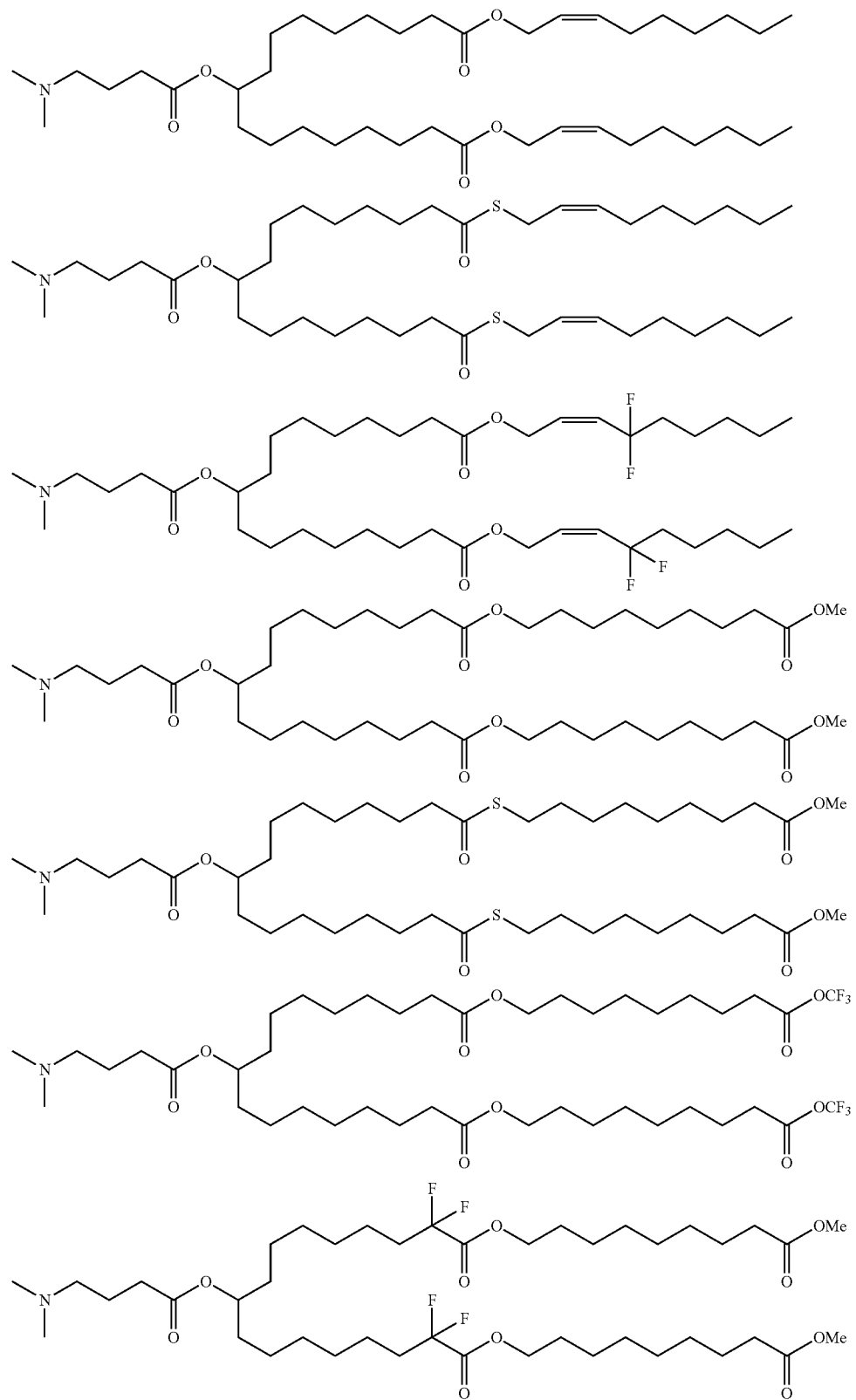

-continued
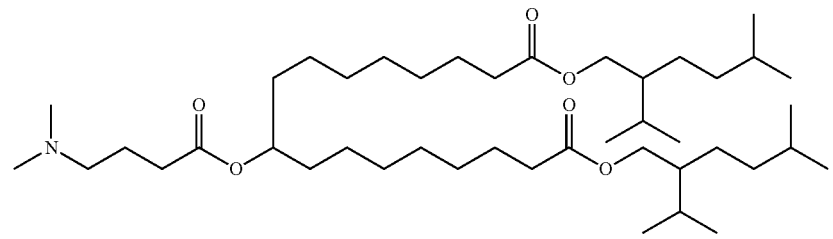
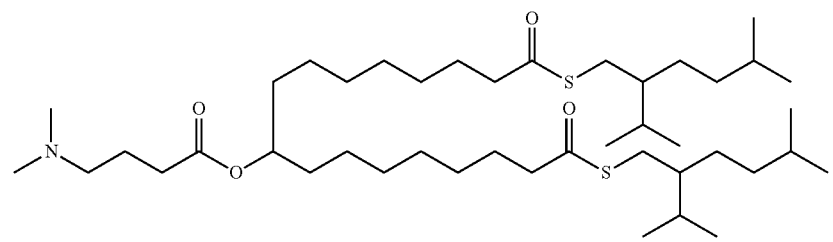
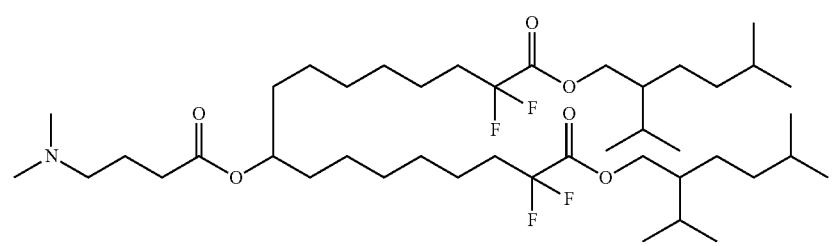
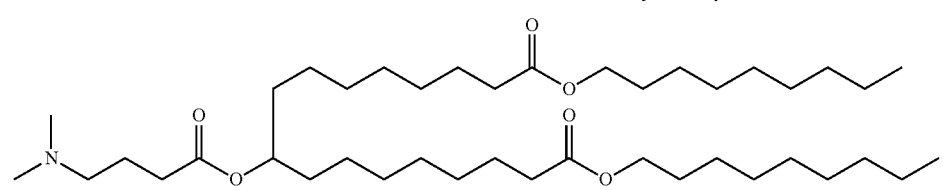
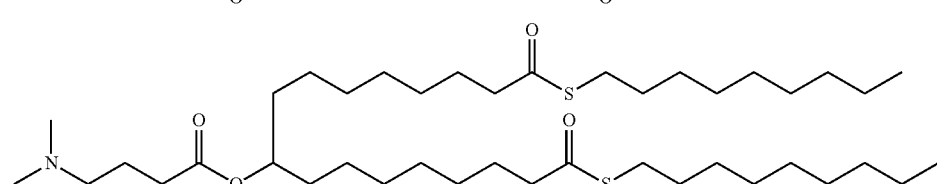
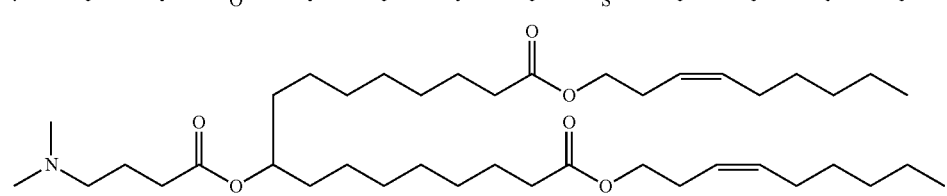
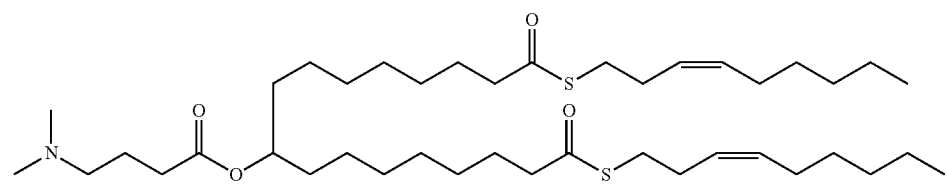
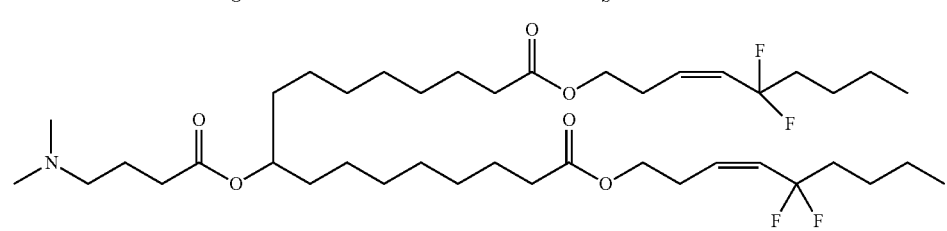

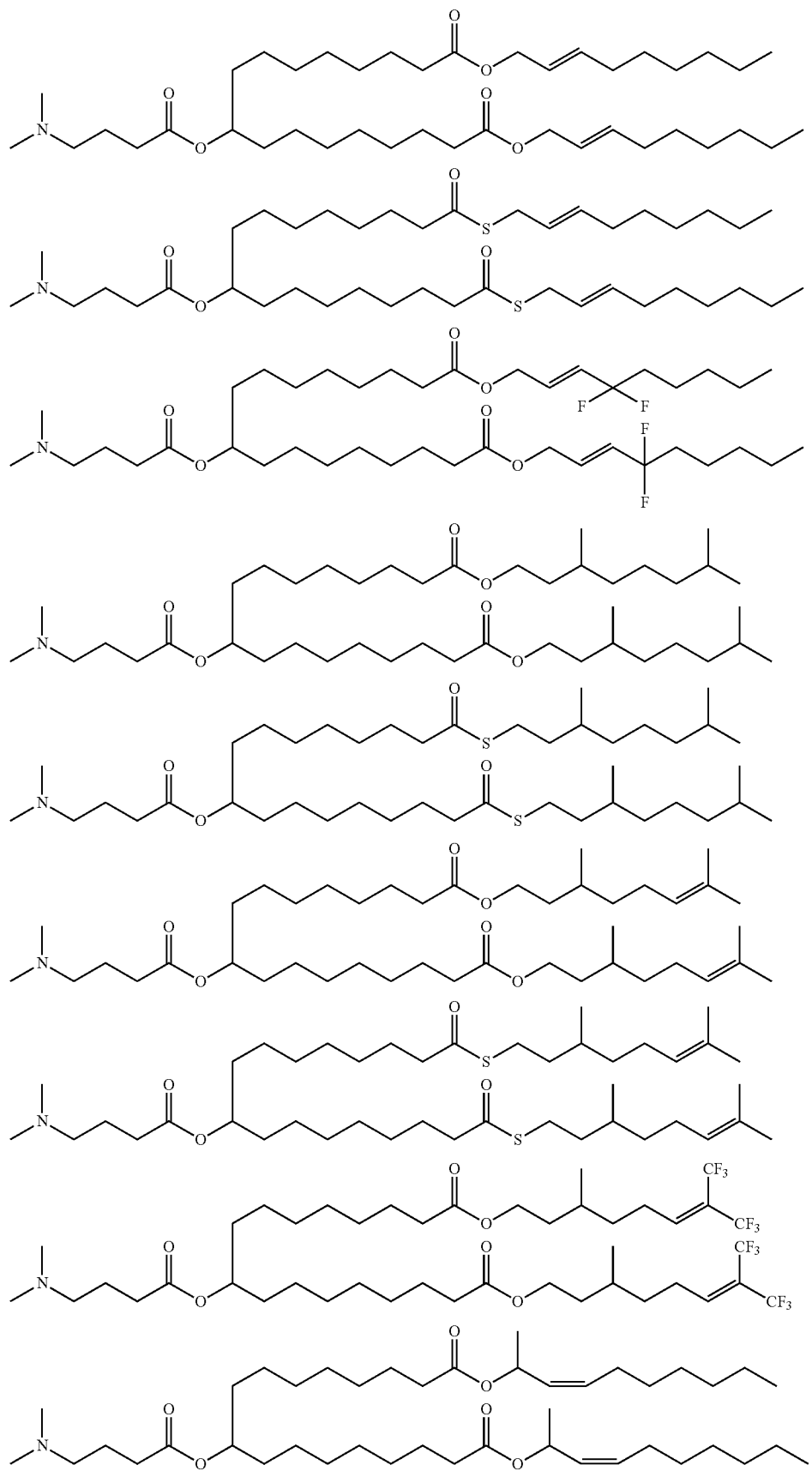

-continued
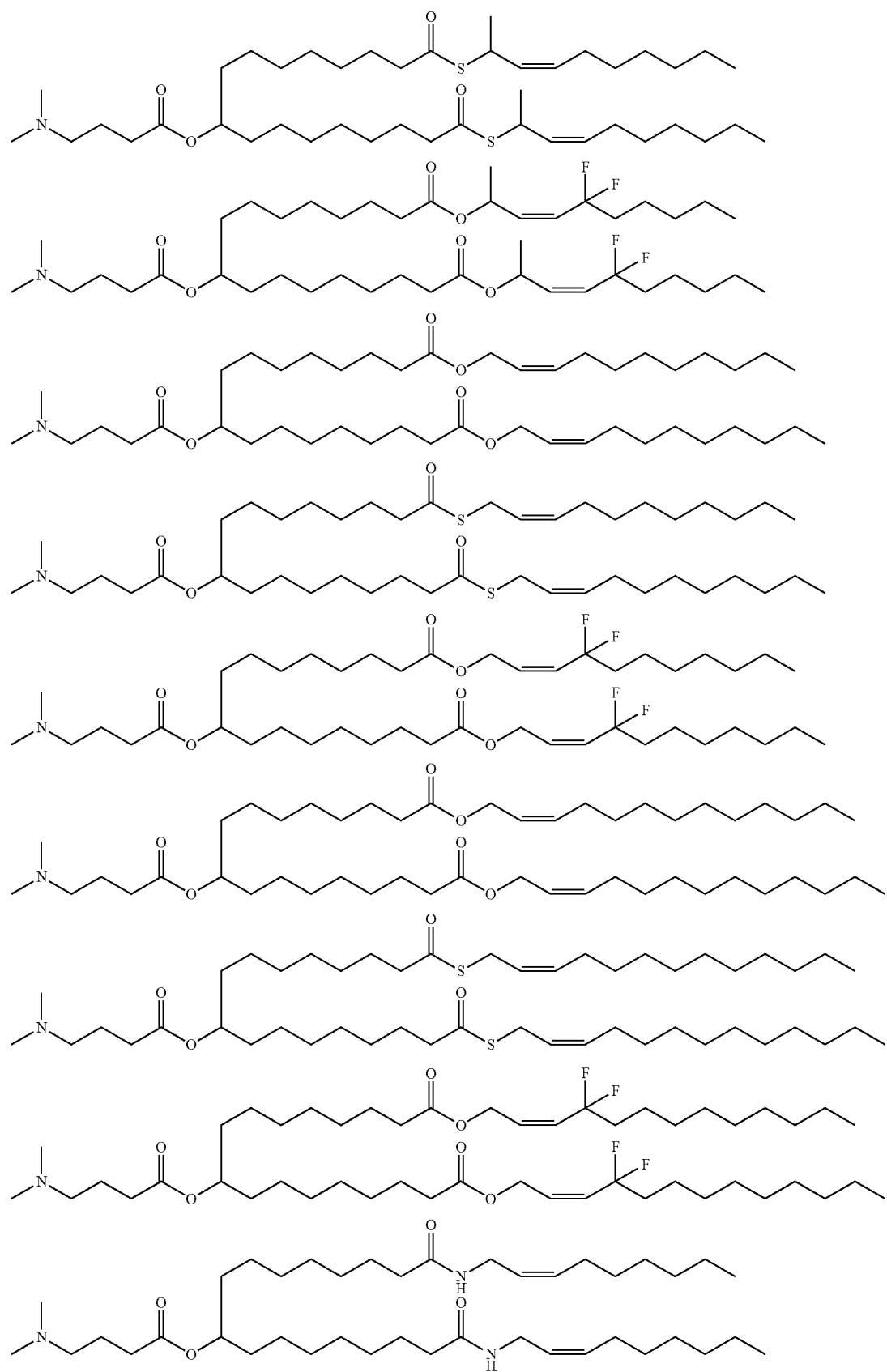

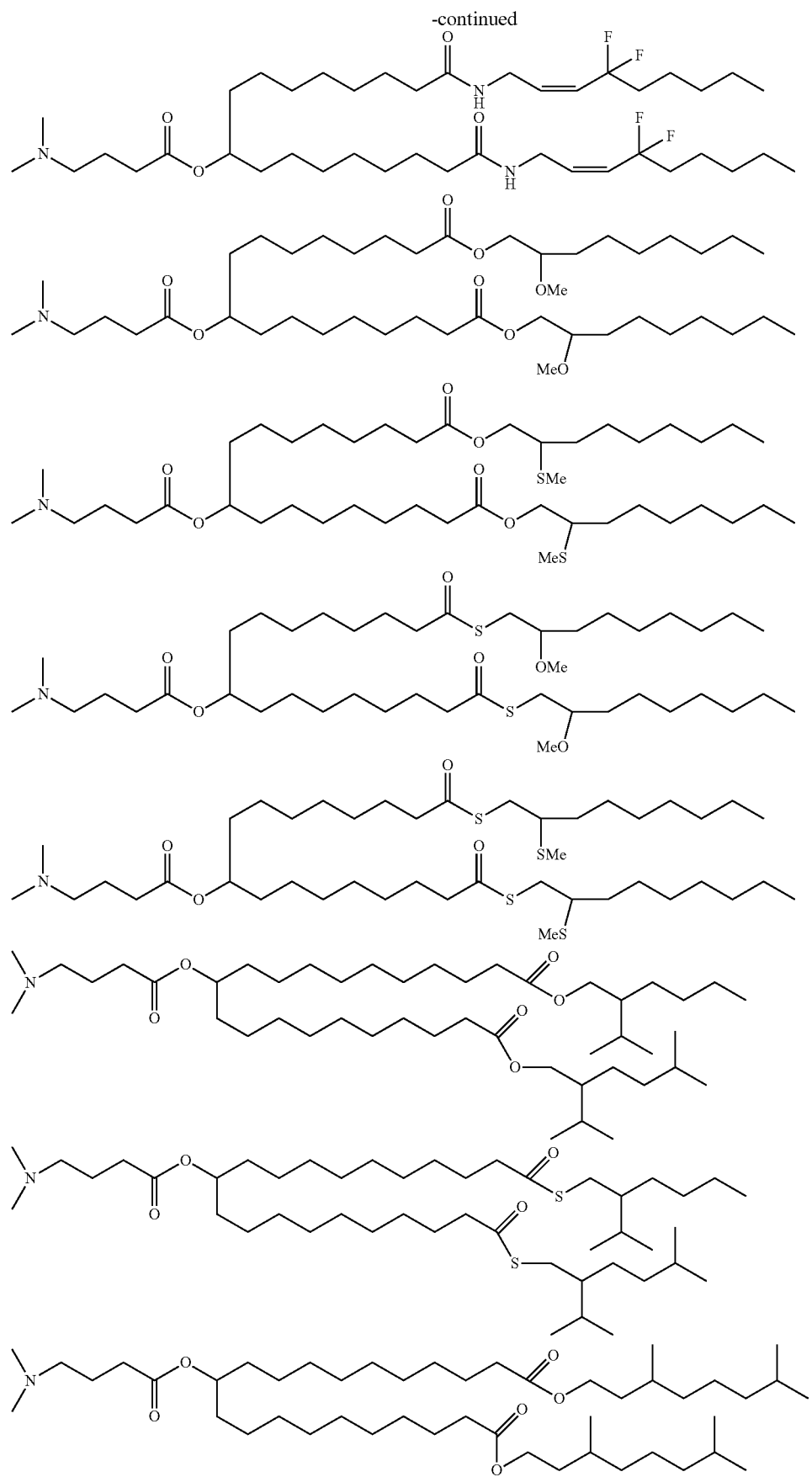

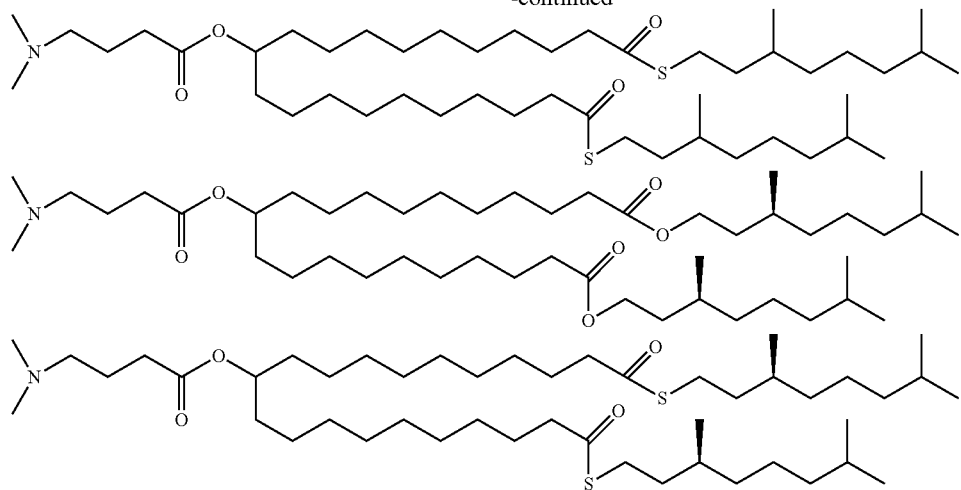
In another embodiment, the cationic lipid of the present invention is selected from the following compounds, and salts thereof (including pharmaceutically acceptable salts thereof):
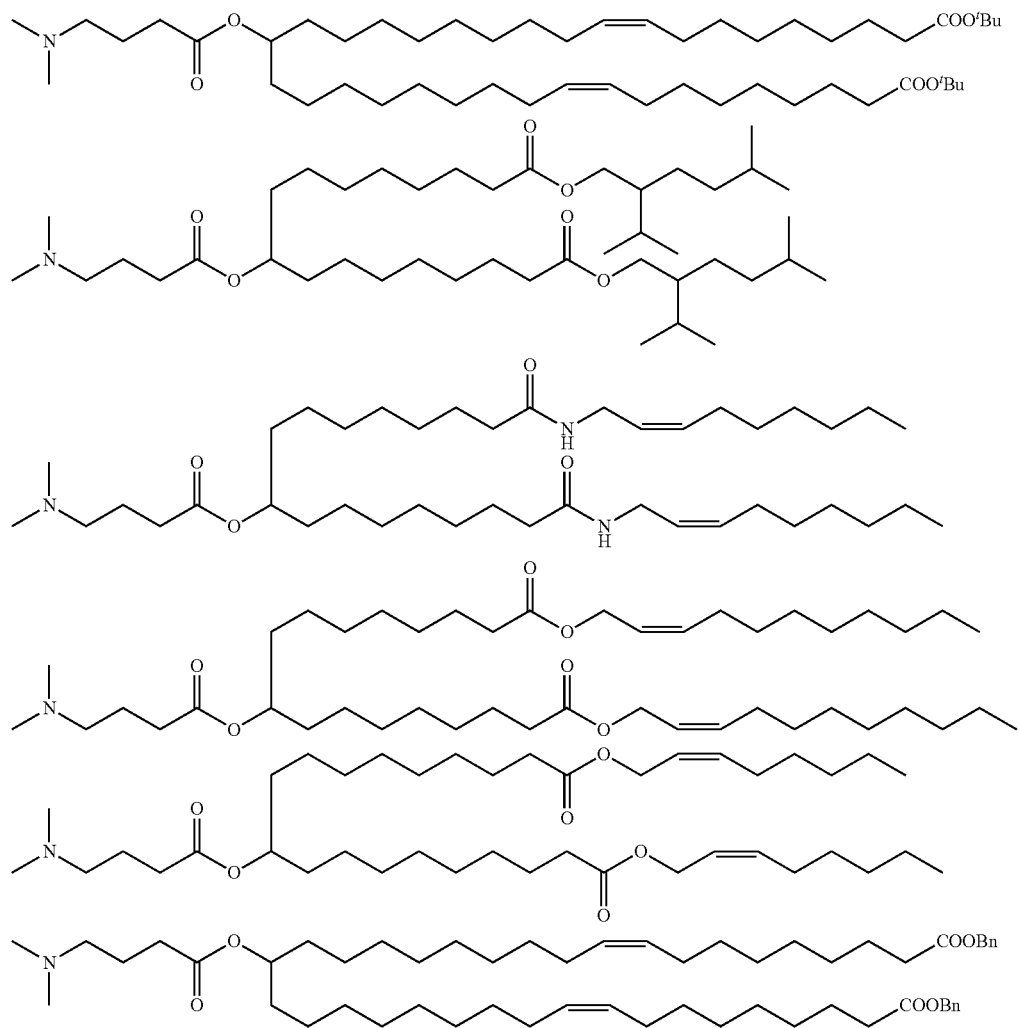

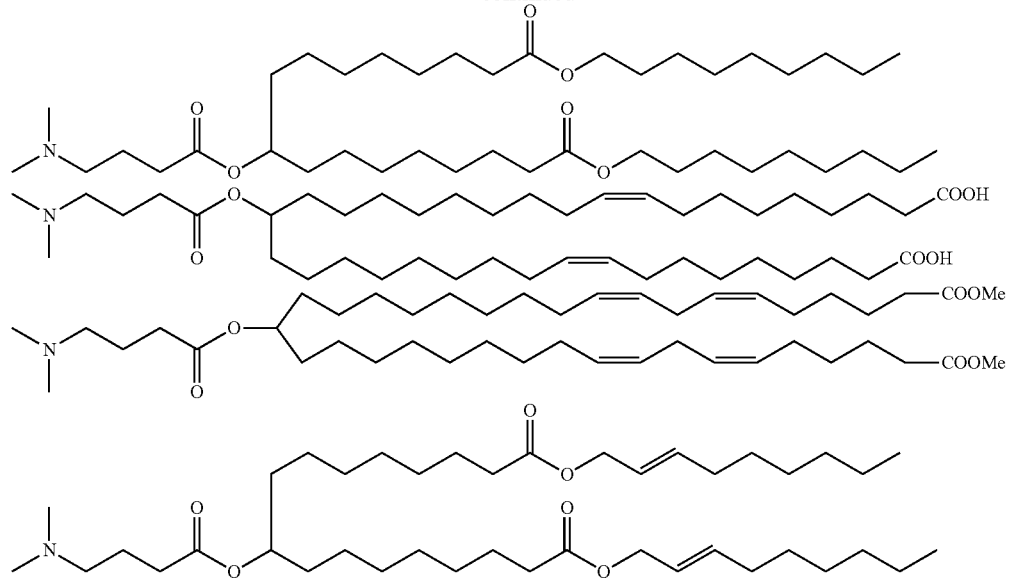
Additional representative cationic lipids include, but are not limited to:
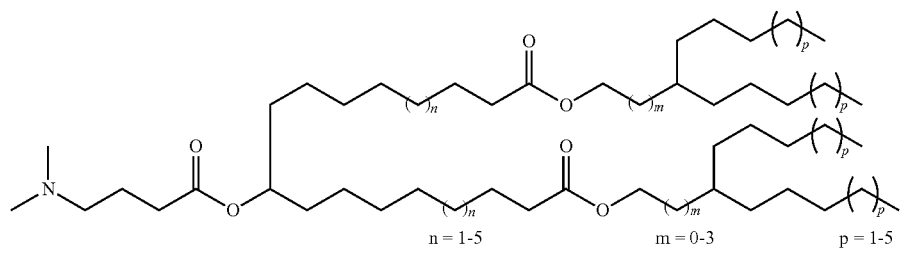
n = 1-5    m = 0-3    p = 1-5
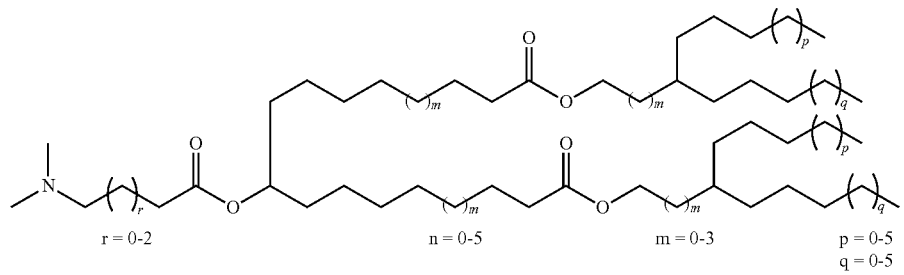
r = 0-2    n = 0-5    m = 0-3    p = 0-5
                                 q = 0-5
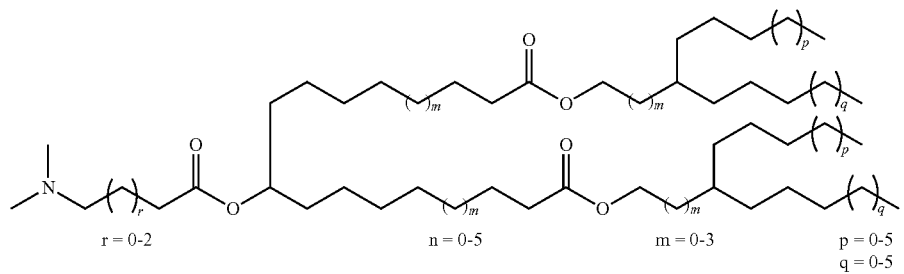
r = 0-2    n = 0-5    m = 0-3    p = 0-5
                                 q = 0-5

-continued
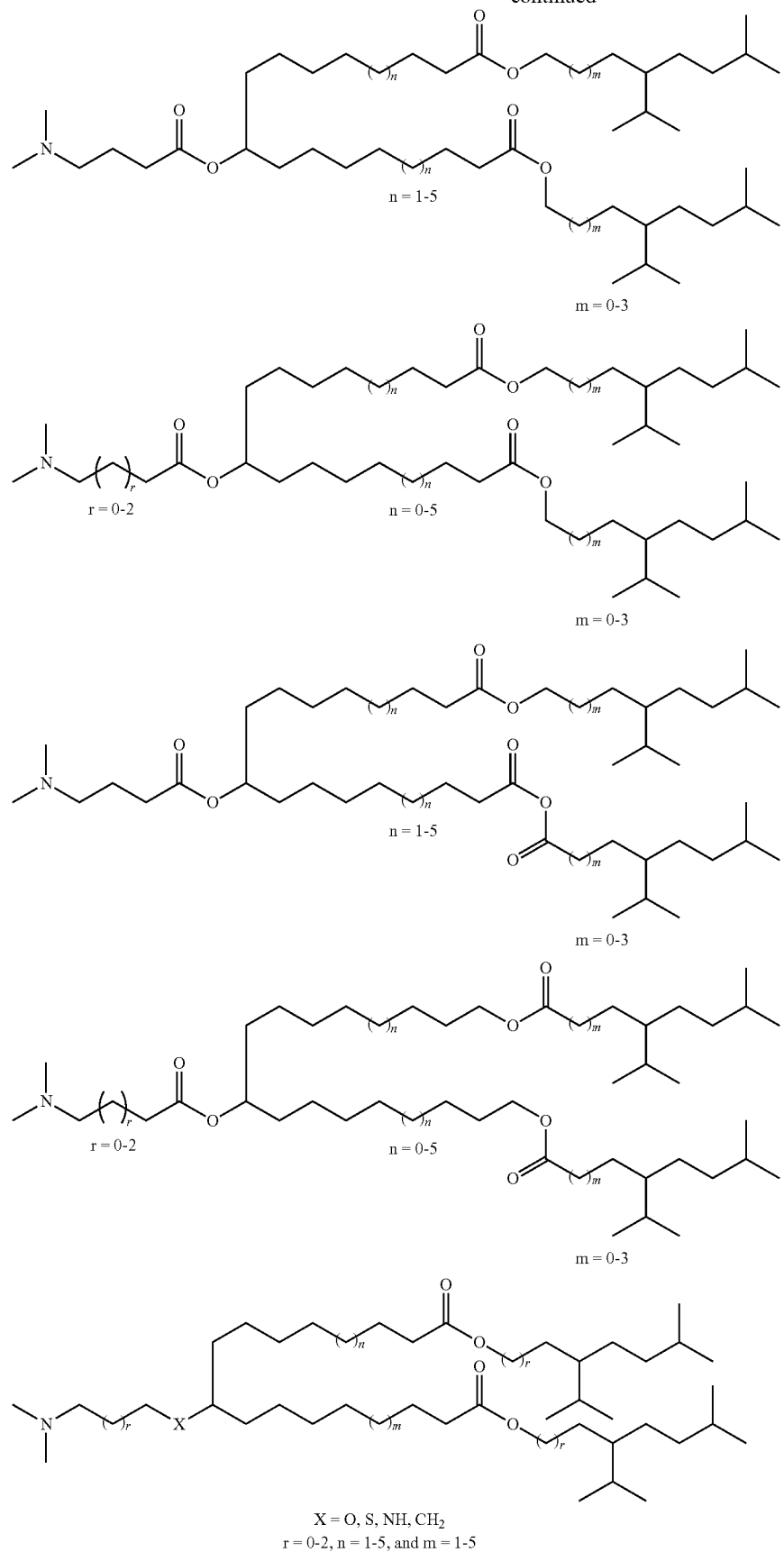

-continued
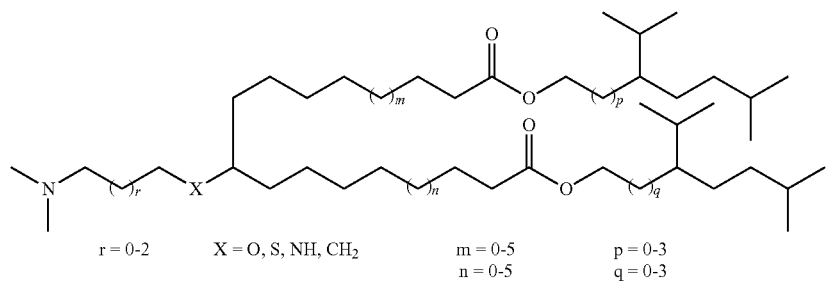
r = 0-2    X = O, S, NH, CH₂    m = 0-5    p = 0-3
                                 n = 0-5    q = 0-3
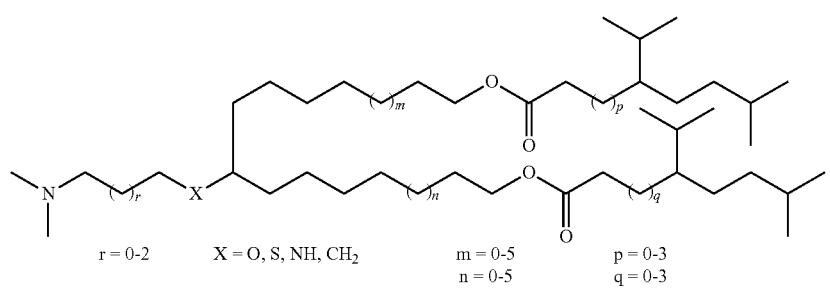
r = 0-2    X = O, S, NH, CH₂    m = 0-5    p = 0-3
                                 n = 0-5    q = 0-3
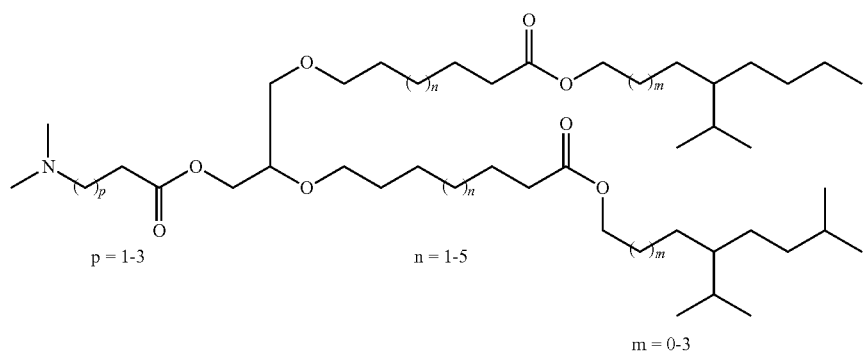
p = 1-3    n = 1-5    m = 0-3
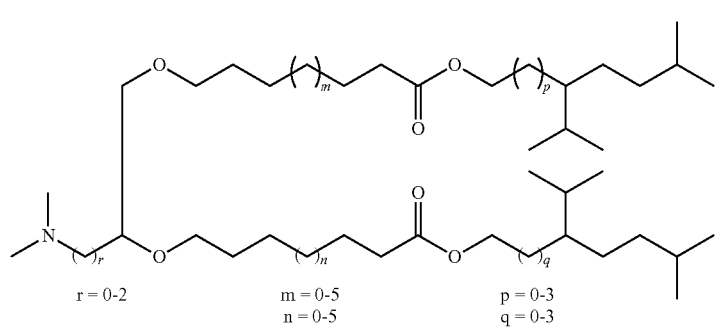
r = 0-2    m = 0-5    p = 0-3
           n = 0-5    q = 0-3
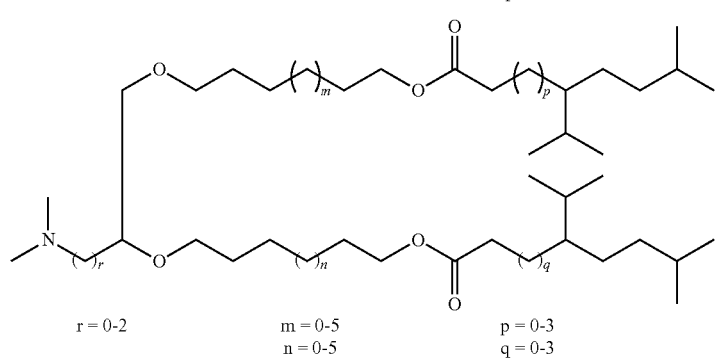
r = 0-2    m = 0-5    p = 0-3
           n = 0-5    q = 0-3

-continued
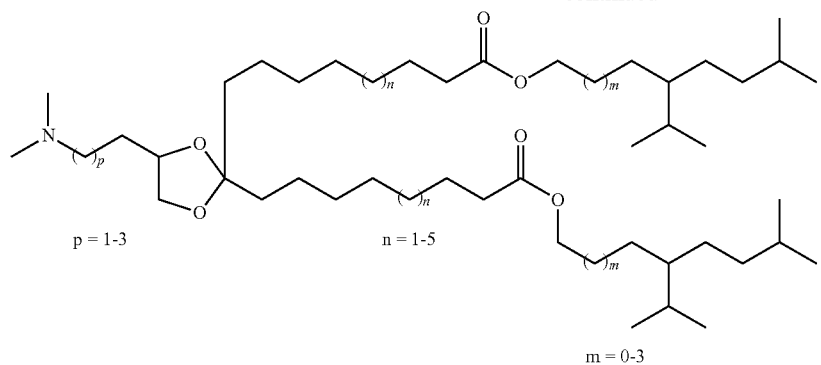
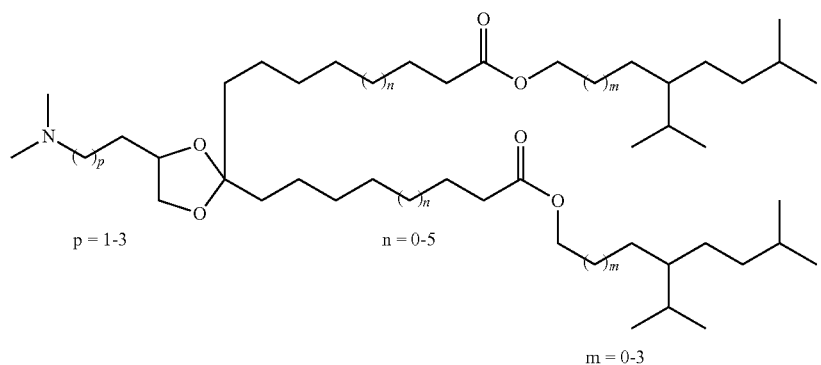
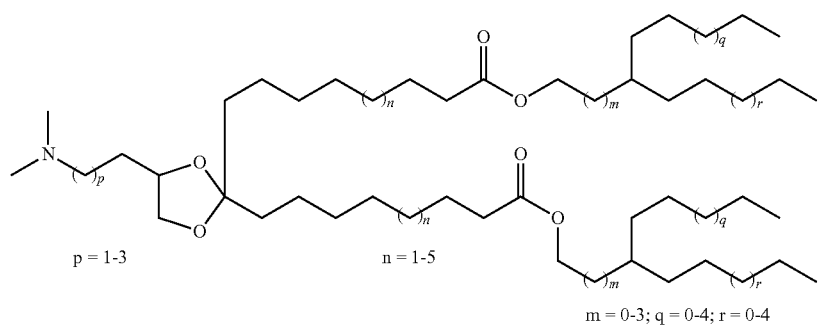
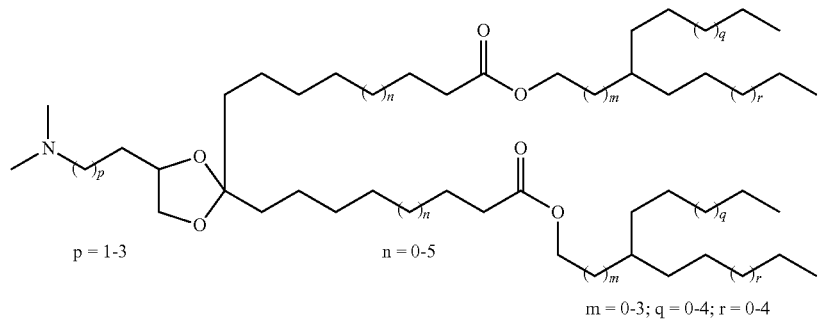
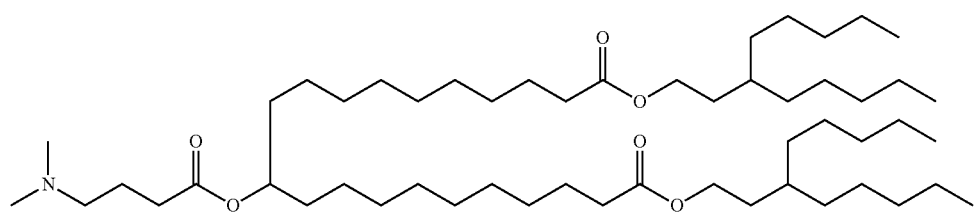

-continued
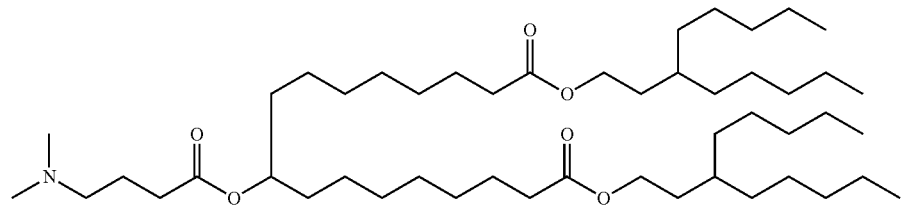
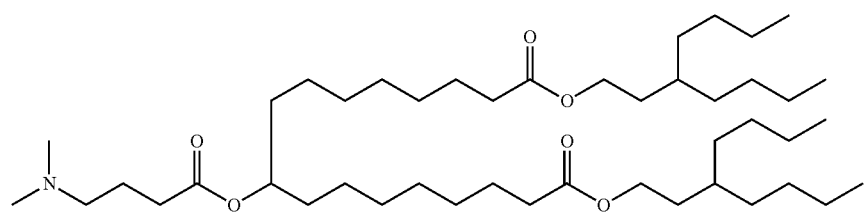
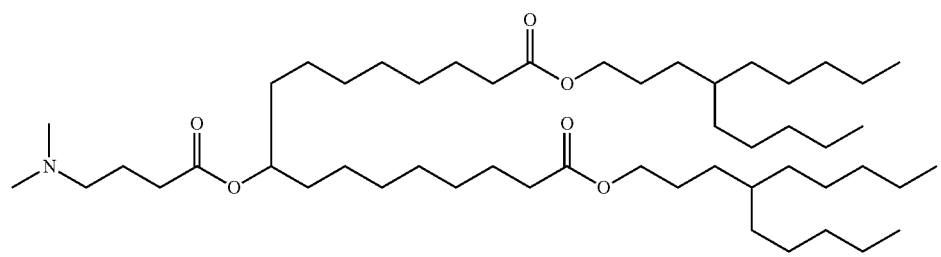
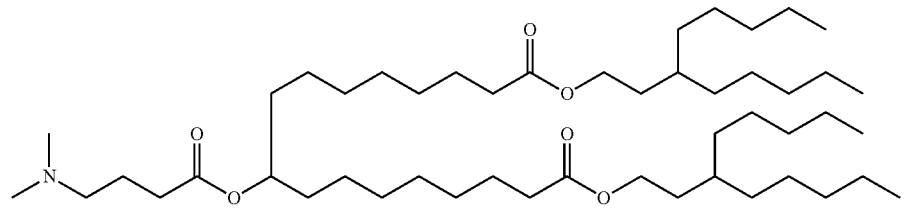
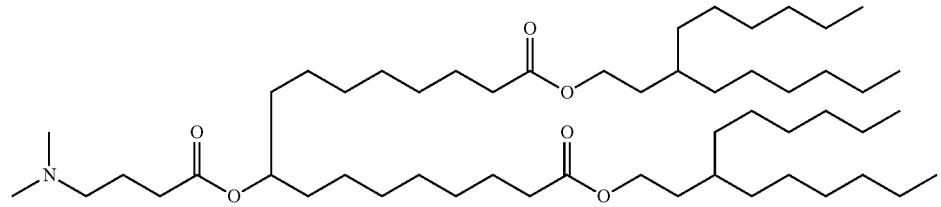
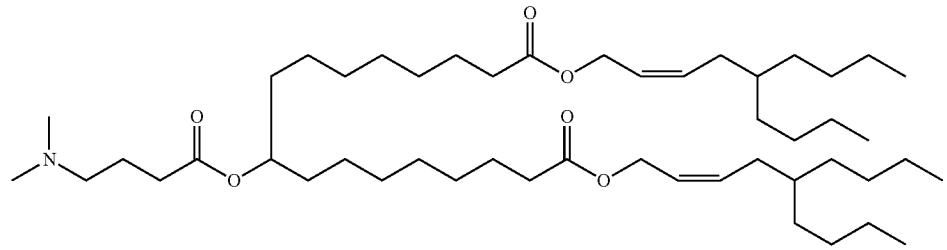
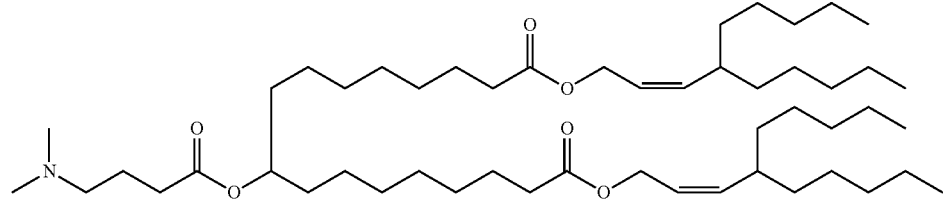

-continued
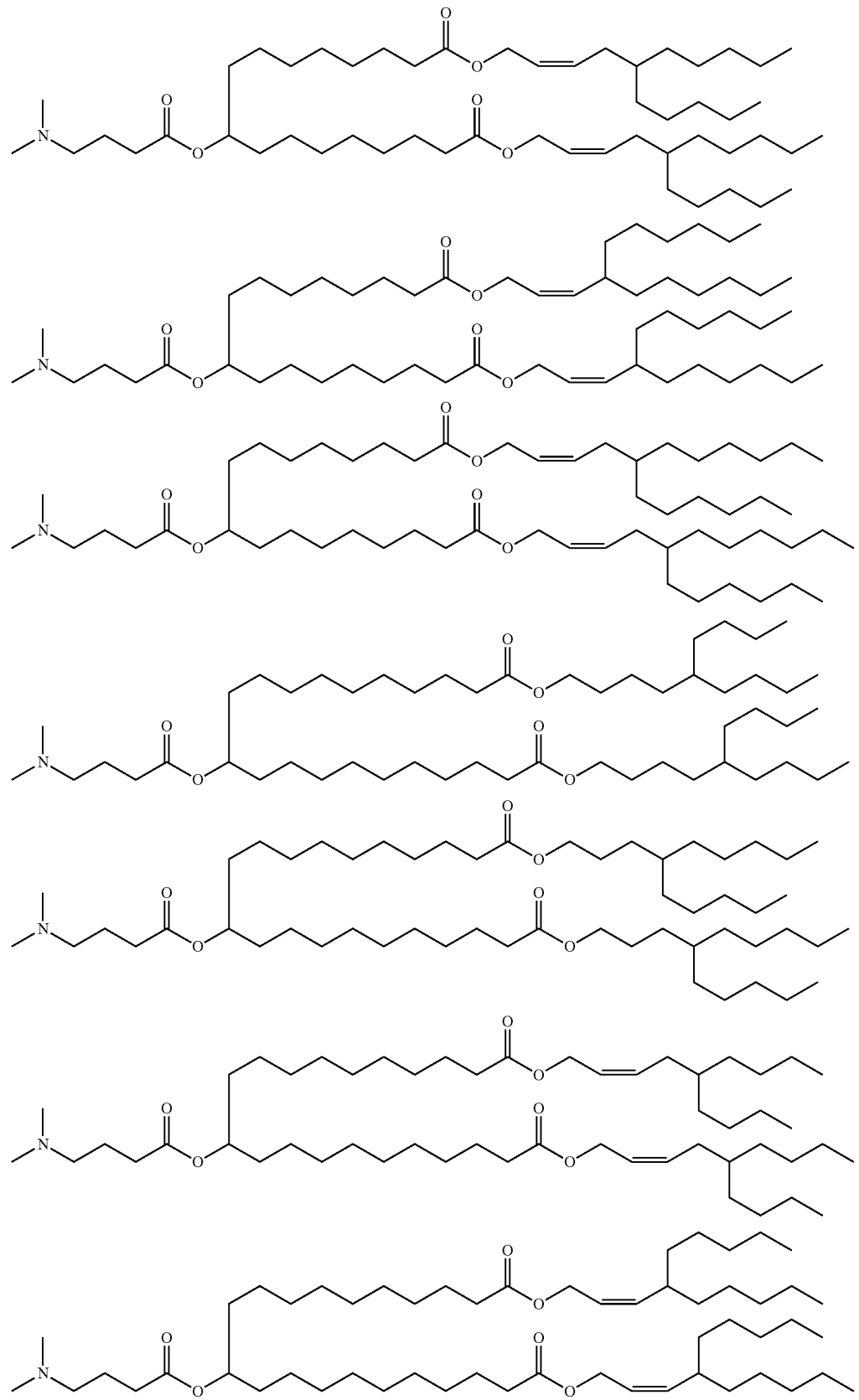

-continued
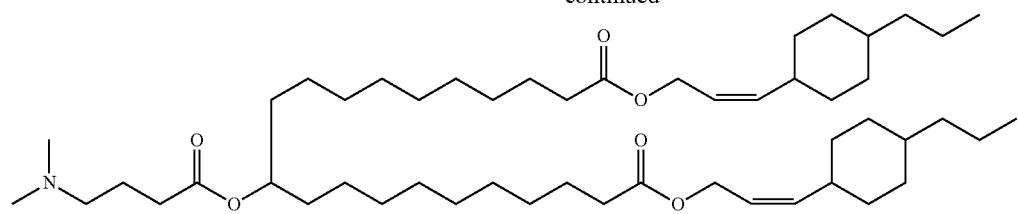
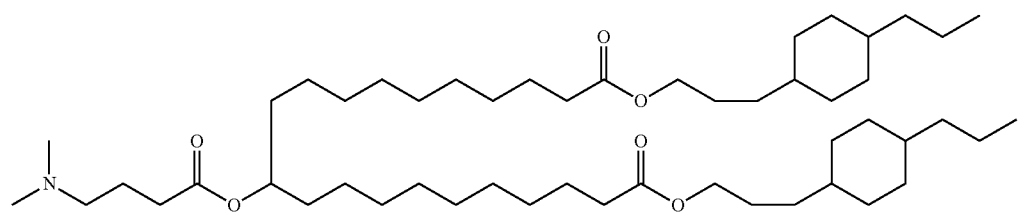
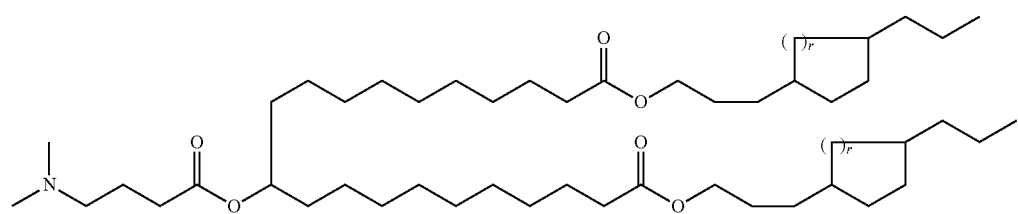
r = 0, 1, or 2
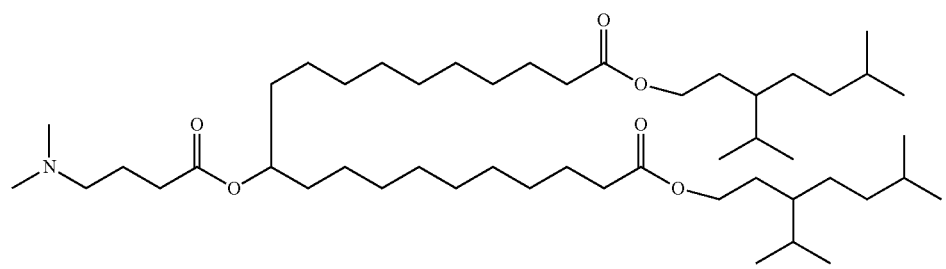
z
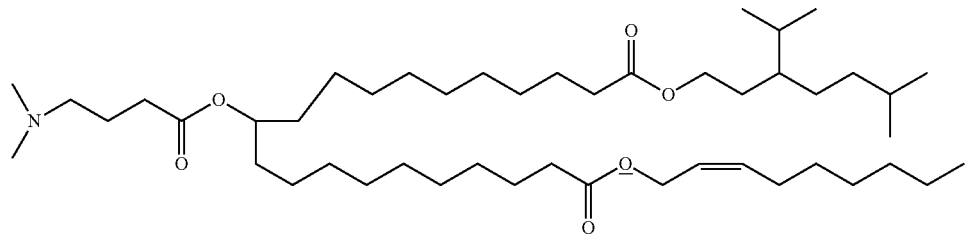
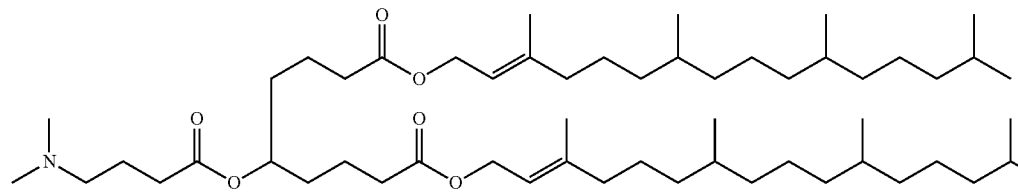
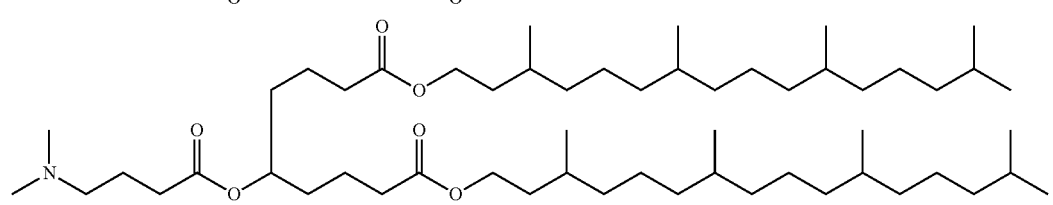

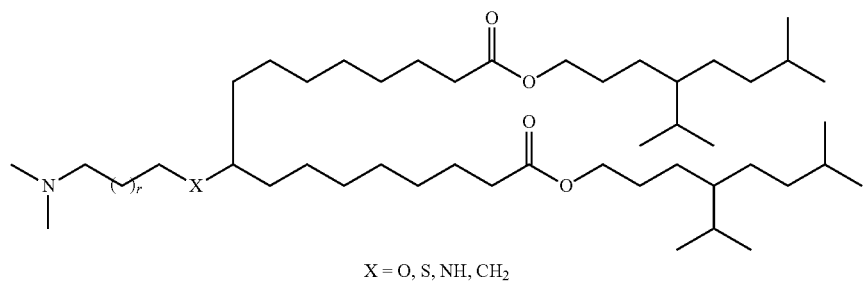
X = O, S, NH, CH₂
r = 0, 1, or 2
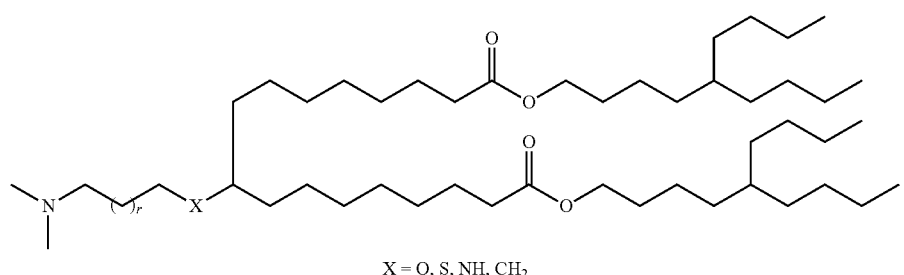
X = O, S, NH, CH₂
r = 0, 1, or 2
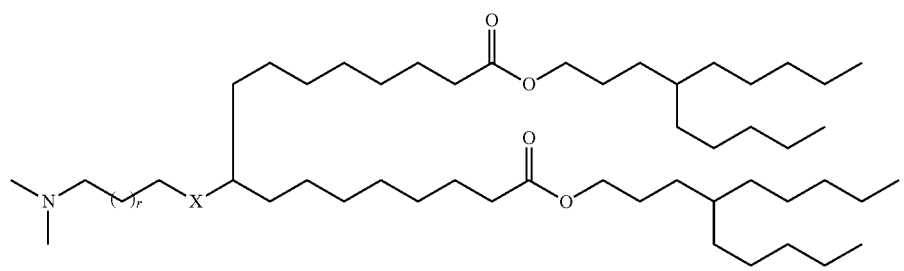
X = O, S, NH, CH₂
r = 0, 1, or 2
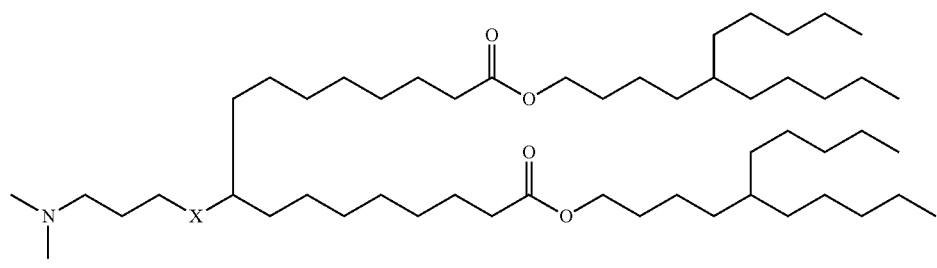
X = O, S, NH, CH₂
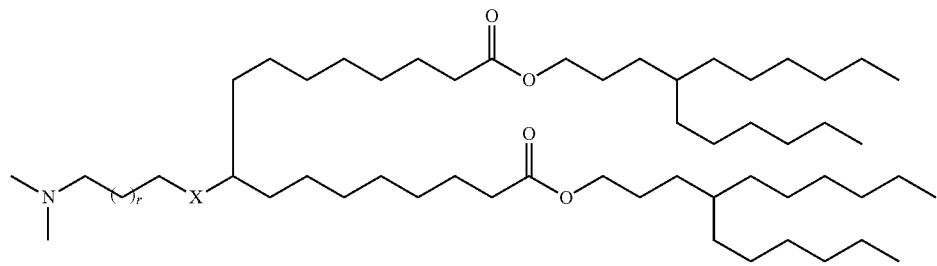
X = O, S, NR, CH₂
r = 0, 1, or 2

-continued
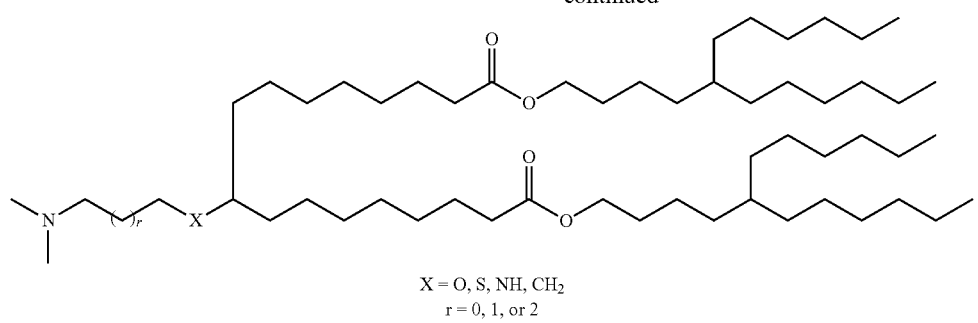
X = O, S, NH, CH$_2$
r = 0, 1, or 2
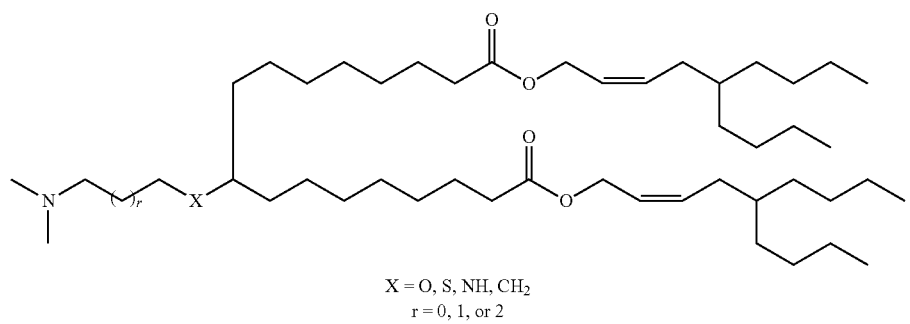
X = O, S, NH, CH$_2$
r = 0, 1, or 2
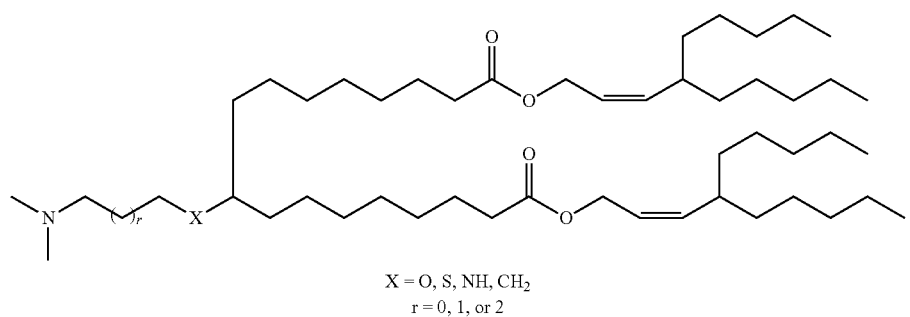
X = O, S, NH, CH$_2$
r = 0, 1, or 2
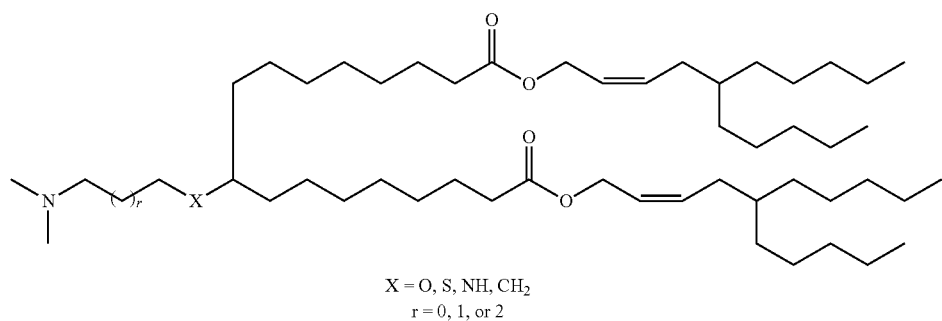
X = O, S, NH, CH$_2$
r = 0, 1, or 2
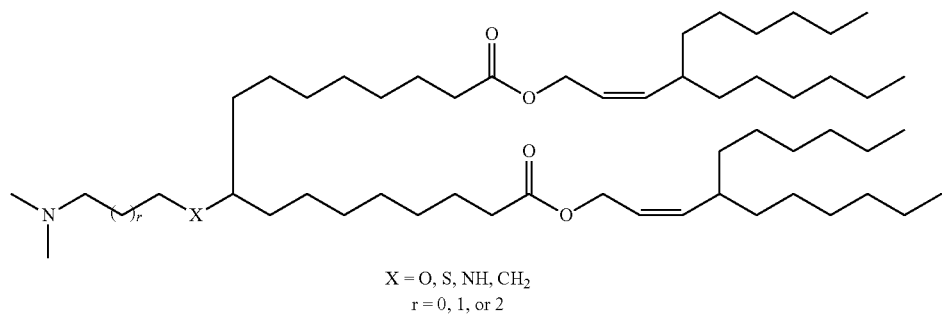
X = O, S, NH, CH$_2$
r = 0, 1, or 2

-continued
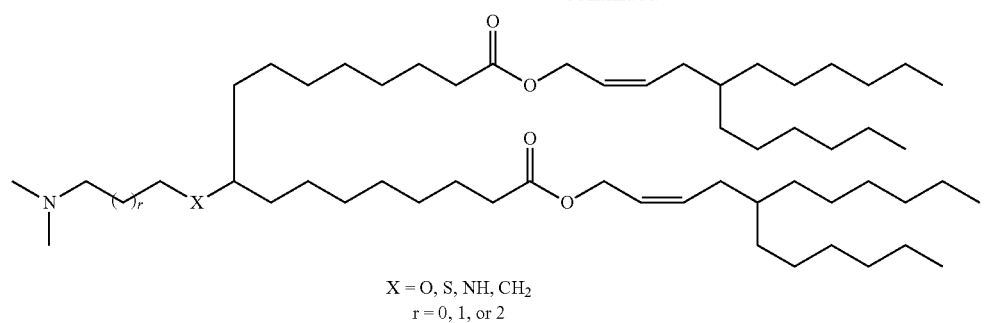
X = O, S, NH, CH₂
r = 0, 1, or 2
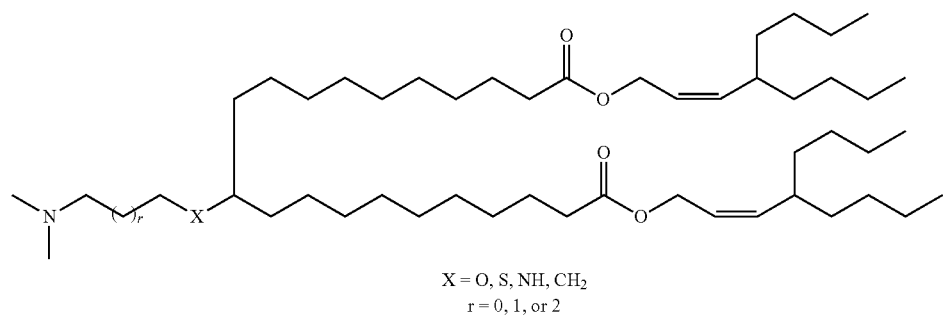
X = O, S, NH, CH₂
r = 0, 1, or 2
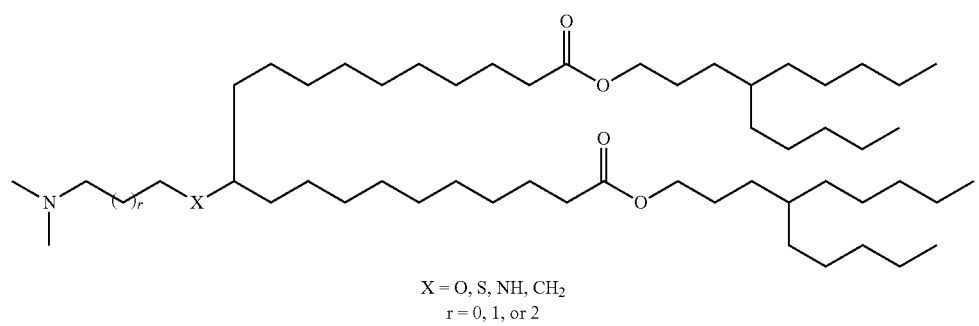
X = O, S, NH, CH₂
r = 0, 1, or 2
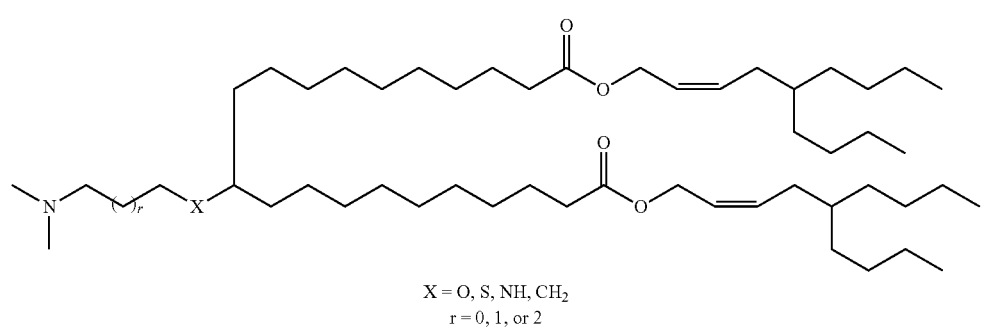
X = O, S, NH, CH₂
r = 0, 1, or 2
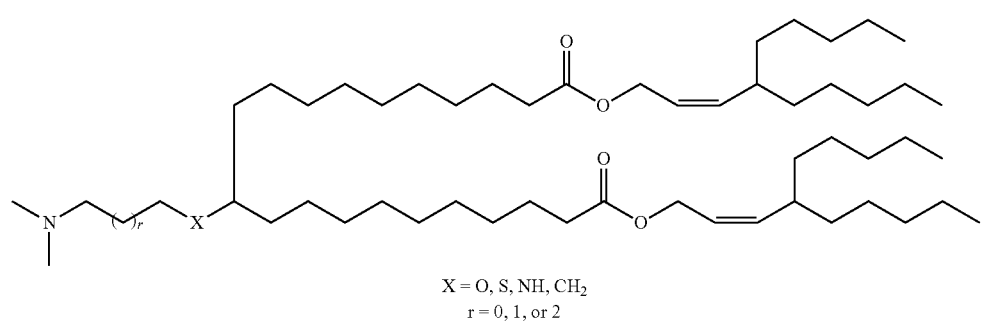
X = O, S, NH, CH₂
r = 0, 1, or 2

-continued
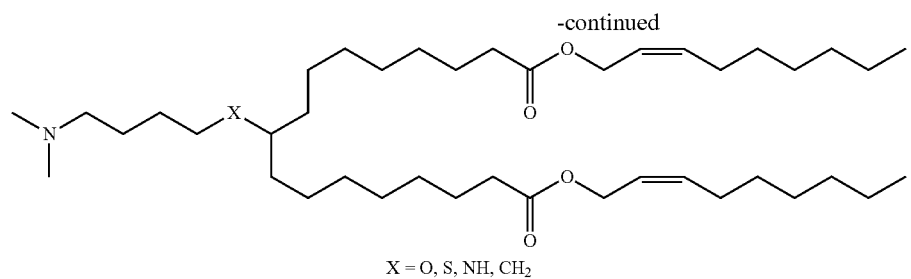
X = O, S, NH, CH₂
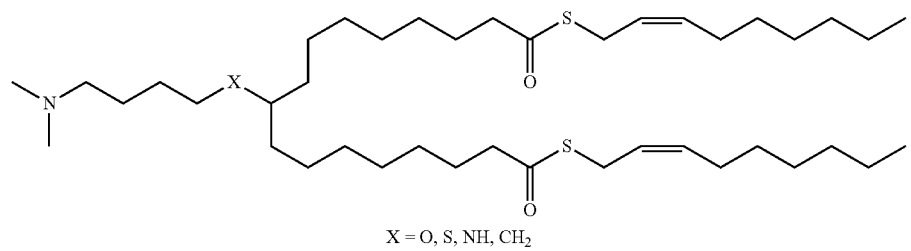
X = O, S, NH, CH₂
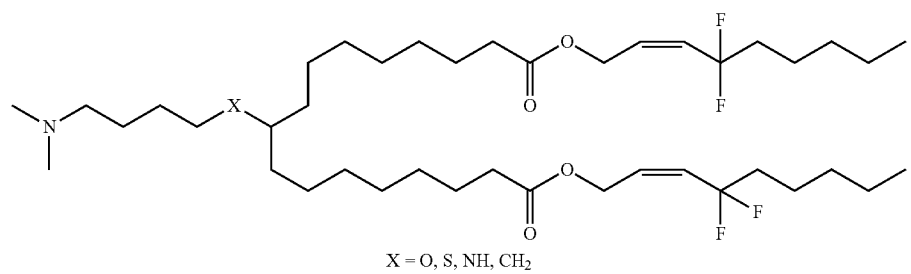
X = O, S, NH, CH₂
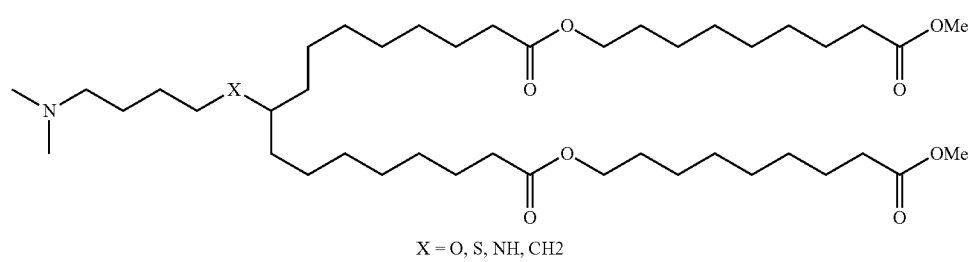
X = O, S, NH, CH2
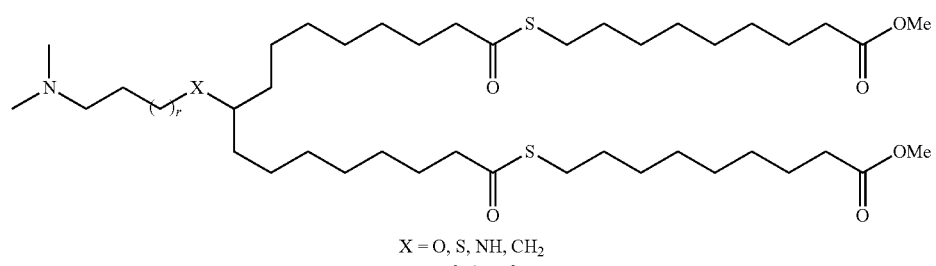
X = O, S, NH, CH₂
r = 0, 1, or 2
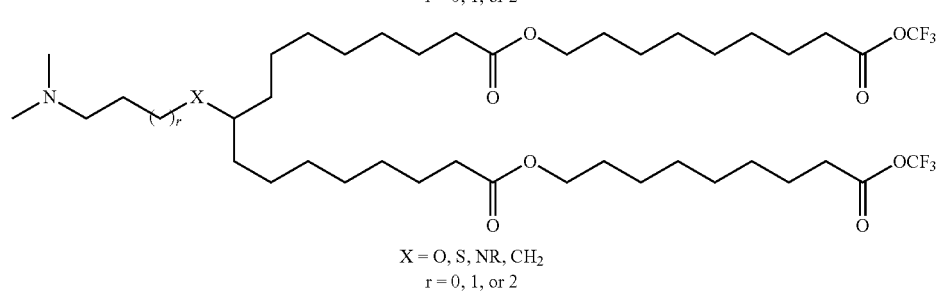
X = O, S, NR, CH₂
r = 0, 1, or 2

-continued
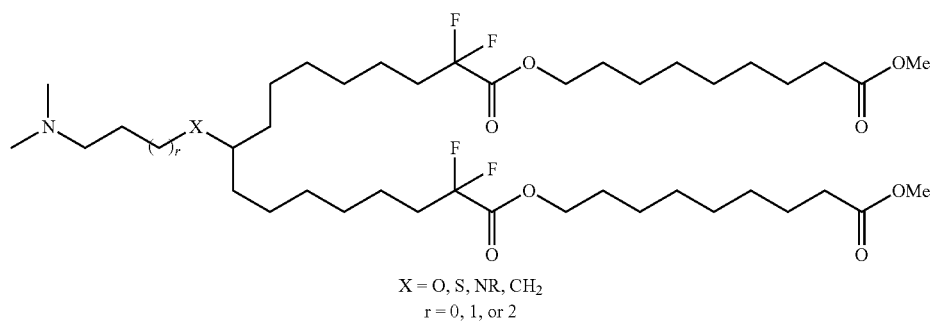
X = O, S, NR, CH$_2$
r = 0, 1, or 2
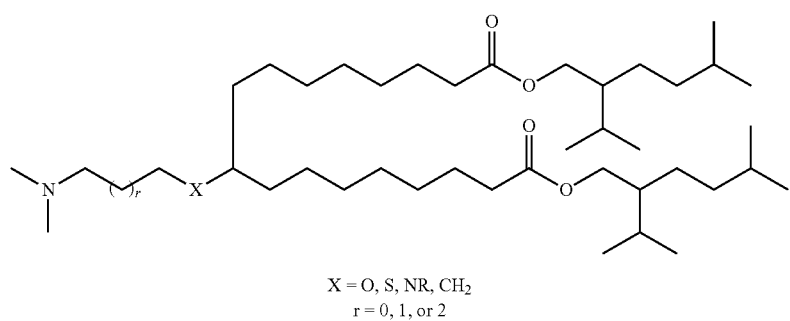
X = O, S, NR, CH$_2$
r = 0, 1, or 2
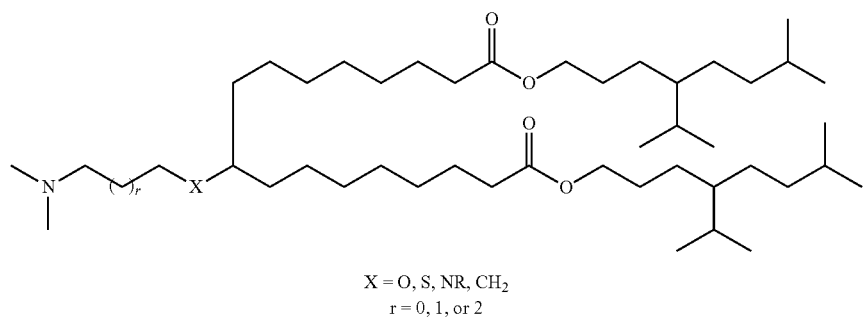
X = O, S, NR, CH$_2$
r = 0, 1, or 2
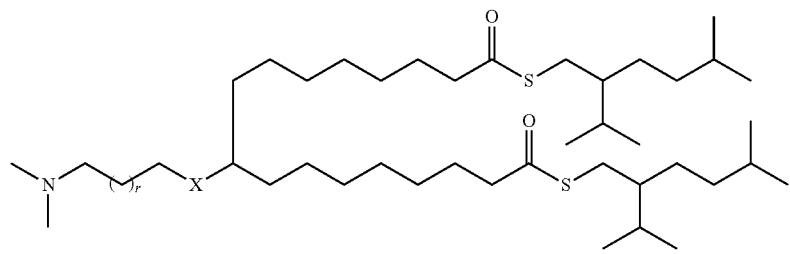
X = O, S, NR, CH$_2$
r = 0, 1, or 2
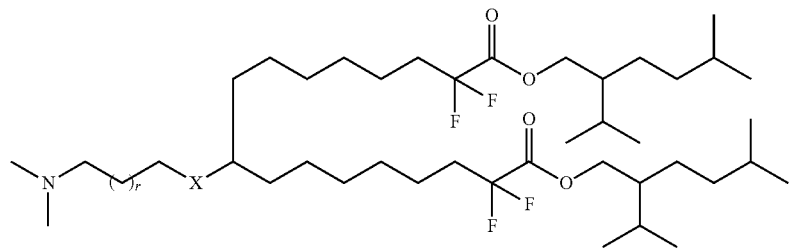
r = 0, 1, or 2

-continued
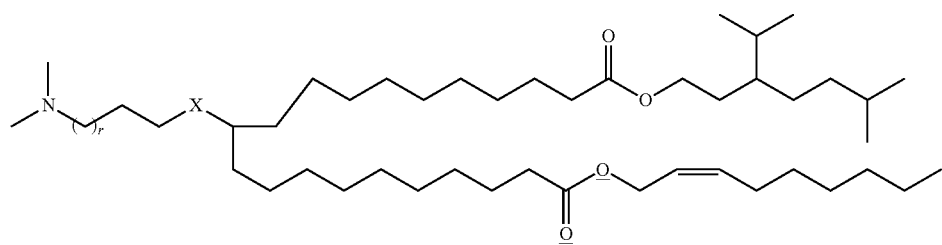
X = O, S, NR, CH₂
r = 0, 1, or 2
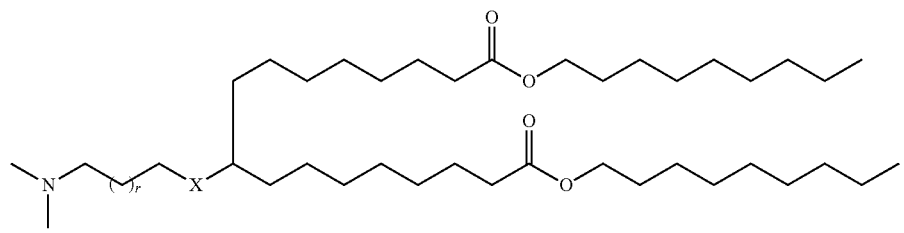
X = O, S, NR, CH₂
r = 0, 1, or 2
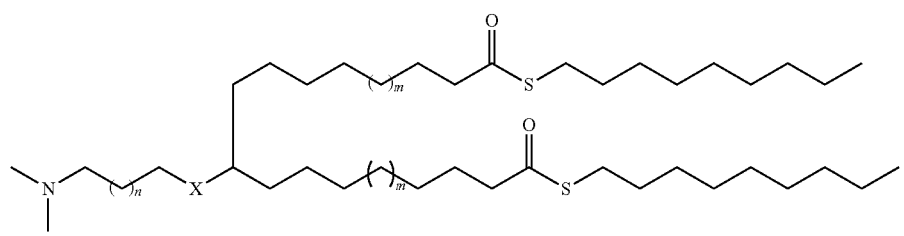
m = 0-5, n = 0, 1, or 2
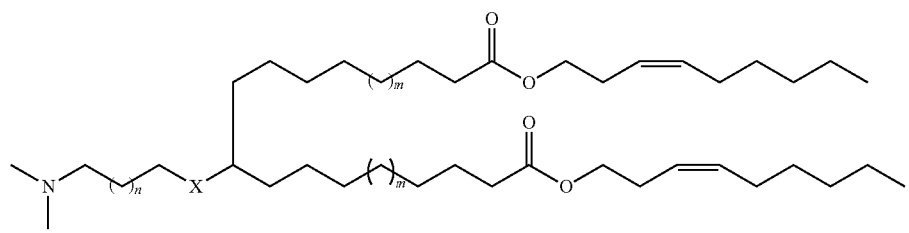
X = O, S, NR, CH₂
m = 0-5, n = 0, 1, or 2
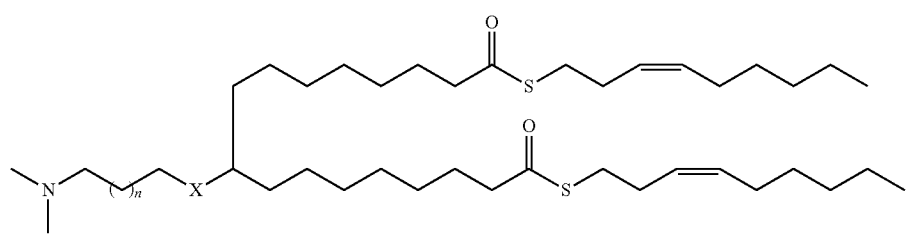
n = 0, 1, or 2
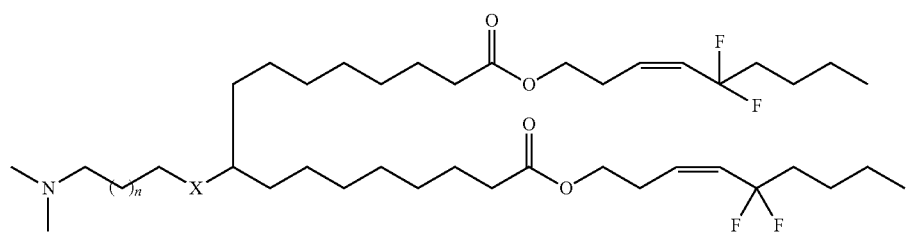
n = 0, 1, or 2

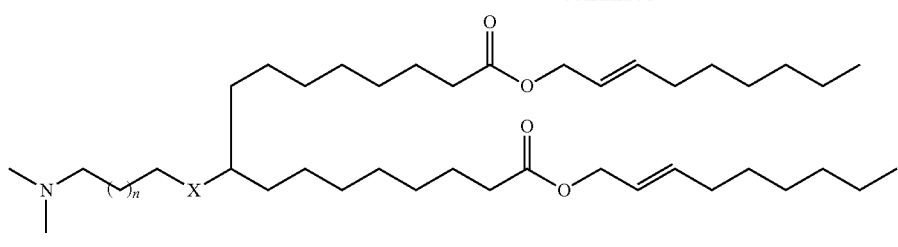
n = 0, 1, or 2
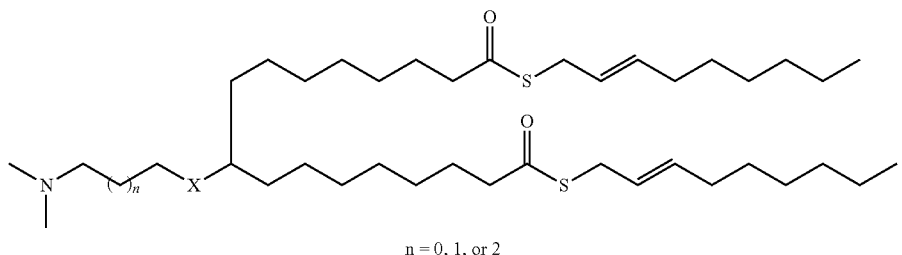
n = 0, 1, or 2
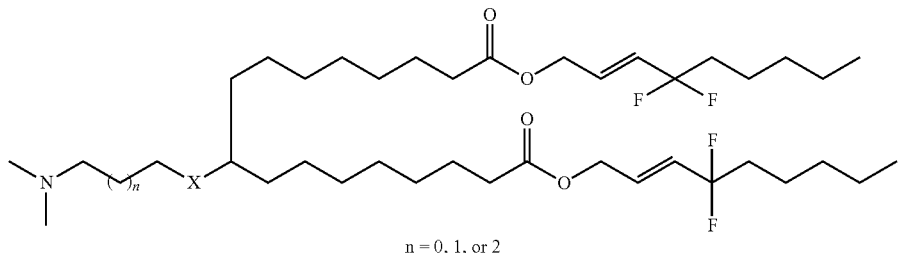
n = 0, 1, or 2
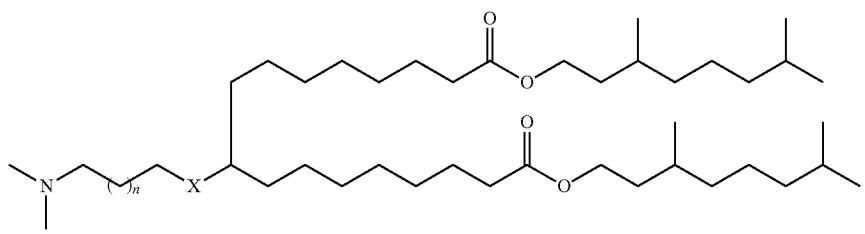
n = 0, 1, or 2
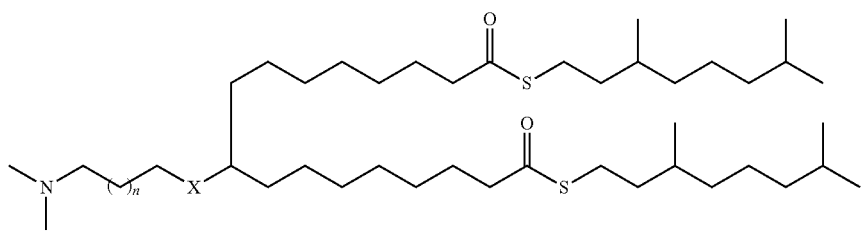
n = 0, 1, or 2
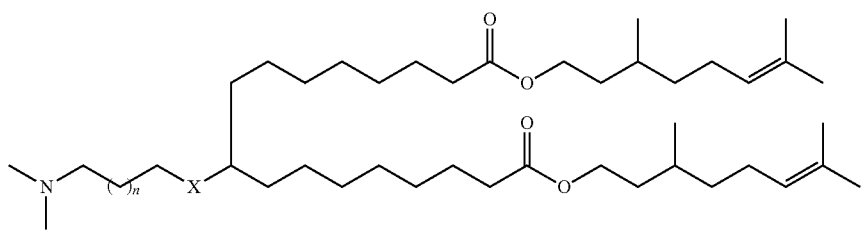
n = 0, 1, or 2

-continued
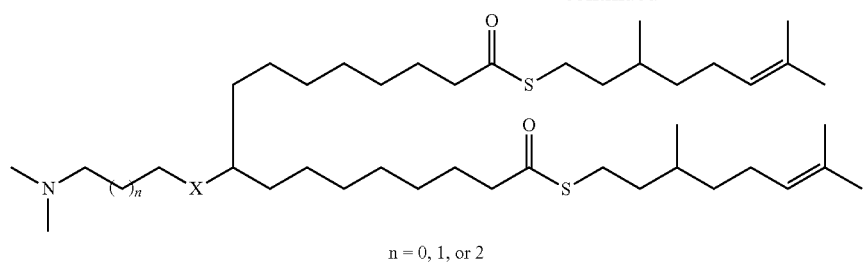
n = 0, 1, or 2
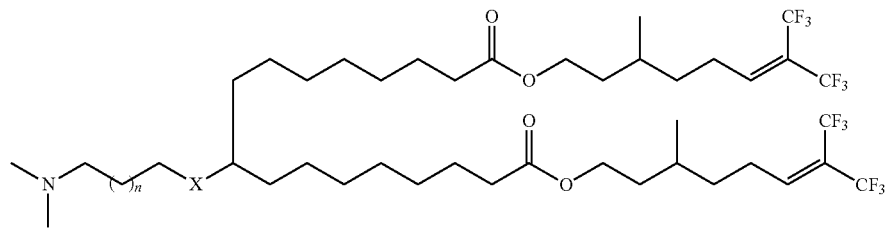
n = 0, 1, or 2
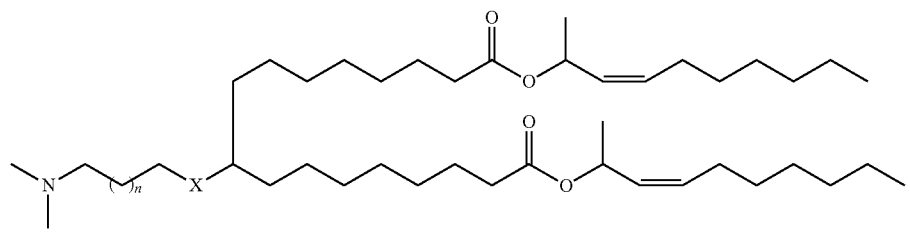
n = 0, 1, or 2
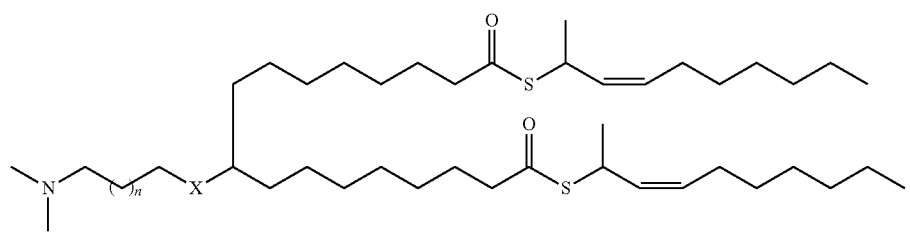
n = 0, 1, or 2
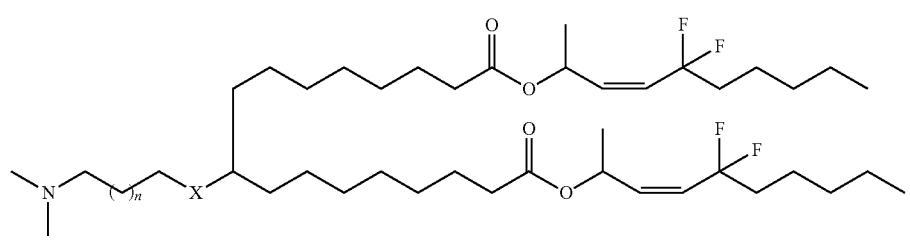
n = 0, 1, or 2
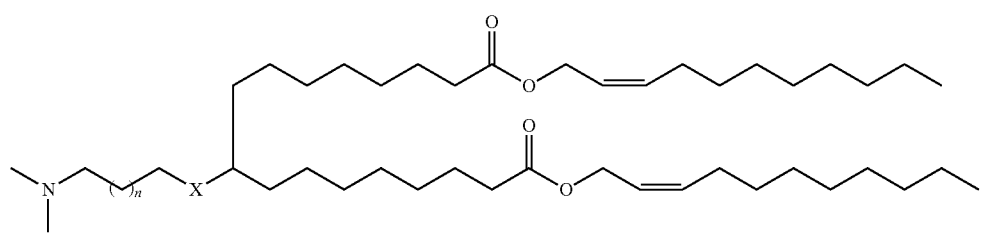
n = 0, 1, or 2

-continued
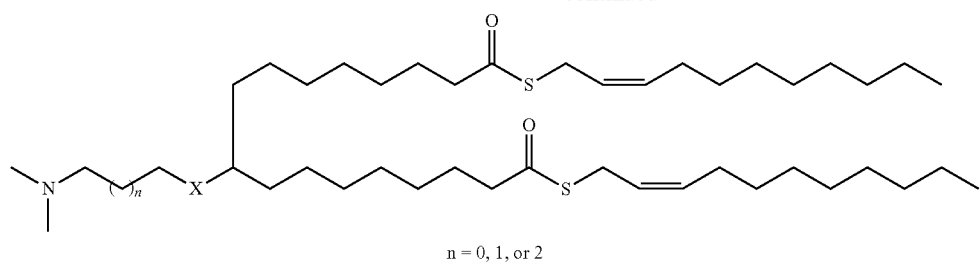
n = 0, 1, or 2
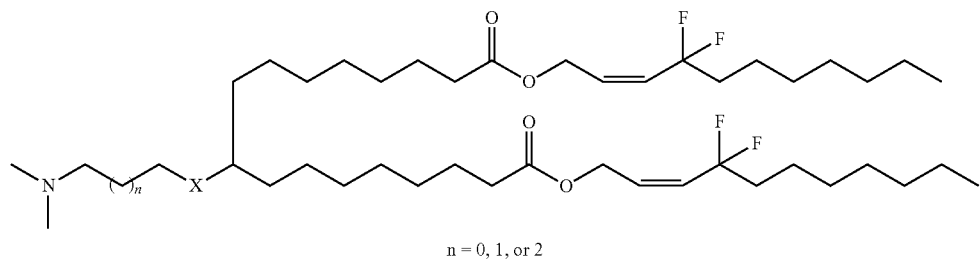
n = 0, 1, or 2
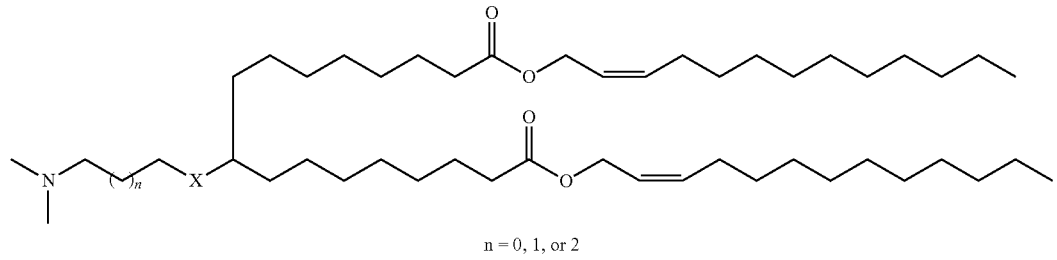
n = 0, 1, or 2
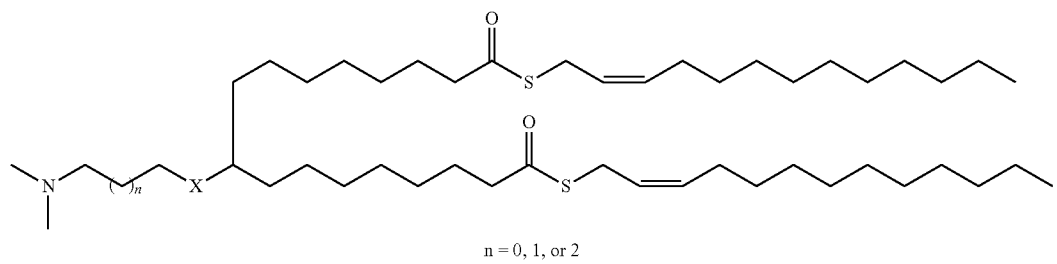
n = 0, 1, or 2
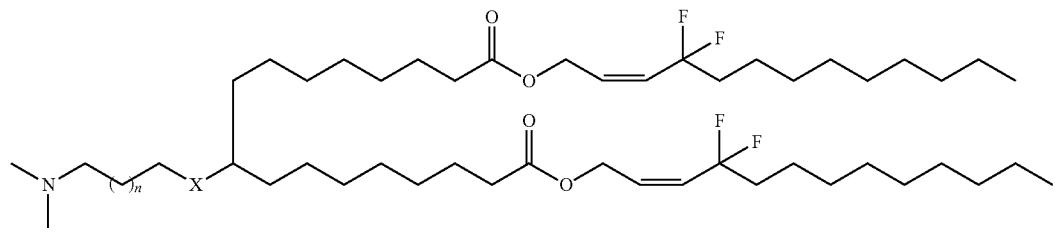
n = 0, 1, or 2
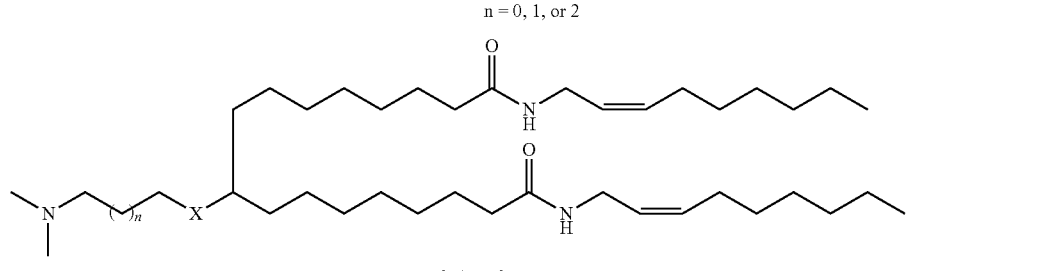
n = 0, 1, or 2

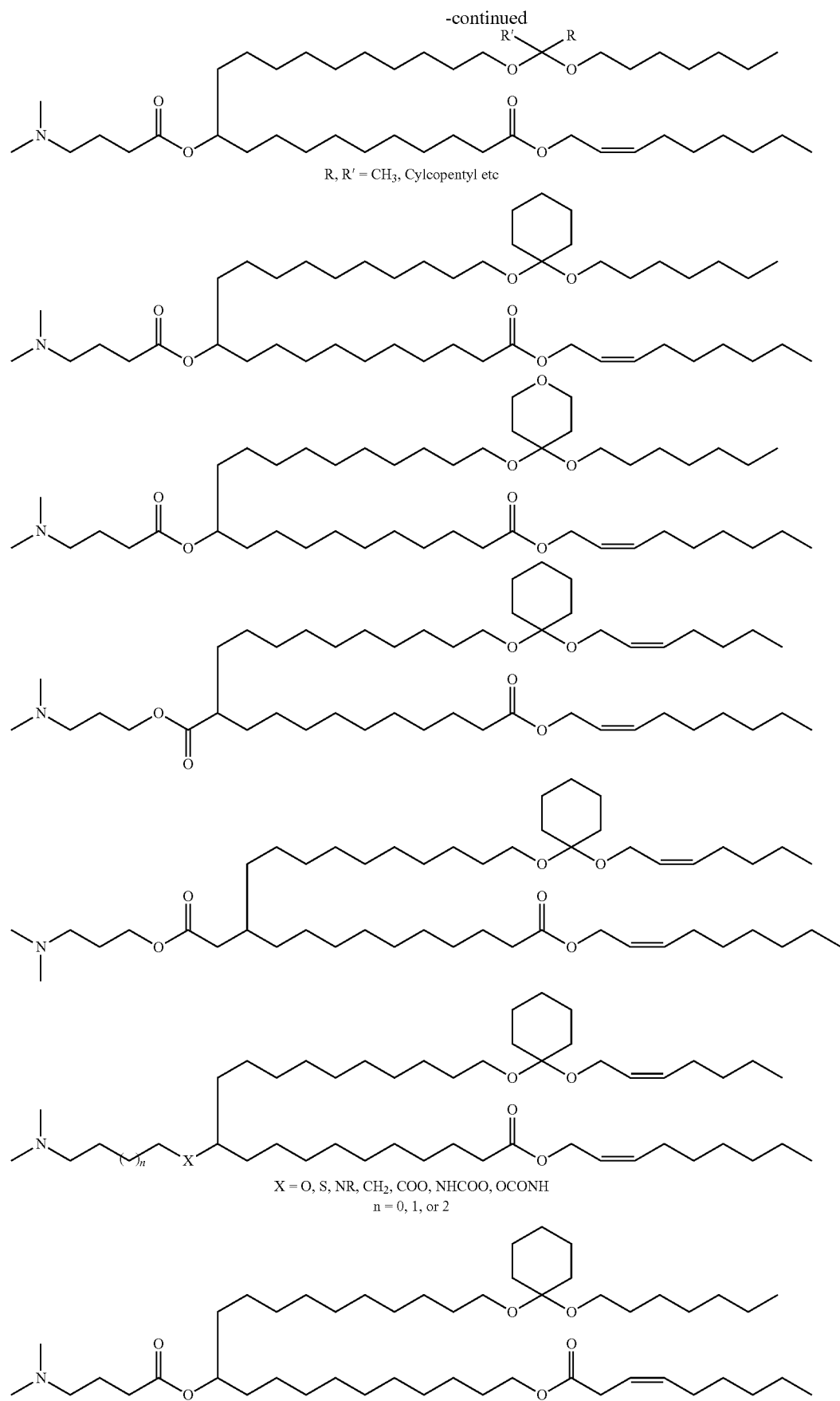

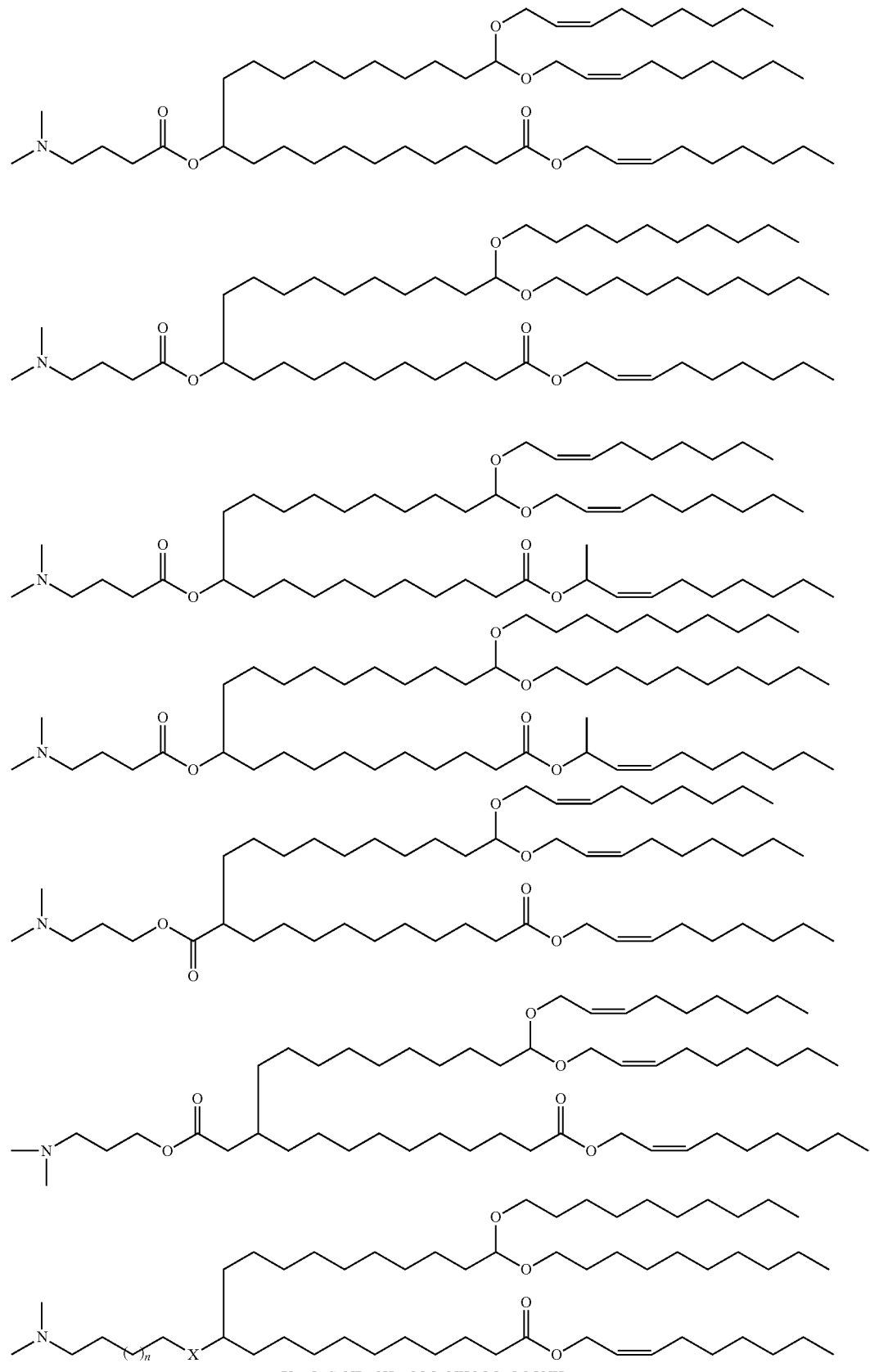
-continued
X = O, S, NR, CH₂, COO, NHCOO, OCONH
n = 0, 1, or 2

-continued
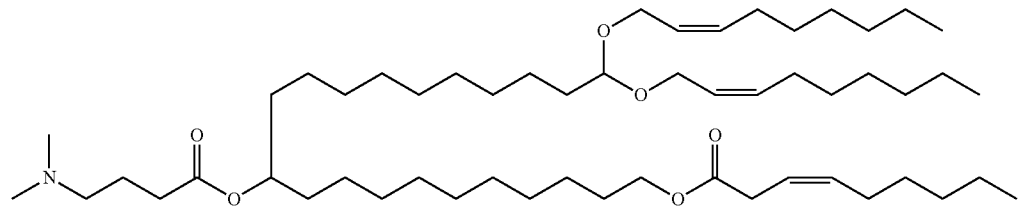
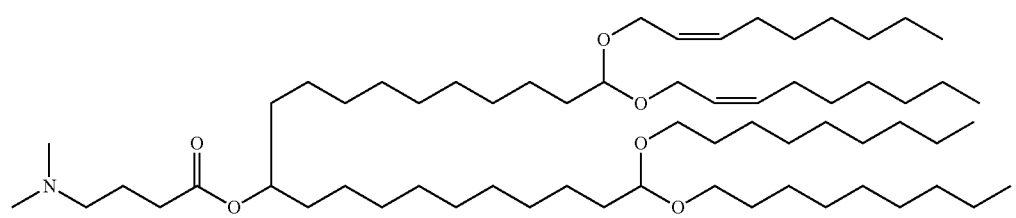
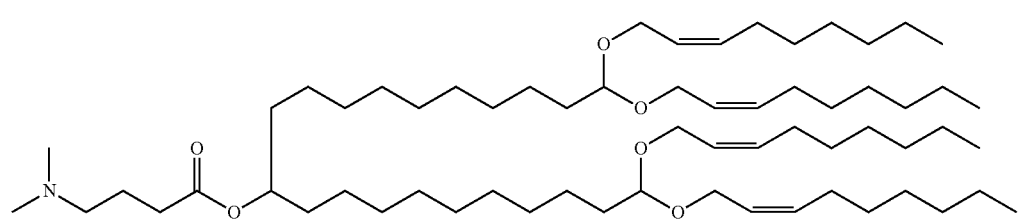
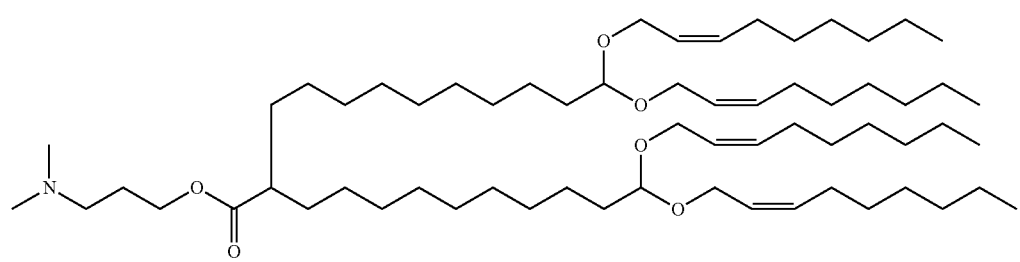
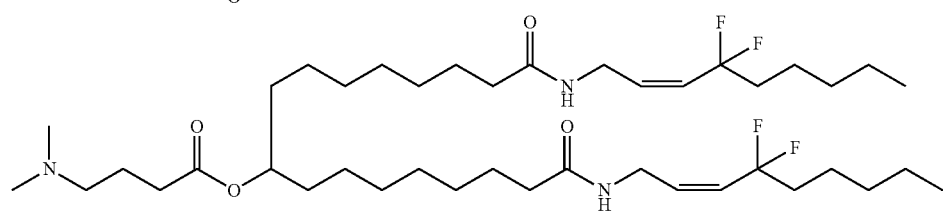
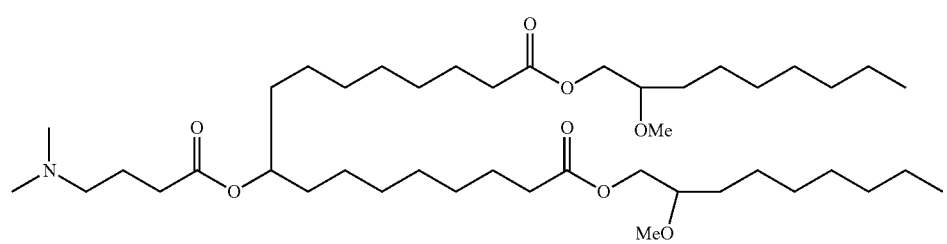
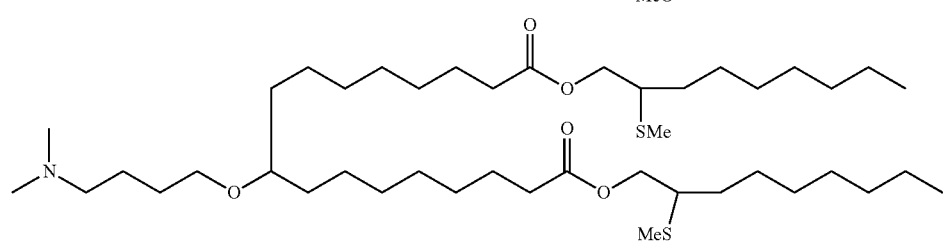

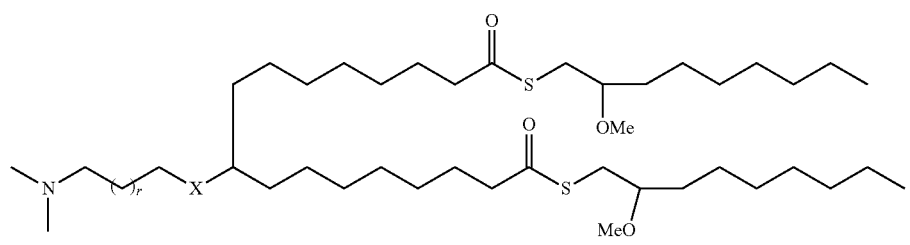
X = O, S, NR, CH₂
r = 0, 1, or 2
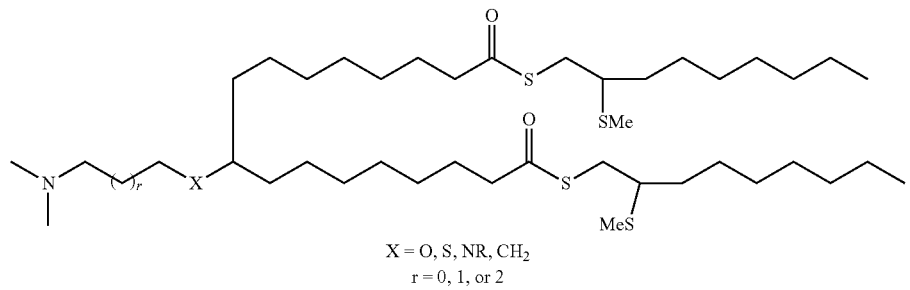
X = O, S, NR, CH₂
r = 0, 1, or 2
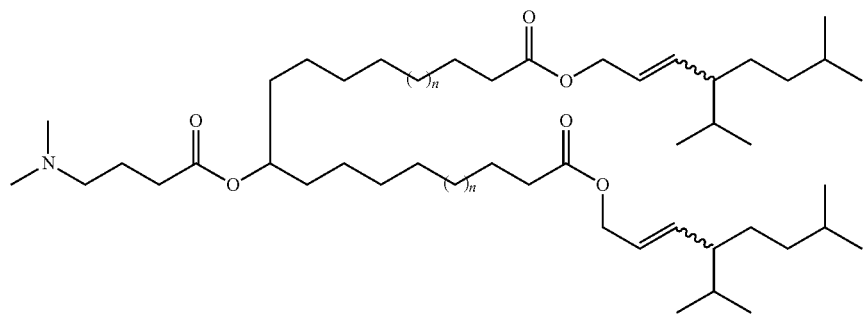
n = 1-5
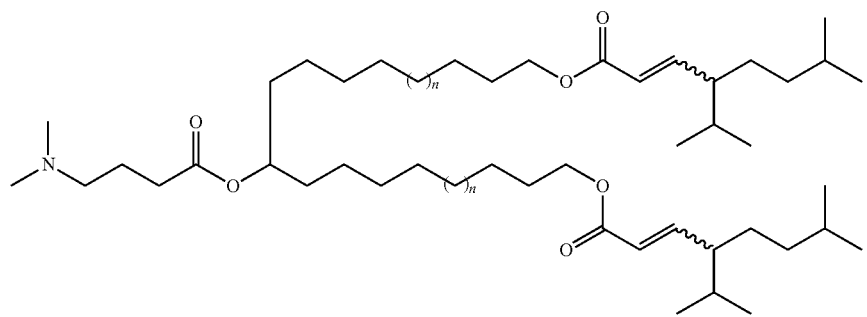
n = 1-5
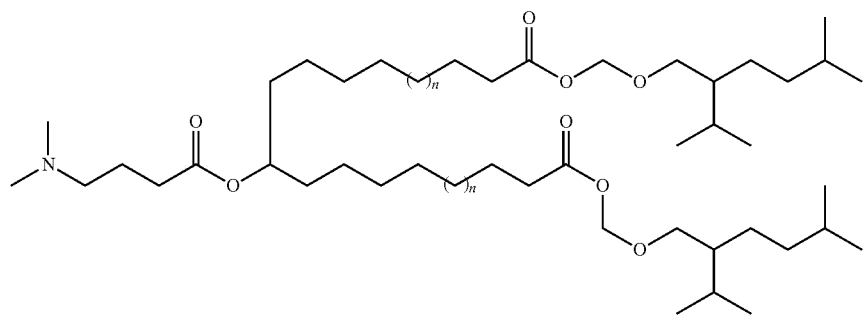
n = 1-5

-continued
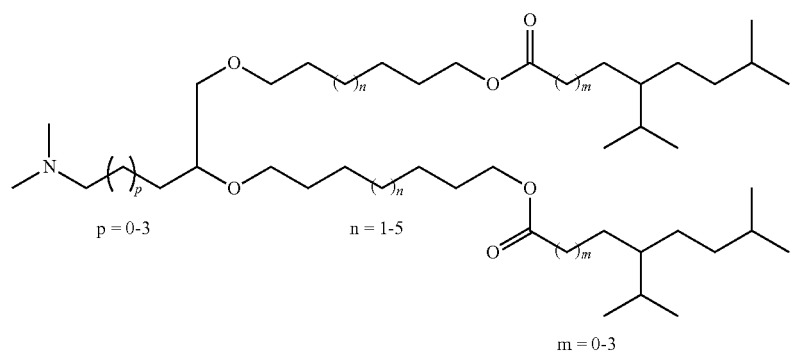
p = 0-3    n = 1-5    m = 0-3
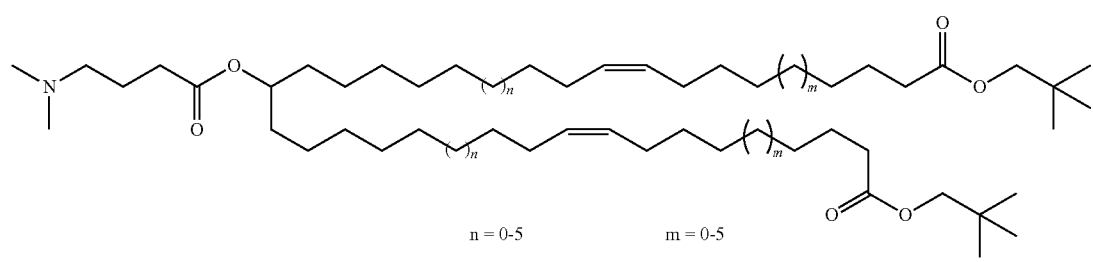
n = 0-5    m = 0-5
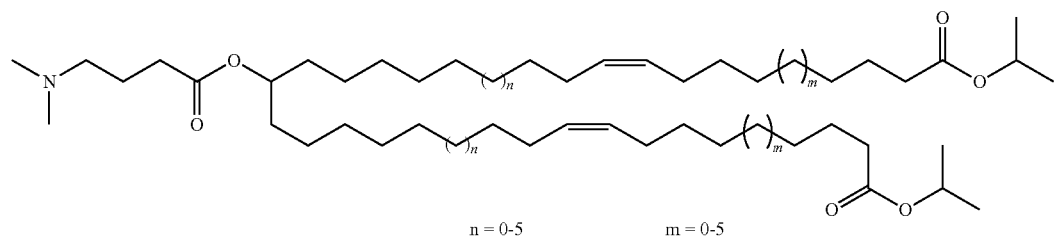
n = 0-5    m = 0-5
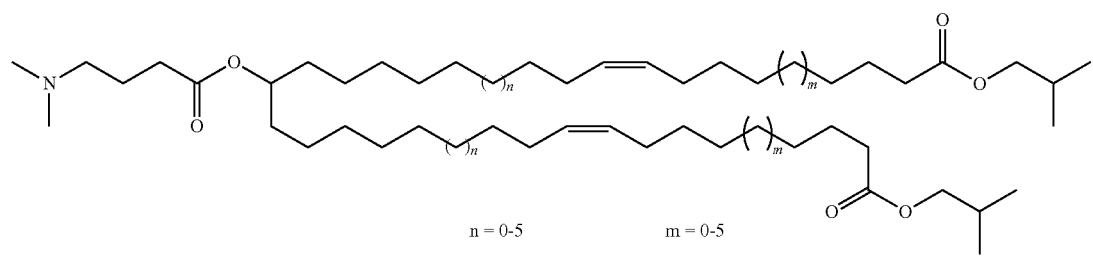
n = 0-5    m = 0-5
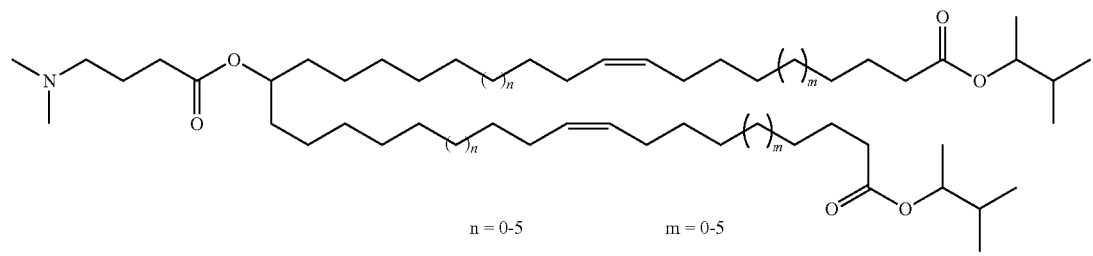
n = 0-5    m = 0-5
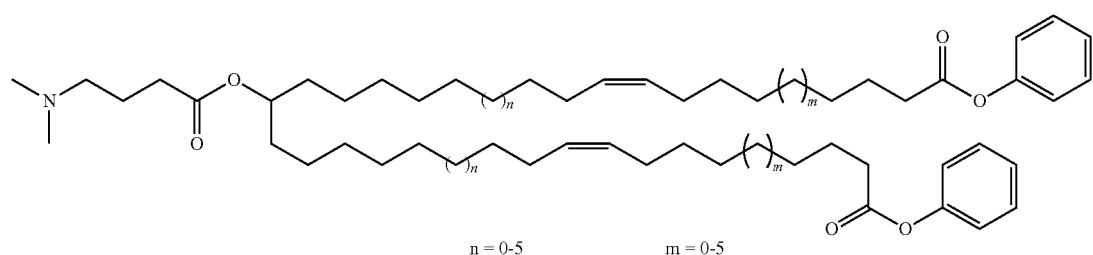
n = 0-5    m = 0-5

-continued
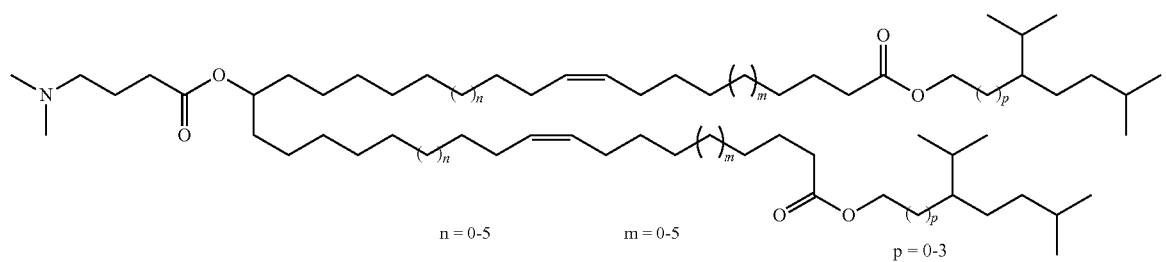
n = 0-5     m = 0-5     p = 0-3
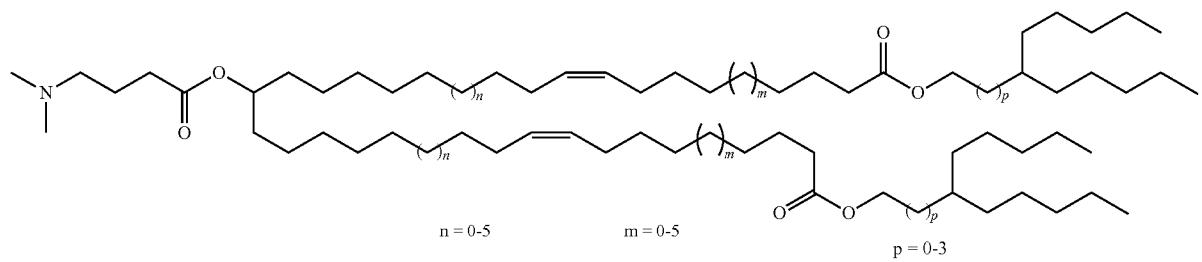
n = 0-5     m = 0-5     p = 0-3
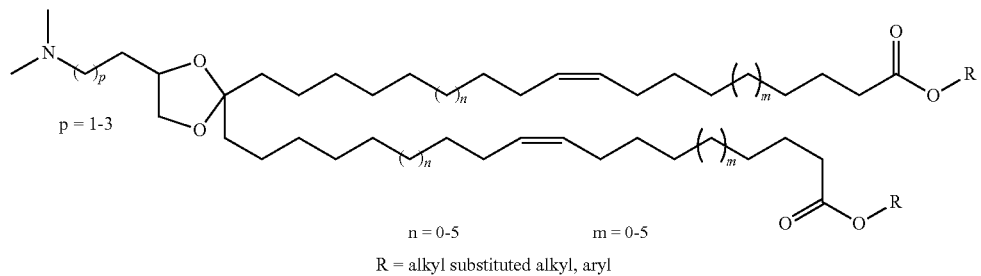
p = 1-3     n = 0-5     m = 0-5
R = alkyl substituted alkyl, aryl
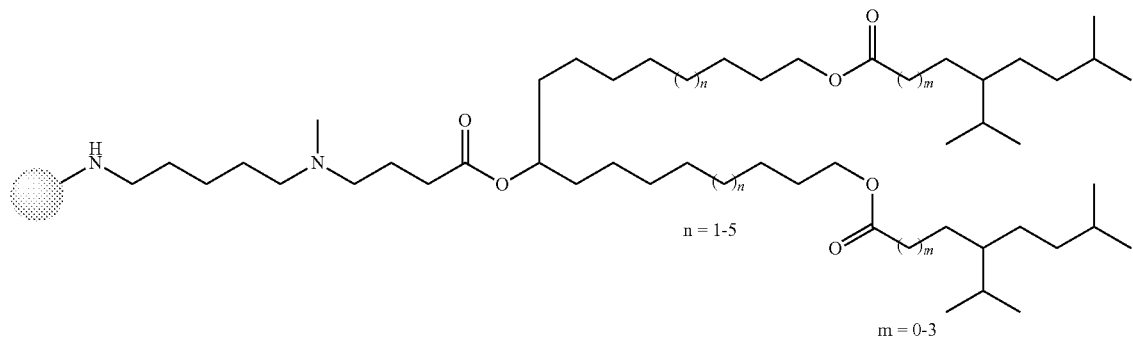
n = 1-5     m = 0-3
● = Bodipy, Alexa-647 or other label (e.g., other fluorescent label)
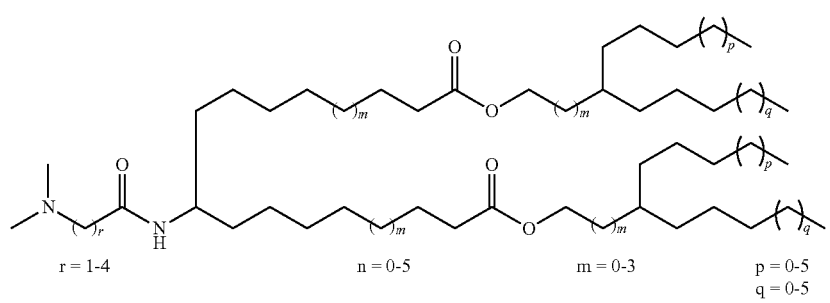
r = 1-4     n = 0-5     m = 0-3     p = 0-5     q = 0-5

-continued

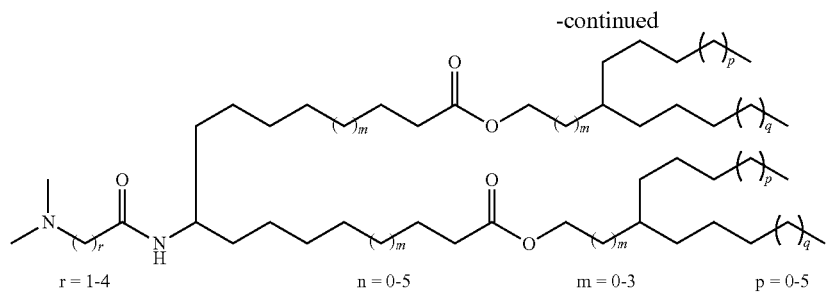

r = 1-4    n = 0-5    m = 0-3    p = 0-5
                                 q = 0-5

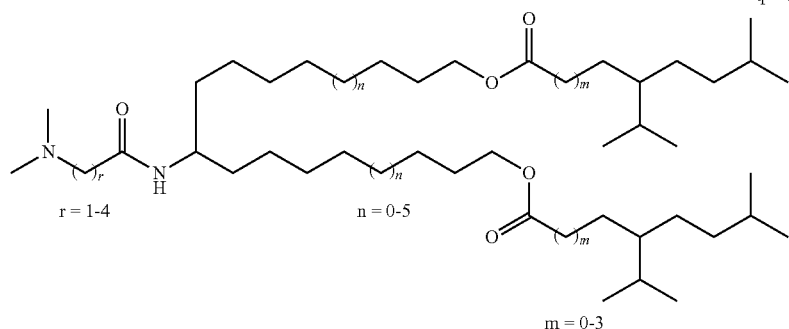

r = 1-4    n = 0-5 m = 0-3

Alternatively, for the compounds above having a head of the formula

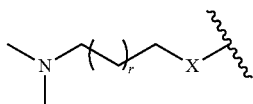

(where X can be, for example, —C(O)O—), the head can have one methylene unit between the X group (or other functional group) and nitrogen atom. For example, the head can be:

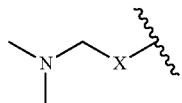

Cationic lipids include those having alternative fatty acid groups and other dialkylamino groups than those shown, including those in which the alkyl substituents are different (e.g., N-ethyl-N-methylamino-, and N-propyl-N-ethyl-amino-).

In certain embodiments, the cationic lipids have at least one protonatable or deprotonatable group, such that the lipid is positively charged at a pH at or below physiological pH (e.g. pH 7.4), and neutral at a second pH, preferably at or above physiological pH. Such lipids are also referred to as cationic lipids. It will, of course, be understood that the addition or removal of protons as a function of pH is an equilibrium process, and that the reference to a charged or a neutral lipid refers to the nature of the predominant species and does not require that all of the lipid be present in the charged or neutral form. The lipids can have more than one protonatable or deprotonatable group, or can be zwitterionic.

In certain embodiments, protonatable lipids (i.e., cationic lipids) have a $pK_a$ of the protonatable group in the range of about 4 to about 11. For example, the lipids can have a $pK_a$ of about 4 to about 7, e.g., from about 5 to about 7, such as from about 5.5 to about 6.8, when incorporated into lipid particles. Such lipids may be cationic at a lower pH formulation stage, while particles will be largely (though not completely) surface neutralized at physiological pH around pH 7.4.

In particular embodiments, the lipids are charged lipids. As used herein, the term "charged lipid" includes, but is not limited to, those lipids having one or two fatty acyl or fatty alkyl chains and a quaternary amino head group. The quaternary amine carries a permanent positive charge. The head group can optionally include an ionizable group, such as a primary, secondary, or tertiary amine that may be protonated at physiological pH. The presence of the quaternary amine can alter the pKa of the ionizable group relative to the pKa of the group in a structurally similar compound that lacks the quaternary amine (e.g., the quaternary amine is replaced by a tertiary amine).

Included in the instant invention is the free form of the cationic lipids described herein, as well as pharmaceutically acceptable salts and stereoisomers thereof. The cationic lipid can be a protonated salt of the amine cationic lipid. The term "free form" refers to the amine cationic lipids in non-salt form. The free form may be regenerated by treating the salt with a suitable dilute aqueous base solution such as dilute aqueous NaOH, potassium carbonate, ammonia and sodium bicarbonate.

The pharmaceutically acceptable salts of the instant cationic lipids can be synthesized from the cationic lipids of this invention which contain a basic or acidic moiety by conventional chemical methods. Generally, the salts of the basic cationic lipids are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the cationic lipids of this invention include non-toxic salts of the cationic lipids of this invention as formed by reacting a basic instant cationic lipids with an inorganic or organic acid. For example, non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, and trifluoroacetic (TFA).

When the cationic lipids of the present invention are acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, and zinc. In one embodiment, the base is selected from ammonium, calcium, magnesium, potassium and sodium. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N¹-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, and tromethamine.

It will also be noted that the cationic lipids of the present invention may potentially be internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

One or more additional cationic lipids, which carry a net positive charge at about physiological pH, in addition to those specifically described above, may also be included in the lipid particles and compositions described herein. Such cationic lipids include, but are not limited to N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3ß-(N—(N',N'-dimethylaminoethane)-carbamoyl)cholesterol ("DC-Chol"), N-(1-(2,3-dioleyloxy)propyl)-N—2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N, N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL).

PEG Lipids

Suitable head groups for the PEG lipids include, but are not limited to those shown in Table 3 below.

TABLE 3

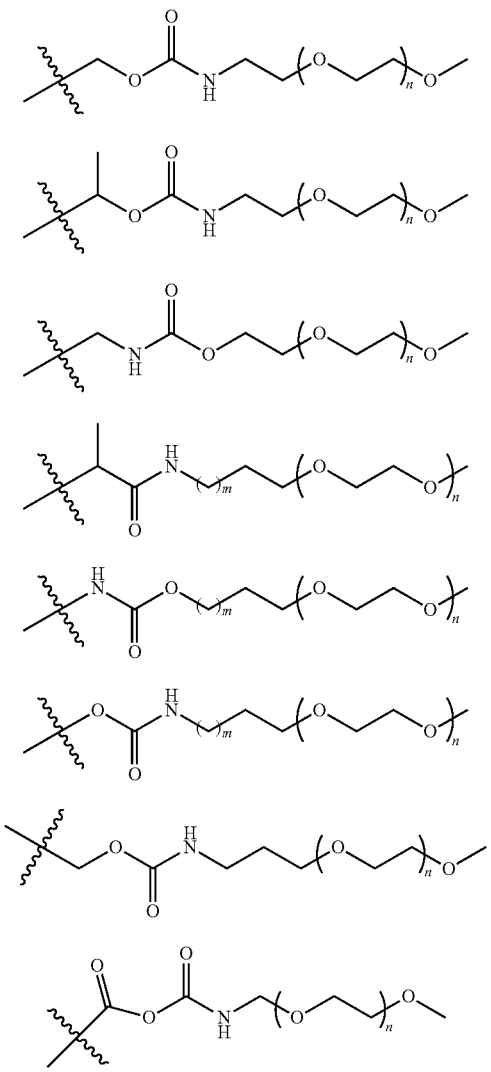

Representative PEG lipids include, but are not limited to:

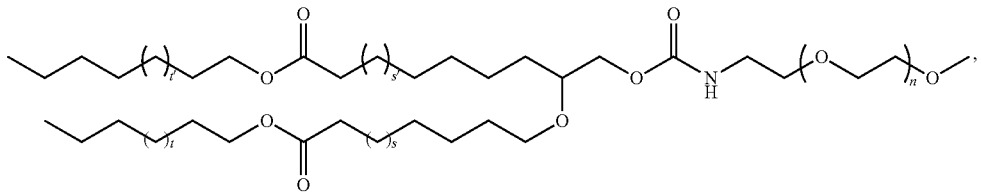

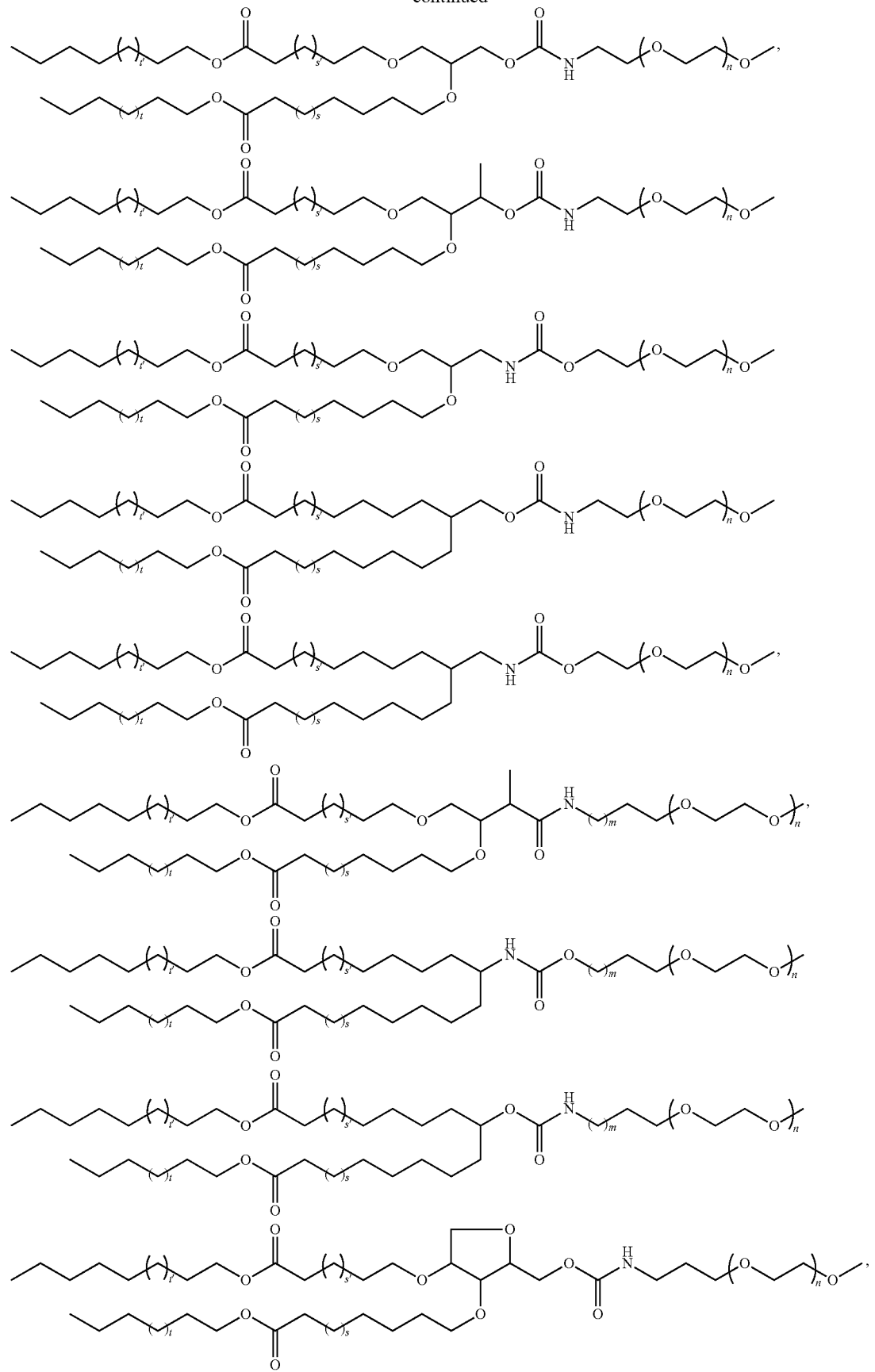

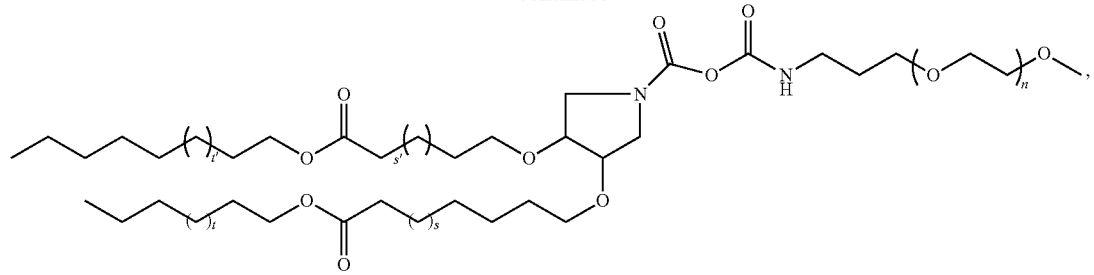
wherein
n is an integer from 10 to 100 (e.g. 20-50 or 40-50);
s, s', t and t' are independently 0, 1, 2, 3, 4, 5, 6 or 7; and m is 1, 2, 3, 4, 5, or 6.
Other representative PEG lipids include, but are not limited to:
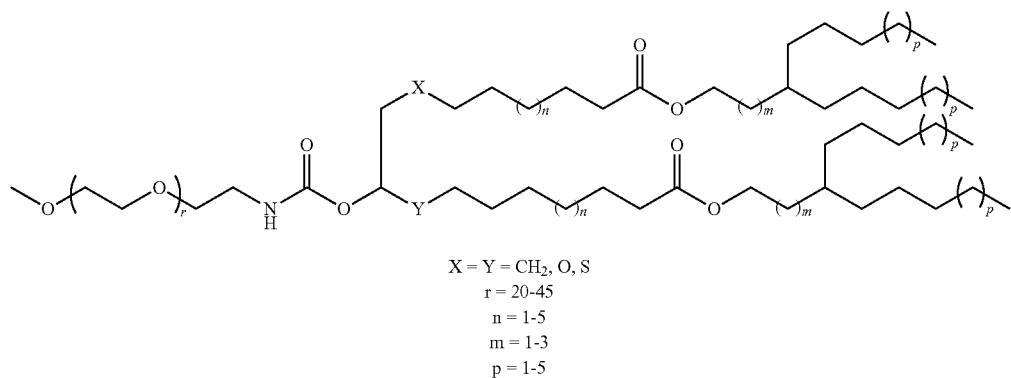
X = Y = CH$_2$, O, S
r = 20-45
n = 1-5
m = 1-3
p = 1-5
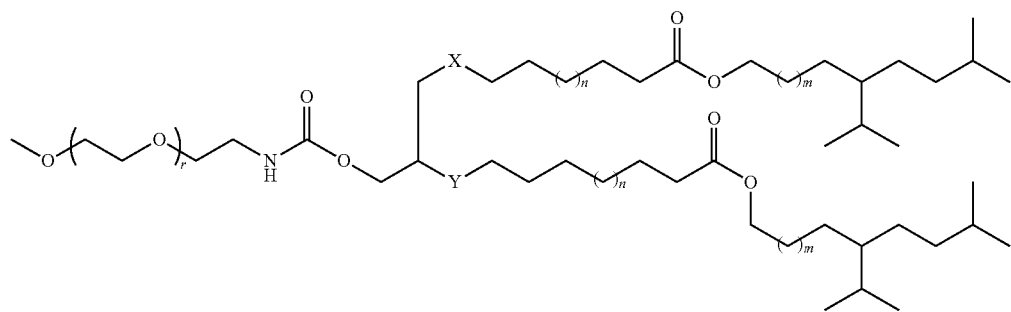
X = Y = CH$_2$, O, S
r = 20-45
n = 1-5
m = 0-3

-continued
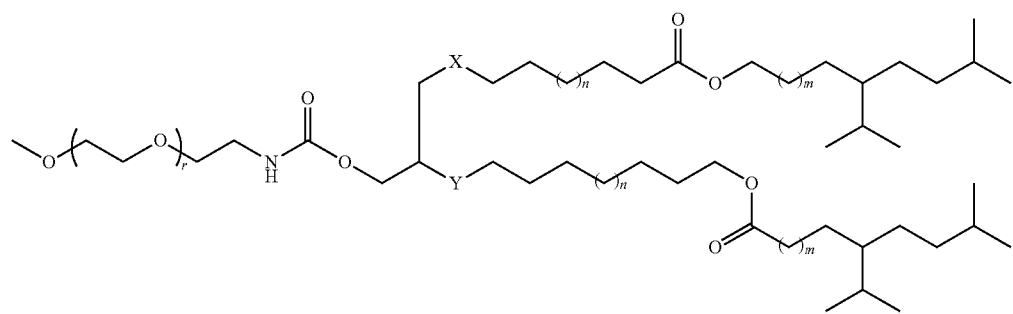
X = Y = CH₂, O, S
r = 20-45
n = 1-5
m = 0-3
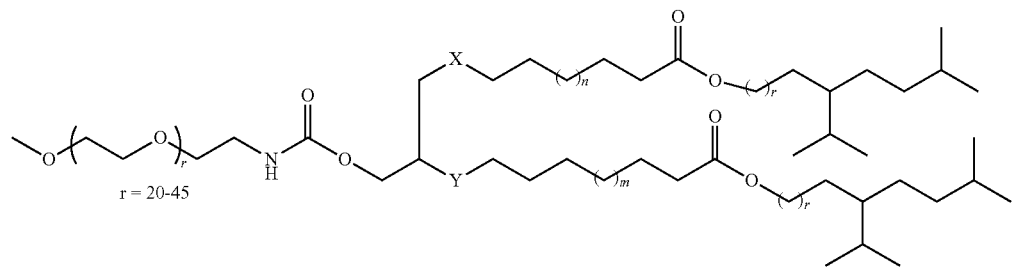
X = Y = CH₂, O, S
m = n = r = 0-10
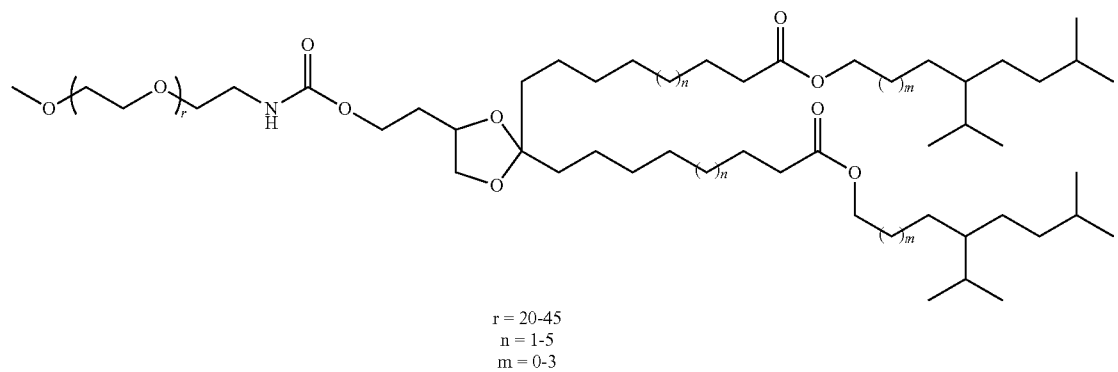
r = 20-45
n = 1-5
m = 0-3
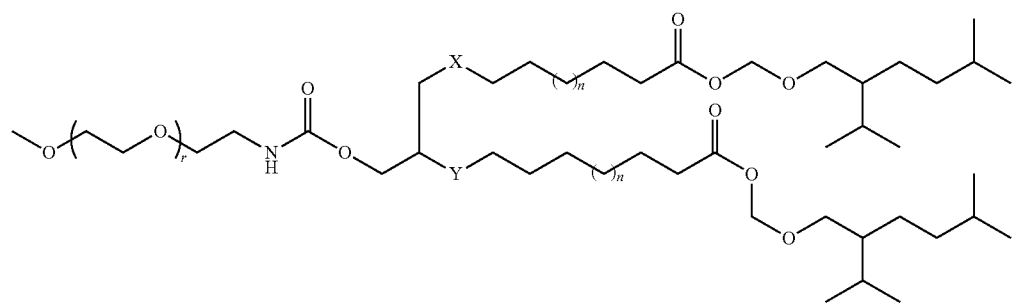
r = 20-45
n = 1-5

-continued
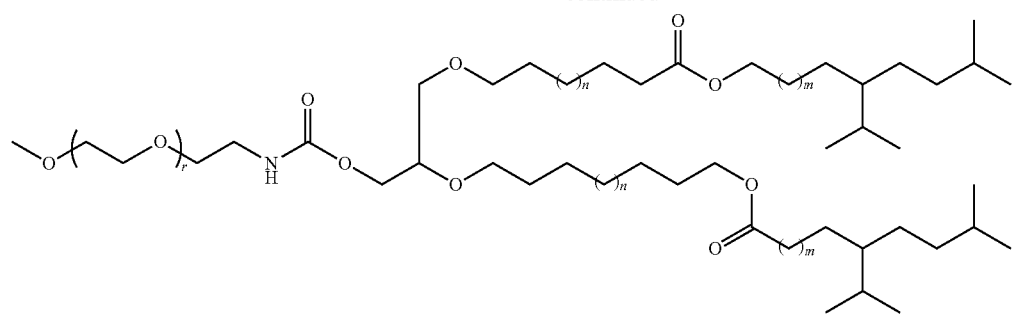
r = 20-45
n = 1-5
m = 0-3
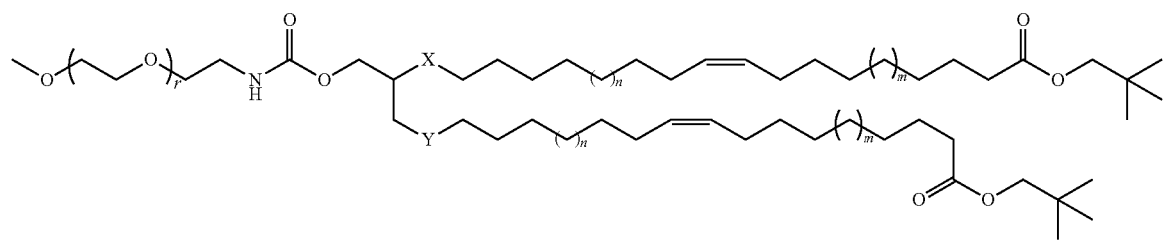
X = Y = O, S, NH, CH₂
r = 20-45
n = 0-5
m = 0-5
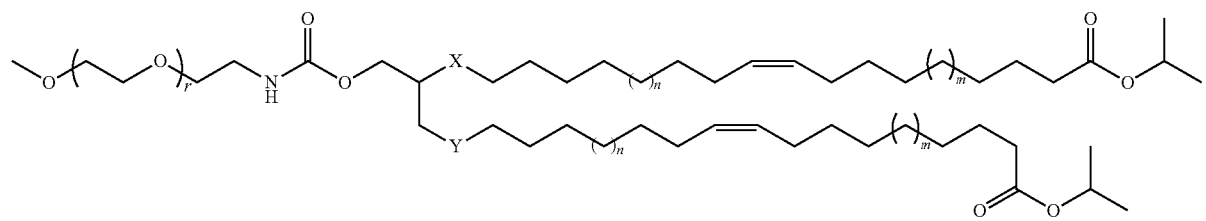
X = Y = O, S, NH, CH₂
r = 20-45
n = 0-5
m = 0-5
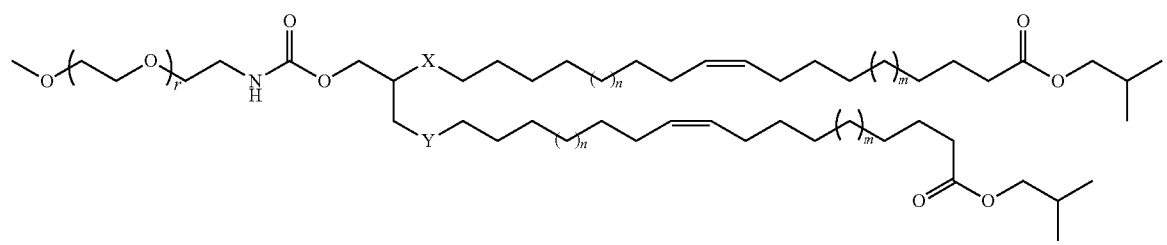
X = Y = O, S, NH, CH₂
r = 20-45
n = 0-5
m = 0-5

-continued

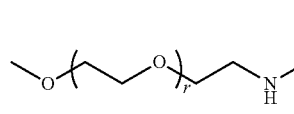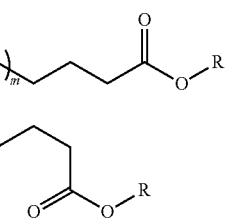

X = Y = O, S, NH, CH$_2$
R = alkyl, substituted alkyl, aryl, benzyl
r = 20-45
n = 0-5
m = 0-5

The Other Lipid Components

The lipid particles and compositions described herein may also include one or more neutral lipids. Neutral lipids, when present, can be any of a number of lipid species which exist either in an uncharged or neutral zwitterionic form at physiological pH. Such lipids include, for example, diacylphosphatidylcholine, diacylphosphatidylethanolamine, ceramide, sphingomyelin, dihydrosphingomyelin, cephalin, and cerebrosides. In one embodiment, the neutral lipid component is a lipid having two acyl groups (e.g., diacylphosphatidylcholine and diacylphosphatidylethanolamine). In one embodiment, the neutral lipid contains saturated fatty acids with carbon chain lengths in the range of $C_{10}$ to $C_{20}$. In another embodiment, the neutral lipid includes mono or diunsaturated fatty acids with carbon chain lengths in the range of $C_{10}$ to $C_{20}$. Suitable neutral lipids include, but are not limited to, DSPC, DPPC, POPC, DOPE, DSPC, and SM.

The lipid particles and compositions described herein may also include one or more lipids capable of reducing aggregation. Examples of lipids that reduce aggregation of particles during formation include polyethylene glycol (PEG)-modified lipids (PEG lipids, such as PEG-DMG and PEG-DMA), monosialoganglioside Gm1, and polyamide oligomers ("PAO") such as (described in U.S. Pat. No. 6,320,017, which is incorporated by reference in its entirety). Suitable PEG lipids include, but are not limited to, PEG-modified phosphatidylethanolamine and phosphatidic acid, PEG-ceramide conjugates (e.g., PEG-CerC14 or PEG-CerC20) (such as those described in U.S. Pat. No. 5,820,873, incorporated herein by reference), PEG-modified dialkylamines and PEG-modified 1,2-diacyloxypropan-3-amines, PEG-modified diacylglycerols and dialkylglycerols, mPEG (mw2000)-diastearoylphosphatidylethanolamine (PEG-DSPE).

The lipid particles and compositions may include a sterol, such as cholesterol.

Lipid Particles

In a further aspect, the present invent relates to lipid particles that include one or more of the cationic lipids described herein. In one embodiment, the lipid particle includes one or more compounds of formula I-VII.

Lipid particles include, but are not limited to, liposomes. As used herein, a liposome is a structure having lipid-containing membranes enclosing an aqueous interior.

Another embodiment is a nucleic acid-lipid particle (e.g., a SNALP) comprising a cationic lipid of the present invention, a non-cationic lipid (such as a neutral lipid), optionally a PEG-lipid conjugate (such as the lipids for reducing aggregation of lipid particles discussed herein), optionally a sterol (e.g., cholesterol), and a nucleic acid. As used herein, the term "SNALP" refers to a stable nucleic acid-lipid particle. A SNALP represents a particle made from lipids, wherein the nucleic acid (e.g., an interfering RNA) is encapsulated within the lipids. In certain instances, SNALPs are useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a SNALP as set forth in International Publication No. WO 00/03683, the disclosure of which is herein incorporated by reference in its entirety.

For example, the lipid particle may include a cationic lipid, a fusion-promoting lipid (e.g., DPPC), a neutral lipid, cholesterol, and a PEG-modified lipid. In one embodiment, the lipid particle includes the above lipid mixture in molar ratios of about 20-70% cationic lipid: 0.1-50% fusion promoting lipid: 5-45% neutral lipid: 20-55% cholesterol: 0.5-15% PEG-modified lipid (based upon 100% total moles of lipid in the lipid particle).

In another embodiment of the lipid particle, the cationic lipid is present in a mole percentage of about 20% and about 60%; the neutral lipid is present in a mole percentage of about 5% to about 25%; the sterol is present in a mole percentage of about 25% to about 55%; and the PEG lipid is PEG-DMA, PEG-DMG, or a combination thereof, and is present in a mole percentage of about 0.5% to about 15% (based upon 100% total moles of lipid in the lipid particle).

In particular embodiments, the molar lipid ratio, with regard to mol % cationic lipid/DSPC/Chol/PEG-DMG or PEG-DMA) is approximately 40/10/40/10, 35/15/40/10 or 52/13/30/5. This mixture may be further combined with a fusion-promoting lipid in a molar ratio of 0.1-50%, 0.1-50%, 0.5-50%, 1-50%, 5%-45%, 10%-40%, or 15%-35%. In other words, when a 40/10/40/10 mixture of lipid/DSPC/Chol/PEG-DMG or PEG-DMA is combined with a fusion-promoting peptide in a molar ratio of 50%, the resulting lipid particles can have a total molar ratio of (mol % cationic lipid/DSPC/Chol/PEG-DMG or PEG-DMA/fusion-promoting peptide) 20/5/20/5/50. In another embodiment, the neutral lipid, DSPC, in these compositions is replaced with POPC, DPPC, DOPE or SM.

In one embodiment, the lipid particles comprise a cationic lipid of the present invention, a neutral lipid, a sterol and a PEG-modified lipid. In one embodiment, the lipid particles include from about 25% to about 75% on a molar basis of cationic lipid, e.g., from about 35 to about 65%, from about 45 to about 65%, about 60%, about 57.5%, about 57.1%, about 50% or about 40% on a molar basis. In one embodiment, the lipid particles include from about 0% to about 15% on a molar basis of the neutral lipid, e.g., from about 3 to about 12%, from about 5 to about 10%, about 15%, about 10%, about 7.5%, about 7.1% or about 0% on a molar basis. In one embodiment, the neutral lipid is DPPC. In one embodiment, the neutral lipid is DSPC. In one embodiment, the formulation includes from about 5% to about 50% on a molar basis of the sterol, e.g., about 15 to about 45%, about 20 to about 40%, about 48%, about 40%, about 38.5%, about 35%, about 34.4%, about 31.5% or about 31% on a molar basis. In one embodiment, the sterol is cholesterol.

The lipid particles described herein may further include one or more therapeutic agents. In a preferred embodiment, the lipid particles include a nucleic acid (e.g., an oligonucleotide), such as siRNA or miRNA.

In one embodiment, the lipid particles include from about 0.1% to about 20% on a molar basis of the PEG-modified lipid, e.g., about 0.5 to about 10%, about 0.5 to about 5%, about 10%, about 5%, about 3.5%, about 1.5%, about 0.5%, or about 0.3% on a molar basis. In one embodiment, the PEG-modified lipid is PEG-DMG. In one embodiment, the PEG-modified lipid is PEG-c-DMA. In one embodiment, the lipid particles include 25-75% of cationic lipid, 0.5-15% of the neutral lipid, 5-50% of the sterol, and 0.5-20% of the PEG-modified lipid on a molar basis.

In one embodiment, the lipid particles include 35-65% of cationic lipid, 3-12% of the neutral lipid, 15-45% of the sterol, and 0.5-10% of the PEG-modified lipid on a molar basis. In one embodiment, the lipid particles include 45-65% of cationic lipid, 5-10% of the neutral lipid, 25-40% of the sterol, and 0.5-5% of the PEG-modified lipid on a molar basis. In one embodiment, the PEG modified lipid comprises a PEG molecule of an average molecular weight of 2,000 Da. In one embodiment, the PEG modified lipid is PEG-distyryl glycerol (PEG-DSG).

In one embodiment, the ratio of lipid:siRNA is at least about 0.5:1, at least about 1:1, at least about 2:1, at least about 3:1, at least about 4:1, at least about 5:1, at least about 6:1, at least about 7:1, at least about 11:1 or at least about 33:1. In one embodiment, the ratio of lipid:siRNA ratio is between about 1:1 to about 35:1, about 3:1 to about 15:1, about 4:1 to about 15:1, or about 5:1 to about 13:1. In one embodiment, the ratio of lipid:siRNA ratio is between about 0.5:1 to about 12:1.

In one embodiment, the lipid particles are nanoparticles. In additional embodiments, the lipid particles have a mean diameter size of from about 50 nm to about 300 nm, such as from about 50 nm to about 250 nm, for example, from about 50 nm to about 200 nm.

In one embodiment, a lipid particle containing a cationic lipid of any of the embodiments described herein has an in vivo half life ($t_{1/2}$) (e.g., in the liver, spleen or plasma) of less than about 3 hours, such as less than about 2.5 hours, less than about 2 hours, less than about 1.5 hours, less than about 1 hour, less than about 0.5 hour or less than about 0.25 hours.

In another embodiment, a lipid particle containing a cationic lipid of any of the embodiments described herein has an in vivo half life ($t_{1/2}$) (e.g., in the liver, spleen or plasma) of less than about 10% (e.g., less than about 7.5%, less than about 5%, less than about 2.5%) of that for the same cationic lipid without the biodegradable group or groups.

Additional Components

The lipid particles and compositions described herein can further include one or more antioxidants. The antioxidant stabilizes the lipid particle and prevents, decreases, and/or inhibits degradation of the cationic lipid and/or active agent present in the lipid particles. The antioxidant can be a hydrophilic antioxidant, a lipophilic antioxidant, a metal chelator, a primary antioxidant, a secondary antioxidant, salts thereof, and mixtures thereof. In certain embodiments, the antioxidant comprises a metal chelator such as EDTA or salts thereof, alone or in combination with one, two, three, four, five, six, seven, eight, or more additional antioxidants such as primary antioxidants, secondary antioxidants, or other metal chelators. In one preferred embodiment, the antioxidant comprises a metal chelator such as EDTA or salts thereof in a mixture with one or more primary antioxidants and/or secondary antioxidants. For example, the antioxidant may comprise a mixture of EDTA or a salt thereof, a primary antioxidant such as a-tocopherol or a salt thereof, and a secondary antioxidant such as ascorbyl palmitate or a salt thereof. In one embodiment, the antioxidant comprises at least about 100 mM citrate or a salt thereof. Examples of antioxidants include, but are not limited to, hydrophilic antioxidants, lipophilic antioxidants, and mixtures thereof. Non-limiting examples of hydrophilic antioxidants include chelating agents (e.g., metal chelators) such as ethylenediaminetetraacetic acid (EDTA), citrate, ethylene glycol tetraacetic acid (EGTA), 1,2-bis(o-aminophenoxy) ethane-N,N,N',N'-tetraacetic acid (BAPTA), diethylene triamine pentaacetic acid (DTPA), 2,3-dimercapto-1-propanesulfonic acid (DMPS), dimercaptosuccinic acid (DMSA), cc-lipoic acid, salicylaldehyde isonicotinoyl hydrazone (SIH), hexyl thioethylamine hydrochloride (HTA), desferrioxamine, salts thereof, and mixtures thereof. Additional hydrophilic antioxidants include ascorbic acid, cysteine, glutathione, dihydrolipoic acid, 2-mercaptoethane sulfonic acid, 2-mercaptobenzimidazole sulfonic acid, 6-hydroxy-2, 5,7,8-tetramethylchroman-2-carboxylic acid, sodium metabisulfite, salts thereof, and mixtures thereof. Non-limiting examples of lipophilic antioxidants include vitamin E isomers such as $\alpha$-, $\beta$-, $\gamma$-, and $\delta$-tocopherols and $\alpha$-, $\beta$-, $\gamma$-, and $\delta$-tocotrienols; polyphenols such as 2-tert-butyl-4-methyl phenol, 2-tert-butyl-5-methyl phenol, and 2-tert-butyl-6-methyl phenol; butylated hydroxyanisole (BHA) (e.g., 2-tert-butyl-4-hydroxyanisole and 3-tert-butyl-4-hydroxyanisole); butylhydroxytoluene (BHT); tert-butylhydroquinone (TBHQ); ascorbyl palmitate; rc-propyl gallate; salts thereof; and mixtures thereof. Suitable antioxidants and formulations containing such antioxidants are described in International Publication No. WO 2011/066651, which is hereby incorporated by reference.

In another embodiment, the lipid particles or compositions contain the antioxidant EDTA (or a salt thereof), the antioxidant citrate (or a salt thereof), or EDTA (or a salt thereof) in combination with one or more (e.g., a mixture of) primary and/or secondary antioxidants such as α-tocopherol (or a salt thereof) and/or ascorbyl palmitate (or a salt thereof).

In one embodiment, the antioxidant is present in an amount sufficient to prevent, inhibit, or reduce the degradation of the cationic lipid present in the lipid particle. For example, the antioxidant may be present at a concentration of at least about or about 0.1 mM, 0.5 mM, 1 mM, 10 mM, 100 mM, 500 mM, 1 M, 2 M, or 5M, or from about 0.1 mM to about 1 M, from about 0.1 mM to about 500 mM, from about 0.1 mM to about 250 mM, or from about 0.1 mM to about 100 mM.

The lipid particles and compositions described herein can further include an apolipoprotein. As used herein, the term "apolipoprotein" or "lipoprotein" refers to apolipoproteins known to those of skill in the art and variants and fragments thereof and to apolipoprotein agonists, analogues or fragments thereof described below.

In a preferred embodiment, the active agent is a nucleic acid, such as a siRNA. For example, the active agent can be a nucleic acid encoded with a product of interest, including but not limited to, RNA, antisense oligonucleotide, an antagomir, a DNA, a plasmid, a ribosomal RNA (rRNA), a micro RNA (miRNA) (e.g., a miRNA which is single stranded and 17-25 nucleotides in length), transfer RNA (tRNA), a small interfering RNA (siRNA), small nuclear RNA (snRNA), antigens, fragments thereof, proteins, peptides, vaccines and small molecules or mixtures thereof. In one more preferred embodiment, the nucleic acid is an oligonucleotide (e.g., 15-50 nucleotides in length (or 15-30 or 20-30 nucleotides in length)). An siRNA can have, for instance, a duplex region that is 16-30 nucleotides long. In another embodiment, the nucleic acid is an immunostimulatory oligonucleotide, decoy oligonucleotide, supermir, miRNA mimic, or miRNA inhibitor. A supermir refers to a single stranded, double stranded or partially double stranded oligomer or polymer of ribonucleic acid (RNA) or deoxyribonucleic acid (DNA) or both or modifications thereof, which has a nucleotide sequence that is substantially identical to an miRNA and that is antisense with respect to its target. miRNA mimics represent a class of molecules that can be used to imitate the gene silencing ability of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression.

The nucleic acid that is present in a lipid-nucleic acid particle can be in any form. The nucleic acid can, for example, be single-stranded DNA or RNA, or double-stranded DNA or RNA, or DNA-RNA hybrids. Non-limiting examples of double-stranded RNA include siRNA. Single-stranded nucleic acids include, e.g., antisense oligonucleotides, ribozymes, microRNA, and triplex-forming oligonucleotides. The lipid particles of the present invention can also deliver nucleic acids which are conjugated to one or more ligands.

Pharmaceutical Compositions

The lipid particles, particularly when associated with a therapeutic agent, may be formulated as a pharmaceutical composition, e.g., which further comprises a pharmaceutically acceptable diluent, excipient, or carrier, such as physiological saline or phosphate buffer.

The resulting pharmaceutical preparations may be sterilized by conventional, well known sterilization techniques. The aqueous solutions can then be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, and tonicity adjusting agents, for example, sodium acetate, sodium lactate, sodium chloride, potassium chloride, and calcium chloride. Additionally, the lipidic suspension may include lipid-protective agents which protect lipids against free-radical and lipid-peroxidative damages on storage. Lipophilic free-radical quenchers, such as α-tocopherol and water-soluble iron-specific chelators, such as ferrioxamine, are suitable.

The concentration of lipid particle or lipid-nucleic acid particle in the pharmaceutical formulations can vary, for example, from less than about 0.01%, to at or at least about 0.05-5% to as much as 10 to 30% by weight.

Methods of Manufacture

Methods of making cationic lipids, lipid particles containing them, and pharmaceutical compositions containing the cationic lipids and/or lipid particles are described in, for example, International Publication Nos. WO 2010/054406, WO 2010/054401, WO 2010/054405, WO 2010/054384, WO 2010/042877, WO 2010/129709, WO 2009/086558, and WO 2008/042973, and U.S. Patent Publication Nos. 2004/0142025, 2006/0051405 and 2007/0042031, each of which is incorporated by reference in its entirety.

For example, in one embodiment, a solution of one or more lipids (including a cationic lipid of any of the embodiments described herein) in an organic solution (e.g., ethanol) is prepared. Similarly, a solution of one or more active (therapeutic) agents (such as, for example an siRNA molecule or a 1:1 molar mixture of two siRNA molecules) in an aqueous buffered (e.g., citrate buffer) solution is prepared. The two solutions are mixed and diluted to form a colloidal suspension of siRNA lipid particles. In one embodiment, the siRNA lipid particles have an average particle size of about 80-90 nm. In further embodiments, the dispersion may be filtered through 0.45/2 micron filters, concentrated and diafiltered by tangential flow filtration.

Definitions

As used herein, the term "cationic lipid" includes those lipids having one or two fatty acid or fatty aliphatic chains and an amino acid containing head group that may be protonated to form a cationic lipid at physiological pH. In some embodiments, a cationic lipid is referred to as an "amino acid conjugate cationic lipid."

A subject or patient in whom administration of the complex is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, and cats, avian species, such as chickens, turkeys, and songbirds, i.e., for veterinary medical use.

Many of the chemical groups recited in the generic formulas above are written in a particular order (for example, —OC(O)—). It is intended that the chemical group is to be incorporated into the generic formula in the order presented unless indicated otherwise. For example, a generic formula of the form —$(R)_i$-$(M^1)_k$-$(R)_m$ where $M^1$ is —C(O)O— and k is 1 refers to —$(R)_i$—C(O)O—$(R)_m$ unless specified otherwise. It is to be understood that when a chemical group is written in a particular order, the reverse order is also contemplated unless otherwise specified. For example, in a generic formula —$(R)_i$-$(M^1)_k$-$(R)_m$ where M is defined as —C(O)NH— (i.e., —$(R)_i$—C(O)—NH—$(R)_m$—), the compound where $M^1$ is —NHC(O)— (i.e., —$(R)_i$—NHC(O)—$(R)_m$) is also contemplated unless otherwise specified.

The term "biodegradable cationic lipid" refers to a cationic lipid having one or more biodegradable groups located in the mid- or distal section of a lipidic moiety (e.g., a hydrophobic chain) of the cationic lipid. The incorporation of the biodegradable group(s) into the cationic lipid results in faster metabolism and removal of the cationic lipid from the body following delivery of the active pharmaceutical ingredient to a target area.

As used herein, the term "biodegradable group" refers to a group that include one or more bonds that may undergo bond breaking reactions in a biological environment, e.g., in an organism, organ, tissue, cell, or organelle. For example, the biodegradable group may be metabolizable by the body of a mammal, such as a human (e.g., by hydrolysis). Some groups that contain a biodegradable bond include, for example, but are not limited to esters, dithiols, and oximes. Non-limiting examples of biodegradable groups are —OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)(C$R^3R^4$)C(O)O—, or —OC(O)(C$R^3R^4$)C(O)—.

As used herein, an "aliphatic" group is a non-aromatic group in which carbon atoms are linked into chains, and is either saturated or unsaturated.

The terms "alkyl" and "alkylene" refer to a straight or branched chain saturated hydrocarbon moiety. In one embodiment, the alkyl group is a straight chain saturated hydrocarbon. Unless otherwise specified, the "alkyl" or "alkylene" group contains from 1 to 24 carbon atoms. Representative saturated straight chain alkyl groups include methyl, ethyl, n-propyl, n-butyl, n-pentyl, and n-hexyl. Representative saturated branched alkyl groups include isopropyl, sec-butyl, isobutyl, tert-butyl, and isopentyl.

The term "alkenyl" refers to a straight or branched chain hydrocarbon moiety having one or more carbon-carbon double bonds. In one embodiment, the alkenyl group contains 1, 2, or 3 double bonds and is otherwise saturated. Unless otherwise specified, the "alkenyl" group contains from 2 to 24 carbon atoms. Alkenyl groups include both cis and trans isomers. Representative straight chain and branched alkenyl groups include ethylenyl, propylenyl, 1-butenyl, 2-butenyl, isobutylenyl, 1-pentenyl, 2-pentenyl, 3-methyl-1-butenyl, 2-methyl-2-butenyl, and 2,3-dimethyl-2-butenyl.

The term "alkynyl" refers to a straight or branched chain hydrocarbon moiety having one or more carbon-carbon triple bonds. Unless otherwise specified, the "alkynyl" group contains from 2 to 24 carbon atoms. Representative straight chain and branched alkynyl groups include acetylenyl, propynyl, 1-butynyl, 2-butynyl, 1-pentynyl, 2-pentynyl, and 3-methyl-1-butynyl.

Unless otherwise specified, the terms "branched alkyl", "branched alkenyl", and "branched alkynyl" refer to an alkyl, alkenyl, or alkynyl group in which one carbon atom in the group (1) is bound to at least three other carbon atoms and (2) is not a ring atom of a cyclic group. For example, a spirocyclic group in an alkyl, alkenyl, or alkynyl group is not considered a point of branching.

Unless otherwise specified, the term "acyl" refers to a carbonyl group substituted with hydrogen, alkyl, partially saturated or fully saturated cycloalkyl, partially saturated or fully saturated heterocycle, aryl, or heteroaryl. For example, acyl groups include groups such as ($C_1$-$C_{20}$)alkanoyl (e.g., formyl, acetyl, propionyl, butyryl, valeryl, caproyl, and t-butylacetyl), ($C_3$-$C_{20}$)cycloalkylcarbonyl (e.g., cyclopropylcarbonyl, cyclobutylcarbonyl, cyclopentylcarbonyl, and cyclohexylcarbonyl), heterocyclic carbonyl (e.g., pyrrolidinylcarbonyl, pyrrolid-2-one-5-carbonyl, piperidinylcarbonyl, piperazinylcarbonyl, and tetrahydrofuranylcarbonyl), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, and benzo[b]thiophenyl-2-carbonyl).

The term "aryl" refers to an aromatic monocyclic, bicyclic, or tricyclic hydrocarbon ring system. Unless otherwise specified, the "aryl" group contains from 6 to 14 carbon atoms. Examples of aryl moieties include, but are not limited to, phenyl, naphthyl, anthracenyl, and pyrenyl.

The terms "cycloalkyl" and "cycloalkylene" refer to a saturated monocyclic or bicyclic hydrocarbon moiety such as cyclopropyl, cyclobutyl, cyclopentyl, and cyclohexyl. Unless otherwise specified, the "cycloalkyl" or "cycloalkylene" group contains from 3 to 10 carbon atoms.

The term "cycloalkylalkyl" refers to a cycloalkyl group bound to an alkyl group, where the alkyl group is bound to the rest of the molecule.

The term "heterocycle" (or "heterocyclyl") refers to a non-aromatic 5- to 8-membered monocyclic, or 7- to 12-membered bicyclic, or 11- to 14-membered tricyclic ring system which is either saturated or unsaturated, and which contains from 1 to 3 heteroatoms if monocyclic, 1-6 heteroatoms if bicyclic, or 1-9 heteroatoms if tricyclic, independently selected from nitrogen, oxygen and sulfur, and wherein the nitrogen and sulfur heteroatoms may be optionally oxidized, and the nitrogen heteroatom may be optionally quaternized. For instance, the heterocycle may be a cycloalkoxy group. The heterocycle may be attached to the rest of the molecule via any heteroatom or carbon atom in the heterocycle. Heterocycles include, but are not limited to, morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, and tetrahydrothiopyranyl.

The term "heteroaryl" refers to an aromatic 5-8 membered monocyclic, 7-12 membered bicyclic, or 11-14 membered tricyclic ring system having 1-3 heteroatoms if monocyclic, 1-6 heteroatoms if bicyclic, or 1-9 heteroatoms if tricyclic, where the heteroatoms are selected from O, N, or S (e.g., carbon atoms and 1-3, 1-6, or 1-9 heteroatoms of N, O, or S if monocyclic, bicyclic, or tricyclic, respectively). The heteroaryl groups herein described may also contain fused rings that share a common carbon-carbon bond.

The term "substituted", unless otherwise indicated, refers to the replacement of one or more hydrogen radicals in a given structure with the radical of a specified substituent including, but not limited to: halo, alkyl, alkenyl, alkynyl, aryl, heterocyclyl, thiol, alkylthio, oxo, thioxy, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and an aliphatic group. It is understood that the substituent may be further substituted. Exemplary substituents include amino, alkylamino, dialkylamino, and cyclic amino compounds.

The term "halogen" or "halo" refers to fluoro, chloro, bromo and iodo.

The following abbreviations may be used in this application:
DSPC: distearoylphosphatidylcholine; DPPC: 1,2-Dipalmitoyl-sn-glycero-3-phosphocholine; POPC: 1-palmitoyl-2-oleoyl-sn-phosphatidylcholine; DOPE: 1,2-dileoyl-sn-3-phosphoethanolamine; PEG-DMG generally refers to 1,2-dimyristoyl-sn-glycerol-methoxy polyethylene glycol (e.g., PEG 2000); TBDPSCl: tert-Butylchlorodiphenylsilane; DMAP: dimethylaminopyridine; HMPA: hexamethylphosphoramide; EDC: 1-ethyl-3-(3-dimethylaminopropyl) carbodiimide; DIPEA: diisopropylethylamine; DCM: dichloromethane; TEA: triethylamine; TBAF: tetrabutylammonium fluoride Methods to prepare various organic groups and protective groups are known in the art and their use and modification is generally within the ability of one of skill in the art (see, for example, Green, T. W. et. al., *Protective Groups in Organic Synthesis* (1999); Stanley R. Sandler and Wolf Karo, *Organic Functional Group Preparations* (1989); Greg T. Hermanson, *Bioconjugate Techniques* (1996); and Leroy G. Wade, *Compendium Of Organic Synthetic Methods* (1980)). Briefly, protecting groups are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

The compounds may be prepared by at least one of the techniques described herein or known organic synthesis techniques.

EXAMPLES

Example 1

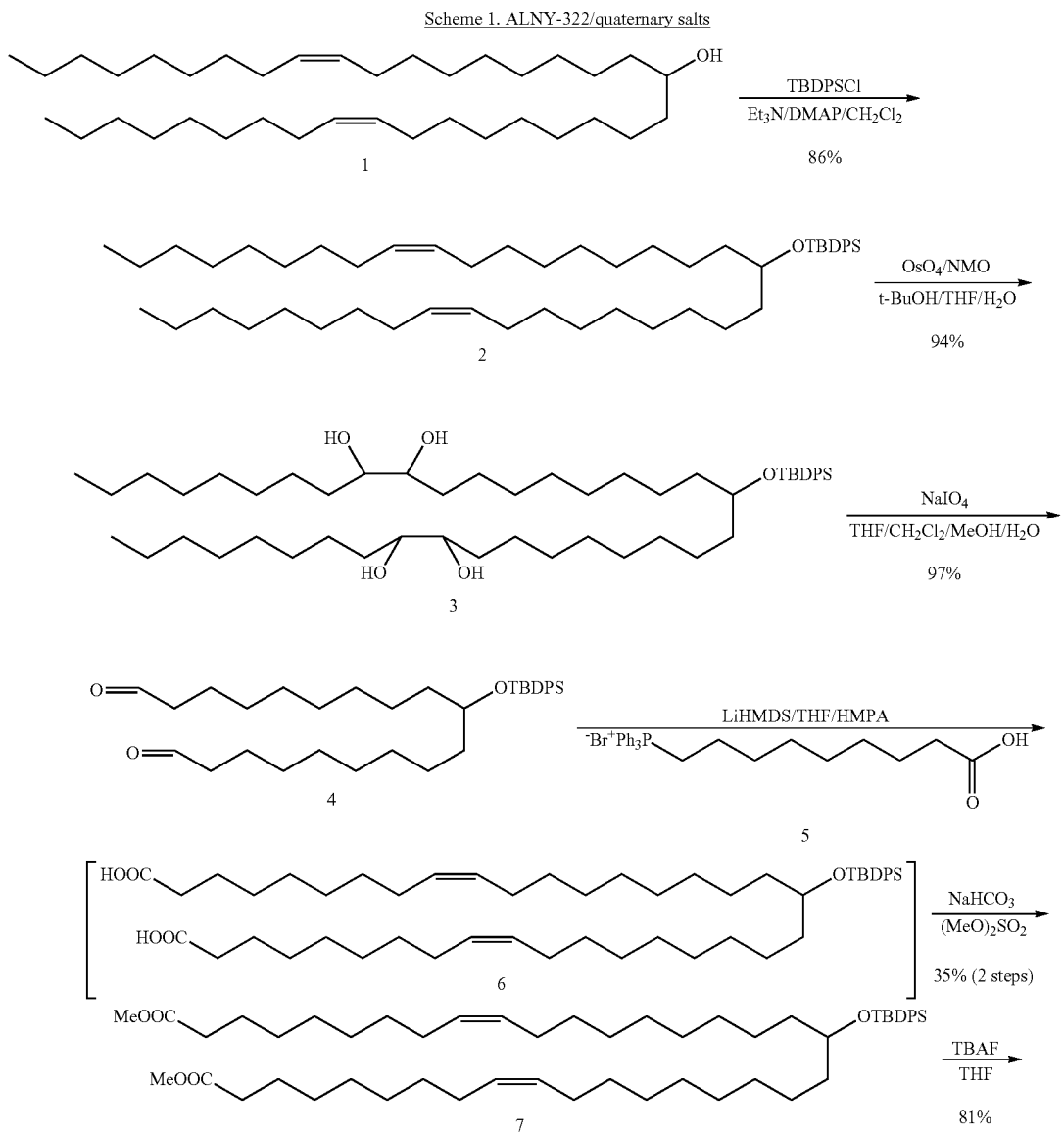

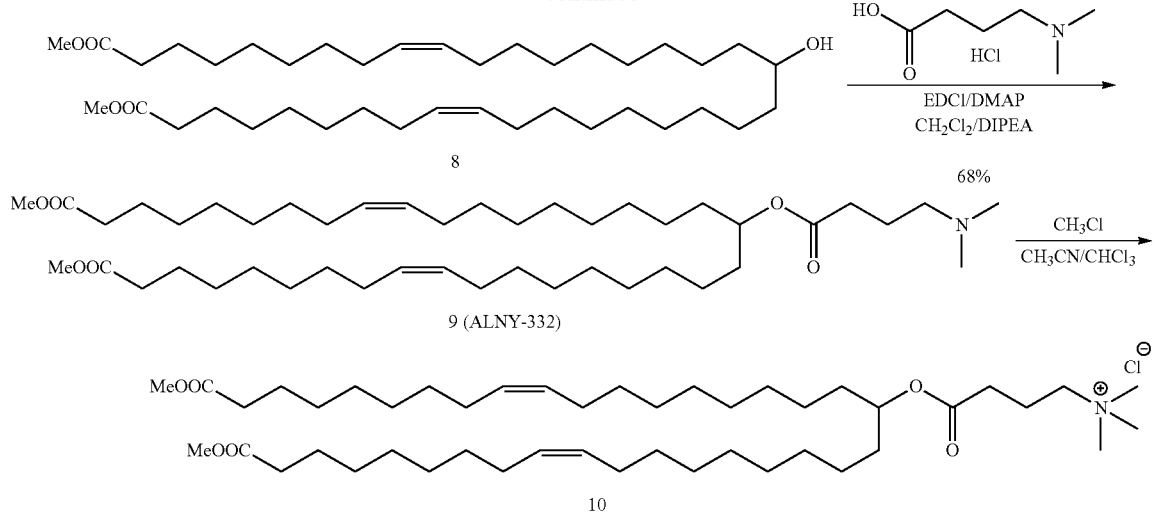

Compound 2: To a solution of compound 1 (10.0 g, 18.8 mmol, see International Publication No. WO 2010/054406) in $CH_2Cl_2$ (80 mL) were added triethylamine (7.86 mL, 56.4 mmol), DMAP (459 mg, 3.76 mmol) and tert-butyl(chloro)diphenylsilane (9.62 mL, 37.6 mmol). The reaction mixture was stirred for 24 hours. The mixture was then diluted with $CH_2Cl_2$ and washed with aqueous saturated $NaHCO_3$ solution. The organic layer was separated and dried over anhydrous $Na_2SO_4$. After filtration and concentration, the crude product was purified by silica gel column chromatography (0-5% EtOAc in hexane) to afford 2 (12.4 g, 16.1 mmol, 86%, $R_f$=0.24 with hexane). $^1H$ NMR (400 MHz, $CDCl_3$) δ 7.66-7.68 (m, 4H), 7.33-7.42 (m, 6H), 5.30-5.39 (m, 4H), 3.67-3.72 (m, 1H), 1.97-2.04 (m, 8H), 1.07-1.42 (m, 52H), 1.05 (s, 9H), 0.88 (t, J=6.8 Hz, 6H).

Compound 3: To a solution of 2 (12.4 g, 16.1 mmol) in tert-butanol (100 mL), THF (30 mL) and $H_2O$ (10 mL) were added 4-methylmorpholine N-oxide (4.15 g, 35.4 mmol) and osmium tetroxide (41 mg, 0.161 mg). The reaction mixture was stirred for 16 hours, then quenched by adding sodium bisulfite. After removing the solvents by evaporation, the residue was extracted with $Et_2O$ (500 mL) and $H_2O$ (300 mL). The organic layer was separated and dried over anhydrous $Na_2SO_4$. After filtration and concentration, the crude was purified by silica gel column chromatography (hexane:EtOAc=1:1, $R_f$=0.49) to afford 3 (12.7 g, 15.1 mmol, 94%). $^1H$ NMR (400 MHz, $CDCl_3$) δ 7.66-7.68 (m, 4H), 7.33-7.43 (m, 6H), 3.67-3.73 (m, 1H), 3.57-3.62 (m, 4H), 1.82 (t, J=5.0 Hz, 4H), 1.10-1.51 (m, 60H), 1.04 (s, 9H), 0.88 (t, J=6.8 Hz, 6H).

Compound 4: To a solution of 3 (12.6 g, 15.0 mmol) in 1,4-dioxane (220 mL), $CH_2Cl_2$ (70 mL), MeOH (55 mL), and $H_2O$ (55 mL) was added $NaIO_4$ (7.70 g, 36.0 mmol). The reaction mixture was stirred for 16 hours at room temperature. The mixture was extracted with $Et_2O$ (500 mL) and $H_2O$ (300 mL). The organic layer was separated and dried over anhydrous $Na_2SO_4$. After filtration and concentration, the crude product was purified by silica gel column chromatography (Hexane:EtOAc=9:1, $R_f$=0.30) to afford 4 (7.98 g, 14.5 mmol, 97%). Molecular weight for $C_{35}H_{54}NaO_3Si$ $(M+Na)^+$ Calc. 573.3740, Found 573.3.

Compound 7: To a solution of 5 (see, Tetrahedron, 63, 1140-1145, 2006; 1.09 g, 2.18 mmol) in THF (20 mL) and HMPA (4 mL), LiHMDS (1 M THF solution, 4.36 mL, 4.36 mmol) was added at −20° C. The resulting mixture was stirred for 20 minutes at the same temperature, then cooled to −78° C. A solution of 4 (500 mg, 0.908 mmol) in THF (4 mL) was added. The mixture was stirred and allowed to warm to room temperature overnight. MS analysis showed the formation of the di-acid (6; $C_{53}H_{85}O_5Si$ $(M-H)^-$ calc. 829.6166, observed 829.5). To the mixture, $NaHCO_3$ (1.10 g, 13.1 mmol) and dimethyl sulfate (1.24 mL, 13.1 mmol) were added and stirred for 2 hours at room temperature. The reaction was quenched by adding saturated $NH_4Cl$ aqueous solution (50 mL) then extracted with $Et_2O$ (2×100 mL). The organic layer was separated and dried over anhydrous $Na_2SO_4$. After filtration and concentration, the crude product was purified by silica gel column chromatography (Hexane:EtOAc=9:1, $R_f$=0.35) to afford 7 (270 mg, 0.314 mmol, 35%). Molecular weight for $C_{55}H_{90}NaO_5Si$ $(M+Na)^+$ Calc. 881.6455, Found 881.6484.

Compound 8: To a solution of 7 (265 mg, 0.308 mmol) in THF (2.5 mL), n-TBAF (1 M THF solution, 0.555 mL, 0.555 mmol) was added. The reaction mixture was stirred for 14 hours at 45° C. After concentration, the mixture was purified by silica gel column chromatography (Hexane:EtOAc=3:1, $R_f$=0.52) to afford 8 (155 mg, 0.250 mmol, 81%). Molecular weight for $C_{39}H_{72}NaO_5$ $(M+Na)^+$ Calc. 643.5277, Found 643.5273.

Compound 9: To a solution of compound 8 (150 mg, 0.242 mmol) and 4-(dimethylamino)butyric acid hydrochloride (49 mg, 0.290 mmol) in $CH_2Cl_2$ (5 mL) were added diisopropylethylamine (0.126 mL, 0.726 mmol), N-(3-dimethylaminopropyl)-N'-ethylcarbodiimide hydrochloride (56 mg, 0.290 mmol) and DMAP (6 mg, 0.0484 mmol). The reaction mixture was stirred at room temperature for 14 hours. The reaction mixture was then diluted with $CH_2Cl_2$ (100 mL) and washed with saturated $NaHCO_3$ aq. (50 mL). The organic layer was dried over $MgSO_4$, filtered and concentrated. The crude product was purified by silica gel column chromatography (0-5% MeOH in $CH_2Cl_2$) to afford compound 9 (121 mg, 0.165 mmol, 68%, $R_f$=0.25 developed with 5% MeOH in $CH_2Cl_2$). Molecular weight for $C_{45}H_{84}NO_6$ $(M+H)^+$ Calc. 734.6299, Found 734.5.

Compound 10: Treatment of compound 9 with $CH_3Cl$ in $CH_3CN$ and $CHCl_3$ can afford compound 10.

Example 2

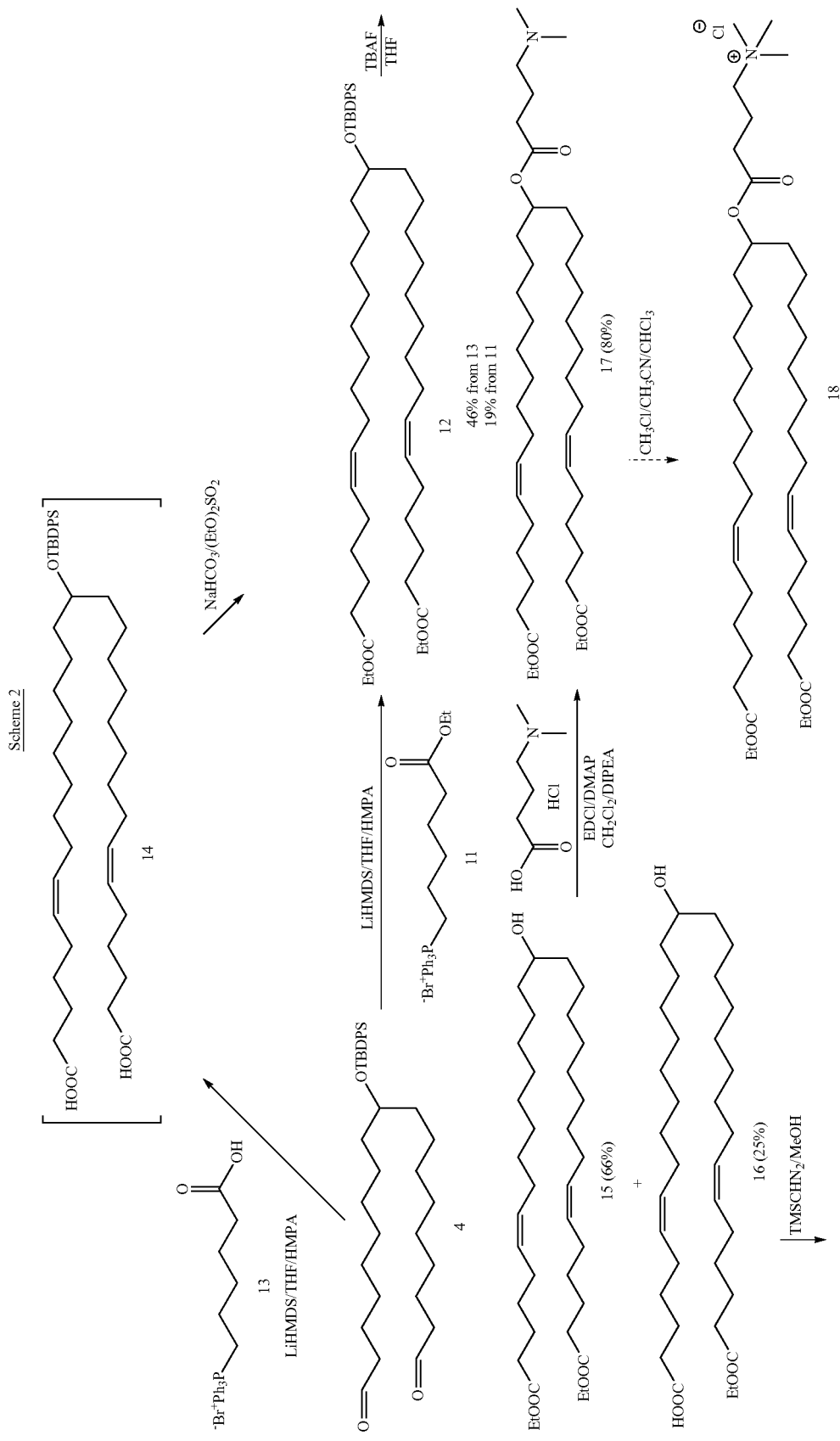

-continued
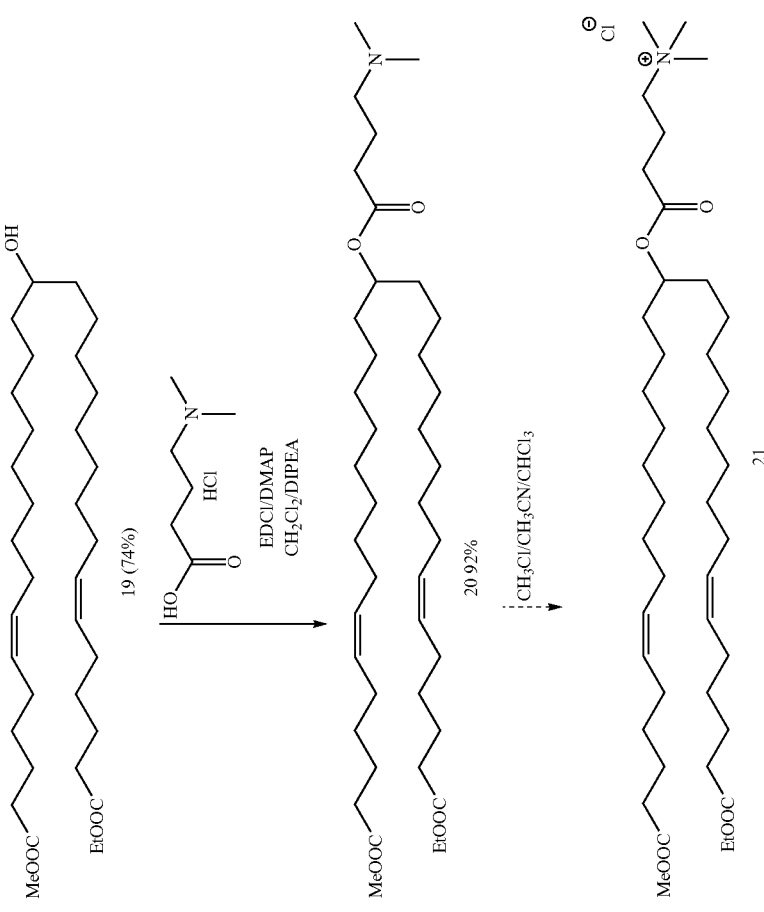

Compound 12: To a solution of 11 (Journal of Medicinal Chemistry (1995), 38, 636-46; 1.25 g, 2.58 mmol) in THF (20 mL) and HMPA (4 mL), LiHMDS (1 M THF solution, 2.58 mL, 2.58 mmol) was added at −20° C. The mixture was stirred for 20 min at the same temperature, then cooled to −78° C. A solution of 4 (500 mg, 0.908 mmol) in THF (9 mL) and HMPA (0.9 mL) was added. The mixture was stirred from −78° C. to room temperature overnight. The reaction was quenched by adding $H_2O$ (40 mL) then extracted with $Et_2O$ (150 mL×3). The organic layer was separated and dried over anhydrous $Na_2SO_4$. After filtration and concentration, the crude was purified by silica gel column chromatography (Hexane:EtOAc=9:1, $R_f$=0.35) to give 12 (136 mg, 0.169 mmol, 19%). Molecular weight for $C_{51}H_{82}NaO_5Si$ $(M+Na)^+$ Calc. 825.5829, Found 825.5.

Using 13 in place of 5, a procedure analogous to that described for compound 7 was followed to afford compound 12 (135 mg, 0.168 mmol, 46%).

Compound 15/Compound 16: To a solution of 12 (800 mg, 0.996 mmol) in THF (5 mL), n-TBAF (1 M THF solution, 5 mL, 5.00 mmol) was added. The reaction mixture was stirred for 16 h at 45° C. After concentration, the mixture was purified by silica gel column chromatography to give 15 (Hexane:EtOAc=3:1, $R_f$=0.46, 372 mg, 0.659 mmol, 66%) and 16 ($CH_2Cl_2$:MeOH=95:5, $R_f$=0.36, 135 mg, 0.251 mmol, 25%). Molecular weight for 15; $C_{35}H_{64}NaO_5$ $(M+Na)^+$ Calc. 587.4651, Found 587.4652. Molecular weight for 16; $C_{33}H_{61}O_5(M+H)^+$ Calc. 537.4519, Found 537.5.

Compound 17: To a solution of compound 15 (164 mg, 0.290 mmol) and 4-(dimethylamino)butyric acid hydrochloride (58 mg, 0.348 mmol) in $CH_2Cl_2$ (5 mL) were added diisopropylethylamine (0.152 mL, 0.870 mmol), N-(3-dimethylaminopropyl)-N'-ethylcarbodiimide hydrochloride (67 mg, 0.348 mmol) and DMAP (7 mg, 0.058 mmol). The reaction mixture was stirred at room temperature for 14 hours. The reaction mixture was diluted with $CH_2Cl_2$ (100 mL) and washed with saturated $NaHCO_3$ aq. (50 mL). The organic layer was dried over $MgSO_4$, filtered and concentrated. The crude was purified by silica gel column chromatography (0-5% MeOH in $CH_2Cl_2$) to give compound 17 (158 mg, 0.233 mmol, 80%, $R_f$=0.24 developed with 5% MeOH in $CH_2Cl_2$). Molecular weight for $C_{45}H_{84}NO_6$ $(M+H)^+$ Calc. 734.6299, Found 734.5.

Compound 18: Treatment of compound 17 with $CH_3Cl$ in $CH_3CN$ and $CHCl_3$ can afford compound 18.

Compound 19: To a solution of 16 (130 mg, 0.242 mmol) in THF (2 mL) and MeOH (2 mL), trimethylsilyldiazomethane (2 M solution in $Et_2O$, 0.158 mL, 0.315 mmol) was added. The reaction mixture was stirred for 14 h. After evaporation, the residue was purified by silica gel column chromatography (Hexane:EtOAc=3:1, $R_f$=0.50) to give 19 (99 mg, 0.180 mmol, 74%). $^1$H NMR (400 MHz, $CDCl_3$) δ 5.29-5.40 (m, 4H), 4.12 (q, J=7.1 Hz, 2H), 3.66 (s, 3H), 3.55-3.59 (m, 1H), 2.30 (dd, J=14.7, 7.2 Hz, 4H), 1.98-2.07 (m, 8H), 1.60-1.68 (m, 4H), 1.23-1.43 (m, 37H).

Compound 20: To a solution of compound 19 (95 mg, 0.168 mmol) and 4-(dimethylamino)butyric acid hydrochloride (42 mg, 0.252 mmol) in $CH_2Cl_2$ (3 mL) were added diisopropylethylamine (0.088 mL, 0.504 mmol), N-(3-dimethylaminopropyl)-N'-ethylcarbodiimide hydrochloride (48 mg, 0.504 mmol) and DMAP (4 mg, 0.034 mmol). The reaction mixture was stirred at room temperature for 14 hours. The reaction mixture was diluted with $CH_2Cl_2$ (100 mL) and washed with saturated $NaHCO_3$ aq. (50 mL). The organic layer was dried over $MgSO_4$, filtered and concentrated. The crude was purified by silica gel column chromatography (0-5% MeOH in $CH_2Cl_2$) to give compound 20 (103 mg, 0.155 mmol, 92%, $R_f$=0.19 developed with 5% MeOH in $CH_2Cl_2$). H NMR (400 MHz, $CDCl_3$) δ 5.29-5.40 (m, 4H), 4.83-4.89 (m, 1H), 4.12 (q, J=7.1 Hz, 2H), 3.67 (s, 3H), 2.28-2.34 (m, 8H), 2.23 (s, 6H), 1.98-2.07 (m, 8H), 1.76-1.83 (m, 2H), 1.60-1.68 (m, 4H), 1.23-1.51 (m, 35H).

Compound 21: Treatment of compound 20 with $CH_3Cl$ in $CH_3CN$ and $CHCl_3$ can afford compound 21.

Example 3: Alternate Synthesis for Di-Aldehyde Intermediate 4

Scheme 3

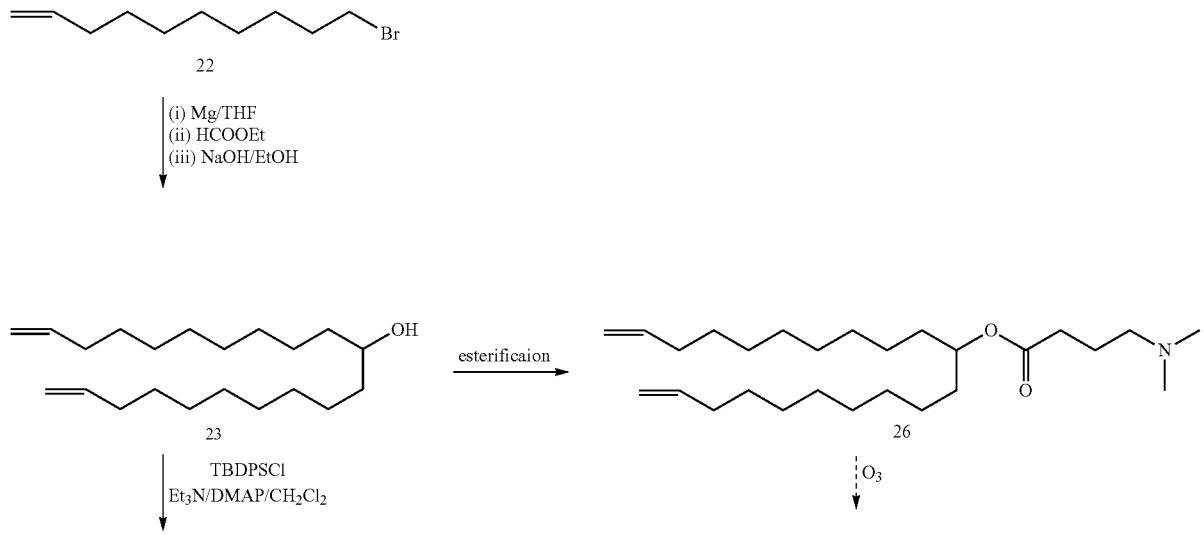

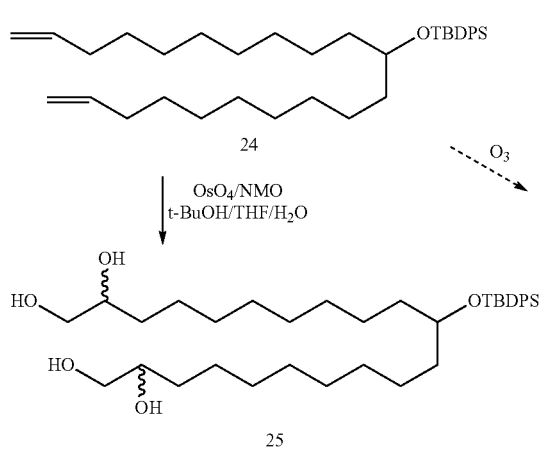
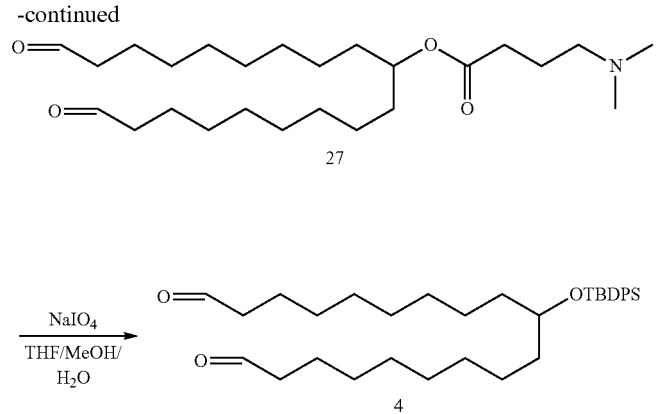
The di-aldehyde 4 can be synthesized as shown in Scheme 3, using 1-bromo-9-decene. Di-aldehyde containing a head group 27 can be useful for the synthesis of terminal ester-substituted lipids using, e.g., a Wittig reaction. Ozonolysis can afford di-aldehyde 4 and 27.
Example 4: Alternate Synthesis for Compound 8
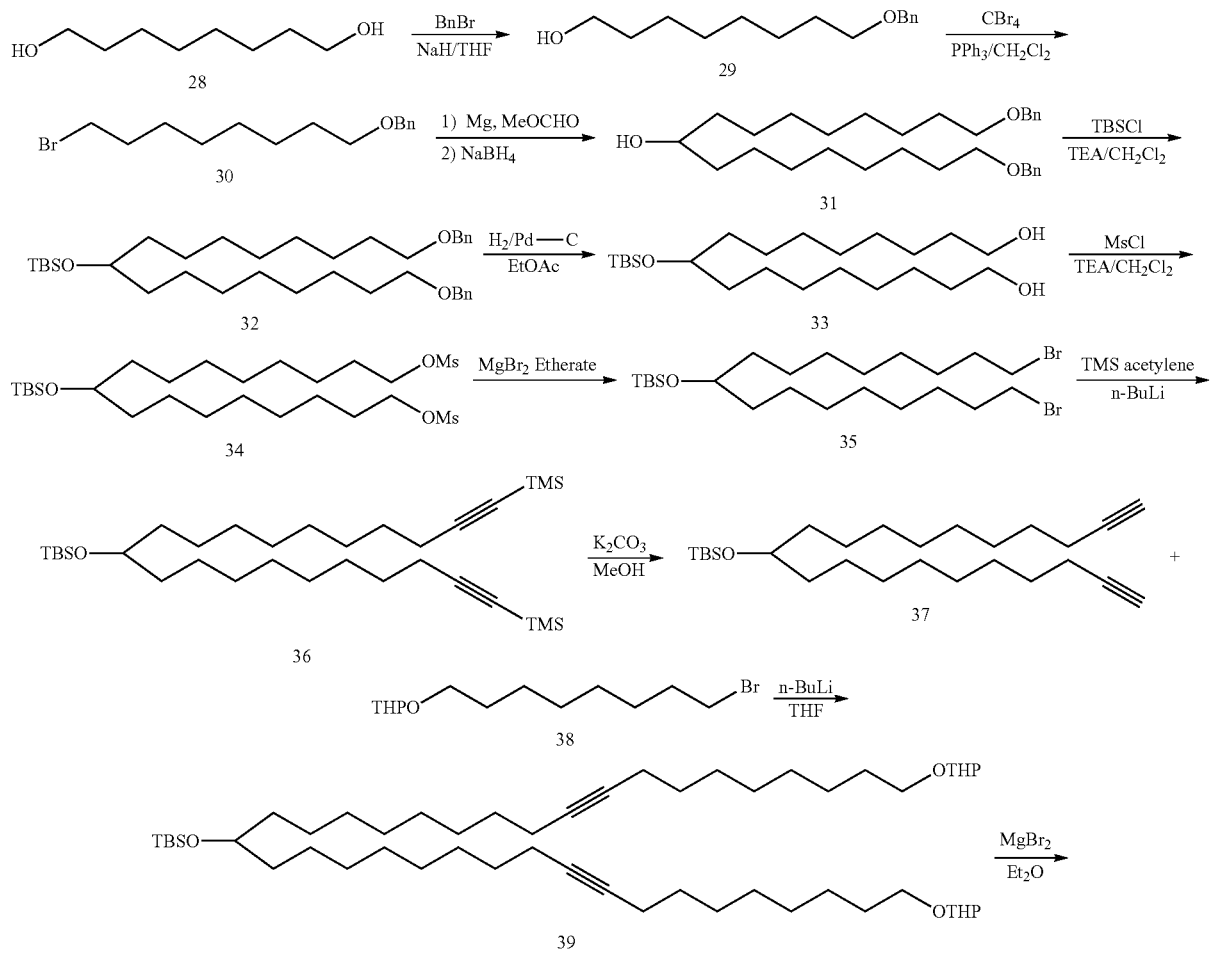

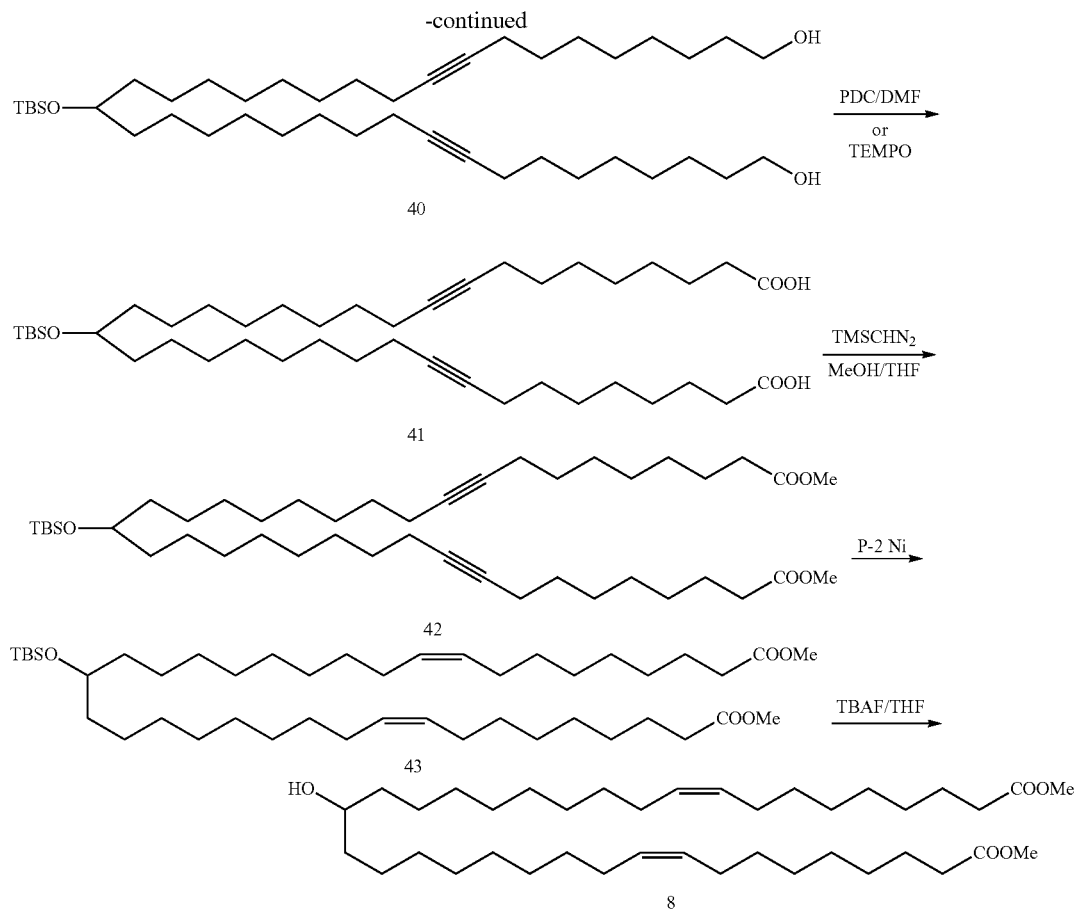

Compound 8 can be synthesized as shown in Scheme 4.

Compound 29: To a stirred suspension of NaH (60% in oil, 82 g, 1.7096 mol) in 500 mL anhydrous DMF, a solution of compound 28 (250 g, 1.7096 mol) in 1.5 L DMF was added slowly using a dropping funnel at 0° C. The reaction mixture was stirred for 30 minutes, then benzyl bromide (208.86 mL, 1.7096 mol) was added slowly under an atmosphere of nitrogen. The reaction was then warmed to ambient temperature and stirred for 10 hours. The mixture was then quenched with crushed ice (~2 kg) and extracted with ethyl acetate (2×1 L). The organic layer was washed with water (1 L) to remove unwanted DMF, dried over $Na_2SO_4$ and evaporated to dryness in vacuo. The crude compound was purified on 60-120 silica gel, eluted with 0-5% MeOH in DCM to afford compound 29 (220 g, 54%) as a pale yellow liquid. $^1$H NMR (400 MHz, $CDCl_3$): δ=7.33-7.24 (m, 5H), 4.49 (s, 2H), 3.63-3.60 (m, 2H), 3.47-3.43 (m, 2H), 1.63-1.51 (m, 4H), 1.39-1.23 (m, 8H).

Compound 30: Compound 29 (133 g, 0.5635 mol) was dissolved in 1.5 L of DCM, $CBr_4$ (280.35 g, 0.8456 mol) was added into this stirring solution and the reaction mixture was cooled to 0° C. under an inert atmosphere. $PPh_3$ (251.03 g, 0.9571 mol) was then added in portions keeping the temperature below 20° C. After complete addition, the reaction mixture was stirred for 3 hours at room temperature. After completion of the reaction, the solid ($PPh_3O$) that precipitated from the reaction mixture was removed by filtration, and the filtrate was diluted with crushed ice (~1.5 kg) and extracted with DCM (3×750 mL). The organic layer was separated, dried over anhydrous $Na_2SO_4$ and distilled under vacuum. The resulting crude compound was chromatographed on 60-120 mesh silica gel column using 0-5% ethyl acetate in hexanes as eluting system to afford compound 30 (150 g, 89%) as pale yellow liquid. H NMR (400 MHz, $CDCl_3$): δ=7.33-7.25 (m, 5H), 4.49 (s, 2H), 3.47-3.41 (m, 2H), 3.41-3.37 (m, 2H), 1.86-1.80 (m, 4H), 1.62-1.56 (m, 2H), 1.42-1.29 (m, 8H).

Compound 31: To freshly activated Mg turnings (24.08 g, 1.003 mol) was added 200 mL anhydrous THF, followed by the addition of pinch of iodine into the mixture under an inert atmosphere. A solution of Compound 30 (150 g, 0.5016 mol) in 1 L of dry THF was added slowly, controlling the exothermic reaction. The reaction was then heated to reflux for 1 hour, then cooled to room temperature. Methyl formate (60.24 g, 1.0033 mol) was then added slowly and the reaction was continued for 2 hours. After completion, the reaction was quenched by slow addition of 10% HCl followed by water (1 L) and extracted with ethyl acetate (3×1 L). The organic layer was taken in 5 litre beaker, diluted with 500 mL of methanol and cooled to 0° C. To this solution, an excess of $NaBH_4$ (~5 eq) was added in portions to ensure hydrolysis of the formate ester which was not cleaved by addition of HCl. The resulting solution was stirred for an hour and then volatilities were removed under vacuum. The residue was taken in water (1 L) and acidified by 10% HCl solution (pH 4). The product was then extracted with ethyl acetate (3×1 L). the organic phase was then dried and concentrated on rotary evaporator to afford the desired compound 31 (57 g, 24%) as solid. $^1$H NMR (400 MHz, $CDCl_3$): δ=7.35-7.32 (m, 8H), 7.29-7.24 (m, 2H), 4.49 (s, 4H), 3.56 (m, 1H), 3.46-3.43 (m, 4H), 1.63-1.56 (m, 4H), 1.44-1.34 (m, 28H). $^{13}$C NMR (100 MHz, CDCl$_3$): δ=138.56, 128.21, 127.49, 127.34, 72.72, 71.76, 70.37, 37.37, 29.64, 29.56, 29.47, 29.33, 26.07, 25.54.

Compound 32: Compound 31 (56 g, 0.1196 mol) was dissolved in 700 mL dry THF and cooled to 0° C. TBSCl (36.06 g, 0.2396 mol) was added slowly followed by the addition of imidazole (32.55 g, 0.4786 mol) under an inert atmosphere. The reaction was then stirred at room temperature for 18 hours. Upon completion, the reaction was quenched with ice (~1 kg) and extracted with ethyl acetate (3×500 mL). The organic layer was separated, washed with saturated NaHCO$_3$ solution to remove acidic impurities, dried over Na$_2$SO$_4$ and evaporated under reduce pressure to afford a crude compound that was purified by silica gel (60-120 mesh) and eluted with 0-10% ethyl acetate hexane to afford (60 g, 82%) of compound 32 as yellowish oil. $^1$H NMR (400 MHz, CDCl$_3$): δ=7.33-7.24 (m, 10H), 4.49 (s, 4H), 3.60-3.57 (m, 1H), 3.46-3.43 (m, 4H), 1.61-1.54 (m, 4H), 1.41-1.26 (m, 28H), 0.87 (s, 9H), 0.02 (s, 6H).

Compound 33: Compound 32 (60 g, 0.1030 mol) was dissolved in 500 mL ethyl acetate and degassed with N$_2$ for 20 minutes. (10 wt %) Pd on carbon (12 g) was added and the reaction was stirred under an atmosphere of hydrogen for 18 hours. After completion, the mixture was filtered through a bed of celite and washed with ethyl acetate. The filtrate was evaporated under vacuum to afford compound 33 (19 g, 46%) that was pure enough to use in the next synthetic sequence. $^1$H NMR (400 MHz, CDCl$_3$): δ=3.64-3.58 (m, 5H), 1.59 (br, 2H), 1.57-1.51 (m, 4H), 1.38-1.22 (m, 28H), 0.87 (s, 9H), 0.02 (s, 6H).

Compound 34: Compound 33 (8.2 g, 0.0199 mol) was dissolved in 100 mL dry DCM and cooled to 0° C. TEA (22.14 mL, 0.1592 mol) was added under an inert atmosphere. After stirring the mixture for 5 minutes, mesyl chloride (4.6 mL, 0.059 mol) was added drop wise and the reaction was stirred further for 3 hours. After completion of the reaction, the mixture was quenched with ice (~200 g) and extracted with DCM (3×75 mL). The organic layer was dried over anhydrous sodium sulfate and evaporated to afford a crude compound which was purified on a 60-120 mesh silica gel column using 0-30% ethyl acetate in hexane as eluting system to afford compound 34 (8.2 g, 73%) as a pale yellow liquid. $^1$H NMR (400 MHz, CDCl$_3$): δ=4.22-4.19 (m, 4H), 3.60-3.58 (m, 1H), 2.99 (s, 6H), 1.75-1.69 (m, 4H), 1.38-1.28 (m, 28H), 0.86 (s, 9H), 0.02 (s, 6H).

Compound 35: To a solution of compound 34 (8.2 g, 0.0146 mol) in 400 mL dry ether was added MgBr$_2$.Et$_2$O (22.74 g, 0.08817 mol) in portions at 0° C. under a nitrogen atmosphere. After complete addition, the reaction mixture was heated to reflux for 28 hours. After completion of reaction, inorganic material formed in the reaction was removed by filtration. The filtrate was evaporated and the resulting crude compound was purified on 60-120 mesh silica gel column using 0-3% ethyl acetate in hexanes as eluting system to afford compound 35 (6.6 g, 85%) as a colorless liquid. $^1$H NMR (400 MHz, CDCl$_3$): δ=3.61-3.58 (m, 1H), 3.41-3.37 (t, 4H, J=6.8 Hz), 1.87-1.80 (m, 4H), 1.42-1.25 (m, 24H), 0.87 (s, 9H), 0.012 (s, 6H).

Compound 36: A solution of ethynyl trimethyl silane (5.3 mL, 0.0378 mol) in 60 mL dry THF was cooled to −78° C. and 1.4 M n-BuLi (23 mL, 0.03405 mol) in hexane was added slowly under an inert atmosphere. The reaction was stirred for 10 minutes, then HMPA (2.3 g, 0.01324 mol) was added and the resulting mixture was then stirred for 2 hours at 0° C., then cooled to −78° C. To this a solution of compound 35 (5 g, 0.0094 mol) in 60 mL dry THF was added slowly and after complete addition, the reaction was warmed to room temperature and maintained for 18 hours. The reaction progress was monitored by $^1$H NMR. After completion, the reaction mixture was cooled to 0° C. and quenched by careful addition of saturated NH$_4$Cl solution (50 mL) followed by water (200 mL). The aqueous phase was extracted with hexane (3×250 mL). The organic layer was dried and solvent removed under vacuum to afford compound 36 (5 g, 94%), which was used without further purification. $^1$H NMR (400 MHz, CDCl$_3$): δ=3.62-3.56 (m, 1H), 2.21-2.17 (m, 4H), 1.49-1.47 (m, 4H), 1.37-1.26 (m, 24H), 0.87 (s, 9H), 0.13 (s, 18H), 0.021 (s, 6H).

Compound 37: To a stirred solution of compound 36 (5 g, 0.0088 mol) in 50 mL methanol, was added K$_2$CO$_3$ (6.1 g, 0.044 mol) in one portion, and the resulting mixture was stirred for 18 hours at ambient temperature. Volatilities were then removed on a rotary evaporator and the crude mixture was diluted with 100 mL water and extracted with hexane (3×100 mL). The organic layer was dried over Na$_2$SO$_4$ and evaporated under vacuum to afford compound 37 (3.5 g, 97%) which was used which was used without further purification. $^1$H NMR (400 MHz, CDCl$_3$): δ=3.60-3.58 (m, 1H), 2.19-2.14 (m, 4H), 1.93-1.92 (m, 2H), 1.54-1.49 (m, 4H), 1.37-1.27 (m, 24H), 0.87 (s, 9H), 0.02 (s, 6H).

Compound 39: Compound 37 (2.5 g, 0.00598 mol) was dissolved in 25 mL dry THF and cooled to −40° C. n-BuLi (1.4 M in hexane 12.9 mL, 0.01794 mol) was added slowly, followed, after a 10 minute interval, by slow addition of HMPA (25 mL). The resulting mixture was maintained for 30 minutes −40° C. under a nitrogen atmosphere. A solution of compound 38 (3.5 g, 1.01196 mol) in 25 mL dry THF was then added drop wise to the cooled reaction mixture. The resulting mixture was warmed to room temperature over 2 hours, then stirred at room temperature for 18 hours. The mixture was then quenched by adding saturated NH$_4$Cl solution (~50 mL) and the product was extracted with ethyl acetate (3×50 mL). The solvent was removed on a rotary evaporator and the resulting crude product was purified by (100-200 mesh) silica gel column using 0-3% ethyl acetate in dichloromethane as eluting system to afford compound 39 (0.9 g, 18%) as a yellow oil. $^1$H NMR (400 MHz, CDCl$_3$): δ=4.56-4.55 (m, 2H), 3.87-3.83 (m, 2H), 3.74-3.68 (m, 2H), 3.59-3.57 (m, 1H), 3.49-3.46 (m, 2H), 3.39-3.33 (m, 2H), 2.13-2.10 (m, 8H), 1.87-1.75 (m, 2H), 1.74-1.66 (m, 2H), 1.57-1.42 (m, 20H), 1.40-1.19 (m, 40H), 0.87 (s, 9H), 0.02 (s, 6H).

Compound 40: To a solution of compound 39 (504 mg, 0.598 mmol) in 10 mL dry ether was added MgBr$_2$Et$_2$O (926 mg, 3.59 mmol). The reaction mixture was stirred for 14 hours, then quenched by adding saturated NaHCO$_3$ aqueous solution. The product was extracted with CH$_2$Cl$_2$. The organic layer was dried over Na$_2$SO$_4$, filtered and concentrated. The crude product was purified by silica gel column chromatography to afford compound 40 (307 mg, 0.455 mmol, 76%, R$_f$=0.36 developed with hexane:EtOAc=2:1). $^1$H NMR (400 MHz, CDCl$_3$) δ 3.59-3.66 (m, 5H), 2.14 (t, J=6.6 Hz, 8H), 1.21-1.59 (m, 52H), 0.88 (s, 9H), 0.03 (s, 6H).

Compound 41: To a stirred solution of 40 (180 mg, 0.267 mmol) in anhydrous DMF (5 mL) was added pyridinium dichromate (603 mg, 1.60 mmol). The reaction mixture was stirred for 48 hours. After dilution with water (20 mL), the mixture was extracted with Et$_2$O (3×40 mL). The organic layer was dried over Na$_2$SO$_4$, filtered and concentrated. The crude product was purified by silica gel column chromatography to afford compound 41 (53 mg, 0.075 mmol, 28%, $R_f$=0.25 developed with $CH_2Cl_2$:MeOH:AcOH=95:4.5:0.5). Molecular weight for $C_{43}H_{77}O_5Si$ (M−H)⁻ Calc. 701.5540, Found 701.5. This compound can be synthesized by TEMPO oxidation.

Compound 42: A procedure analogous to that described for compound 19 afforded compound 42 (23 mg 0.032 mmol, 21% from compound 40). ¹H NMR (400 MHz, $CDCl_3$) δ 3.67 (s, 6H), 3.59-3.62 (m, 1H), 2.30 (t, J=7.5 Hz, 4H), 2.13 (t, J=6.8 Hz, 8H), 1.27-1.64 (m, 48H), 0.88 (s, 9H), 0.03 (s, 6H).

Reduction using P-2 nickel conditions can give compound 43 and subsequent deprotection by TBAF can afford compound 8.

Example 5: Alternate Synthesis for Compound 8

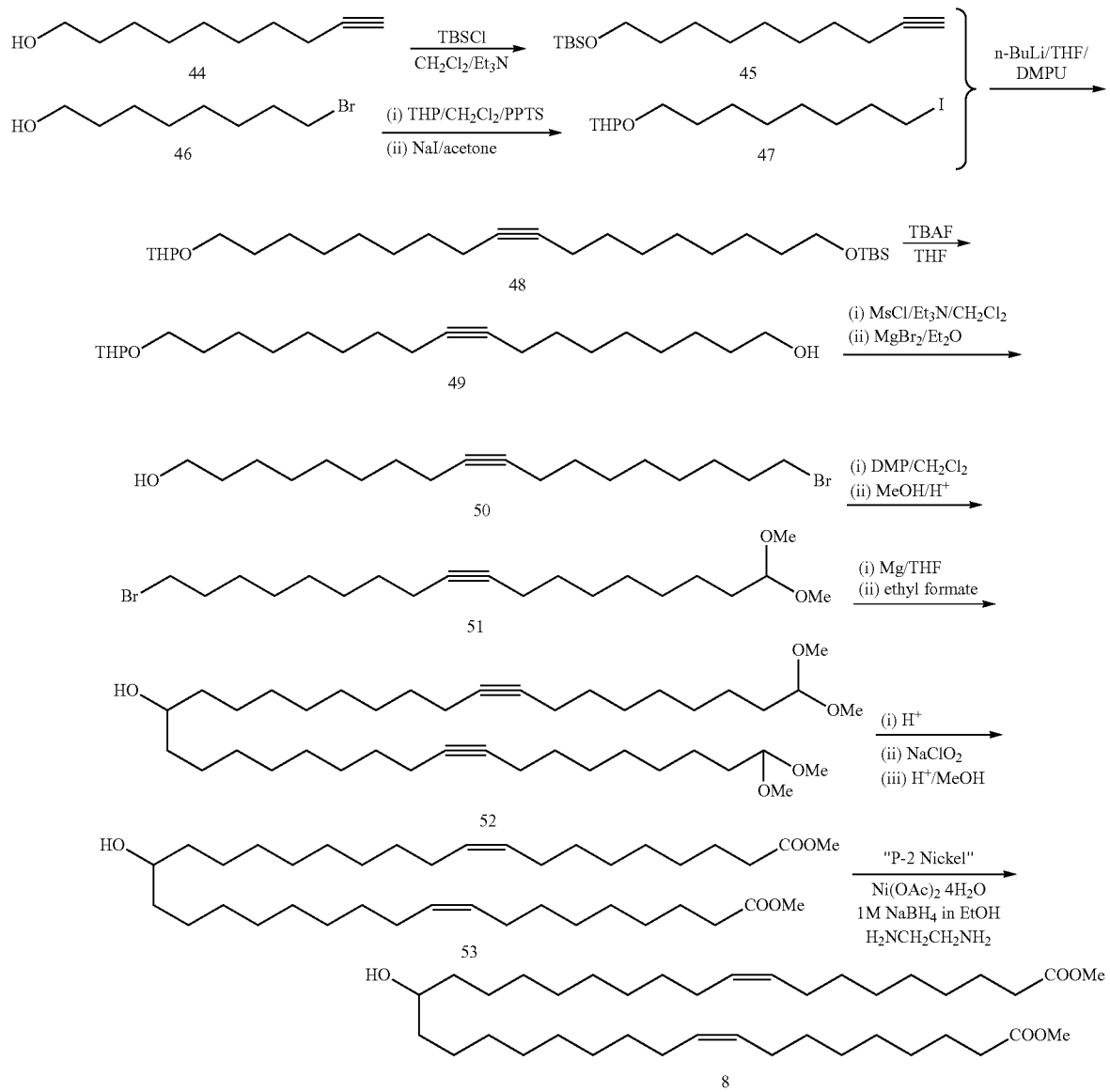

Compound 8 can be synthesized as shown in Scheme 5. The bromide 51 can be converted to its Grignard reagent then coupled with ethyl formate to afford compound 52. Subsequent acid treatment, oxidation, and reduction can give compound 8.

Example 6: Alternate Synthesis for Compound 8

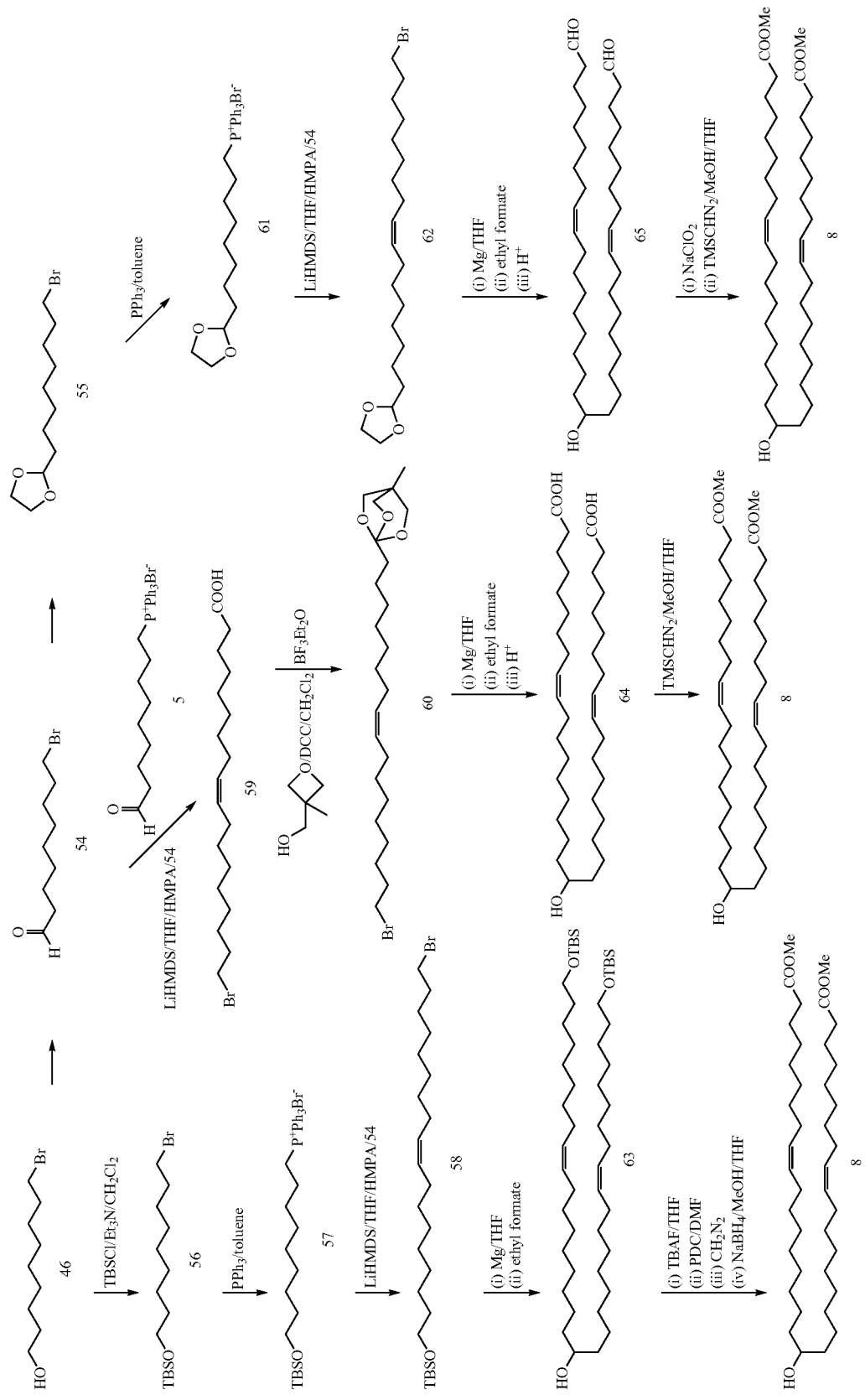

Compound 8 can be synthesized as shown in Scheme 6. Either bromides of compound 58, 60, or 62 can be reacted with ethyl formate to generate terminal-functionalized di-olefin chain. Compound 8 can then be prepared from the diolefin chain compounds using standard chemical reactions.

Example 7: General Synthetic Scheme for Terminal Ester Lipids

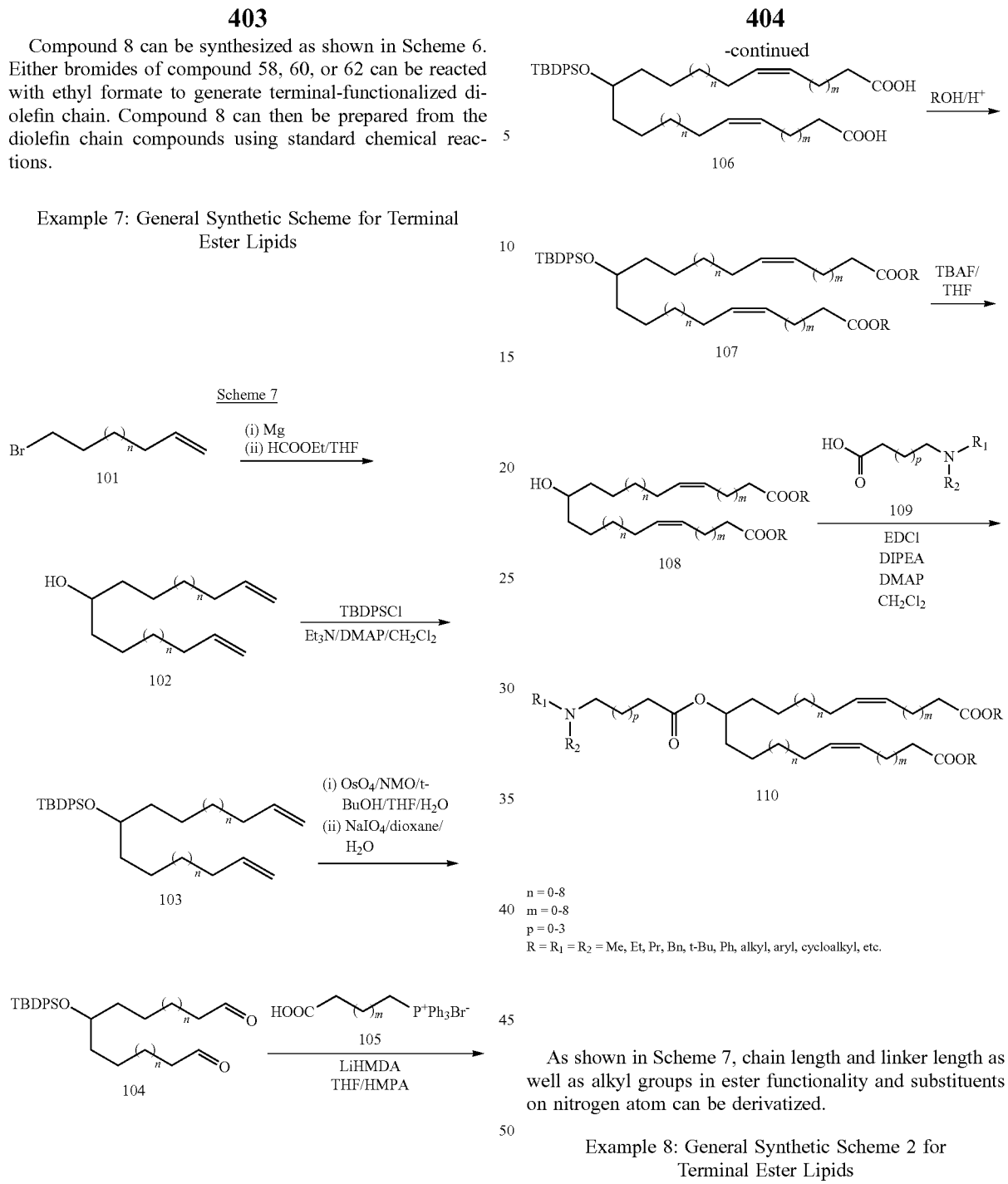

As shown in Scheme 7, chain length and linker length as well as alkyl groups in ester functionality and substituents on nitrogen atom can be derivatized.

Example 8: General Synthetic Scheme 2 for Terminal Ester Lipids

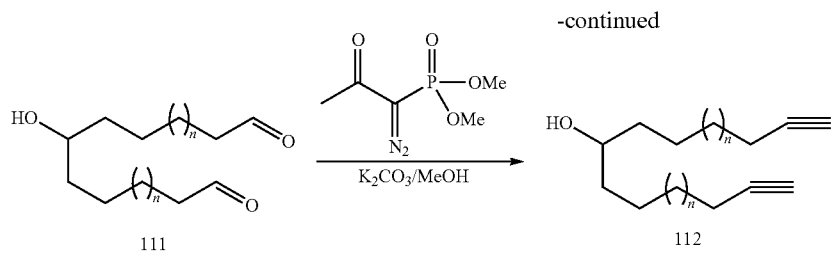
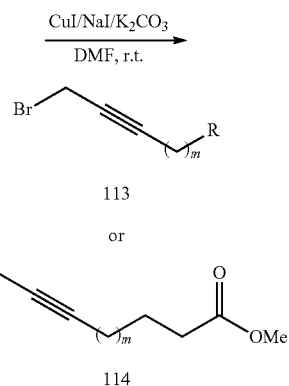
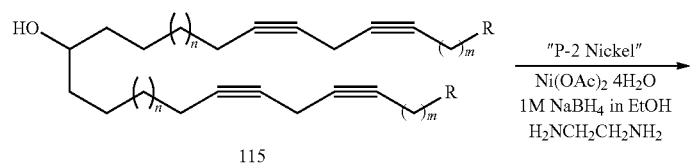
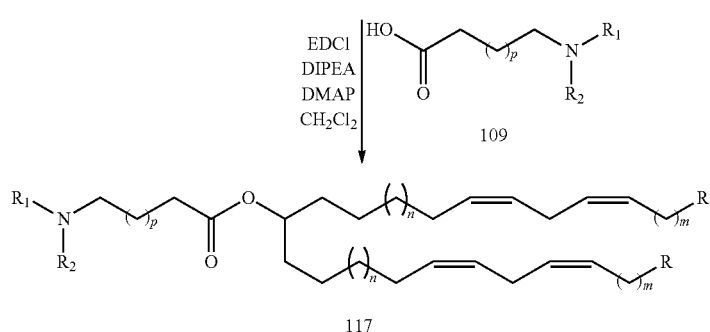

n = 0-8
m = 0-8
p = 0-3
R = Me, Et, Pr, Bn, t-Bu, Ph, alkyl, aryl, cycloalkyl, and alkyl esters, etc.
$R_1 = R_2$ = Me, Et, Pr, Bn, t-Bu, Ph, alkyl, aryl, cycloalkyl As shown in Scheme 8, copper-mediated coupling affords di-yne containing lipid chain with terminal functional groups, which can be easily reduced to generate di-ene containing lipid chains. The length of linker and lipid chain as well as functional substituent groups (R, $R_1$, $R_2$) can be derivatized.

Example 9: Synthesis of Terminal Benzyl Ester Lipid

Scheme 9

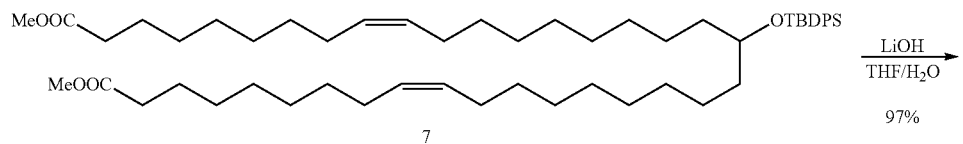

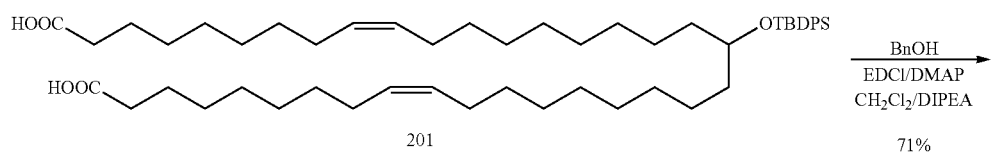

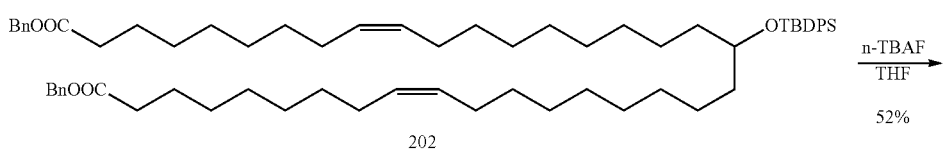

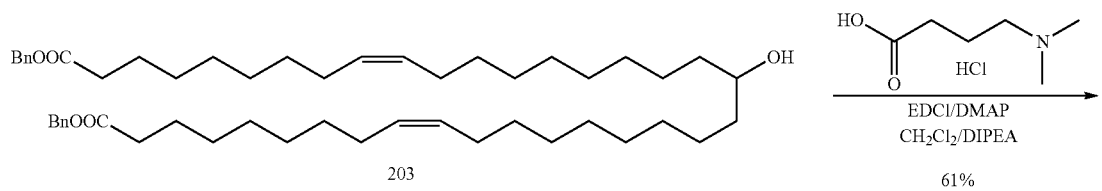

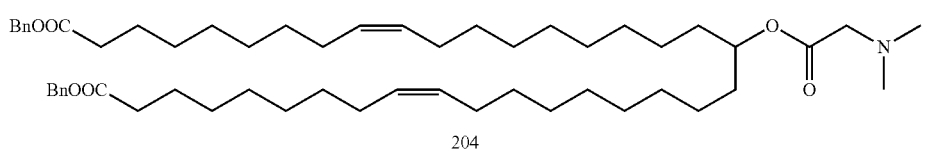

Compound 201: Compound 7 (1.30 g, 1.51 mmol) was treated with lithium hydroxide monohydrate (317 mg, 7.55 mmol) in THF (25 mL) and H$_2$O (5 mL) for 12 h. Amberlite IR-120 (plus) ion exchange resin was added then stirred for 10 minutes. The resulting clear solution was filtered, washed with THF/H$_2$O and evaporated. Co-evaporation with toluene gave the compound 201 (1.22 g, 1.47 mmol, 97%). Molecular weight for C$_{53}$H$_{85}$O$_5$Si (M−H)$^-$ Calc. 829.6166, Found 829.5.

Compound 202: A procedure analogous to that described for compound 9 was followed with benzylalcohol and 201 (101 mg, 0.121 mmol) to afford compound 202 (87 mg, 0.0860 mmol, 71%). $^1$H NMR (400 MHz, CDCl$_3$) δ 7.68-7.66 (m, 4H), 7.42-7.30 (m, 16H), 5.38-5.30 (m, 4H), 5.11 (s, 4H), 3.71-3.68 (m, 1H), 2.35 (t, J=7.6 Hz, 4H), 2.04-1.97 (m, 8H), 1.66-1.62 (m, 4H), 1.40-1.07 (m, 44H), 1.04 (s, 9H).

Compound 203: A procedure analogous to that described for compound 8 was followed with 202 (342 mg, 0.338 mmol) to afford compound 202 (136 mg, 0.176 mmol, 52%). H NMR (400 MHz, CDCl$_3$) δ 7.38-7.30 (m, 10H), 5.38-5.30 (m, 4H), 5.11 (s, 4H), 3.57 (brs, 1H), 2.35 (t, J=7.6 Hz, 4H), 2.01-1.98 (m, 8H), 1.66-1.60 (m, 4H), 1.45-1.25 (m, 44H).

Compound 204: A procedure analogous to that described for compound 9 was followed with 203 (133 mg, 0.172 mmol) to afford compound 204 (93 mg, 0.105 mmol, 61%). H NMR (400 MHz, CDCl$_3$) δ 7.38-7.26 (m, 10H), 5.38-5.30 (m, 4H), 5.11 (s, 4H), 4.88-4.83 (m, 1H), 2.37-2.27 (m, 8H), 2.22 (s, 6H), 2.03-1.97 (m, 8H), 1.81-1.26 (m, 50H).

Example 10: Synthesis of Terminal t-Butyl Ester Lipid and the Derivatives

Compound 206: A procedure analogous to that described for compound 12 was followed with 205 (3.80 g, 0.7.61 mmol) and 4 (1.75 g, 3.17 mmol) to afford compound 206 (2.00 g, 2.12 mmol, 67%). $^1$H NMR (400 MHz, CDCl$_3$) δ 7.68-7.66 (m, 4H), 7.42-7.33 (m, 6H), 5.39-5.31 (m, 4H), 3.71-3.68 (m, 1H), 2.20 (t, J=7.6 Hz, 4H), 2.01-1.98 (m, 8H), 1.59-1.55 (m, 4H), 1.44 (s, 18H), 1.41-1.11 (m, 44H), 1.04 (s, 9H).

Compound 207: A procedure analogous to that described for compound 8 was followed with 206 (265 mg, 0.281 mmol) to afford compound 207 (161 mg, 0.228 mmol, 81%). $^1$H NMR (400 MHz, CDCl$_3$) δ 5.38-5.30 (m, 4H), 3.58 (brs, 1H), 2.20 (t, J=7.4 Hz, 4H), 2.01-1.98 (m, 8H), 1.59-1.55 (m, 4H), 1.44 (s, 18H), 1.35-1.26 (m, 44H).

Compound 208: A procedure analogous to that described for compound 9 was followed with 207 (158 mg, 0.224

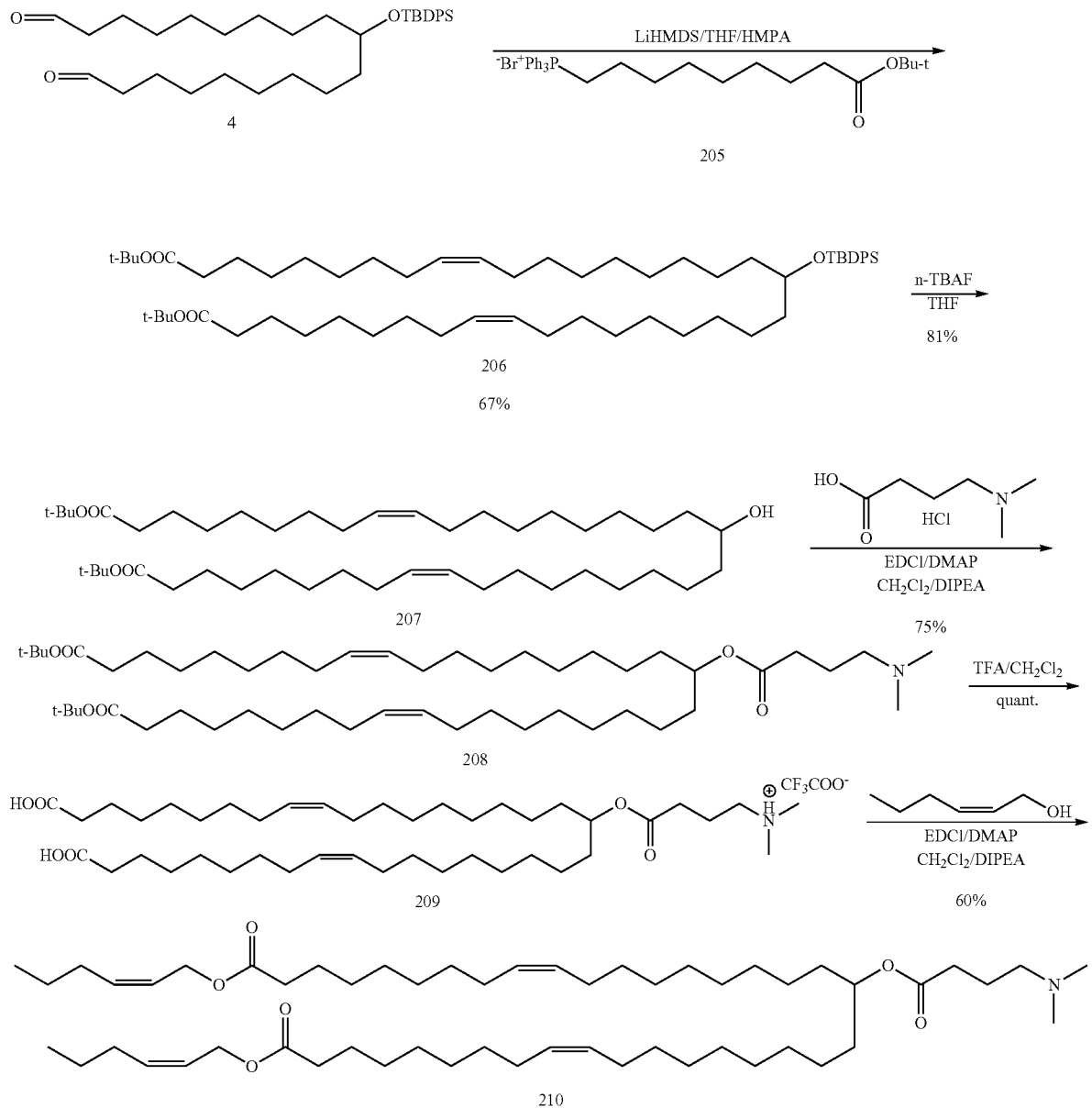

Scheme 10 mmol) to afford compound 208 (138 mg, 0.169 mmol, 75%). Molecular weight for $C_{51}H_{96}NO_6$ $(M+H)^+$ Calc. 818.7238, Found 818.7.

Compound 209: Compound 208 (148 mg, 0.181 mmol) was treated with TFA (1.5 mL) in $CH_2Cl_2$ (6 mL) for 2.5 h. After evaporation and co-evaporation with toluene gave the compound 209 (154 mg, quant.). Molecular weight for $C_{43}H_{80}NO_6$ $(M+H)^+$ Calc. 706.5980, Found 706.5.

Compound 210: A procedure analogous to that described for compound 9 was followed with 209 (0.061 mmol) and cis-2-Hexen-1-ol (18.3 mg, 0.183 mmol) to afford compound 210 (32 mg, 0.0368 mmol, 60%). Molecular weight for $C_{55}H_{100}NO_6$ $(M+H)^+$ Calc. 870.7551, Found 870.5.

Example 11: Synthesis of Internal Ester/Amide Lipids-1

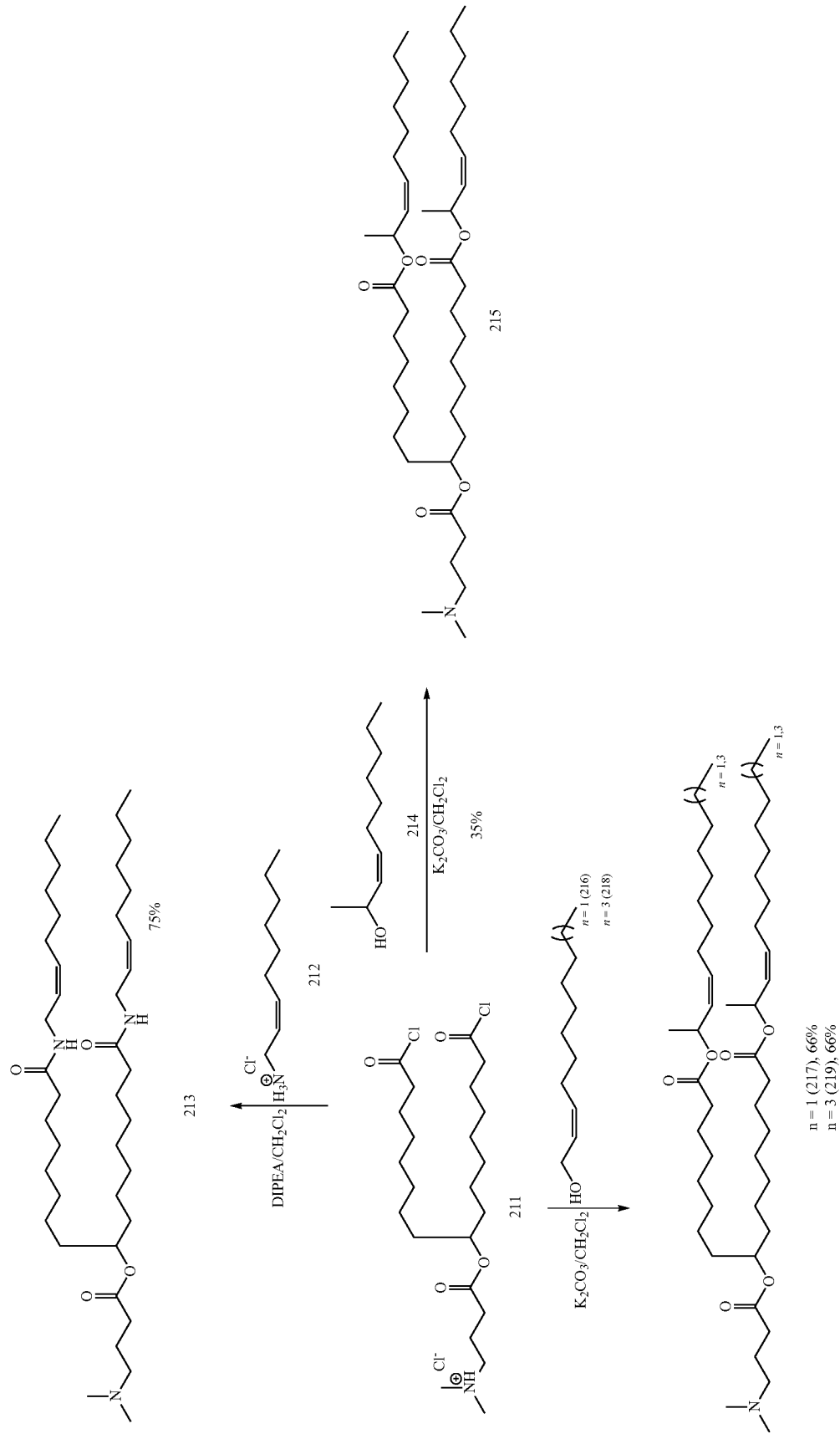
Scheme 11

Compound 213: Compound 211 (503 mg, 1.0 mmol) was treated with 212 (533 mg, 3.0 mmol) in $CH_2Cl_2$ (35 mL) and DIPEA (1.74 mL, 10 mmol) for 14 h. Aqueous work-up then column chromatography gave compound 213 (506 mg, 0.748 mmol, 75%). Molecular weight for $C_{41}H_{78}N_3O_4$ $(M+H)^+$ Calc. 676.5992, Found 676.4.

Compound 215: Compound 211 (503 mg, 1.0 mmol) was treated with 214 (469 mg, 3.0 mmol) and $K_2CO_3$ (1.38 g, 10 mmol) in $CH_2Cl_2$ (35 mL) for 14 h. Aqueous work-up then column chromatography gave compound 215 (244 mg, 0.346 mmol, 35%). Molecular weight for $C_{43}H_{80}NO_6$ $(M+H)^+$ Calc. 706.5986, Found 706.4.

Compound 217: Compound 211 (425 mg, 0.845 mmol) was treated with 216 (525 mg, 3.08 mmol) and $K_2CO_3$ (1.17 g, 8.45 mmol) in $CH_2Cl_2$ (35 mL) for 14 h. Aqueous work-up then column chromatography gave compound 217 (407 mg, 0.554 mmol, 66%). Molecular weight for $C_{45}H_{84}NO_6$ $(M+H)^+$ Calc. 734.6299, Found 734.4.

Compound 219: Compound 211 (503 mg, 1.0 mmol) was treated with 218 (595 mg, 3.0 mmol) and $K_2CO_3$ (1.38 g, 10 mmol) in $CH_2Cl_2$ (35 mL) for 14 h. Aqueous work-up then column chromatography gave compound 219 (519 mg, 0.657 mmol, 66%). Molecular weight for $C_{49}H_{92}NO_6$ $(M+H)^+$ Calc. 790.6925, Found 790.7.

Example 12: Synthesis of Internal Ester Lipid-223

Compound 221: A procedure analogous to that described for compound 9 was followed with 220 (390 mg, 1.93 mmol) and 218 (765 mg, 3.86 mmol) to afford compound 221 (878 mg, 1.56 mmol, 81%). $^1$H NMR (400 MHz, $CDCl_3$) δ 5.67-5.61 (m, 2H), 5.54-5.48 (m, 2H), 4.62 (d, J=6.8 Hz, 4H), 2.47 (t, J=7.2 Hz, 4H), 2.33 (t, J=7.2 Hz, 4H), 2.12-2.06 (m, 4H), 1.93-1.86 (m, 4H), 1.38-1.26 (m, 32H), 0.88 (t, J=6.8 Hz, 6H).

Compound 222: Compound 221 (318 mg, 0.565 mmol) was treated with $NaBH(OAc)_3$ (360 mg, 1.70 mmol) in $CH_2Cl_2$ (5 mL) and AcOH (0.2 mL) for 16 h. After evaporation, column chromatography gave compound 222 (141 mg, 0.250 mmol, 44%). Molecular weight for $C_{35}H_{65}O_5$ $(M+H)^+$ Calc. 565.4832, Found 565.4.

Compound 223: A procedure analogous to that described for compound 9 was followed with 222 (137 mg, 0.243 mmol) to afford compound 223 (137 mg, 0.202 mmol, 83%). Molecular weight for $C_{41}H_{76}NO_6$ $(M+H)^+$ Calc. 678.5673, Found 678.5.

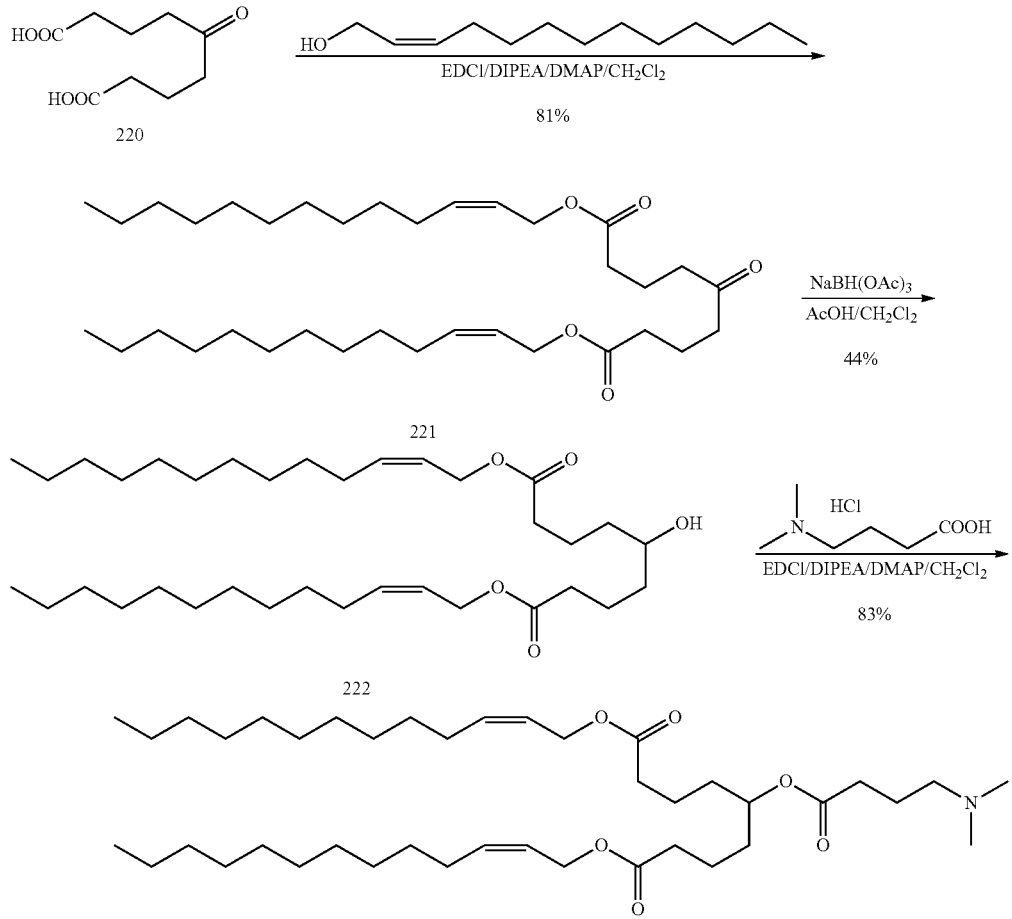

Example 13: Synthesis of Internal Ester Lipid-227

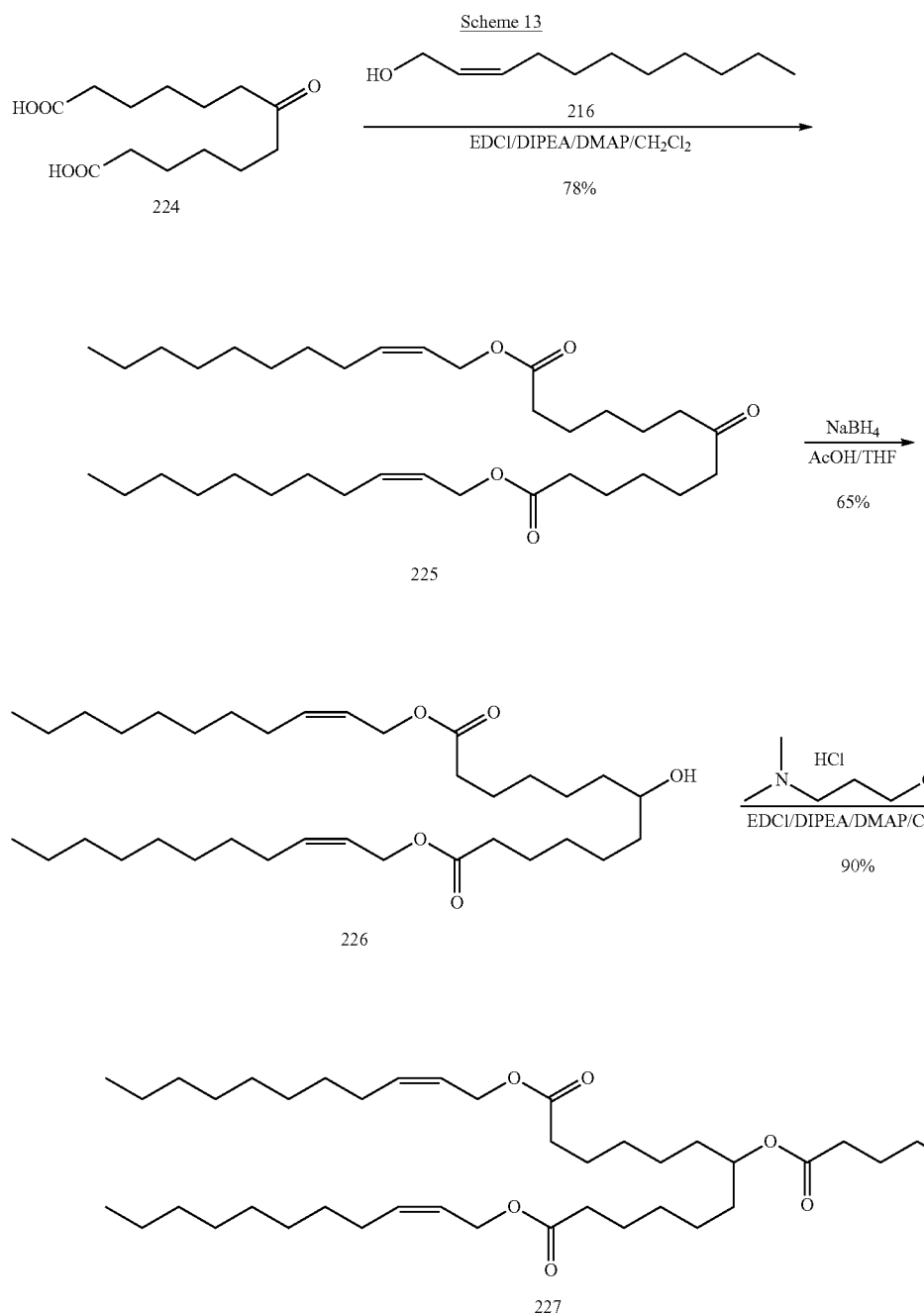

Compound 225: A procedure analogous to that described for compound 9 was followed with 224 (200 mg, 0.774 mmol) and 216 (264 mg, 1.55 mmol) to afford compound 225 (341 mg, 0.606 mmol, 78%). Molecular weight for $C_{35}H_{62}NaO_5$ (M+Na)$^+$ Calc. 585.4495, Found 585.5.

Compound 226: Compound 225 (283 mg, 0.503 mmol) was treated with NaBH$_4$ (57 mg, 1.51 mmol) in THF (5 mL) and AcOH (0.2 mL) for 8 h. After evaporation, column chromatography gave compound 226 (185 mg, 0.328 mmol, 65%). Molecular weight for $C_{35}H_{64}NaO_5$ (M+Na)$^+$ Calc. 587.4651, Found 587.3.

Compound 227: A procedure analogous to that described for compound 9 was followed with 226 (230 mg, 0.407 mmol) to afford compound 227 (248 mg, 0.366 mmol, 90%). Molecular weight for $C_{41}H_{76}NO_6$ (M+H)$^+$ Calc. 678.5673, Found 678.5.

Example 14: Synthesis of Terminal Ester Lipid with Linoleyl Chain-232

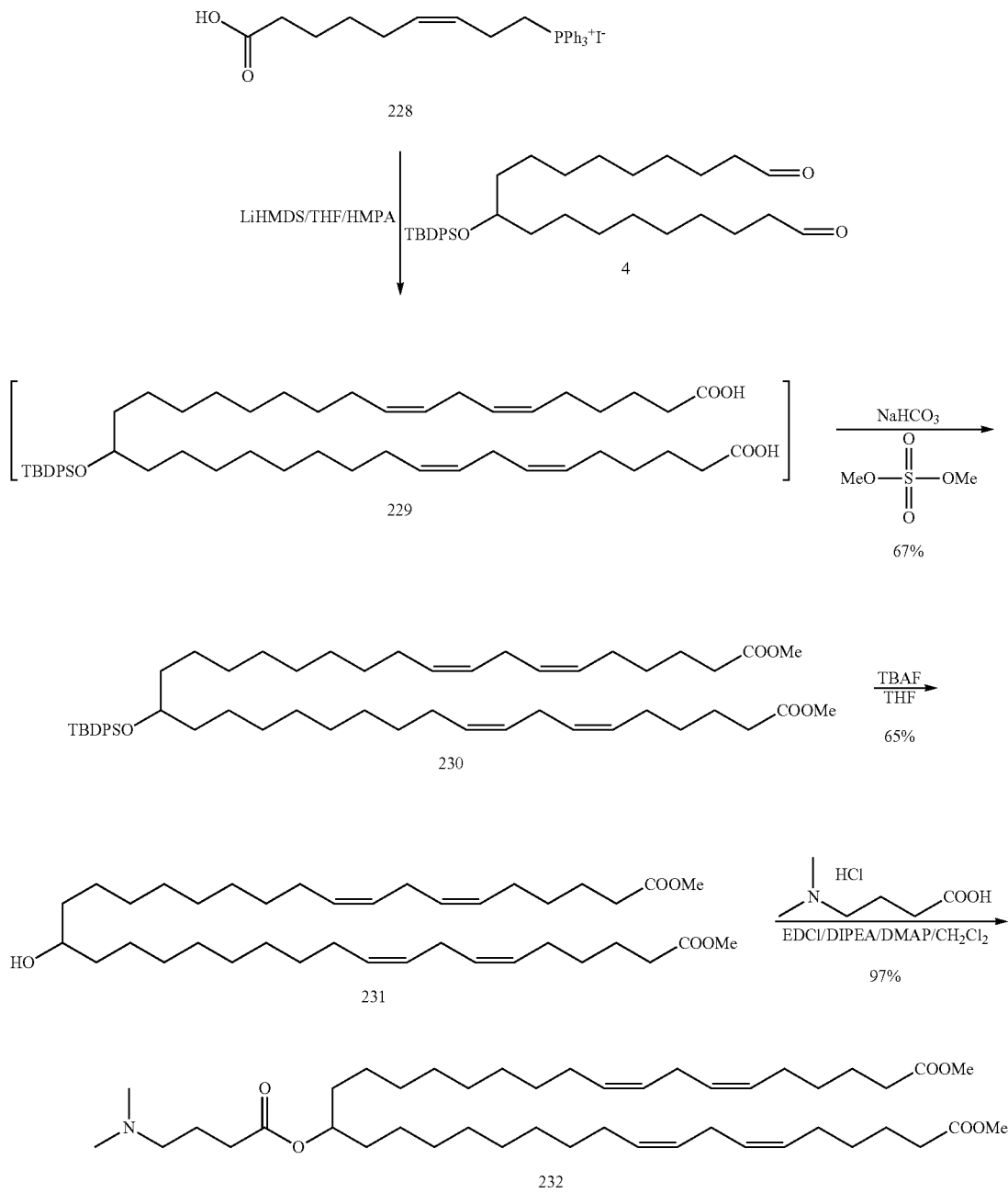

Compound 230: A procedure analogous to that described for compound 7 was followed with 228 (3.27 g, 6.0 mmol) and 4 (1.27 g, 2.30 mmol) to afford compound 230 (1.31 g, 1.53 mmol, 67%). $^1$H NMR (400 MHz, CDCl$_3$) δ 7.68-7.66 (m, 4H), 7.42-7.33 (m, 6H), 5.42-5.29 (m, 8H), 3.71-3.68 (m, 1H), 3.66 (s, 6H), 2.77 (t, J=5.8 Hz, 4H), 2.33-2.28 (m, 4H), 2.11-2.01 (m, 8H), 1.69-1.60 (m, 4H), 1.43-1.10 (m, 32H), 1.04 (s, 9H).

Compound 231: A procedure analogous to that described for compound 8 was followed with 230 (1.30 g, 1.52 mmol) to afford compound 231 (611 mg, 0.990 mmol, 65%). $^1$H NMR (400 MHz, CDCl$_3$) δ 5.41-5.29 (m, 8H), 3.67 (s, 6H), 3.58 (brs, 1H), 2.77 (t, J=5.8 Hz, 4H), 2.32 (t, J=7.4 Hz, 4H), 2.10-2.00 (m, 8H), 1.69-1.60 (m, 4H), 1.43-1.29 (m, 32H).

Compound 232: A procedure analogous to that described for compound 9 was followed with 231 (520 mg, 0.843 mmol) to afford compound 232 (600 mg, 0.822 mmol, 97%). Molecular weight for $C_{45}H_{80}NO_6$ (M+H)$^+$ Calc. 730.5986, Found 730.5.

Example 15: Synthesis of Terminal Ester Lipid with Linoleyl Chain-232

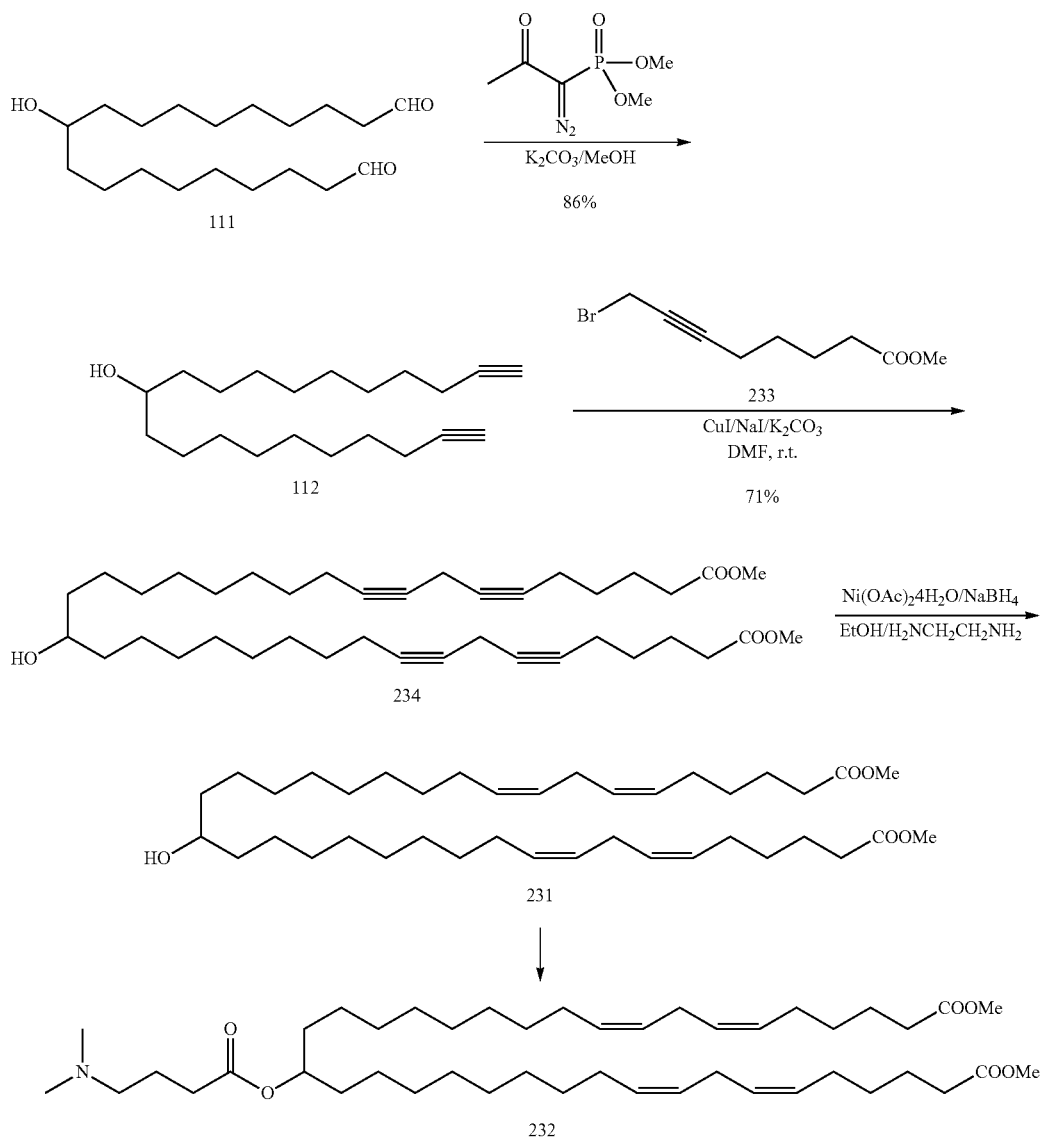

Compound 231 was also synthesized as shown Scheme 15.

Compound 112: Compound 111 (840 mg, 2.69 mmol) was treated with dimethyl (1-diazo-2-oxopropyl)phosphonate (0.970 mL, 6.46 mmol) and K$_2$CO$_3$ (1.49 g, 10.8 mmol) in MeOH (40 mL) for 6 h. Aqueous work-up then column chromatography gave compound 112 (700 mg, 2.30 mmol, 86%). $^1$H NMR (400 MHz, CDCl$_3$) δ 3.58 (brs, 1H), 2.18 (td, J=7.1, 2.6 Hz, 4H), 1.94 (t, J=2.6 Hz, 2H), 1.56-1.25 (m, 28H).

Compound 234: Compound 112 (207 mg, 0.680 mmol) was treated with 233 (316 mg, 1.36 mmol), K$_2$CO$_3$ (282 mg, 2.04 mmol), NaI (408 mg, 2.72 mmol) and CuI (518 mg, 2.72 mmol) in DMF (3.5 mL) for 18 h. Aqueous work-up then column chromatography gave compound 234 (292 mg, 0.480 mmol, 71%). Molecular weight for C$_{39}$H$_{61}$O$_5$(M+H)$^+$ Calc. 609.4519, Found 609.5.

Compound 231: To a stirred solution of nickel(II) acetate tetrahydrate (533 mg, 2.14 mmol) in EtOH (28.5 mL), 1 M solution of NaBH$_4$ in EtOH (2.14 mL) was added at room temperature. After 30 min, ethylenediamine (0.574 mL, 8.57 mmol) and a solution of 234 (290 mg, 0.476 mmol) in EtOH (3 mL) was added then stirred for 1 h. The reaction mixture was filtered through Celite and evaporated. Aqueous work-up then column chromatography gave compound 231 (219 mg, 0.355 mmol, 75%). Molecular weight for C$_{39}$H$_{69}$O$_5$ (M+H)$^+$ Calc. 617.5145, Found 617.3.

Example 16: Synthesis of Internal Oxime Lipid-238

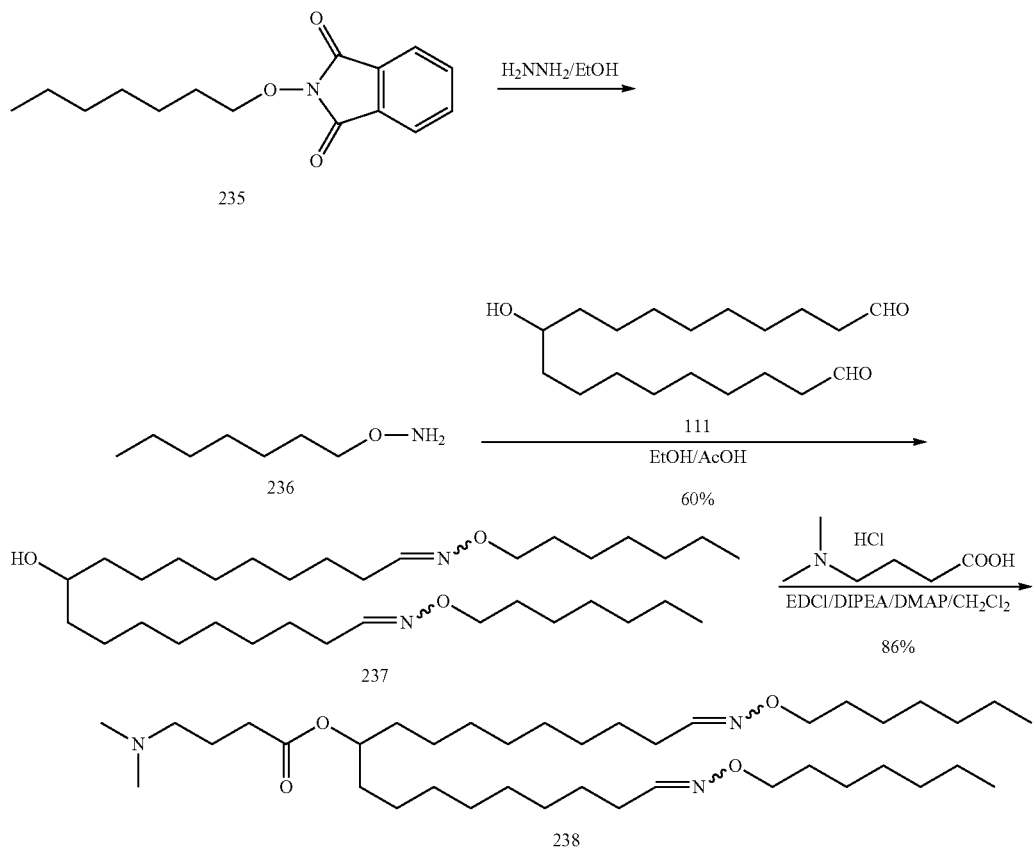

Compound 237: Compound 235 (465 mg, 1.78 mmol) was treated with hydrazine monohydrate (64-65%, 0.135 mL, 1.78 mmol) in EtOH (15 mL) for 4 h. After filtration then evaporation, the crude was re-suspended in EtOH (5 mL). To this solution was added compound 111 (160 mg, 0.512 mmol) and AcOH (a few drops). Aqueous work-up then column chromatography gave compound 237 (165 mg, 0.306 mmol, 60%). Molecular weight for $C_{33}H_{67}N_2O_3$ $(M+H)^+$ Calc. 539.5152, Found 539.3.

Compound 238: A procedure analogous to that described for compound 9 was followed with 237 (162 mg, 0.301 mmol) to afford compound 238 (168 mg, 0.258 mmol, 86%). Molecular weight for $C_{39}H_{78}N_3O_4$ $(M+H)^+$ Calc. 652.5992, Found 652.4.

Example 17

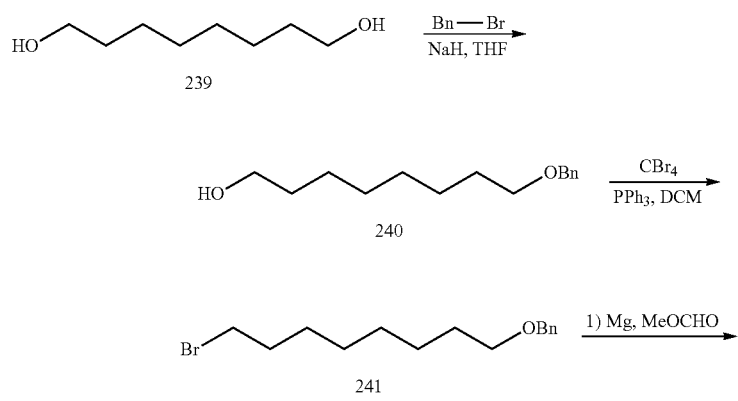

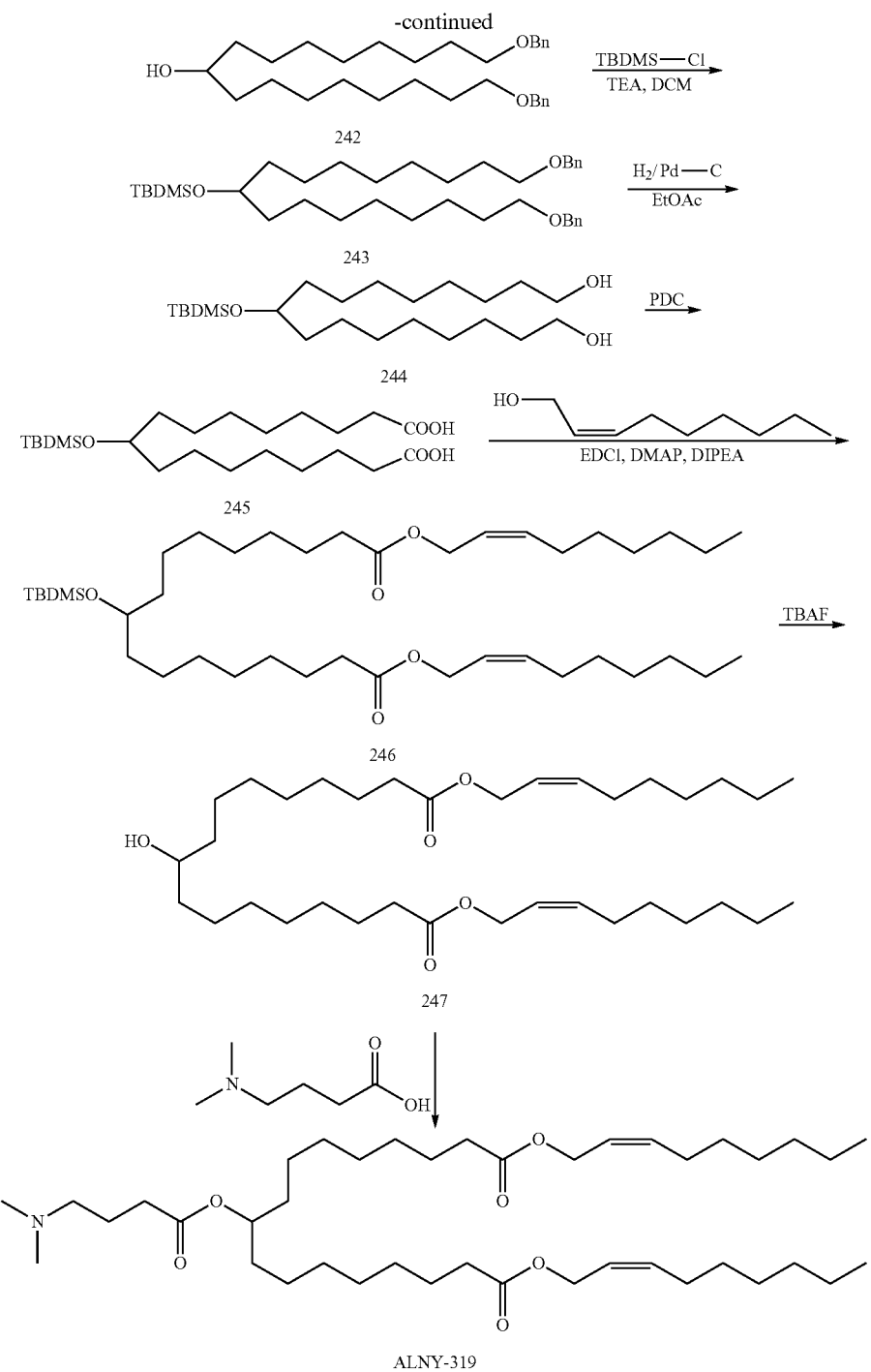

ALNY-319

8-benzyloxy-octan-1-ol (240): To a stirred suspension of NaH (60% in oil, 82 g, 1.7096 mol) in 500 mL anhydrous DMF, a solution of compound 239 (250 g, 1.7096 mol) in 1.5 L DMF was added slowly using a dropping funnel at 0° C. The reaction mixture was stirred for 30 minutes, then benzyl bromide (208.86 mL, 1.7096 mol) was added slowly under a nitrogen atmosphere. The reaction was then warmed to ambient temperature and stirred for 10 hours. After completion of reaction, the mixture was quenched with crushed ice (~2 kg) and extracted with ethyl acetate (2×1 L). The organic layer washed with water (1 L) to remove unwanted DMF, dried over $Na_2SO_4$ and evaporated to dryness under vacuum. The crude compound was purified on 60-120 silica gel, eluted with 0-5% MeOH in DCM to afford compound 240 (220 g, 54%) as pale yellow liquid. $H^1$ NMR (400 MHz, $CDCl_3$): δ=7.33-7.24 (m, 5H), 4.49 (s, 2H), 3.63-3.60 (m, 2H), 3.47-3.43 (m, 2H), 1.63-1.51 (m, 4H), 1.39-1.23 (m, 8H).

(8-bromo-octyloxymethyl)-benzene (241): Compound 240 (133 g, 0.5635 mol) was dissolved in 1.5 L of DCM, $CBr_4$ (280.35 g, 0.8456 mol) was added to this stirring solution and the reaction mixture was cooled to 0° C. under an inert atmosphere. PPh$_3$ (251.03 g, 0.9571 mol) was then added in portions maintaining the temperature below 20° C. and after complete addition, the reaction mixture was stirred for 3 hours at room temperature. After completion of reaction, solid (PPh$_3$O) precipitated out from the reaction mixture was isolated by filtration and the filtrate was diluted with crushed ice (~1.5 kg) and extracted with DCM (3×750 mL). The organic layer was separated, dried over anhydrous Na$_2$SO$_4$ and distilled under vacuum. The resulting crude compound was chromatographed on 60-120 mesh silica gel column using 0-5% ethyl acetate in hexanes as eluting system to afford compound 241 (150 g, 89%) as pale yellow liquid. $^1$H NMR (400 MHz, CDCl$_3$): δ=7.33-7.25 (m, 5H), 4.49 (s, 2H), 3.47-3.41 (m, 2H), 3.41-3.37 (m, 2H), 1.86-1.80 (m, 4H), 1.62-1.56 (m, 2H), 1.42-1.29 (m, 8H).

1, 17-bis-benzyloxy-heptadecan-9-ol (242): To freshly activated Mg turnings (24.08 g, 1.003 mol) was added 200 mL anhydrous THF, followed by the addition of pinch of iodine into the mixture under inert atmosphere. After initiation of the Grignard formation a solution of Compound 241 (150 g, 0.5016 mol) in 1 L of dry THF was added slowly controlling the exothermic reaction. After complete addition, the reaction was heated to reflux for 1 hour, then cooled to room temperature. Methyl formate (60.24 g, 1.0033 mol) was then added slowly and reaction was continued for 2 hours. After completion, the reaction was quenched by slow addition of 10% HCl followed by water (1 L) and extracted with ethyl acetate (3×1 L). The organic layer was taken in 5 litre beaker, diluted with 500 mL of methanol and cooled to 0° C. To this solution excess of NaBH$_4$ (~5 eq) was added in portions to ensure the hydrolysis of formate ester which was not cleaved by addition of HCl. The resulting solution was stirred for an hour and then volatilities were removed under vacuum. The residue was taken in water (1 L) and acidified by 10% HCl solution (PH 4). The product was then extracted with ethyl acetate (3×1 L). The organic phase was then dried and concentrated on rotary evaporator to afford compound 242 (57 g, 24%) as solid. $^1$H NMR (400 MHz, CDCl$_3$): δ=7.35-7.32 (m, 8H), 7.29-7.24 (m, 2H), 4.49 (s, 4H), 3.56 (m, 1H), 3.46-3.43 (m, 4H), 1.63-1.56 (m, 4H), 1.44-1.34 (m, 28H). C$^{13}$ NMR (100 MHz, CDCl$_3$): δ=138.56, 128.21, 127.49, 127.34, 72.72, 71.76, 70.37, 37.37, 29.64, 29.56, 29.47, 29.33, 26.07, 25.54.

[9-benzyloxy-1-(8-benzyloxy-octyl)-nonyloxy]-tert-butyl-dimethyl-silane (243): Compound 242 (56 g, 0.1196 mol) was dissolved in 700 mL of anhydrous THF and cooled to 0° C. TBMS-Cl (36.06 g, 0.2396 mol) was added slowly followed by addition of imidazole (32.55 g, 0.4786 mol) under an inert atmosphere. The reaction was then stirred at room temperature for 18 hours, then quenched with ice (~1 kg). The product was extracted with ethyl acetate (3×500 mL). The organic layer was separated, washed with saturated NaHCO$_3$ solution to remove the acidic impurity, dried over Na$_2$SO$_4$ and evaporated under reduce pressure to obtain crude compound which was purified by silica gel (60-120 mesh) and eluted with 0-10% ethyl acetate hexane to afford (60 g, 82%) of compound 243 as yellowish oil. H NMR (400 MHz, CDCl$_3$): δ=7.33-7.24 (m, 10H), 4.49 (s, 4H), 3.60-3.57 (m, 1H), 3.46-3.43 (m, 4H), 1.61-1.54 (m, 4H), 1.41-1.26 (m, 28H), 0.87 (s, 9H), 0.02 (s, 6H)

9-(tert-butyl-dimethyl-silanyloxy)-heptadecane-1, 17-diol (244): Compound 243 (60 g, 0.1030 mol) was dissolved in 500 mL ethyl acetate and degassed with N$_2$ for 20 min. (10 wt %) Pd on carbon (12 g) was added and reaction was stirred under an atmosphere of hydrogen for 18 hours. After completion, the mixture was filtered through a bed of celite and washed with ethyl acetate. The filtrate was evaporated under vacuum. Compound 244 (19 g, 46%) thus obtained was pure enough to carry out the next reaction. $^1$H NMR (400 MHz, CDCl$_3$): δ=3.64-3.58 (m, 5H), 1.59 (br, 2H), 1.57-1.51 (m, 4H), 1.38-1.22 (m, 28H), 0.87 (s, 9H), 0.02 (s, 6H).

9-(tert-butyl-dimethyl-silanyloxy)-heptadecanedioic acid (245): To a stirred solution of 244 (2 g, 0.0049 mol) in anhydrous DMF (40 mL) was added pyridinium dichromate (2.7 g, 0.0074 mol) at 0° C. under an inert atmosphere. The reaction mixture was then allowed to warm to room temperature over a period of 10-15 minutes and continued for 24 hours. Then, the reaction was diluted with water (100 mL). The aqueous phase was extracted using DCM (3×40 mL). The organic phase was washed with brine (1x 25 mL) and concentrated under vacuum to afford crude acid which was then purified by (100-200 mesh) silica gel column using 0-30% ethyl acetate in hexanes system. Pure product (245) was obtained (0.7 g, 33%) as a pale yellow oil. $^1$H NMR (400 MHz, CDCl$_3$): δ=3.61-3.56 (m, 1H), 2.35-2.32 (m, 4H), 1.64-1.59 (m, 4H), 1.40-1.19 (m, 24H), 0.86 (s, 9H), 0.017 (s, 6H); LC-MS [M+H]—431.00; HPLC (ELSD) purity—96.94%

Di((Z)-non-2-en-1-yl) 9-((tert-butyldimethylsilyl)oxy) heptadecanedioate (246): The diacid 245 (0.42 g, 0.97 mmol) was dissolved in 20 mL of dichloromethane and to it cis-2-nonen-1-ol (0.35 g, 2.44 mmol) was added followed by Hunig's base (0.68 g, 4.9 mmol) and DMAP (12 mg). To this mixture EDCI (0.47 g, 2.44 mmol) was added and the reaction mixture was stirred at room temperature overnight. The reaction mixture was then diluted with CH$_2$Cl$_2$ (40 mL) and washed with saturated NaHCO$_3$ (50 mL), water (60 mL) and brine (60 mL). The combined organic layers were dried over anhydrous Na$_2$SO$_4$ and solvents were removed in vacuo. The crude product thus obtained was purified by Combiflash Rf purification system (40 g silicagel, 0-10% MeOH in CH$_2$Cl$_2$) to afford the pure product 246 (0.35 g, 53%) as a colorless oil. $^1$H NMR (400 MHz, CDCl$_3$): δ $^1$H NMR (400 MHz, CDCl$_3$) δ 5.64 (dt, J=10.9, 7.4 Hz, 2H), 5.58-5.43 (m, 2H), 4.61 (d, J=6.8 Hz, 4H), 3.71-3.48 (m, 1H), 2.30 (t, J=7.6 Hz, 4H), 2.20-1.98 (m, 4H), 1.71-1.53 (m, 4H), 1.31 (ddd, J=8.3, 7.0, 3.7 Hz, 34H), 1.07-0.68 (m, 14H), 0.02 (s, 5H). $^{13}$C NMR (101 MHz, CDCl$_3$) δ 178.18, 139.81, 127.78, 81.73, 81.42, 81.10, 76.72, 64.59, 41.52, 41.32, 38.76, 36.09, 34.10, 33.93, 33.80, 33.70, 33.59, 33.55, 33.26, 31.95, 30.34, 29.69, 29.58, 29.39, 27.01, 22.56, 18.48, 0.01.

Di((Z)-non-2-en-1-yl) 9-hydroxyheptadecanedioate (247): The silyl protected diester 246 (0.3 g, 0.44 mmol) was dissolved in 1 M solution of TBAF in THF (6 mL) and the solution was kept at 40° C. for two days. The reaction mixture was diluted with water (60 mL) and extracted with ether (2×50 mL). The combined organic layers were concentrated and the thus obtained crude product was purified by column to isolate the pure product (0.097 g, 39%). $^1$H NMR (400 MHz, CDCl$_3$) δ 5.64 (dt, J=10.9, 7.4 Hz, 2H), 5.52 (dt, J=11.0, 6.8 Hz, 2H), 4.61 (d, J=6.8 Hz, 4H), 3.57 (s, 1H), 2.30 (t, J=7.5 Hz, 4H), 2.09 (q, J=7.1 Hz, 4H), 1.75-1.53 (m, 4H), 1.53-1.06 (m, 36H), 0.88 (t, J=6.8 Hz, 6H). $^{13}$C NMR (101 MHz, CDCl$_3$) δ 173.98, 135.64, 123.57, 77.54, 77.22, 76.91, 72.14, 60.41, 37.69, 34.54, 31.89, 29.70, 29.60, 29.44, 29.29, 29.07, 27.76, 25.80, 25.15, 22.82, 14.29.

Di((Z)-non-2-en-1-yl) 9-((4-(dimethylamino)butanoyl) oxy)heptadecanedioate: The alcohol 247 (0.083 g, 0.147 mmol) was dissolved in 20 mL of dichloromethane and to it dimethylaminobutyric acid hydrochloride (0.030 g, 0.176 mmol) was added followed by Hunig's base (0.045 g, 0.44 mmol) and DMAP (2 mg). To this mixture EDCI (0.034 g, 0.176 mmol) was added and the reaction mixture was stirred at room temperature overnight and the TLC (silica gel, 10% MeOH in CH$_2$Cl$_2$) showed complete disappearance of the starting alcohol. The reaction mixture was diluted with CH$_2$Cl$_2$ (40 mL) and washed with saturated NaHCO$_3$ (50 mL), water (60 mL) and brine (60 mL). The combined organic layers were dried over anhyd. Na$_2$SO$_4$ and solvents were removed in vacuo. The crude product thus obtained was purified by Combiflash Rf purification system (40 g silicagel, 0-10% MeOH in CH$_2$Cl$_2$) to isolate the pure product (0.062 g, 62%) as a colorless oil. $^1$H NMR (400 MHz, CDCl$_3$) δ 5.74-5.58 (m, 2H), 5.51 (dtt, J=9.7, 6.8, 1.3 Hz, 2H), 4.95-4.75 (m, 1H), 4.61 (d, J=6.8 Hz, 4H), 2.35-2.24 (m, 8H), 2.22 (d, J=7.9 Hz, 6H), 2.09 (q, J=6.9 Hz, 4H), 1.83-1.72 (m, 2H), 1.60 (dd, J=14.4, 7.2 Hz, 4H), 1.49 (d, J=5.7 Hz, 4H), 1.41-1.13 (m, 30H), 0.88 (t, J=6.9 Hz, 6H). $^{13}$C NMR (101 MHz, CDCl$_3$) δ 173.72, 173.36, 135.40, 123.35, 74.12, 60.18, 58.95, 45.46, 34.30, 34.11, 32.45, 31.67, 29.38, 29.35, 29.17, 29.07, 28.84, 27.53, 25.28, 24.93, 23.16, 22.59, 14.06. MW calc. for C$_{41}$H$_{75}$NO$_6$ (MH$^+$): 678.04, found: 678.5.

Example 18

The following shorter route was used for the synthesis of analogs of Compound 1 of the present invention The commercial 9-bromonon-1-ene 248 was treated with magnesium to form the corresponding Grignard reagent which was reacted with ethylformate to give the corresponding adduct 249 which on treatment with bromobutyryl chloride to provide the bromoester 250. The bromoester 250 on treatment with RuO$_4$ provided the diacid 251. The bromodiacid 251 on treatment with dimethylamine provided the amino diacid 252. The diacid 252 on treatment with oxalyl chloride in the presence of DMF provided the diacid chlorides 253. The lipids 254a-n were synthesized by treating the acid Chloride 253 with respective alcohols.

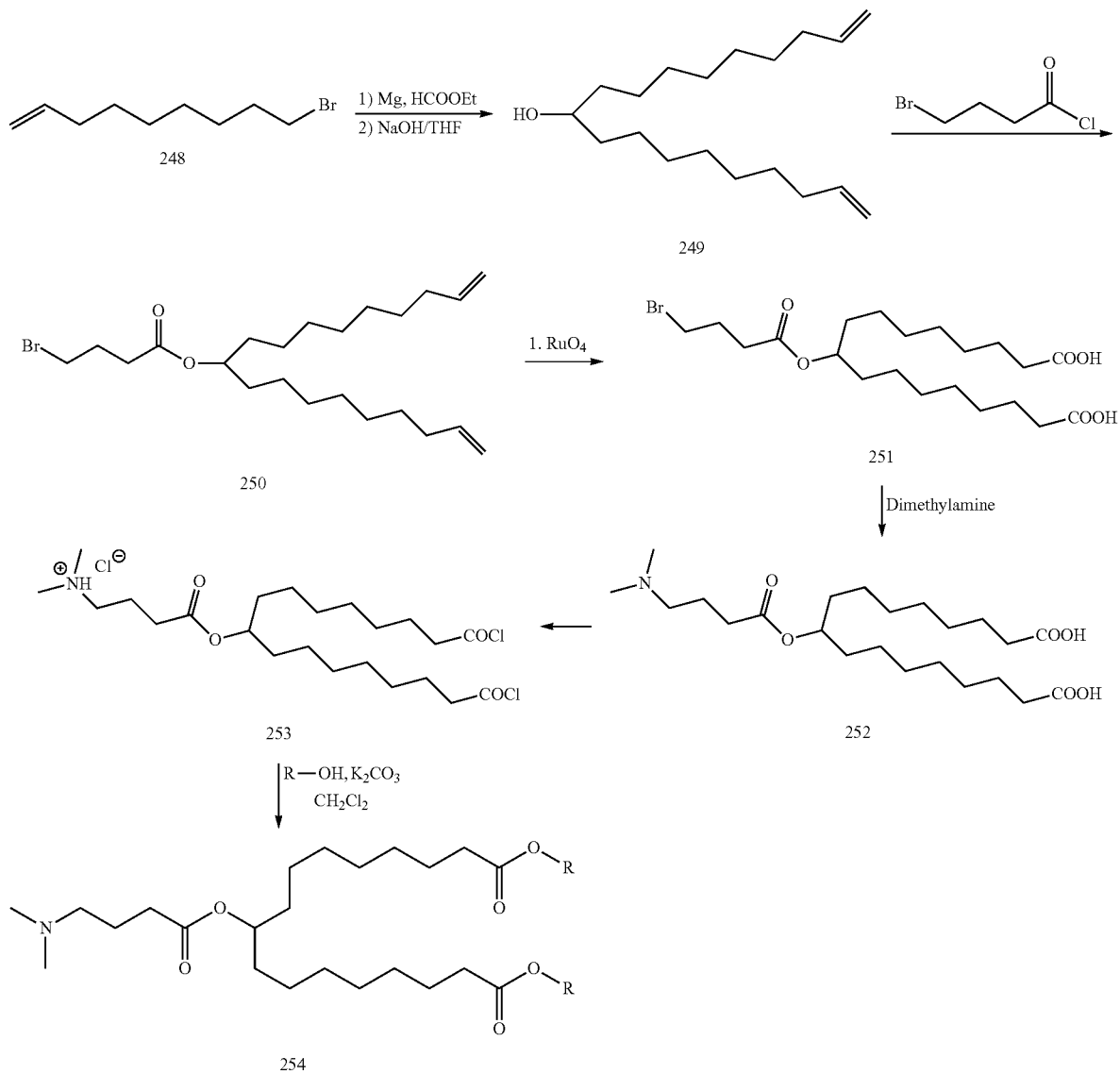

Scheme 18

| No | Starting Alcohol (ROH) |
|---|---|
| 254a | HO–CH₂–CH=CH–(CH₂)₅–CH₃ (cis) |
| 254aS | HS–CH₂–CH=CH–(CH₂)₅–CH₃ (cis) |
| 254aF | HO–CH₂–CH=CH–CF₂–(CH₂)₄–CH₃ (cis) |
| 254b | HO–(CH₂)₇–C(=O)–OMe |
| 254bS | HS–(CH₂)₇–C(=O)–OMe |
| 254bF | HO–(CH₂)₇–C(=O)–OCF₃ |
| 254bF2 | HO–(CH₂)₈–C(=O)–OMe |
| 254c | HO–CH₂–CH(iPr)–CH₂–CH₂–CH(CH₃)₂ |
| 254cS | HS–CH₂–CH(iPr)–CH₂–CH₂–CH(CH₃)₂ |
| 254cF | HO–CH₂–CH(iPr)–CH₂–CH₂–CH(CH₃)₂ |
| 254d | HO–(CH₂)₉–CH₃ (saturated chain) |
| 254ds | HS–(CH₂)₉–CH₃ |
| 254e | HO–(CH₂)₃–CH=CH–(CH₂)₄–CH₃ (cis) |
| 254es | HS–(CH₂)₃–CH=CH–(CH₂)₄–CH₃ (cis) |
| 254eF | HO–(CH₂)₃–CH=CH–CF₂–(CH₂)₃–CH₃ (cis) |
| 254f | HO–CH₂–CH=CH–(CH₂)₅–CH₃ (trans) |
| 254fs | HS–CH₂–CH=CH–(CH₂)₅–CH₃ (trans) |

-continued
| | |
|---|---|
| 254fF | 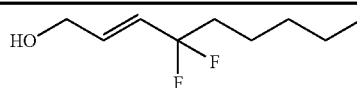 |
| 254g | 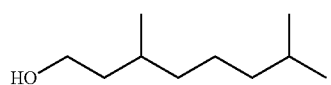 |
| 254gs | 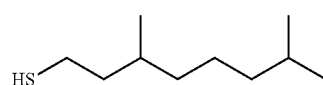 |
| 254h | 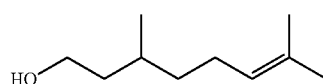 |
| 254hs | 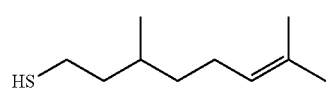 |
| 254hF | 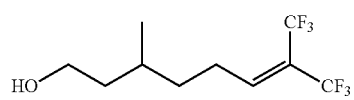 |
| 254i | 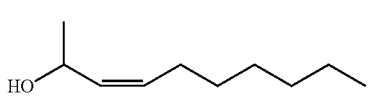 |
| 254is | 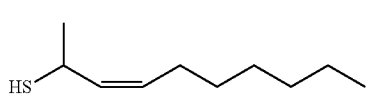 |
| 254iF | 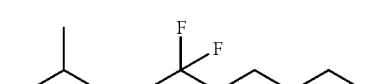 |
| 254j | 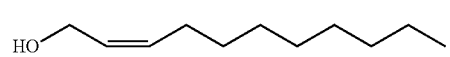 |
| 254js | 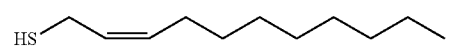 |
| 254jF | 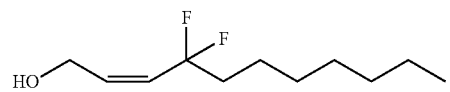 |
| 254k | 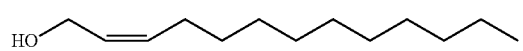 |
| 254ks | 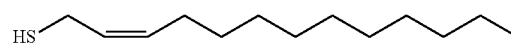 |
| 254kS | 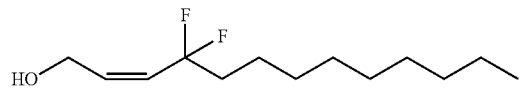 [SMILES: CCCCCCCCCC(F)(F)/C=C\CO] |
| 254l | 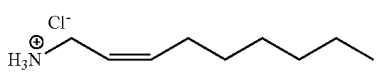 |
| 254lF | 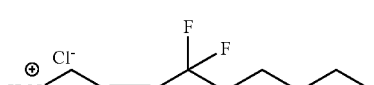 |
| 254m | 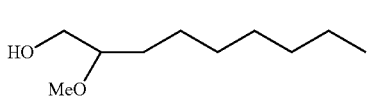 |

| | |
|---|---|
| 254ms | 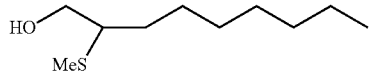 |
| 254ns | 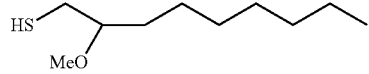 |
| 254os | 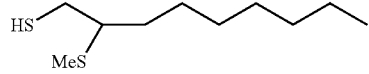 |
| No | Product |
|---|---|
| 254a | 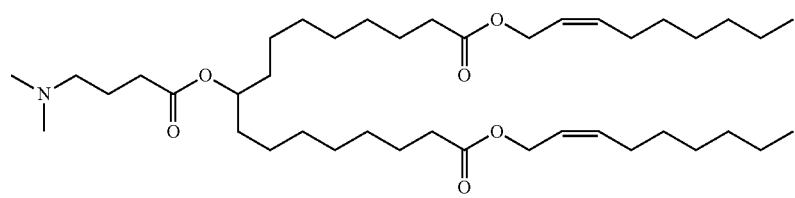 [SMILES: CCCCCC/C=C\CSC(=O)CCCCCCCC(CCCCCCCC(=O)SC/C=C\CCCCCC)OC(=O)CCCN(C)C] |
| 254aS | 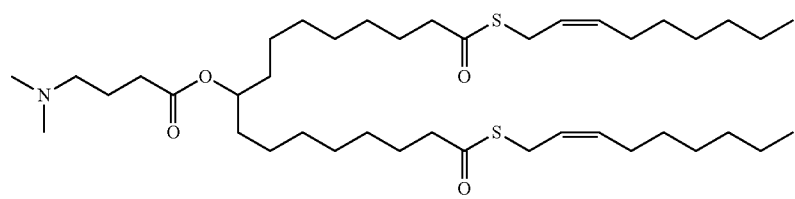 |
| 254aF | 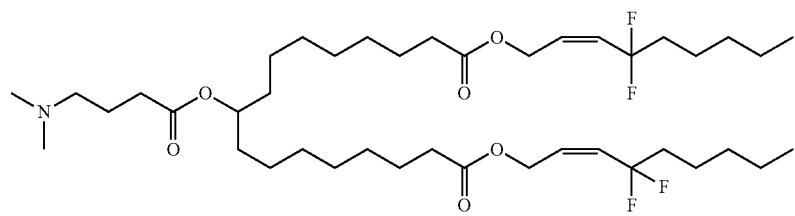 [SMILES: CCCCCC(F)(F)/C=C\COC(=O)CCCCCCCC(CCCCCCCC(=O)OC/C=C\C(F)(F)CCCCC)OC(=O)CCCN(C)C] |
| 254b | 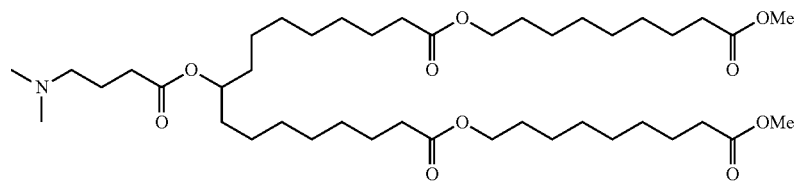 |
| 254bS | 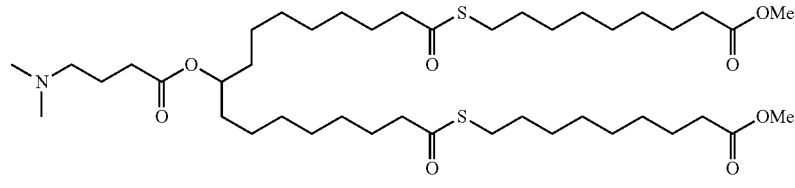 [SMILES: COC(=O)CCCCCCCCOC(=O)CCCCCCCC(CCCCCCCC(=O)OCCCCCCCCC(=O)OC)OC(=O)CCCN(C)C] |
| 254bF | 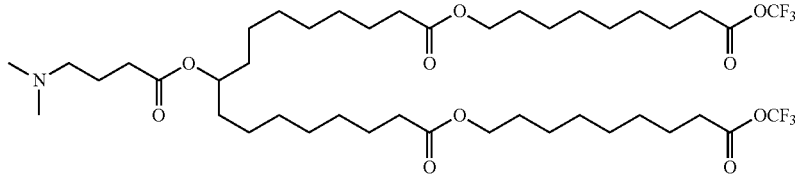 [SMILES: CN(C)CCCC(=O)OC(CCCCCCCC(=O)OCCCCCCCCC(=O)OC(F)(F)F)CCCCCCCC(=O)OCCCCCCCCC(=O)OC(F)(F)F] |

254bF2 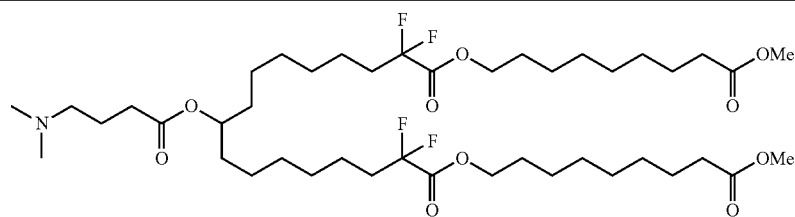
254c 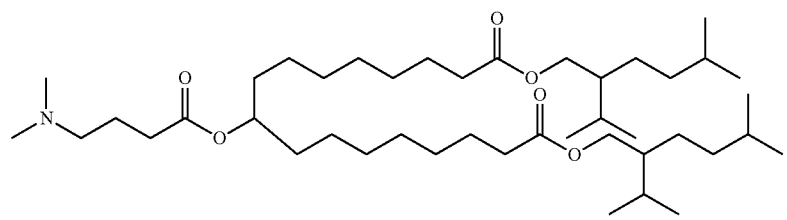 [SMILES: CC(C)CCC(COC(=O)CCCCCCCC(CCCCCCCC(=O)OCC(CCC(C)C)C(C)C)OC(=O)CCCN(C)C)C(C)C]
254cS 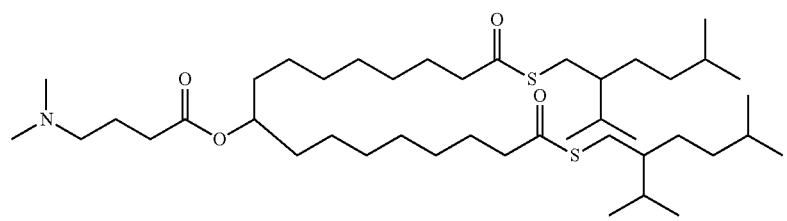
254cF 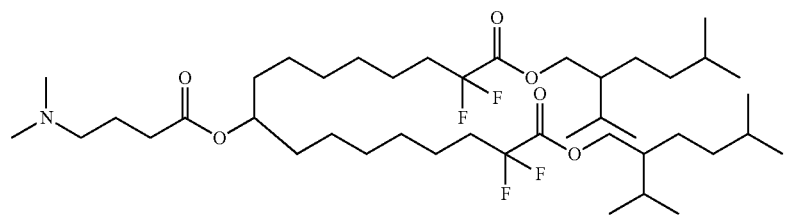 [SMILES: CC(C)CCC(COC(=O)C(F)(F)CCCCCCC(CCCCCCC(F)(F)C(=O)OCC(CCC(C)C)C(C)C)OC(=O)CCCN(C)C)C(C)C]
254d 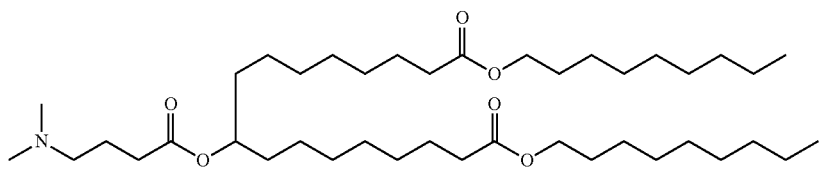 [SMILES: CCCCCCCCCOC(=O)CCCCCCCC(CCCCCCCC(=O)OCCCCCCCCC)OC(=O)CCCN(C)C]
254ds 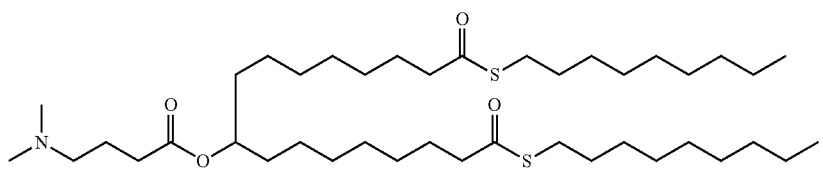 [SMILES: CCCCCCCCCSC(=O)CCCCCCCC(CCCCCCCC(=O)SCCCCCCCCC)OC(=O)CCCN(C)C]
254e 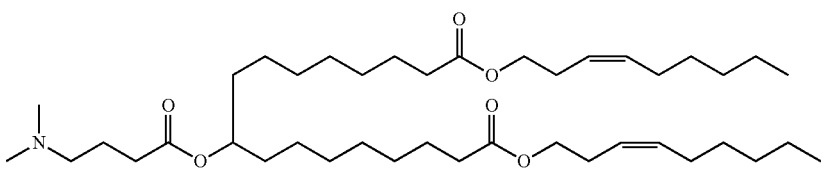
254es 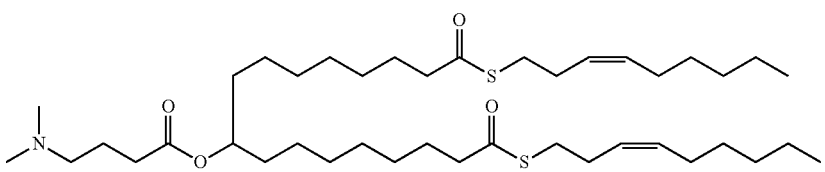 [SMILES: CCCCC/C=C\CCSC(=O)CCCCCCCC(CCCCCCCC(=O)SCC/C=C\CCCCC)OC(=O)CCCN(C)C]

254eF
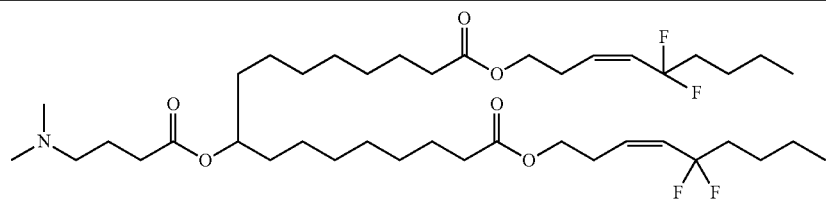
254f
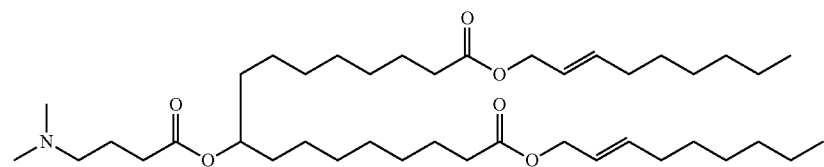 [SMILES: CCCCCC/C=C/COC(=O)CCCCCCCC(CCCCCCCC(=O)OC/C=C/CCCCCC)OC(=O)CCCN(C)C]
254fs
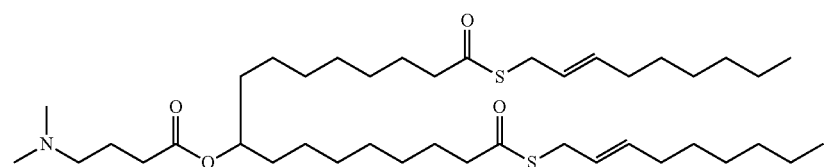 [SMILES: CCCCCC/C=C/CSC(=O)CCCCCCCC(CCCCCCCC(=O)SC/C=C/CCCCCC)OC(=O)CCCN(C)C]
254fF
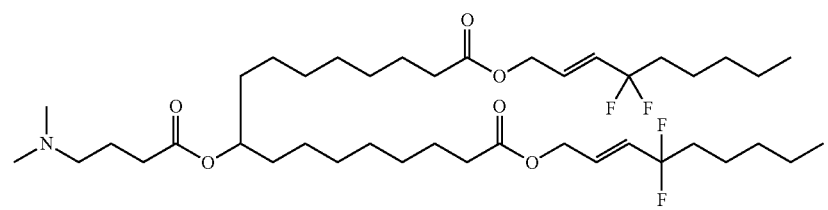 [SMILES: CCCCCC(F)(F)/C=C/COC(=O)CCCCCCCC(CCCCCCCC(=O)OC/C=C/C(F)(F)CCCCC)OC(=O)CCCN(C)C]
254g
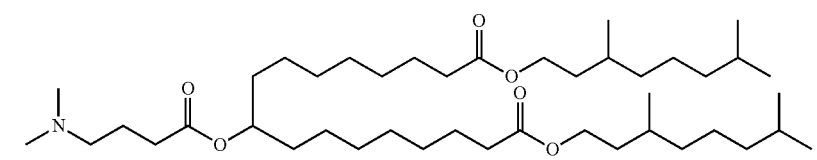 [SMILES: CC(C)CCCC(C)CCOC(=O)CCCCCCCC(CCCCCCCC(=O)OCCC(C)CCCC(C)C)OC(=O)CCCN(C)C]
254gs
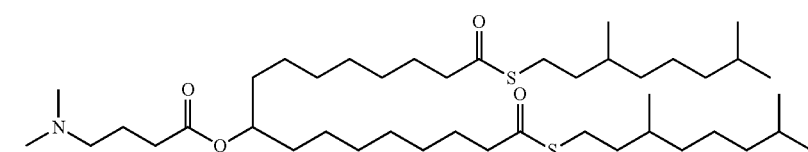
254h
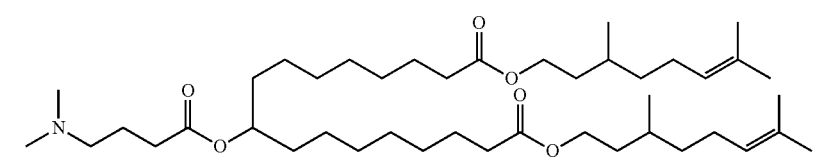 [SMILES: CC(C)=CCCC(C)CCOC(=O)CCCCCCCC(CCCCCCCC(=O)OCCC(C)CCC=C(C)C)OC(=O)CCCN(C)C]
254hs
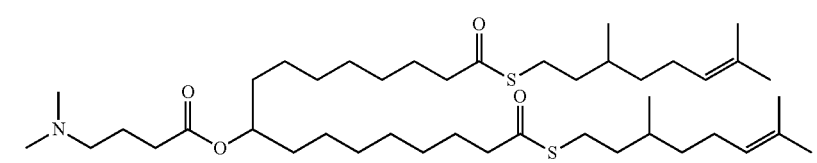 [SMILES: CC(C)=CCCC(C)CCSC(=O)CCCCCCCC(CCCCCCCC(=O)SCCC(C)CCC=C(C)C)OC(=O)CCCN(C)C]
254hF
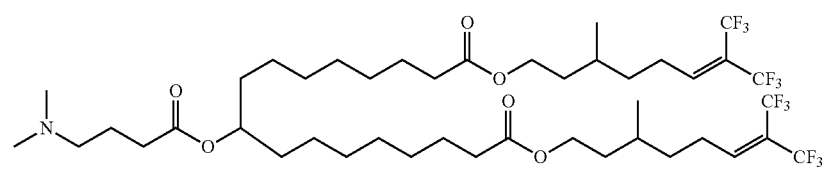 [SMILES: CC(CCC=C(C(F)(F)F)C(F)(F)F)CCOC(=O)CCCCCCCC(CCCCCCCC(=O)OCCC(C)CCC=C(C(F)(F)F)C(F)(F)F)OC(=O)CCCN(C)C]

-continued
254i
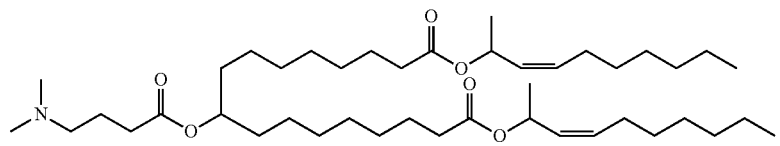
254is
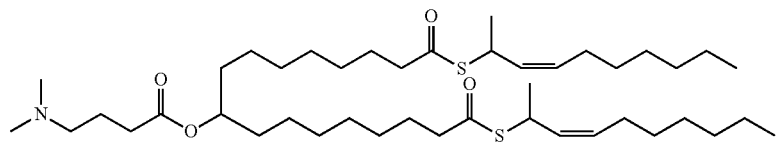 [SMILES: CCCCCC/C=C\C(C)SC(=O)CCCCCCCC(CCCCCCCC(=O)SC(C)/C=C\CCCCCC)OC(=O)CCCN(C)C]
254iF
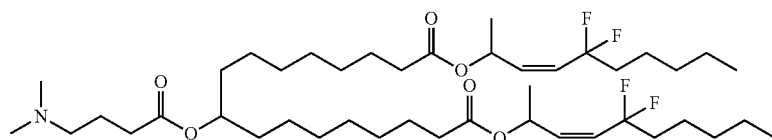
254j
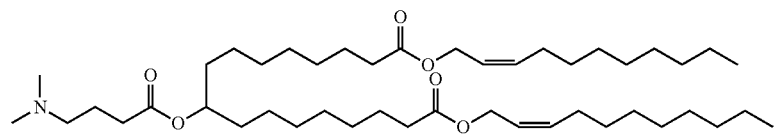 [SMILES: CCCCCCCC/C=C\COC(=O)CCCCCCCC(CCCCCCCC(=O)OC/C=C\CCCCCCCC)OC(=O)CCCN(C)C]
254js
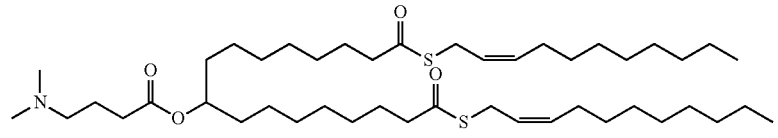 [SMILES: CCCCCCCC/C=C\CSC(=O)CCCCCCCC(CCCCCCCC(=O)SC/C=C\CCCCCCCC)OC(=O)CCCN(C)C]
254jF
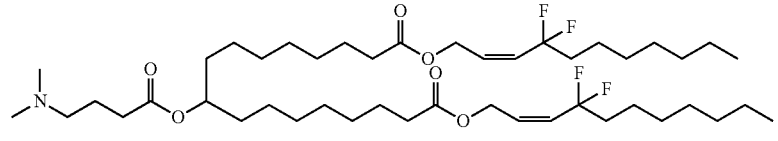 [SMILES: CCCCCCCC(F)(F)/C=C\COC(=O)CCCCCCCC(CCCCCCCC(=O)OC/C=C\C(F)(F)CCCCCCC)OC(=O)CCCN(C)C]
254k
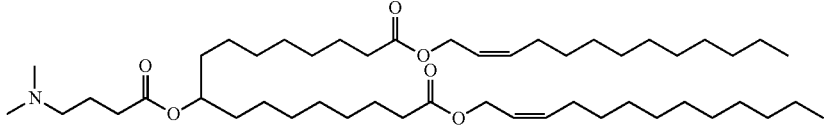
254ks
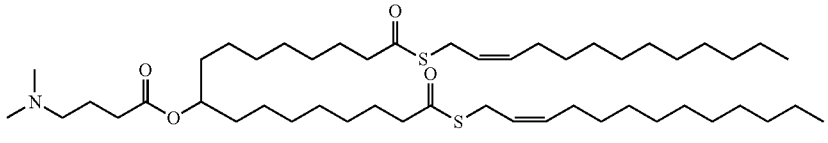 [SMILES: CCCCCCCCCC/C=C\CSC(=O)CCCCCCCC(CCCCCCCC(=O)SC/C=C\CCCCCCCCCC)OC(=O)CCCN(C)C]
254kS
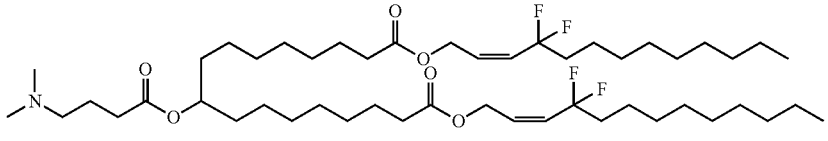 [SMILES: CCCCCCCCCC(F)(F)/C=C\COC(=O)CCCCCCCC(CCCCCCCC(=O)OC/C=C\C(F)(F)CCCCCCCCC)OC(=O)CCCN(C)C]
254l
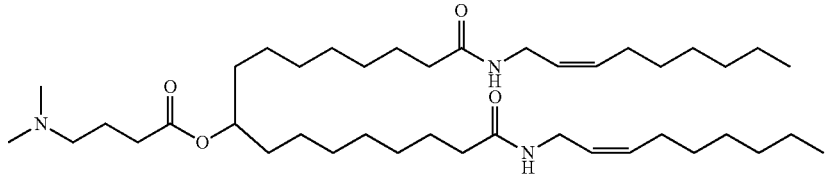 [SMILES: CCCCCC/C=C\CNC(=O)CCCCCCCC(CCCCCCCC(=O)NC/C=C\CCCCCC)OC(=O)CCCN(C)C]

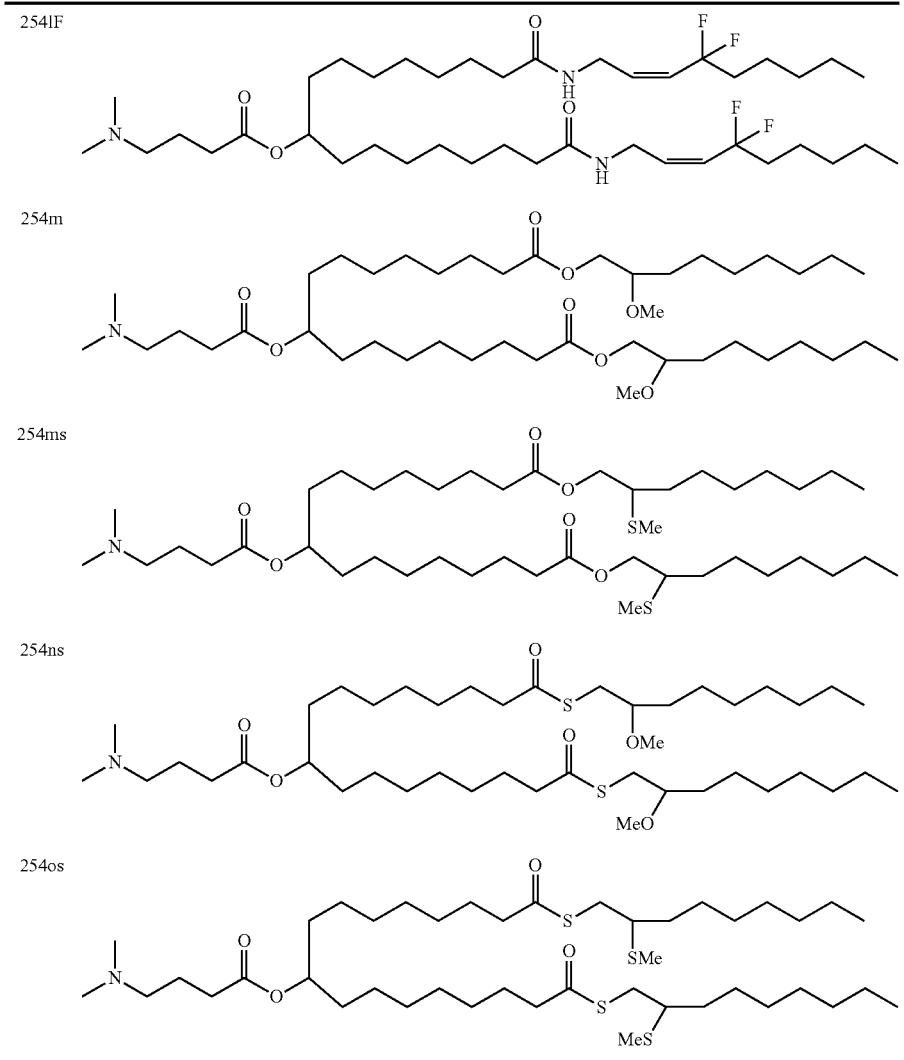

Synthesis of nonadeca-1,18-dien-10-ol (249)

To a flame dried 500 mL RB flask, freshly activated Mg turnings (9 g) were added and the flask was equipped with a magnetic stir bar, an addition funnel and a reflux condenser. This set-up was degassed and flushed with argon and 100 mL of anhydrous ether was added to the flask via syringe. The bromide 3 (51.3 g, 250 mmol) was dissolved in anhydrous ether (100 mL) and added to the addition funnel. About 5 mL of this ether solution was added to the Mg turnings while stirring vigorously. An exothermic reaction was noticed (to confirm/accelerate the Grignard reagent formation, 5 mg of iodine was added and immediate decolorization was observed confirming the formation of the Grignard reagent) and the ether started refluxing. The rest of the solution of the bromide was added dropwise while keeping the reaction under gentle reflux by cooling the flask in water. After the completion of the addition the reaction mixture was kept at 35 TC for 1 hour and then cooled in ice bath. Ethyl formate (9 g, 121 mmol) was dissolved in anhydrous ether (100 mL) and transferred to the addition funnel and added dropwise to the reaction mixture with stirring. An exothermic reaction was observed and the reaction mixture started refluxing. After the initiation of the reaction the rest of the ethereal solution of formate was quickly added as a stream and the reaction mixture was stirred for a further period of 1 h at ambient temperature. The reaction was quenched by adding 10 mL of acetone dropwise followed by ice cold water (60 mL). The reaction mixture was treated with aq. $H_2SO_4$ (10% by volume, 300 mL) until the solution became homogeneous and the layers were separated. The aq. phase was extracted with ether (2×200 mL). The combined ether layers were dried ($Na_2SO_4$) and concentrated to afford the crude product which was purified by column (silica gel, 0-10% ether in hexanes) chromatography. The product fractions were evaporated to provide the pure product 249 as a white solid (30.6 g, 90%). $^1$H NMR (400 MHz, $CDCl_3$) δ 7.26 (s, 1H), 5.81 (ddt, J=16.9, 10.2, 6.7 Hz, 8H), 5.04-4.88 (m, 16H), 3.57 (dd, J=7.6, 3.3 Hz, 4H), 2.04 (q, J=6.9 Hz, 16H), 1.59 (s, 1H), 1.45 (d, J=7.5 Hz, 8H), 1.43-1.12 (m, 94H), 0.88 (t, J=6.8 Hz, 2H). $^{13}$C NMR (101 MHz, $cdcl_3$) δ 139.40, 114.33, 77.54, 77.22, 76.90, 72.21, 37.70, 34.00, 29.86, 29.67, 29.29, 29.12, 25.85.

Synthesis of nonadeca-1,18-dien-10-yl 4-bromobutanoate (250)

To a solution of the alcohol 249 (5.6 g, 20 mol) in anhydrous DCM (300 mL) was added slowly and carefully Bromobutyryl chloride (20 mmol) at 0° C. under inert atmosphere. The reaction mixture was warmed to room temperature, stirred for 20 h and monitored by TLC (silica gel, 10% ethyl acetate in hexanes). Upon completion of the reaction, mixture was diluted with water (400 mL) and organic layer was separated out. Organic phase was then washed with sat. solution of $NaHCO_3$ (1×400 mL) followed by brine (1×100 mL) and concentrated under vacuum. Crude product was then purified by silica gel (100-200 mesh) column, eluted with 2-3% ethyl acetate in hexane solution to give 6 g (90%) of desired product 250 as colorless liquid. H NMR (400 MHz, $CDCl_3$) δ 5.80 (ddt, J=16.9, 10.2, 6.7 Hz, 2H), 5.05-4.81 (m, 5H), 3.46 (t, J=6.5 Hz, 2H), 2.48 (t, J=7.2 Hz, 2H), 2.17 (p, J=6.8 Hz, 2H), 2.11-1.93 (m, 4H), 1.65-1.44 (m, 4H), 1.43-1.17 (m, 19H). $^{13}C$ NMR (101 MHz, $cdcl_3$) δ 172.51, 139.37, 114.35, 77.54, 77.23, 76.91, 74.86, 34.31, 33.99, 33.01, 32.96, 29.65, 29.56, 29.24, 29.09, 28.11, 25.52.

Synthesis of 9-((4-bromobutanoyl)oxy)heptadecanedioic acid (251)

To a solution of the bromoester 250 (12.1 g, 28.2 mmol) in dichloromethane (300 mL) and acetonitrile (300 mL), $RuCl_3$ (1.16 g, 5 mol %) was added and the mixture was cooled to 10° C. and sodium metaperiodate (60 g) in water (400 mL) was added dropwise. It was stirred at 10° C. for 20 hr. The reaction mixture was diluted with water, The layers were separated and to the organic layer, was added saturated brine solution with stirring followed by 3% sodium sulfide solution drop wise for the decolourisation (dark green to pale yellow). The layers were separated, the organic layer was dried over sodium sulfate and evaporated at reduced pressure to afford pure product. MW calcd for $C_{20}H_{35}BrO_7$ 467.39; Found 465.4 (M−2H). H NMR (400 MHz, DMSO) δ 11.94 (s, 2H), 4.88-4.69 (m, 1H), 3.53 (t, J=6.6 Hz, 2H), 2.43 (t, J=7.2 Hz, 2H), 2.17 (t, J=7.4 Hz, 4H), 2.09-1.95 (m, 2H), 1.90 (s, 3H), 1.46 (s, 7H), 1.23 (s, 15H).

Synthesis of 9-((4-(dimethylamino)butanoyl)oxy)heptadecanedioic acid (252)

The Bromoacid 251 (2 mmol) is dissolved in 2M solution of dimethylamine in THF (20 mL) and to it 1 g of anhydrous $K_2CO_3$ was added and the mixture was heated in a pressure bottle at 50° C. overnight. The TLC showed the completion of the reaction. The reaction mixture was acidified with acetic acid and diluted with water (100 mL) and extracted with dichloromethane (2×60 mL). The combined organic layers were concentrated dried and used as such in the next reaction. MW calcd for $C_{23}H_{43}NO_6$ 429.59; Found 430.6 (MH)⁺. 1H NMR (400 MHz, DMSO) δ 11.87-11.82 (m, 7H), 5.75 (d, J=0.7 Hz, 15H), 4.85-4.69 (m, 38H), 3.64-3.55 (m, 12H), 3.35-2.83 (m, 106H), 3.01-2.90 (m, 59H), 2.94 (ddd, J=30.6, 7.7, 4.0 Hz, 63H), 2.90-2.73 (m, 9H), 2.70 (s, 221H), 2.57-2.46 (m, 91H), 2.44-2.30 (m, 76H), 2.17 (t, J=7.3 Hz, 147H), 1.89 (tq, J=15.5, 7.6 Hz, 88H), 1.79-1.69 (m, 13H), 1.65-1.32 (m, 311H), 1.28 (d, J=46.0 Hz, 598H).

Synthesis of 9-((4-(dimethylamino)butanoyl)oxy)heptadecanedioyl chloride (253)

The diacid 252 is converted to the corresponding diacid chloride 253 by treating it with oxalyl chloride in dichloromethane in the presence of catalytic DMF and the crude acid chloride obtained after the concentration of the reaction mixture was used as such for the coupling with different alcohols.

General Procedure for the Synthesis of Cationic Lipids 254a-n

To a solution of the acid chloride 253 (500 mg, 1 mmol) in dichloromethane (30 mL) the corresponding alcohol (5 equivalent) was added at room temperature followed by solid $K_2CO_3$ (1 g) and the solution was stirred for 16 h at room temperature. The reaction mixture was diluted with dichloromethane (100 mL) and washed with satd. $NaHCO_3$ (100 mL) and the organic layer was dried (Anhyd. $Na_2SO_4$) and concentrated to obtain the crude product which was purified by Combiflash Rf purification system.

Compound 254b: By using the above procedure the lipid 254b was isolated in 72% yield (554 mg). 1H NMR (400 MHz, CDCl3) δ 4.91-4.78 (m, 1H), 4.05 (t, J=6.7 Hz, 4H), 3.81 (s, 6H), 3.63 (t, J=6.4 Hz, 1H), 2.29 (dt, J=15.2, 7.5 Hz, 8H), 2.21 (s, 6H), 1.84-1.69 (m, 2H), 1.57 (dt, J=13.4, 5.2 Hz, 9H), 1.53-1.40 (m, 4H), 1.27 (s, 43H). 13C NMR (101 MHz, cdcl3) δ 174.45, 174.13, 173.59, 77.54, 77.22, 76.91, 74.34, 64.54, 59.17, 51.65, 45.67, 34.56, 34.35, 34.27, 32.67, 29.59, 29.40, 29.33, 29.31, 29.25, 28.83, 26.06, 25.51, 25.18, 25.11, 23.38. MW calcd for $C_{43}H_{79}NO_{10}$ 770.09; Found 770.68.

Compound 254c: By using the above procedure the lipid 254c was isolated in 69% (490 mg). 1H NMR (400 MHz, CDCl3) δ 5.71-5.36 (m, 4H), 4.89-4.72 (m, 1H), 4.59 (d, J=6.8 Hz, 4H), 2.26 (ddd, J=22.3, 13.0, 8.6 Hz, 9H), 2.19 (s, 6H), 2.12-1.95 (m, 4H), 1.82-1.68 (m, 2H), 1.63-1.37 (m, 8H), 1.37-1.00 (m, 32H), 0.85 (t, J=6.8 Hz, 6H). 13C NMR (101 MHz, cdcl3) δ 173.94, 173.57, 135.61, 123.57, 77.54, 77.22, 76.91, 74.34, 60.40, 59.16, 45.65, 34.52, 34.33, 32.66, 31.88, 29.59, 29.57, 29.38, 29.28, 29.06, 27.75, 25.49, 25.14, 23.35, 22.81, 14.28. MW calcd for $C_{43}H_{83}NO_6$: 710.12; Found 710.81.

Compound 254d: By using the above procedure the lipid 254d was isolated in 67% yield (456 mg). 1H NMR (400 MHz, CDCl3) δ 4.92-4.78 (m, 1H), 4.05 (t, J=6.7 Hz, 4H), 3.63 (t, J=6.4 Hz, 1H), 2.39-2.24 (m, 8H), 2.21 (s, 6H), 1.89-1.70 (m, 2H), 1.69-1.54 (m, 8H), 1.51 (dd, J=17.2, 6.3 Hz, 4H), 1.27 (s, 42H), 0.88 (t, J=6.8 Hz, 6H). MW calcd for: $C_{41}H_{79}NO_6$: 682.07; Found 682.96.

Compound 254e: By using the above procedure the lipid 254e was isolated in 70% (474 mg). 1H NMR (400 MHz, CDCl3) δ 5.49 (ddd, J=12.9, 9.8, 7.3 Hz, 2H), 5.40-5.23 (m, 2H), 4.92-4.77 (m, 1H), 4.05 (t, J=6.9 Hz, 4H), 2.32 (ddd, J=23.4, 14.5, 7.1 Hz, 12H), 2.21 (s, 6H), 2.07-1.91 (m, 4H), 1.84-1.70 (m, 2H), 1.66-1.39 (m, 8H), 1.40-1.15 (m, 26H), 0.88 (t, J=6.8 Hz, 5H). MW calc. for $C_{41}H_{75}NO_6$ (MH⁺): 678.04, found: 678.5.

Compound 254f: By using the above procedure the lipid 254f was isolated in 73% (559 mg). 1H NMR (400 MHz, CDCl3) δ 5.87-5.62 (m, 2H), 5.55 (dtt, J=9.1, 6.4, 1.3 Hz, 2H), 4.93-4.75 (m, 1H), 4.50 (dd, J=6.5, 0.6 Hz, 4H), 2.40-2.17 (m, 13H), 2.12-1.95 (m, 4H), 1.89-1.67 (m, 2H), 1.69-1.44 (m, 7H), 1.41-1.12 (m, 25H), 0.88 (t, J=6.9 Hz, 5H). MW calc. for $C_{41}H_{75}NO_6$ (MH⁺): 678.04, found: 678.5.

Compound 254 g: By using the above procedure the lipid 254 g was isolated in 63% (432 mg). 1H NMR (400 MHz, CDCl3) δ 4.93-4.77 (m, 1H), 4.20-3.95 (m, 4H), 2.44-2.23 (m, 8H), 2.21 (s, 6H), 1.84-1.66 (m, 3H), 1.68-1.34 (m, 15H), 1.35-1.17 (m, 20H), 1.17-1.04 (m, 5H), 0.88 (dd, J=12.4, 6.6 Hz, 16H). MW calcd for $C_{43}H_{83}NO_6$: 710.12; Found 710.81.

Compound 254h: By using the above procedure the lipid 254h was isolated in 66% (466 mg). 1H NMR (400 MHz, CDCl3) δ 5.08 (ddd, J=7.1, 5.9, 1.3 Hz, 2H), 4.91-4.75 (m, 1H), 4.22-3.97 (m, 4H), 2.39-2.22 (m, 8H), 2.23 (d, J=16.7 Hz, 7H), 2.09-1.84 (m, 4H), 1.86-1.71 (m, 3H), 1.71-1.02 (m, 44H), 0.91 (t, J=4.9 Hz, 6H). MW calcd for $C_{43}H_{79}NO_6$: 706.12; Found 706.81.

Example 19

In another approach the following synthetic approach is used for the synthesis of Compound 1 of the present invention.

Scheme 19

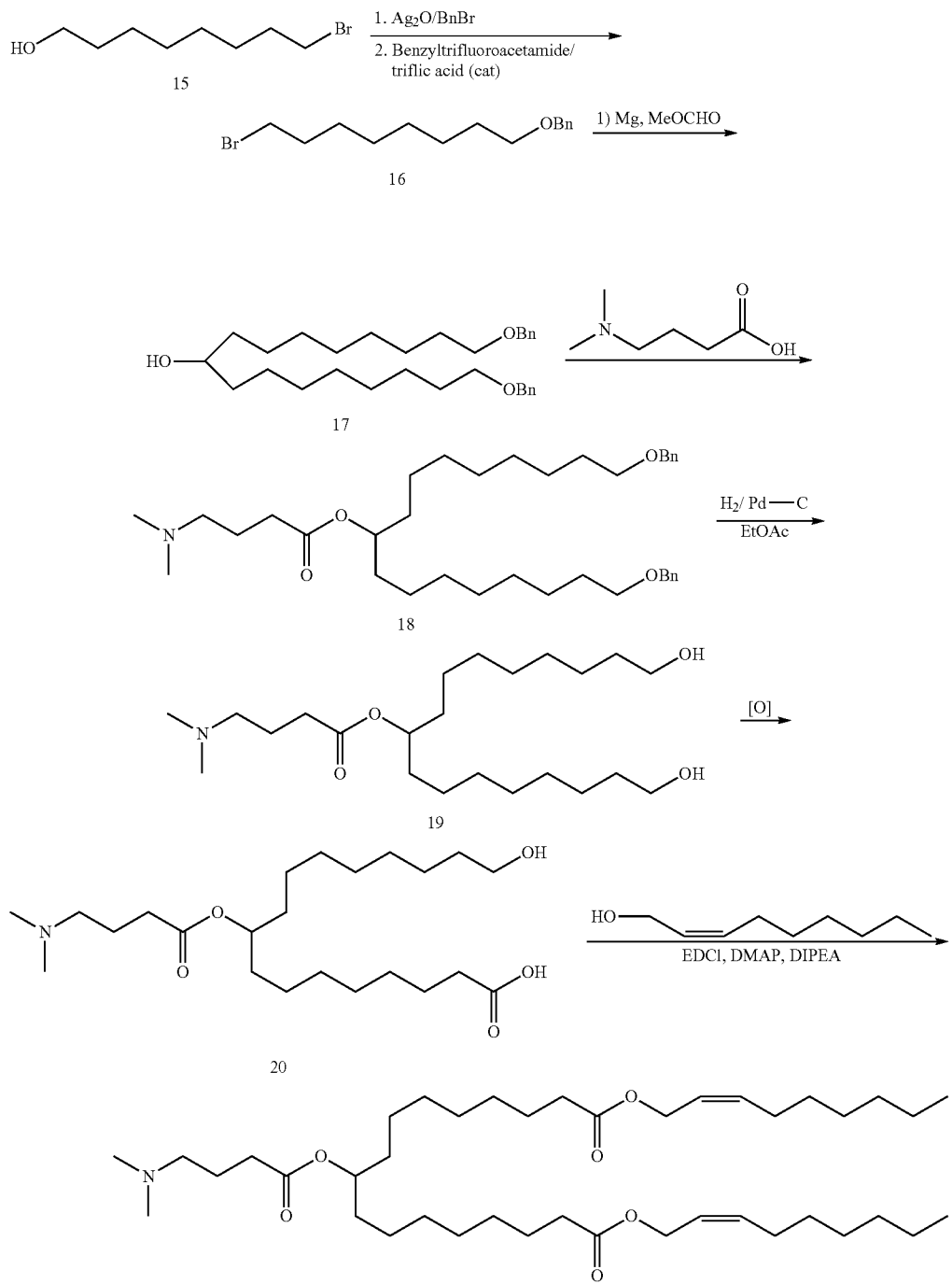

Example 20
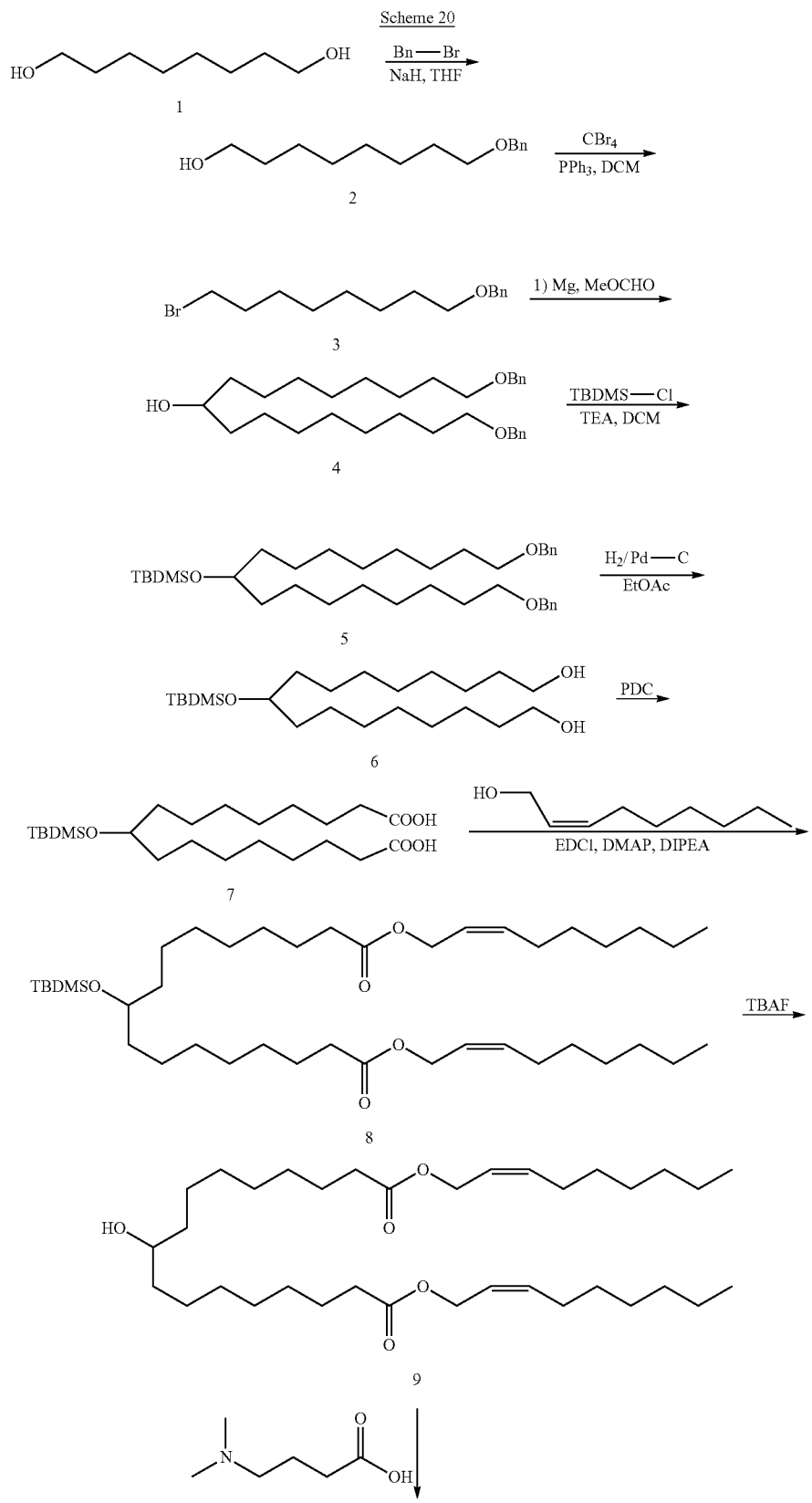
Scheme 20

-continued

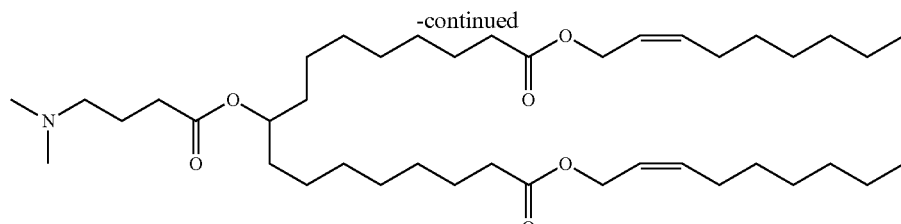

ALNY-319

8-benzyloxy-octan-1-ol (2): To a stirred suspension of NaH (60% in oil, 82 g, 1.7096 mol) in 500 mL anhydrous DMF, a solution of compound 1 (250 g, 1.7096 mol) in 1.5 L DMF was added slowly with dropping funnel at 0° C. Reaction mixture was stirred for 30 min and to it Benzyl bromide (208.86 mL, 1.7096 mol) was added slowly under nitrogen atmosphere. Reaction was then warmed to ambient temperature and stirred for 10 h. After completion of reaction, mixture was quenched with crushed ice (~2 kg) and extracted with Ethyl acetate (2×1 L). Organic layer washed with water (1 L) to remove unwanted DMF, dried over $Na_2SO_4$ and evaporated to dryness under vacuum. The crude compound was purified on 60-120 silica gel, eluted with 0-5% MeOH in DCM to afford compound 2 (220 g, 54%) as pale yellow liquid. $H^1$ NMR (400 MHz, $CDCl_3$): δ=7.33-7.24 (m, 5H), 4.49 (s, 2H), 3.63-3.60 (m, 2H), 3.47-3.43 (m, 2H), 1.63-1.51 (m, 4H), 1.39-1.23 (m, 8H).

(8-bromo-octyloxymethyl)-benzene (3): Compound 2 (133 g, 0.5635 mol) was dissolved in 1.5 L of DCM, $CBr_4$ (280.35 g, 0.8456 mol) was added into this stirring solution and reaction mixture was cooled to 0° C. under inert atmosphere. $PPh_3$ (251.03 g, 0.9571 mol) was then added in portions keeping the temperature below 20° C. and after complete addition reaction was stirred for 3 h at room temperature and monitored by TLC. After completion of reaction, solid ($PPh_3O$) precipitated out from the reaction mixture was filtered off and filtrate was diluted with crushed ice (~1.5 kg) and extracted with DCM (3×750 mL). Organic layer was separated, dried over an. $Na_2SO_4$ and distilled under vacuum. Resulting crude compound was chromatographed on 60-120 mesh silica gel column using 0-5% ethyl acetate in hexanes as eluting system to give compound 3 (150 g, 89%) as pale yellow liquid. $H^1$ NMR (400 MHz, $CDCl_3$): δ=7.33-7.25 (m, 5H), 4.49 (s, 2H), 3.47-3.41 (m, 2H), 3.41-3.37 (m, 2H), 1.86-1.80 (m, 4H), 1.62-1.56 (m, 2H), 1.42-1.29 (m, 8H).

1, 17-bis-benzyloxy-heptadecan-9-ol (4): To freshly activated Mg turnings (24.08 g, 1.003 mol) was added 200 mL anhydrous THF was added followed by the addition of pinch of iodine into the mixture under inert atmosphere. After initiation of the Grignard formation a solution of Compound 3 (150 g, 0.5016 mol) in 1 L of dry THF was added slowly controlling the exothermic reaction. After complete addition reaction was refluxed for 1 h and then cooled to room temperature. (60.24 g, 1.0033 mol) methyl formate was then added slowly and reaction was continued for 2 h. After completion, the reaction was quenched by slow addition of 10% HCl followed by water (1 L) and extracted with Ethyl Acetate (3×1 L). Organic layer was taken in 5 lit beaker, diluted with 500 mL of methanol and cooled to 0° C. To this solution excess of $NaBH_4$ (~5 eq) was added in portions to ensure the hydrolysis of formate ester which was not cleaved by addition of HCl. Resulting solution was stirred for an hour and then volatilities were stripped off under vacuum. Residue was taken in water (1 L) and acidified by 10% HCl solution (PH 4). Product was then extracted out with ethyl acetate (3×1 L). Organic phase was then dried and concentrated on rotary evaporator to get the desired compound 4 (57 g, 24%) as solid. $H^1$ NMR (400 MHz, $CDCl_3$): δ=7.35-7.32 (m, 8H), 7.29-7.24 (m, 2H), 4.49 (s, 4H), 3.56 (m, 1H), 3.46-3.43 (m, 4H), 1.63-1.56 (m, 4H), 1.44-1.34 (m, 28H). $C^3$ NMR (100 MHz, $CDCl_3$): δ=138.56, 128.21, 127.49, 127.34, 72.72, 71.76, 70.37, 37.37, 29.64, 29.56, 29.47, 29.33, 26.07, 25.54.

[9-benzyloxy-1-(8-benzyloxy-octyl)-nonyloxy]-tert-butyl-dimethyl-silane (5): Compound 4 (56 g, 0.1196 mol) was dissolved in 700 mL of anhydrous THF and cooled to 0° C. TBMS-Cl (36.06 g, 0.2396 mol) was added slowly followed by addition of Imidazole (32.55 g, 0.4786 mol) under inert atmosphere. Reaction was then stirred at room temperature for 18 h. Reaction was judged complete by TLC and then quenched with ice (~1 kg) and extracted with Ethyl acetate (3×500 mL). Organic layer was separated, washed with Sat $NaHCO_3$ solution to remove the acidic impurity, dried over $Na_2SO_4$ and evaporated under reduce pressure to obtain crude compound which was purified by silica gel (60-120 mesh) and eluted with 0-10% ethyl acetate hexane to yield (60 g, 82%) of compound 5 as yellowish oil. $H^1$ NMR (400 MHz, $CDCl_3$): δ=7.33-7.24 (m, 10H), 4.49 (s, 4H), 3.60-3.57 (m, 1H), 3.46-3.43 (m, 4H), 1.61-1.54 (m, 4H), 1.41-1.26 (m, 28H), 0.87 (s, 9H), 0.02 (s, 6H)

9-(tert-butyl-dimethyl-silanyloxy)-heptadecane-1, 17-diol (6): Compound 5 (60 g, 0.1030 mol) was dissolved in 500 mL ethyl acetate and degassed with $N_2$ for 20 min. (10 wt %) Pd on carbon (12 g) was added and reaction was stirred under $H_2$ atmosphere for 18 h. After completion of reaction (by TLC) mixture was filtered through celite bed and washed with ethyl acetate. Filtrate was evaporated under vacuum. The compound 6 (19 g, 46%) thus obtained was pure enough to carry out the next reaction. $H^1$ NMR (400 MHz, $CDCl_3$): δ=3.64-3.58 (m, 5H), 1.59 (br, 2H), 1.57-1.51 (m, 4H), 1.38-1.22 (m, 28H), 0.87 (s, 9H), 0.02 (s, 6H).

9-(tert-butyl-dimethyl-silanyloxy)-heptadecanedioic acid (7): To a stirred solution of 6 (2 g, 0.0049 mol) in anhydrous DMF (40 mL) was added pyridinium dichromate (2.7 g, 0.0074 mol) at 0° C. under inert atmosphere. Reaction mixture was then allowed to warm to room temperature over a period of 10-15 minutes and continued for 24 h. Progress of the reaction was monitored by TLC. After complete oxidation reaction was diluted with water (100 mL). Aqueous phase was extracted with DCM (3×40 mL). Organic phase was washed with brine (lx 25 mL) and concentrated under vacuum to afford crude acid which was then purified by (100-200 mesh) silica gel column using 0-30% ethyl acetate in hexanes system. Pure product 26-003 was obtained (0.7 g, 33%) as pale yellow oil. H NMR (400 MHz, $CDCl_3$): δ=3.61-3.56 (m, 1H), 2.35-2.32 (m, 4H), 1.64-1.59

(m, 4H), 1.40-1.19 (m, 24H), 0.86 (s, 9H), 0.017 (s, 6H); LC-MS [M+H]—431.00; HPLC (ELSD) purity—96.94%

Di((Z)-non-2-en-1-yl) 9-((tert-butyldimethylsilyl)oxy)heptadecanedioate (8): The diacid 7 (0.42 g, 0.97 mmol) was dissolved in 20 mL of dichloromethane and to it cis-2-nonen-1-ol (0.35 g, 2.44 mmol) was added followed by Hunig's base (0.68 g, 4.9 mmol) and DMAP (12 mg). To this mixture EDCI (0.47 g, 2.44 mmol) was added and the reaction mixture was stirred at room temperature overnight and the TLC (silica gel, 5% MeOH in $CH_2Cl_2$) showed complete disappearance of the starting acid. The reaction mixture was diluted with $CH_2Cl_2$ (40 mL) and washed with saturated $NaHCO_3$ (50 mL), water (60 mL) and brine (60 mL). The combined organic layers were dried over anhyd. $Na_2SO_4$ and solvents were removed in vacuo. The crude product thus obtained was purified by Combiflash Rf purification system (40 g silicagel, 0-10% MeOH in $CH_2Cl_2$) to isolate the pure product 8 (0.35 g, 53%) as a colorless oil. $^1$H NMR (400 MHz, $CDCl_3$): δ $^1$H NMR (400 MHz, $CDCl_3$) δ 5.64 (dt, J=10.9, 7.4 Hz, 2H), 5.58-5.43 (m, 2H), 4.61 (d, J=6.8 Hz, 4H), 3.71-3.48 (m, 1H), 2.30 (t, J=7.6 Hz, 4H), 2.20-1.98 (m, 4H), 1.71-1.53 (m, 4H), 1.31 (ddd, J=8.3, 7.0, 3.7 Hz, 34H), 1.07-0.68 (m, 14H), 0.02 (s, 5H). $^{13}$C NMR (101 MHz, $CDCl_3$) δ 178.18, 139.81, 127.78, 81.73, 81.42, 81.10, 76.72, 64.59, 41.52, 41.32, 38.76, 36.09, 34.10, 33.93, 33.80, 33.70, 33.59, 33.55, 33.26, 31.95, 30.34, 29.69, 29.58, 29.39, 27.01, 22.56, 18.48, 0.01.

Di((Z)-non-2-en-1-yl) 9-hydroxyheptadecanedioate (9): The silyl protected diester 8 (0.3 g, 0.44 mmol) was dissolved in 1 M solution of TBAF in THF (6 mL) and the solution was kept at 40° C. for two days after which the TLC showed the completion of the reaction. The reaction mixture was diluted with water (60 mL) and extracted with ether (2×50 mL). The combined organic layers were concentrated and the thus obtained crude product was purified by column to isolate the pure product (0.097 g, 39%). $^1$H NMR (400 MHz, $CDCl_3$) δ 5.64 (dt, J=10.9, 7.4 Hz, 2H), 5.52 (dt, J=11.0, 6.8 Hz, 2H), 4.61 (d, J=6.8 Hz, 4H), 3.57 (s, 1H), 2.30 (t, J=7.5 Hz, 4H), 2.09 (q, J=7.1 Hz, 4H), 1.75-1.53 (m, 4H), 1.53-1.06 (m, 36H), 0.88 (t, J=6.8 Hz, 6H). $^{13}$C NMR (101 MHz, $CDCl_3$) δ 173.98, 135.64, 123.57, 77.54, 77.22, 76.91, 72.14, 60.41, 37.69, 34.54, 31.89, 29.70, 29.60, 29.44, 29.29, 29.07, 27.76, 25.80, 25.15, 22.82, 14.29.

Di((Z)-non-2-en-1-yl) 9-((4-(dimethylamino)butanoyl)oxy)heptadecanedioate: The alcohol 9 (0.083 g, 0.147 mmol) was dissolved in 20 mL of dichloromethane and to it dimethylaminobutyric acid hydrochloride (0.030 g, 0.176 mmol) was added followed by Hunig's base (0.045 g, 0.44 mmol) and DMAP (2 mg). To this mixture EDCI (0.034 g, 0.176 mmol) was added and the reaction mixture was stirred at room temperature overnight and the TLC (silica gel, 10% MeOH in $CH_2Cl_2$) showed complete disappearance of the starting alcohol. The reaction mixture was diluted with $CH_2Cl_2$ (40 mL) and washed with saturated $NaHCO_3$ (50 mL), water (60 mL) and brine (60 mL). The combined organic layers were dried over anhyd. $Na_2SO_4$ and solvents were removed in vacuo. The crude product thus obtained was purified by Combiflash Rf purification system (40 g silicagel, 0-10% MeOH in $CH_2Cl_2$) to isolate the pure product (0.062 g, 62%) as a colorless oil. $^1$H NMR (400 MHz, $CDCl_3$) δ 5.74-5.58 (m, 2H), 5.51 (dtt, J=9.7, 6.8, 1.3 Hz, 2H), 4.95-4.75 (m, 1H), 4.61 (d, J=6.8 Hz, 4H), 2.35-2.24 (m, 8H), 2.22 (d, J=7.9 Hz, 6H), 2.09 (q, J=6.9 Hz, 4H), 1.83-1.72 (m, 2H), 1.60 (dd, J=14.4, 7.2 Hz, 4H), 1.49 (d, J=5.7 Hz, 4H), 1.41-1.13 (m, 30H), 0.88 (t, J=6.9 Hz, 6H). $^{13}$C NMR (101 MHz, $CDCl_3$) δ 173.72, 173.36, 135.40, 123.35, 74.12, 60.18, 58.95, 45.46, 34.30, 34.11, 32.45, 31.67, 29.38, 29.35, 29.17, 29.07, 28.84, 27.53, 25.28, 24.93, 23.16, 22.59, 14.06. MW calc. for $C_{41}H_{75}NO_6$ (MH$^+$): 678.04, found: 678.5.

In another embodiment the following shorter route was used for the synthesis of the di((Z)-non-2-en-1-yl) 9-((4-(dimethylamino)butanoyl)oxy)heptadecanedioate. The commercial 9-bromonon-1-ene 10 was treated with magnesium to form the corresponding Grignard reagent which was reacted with ethylformate to give the corresponding adduct 11 which on treatment with bromobutyryl chloride to provide the bromoester 12. The bromoester 12 on treatment with $RuO_4$ provided the diacid 13. The bromodiacid 13 on treatment with dimethylamine provided the amino diacid 14. The aminodiacid 14 on coupling with the alcohol 15 provided the product in good yields.

Example 21

Scheme 21

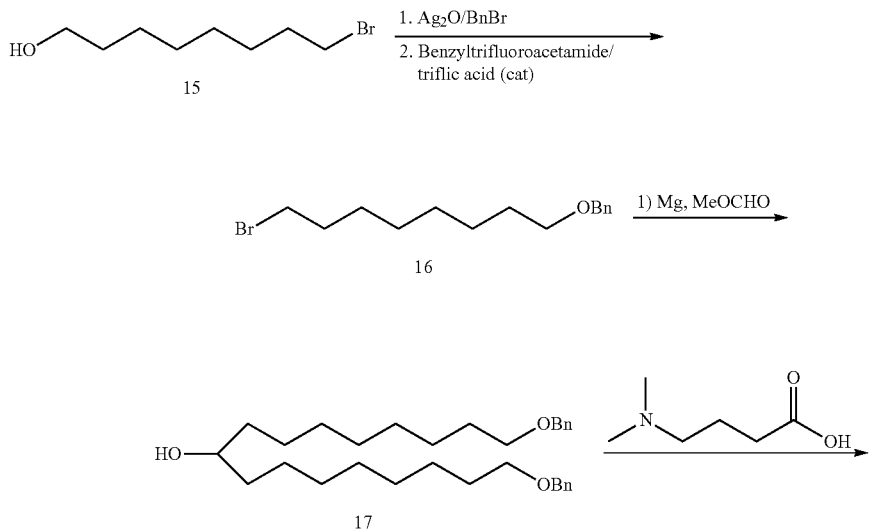

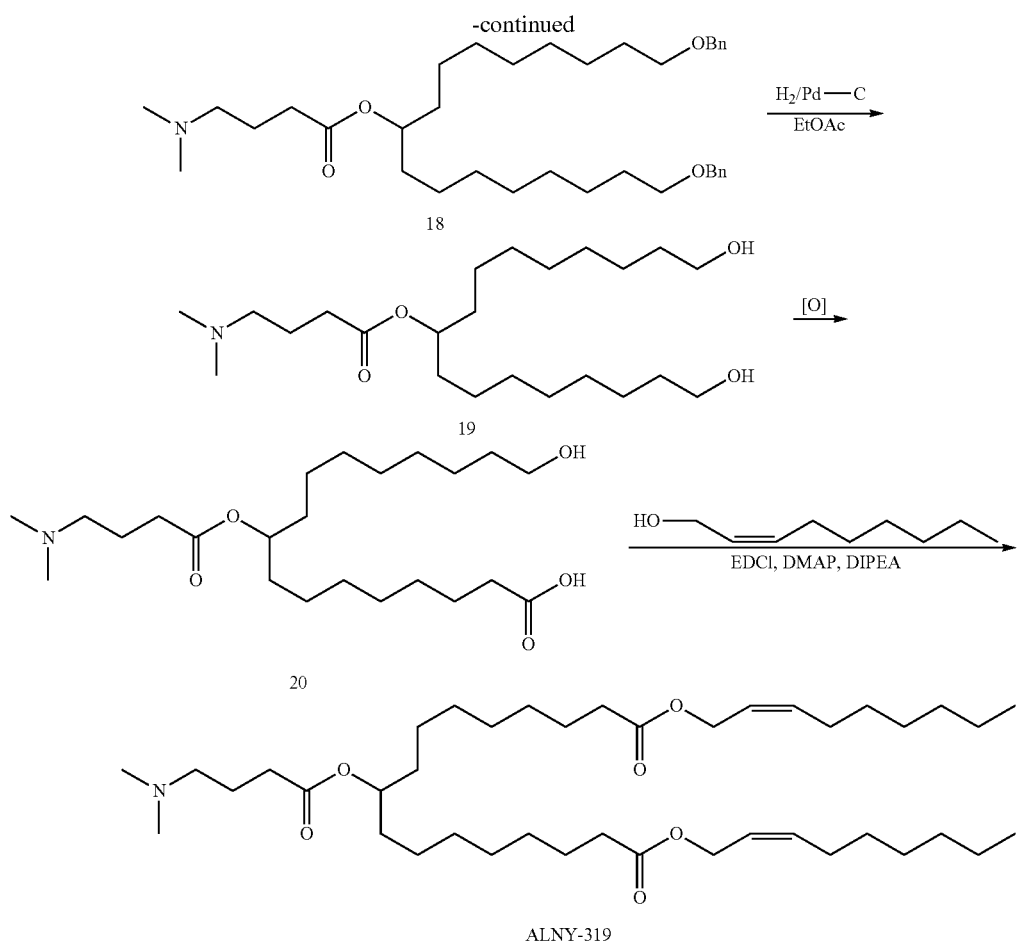
Example 22
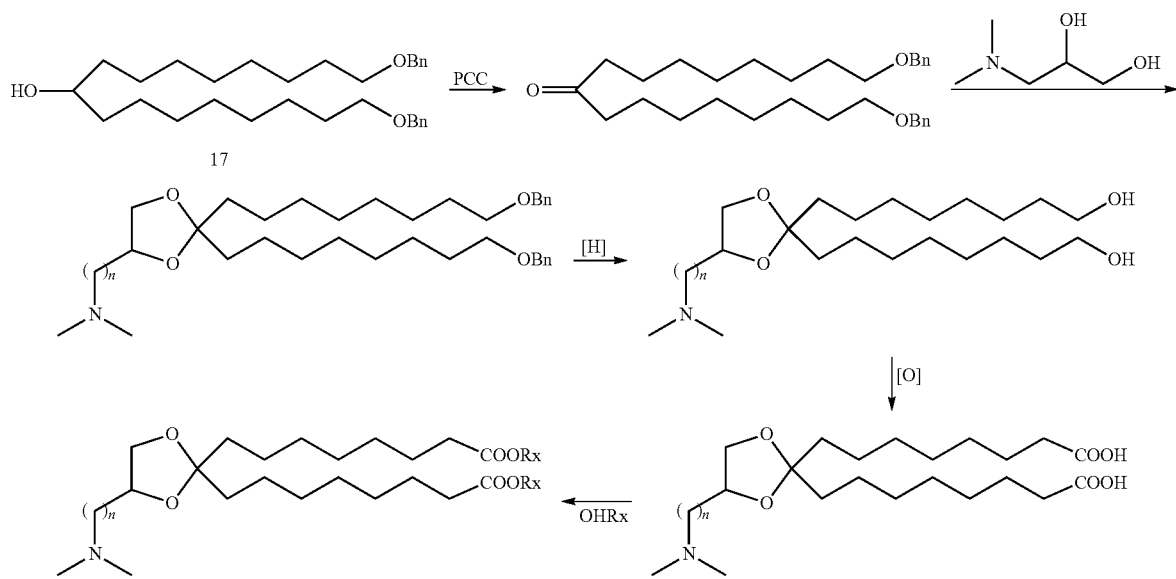
Scheme 22

Example 23
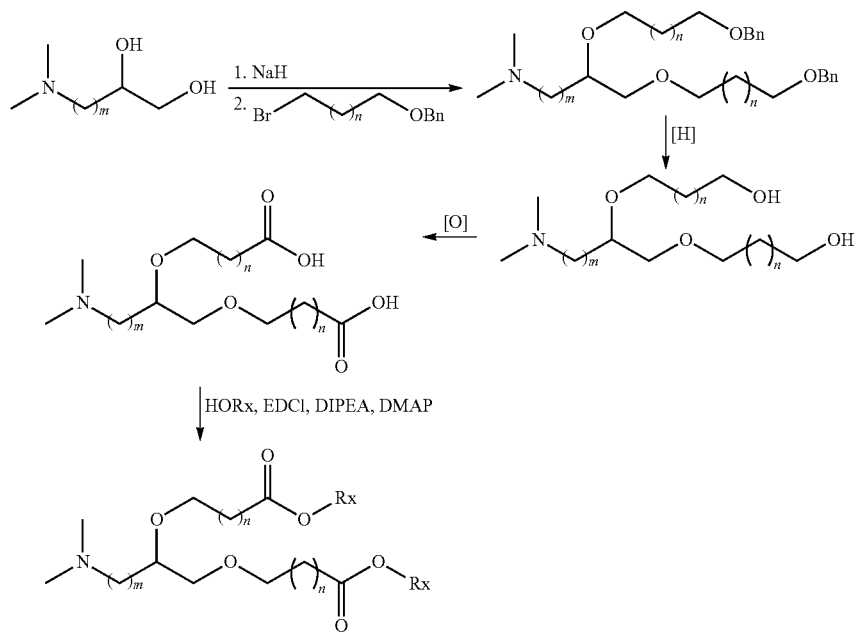
Scheme 23
Example 24
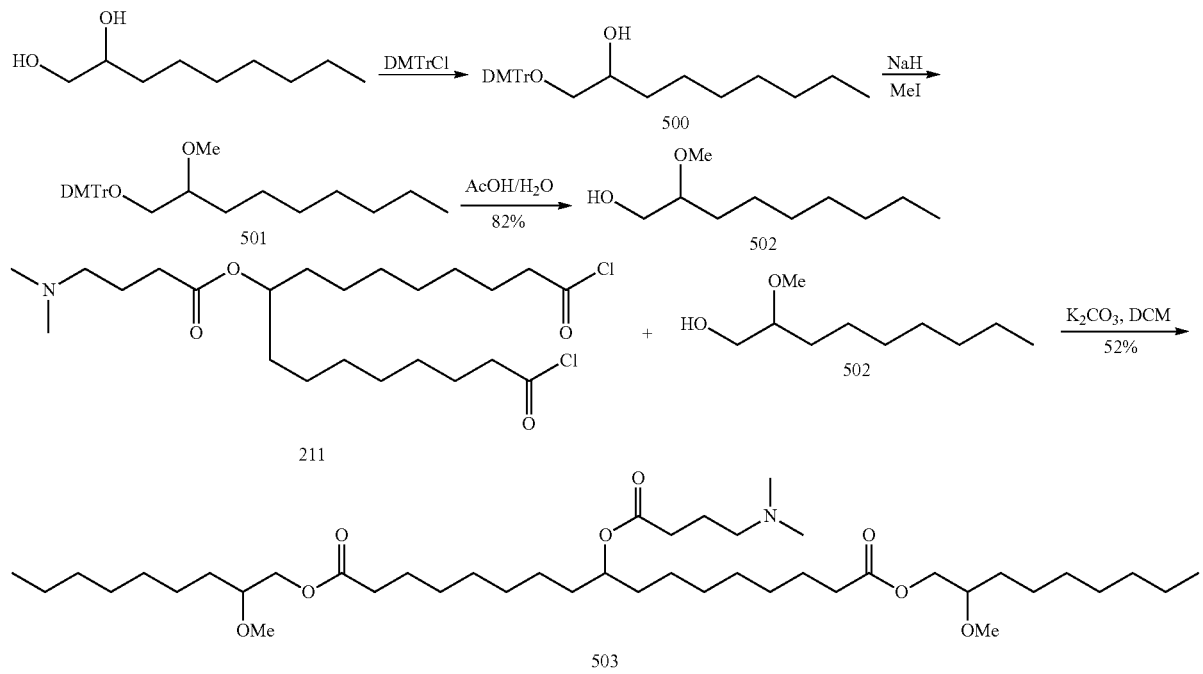
Scheme 24
Compound 501: To a stirred solution of 2-hydroxy 1-octanol 5 g (31.25 mmol), DMAP 0.38 g (3.1 mmol) in dry pyridine (100 mL) was added DMTr-Cl and stirred at room temperature for 14 h. 10 mL of water was added and extracted with ethyl acetate, washed with saturated NaHCO$_3$ and brine. The organic layer was dried over Na$_2$SO$_4$ and concentration of the solvent gave 20 g of crude product 500 which was co-evaporated with toluene twice and used for the next step without further purification. To the above crude DMTr ether in dry THF (250 mL) were added NaH and iodo methane at 0° C. and then brought to room temperature over 30 min. and then stirred for two days. 5 mL of water was added and concentrated followed by column chromatography (0-30% ethyl acetate in hexane) gave the corresponding product 501 (10.25 g, R$_f$: 0.45, 20% ethyl acetate in hexane) and 8.4 g of recovered starting material 500. $^1$H NMR (400 MHz, CDCl$_3$) δ 7.47-6.8 (m, 13H), 3.79 (s, 6H), 3.42 (s, 3H), 3.29-3.26 (m, 1H), 3.13-3.04 (m, 2H), 1.55-1.47 (m, 2H), 1.3-1.2 (m, 10H), 0.89 (t, J=6.4 Hz, 3H).

Alcohol 502: The compound 501 (10.25 g, 21.5 mmol) was dissolved in 75 mL of 80% acetic acid and stirred at room temperature for 14 h. 10 mL of methanol was added and concentrated, followed by column chromatography (0-50% ethyl acetate in hexane) yielded the expected product 502 as colorless oil (1.8 g, 82%, R$_f$: 0.3, 30% ethyl acetate in hexane). $^1$H NMR (400 MHz, CDCl$_3$) δ 3.71-3.65 (m, 1H), 3.5-3.45 (m, 1H), 3.41 (s, 3H), 3.28-3.25 (m, 1H), 1.93-1.9 (m, 1H), 1.45-1.41 (m, 2H), 1.39-1.27 (m, 10H), 0.88 (s, J=6.8 Hz, 3H).

Compound 503: Compound 503 was synthesized following general experimental procedure for compound 213. 0.3 g as pale yellow oil (52%, R$_f$=0.2, 5% methanol in dichloromethane). $^1$H NMR (400 MHz, CDCl$_3$) δ 4.87-4.84 (m, 1H), 4.18-4.00 (m, 4H), 3.4 (s, 6H), 3.37-3.19 (m, 2H), 2.34-2.26 (m, 6H), 2.2 (s, 6H), 1.8-1.6 (m, 2H), 1.63-1.2 (m, 50H), 0.88 (s, J=6.8 Hz, 6H).

Example 25

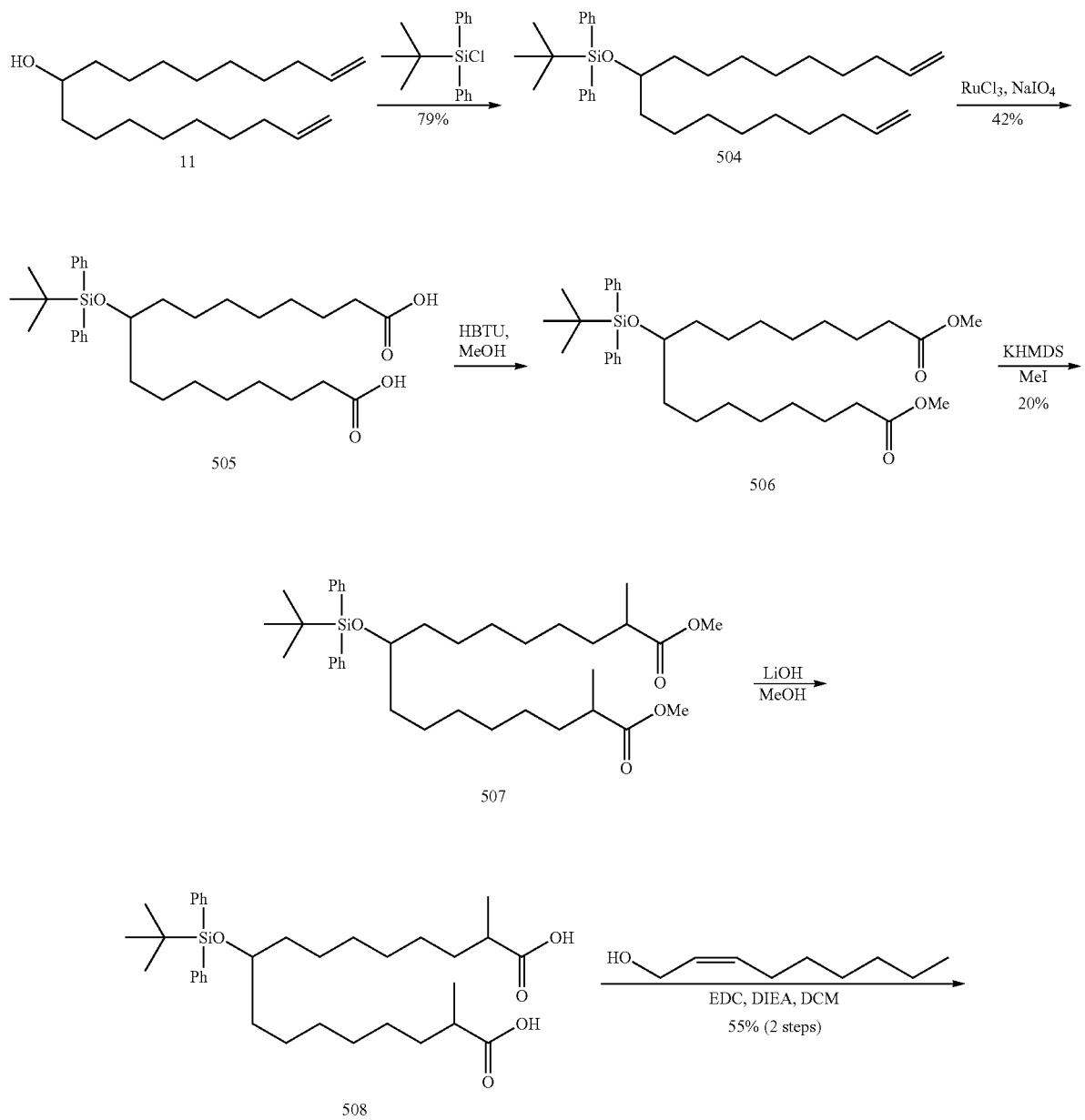

Scheme 25

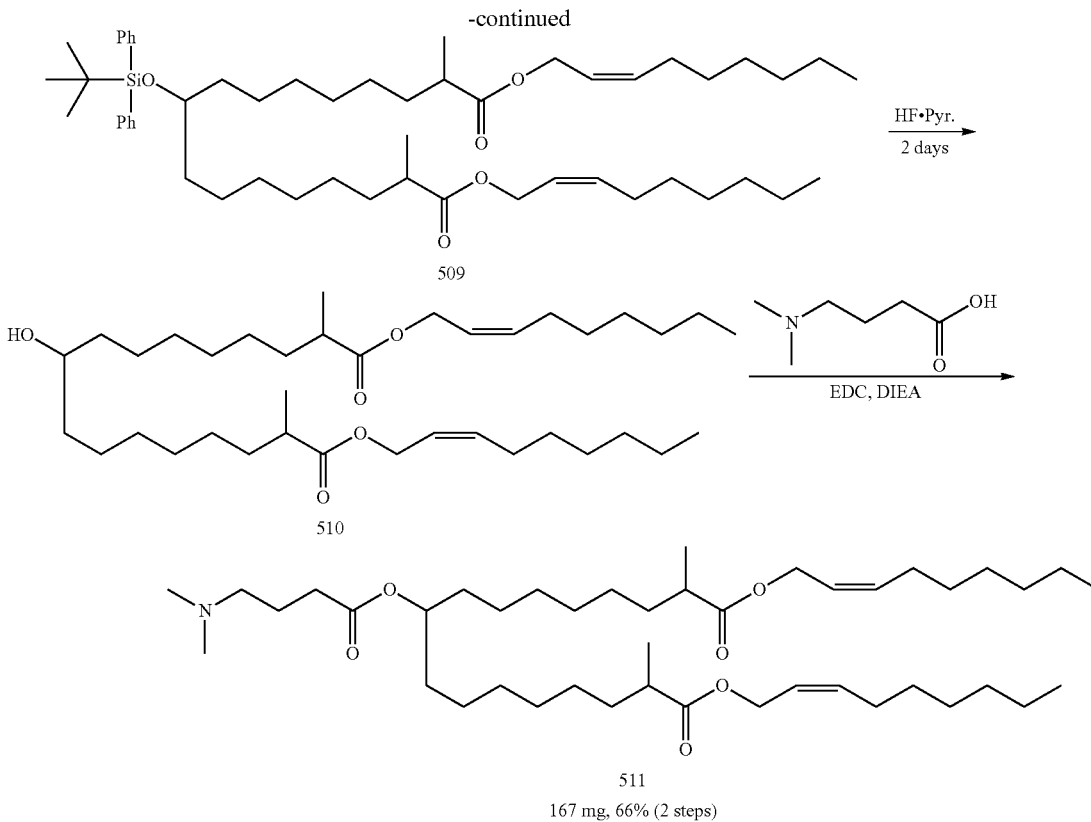

Compound 504: To a stirred solution of alcohol 11 (4.01 g, 22.25 mmol), TBDPS-Cl (12.24 g, 44.5 mmol) and DMAP (0.54 g, 4.42 mmol) was added triethyl amine (8.99 g, 90 mmol) and stirred at room temper for 14 h. To the above solution was added imidazole (1.51 g, 22.25 mmol) and continued to stir for 14 h at room temperature. 20 mL of water was added and extracted with DCM followed by washing with 2N HCl, brine and dried over anhydrous $Na_2SO_4$. Concentration of the solvent gave the crude product which was purified by column chromatography (0-10% ethyl acetate in hexane) to yield compound 504 (7.38 g, 79%, $R_f$: 0.8, 5% ethyl acetate in hexane). $^1$H NMR (400 MHz, CDCl$_3$) δ 7.68-7.66 (m, 4H), 7.43-7.33 (m, 6H), 5.86-5.76 (m, 2H), 5.02-4.91 (m, 4H), 3.73-3.67 (m, 1H), 2.04-1.99 (m, 4H), 1.42-1.08 (m, 24H), 1.05 (s, 9H).

Compound 505: To a stirred solution of diene 504 (7.38 g, 17.6 mmol) and RuCl$_3$ (0.18 g, 0.88 mmol) in 400 mL of DCM/CH$_3$CN(1:1) was added NaIO$_4$ (37.6 g, 176 mmol) dissolved in 400 mL of water drop wise around 5° C. over 30 min. and stirred at room temperature for 3 h. The organic layer was separated followed by washing with 3% Na$_2$S solution (100 mL), water (250 mL) brine and dried over anhydrous Na$_2$SO$_4$. Concentration of the solvent gave the crude product 505 (4 g, 42%, $R_f$: 0.3, 40% ethyl acetate in hexane), which was used for the next step without further purification.

Compound 506: To a stirred solution of the acid 505 (4 g, 7.22 mmol), HBTU (6.02 g, 15.88 mmol), HOBt (2.14 g, 15.88 mmol) and DMAP (88 mg, 0.72 mmol) in 75 mL of dry DCM was added 5 mL of methanol and stirred at room temperature for 14 h. 10 mL of water was added followed by extraction with DCM (3×50 mL), washing with saturated NaHCO$_3$, water, brine and dried over anhydrous Na$_2$SO$_4$. Concentration of the solvent gave the crude product which was purified by column chromatography (0-30% ethyl acetate in hexane) to yield compound 506 (2 g, 47.6%, $R_f$: 0.3, 10% ethyl acetate in hexane). $^1$H NMR (400 MHz, CDCl$_3$) δ 7.67-7.65 (m, 4H), 7.41-7.33 (m, 6H), 3.70-3.64 (m, 1H), 3.66 (s, 6H), 2.28 (t, J=7.2 Hz, 4H), 1.63-1.07 (m, 24H), 1.04 (s, 9H).

Compound 507: To a stirred solution of dimethyl ester 506 (1.0 g, 1.79 mmol) in dry THF (20 mL) were added KHMDS (0.752 g, 3.76 mmol) and methyl iodide (0.762 g, 5.37 mmol) at 0° C. and then brought to room temperature over 30 min. and stirred for 24 h. 10 mL of sat. NH$_4$Cl solution was added followed by extraction with ethyl acetate (3×50 mL), washing with water, brine and dried over anhydrous Na$_2$SO$_4$. Concentration of the solvent gave the crude product, which was purified by column chromatography (0-5% ethyl acetate in hexane) to obtain the product 507 (0.218 g, 20%, $R_f$: 0.8, 5% ethyl acetate in hexane). $^1$H NMR (400 MHz, CDCl$_3$) δ 7.68-7.65 (m, 4H), 7.41-7.33 (m, 6H), 3.70-3.67 (m, 1H), 3.67 (s, 6H), 2.43-2.38 (m, 2H), 1.59-1.07 (m, 24H), 1.13 (d, J=7.2 Hz, 6H), 1.04 (s, 9H).

Compound 509: To a stirred solution of methyl ester 507 (0.4 g, 0.66 mmol) in 10 mL of MeOH/THF (1:1) was added LiOH (0.079 g, 3.27 mmol) in 1 mL of water and stirred at room temperature for 24 h. To the above solution was added KOH (0.183 g, 3.27 mmol) in 1 mL of water and stirred for another 2 days. 2 mL of sat. NH$_4$Cl solution was added followed by extraction with ethyl acetate (3×25 mL), washing with water, brine and dried over anhydrous Na$_2$SO$_4$. Concentration of the solvent gave the crude product 508 (0.45 g, $R_f$: 0.2, 10% ethyl acetate in hexane), which was used for the next step without further purification. To a stirred solution of the above di-acid 508 (0.45 g), cis-2-

Nonen-1-ol (0.66 g, 4.6 mmol) and EDC.HCl (0.82 g, 4.6 mmol) in dry DCM (15 mL) was added DIEA (1.2 g, 9.24 mmol) and stirred at room temperature for 3 days. 10 mL of water was added followed by extraction with DCM followed by washing with 2N HCl, brine and dried over anhydrous Na$_2$SO$_4$. Concentration of the solvent gave the crude product which was purified by column chromatography (0-10% ethyl acetate in hexane) to yield compound 509 (0.3 g, 55%, R$_f$: 0.5, 3% ethyl acetate in hexane). $^1$H NMR (400 MHz, CDCl$_3$) δ 7.67-7.65 (m, 4H), 7.42-7.33 (m, 6H), 5.67-5.6 (m, 2H), 5.55-5.49 (m, 2H), 4.615 (d, J=4 Hz, 4H), 3.71-3.65 (m, 1H), 2.44-2.35 (m, 2H), 2.10 (q, J=8.0 Hz, 4H), 1.64-1.07 (m, 40H), 1.13 (d, J=8.0 Hz, 6H), 1.04 (s, 9H), 0.86 (t, J=10 Hz, 6H).

EDC.HCl (0.39 g, 2.04 mmol) and DMAP (0.06 g, 0.51 mmol) in dry DCM (10 mL) was added DIEA (0.5 g, 3.88 mmol) and stirred at room temperature for 2 days. 10 mL of water was added followed by extraction with DCM (3×25 mL), washing with saturated NaHCO$_3$, water, brine and dried over anhydrous Na$_2$SO$_4$. Concentration of the solvent gave the crude product which was purified by column chromatography (0-30% ethyl acetate in 1% TEA containing hexane) to yield compound 511 (0.167 g, 66%, R$_f$: 0.4, 10% MeOH in DCM). Molecular weight for C$_{43}$H$_{79}$NO$_6$ (M+H)$^+$ Calc. 706.59, Found 706.5.

Example 26

Scheme 26

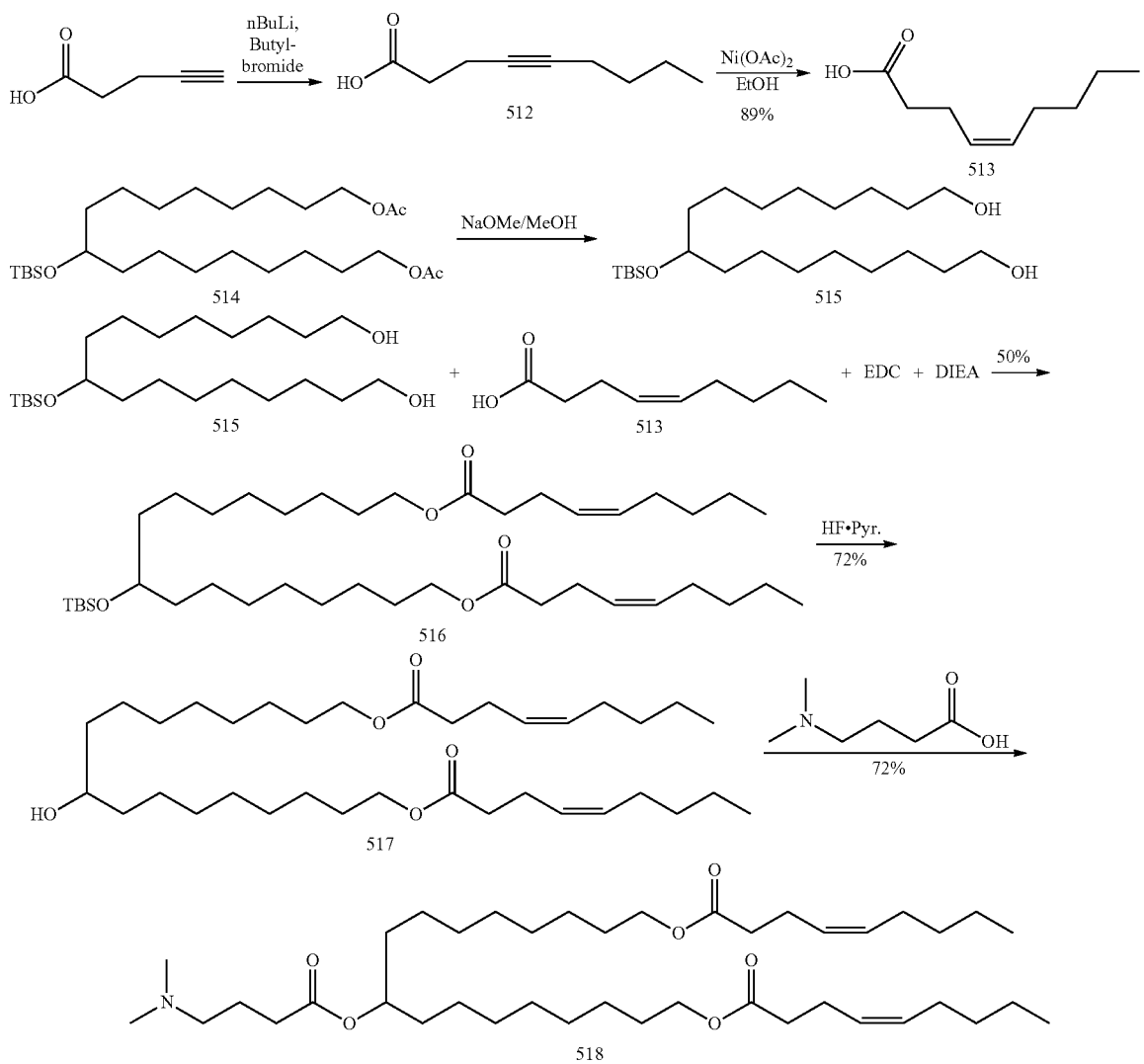

Compound 511: To a stirred solution of silyl ether 509 (0.3 g, 0.36 mmol) in dry THF were added pyridine (1 mL) and HF.Pyr., (1 mL) drop wise and stirred at 45° C. for 48 h. The solvent was evaporated and used for the next step without purification.

To a stirred solution of the above crude alcohol 510, N,N-Dimethyl amino butyric acid (0.34 g, 2.04 mmol), Compound 512: To a stirred solution of 4-Pentynoic acid in 100 mL of THF/HMPA (4:1) at −78° C. was added nBuLi (3.1 g, 49 mmol) drop wise and stirred for 30 min. Then the reaction mixture was brought to 0° C. and stirred for 2 h. Again, the reaction mixture was cooled to −78° C. and n-butyl bromide (3.07 g, 22.44 mmol) was added drop wise and stirred at room temperature for 14 h. 10 mL of sat.

NH₄Cl solution was added followed by extraction with ethyl acetate (3×25 mL), washing with water, brine and dried over anhydrous Na₂SO₄. Concentration of the solvent gave the crude product, which was purified by column chromatography (0-30% ethyl acetate in hexane) to yield compound 512 (0.4 g, R$_f$: 0.8, 30% ethyl acetate in hexane). ¹H NMR (400 MHz, CDCl₃) δ 2.59-2.55 (m, 2H), 2.49-2.44 (m, 2H), 2.16-2.11 (m, 2H), 1.49-1.34 (m, 4H), 0.9 (t, J=6.0 Hz, 3H).

Compound 513: To a suspension of Ni(OAc)₂ (0.45 g, 2.53 mmol) in EtOH (20 mL) was added NaBH₄ (0.096 g, 12.65 mmol) portion wise at room temperature and stirred for 15 min. under H₂ atm. Filtered off the solid followed by concentration of the solvent gave compound 513 (0.35 g, 88.6%, R$_f$: 0.6, 20% ethyl acetate in hexane). ¹H NMR (400 MHz, CDCl₃) δ 10.88 (br s, 1H), 5.47-5.41 (m, 1H), 5.35-5.31 (m, 1H), 2.43-2.33 (m, 4H), 2.07-2.03 (m, 2H), 1.36-2.27 (m, 4H), 0.9 (t, J=8.0 Hz, 3H).

Compound 515: To a stirred solution of di-acetate 514 (1.5 g, 3.09 mmol) in MeOH (100 mL) was added a piece of sodium metal (0.05 g, 2.17 mmol) and stirred at room temperature for 14 h. Neutralized with dry ice and concentrated followed by extraction with ethyl acetate (3×50 mL), washing with water, dried over anhydrous Na₂SO₄. Concentration of the solvent gave the crude product 515 (1.1 g, 88.7%), which was used for the next step without purification.

Compound 516: To a stirred solution of the above diol 515 (0.4 g, 1 mmol), 513 (0.341 g, 2.19 mmol), DMAP (0.1 g, 0.82 mmol) and EDC.HCl (0.57 g, 2.98 mmol) in dry DCM (15 mL) was added DIEA (5.97 g, 6 mmol) and stirred at room temperature for 2 days. 10 mL of water was added followed by extraction with ethyl acetate followed by washing with 1N HCl, brine and dried over anhydrous Na₂SO₄. Concentration of the solvent gave the crude product which was purified by column chromatography (0-10% ethyl acetate in hexane) to yield compound 516 (0.335 g, 50%, R$_f$: 0.6, 5% ethyl acetate in hexane). ¹H NMR (400 MHz, CDCl₃) δ 5.45-5.38 (m, 2H), 5.36-5.29 (m, 2H), 4.06 (t, J=8 Hz, 4H), 3.63-3.58 9m, 1H), 2.39-2.31 (m, 8H), 2.07-2.02 (m, 4H), 1.65-1.57 (m, 4H), 1.4-1.28 (m, 32H), 0.9 (t, J=6.0 Hz, 6H), 0.88 (s, 9H), 0.03 (s, 6H).

Compound 517: To a stirred solution of silyl ether 516 (0.3 g, 0.36 mmol) in dry THF (5 mL) were added pyridine (1 mL) and HF.Pyr. (1 mL) drop wise and stirred at 45° C. for 24 h. The solvent was evaporated followed by purification by column chromatography gave product 517 (0.2 g, 72%, R$_f$: 0.4, 10% ethyl acetate in hexane). ¹H NMR (400 MHz, CDCl₃) δ 5.43-5.36 (m, 2H), 5.34-5.27 (m, 2H), 4.04 (t, J=8 Hz, 4H), 3.59-3.53 (m, 1H), 2.37-2.3 (m, 8H), 2.05-2.0 (m, 4H), 1.61-1.29 (m, 37H), 0.88 (t, J=8.0 Hz, 6H).

Compound 518: To a stirred solution of the alcohol 517 (0.2 g, 0.355 mmol), N,N-Dimethyl amino butyric acid (0.36 g, 2.14 mmol), EDC.HCl (0.406 g, 2.14 mmol) and DMAP (0.043 g, 0.36 mmol) in dry DCM (10 mL) was added DIEA (0.55 g, 4.26 mmol) and stirred at room temperature for 2 days. 10 mL of water was added followed by extraction with DCM (3×25 mL), washing with saturated NaHCO₃, water, brine and dried over anhydrous Na₂SO₄. Concentration of the solvent gave the crude product which was purified by column chromatography (0-30% ethyl acetate in 1% TEA containing hexane) to yield compound 518 (0.172 g, 72%, R$_f$: 0.2, 5% MeOH in DCM). H NMR (400 MHz, CDCl₃) δ 5.43-5.36 (m, 2H), 5.32-5.27 (m, 2H), 4.87-4.83 (m, 1H), 4.03 (t, J=6 Hz, 4H), 2.36-2.2 (m, 6H), 2.32 (s, 6H), 2.03-1.25 (m, 40H), 0.88 (t, J=6.0 Hz, 6H).

Example 27

Scheme 27

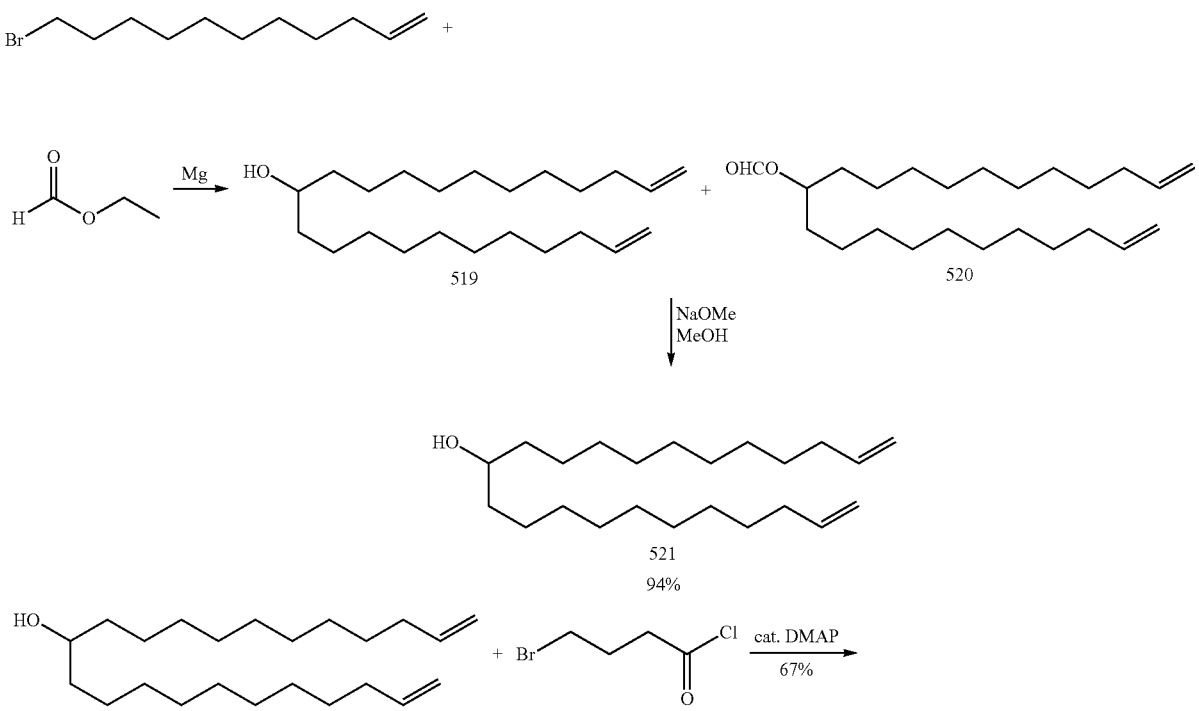

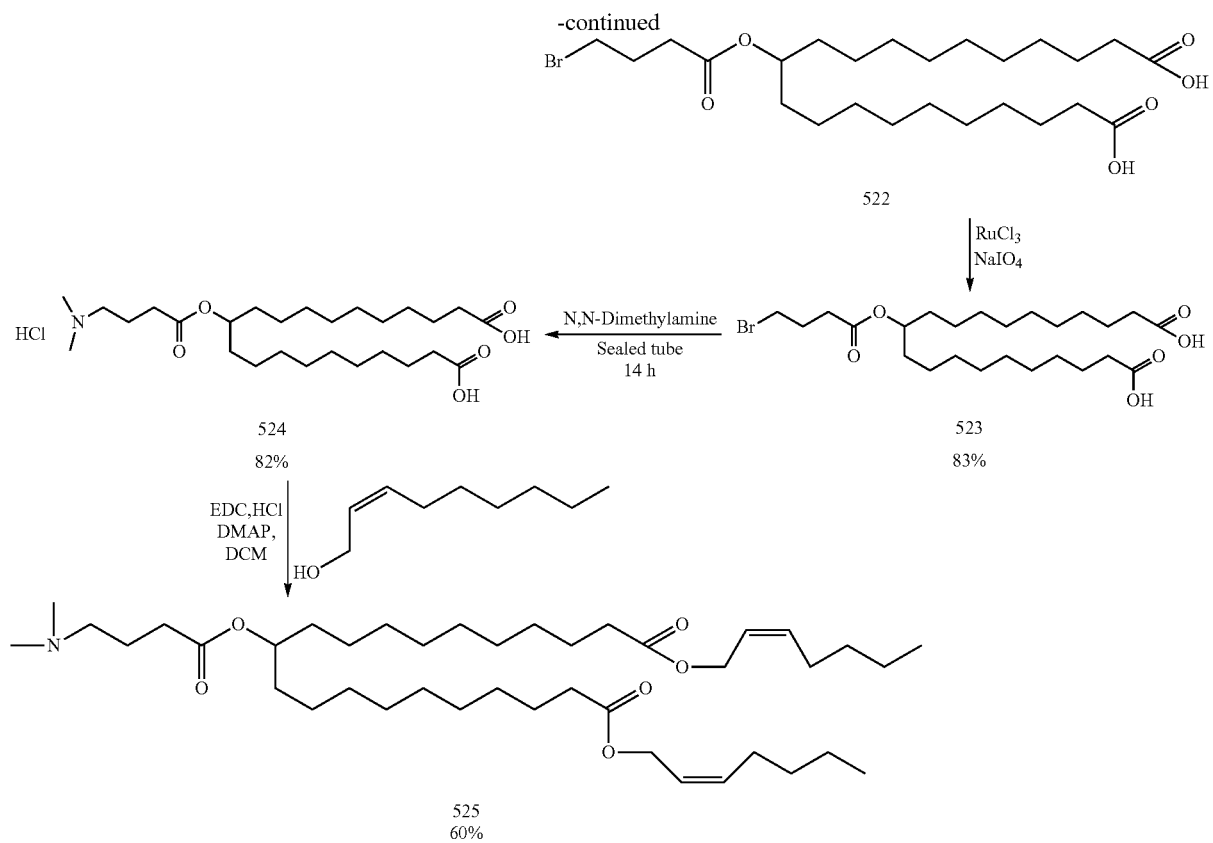

Compound 521: To a suspension of Mg in Et₂O was added alkyl bromide (25 g, 107.7 mmol) drop wise at 40° C. over one hour. Ethyl formate was added to the above reaction mixture at 0-5° C. and then the reaction mixture was stirred at room temperature for 14 h. The reaction mixture was poured onto the ice cold sat. NH₄Cl solution followed by extraction with Et₂O (3×250 mL), washing with water, brine and dried over anhydrous Na₂SO₄. Concentration of the solvent gave the crude product, which was re-dissolved in MeOH (250 mL) and a small piece of sodium (0.1 g) was added and stirred at room temperature for 14 h. The solvent was evaporated and 100 mL of water was added followed by filtration of the solid, washing with water (2×100 mL) gave pale yellow powder 521 (17 g, 94%, %, $R_f$: 0.8, 10% ethyl acetate in hexane). ¹H NMR (400 MHz, CDCl₃) δ 5.84-5.74 (m, 2H), 5.0-4.89 (m, 4H), 3.64-3.49 (m, 1H), 2.04-1.99 (m, 4H), 1.79 (br s, 1H), 1.44-1.23 (m, 32H).

Compound 522: To a stirred solution of 521 (10 g, 29.73 mmol) and DMAP (0.1 g, 0.82 mmol) in dry DCM (50 mL) was added 4-bromo butyryl chloride (6.56 g, 35.68 mmol) and stirred at room temperature for 14 h. 5 mL of saturated NaHCO₃ was added and the organic layer was separated and dried over anhydrous Na₂SO₄. Concentration of the solvent gave the crude product which was purified by column chromatography (0-10% ethyl acetate in hexane) to yield compound 522 (9.6 g, 66.7%, $R_f$: 0.9, 5% ethyl acetate in hexane).

Compound 524: Oxidation was carried out to get compound 523 (8.6 g, 83.5%, $R_f$: 0.1, 5% MeOH in DCM) following same experimental procedure as for compound 505. This crude material was dissolved in 2N N,N-dimethyl amine in THF (20 mL) and heated to 60° C. in a sealed tube for 14 h. Concentrated the reaction mixture and then pH of the reaction mixture was brought to 3. This mixture was freeze-dried to obtain compound 524 as HCl salt (4 g, 82%). Molecular weight for C27H51NO6 (M+H)⁺ Calc. 486.37, Found 486.2. H NMR (400 MHz, CDCl₃) δ 4.94-4.89 (m, 1H), 3.32-3.3 (m, 2H), 3.2-3.16 (m, 2H), 2.91 (s, 6H), 2.47 (t, J=8 Hz, 2H), 2.28 (t, J=8 Hz, 4H), 2.05-1.97 (m, 2H), 1.61-1.56 (8H), 1.4-1.25 (m, 22H).

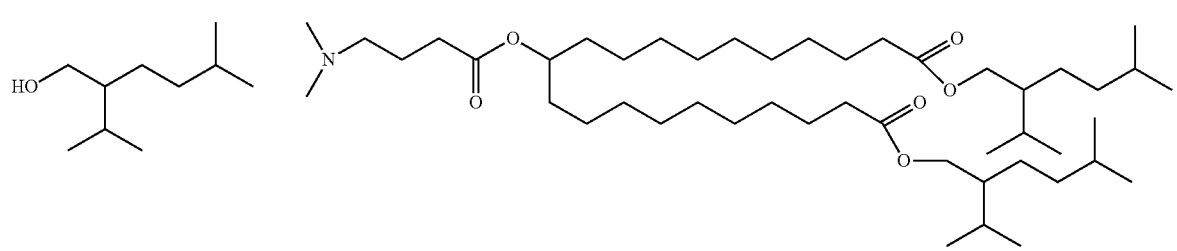

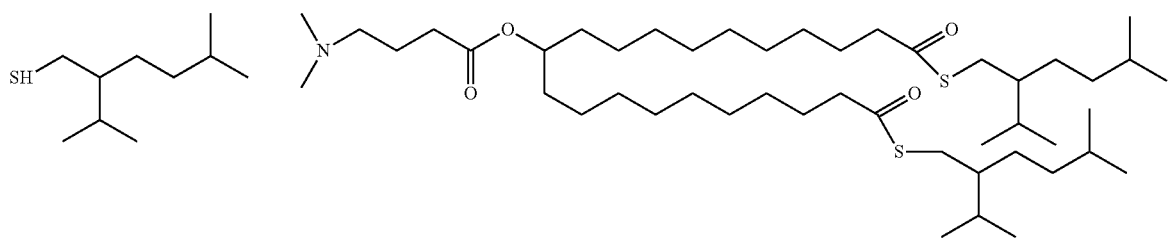

526s

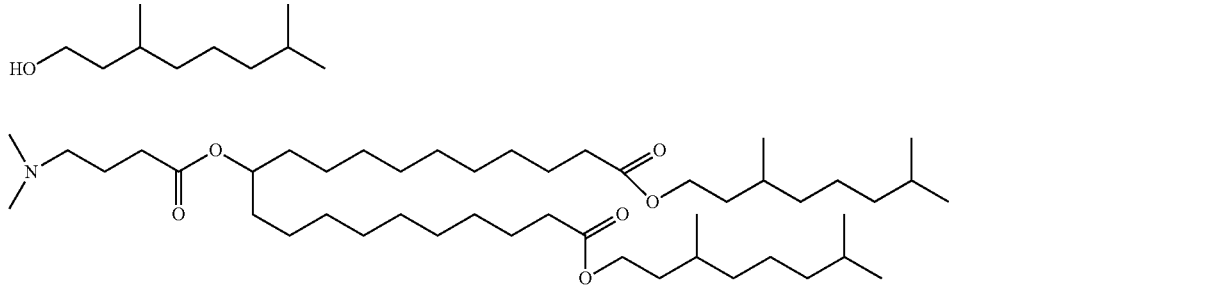

527

527s

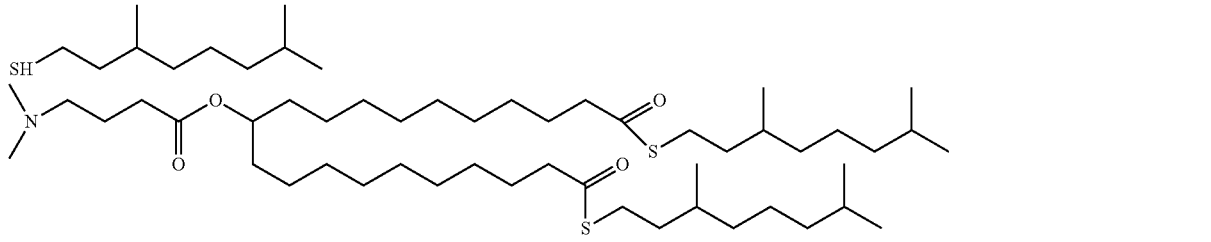

528

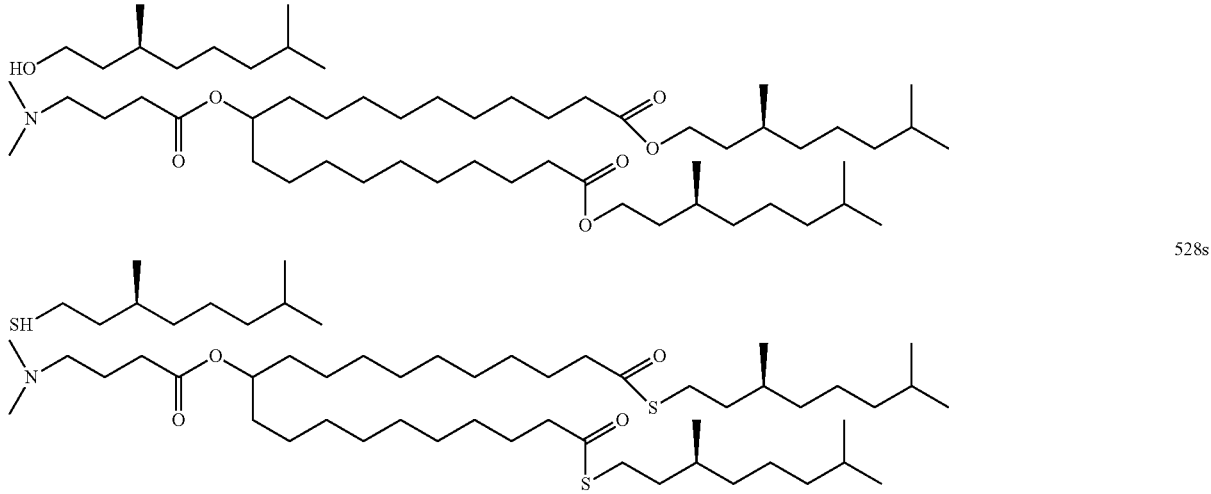

528s

Synthesis of Ester 525, 526, 527 and 528:

The title compounds were synthesized following the experimental procedure as for compound 516.

Compound 525: (0.75 g, 60%, $R_f$: 0.3, 5% MeOH in DCM). H NMR (400 MHz, CDCl$_3$) δ 5.65-5.59 (m, 2H), 5.53-5.47 (m, 2H), 4.87-4.81 (m, 1H), 4.595 (d, J=4.0 Hz, 4H), 2.43-2.25 (m, 8H), 2.2 (s, 6H), 2.1-2.03 (m, 4H), 1.81-1.73 (m, 2H), 1.61-1.56 (m, 4H), 1.48-1.47 (m, 4H), 1.36-1.23 (m, 32H), 0.86 (t, J=8.0 Hz, 6H).

Compound 526: (0.358 g, 60.9%, $R_f$: 0.5, 5% MeOH in DCM). H NMR (400 MHz, CDCl$_3$) δ 4.87-4.81 (m, 1H), 4.07-3.95 (m, 4H), 2.32-2.24 (m, 6H), 2.2 (s, 6H), 1.80-1.69 (m, 4H), 1.6-1.14 (m, 46H), 0.88-0.84 (m, 24H).

Compound 527: (0.258 g, 56.8%, $R_f$: 0.5, 5% MeOH in DCM). Molecular weight for C47H91NO6 (M+H)$^+$ Calc. 766.23; Found: 766.7. $^1$H NMR (400 MHz, CDCl$_3$) δ 4.86-4.80 (m, 1H), 4.12-4.02 (m, 4H), 2.31-2.23 (m, 8H), 2.19 (s, 6H), 1.80-1.72 (m, 2H), 1.66-1.06 (m, 52H), 0.87 (d, J=8.0 Hz, 6H), 0.84 (d, J=8.0 Hz, 12H).

Compound 528: (0.3 g, 68.1%, $R_f$: 0.5, 5% MeOH in DCM). Molecular weight for C47H91NO6 (M+H)$^+$ Calc. 766.23; Found: 766.7. $^1$H NMR (400 MHz, CDCl$_3$) δ 4.86-4.80 (m, 1H), 4.12-4.02 (m, 4H), 2.31-2.21 (m, 8H), 2.19 (s, 6H), 1.79-1.72 (m, 2H), 1.66-0.98 (m, 52H), 0.87 (d, J=8.0 Hz, 6H), 0.835 (d, J=4.0 Hz, 12H).

Example 28
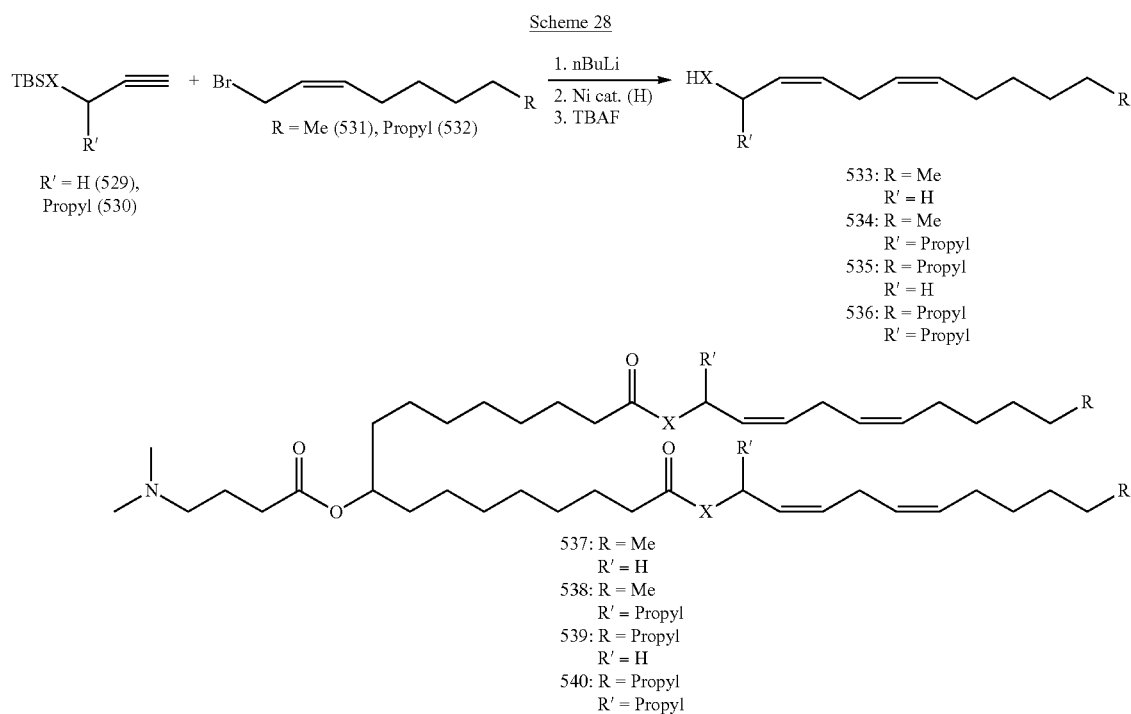
X = O or S
Synthesis of compounds 533, 534, 535 and 536: The title compounds (1 mmol) are synthesized following the experimental procedure of compound 513 except de-silylation step and it is done using TBAF in THF at room temperature.
Synthesis of compounds 537, 538, 539 and 540: The title compounds (1 mmol) are synthesized following the experimental procedure of compound 525.
Example 29
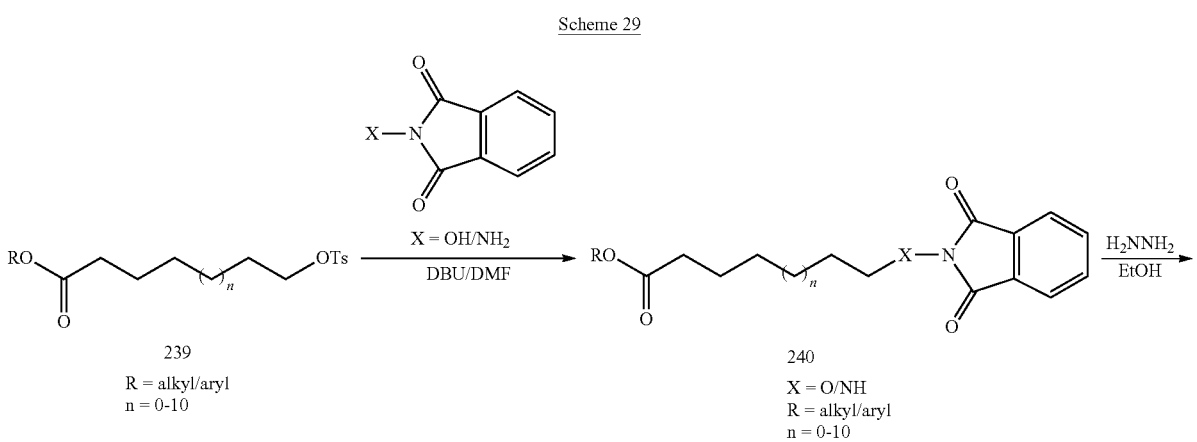

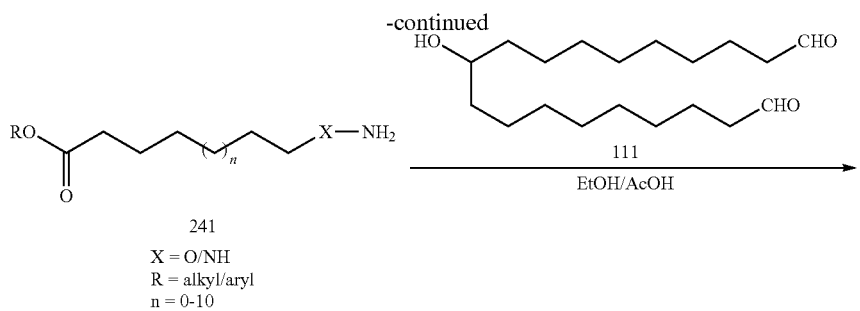
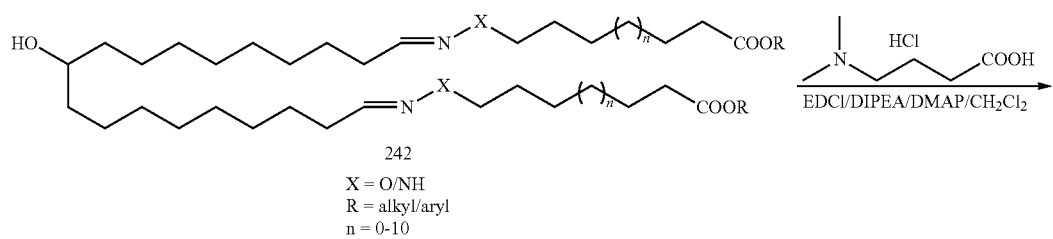
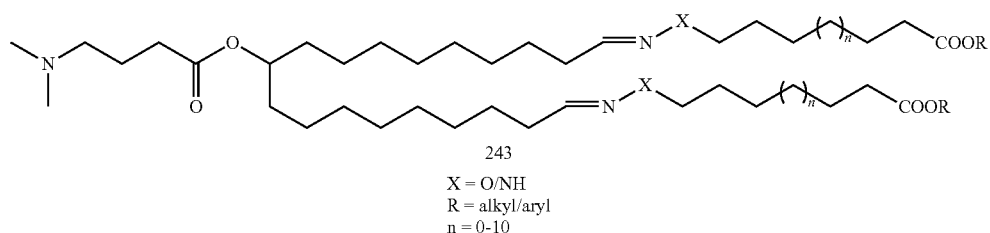
Compound 243 (X═O/NH, R=alkyl/aryl) can be synthesized as shown in Scheme 16-2. Tosyl group of 239 can be replaced with phthalimide group by nucleophilic substitution. After deprotection followed by coupling with 111 under acidic conditions, 242 can be synthesized. Standard esterification gives cationic lipid 243 and its analogs.
Example 30: Synthesis of Ester-Containing Lipids
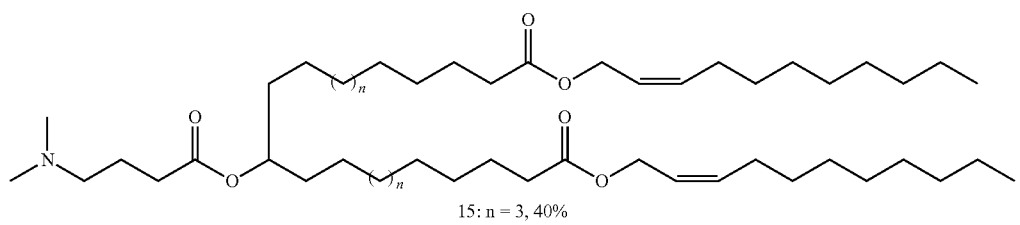
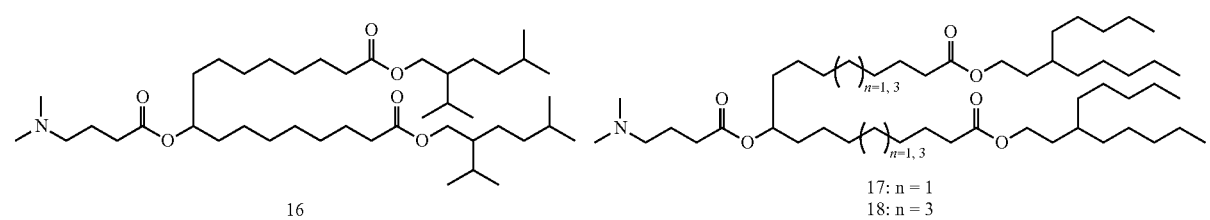

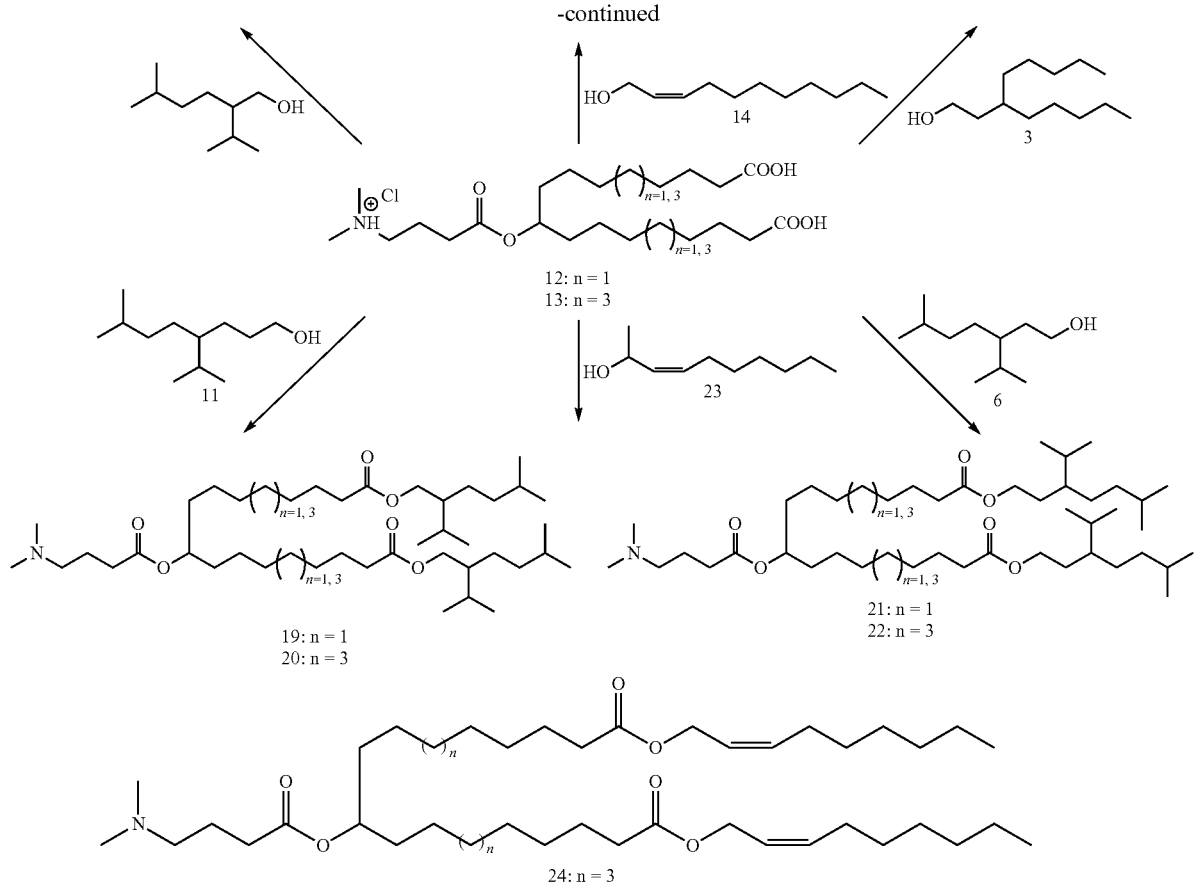

Compound 15: Compound 13 (503 mg, 1.0 mmol) was treated with 14 (469 mg, 3.0 mmol) in the presence of EDCI (2.30 g, 12.0 mmol), DMAP (235 mg, 1.92 mmol) and DIEA (8.34 mL, 47.9 mmol) in $CH_2Cl_2$ (50 mL) for 14 h. Aqueous work-up then column chromatography gave compound 15 (1.22 g, 1.54 mmol, 40%).

Molecular weight for $C_{49}H_{92}NO_6$ $(M+H)^+$ Calc. 790.6925, Found 790.7.

Compound 16: This compound was synthesized from 13 and tetrahydrolavandulol using a procedure analogous to that described for compound 15. Yield: 0.358 g, 61%. $^1H$ NMR (400 MHz, $CDCl_3$) δ 4.87-4.81 (m, 1H), 4.07-3.95 (m, 4H), 2.32-2.24 (m, 6H), 2.2 (s, 6H), 1.80-1.69 (m, 4H), 1.6-1.14 (m, 46H), 0.88-0.84 (m, 24H).

Compound 17: This compound was synthesized from 12 (1.0 g, 2.15 mmol) and 3 (1.03 g, 5.16 mmol) using a procedure analogous to that described for compound 15.

Yield: 856 mg (50%). $^1H$ NMR (400 MHz, $CDCl_3$) δ 4.91-4.79 (m, 1H), 4.08 (t, J=7.1 Hz, 4H), 2.35-2.25 (m, 14H), 1.89-1.76 (m, 2H), 1.67-1.13 (m, 62H), 0.88 (t, J=7.0 Hz, 12H). $^{13}C$ NMR (100 MHz, $CDCl_3$) δ 174.08, 74.45, 63.08, 45.27, 34.76, 34.56, 34.28, 33.70, 32.61, 32.39, 29.54, 29.36, 29.28, 26.36, 25.47, 25.13, 22.83, 14.26. Molecular weight for $C_{49}H_{96}NO_6$ $(M+H)^+$ Calc. 794.7238, Found 794.6.

Compound 18: This compound was synthesized from 13 (1.0 g, 2.15 mmol) and 3 (1 g) using a procedure analogous to that described for compound 15.

Yield: 1 g (59%). $^1H$ NMR (400 MHz, $CDCl_3$) δ 4.94-4.74 (m, 1H), 4.17-3.85 (m, 4H), 2.46-2.19 (m, 12H), 1.93-1.79 (m, 2H), 1.74-1.45 (m, 10H), 1.37 (d, J=20.2 Hz, 2H), 1.35-1.13 (m, 44H), 0.88 (t, J=6.9 Hz, 12H). $^{13}C$ NMR (101 MHz, $CDCl_3$) δ 174.19, 77.53, 77.21, 76.90, 63.12, 34.81, 34.66, 34.35, 33.76, 32.66, 32.45, 29.76, 29.73, 29.63, 29.48, 29.39, 26.42, 25.57, 25.23, 22.89, 14.32. Molecular weight for $C_{53}H_{103}NO_6$ $(M+H)^+$ Calc. 850.38, Found 850.7.

Compound 19: This compound was synthesized from 12 and 11 using a procedure analogous to that described for compound 15.

Yield: 860 mg (51%). $^1H$ NMR (400 MHz, $CDCl_3$) δ 4.90-4.81 (m, 1H), 4.04 (t, J=6.8 Hz, 4H), 2.37-2.17 (m, 14H), 1.84-1.06 (m, 48H), 0.93-0.78 (m, 24H). $^{13}C$ NMR (100 MHz, $CDCl_3$) δ 174.06, 74.35, 65.51, 64.91, 59.05, 45.51, 43.77, 37.10, 34.55, 34.29, 32.55, 29.54, 29.37, 29.34, 29.28, 28.58, 28.19, 26.99, 26.74, 25.47, 25.15, 22.90, 22.82, 19.60, 19.41, 19.28. Molecular weight for $C_{47}H_{92}NO_6$ $(M+H)^+$ Calc. 766.6925, Found 766.5.

Compound 20: This compound was synthesized from 13 and 11 using a procedure analogous to that described for compound 15.

$^1H$ NMR (400 MHz, $CDCl_3$) δ 4.86 (p, J=6.2 Hz, 1H), 4.04 (t, J=6.7 Hz, 4H), 2.38-2.17 (m, 14H), 1.84-1.07 (m, 56H), 0.93-0.76 (m, 24H). $^{13}C$ NMR (100 MHz, $CDCl_3$) δ 174.11, 173.46, 74.44, 64.90, 59.06, 45.51, 43.77, 37.11, 34.59, 34.32, 32.57, 29.71, 29.67, 29.57, 29.43, 29.34, 28.58, 28.20, 27.00, 26.75, 25.51, 25.20, 22.90, 22.82, 19.41, 19.28. Molecular weight for $C_{51}H_{100}NO_6$ $(M+H)^+$ Calc. 822.7551, Found 822.6.

Compound 21: This compound was synthesized from 12 and 6 using a procedure analogous to that described for compound 15.

$^1$H NMR (400 MHz, CDCl$_3$) δ 4.91-4.78 (m, 1H), 4.15-3.98 (m, 4H), 2.39-2.18 (m, 14H), 1.84-1.11 (m, 44H), 0.92-0.77 (m, 24H). $^{13}$C NMR (100 MHz, CDCl$_3$) δ 174.06, 173.44, 74.36, 63.73, 59.03, 45.48, 41.00, 36.98, 34.56, 34.29, 32.54, 29.60, 29.54, 29.49, 29.36, 29.28, 28.52, 25.47, 25.13, 23.15, 22.85, 22.81, 19.49, 18.89. Molecular weight for C$_{45}$H$_{88}$NO$_6$ (M+H)$^+$ Calc. 738.6612, Found 738.6.

Compound 22: This compound was synthesized from 13 and 6 using a procedure analogous to that described for compound 15.

Yield: 900 mg (57%). $^1$H NMR (400 MHz, CDCl$_3$) δ 4.92-4.78 (m, 1H), 4.15-3.91 (m, 4H), 3.33-3.08 (m, 1H), 2.36-2.15 (m, 14H), 1.79 (dq, J=14.3, 7.2 Hz, 2H), 1.74-1.55 (m, 8H), 1.55-1.37 (m, 9H), 1.35-0.95 (m, 36H), 0.96-0.61 (m, 27H). $^{13}$C NMR (101 MHz CDCl$_3$) δ 174.16, 173.52, 77.54, 77.22, 76.91, 74.48, 63.76, 59.10, 45.55, 42.02, 41.04, 38.75, 37.09, 37.02, 34.65, 34.36, 32.62, 30.71, 29.75, 29.72, 29.64, 29.62, 29.53, 29.48, 29.44, 29.38, 28.56, 28.45, 25.56, 25.23, 23.59, 23.23, 22.90, 22.86, 19.54, 19.03, 18.94. Molecular weight for C$_{49}$H$_{95}$NO$_6$ (M+H)$^+$ Calc. 794.2817, Found 794.7.

Compound 24: This compound was synthesized from 13 and 23 using a procedure analogous to that described for compound 15.

Yield: 0.567 g (30%). $^1$H NMR (400 MHz, CDCl$_3$) δ 4.85 (p, J=6.1 Hz, 1H), 4.20-3.93 (m, 4H), 2.41-2.18 (m, 13H), 1.92-1.72 (m, 2H), 1.56 (ddd, J=27.4, 16.4, 5.8 Hz, 12H), 1.39 (s, 2H), 1.25 (s, 54H), 0.91 (dt, J=13.7, 6.4 Hz, 11H). $^{13}$C NMR (101 MHz, CDCl$_3$) δ 174.18, 173.51, 77.54, 77.23, 76.91, 74.50, 63.12, 59.10, 45.55, 34.81, 34.66, 34.38, 33.76, 32.67, 32.62, 32.45, 29.77, 29.73, 29.64, 29.49, 29.39, 26.42, 25.57, 25.24, 23.23, 22.89, 14.32. Molecular weight for C$_{47}$H$_{88}$NO$_6$ (M+H)$^+$ Calc. 762.6612, Found 762.5.

Example 31: Synthesis of Alcohol Components

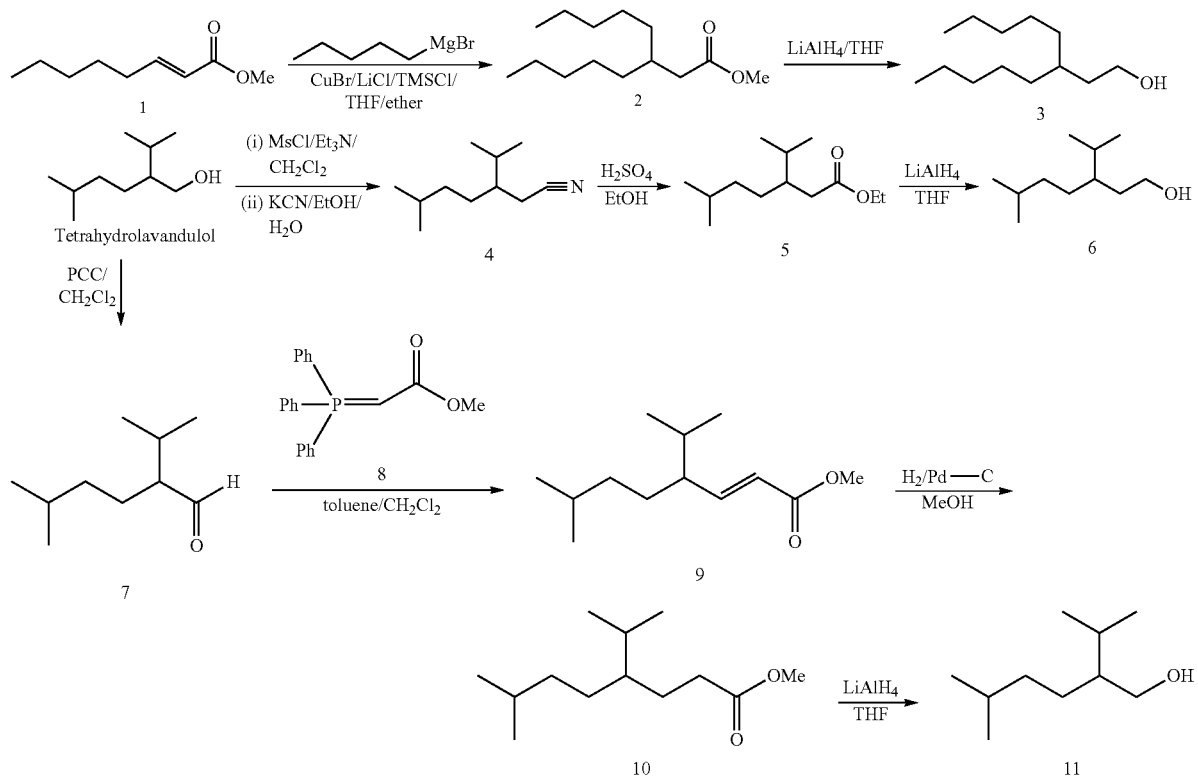

Compound 2: Compound 2 was synthesized from 1 using a procedure analogous to that described in Journal of the Organic Chemistry, 2009, 1473. $^1$H NMR (400 MHz, CDCl$_3$) δ 3.66 (s, 3H), 2.23 (d, J=6.9 Hz, 2H), 1.84 (brs, 1H), 1.27 (d, J=11.5 Hz, 16H), 0.88 (t, J=6.8 Hz, 6H). $^{13}$C NMR (100 MHz, CDCl$_3$) δ 174.29, 51.49, 39.25, 35.22, 34.00, 32.24, 26.34, 22.77, 14.22.

Compound 3: To a suspension of LiAlH$_4$ (2.84 g, 74.9 mmol) in THF (85 mL) was added a solution of compound 2 (8.55 g, 37.4 mmol) in THF (25 mL). The reaction mixture was refluxed overnight. Aqueous workup then column chromatography gave pure compound 3 (7.35 g, 36.7 mmol, 98%) as a colorless oil. $^1$H NMR (400 MHz, CDCl$_3$) δ 3.66 (t, J=7.0 Hz, 2H), 1.59-1.12 (m, 19H), 0.88 (t, J=6.9 Hz, 6H).

Compound 4: Tetrahydrolavandulol (10.1 g, 63.8 mmol) was treated with methansulfonyl chloride (6.38 mL) in CH$_2$Cl$_2$ (200 mL) and Et$_3$N (17.6 mL). Aqueous workup gave the crude mesylate, which was treated with KCN (4.98 g, 76.5 mmol) in EtOH (90 mL) and H$_2$O (10 mL). Aqueous workup then column chromatography gave pure compound 4 (8.36 g, 50.0 mmol, 72%) as a colorless oil.

$^1$H NMR (400 MHz, CDCl$_3$) δ 2.38-2.23 (m, 2H), 1.86-1.78 (m, 1H), 1.59-1.42 (m, 3H), 1.40-1.07 (m, 3H), 0.93-0.89 (m, 12H). $^{13}$C NMR (100 MHz, CDCl$_3$) δ 119.73, 41.69, 36.46, 30.10, 28.44, 28.33, 22.82, 22.59, 19.62, 19.11, 19.05.

Compound 6: The cyano derivative 4 was converted to the ethyl ester under acidic conditions to give compound 5 and the ester was reduced by LiAlH$_4$ in THF to give compound 6.

Compound 7: Tetrahydrolavandulol (98.1 g, 51.2 mmol) was oxidized with PCC (16.6 g, 76.8 mmol) in CH$_2$Cl$_2$ (200 mL). Aqueous workup then column chromatography gave pure compound 7 (6.19 g, 39.6 mmol, 77%) as a colorless oil.

$^1$H NMR (400 MHz, CDCl$_3$) δ 9.60 (d, J=3.1 Hz, 1H), 2.05-1.79 (m, 1H), 1.71-1.36 (m, 4H), 1.23-1.04 (m, 2H), 1.02-0.82 (m, 12H).

Compound 9: To a solution of compound 7 (2.0 g, 12.8 mmol) in toluene (40 mL) and CH$_2$Cl$_2$ (18 mL) and was added 8 (3.96 g, 11.8 mmol). The mixture was heated at 70° C. overnight. Column chromatography gave pure compound 9 (1.40 g, 6.59 mmol, 51%) as a colorless oil.

$^1$H NMR (400 MHz, CDCl$_3$) δ 6.77 (dd, J=15.6, 9.9 Hz, 1H), 5.76 (d, J=15.6 Hz, 1H), 3.73 (s, 3H), 1.97-1.83 (m, 1H), 1.72-1.64 (m, 1H), 1.54-1.40 (m, 2H), 1.37-1.22 (m, 1H), 1.18-0.97 (m, 2H), 0.94-0.78 (m, 12H). $^{13}$C NMR (100 MHz, CDCl$_3$) δ 167.19, 152.54, 121.70, 51.53, 49.66, 36.95, 31.76, 29.49, 28.29, 22.92, 22.54, 20.84, 19.24.

Compound 10: To a solution of compound 9 (1.0 g, 4.71 mmol) in MeOH (15 mL) was added Pd—C (125 mg). The mixture was stirred under H$_2$ atmosphere overnight. The mixture was filtered over Celite then evaporated to give pure compound 10 (924 mg, 4.31 mmol, 92%) as a colorless oil.

$^1$H NMR (400 MHz, CDCl$_3$) δ 3.67 (s, 3H), 2.41-2.16 (m, 2H), 1.74-1.57 (m, 2H), 1.57-1.42 (m, 2H), 1.33-1.02 (m, 5H), 0.88-0.83 (m, 12H). $^{13}$C NMR (100 MHz, CDCl$_3$) δ 174.78, 51.62, 43.71, 36.97, 32.69, 29.23, 28.56, 27.94, 25.92, 22.85, 22.79, 19.32, 19.19.

Compound 11: To a suspension of LiAlH$_4$ (444 mg, 11.7 mmol) in THF (12 mL) was added a solution of compound 10 (1.25 g, 5.83 mmol) in THF (8 mL). The reaction mixture was refluxed overnight. Aqueous workup gave the crude compound 11 (1.1 g) as a colorless oil.

$^1$H NMR (400 MHz, CDCl$_3$) δ 3.63 (t, J=6.7 Hz, 2H), 1.74-1.66 (m, 1H), 1.60-1.45 (m, 3H), 1.37-1.05 (m, 7H), 0.88-0.82 (m, 12H). $^{13}$C NMR (100 MHz, CDCl$_3$) δ 63.75, 44.00, 37.16, 31.22, 29.40, 28.61, 28.28, 26.62, 22.90, 22.82, 19.43, 19.28.

Example 32: Synthesis of Ester-Containing Lipids

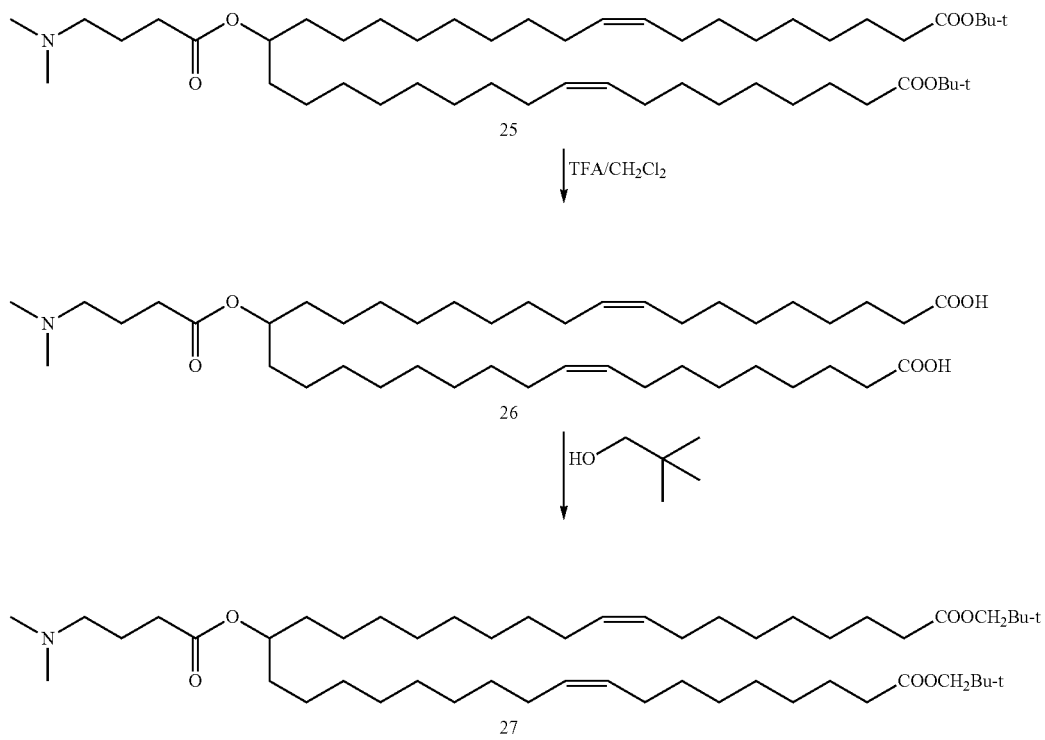

Compound 26: Compound 25 (840 mg, 1.03 mmol) was stirred in TFA (9 mL) and CH$_2$Cl$_2$ (36 mL) for 3 h at room temperature. Evaporation of the solvents and co-evaporation with toluene 3 times gave compound 26.

Molecular weight for C$_{43}$H$_{80}$NO$_6$ (M+H)$^+$ Calc. 706.5986, Found 706.4.

Compound 27: Compound 26 from the previous step was treated with 2,2-dimethylpropanol (363 mg, 4.12 mmol) in the presence of EDCI (592 mg, 3.09 mmol), DMAP (50 mg, 0.412 mmol) and DIEA (1.44 mL, 8.24 mmol) in CH$_2$Cl$_2$ (10 mL) for 14 h. Aqueous work-up then column chromatography gave compound 27 (575 mg, 0.679 mmol, 66%).

$^1$H NMR (400 MHz, CDCl$_3$) δ 5.40-5.28 (m, 4H), 4.91-4.81 (m, 1H), 3.76 (s, 4H), 2.34-2.27 (m, 8H), 2.22 (s, 6H), 2.03-1.97 (m, 8H), 1.83-1.26 (m, 50H), 0.94 (s, 18H). $^{13}$C NMR (100 MHz, CDCl$_3$) δ 174.14, 173.53, 130.09, 129.92, 74.41, 73.72, 59.12, 45.61, 34.60, 34.32, 32.64, 31.45, 29.93, 29.85, 29.71, 29.68, 29.48, 29.32, 29.28, 27.39, 27.33, 26.62, 25.52, 25.22, 23.32.

Molecular weight for C$_{53}$H$_{100}$NO$_6$ (M+H)$^+$ Calc. 846.7551, Found 846.5.

Example 33: Synthesis of Quaternary Lipids
A. The amino lipids synthesized in Examples 31 and 32 can be converted to the corresponding quaternary lipids as shown below by treatment with $CH_3Cl$ in $CH_3CN$ and $CHCl_3$.
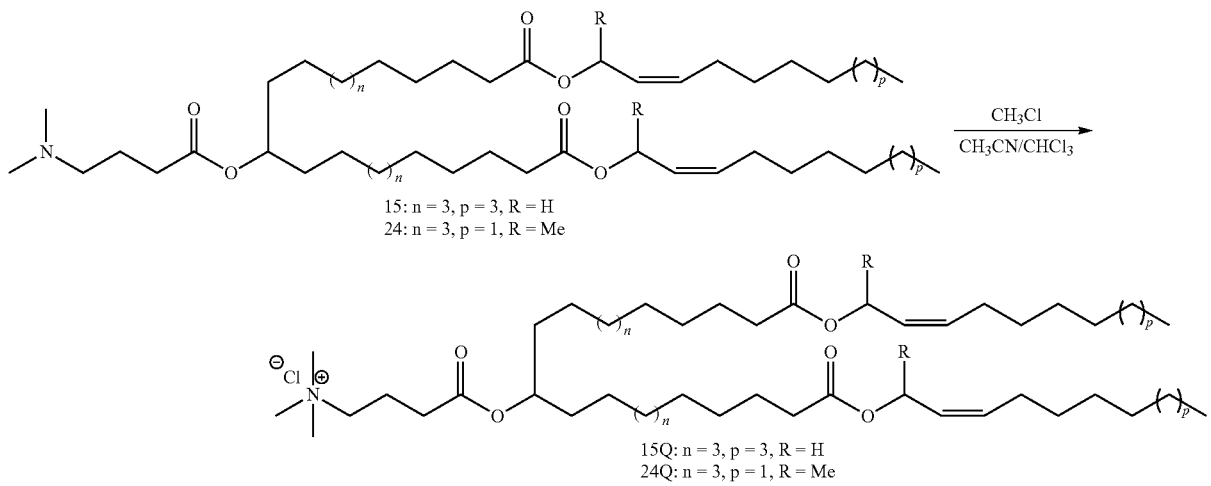
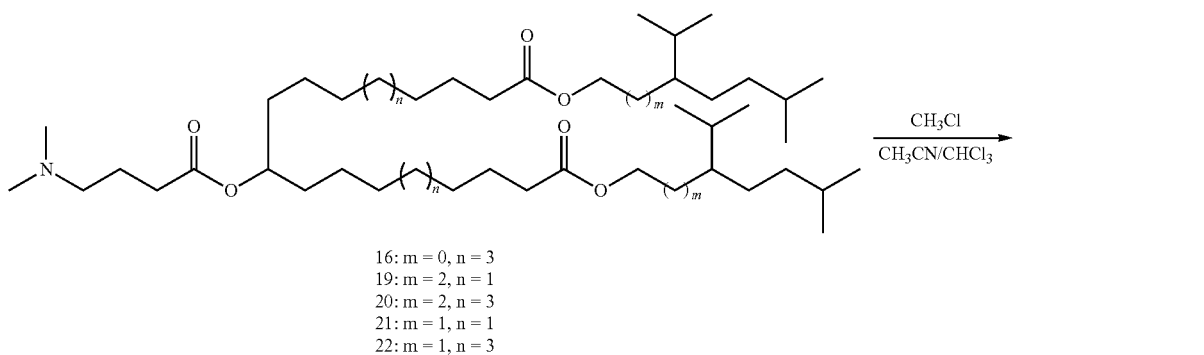
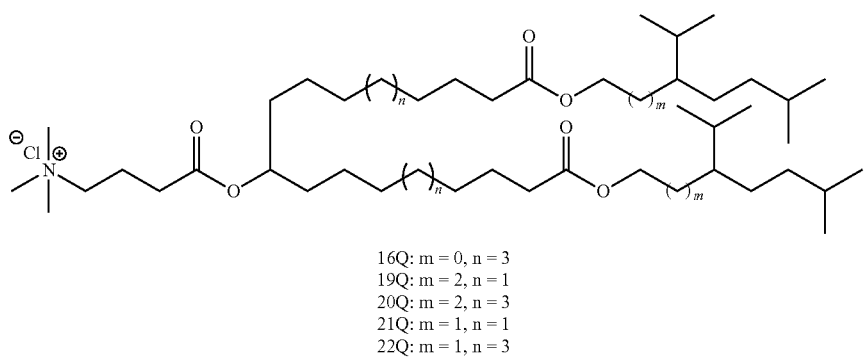
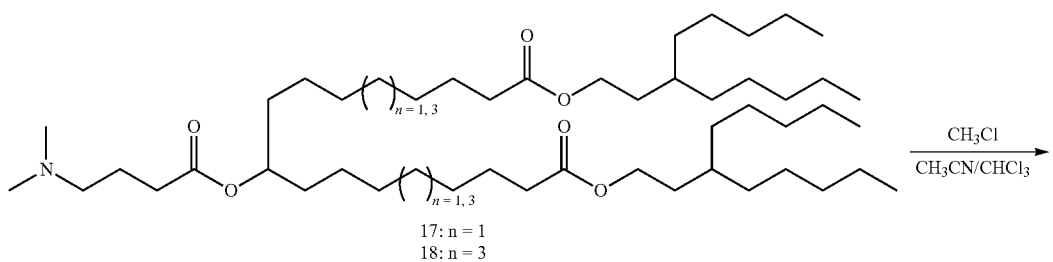

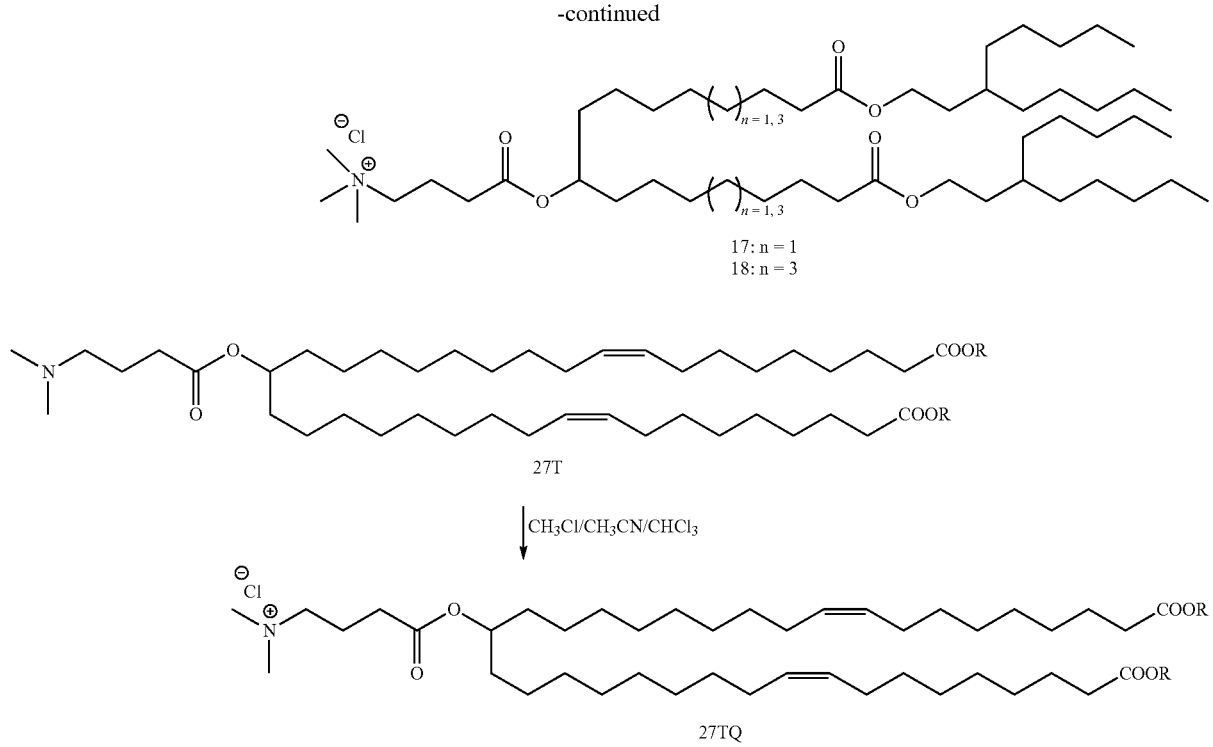
R = Me, Et, iPr, t-Bu, other alkyl/allyl groups
B. Synthesis of BODIPY-Lipid Conjugates
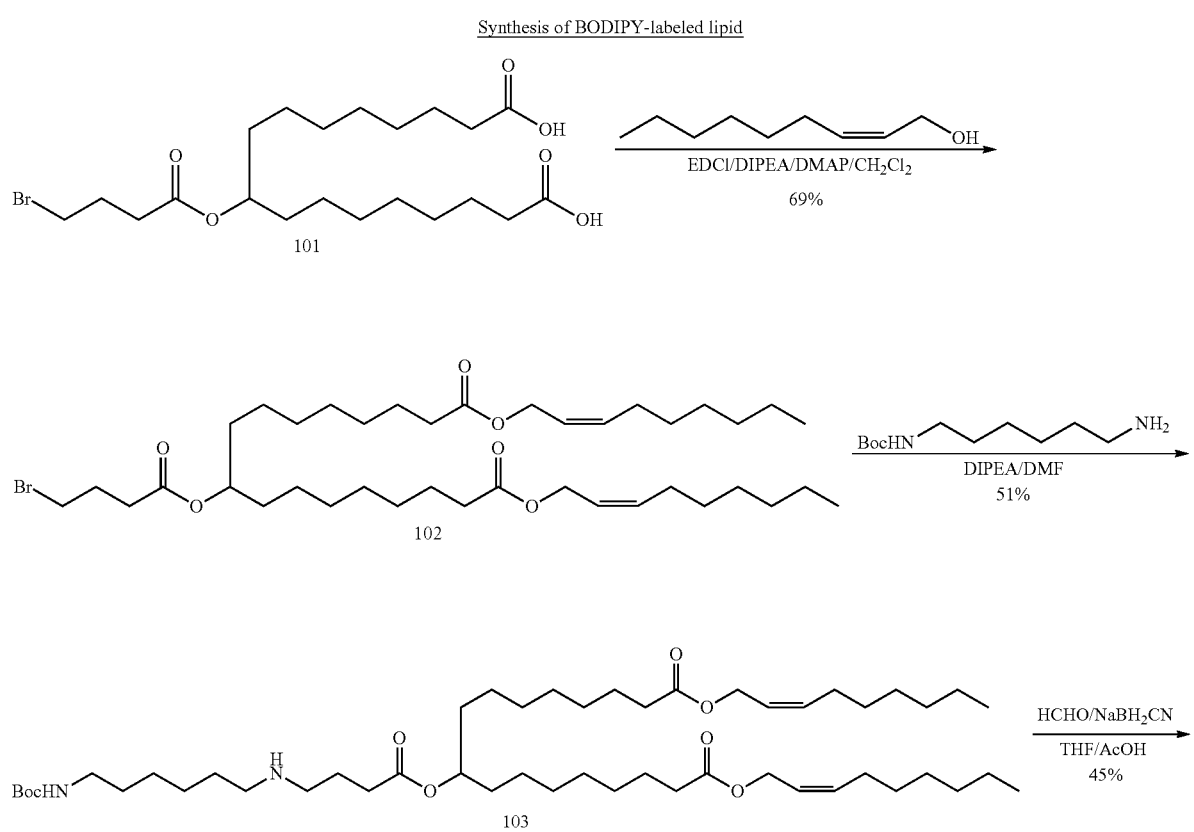

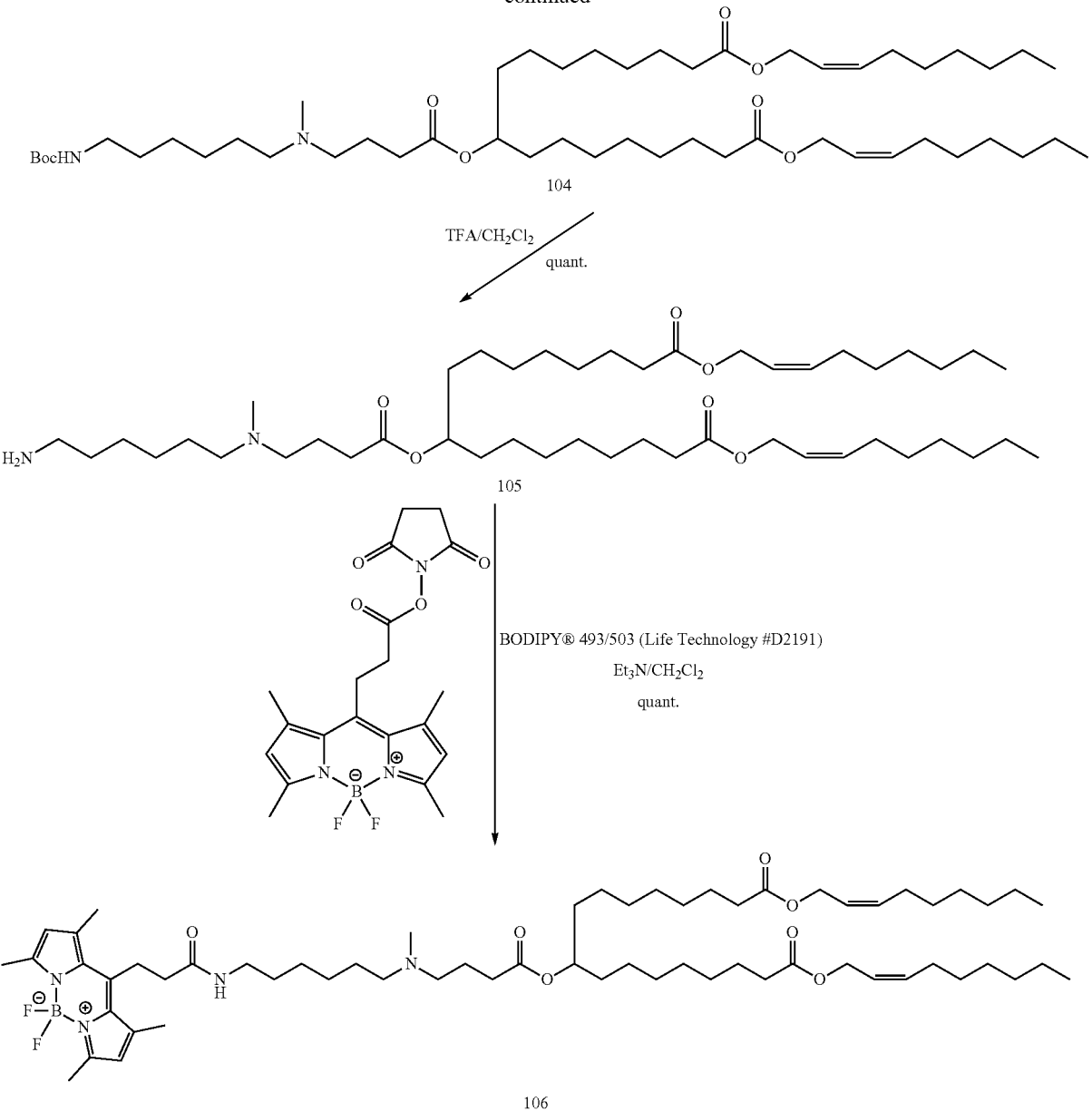

Compound 102: To a solution of compound 101 (2.00 g, 4.30 mmol) and cis-2-nonen-1-ol (1.81 mL, 10.7 mmol) in CH$_2$Cl$_2$ (20 mL) were added diisopropylethylamine (3.00 mL, 17.2 mmol), N-(3-dimethylaminopropyl)-N'-ethylcarbodiimide hydrochloride (2.06 g, 10.7 mmol) and DMAP (106 mg, 0.868 mmol). The reaction mixture was stirred at room temperature for 18 hours. The reaction mixture was diluted with CH$_2$Cl$_2$ (200 mL) and washed with saturated NaHCO$_3$ aq. (100 mL). The organic layer was dried over MgSO$_4$, filtered and concentrated. The crude was purified by silica gel column chromatography (0-5% EtOAc in Hexane) to give compound 102 (2.11 g, 2.96 mmol, 69%, R$_f$=0.45 developed with 10% EtOAc in Hexane).

$^1$H NMR (500 MHz, CDCl$_3$) δ 5.67-5.61 (m, 2H), 5.54-5.49 (m, 2H), 4.89-4.84 (m, 1H), 4.62 (d, J=6.5 Hz, 4H), 3.46 (t, J=6.5 Hz, 2H), 2.48 (t, J=7.3 Hz, 2H), 2.30 (t, J=7.5 Hz, 4H), 2.20-2.14 (m, 2H), 2.12-2.04 (m, 4H), 1.63-1.60 (m, 4H), 1.51-1.50 (m, 4H), 1.37-1.27 (m, 32H), 0.88 (t, J=6.8 Hz, 6H). $^{13}$C NMR (100 MHz, CDCl$_3$) δ 173.90, 172.45, 135.58, 123.51, 74.74, 60.36, 34.47, 34.24, 32.93, 32.91, 31.83, 29.54, 29.48, 29.31, 29.21, 29.01, 28.03, 27.70, 25.43, 25.08, 22.76, 14.23.

Molecular weight for C$_{39}$H$_{69}$BrNaO$_6$ (M+Na)$^+$ Calc. 735.42, Found 735.2.

Compound 103: To a solution of 102 (2.11 g, 2.96 mmol) in DMF (20 mL) was added a solution of N-Boc-1,6-diaminohexane (670 mg, 3.10 mmol) in DMF (20 mL) at 0° C. The mixture was stirred for 18 hours at room temperature. Then additional N-Boc-1,6-diaminohexane (160 mg, 0.740 mmol) in DMF (1 mL) was added and the mixture was stirred for 12 hour. The reaction was quenched by adding saturated NaHCO$_3$ aq. (100 mL) then extracted with Et$_2$O (150 mL×3). The organic layer was separated and dried over anhydrous MgSO$_4$. After filtration and concentration, the crude was purified by silica gel column chromatography (5% MeOH in $CH_2Cl_2$, $R_f$=0.24) to give 103 (1.28 g, 1.51 mmol, 51%).

$^1H$ NMR (400 MHz, $CDCl_3$) δ 5.67-5.61 (m, 2H), 5.55-5.50 (m, 2H), 4.88-4.81 (m, 1H), 4.61 (d, J=6.8 Hz, 4H), 4.54 (brs, 1H), 3.11-3.08 (m, 2H), 2.67-2.59 (m, 4H), 2.35 (t, J=7.4 Hz, 2H), 2.29 (t, J=7.6 Hz, 4H), 2.10-2.07 (m, 4H), 1.84-1.81 (m, 4H), 1.63-1.57 (m, 4H) 1.50-1.47 (m, 8H), 1.44 (s, 9H), 1.38-1.27 (m, 34H), 0.88 (t, J=6.8 Hz, 6H). $^{13}C$ NMR (100 MHz, $CDCl_3$) δ 173.90, 173.53, 135.57, 123.50, 74.49, 60.36, 49.82, 49.29, 40.64, 34.47, 34.24, 32.68, 31.83, 30.16, 29.89, 29.54, 29.50, 29.33, 29.23, 29.01, 28.58, 27.69, 27.11, 26.80, 25.44, 25.37, 25.09, 22.76, 14.23.

Molecular weight for $C_{50}H_{93}N_2O_8$ $(M+H)^+$ Calc. 849.69, Found 849.5.

Compound 104: To a solution of 103 (1.16 g, 1.37 mmol) in THF (20 mL) were added formaldehyde (37 wt. % in $H_2O$, 0.306 mL, 4.11 mmol), sodium cyanoborohydride (1 M solution in THF, 2.06 mL, 2.06 mmol) and acetic acid (0.008 mL, 0.137 mmol) at 0° C. The mixture was stirred at room temperature for 17 hours. The reaction was quenched by adding saturated $NaHCO_3$ aq. (50 mL) then extracted with $Et_2O$ (100 mL×3). The organic layer was separated and dried over anhydrous $MgSO_4$. After filtration and concentration, the crude was purified by silica gel column chromatography (8% MeOH in $CH_2Cl_2$, $R_f$=0.46) to give 104 (531 mg, 0.615 mmol, 45%).

$^1H$ NMR (400 MHz, $CDCl_3$) δ 5.66-5.60 (m, 2H), 5.53-5.47 (m, 2H), 4.86-4.80 (m, 1H), 4.61-4.59 (m, 5H), 3.12-3.07 (m, 2H), 2.89-2.78 (m, 4H), 2.62 (s, 3H), 2.40 (t, J=6.8 Hz, 2H), 2.28 (t, J=7.4 Hz, 4H), 2.11-2.06 (m, 4H), 1.99-1.92 (m, 2H), 1.69-1.27 (m, 57H), 0.87 (t, J=6.8 Hz, 6H). $^{13}C$ NMR (100 MHz, $CDCl_3$) δ 173.86, 172.45, 156.18, 135.55, 123.45, 75.24, 60.32, 56.68, 55.83, 40.72, 40.36, 34.40, 34.09, 31.79, 31.29, 29.92, 29.49, 29.41, 29.26, 29.17, 28.96, 28.55, 27.65, 26.49, 26.30, 25.41, 25.02, 24.79, 22.71, 20.12, 14.19.

Molecular weight for $C_{51}H_{95}N_2O_8$ $(M+H)^+$ Calc. 863.71, Found 863.6.

Compound 105: To a solution of compound 104 (525 mg, 0.608 mmol) in $CH_2Cl_2$ (8 mL) was added trifluoroacetic acid (2 mL) at 0° C. The reaction mixture was stirred at 0° C. for 1 hour and at room temperature for 3 hours. The reaction mixture was evaporated and co-evaporated with toluene 3 times then dried in vacuo overnight to give compound 105 (603 mg, 0.603 mmol calculated as 2 TFA salt, quantitatively, $R_f$=0.24 developed with 8% MeOH in $CH_2Cl_2$).

$^1H$ NMR (400 MHz, $CDCl_3$) δ 8.06 (brs, 1H), 5.68-5.61 (m, 2H), 5.55-5.49 (m, 2H), 4.87-4.81 (m, 1H), 4.62 (d, J=6.8 Hz, 4H), 4.28 (brs, 3H), 3.20-3.02 (m, 6H), 2.82 (d, J=4.0 Hz, 3H), 2.45-2.40 (m, 2H), 2.30 (t, J=7.4 Hz, 4H), 2.12-2.00 (m, 6H), 1.78-1.22 (m, 52H), 0.88 (t, J=6.8 Hz, 6H). $^{13}C$ NMR (100 MHz, $CDCl_3$) δ 174.04, 172.08, 161.84, 161.47, 135.63, 123.44, 117.60, 114.71, 75.56, 60.41, 55.69, 55.27, 39.94, 39.64, 34.44, 34.06, 31.82, 30.72, 29.53, 29.43, 29.28, 29.19, 29.00, 27.69, 26.58, 25.42, 25.27, 25.05, 24.60, 23.06, 22.75, 19.00, 14.22.

Molecular weight for $C_{46}H_{87}N_2O_6$ $(M+H)^+$ Calc. 763.66, Found 763.4.

Compound 106: To a solution of 105 (23.8 mg, 0.0240 mmol, calculated as 2TFA salt) in $CH_2Cl_2$ (1 mL) and $Et_3N$ (0.050 mL, 0.360 mmol) was added a solution of BODIPY® 493/503 (10 mg, 0.0240 mmol, Life Technology #D2191) in $CH_2Cl_2$ (2 mL). The reaction mixture was stirred for 1 h. The reaction mixture was loaded onto silica gel column chromatography and eluted with 0-5% MeOH in $CH_2Cl_2$. The product color fractions were collected (5% MeOH in $CH_2Cl_2$, $R_f$=0.36) to give 106 (26 mg, 0.024 mmol, quantitatively).

$^1H$ NMR (400 MHz, $CDCl_3$) δ 6.05 (s, 2H), 5.67-5.61 (m, 2H), 5.54-5.48 (m, 2H), 4.85-4.82 (m, 1H), 4.61 (d, J=6.8 Hz, 4H), 3.37-3.32 (m, 2H), 3.27-3.22 (m, 2H), 2.51-2.44 (m, 17H), 2.34-2.27 (m, 8H), 2.12-2.06 (m, 4H), 1.60-1.21 (m, 52H), 0.88 (t, J=6.8 Hz, 6H).

Molecular weight for $C_{62}H_{104}BF_2N_4O_7$ $(M+H)^+$ Calc. 1065.80, Found 1065.5.

Example 34: Multi-Ester Containing Lipids and Acetal Linked Lipids

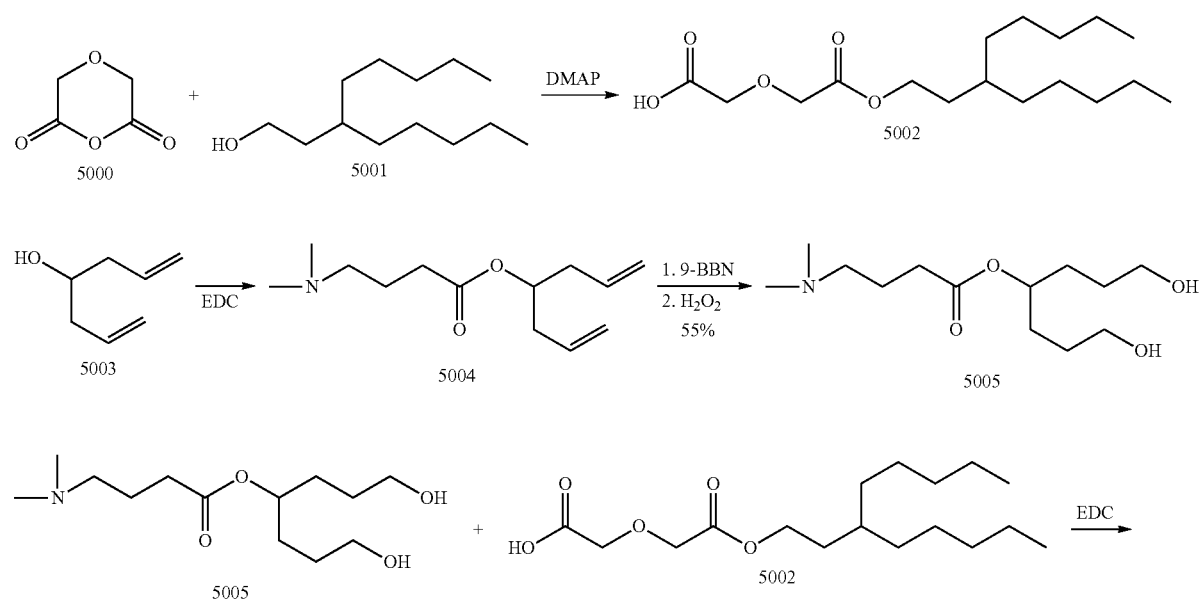

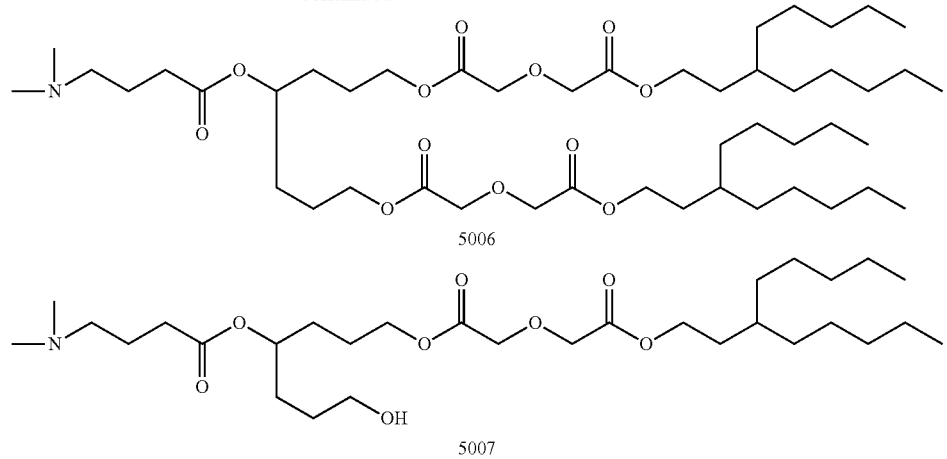

Synthesis of compound 5002: To a stirred solution of alcohol 5001 (1.0 g, 5.15 mmol), Glycolic anhydride 5000 (5.66 mmol) in DCM (20 mL) was added DMAP (1.26 g, 10.41 mmol) and stirred at room temperature for 48 h. The reaction mixture was concentrated followed by column purification gave the corresponding product 5002 (1.4 g, 86%) as DMAP salt. LCMS: Calculated: 316.22 (M$^+$), Found: 315.1 (M$^+$−1).

Synthesis of compound 5004: To a stirred solution of alcohol 5003 (5.0 g, 44.6 mmol), 4-(Dimethylamino)butyric acid hydrochloride (8.1 g, 48.3 mmol) and EDC (10.3 g, 53.6 mmol) in DCM (100 mL) was added DIEPA (23 g, 178.3 mmol) and stirred at room temperature overnight. After usual work up, the crude product was purified by column chromatography (9.0 g, 90%).

Synthesis of compound 5005: To a stirred solution of diene 5004 (4.0 g, 18 mmol) in 10 mL of THF was added 9-BBN and stirred overnight. To the above solution was added 6.6 mL of 3M NaOAc and 7.4 mL of 30% $H_2O_2$ at 0-5° C. The reaction mixture was stirred at room temperature overnight. After usual work up, the crude material was purified by column chromatography to get 5005 (2.6 g, 55%) as viscous oil. LCMS: Calculated: 261.19 (M$^+$), Found: 262.1 (M$^+$+1).

Synthesis of compound 5006 and 5007: To a stirred solution of diene 5005 (260 mg, 1 mmol), acid 5002 (1.0 g, 2.28 mmol), EDC (387 mg, 2 mmol) in 10 mL of DCM was added DIEA (516 mg, 4 mmol) and stirred overnight. After usual work up, the crude material was purified by column chromatography to get 5006 (0.1 g, 12%) and 5007 (0.2 g, 36%). LCMS for compound 5006: Calculated: 857.62 (M$^+$), Found: 858.5 (M$^+$+1), 880.5 (M$^+$+Na). LCMS for compound 5007: Calculated: 559.4 (M$^+$), Found: 560.4 (M$^+$+1).

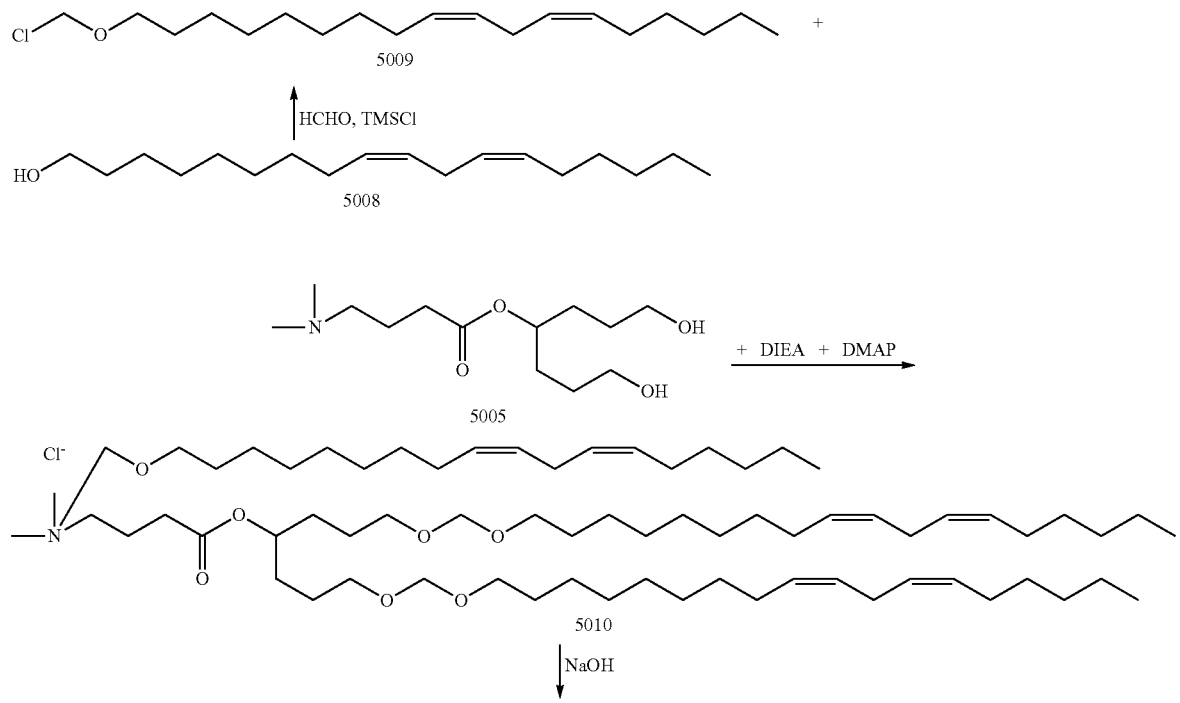

-continued

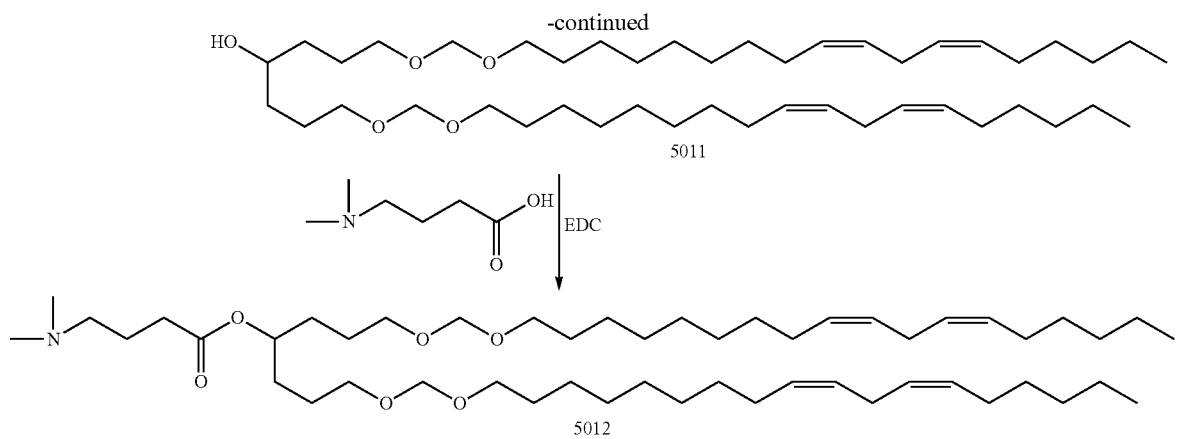

Synthesis of compound 5011: To a stirred solution of alcohol 5008 (2.66 g 10 mmol) in 5 mL of Chlorotrimethylsilane was added paraformaldehyde (0.3 g, 10 mmol) and stirred at room temperature overnight. The excess Chlorotrimethylsilane was evaporated followed by drying under reduced pressure gave the corresponding product 5009 and used for next step without purification. The compound 5009 was added dropwise to the solution of diol (261 mg, 1 mmol), DIEA (2.5 g, 19.4 mmol) and DMAP (20 mg, 0.16 mmol) in DCM (10 mL) and stirred overnight. Concentration of the solvent gave the crude product 5010, which was dissolved in 5 mL of THF and 2 mL of 1N NaOH was added and stirred for 2 days at room temperature. After usual work up, the crude material was purified by column chromatography to get the corresponding product 5011 (200 mg, 28%). LCMS for compound 5010: Calculated: 1131.95 ($M^+$), Found: 1096.98 ($M^+$–$Cl^-$)). LCMS for compound 5011: Calculated: 704.63 ($M^+$), Found: 727.5 ($M^+$+Na).

Synthesis of compound 5012: To a stirred solution of alcohol 5011 (200 mg, 0.284 mmol), 4-(Dimethylamino) butyric acid hydrochloride (103 mg, 0.57 mmol), EDC (109 mg, 0.57 mmol) in 10 mL of DCM was added DIEA (294 mg, 4 mmol) and stirred overnight. After usual work up, the crude material was purified by column chromatography to get 5012 (190 mg, 85%). LCMS for compound 5012: Calculated: 817.72 ($M^+$), Found: 818.5 ($M^+$+Na).

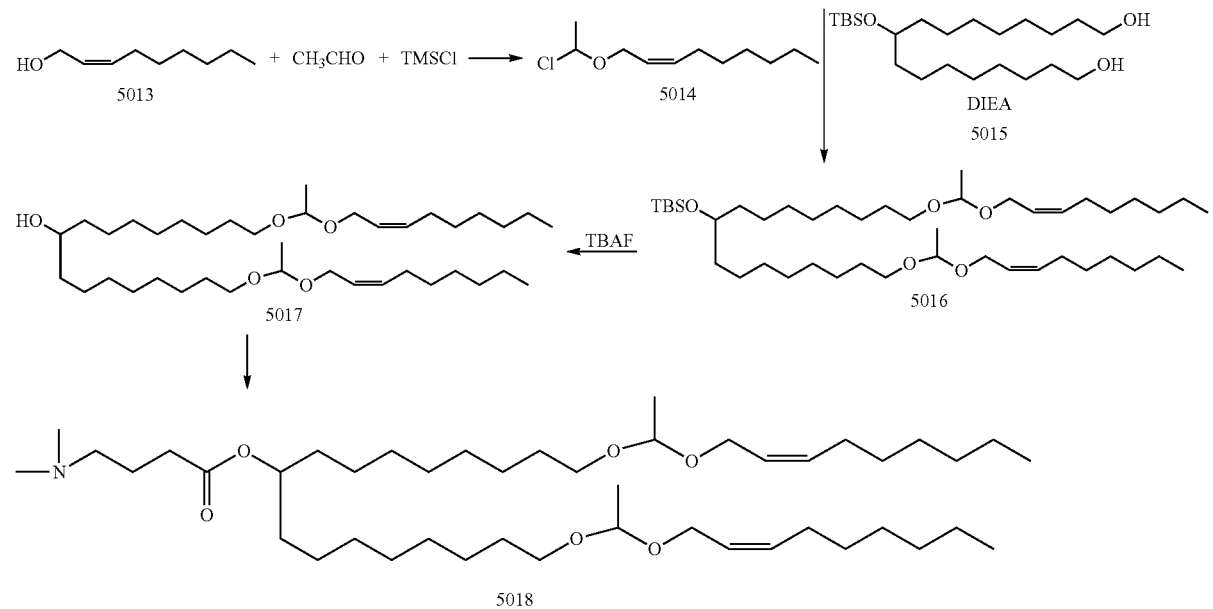

Synthesis of compound 5016: To a stirred solution of alcohol 5013 (1.0 g 7.03 mmol) in 5 mL of Chlorotrimethylsilane was added acetaldehyde (0.3 g, 7.03 mmol) and stirred at room temperature for 2 h. The excess Chlorotrimethylsilane was evaporated followed by drying under reduced pressure gave the corresponding product 5014 and used for next step without purification. The compound 5014 was added dropwise to the solution of diol 5015 (223 mg, 0.55 mmol), DIEA (2 mL g, 11.5 mmol) and DMAP (20 mg, 0.16 mmol) in DCM (10 mL) and stirred overnight. 10 mL of water was added followed by extraction with DCM (3×30 mL), washed with water, saturated $NaHCO_3$, brine and dried over anhydrous $Na_2SO_4$. Concentration of the solvent gave the crude product, which was used for the next step without purification. LCMS for compound 5016: Calculated: 738.66 ($M^+$), Found: 761.5 ($M^+$+Na).

Synthesis of compound 5017: To a stirred solution of alcohol 5016 in 5 mL of THF was added 0.54 mL of 1M TBAF in THF (0.54 mmol) and stirred for 2 days at room temperature. After usual work up, the crude material was purified by column chromatography to get 5017. However, it contains some inseparable impurity and hence used for next step without further purification. LCMS for compound 5017: Calculated: 624.57 ($M^+$), Found: 647.5 ($M^++Na$).

Synthesis of compound 5018: To a stirred solution of alcohol 5017 (0.55 mmol), 4-(Dimethylamino)butyric acid hydrochloride (116 mg, 0.64 mmol), EDC (123 mg, 0.64 mmol) in 10 mL of DCM was added DIEA (165 mg, 1.28 mmol) and stirred for 2 days. After usual work up, the crude material is purified by column chromatography (0-10% MeOH in 1% $Et_3N$ containing DCM) to get 5018 (300 mg, 75% from 5015). LCMS for compound 5018: Calculated: 737.65 ($M^+$), Found: 738.6 ($M^++1$), 760.5 ($M^++Na^+$).

Example 35: Preparation of Lipid Nanoparticles

The cationic lipids described herein are used to formulate liposomes containing the AD-1661 duplex (shown in the table below) using an in-line mixing method as described in International Publication No. WO 2010/088537, which is incorporated by reference in its entirety. The lipid nanoparticles had the formulation shown in the table below.

| Component | Mole Percentage (Based on 100% of the lipid components in the LNP) |
|---|---|
| Cationic lipid | 50% |
| Distearoylphosphatidylcholine (DSPC) | 10% |
| Cholesterol | 38.5% |
| 1-(monomethoxy-polyethyleneglycol)-2,3-dimyristoylglycerol (PEG-DMG) (with an average PEG molecular weight of 2000) | 1.5% |
| siRNA (AD-1661) | — |

The siRNA AD-1661 duplex has the sequence shown below.

| Duplex | Sequence 5'-3' | SEQ ID NO: | Target |
|---|---|---|---|
| AD-1661 | GGAfUfCAfUfCfUfCfUfCAAGfUfCf UfUAfCdTsdT | 1 | FVII |
|  | GfUAAGAfCfUfUGAGAfUGAfUf CfCdTsdT | 2 |  |

Lower case is 2'OMe modification and Nf is a 2'F modified nucleobase, dT is deoxythymidine, s is phosphothioate The lipid nanoparticles was prepared as follows. Cationic lipid, DSPC, cholesterol, and PEG-DMG in the ratio recited in the table above were solubilized in ethanol at a total lipid concentration of 25 mg/mL.

A siRNA stock solution was prepared by solubilizing the siRNA AD-1661 in a low pH acetate or citrate buffer (pH=4) at 0.8 mg/mL.

The stock solutions should be completely clear and the lipids should be completely solubilized before combining with the siRNA. Therefore, if it was determined appropriate, the stock solutions were heated to completely solubilize the lipids.

The individual stock solutions were combined by pumping each solution to a T-junction (i.e., by in-line mixing). Specifically, the ethanol solution (at 5 ml/min, via 0.01 in. PEEK tube) and aqueous buffer solution (at 15 mL/min, via 0.02 in. PEEK tube) were mixed through a T-junction (PEEK Tee body, IDEX).

After the T-junction a single tubing is placed where the combined stream will emit. Ethanol is removed and exchanged for PBS by dialysis. The lipid formulations are then concentrated using centrifugation or diafiltration to an appropriate working concentration.

Lipid nanoparticles containing the cationic lipids listed in the table in Example 36 were prepared as described above.

Example 36: Efficacy of Lipid Nanoparticles

Factor VII (FVII), a prominent protein in the coagulation cascade, is synthesized in the liver (hepatocytes) and secreted into the plasma. FVII levels in plasma can be determined by a simple, plate-based colorimetric assay. As such, FVII represents a convenient model for determining siRNA-mediated downregulation of hepatocyte-derived proteins.

Test formulations of the lipid nanoparticles prepared in Example 35 were initially assessed for their FVII knockdown in female 7-9 week old, 15-25 g, female C57Bl/6 mice at 0.1, 0.3, 1.0 and 5.0 mg/kg with 3 mice per treatment group. All studies included animals receiving either phosphate-buffered saline (PBS, control group) or a benchmark formulation. Formulations were diluted to the appropriate concentration in PBS immediately prior to testing. Mice were weighed and the appropriate dosing volumes calculated (10 μl/g body weight). Test and benchmark formulations as well as PBS (for control animals) were administered intravenously via the lateral tail vein. Animals were anesthetised 24 hours later with an intraperitoneal injection of ketamine/xylazine and 500-700 μl of blood was collected by cardiac puncture into serum separator tubes (BD Microtainer). Blood was centrifuged at 2,000×g for 10 minutes at 15° C. and serum was collected and stored at −70° C. until analysis. Serum samples were thawed at 37° C. for 30 minutes, diluted in PBS and aliquoted into 96-well assay plates. Factor VII levels were assessed using a chromogenic assay (Biophen FVII kit, Hyphen BioMed) according to the manufacturer's instructions and absorbance was measured in a microplate reader equipped with a 405 nm wavelength filter. Plasma FVII levels were quantified and $ED_{50}$ values (dose resulting in a 50% reduction in plasma FVII levels compared to control animals) were calculated using a standard curve generated from a pooled sample of serum from control animals. Those formulations of interest showing high levels of FVII knockdown ($ED_{50}$<<0.1 mg/kg) were re-tested in independent studies at a lower dose range to confirm potency and establish $ED_{50}$ levels.

The following table shows $ED_{50}$ values for some of the cationic lipids described herein. Two asterisks (**) indicates an $ED_{50}$ value between 0.001 and 0.10. One asterisk (*) indicates an $ED_{50}$ value greater than 0.10.

| ED50 | Cationic Lipid |
|---|---|
| ** | 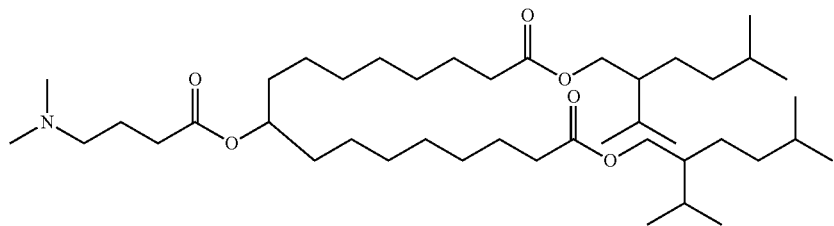 |
| ** | 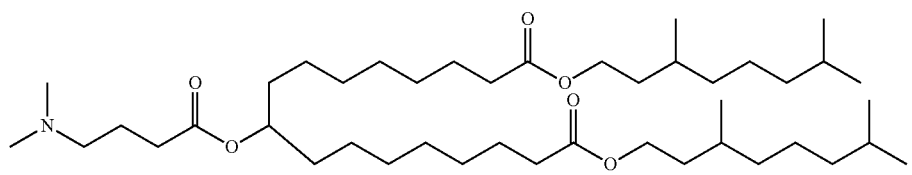 [SMILES: CC(C)CCCC(C)CCOC(=O)CCCCCCCC(CCCCCCCC(=O)OCCC(C)CCCC(C)C)OC(=O)CCCN(C)C] |
| ** | 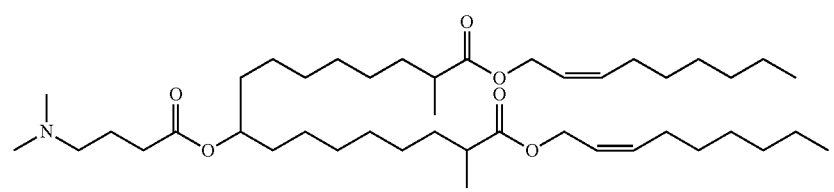 [SMILES: CCCCCC/C=C\COC(=O)C(C)CCCCCCC(CCCCCCC(C)C(=O)OC/C=C\CCCCCC)OC(=O)CCCN(C)C] |
| ** | 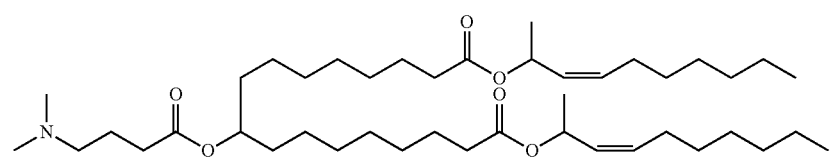 [SMILES: CCCCCC/C=C\C(C)OC(=O)CCCCCCCC(CCCCCCCC(=O)OC(C)/C=C\CCCCCC)OC(=O)CCCN(C)C] |
| ** | 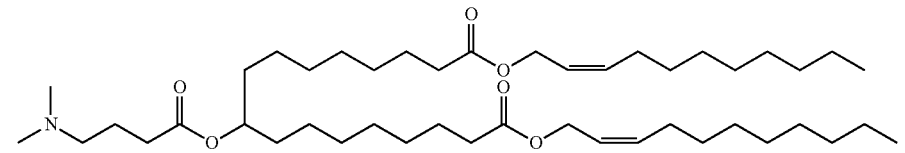 [SMILES: CCCCCCCC/C=C\COC(=O)CCCCCCCC(CCCCCCCC(=O)OC/C=C\CCCCCCCC)OC(=O)CCCN(C)C] |
| ** | 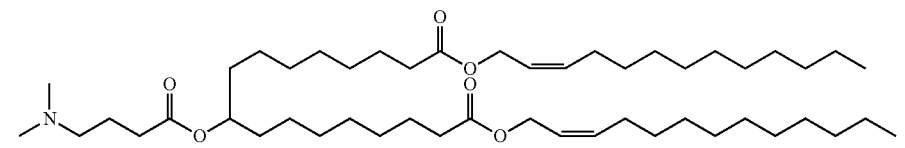 [SMILES: CCCCCCCCCC/C=C\COC(=O)CCCCCCCC(CCCCCCCC(=O)OC/C=C\CCCCCCCCCC)OC(=O)CCCN(C)C] |
| ** | 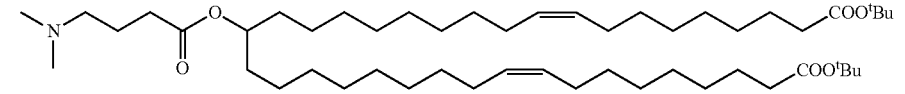 |
| ** | 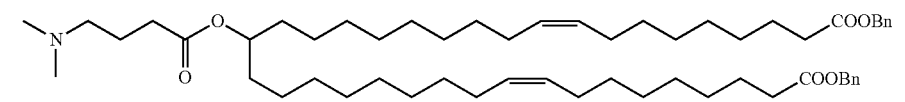 |
| * | 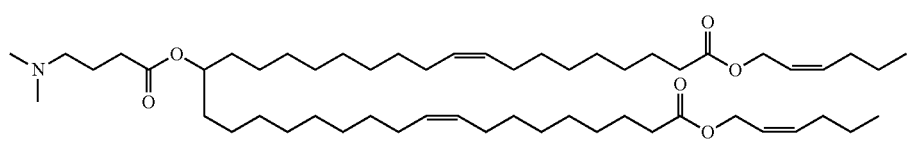 [SMILES: CCC/C=C\COC(=O)CCCCCCC/C=C\CCCCCCCCC(CCCCCCCC/C=C\CCCCCCCC(=O)OC/C=C\CCC)OC(=O)CCCN(C)C] |
| ** | 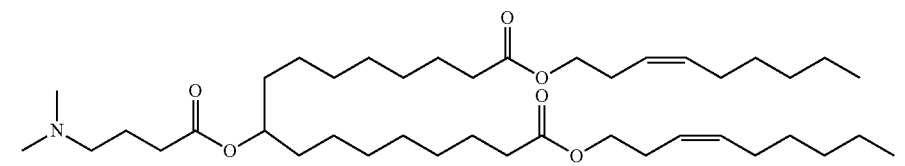 [SMILES: CCCCC/C=C\CCOC(=O)CCCCCCCC(CCCCCCCC(=O)OCC/C=C\CCCCC)OC(=O)CCCN(C)C] |

-continued
| ED$_{50}$ | Cationic Lipid |
|---|---|
| * | 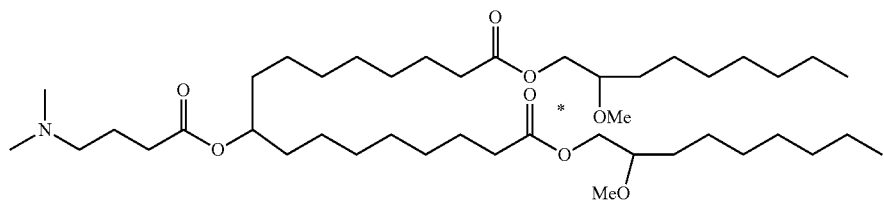 [SMILES: CCCCCCCC(COC(=O)CCCCCCCC(CCCCCCCC(=O)OCC(CCCCCCC)OC)OC(=O)CCCN(C)C)OC] |
| ** | 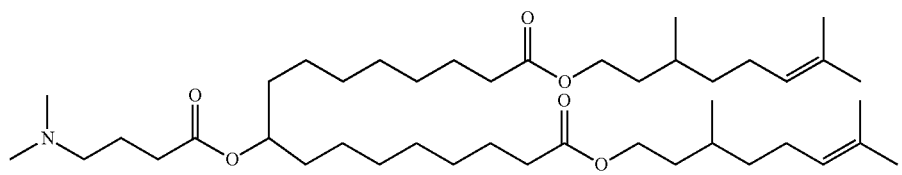 [SMILES: CC(C)=CCCC(C)CCOC(=O)CCCCCCCC(CCCCCCCC(=O)OCCC(C)CCC=C(C)C)OC(=O)CCCN(C)C] |
| ** | 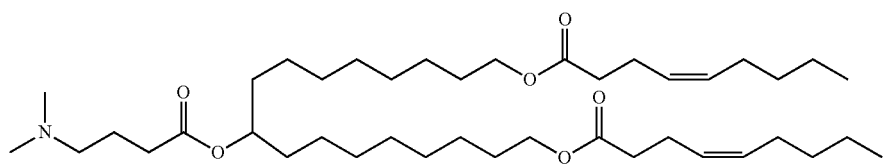 [SMILES: CCCC/C=C\CCC(=O)OCCCCCCCCC(CCCCCCCCOC(=O)CC/C=C\CCCC)OC(=O)CCCN(C)C] |
| ** | 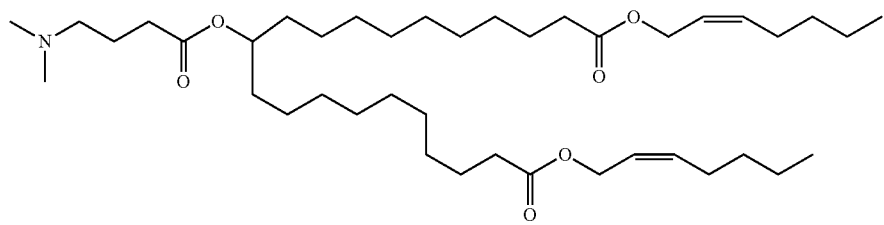 [SMILES: CCCC/C=C\COC(=O)CCCCCCCCCC(CCCCCCCCCC(=O)OC/C=C\CCCC)OC(=O)CCCN(C)C] |
| ** | 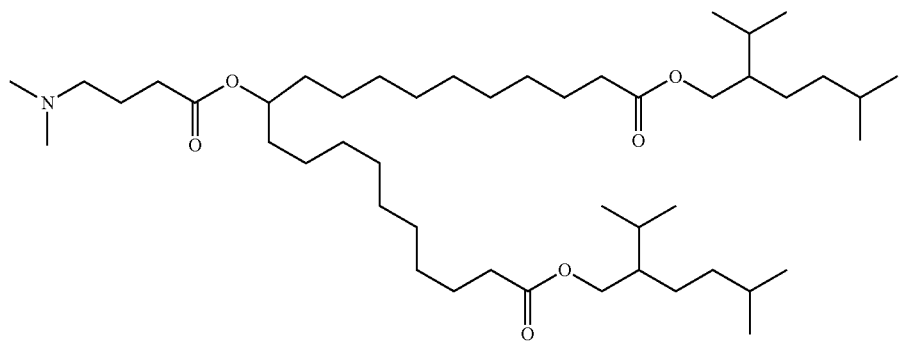 [SMILES: CC(C)CCC(COC(=O)CCCCCCCCCC(CCCCCCCCCC(=O)OCC(CCC(C)C)C(C)C)OC(=O)CCCN(C)C)C(C)C] |
| ** | 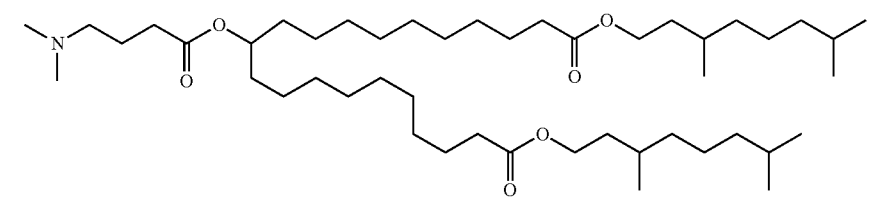 [SMILES: CC(C)CCCC(C)CCOC(=O)CCCCCCCCCC(CCCCCCCCCC(=O)OCCC(C)CCCC(C)C)OC(=O)CCCN(C)C] |
| ** | 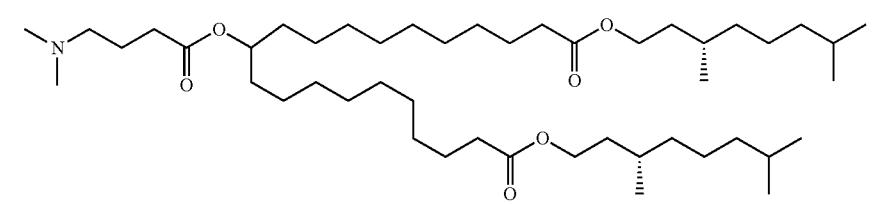 [SMILES: CC(C)CCC[C@H](C)CCOC(=O)CCCCCCCCCC(CCCCCCCCCC(=O)OCC[C@@H](C)CCCC(C)C)OC(=O)CCCN(C)C] |

| ED$_{50}$ | Cationic Lipid |
|---|---|
| ** | |
| ** | |
| ** | |
| ** | |
| ** | |
| ** | |
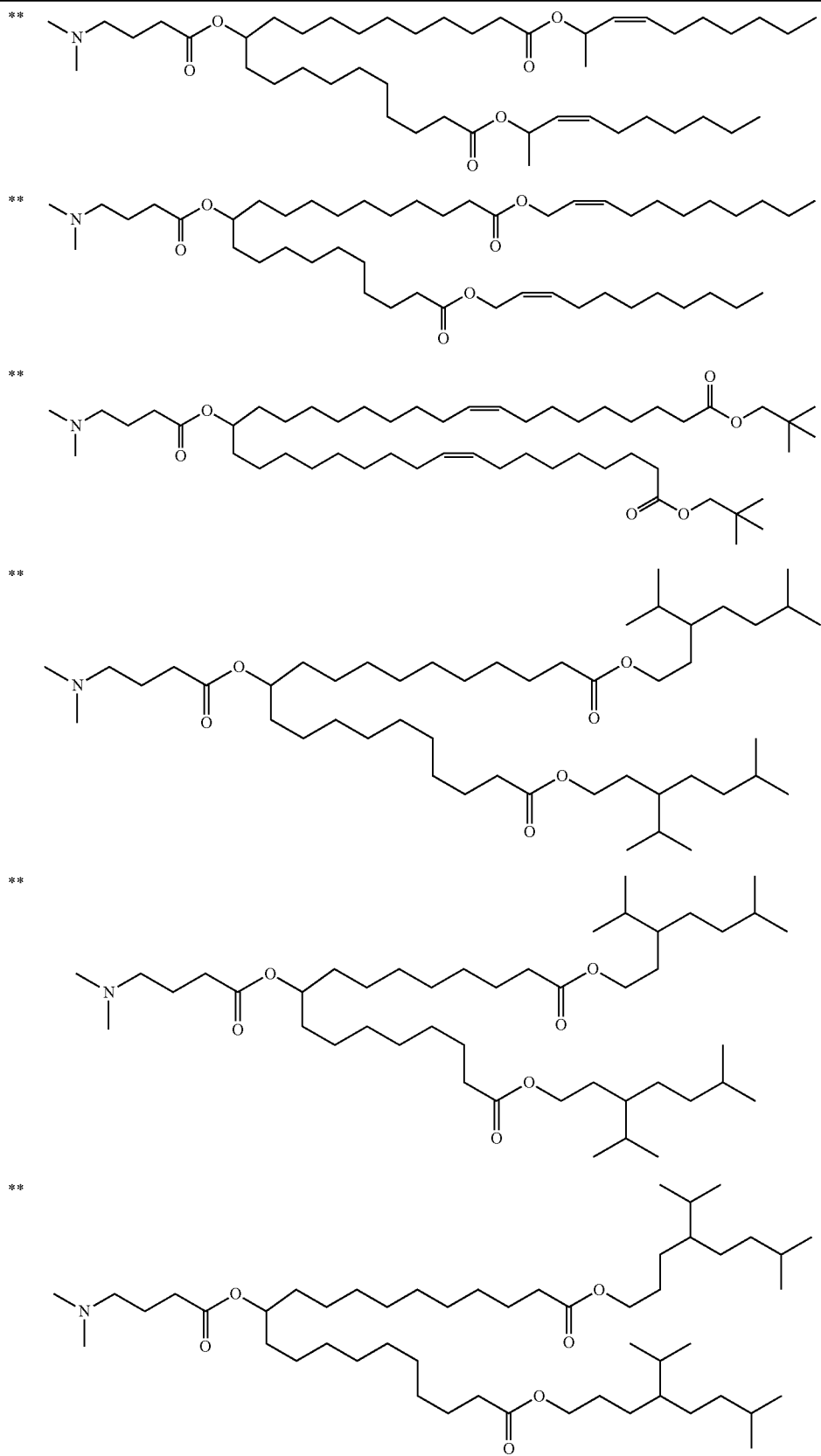

-continued

| ED$_{50}$ | Cationic Lipid |
|---|---|
| ** | 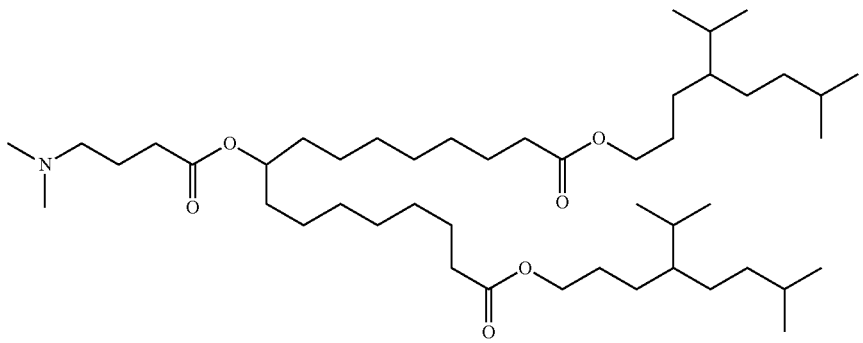 [SMILES: CC(C)CCC(CCCOC(=O)CCCCCCCC(CCCCCCCC(=O)OCCCC(CCC(C)C)C(C)C)OC(=O)CCCN(C)C)C(C)C] |
| ** | 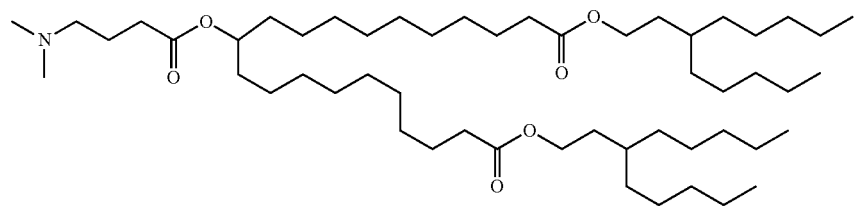 [SMILES: CCCCCC(CCCCC)CCOC(=O)CCCCCCCCCC(CCCCCCCCCC(=O)OCCC(CCCCC)CCCCC)OC(=O)CCCN(C)C] |
| ** | 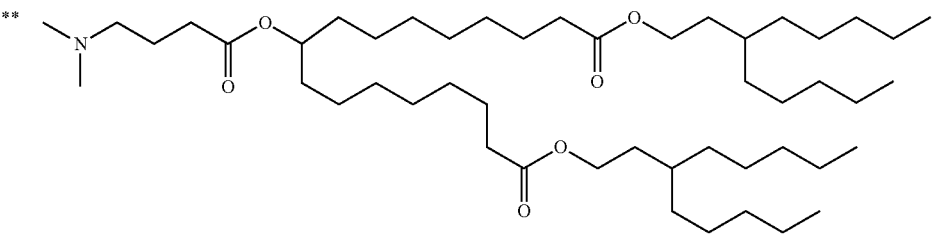 |

Example 37: Hydrophobicity and Stability

The log P values for the biodegradable cationic lipids listed in the table below were calculated using the software available at http://www.molinspiration.com/services/logp.html from Molinspiration Cheminformatics of Slovensky Grob, Slovak Republic.

Furthermore, the HPLC retention time for each biodegradable cationic lipid was measured in lipid nanoparticles prepared from them. The lipid nanoparticles were prepared as described in Example 35 using AD-1661 as the payload. The retention times are reported in the table below relative to the retention time for cholesterol.

The HPLC buffer used was a mixture of two solutions (Solution #1 and Solution #2).

Solution #1: 80% methanol/20% 10 mM NH$_4$HCO$_3$
Solution #2: 80% methanol/20% isopropanol The ratios of the two solutions in the mixture changed over time as indicated in the table below.

| Time (min) | Solution #1 (vol %) | Solution #2 (vol %) |
|---|---|---|
| 0 | 70 | 30 |
| 4 | 10 | 90 |
| 6 | 10 | 90 |
| 6.1 | 70 | 30 |
| 8 | 70 | 30 |

The size of the lipid nanoparticles was measured before and after undergoing dialysis overnight. In general, greater changes in lipid nanoparticle size are indicative of lesser stability.

Dynamic laser light scattering was used to determine the lipid nanoparticle size (expressed as the intensity weighted diameter) with a Zetasizer (Malvern Instruments, Inc. of Westborough, Mass.). All measurements were made at 532 nm wavelength at the scattering angle of 1730 using normal resolution mode as the analysis model.

The results of these experiments are provided in the table below.
| Cationic Lipid | logP | t(lipid)-t(chol) | LNPs Size (nm) change |
|---|---|---|---|
| 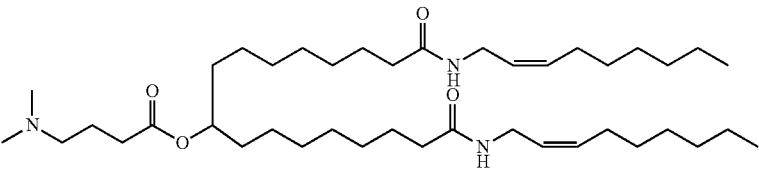 [SMILES: CCCCCC/C=C\CNC(=O)CCCCCCCC(CCCCCCCC(=O)NC/C=C\CCCCCC)OC(=O)CCCN(C)C] | 9.647 | −1.4 | 107 -> 260 |
| 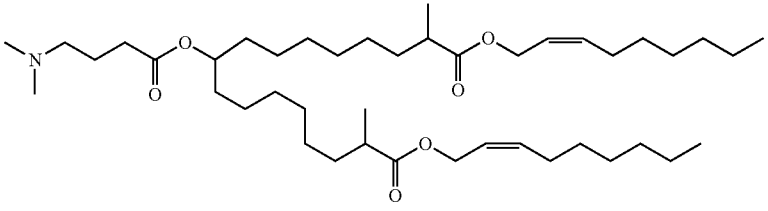 [SMILES: CCCCCC/C=C\COC(=O)C(C)CCCCCCC(CCCCCCC(C)C(=O)OC/C=C\CCCCCC)OC(=O)CCCN(C)C] | 9.972 | 0.848 | 73 -> 77 |
| 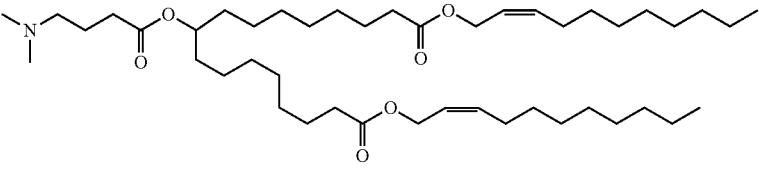 [SMILES: CCCCCCCC/C=C\COC(=O)CCCCCCCC(CCCCCCCC(=O)OC/C=C\CCCCCCCC)OC(=O)CCCN(C)C] | 10.093 | 1.44 | 60 -> 67 |
| 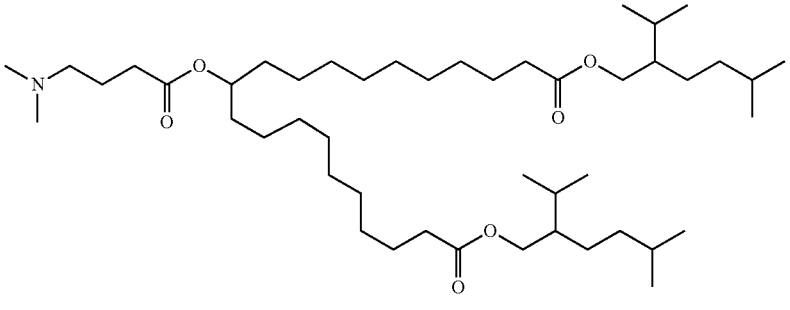 [SMILES: CC(C)CCC(COC(=O)CCCCCCCCCC(CCCCCCCCCC(=O)OCC(CCC(C)C)C(C)C)OC(=O)CCCN(C)C)C(C)C] | 10.201 | 1.751 | 59 -> 60 |
| 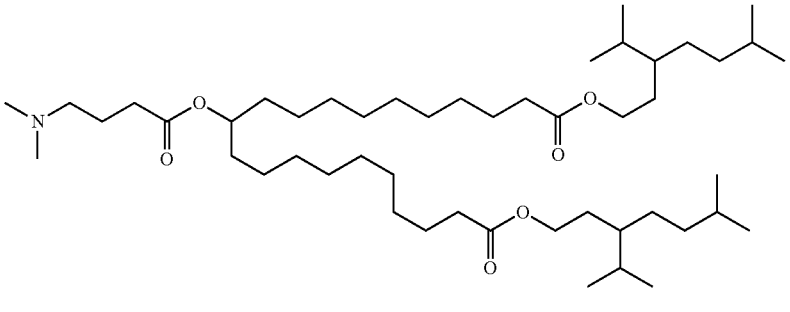 [SMILES: CC(C)CCC(CCOC(=O)CCCCCCCCCC(CCCCCCCCCC(=O)OCCC(CCC(C)C)C(C)C)OC(=O)CCCN(C)C)C(C)C] | 10.259 | 2.106 | |
| 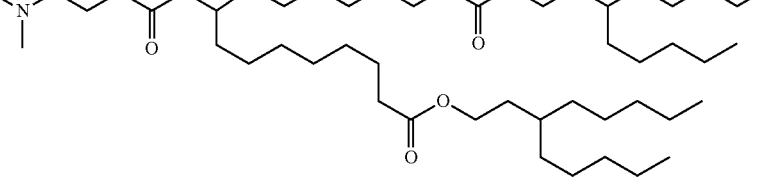 | 10.313 | 2.365 | 56 -> 56 |

| Cationic Lipid | logP | t(lipid)-t(chol) | LNPs Size (nm) change |
|---|---|---|---|
| 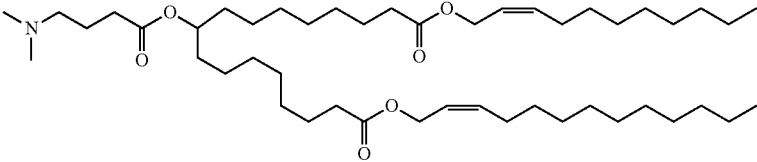 | 10.315 | 2.219 | 68 -> 67 |
| 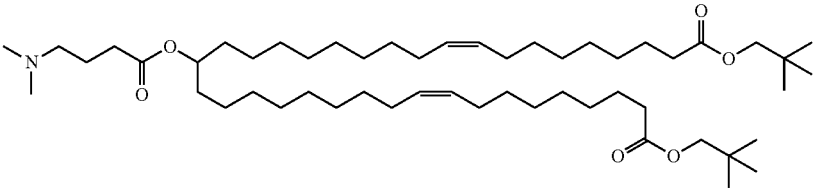 [SMILES: CN(C)CCCC(=O)OC(CCCCCCCC/C=C\CCCCCCCC(=O)OCC(C)(C)C)CCCCCCCC/C=C\CCCCCCCC(=O)OCC(C)(C)C] | 10.416 | 2.707 | |
| 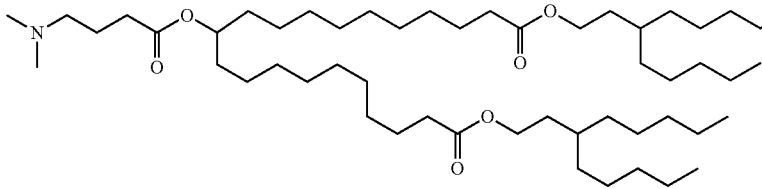 | 10.495 | 3.178 | |

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A lipid particle comprising:
   (i) a nucleic acid,
   (ii) 35-65 mol % of a protonatable lipid compound,
   (iii) 3-12 mol % distearoylphosphatidylcholine (DSPC),
   (iv) 15-45 mol % cholesterol, and
   (v) 0.5-10 mol % of a PEG-modified lipid,
   wherein the mol % is based on 100% total moles of lipids in the lipid particle,
   wherein the protonatable lipid compound comprises a head group, hydrophobic tails, and a central moiety to which the head group and the hydrophobic tails are directly bonded, wherein:
   the central moiety is a nitrogen atom;
   the hydrophobic tails consist of two hydrophobic tails;
   each of the two hydrophobic tails has the formula —$R^{12}$-$M^1$-$R^{13}$, wherein
   $R^{12}$ is a $C_4$-$C_{14}$ alkyl group, $M^1$ is a —OC(O)— group, and $R^{13}$ is a $C_{10}$-$C_{20}$ branched alkyl group;
   the chain length of formula —$R^{12}$-$M^1$-$R^{13}$ is at most 21 atoms; and
   the total carbon atom content of each hydrophobic tail is 21 to 26 carbon atoms.

2. The lipid particle of claim 1, wherein $R^{13}$ is branched at the alpha position relative to the —OC(O)— group.

3. The lipid particle of claim 2, wherein the chain length of formula —$R^{12}$-$M^1$-$R^{13}$ is 17 atoms.

4. The lipid particle of claim 2, wherein the nucleic acid comprises RNA.

5. A lipid particle comprising:
   (i) a nucleic acid,
   (ii) 35-65 mol % of a protonatable lipid compound,
   (iii) 3-12 mol % distearoylphosphatidylcholine (DSPC),
   (iv) 15-45 mol % cholesterol, and
   (v) 0.5-10 mol % of a PEG-modified lipid, wherein the PEG-modified lipid is 1-(monomethoxy-polyethylene glycol)-2,3-dimyristoyl glycerol (PEG-DMG),
   wherein the mol % is based on 100% total moles of lipids in the lipid particle,
   wherein the protonatable lipid compound comprises a head group, hydrophobic tails, and a central moiety to which the head group and the two hydrophobic tails are directly bonded, wherein:
   the central moiety is a nitrogen atom;
   the hydrophobic tails consist of two hydrophobic tails;
   each of the two hydrophobic tails independently consists of a first hydrophobic chain, an ester group, and a second hydrophobic chain, wherein the first and second hydrophobic chains are aliphatic and linked by the ester group, and the first hydrophobic chain is bonded directly to the central moiety, wherein each ester group is —C(O)O—;

wherein each hydrophobic tail has a total carbon atom content from 17 to 26 carbon atoms; and wherein one hydrophobic tail has the formula:

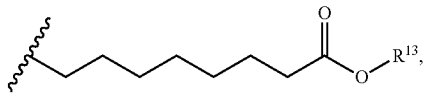

wherein $R^{13}$ is a $C_{13}$-$C_{17}$ branched alkyl; and the chain length of the one hydrophobic tail is from 18 to 20 atoms.

6. The lipid particle of claim 5, wherein, $R^{13}$ is a $C_{17}$ branched alkyl.

7. The lipid particle of claim 6, wherein the hydrophobic tail having the formula:

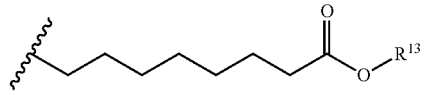

has a chain length of 18 atoms.

8. The lipid particle of claim 5, wherein $R^{13}$ is branched at the alpha position relative to the —C(O)O— group.

9. The lipid particle of claim 8, wherein the nucleic acid comprises RNA.

10. The lipid particle of claim 8, wherein the head group consists of a saturated aliphatic group and a hydroxyl group.

11. The lipid particle of claim 2, wherein the head group consist of a saturated aliphatic group and a hydroxyl group.

12. A method for preparing a lipid particle mixture comprising mixing a first solution comprising an organic solvent, a protonatable lipid compound, distearoylphosphatidylcholine (DSPC), cholesterol, and a PEG-modified lipid, with a second solution comprising a nucleic acid and water to form a lipid particle mixture, wherein the lipid particle comprises (i) the nucleic acid,
(ii) 35-65 mol % of the protonatable lipid compound,
(iii) 3-12 mol % distearoylphosphatidylcholine (DSPC),
(iv) 15-45 mol % cholesterol, and
(v) 0.5-10 mol % of the PEG-modified lipid,
wherein the mol % is based on 100% total moles of lipids in the lipid particle,
wherein the protonatable lipid compound comprises a head group, hydrophobic tails, and a central moiety to which the head group and the hydrophobic tails are directly bonded, wherein:
the central moiety is a nitrogen atom;
the hydrophobic tails consist of two hydrophobic tails,
each of the two hydrophobic tails has the formula —$R^{12}$-$M^1$-$R^{13}$ wherein $R^{12}$ is a $C_4$-$C_{14}$ alkyl group, $M^1$ is a —OC(O)—, and $R^{13}$ is a $C_{10}$-$C_{20}$ branched alkyl group;
the chain length of formula —$R^{12}$-$M^1$-$R^{13}$ is at most 21 atoms; and
the total carbon atom content of each hydrophobic tail is 21 to 26 carbon atoms.

13. The method of claim 12, wherein $R^{13}$ is branched at the alpha position relative to the —OC(O)— group.

14. The method of claim 13, wherein the organic solvent comprises ethanol and the second solution comprises an aqueous buffer.

15. The method of claim 14, wherein the aqueous buffer is a citrate buffer.

16. The method of claim 15, further comprising dialyzing or diafiltering the lipid particle mixture.

17. The method of claim 13, wherein the nucleic acid comprises RNA.

18. The method of claim 13, wherein the chain length of formula —$R^{12}$-$M^1$-$R^{13}$ is 17 atoms.

19. The method of claim 13, wherein the head group consists of a saturated aliphatic group and a hydroxyl group.

20. A method for preparing a lipid particle mixture comprising mixing a first solution comprising an organic solvent, a protonatable lipid compound, distearoylphosphatidylcholine (DSPC), cholesterol, and a PEG-modified lipid, with a second solution comprising a nucleic acid and water to form a lipid particle mixture, wherein the lipid particle comprises (i) a nucleic acid,
(ii) 35-65 mol % of a protonatable lipid compound,
(iii) 3-12 mol % distearoylphosphatidylcholine (DSPC),
(iv) 15-45 mol % cholesterol, and
(v) 0.5-10 mol % of the PEG-modified lipid, wherein the PEG-modified lipid is 1-(monomethoxy-polyethylene glycol)-2,3-dimyristoyl glycerol (PEG-DMG),
wherein the mol % is based on 100% total moles of lipids in the lipid particle,
wherein the protonatable lipid compound comprises a head group, hydrophobic tails, and a central moiety to which the head group and the hydrophobic tails are directly bonded, wherein:
the central moiety is a nitrogen atom;
the hydrophobic tails consist of two hydrophobic tails;
each of the two hydrophobic tails independently consists of a first hydrophobic chain, an ester group, and a second hydrophobic chain, wherein the first and second hydrophobic chains are aliphatic and linked by the ester group, and the first hydrophobic chain is bonded directly to the central moiety, wherein each ester group is —C(O)O—;
wherein each hydrophobic tail has a total carbon atom content from 17 to 26 carbon atoms; and
wherein one hydrophobic tail has the formula:

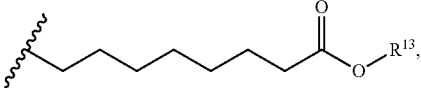

wherein:
$R^{13}$ is a $C_{13}$-$C_{17}$ branched alkyl; and
the chain length of the one hydrophobic tail is from 18 to 20 atoms.

21. The method of claim 20, wherein $R^{13}$ is a $C_{17}$ branched alkyl.

22. The method of claim 21, wherein the hydrophobic tail having the formula:

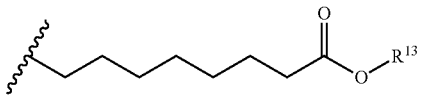

has a chain length of 18 atoms.

23. The method of claim 20, wherein $R^{13}$ is branched at the alpha position relative to the —C(O)O— group.

24. The method of claim 23, wherein the nucleic acid comprises RNA.

25. The method of claim 23, wherein the head group consists of a saturated aliphatic group and a hydroxyl group.

26. The method of claim 21, wherein the organic solvent comprises ethanol and the second solution comprises an aqueous buffer.

27. The method of claim 26, wherein the aqueous buffer is a citrate buffer.

28. The method of claim 27, further comprising dialyzing or diafiltering the lipid particle mixture.

* * * * *

UNITED STATES PATENT AND TRADEMARK OFFICE
CERTIFICATE OF CORRECTION

PATENT NO. : 11,633,480 B2
APPLICATION NO. : 17/651023
DATED : April 25, 2023
INVENTOR(S) : Martin Maier et al.

It is certified that error appears in the above-identified patent and that said Letters Patent is hereby corrected as shown below:

On the Title Page

Item (72) Inventor, should read:
--(72) Inventors: Martin Maier, Cambridge, MA (US); Muthusamy Jayaraman, Cambridge, MA (US); Akin Akinc, Cambridge, MA (US); Shigeo Matsuda, Cambridge, MA (US); Pachamuthu Kandasamy, Malden, MA (US); Kallanthottathil G. Rajeev, Cambridge, MA (US); Muthiah Manoharan, Cambridge, MA (US); Jayaprakash K. Nair, Wayland, MA (US); Thomas A. Baillie, Seattle, WA (US)--

Signed and Sealed this
Thirtieth Day of January, 2024

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (3)..(4)
<223> OTHER INFORMATION: 2'F modified nucleobase
<220> FEATURE:
<221> NAME/KEY: modified_base
<222> LOCATION: (6)..(9)
<223> OTHER INFORMATION: 2'F modified nucleobase
<220> FEATURE:
<221> NAME/KEY: modified_base
<222> LOCATION: (13)..(16)
<223> OTHER INFORMATION: 2'F modified nucleobase
<220> FEATURE:
<221> NAME/KEY: modified_base
<222> LOCATION: (18)..(18)
<223> OTHER INFORMATION: 2'F modified nucleobase
<220> FEATURE:
<221> NAME/KEY: modified_base
<222> LOCATION: (20)..(21)
<223> OTHER INFORMATION: Deoxythymidine
<220> FEATURE:
<221> NAME/KEY: misc_feature
```

```
<222> LOCATION: (20)..(21)
<223> OTHER INFORMATION: Phosphothioate bond

<400> SEQUENCE: 1
ggaucaucuc aagucuuact t                                              21

<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'F modified nucleobase
<220> FEATURE:
<221> NAME/KEY: modified_base
<222> LOCATION: (6)..(8)
<223> OTHER INFORMATION: 2'F modified nucleobase
<220> FEATURE:
<221> NAME/KEY: modified_base
<222> LOCATION: (13)..(13)
<223> OTHER INFORMATION: 2'F modified nucleobase
<220> FEATURE:
<221> NAME/KEY: modified_base
<222> LOCATION: (16)..(18)
<223> OTHER INFORMATION: 2'F modified nucleobase
<220> FEATURE:
<221> NAME/KEY: modified_base
<222> LOCATION: (20)..(21)
<223> OTHER INFORMATION: Deoxythymidine
<220> FEATURE:
<221> NAME/KEY: misc_feature
<222> LOCATION: (20)..(21)
<223> OTHER INFORMATION: Phosphothioate bond

<400> SEQUENCE: 2
guaagacuug agaugaucct t                                              21
```